(12) United States Patent
Wittman et al.

(10) Patent No.: US 7,081,454 B2
(45) Date of Patent: Jul. 25, 2006

(54) TYROSINE KINASE INHIBITORS

(75) Inventors: Mark D. Wittman, Wallingford, CT (US); Neelakantan Balasubramanian, Madison, CT (US); Upender Velaparthi, North Haven, CT (US); Kurt Zimmermann, Durham, CT (US); Mark G. Saulnier, Higgannum, CT (US); Peiying Liu, Madison, CT (US); Xiaopeng Sang, Glastonbury, CT (US); David B. Frennesson, Nauatuck, CT (US); Karen M. Stoffan, Hartford, CT (US); James G. Tarrant, Hamden, CT (US); Anne Marinier, Kirkland (CA); Stephan Roy, St-Lambert (CA)

(73) Assignee: Bristol-Myers Squibb Co., Princeton, NJ (US)

( * ) Notice: Subject to any disclaimer, the term of this patent is extended or adjusted under 35 U.S.C. 154(b) by 255 days.

(21) Appl. No.: 10/263,448

(22) Filed: Oct. 2, 2002

(65) Prior Publication Data

US 2004/0044203 A1    Mar. 4, 2004

Related U.S. Application Data

(63) Continuation-in-part of application No. 10/105,599, filed on Mar. 25, 2002, now abandoned.

(60) Provisional application No. 60/279,327, filed on Mar. 28, 2001.

(51) Int. Cl.
*C07D 267/10* (2006.01)
*C07D 413/14* (2006.01)
*A61K 31/553* (2006.01)
*A66K 31/5377* (2006.01)

(52) U.S. Cl. ............... 514/211.15; 514/235.2; 540/544; 544/124

(58) Field of Classification Search .......... 514/234.5, 514/253.12, 318, 278, 322, 211.15, 218, 256, 514/235.2; 540/544, 553; 544/131, 333, 544/361, 124; 546/273.4
See application file for complete search history.

(56) References Cited

U.S. PATENT DOCUMENTS 5,650,415 A    7/1997    Tang et al.

FOREIGN PATENT DOCUMENTS

| EP | 0 385 850 | 9/2000 |
|---|---|---|
| WO | WO 99/60023 | 11/1999 |
| WO | WO 00/02871 | 1/2000 |
| WO | WO 00/08202 | 2/2000 |
| WO | WO 00/12089 | 3/2000 |
| WO | WO 00/17203 | 3/2000 |
| WO | WO 00/20023 | 4/2000 |
| WO | WO 00/23469 | 4/2000 |
| WO | WO 00/35455 | 6/2000 |
| WO | WO 00/53605 | 9/2000 |
| WO | WO 01/17995 | 3/2001 |
| WO | WO 01/60816 | 8/2001 |
| WO | WO 01/72751 | 10/2001 |

OTHER PUBLICATIONS

Parrizas, et al. (1997) Endocrinology 138: 1427-1433.
Blum, et al. (2000) Biochemistry 39:15705-15712.
Gungor, et al. (1992(J. Med. Chem. 35:4455-4463.
Sahal, et al. (1988) Archives of Biochemistry and Biophysics 260: 416-426.
Chimirri et al., Heterocycles, vol. 53, No. 3, pp. 613-620, 2000.
Nawwar et al., Chemical Abstract No. 164052r, vol. 120, No. 13, Mar. 28, 1994.
Pednekar et al., Chemical Abstracts No. 182731b, vol. 96, No. 22, May 31, 1982.

*Primary Examiner*—Kamal A. Saeed
*Assistant Examiner*—Rebecca Anderson
(74) *Attorney, Agent, or Firm*—Maureen S. Gibbons

(57) ABSTRACT

The present invention provides compounds of formula I

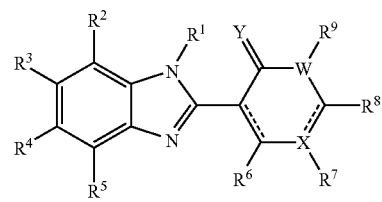

and pharmaceutically acceptable salts thereof.

The formula I compounds inhibit tyrosine kinase enzymes thereby making them useful as anti-cancer agents. The formula I compounds are also useful for the treatment of other diseases which can be treated by inhibiting tyrosine kinase enzymes.

20 Claims, No Drawings

TYROSINE KINASE INHIBITORS

RELATED APPLICATIONS

This application is a continuation in part of U.S. Ser. No. 10/105,599 filed Mar. 25, 2002, now abandoned, which claims priority to U.S. application Ser. No. 60/279,327 filed Mar. 28, 2001.

FIELD OF INVENTION

The present invention relates generally to the field of tyrosine kinase enzyme inhibition using novel small molecules.

BACKGROUND OF THE INVENTION

Tyrosine Kinases are a class of enzymes, which catalyze the transfer of the terminal phosphate of adenosine triphosphate to the phenolic hydroxyl group of a tyrosine residue present in the target protein. Tyrosine kinases play a critical role in signal transduction for several cellular functions including cell proliferation, carcinogenesis, apoptosis, and cell differentiation (Plowman, G. D.; Ullrich, A.; Shawver, L. K.: Receptor Tyrosine Kinases As Targets For Drug Intervention. *DN&P* (1994) 7: 334–339). Therefore inhibitors of these enzymes would be useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, HER-2, IGF-1R, IR, LCK, MET, PDGF, Src, and VEGF (Traxler, P. M. Protein Tyrosine Kinase Inhibitors in Cancer Treatment. *Exp. Opin. Ther. Patents* (1997) 7: 571–588; incorporated herein by reference). Hence, there is an ongoing need to investigate novel compounds that can be used to regulate or inhibit tyrosine kinase enzymes.

SUMMARY OF THE INVENTION

The present invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, angiogenic diseases and immunologic disorders (Powis, G.; Workman, P. Signaling targets For The Development of Cancer Drugs. *Anti-Cancer Drug Design* (1994), 9: 263–277; Merenmies, J.; Parada, L. F.; Henkemeyer, M. Receptor Tyrosine Kinase Signaling in Vascular Development. *Cell Growth Differ* (1997) 8: 3–10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50–63; all herein incorporated by reference).

A compound according to formula I

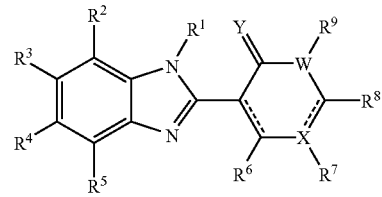

its enantiomers, diastereomers, pharmaceutically acceptable salts, hydrates, prodrugs and solvates thereof;

wherein

X is selected from the group consisting of N, C, $C_1$–$C_3$ alkyl, $C_1$–$C_3$ alkyl substituted with one or more $R^7$ and a direct bond;

Y is selected from the group consisting of O and S;

W is selected from the group consisting of N, C, O, and S; provided that if W is O or S, $R^9$ is absent;

$R^1$, $R^2$, $R^3$, $R^4$, $R^5$, $R^6$, $R^7$, $R^8$, $R^9$ are each independently selected from the group consisting of H, $C_{1-6}$ alkyl, alkenyl, alkynyl, cycloalkyl, heterocycloalkyl, halo, amino, —$OR^{60}$, —$NO_2$, —OH, —$SR^{60}$, —$NR^{60}R^{61}$, —CN, —$CO_2R^{60}$, —$CONR^{60}OR^{61}$, $OCONR^{60}R^{61}$, —$NR^{62}CONR^{60}R^{61}$, —$NR^{60}SO_2R^{61}$, —$SO_2NR^{60}R^{61}$, —$SO_2R^{63}$, —$C(NR^{62})NR^{60}R^{61}$, aryl, heteroaryl, —$(CH_2)_nOR^{60}$, —$(CH_2)_nNR^{60}R^{61}$, —$(CH_2)_nSR^{60}$, —$(CH_2)_n$ aryl, —$(CH_2)_n$ heteroaryl, —$(CH_2)_n$ heterocycloalkyl, —NH—Z-aryl, and —NH—Z-heteroaryl; wherein n is 1 to 3; and Z is selected from the group consisting of $C_1$–$C_4$ alkyl, alkenyl, and alkynyl chain; Z having one or more hydroxy, thiol, alkoxy, thioalkoxy, amino, halo, $NR^{60}SO_2R^{61}$ groups; Z optionally incorporating one or more groups selected from the group consisting of CO, CNOH, $CNOR^{60}$, $CNNR^{60}$, $CNNCOR^{60}$ and $CNNSO_2R^{60}$; and $R^{60}$, $R^{61}$, $R^{62}$, and $R^{63}$ are independently selected from the group consisting of H, alkyl, alkenyl, alkynyl, cycloalkyl, cycloalkylalkyl, hydroxy, alkoxy, aryl, heteroaryl, heteroarylalkyl, and alkyl-$R^{25}$;

$R^{25}$ is hydrogen, alkenyl, hydroxy, thiol, alkoxy, thioalkoxy, amino, alkylamino, dialkylamino, aryl, heteroaryl, cyano, halo, sulfoxy, sulfonyl, —$NR^{30}COOR^{31}$, —$NR^{30}C(O)R^{31}$, —$NR^{30}SO_2R^{31}$, —$C(O)NR^{30}R^{31}$, heteroaryl or heterocycloalkyl; and $R^{30}$ and $R^{31}$ are, independently, hydrogen, alkyl, or cycloalkyl.

In preferred embodiments, $R^1$, $R^7$, $R^8$ and $R^9$ are H; $R^2$ and $R^4$ are H or F; Y is O; X is selected from the group consisting of N and CH; W is N; $R^5$ is selected from the group consisting of H, methyl, ethyl, isopropyl, secondary butyl, cyclopropyl, F, and $CF_3$; $R^6$ is selected from the group consisting of H, 2-aminomethylpyridine, $NHCH_2CH(OH)$ aryl, and $NHCH(CH_2OH)CH_2$aryl; and $R^3$ is selected from the group consisting of $OR^{60}$, $C(NH)NHR^{60}$, $C(O)NHR^{60}$ imidazole, imidazoline, tetrahydropyrimidine, piperazine, morpholine, homomorpholine, piperidine, pyrrolidine, homopiperazine and amino; wherein $R^{60}$ is selected from the group consisting of H, alkyl, cycloalkyl, heterocycloalkyl, and alkyl-$R^{25}$.

Preferably, $R^3$ is —$OR^{60}$ and $R^{60}$ is alkyl, or -alkyl-$R^{25}$, such as methyl, —$(CH_2)_nCH_2OH$, or —$(CH_2)_nCH_2N(CH_2CH_2)_2O$, and n is 0, 1, or 2.

In some embodiments, $R^{25}$ is morpholine,

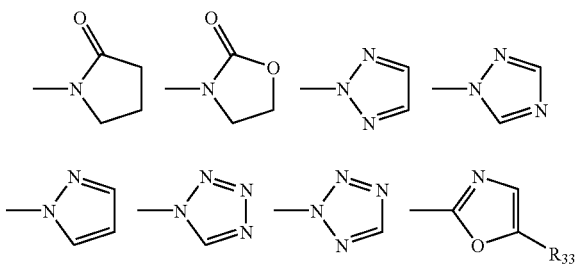

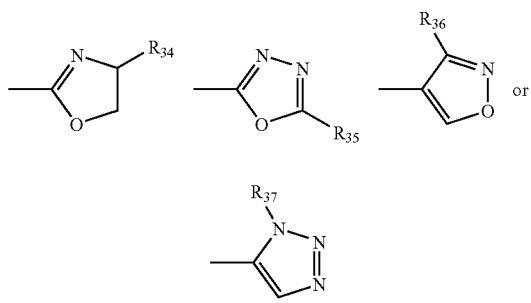

wherein $R^{33}$, $R^{34}$, $R^{35}$, $R^{36}$, and $R^{37}$ are hydrogen, alkyl, or substituted alkyl.

According to some embodiments of the present invention, $R^3$ is piperazine, homopiperazine, 3-methylpiperazine, or 3,5-dimethylpiperazine being optionally substituted at the 4-N position with a compound selected from the group consisting of alkyl, cycloalkyl, cycloalkylalkyl, alkyl-$R^{25}$, —C(O)—$R^{15}$, or —CO$_2$$R^{15}$ wherein $R^{15}$ is hydrogen, alkyl, aryl, alkyl-$R^{25}$, amino or aryl. Preferred piperazines are substituted with methyl, ethyl, CH$_2$-cyclopropyl, hydroxyethyl, 2-dimethylaminoethyl, 2-diethylaminoethyl, 2-aminoethyl, 2-methylaminoethyl, 2-ethylaminoethyl, methoxyethyl, ethoxyethyl, thiomethoxyethyl, morpholine, and morpholinylethyl.

$R^3$ may be an amino group selected from the group consisting of hydroxyalkylamino, amino alkylamino, dialkylaminoalkylamino, and heterocycloalkylalkylamino. Preferred amino groups include NHCH$_2$CH$_2$OH, NMeCH$_2$CH$_2$OH, NEtCH$_2$CH$_2$OH, NHCH$_2$CH$_2$NH$_2$, NMeCH$_2$CH$_2$NH$_2$, NEtCH$_2$CH$_2$NH$_2$, NHCH$_2$CH$_2$NMe$_2$, NMeCH$_2$CH$_2$NMe$_2$, NEtCH$_2$CH$_2$NMe$_2$, NHCH$_2$CH$_2$NEt$_2$, NMeCH$_2$CH$_2$NEt$_2$, NEtCH$_2$CH$_2$NEt$_2$, NHCH$_2$CH$_2$N(CH$_2$CH$_2$)$_2$O, NMeCH$_2$CH$_2$N(CH$_2$CH$_2$)$_2$O, and NEtCH$_2$CH$_2$N(CH$_2$CH$_2$)$_2$O.

According to some embodiments of the present invention, $R^3$ is piperidine, optionally substituted with hydroxy, thiol, amino, alkylamino, dialkylamino, alkoxy, thioalkoxy, 1,3 dioxolane, 1,3 dioxane, —NHC(O)$R^{15}$, —NHCO$_2$$R^{15}$, wherein $R^{15}$ is hydrogen, alkyl, aryl or alkyl-$R^{25}$ or morpholine, thiomorpholine, sulfoxymorpholine, sulfonylmorpholine, or homomorpholine, or a substituted morpholine, thiomorpholine, sulfoxymorpholine, sulfonylmorpholine, or homomorpholine. The morpholine, thiomorpholine, sulfoxymorpholine, sulfonyl morpholine, or homomorpholine is optionally substituted with hydroxy, thiol, amino, alkylamino, dialkylamino, alkoxy, thioalkoxy, alkyl-$R^{25}$, —NHC(O)$R^{15}$, —NHCO$_2$$R^{15}$, wherein $R^{15}$ is hydrogen, alkyl, aryl or alkyl-$R^{25}$.

In some embodiments of the present invention, $R^3$ is an optionally substituted pyrrolidine that may be selected from the group consisting of 3-hydroxyl pyrrolidine, 3-alkoxy pyrrolidine, and 3-alkylamino pyrrolidine, 3-dialkylamino pyrrolidine.

According to one embodiment of the present invention, $R^6$ is selected from the group consisting of H, 2-aminomethylpyridine, NHCH$_2$CH(OH)aryl, and NHCH(CH$_2$OH)CH$_2$aryl. Preferred aryl groups include substituted phenyl wherein the phenyl is substituted with at least one Br, Cl, F, —CN, methoxy, or —NHSO$_2$CH$_3$.

According to some embodiments of the present invention, $R^6$ is

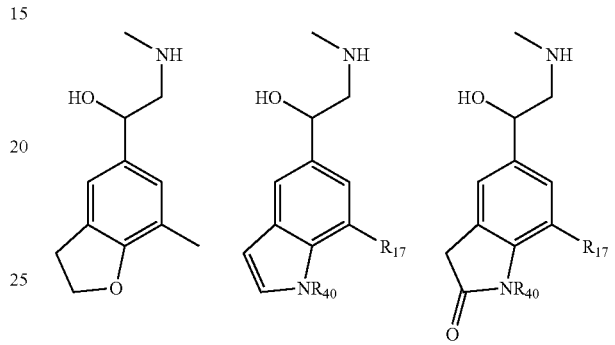

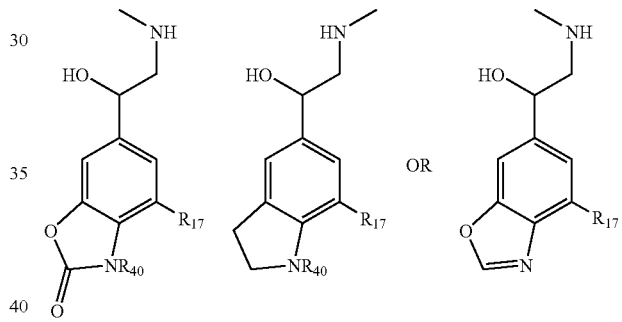

wherein $R^{17}$ is H, Br, Cl, or F and $R^{40}$ is H or alkyl.

Compounds of the present invention may have the formula:

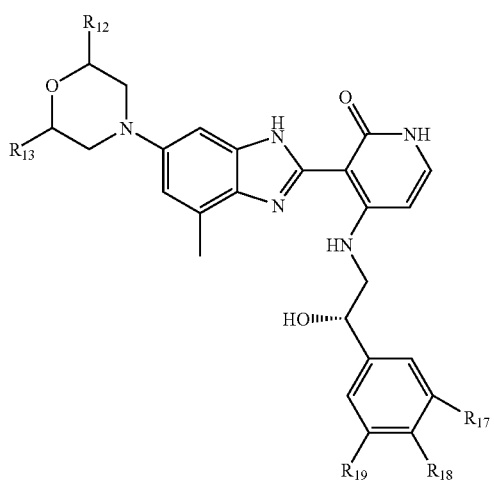

In preferred embodiments, $R^{12}$ is hydrogen, methyl, hydroxymethyl, methoxymethyl, $CH_2F$, $CH_2CN$, $CO_2H$, or —$CONR^{30}R^{31}$; $R^{13}$ is H or methyl; $R^{17}$ is Br, F, or Cl; $R^{18}$ is methoxy or fluoro; and $R^{19}$ is H; or $R^{18}$ and $R^{19}$ together form 4-O, 5 dihydrofuranyl.

According to one embodiment of the present invention, compounds have the formula:

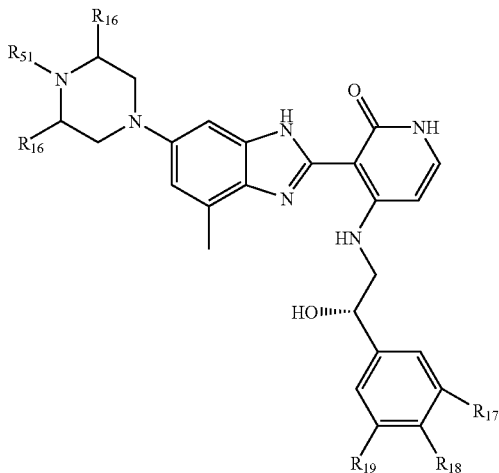

wherein $R^{51}$ is hydrogen, alkyl, aryl, or -alkyl-$R^{25}$ and the remaining substituents are as defined above. The compound according to claim 30 wherein $R^{51}$ is hydrogen, methyl, ethyl, or $(CH_2)_nCH_2$—$R^{25}$ wherein $R^{25}$ is OH, OMe, F, CN, $CF_3$, $SOCH_3$ or $SO_2CH_3$, wherein n is 0 or 1. Preferably, $R^{51}$ is methoxyethyl and $R^6$ is —$NHCH_2CHOH$-aryl. In some embodiments, $R^{51}$ is cyanoethyl, hydroxyethyl, $CH_2CH_2SOCH_3$, $CH_2CH_2CH_2F$, $CH_2CH_2CH_2CN$, or $CH_2CH_2CF_3$; $R^{16}$ and $R^{19}$ are H; $R^{17}$ is Br, or Cl; and $R_{18}$ is hydrogen or methoxy.

According to one embodiment of the present invention, compounds have the formula:

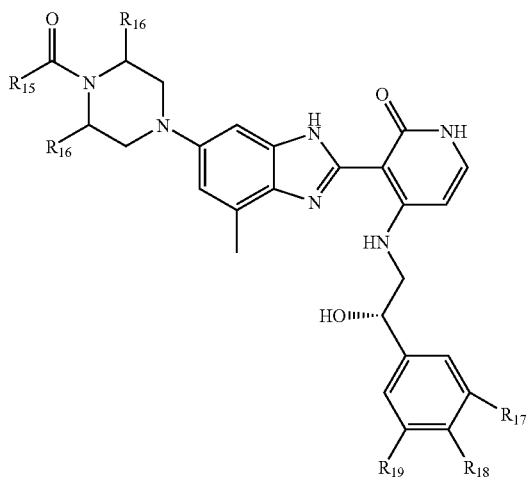

wherein $R^{15}$ is hydrogen, alkyl, aryl or alkyl-$R^{25}$;

each $R^{16}$ is independently hydrogen or methyl and the remaining substituents are as defined above. In preferred embodiments, $R^{15}$ is hydrogen or methyl; $R^{17}$ is bromo, chloro or fluoro; $R^{18}$ is hydrogen or methoxy; and $R^{19}$ is hydrogen.

According to one embodiment of the present invention, compounds have the formula:

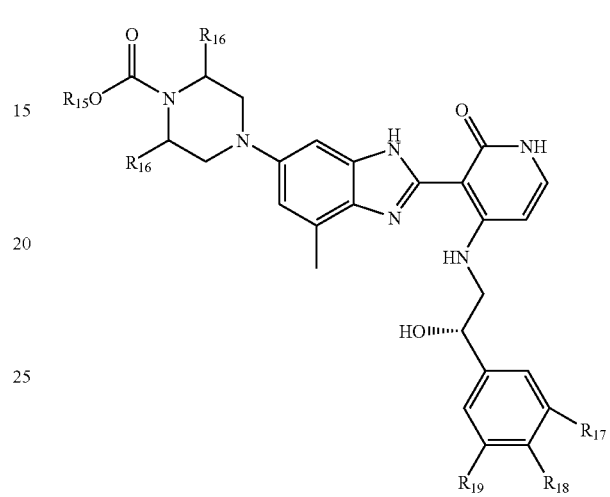

wherein the substituents are as defined above. In preferred embodiments, $R^{15}$ is hydrogen, methyl, ethyl, or —$(CH_2)_n$ CH$^2$—$R^{25}$ wherein n is 0, 1, or 2; and $R^{25}$ is OH, OMe, F, CN, $CF_3$, $SOCH_3$ or $SO_2CH_3$, —$NR^{30}COR^{31}$, —$NR^{30}COOR^{31}$, —$NR^{30}SO_2R^{31}$, —$C(O)NR^{30}R^{31}$, or has the formula:

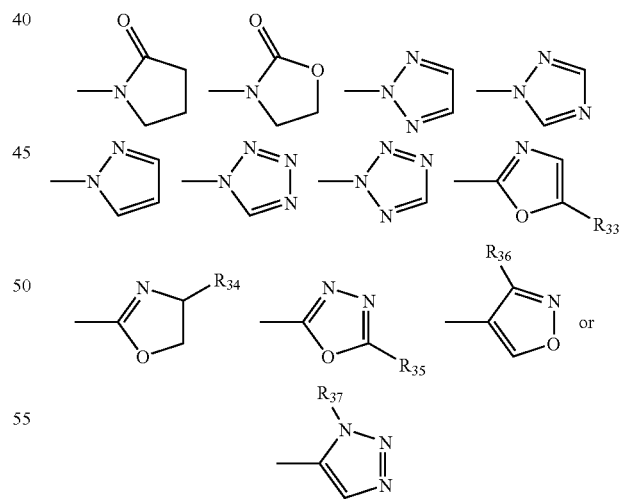

wherein $R^{33}$, $R^{34}$, $R^{35}$, $R^{36}$, and $R^{37}$ are hydrogen, alkyl, or substituted alkyl. In some preferred embodiments, $R^{15}$ is ethyl, methoxyethyl, $CH_2CH_2F$, or $CH_2CH_2CN$; $R^{17}$ is bromo or chloro; $R^{18}$ is methoxy or hydrogen; and $R^{19}$ is hydrogen.

According to some embodiments of the present invention, compounds have the formula:

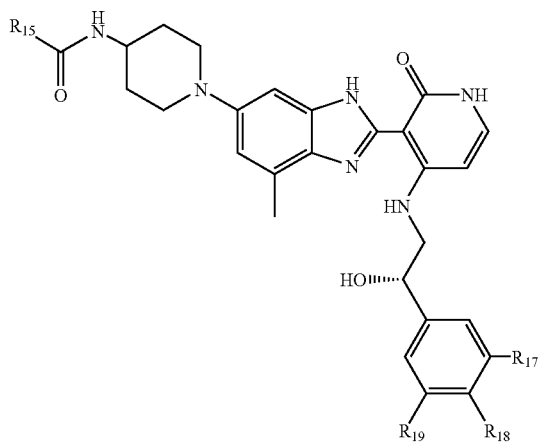

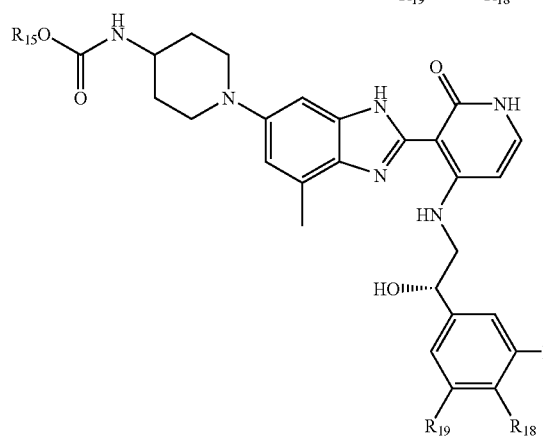

wherein the substituents are as defined above. Preferably, $R^{15}$ is —$(CH_2)nCH_2R^{25}$ n is 0, 1, 2 or 3 and $R^{25}$ is OH, OMe, F, CN, $CF_3$, $SOCH_3$ or $SO_2CH_3$, —$NR^{30}COOR^{31}$, —$NR^{30}C(O)R^{31}$, —$NR^{30}SO_2R^{31}$, —$C(O)NR^{31}R^{32}$ or has the formula:

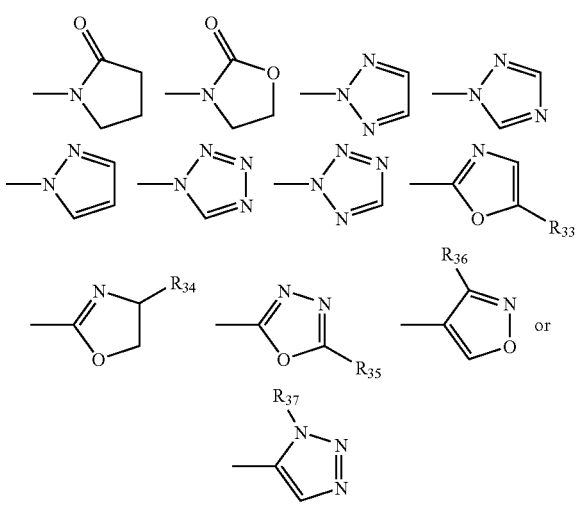

wherein $R^{33}$, $R^{34}$, $R^{35}$, $R^{36}$, and $R^{37}$ are hydrogen, alkyl, or substituted alkyl. More preferably, $R^{15}$ is methyl, ethyl, $CH_2F$, methoxyethyl, $CH_2CH_2F$, or $CH_2CH_2CH_2SOCH_3$; $R^{17}$ is bromo; $R^{18}$ is hydrogen, methoxy, or fluoro; and $R^{19}$ is H.

According to some embodiments of the present invention compounds have the formula:

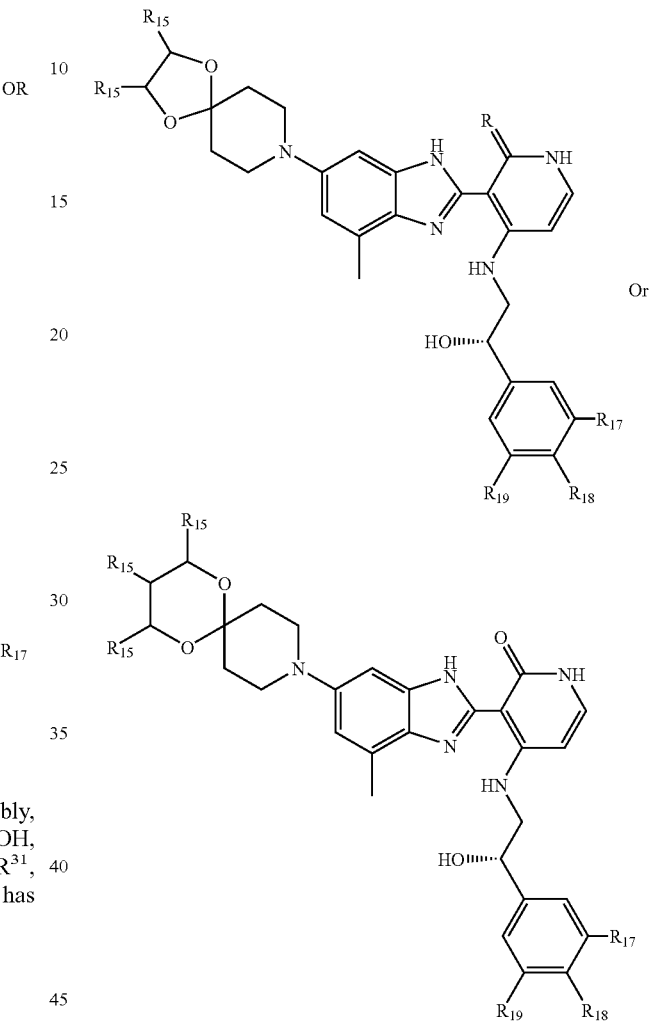

In one preferred embodiment of the present invention, compounds have the following formula:

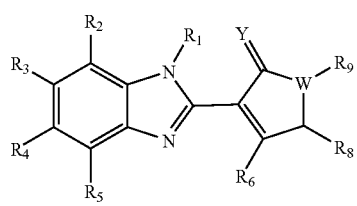

wherein

Y is selected from the group consisting of O and S;

W is selected from the group consisting of N, C, O, and S; provided that if W is O or S, $R^9$ is absent;

$R^1$, $R^2$, $R^3$, $R^4$, $R^5$, $R^6$, $R^8$, $R^9$ are each independently selected from the group consisting of H, $C_{1-6}$ alkyl, alkenyl, alkynyl, cycloalkyl, heterocycloalkyl, halo, amino, —OR$^{60}$, —NO$_2$, —OH, —SR$^{60}$, —NR$^{60}$R$^{61}$, —CN, —CO$_2$R$^{60}$, —CONR$^{60}$R$^{61}$, OCONR$^{60}$R$^{61}$, —NR$^{62}$CONR$^{60}$R$^{61}$, —NR$^{60}$SO$_2$R$^{61}$, —SO$_2$NR$^{60}$R$^{61}$, —SO$_2$R$^{63}$, —C(NR$^{62}$)NR$^{60}$R$^{61}$, aryl, heteroaryl, —(CH$_2$)$_n$OR$^{60}$, —(CH$_2$)$_n$NR$^{60}$R$^{61}$, —(CH$_2$)$_n$SR$^{60}$, —(CH$_2$)$_n$ aryl, —(CH$_2$)$_n$ heteroaryl, —(CH$_2$)$_n$ heterocycloalkyl, —NH—Z-aryl, and —NH—Z-heteroaryl;

wherein n is 1 to 3; and

Z is selected from the group consisting of C$_1$–C$_4$ alkyl, alkenyl, and alkynyl chain; Z having one or more hydroxy, thiol, alkoxy, thioalkoxy, amino, halo, NR$^{60}$S$_2$R$^{61}$ groups; Z optionally incorporating one or more groups selected from the group consisting of CO, CNOH, CNOR$^{60}$, CNNR$^{60}$, CNNCOR$^{60}$ and CNNSO$_2$R$^{60,}$ and R$^{60}$, R$^{61}$, R$^{62}$, and R$^{63}$ are independently selected from the group consisting of H, alkyl, alkenyl, alkynyl, cycloalkyl, cycloalkylalkyl, hydroxy, alkoxy, aryl, heteroaryl, heteroarylalkyl, and alkyl-R$^{25}$;

R$^{25}$ is hydrogen, alkenyl, hydroxy, thiol, alkoxy, thioalkoxy, amino, alkylamino, dialkylamino, aryl, heteroaryl, cyano, halo, sulfoxy, sulfonyl, —NR$^{30}$COOR$^{31}$, —NR$^{30}$C(O)R$^{31}$, —NR$^{30}$SO$_2$R$^{31}$, —C(O)NR$^{30}$R$^{31}$, heteroaryl or heterocycloalkyl; and R$^{30}$ and R$^{31}$ are, independently, hydrogen, alkyl, or cycloalkyl.

In addition to being used as single agents, it is contemplated that tyrosine kinase inhibitors can enhance the activity of cytotoxic or cytostatic treatments when used in combination with standard therapies known in the art.

The invention also provides a pharmaceutical composition comprising a compound of formula I, as defined above, and a pharmaceutically acceptable carrier.

The invention further provides a pharmaceutical composition comprising a compound of formula I, as defined above, in combination with pharmaceutically acceptable carrier and at least one other anti-cancer agent optionally formulated as a fixed dose.

Additionally provided is a method of treating a condition associated with at least one tyrosine kinase enzyme comprising administering to a mammalian species in need of such treatment an effective amount of a compound of formula I, as defined above. Furthermore, the invention provides a method of treating a condition associated with at least one tyrosine kinase enzyme comprising administering to a mammalian species at least one other anti-cancer agent in combination with a compound of formula I, as defined above.

DESCRIPTION

The present invention provides for compounds of formula I, as defined above, pharmaceutical compositions employing such compounds and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: hydroxy, halo (such as F, Cl, Br, I), haloalkyl (such as CCl$_3$ or CF$_3$), alkoxy, alkylthio, cyano, carboxy (—COOH), alkylcarbonyl (—C(O)R), alkoxycarbonyl (—OCOR), amino, carbamoyl (—NHCOOR or —OCONHR), urea (—NHCONHR), thiol, (—SH), sulfoxy, sulfonyl, aryl, heteroaryl, and heterocycloalkyl. Alkyl groups as defined may also comprise one or more carbon to carbon double bonds or one or more carbon to carbon triple bonds. Alkyl groups may also be represented by the formula alkyl-R$^{25}$. In preferred embodiments, the alkyl group is a methyl, ethyl, propyl or butyl group and include substituted methyl, ethyl, propyl or butyl groups.

The term "alkenyl" herein alone or as part of another group refers to a hydrocarbon radical straight, branched or cyclic containing from 2 to 12 carbon atoms and at least one carbon to carbon double bond. An alkenyl group may be optionally substituted in the same manner as described for an alkyl group.

The term "alkynyl" herein alone or as part of another group refers to a hydrocarbon radical straight, branched or cyclic containing from 2 to 12 carbon atoms and at least one carbon to carbon triple bond. An alkynyl group may be optionally substituted in the same manner as described for an alkyl group.

The term "alkoxy" as used alone or in combination herein refers to a straight or branched chain alkyl group covalently bonded to the parent molecule through an oxygen atom linkage containing from one to ten carbon atoms and the terms "C$_{1-6}$ alkoxy" and "lower alkoxy" refer to such groups containing from one to six carbon atoms, examples include, but are not limited to, methoxy, ethoxy, propoxy, isopropoxy, butoxy, t-butoxy and the like. The term "optionally substituted" when used in connection with an alkoxy substituent refers to the replacement of up to two hydrogens, preferably on different carbon atoms with a radical selected form the group of lower alkyl, phenyl, cyano, halo, trifluoromethyl, nitro, hydroxy, alkanoyl, amino, monoalkyl amino and dialkylamino. Alkoxy groups may be substituted in the same manner that alkyl groups can be substituted as described above.

The term "sulfoxy" herein alone or as part of a group refers to —SO and may be substituted with, for example, alkyl or aryl groups.

The term "sulfonyl" herein alone or as part of a group refers to —SO$_2$ and may be substituted with alkyl or aryl groups.

The term "amino" herein alone or as part of another group refers to —NH$_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. Preferred substituents include alkylamino and dialkylamino, such as methylamino, ethylamino, dimethylamino, and diethylamino. These substituents may be further substituted with a carboxylic acid or any of the alkyl or aryl substituents set out herein. In addition, the amino substituents may be taken together with the nitrogen atom to which they are attached to form 1-pyrrolidinyl, 1-piperidinyl, 1-azepinyl, 4-morpholinyl, 4-thiamorpholinyl, 4-sulfoxymorpholine, 4-sulfonylmorpholine, 1-piperazinyl, 4-alkyl-1-piperazinyl, 4-arylalkyl-1-piperazinyl, 4-diarylalkyl-1-piperazinyl, 1-homopiperazinyl, 4-alkyl-1-homopiperazinyl, 4-arylalkyl-1-homopiperazinyl, 4-diarylalkyl-1-homopiperazinyl; 1-pyrrolidinyl, 1-piperidinyl, or 1-azepinyl, optionally substituted with alkyl, alkoxy, alkylthio, halo, trifluoromethyl or hydroxy.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, alkynyl, alkoxy, hydroxy, carboxy, carbamoyl, alkyloxycarbonyl, alkylaminocarbonyl, nitro, trifluoromethyl, amino, cycloalkyl, cyano, alkyl $S(O)_m$ (m=0, 1, 2), or thiol. Aryl groups may also be substituted with heterocycloalkyl and heterocycloaryl groups to form fused rings, such as dihydrobenzfuranyl, oxindolyl, indolyl, indolinyl, oxindolyl, benzoxazolidinonyl, benzoxazolinyl and benzoxazolidinone.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, preferably one, selected from the group consisting of halo, alkyl, substituted alkyl, alkenyl, alkynyl, nitro, cyano, oxo (=O), hydroxy, alkoxy, thioalkyl, —CO₂H, —OC(=O)H, CO₂-alkyl, —OC(=O)alkyl, =N—OH, =N—O-alkyl, aryl, heteroaryl, heterocyclo, a five or six membered ketal (i.e. 1,3-dioxolane or 1,3-dioxane), —NR'R", —C(=O)NR'R", —OC(=O)NR'R", —NR'CO₂'R", —NR'C(=O)R", —SO₂NR'R", and —NR'SO₂'R", wherein each of R' and R" is independently selected from hydrogen, alkyl, substituted alkyl, and cycloalkyl, or R' and R" together form a heterocyclo or heteroaryl ring. Cycloalkyl groups may also be substituted with hetero atoms such as O, N, and S to form heterocycloalkyl groups. Preferred heterocycloalkyl groups include optionally substituted morpholine, homomorpholine (7 membered ring), thiomorpholine, piperazine, homopiperazine (7 membered ring), and piperidine.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, hydroxy, alkoxy, thioalkyl, —CO₂H, —OC(=O)H, —CO₂-alkyl, —OC(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —OC(=O)NR'R", —NR'CO₂'R", —NR'C(=O)R", —SO₂NR'R", and —NR'SO₂R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrrolidinyl, imidazolinyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, and the like.

Exemplary bicyclic heteroaryl groups include indolyl, indolinyl, oxindolyl, benzoxazolidinone, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

The term "halogen" or "halo" herein alone or as part of another group refers to chlorine, bromine, fluorine or iodine selected on an independent basis.

The term "hydroxy" herein alone or as part of another group refers to —OH.

The term "thioalkoxy" herein alone or as part of another group refers to an alkyl group as defined herein attached to the parent molecular group through a sulfur atom. Examples of thioalkoxy include, but are not limited to, thiomethoxy, thioethoxy, and the like.

Abbreviations: "Ph" represents phenyl; "Me" represents methyl; and "Et" represents ethyl.

An "anti-cancer agent" as used herein includes known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; antimetabolites, such as methotrexate; tyrosine kinase inhibitors such as Iressa and OSI-774; angiogenesis inhibitors; EGF inhibitors; VEGF inhibitors; CDK inhibitors; Her1/2 inhibitors and monoclonal antibodies directed against growth factor receptors such as erbitux (EGF) and herceptin (Her2).

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

When $C_{1-6}$ alkyl, alkenyl, alkynyl, cycloalkyl are substituted, they are preferably substituted with one or more hydroxy, cyano, carbamoyl, hydroxy, alkoxy, thiol, alkenyl, thioalkoxy, amino, alkylamino, amido, sulfonyl, sulfoxy, sulfonamido, halo, heterocycloalkyl, aryl or heteroaryl.

When aryl or heteroaryl are substituted, they are preferably substituted with one or more alkyl, alkenyl, alkynyl, cyano, carbamoyl, hydroxy, alkoxy, thioalkoxy, amino, amido, sulfonamido, halo or with R', R" wherein R', R" form a ring that is fused to the aryl group. When CH$_2$aryl or heteroaryl are substituted, they are preferably substituted with one or more alkyl, alkyenyl, alkynyl, cyano, carbamoyl, hydroxy, alkoxy, thioalkoxy, amino, amido, sulfonamido, or halogen.

When NH—Z-aryl or NH—Z-heteroaryl groups are substituted, they are preferably substituted with one or more alkyl, alkenyl, alkynyl, hydroxy, alkoxy, thioalkoxy, amino, halogen, nitro, nitrile, carboxylate, alkoxycarbonyl, carbamoyl, ester, amide, aryl, or heteroaryl The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "alkyl-$R^{25}$" includes optionally substituted alkyl groups such as methyl, ethyl, propyl, and butyl, attached to an $R^{25}$group. $R^{25}$ generally includes hydrogen, alkenyl, hydroxy, thiol, alkoxy, thioalkoxy, amino, alkylamino, dialkylamino, aryl, heteroaryl, cyano, halo, sulfoxy, sulfonyl, —NHCOOH, —NHC(O)—, —NHSO$_2$—, —C(O)NH$_2$, heteroaryl or heterocycloalkyl groups such as morpholinyl or group having the formula:

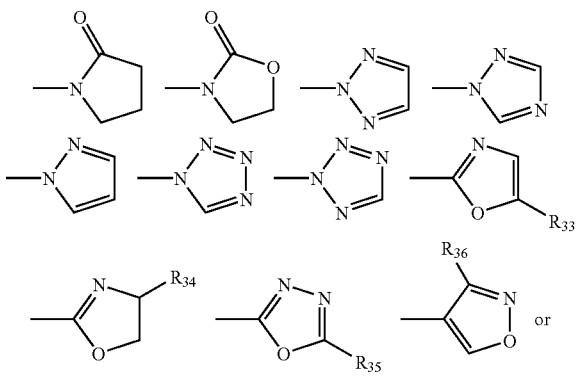

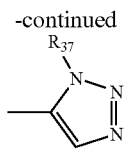

The terms "imidazole" and "imidazoline" herein alone or as part of another group includes substituted imidazoles and substituted imidazolines. Similarly, the term "tetrahydropyrimidine" includes substituted tetrahydropyrimidines. Likewise, the terms "piperazine", "piperidine" "morpholines", "homopiperazines", "homomorpholines" and "pyrrolidine" include substituted piperazines, substituted piperidines, substituted morpholines, substituted homomorpholines and substituted pyrrolidines, respectively.

Compounds of the present invention have the general formula I:

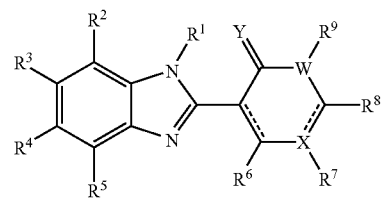

its enantiomers, diastereomers, pharmaceutically acceptable salts, hydrates, prodrugs and solvates thereof;

wherein

X is selected from the group consisting of N, C, $C_1$–$C_3$ alkyl, $C_1$–$C_3$ alkyl substituted with one or more $R^7$ and a direct bond;

Y is selected from the group consisting of O and S;

W is selected from the group consisting of N, C, O, and S, provided that when W is O or S, $R^9$ is absent;

$R^1$, $R^2$, $R^3$, $R^4$, $R^5$, $R^6$, $R^7$, $R^8$, $R^9$ are each independently selected from the group consisting of H, $C_{1-6}$ alkyl, alkenyl, alkynyl, cycloalkyl, heterocycloalkyl, halo, amino, OR$^{60}$, NO$_2$, OH, SR$^{60}$, NR$^{60}$R$^{61}$, CN, CO$_2$R$^{60}$, CONR$^{60}$R$^{61}$, CO$_2$NR$^{60}$R$^{61}$, NR$^{62}$CONR$^{60}$R$^{61}$, NR$^{60}$SO$_2$R$^{61}$, SO$_2$NR$^{60}$R$^{61}$, C(NR$^{62}$)NR$^{60}$R$^{61}$, aryl, heteroaryl, (CH$_2$)$_n$OR$^{60}$, (CH$_2$)$_n$NR$^{60}$OR$^{61}$, (CH$_2$)$_n$SR$^{60}$, (CH$_2$)$_n$ aryl, (CH$_2$)$_n$ heteroaryl, (CH$_2$)$_n$ heterocycloalkyl, NH—Z-aryl, and NH—Z-heteroaryl;

wherein n is 1 to 3; and

Z is selected from the group consisting of $C_1$–$C_4$ alkyl, alkenyl, and alkynyl chain; Z having one or more hydroxy, thiol, alkoxy, thioalkoxy, amino, halo, NR$^{60}$SO$_2$R$^{61}$ groups; Z optionally incorporating one or more groups selected from the group consisting of CO, CNOH, CNOR$^{60}$, CNNR$^{60}$, CNNCOR$^{60}$ and CNNSO$_2$R$^{60}$; and $R^{60}$, $R^{61}$, $R^{62}$ and $R^{63}$ are independently selected from the group consisting of H, alkyl, alkenyl, alkynyl, cycloalkyl, cycloalkylalkyl, hydroxy, alkoxy, aryl, heteroaryl, heteroarylalkyl, and alkyl-$R^{25}$ wherein $R^{25}$ is hydrogen, alkenyl, hydroxy, thiol, alkoxy, thioalkoxy, amino, alkylamino, dialkylamino, aryl, heteroaryl, cyano, halo, sulfoxy, sulfonyl, —NR$^{30}$COOR$^{31}$, —NR$^{30}$C(O)R$^{31}$, NR$^{30}$SO$_2$R$^{31}$, —C(O)NR$^{30}$R$^{31}$, heteroaryl or heterocycloalkyl; and $R^{30}$ and $R^{31}$ are, independently, hydrogen, alkyl, or cycloalkyl.

In some embodiments of the present invention, $R^3$ is —$OR^{60}$. $R^{60}$ is alkyl, or -alkyl-$R^{25}$, wherein $R^{25}$ is hydrogen, alkenyl, hydroxy, thiol, alkoxy, thioalkoxy, amino, halo, cyano, alkylsulfoxy, alkylsulfonyl, —$R^{30}COOR^{31}$, —$NR^{30}C(O)R^{31}$, —$NR^{30}SO_2R^{31}$, —$C(O)NR^{30}R^{31}$, heteroaryl or heterocycloalkyl; and $R_{30}$ and $R_{31}$ are, independently, hydrogen, alkyl, or cycloalkyl. In preferred embodiments, $R^{60}$ is methyl, —$(CH_2)_nCH_2OH$, or —$(CH_2)_nCH_2N(CH_2CH_2)_2O$, and n is 0, 1, or 2.

In some embodiments, $R^3$ is piperazine, homopiperazine, 3-methylpiperazine, or 3,5-dimethylpiperazine being optionally substituted at the 4-N position with a compound selected from the group consisting of alkyl, aryl, cycloalkyl, cycloalkylalkyl, heterocycloalkyl, alkyl-$R^{25}$, —$C(O)$—$R^{15}$, or —$CO_2R^{15}$ wherein $R^{15}$ is hydrogen, alkyl, aryl, alkyl-$R^{25}$, amino or aryl; and $R^{25}$ is hydrogen, alkenyl, hydroxy, thiol, alkoxy, thioalkoxy, amino, alkylamino, dialkylamino, cyano, halo, sulfoxy, sulfonyl, arylsulfonyl, —$NR^{30}COOR^{31}$, —$NR^{30}C(O)R^{31}$, —$NR^{30}SO_2R^{31}$, —$C(O)NR^{30}R^{31}$, heteroaryl or heterocycloalkyl and $R^{30}$ and $R^{31}$ are, independently, hydrogen, alkyl, or cycloalkyl. In preferred embodiments, piperazine is substituted with Me, $CH_2$cyclopropyl, $CH_2CH_2NMe_2$, $CH_2CH_2NEt_2$, $CH_2CH_2NH_2$, $CH_2CH_2NHMe$, $CH_2CH_2NHEt$, N—$CH_2CH_2N(CH_2CH_2)_2O$, $(CH_2)_nCH_2$—$R_{25}$ wherein $R^{25}$ is OH, OMe, F, CN, $CF_3$, $SOCH_3$ or $SO_2CH_3$, wherein n is 0, 1, or 2.

In some embodiments, $R^3$ is an amino group. Preferred amino groups include $NHCH_2CH_2OH$, $NMeCH_2CH_2OH$, $NEtCH_2CH_2OH$, $NHCH_2CH_2NH_2$, $NMeCH_2CH_2NH_2$, $NEtCH_2CH_2NH_2$, $NHCH_2CH_2NMe_2$, $NMeCH_2CH_2NMe_2$, $NEtCH_2CH_2NMe_2$, $NHCH_2CH_2NEt_2$, $NMeCH_2CH_2NEt_2$, $NEtCH_2CH_2NEt_2$, $NHCH_2CH_2N(CH_2CH_2)_2O$, $NMeCH_2CH_2N(CH_2CH_2)_2O$, $NEtCH_2CH_2N(CH_2CH_2)_2O$.

In some embodiments, $R^3$ is an optionally substituted piperidine. Preferred substituents are selected from the group consisting of hydroxy, thiol, amino, alkylamino, dialkylamino, alkoxy, thioalkoxy, 1,3 dioxolane (—$OCHR^{15})_2$, 1,3 dioxane (—$OCHR^{15}CHR^{15}CHR^{15}O$—)—$NHC(O)R^{15}$, —$NHCO_2R^{15}$, wherein $R^{15}$ is hydrogen, alkyl or alkyl-$R^{25}$.

In some embodiments $R^3$ is an optionally substituted morpholine, homomorpholine, thiomorpholine, sulfoxymorpholine, or sulfonylmorpholine. Preferred substituents include hydroxy, thiol, amino, alkylamino, dialkylamino, alkoxy, thioalkoxy, alkyl-$R^{25}$, —$NHC(O)R^{15}$, —$NHCO_2R^{15}$, wherein $R^{15}$ is hydrogen, alkyl or alkyl-$R^{25}$ wherein $R^{25}$.

In some embodiments, $R^3$ is a pyrrolidine. Preferred pyrrolidines include, 3-hydroxyl pyrrolidine, 3- alkoxy pyrrolidine, and 3-alkylamino pyrrolidine.

According to one embodiment of the present invention, $R^3$ is an optionally substituted N-tetrahydropyrimidine or N-imidazoline wherein the substituents are, preferably, alkyl, hydroxyalkyl, alkoxyalkyl, haloalkyl, cyanoalkyl, carboxyl, or carboxamide.

In some embodiments, $R^6$ is selected from the group consisting of H, 2-aminomethylpyridine, $NHCH_2CH(OH)$aryl, and $NHCH(CH_2OH)CH_2$aryl, wherein the aryl group is optionally substituted. In preferred embodiments, the aryl group is substituted with Br, Cl, F, CN, or methoxy. In some embodiments, $R^6$ has one of the following formulae:

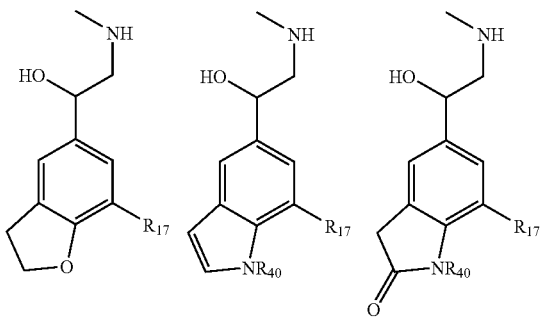

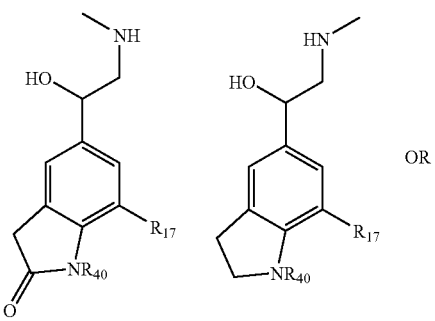

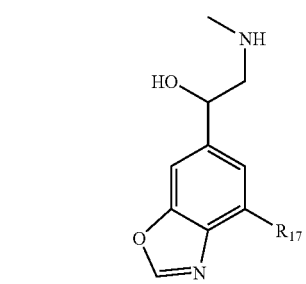

wherein $R^{40}$ is hydrogen or alkyl, preferably methyl, and $R^{17}$ is hydrogen or halogen, such as Br, Cl or F.

Preferred compounds of the present invention have one of the following formulae:

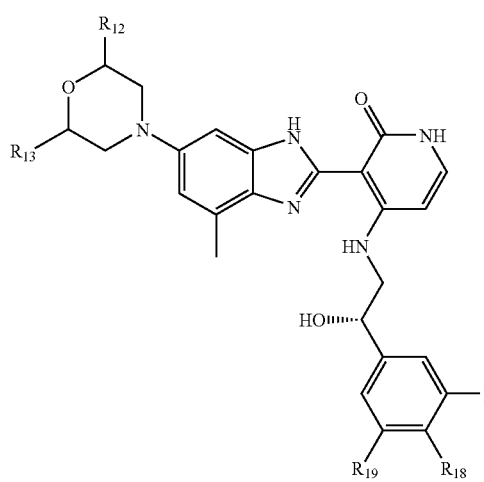

II

III
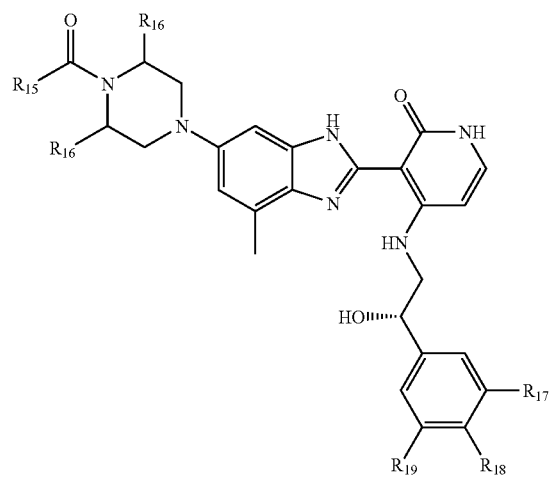
VI
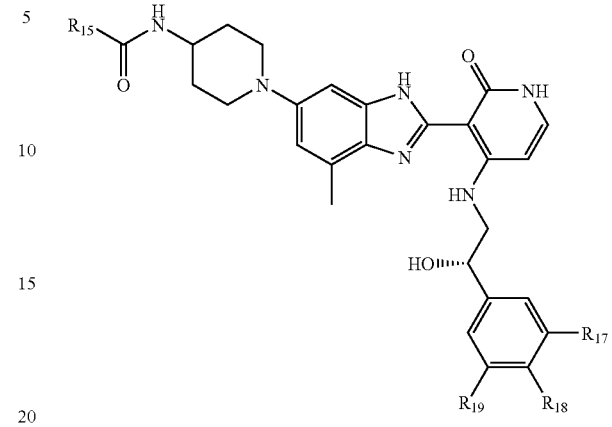
IV
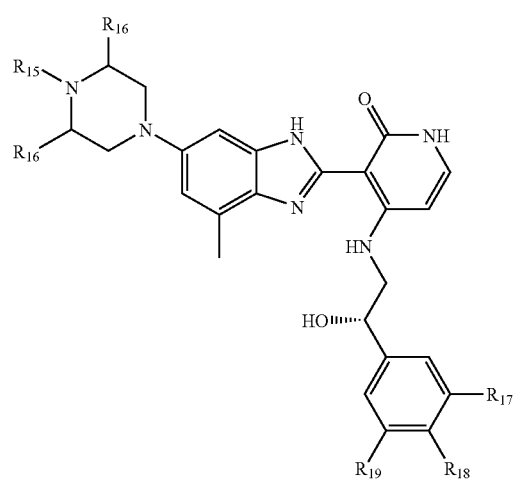
VII
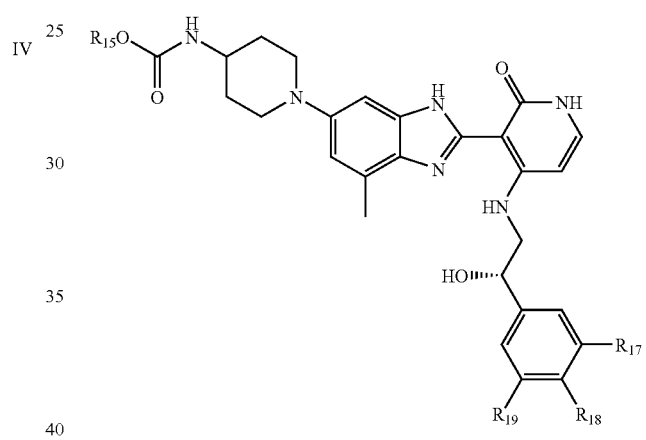
V
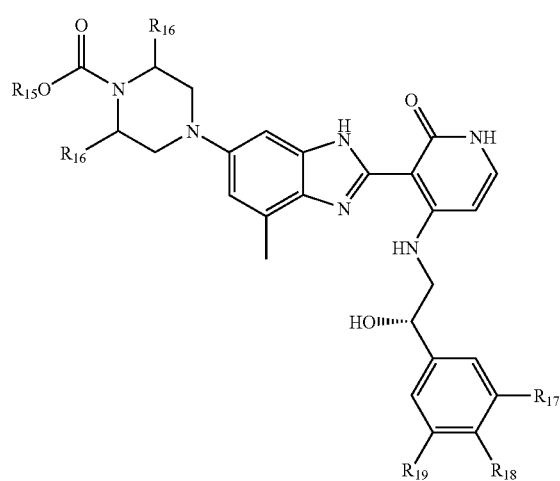
VIII
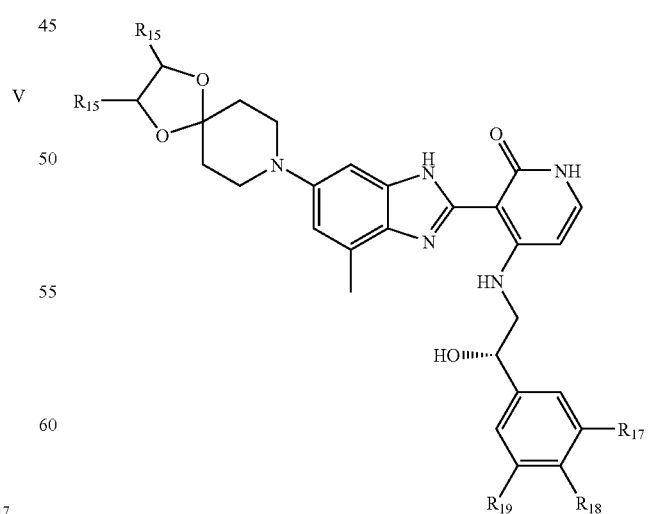
or -continued

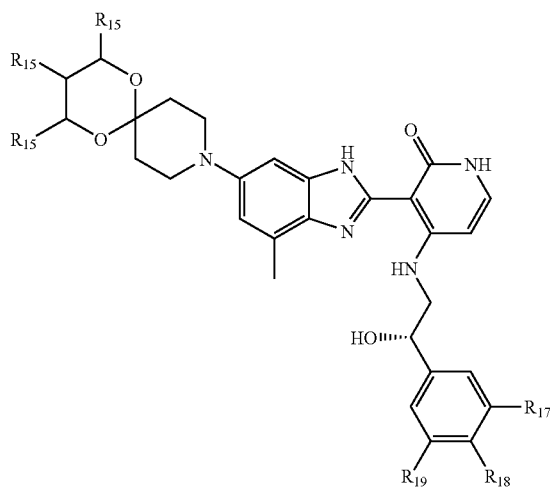

IX wherein $R^{12}$ and $R^{13}$ are, independently, hydrogen, alkyl, or alkyl-$R^{25}$;

$R^{15}$ is hydrogen, alkyl, or alkyl-$R^{25}$;

$R^{16}$ is independently, hydrogen or methyl;

$R^{17}$, $R^{18}$ and $R^{19}$ are, independently, hydrogen, halogen, or alkoxy, or $R^{18}$ and $R^{19}$ together form a heterocycloalkyl or heteroaryl group;

$R^{25}$ is hydrogen, cycloalkyl, hydroxy, thiol, alkenyl, alkoxy, thioalkoxy, amino, halo, cyano, sulfoxy, sulfonyl, —$NR^{30}COOR^{31}$, —$NR^{30}C(O)R^{31}$, —$NR^{30}SO_2R^{31}$, —$C(O)NR^{30}R^{31}$, heteroaryl or heterocycloalkyl; and $R^{30}$ and $R^{31}$ are, independently, hydrogen, alkyl, or cycloalkyl.

In preferred embodiments, $R^{12}$ is hydrogen, methyl, hydroxymethyl, methoxymethyl, alkyl-$R^{25}$, $CH_2F$, $CH_2CN$, $CO_2H$, or —$CONR^{30}R^{31}$;

$R^{13}$ is H;

$R^{17}$ is Br, Cl or F;

$R^{18}$ is halo or methoxy; and $R^{19}$ is H.

According to one embodiment of the present invention, compounds have the formula:
following formula:

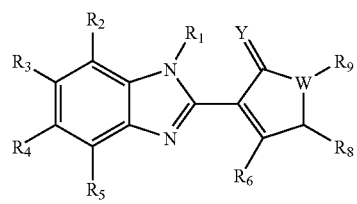

wherein

Y is selected from the group consisting of O and S;

W is selected from the group consisting of N, C, O, and S; provided that if W is O or S, $R^9$ is absent;

$R^1$, $R^2$, $R^3$, $R^4$, $R^5$, $R^6$, $R^8$, $R^9$ are each independently selected from the group consisting of H, $C_{1-6}$ alkyl, alkenyl, alkynyl, cycloalkyl, heterocycloalkyl, halo, amino, —$OR^{60}$, —$NO_2$, —OH, —$SR^{60}$, —$NR^{60}OR^{61}$, —CN, —$CO_2R^{60}$, —$CONR^{60}R^{61}$, $OCONR^{60}R^{61}$, —$NR^{62}CONR^{60}R^{61}$, —$NR^{60}SO_2R^{61}$, —$SO_2NR^{60}R^{61}$, —$SO_2R^{63}$, —$C(NR^{62})NR^{60}R^{61}$, aryl, heteroaryl, —$(CH_2)_nOR^{60}$, —$(CH_2)_nNR^{60}R^{61}$, —$(CH_2)_nSR^{60}$, —$(CH_2)_n$ aryl, —$(CH_2)_n$ heteroaryl, —$(CH_2)_n$ heterocycloalkyl, —NH—Z-aryl, and —NH—Z-heteroaryl; wherein n is 1 to 3; and Z is selected from the group consisting of $C_1$–$C_4$ alkyl, alkenyl, and alkynyl chain; Z having one or more hydroxy, thiol, alkoxy, thioalkoxy, amino, halo, $NR^{60}SO_2R^{61}$ groups; Z optionally incorporating one or more groups selected from the group consisting of CO, CNOH, $CNOR^{60}$, $CNNR^{60}$, $CNNCOR^{60}$ and $CNNSO_2R^{60}$; and $R^{60}$, $R^{61}$, $R^{62}$, and $R^{63}$ are independently selected from the group consisting of H, alkyl, alkenyl, alkynyl, cycloalkyl, cycloalkylalkyl, hydroxy, alkoxy, aryl, heteroaryl, heteroarylalkyl, and alkyl-$R^{25}$;

$R^{25}$ is hydrogen, alkenyl, hydroxy, thiol, alkoxy, thioalkoxy, amino, alkylamino, dialkylamino, aryl, heteroaryl, cyano, halo, sulfoxy, sulfonyl, —$NR^{30}COOR^{31}$, —$NR^{30}C(O)R^{31}$, —$NR^{30}SO_2R^{31}$, —$C(O)NR^{30}R^{31}$, heteroaryl or heterocycloalkyl; and $R^{30}$ and $R^{31}$ are, independently, hydrogen, alkyl, or cycloalkyl. In preferred embodiments, $R^1$ is —$CO_2R^{60}$, $R^2$, $R^4$, $R^5$ and $R^8$ are H or methyl, $R^3$ is a heterocycloalkyl and $R^6$ is —$NH(CH)_2OH$-aryl. Preferred heterocycles include morpholine or homomorpholine.

Suitable examples of salts of the compounds according to the invention include inorganic or organic acids. These include, but are not limited to, hydrochloride, hydrobromide, sulfate, methanesulfonate, maleate, fumarate, phosphate and other pharmaceutically acceptable salts. Salts which are unsuitable for pharmaceutical uses but which can be employed, for example, for the isolation or purification of free compounds of formula I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of formula I. Various forms of prodrugs are well known in the art. For examples of such prodrug derivatives, see:

(a) Design of Prodrugs, edited by H. Bundgaard (Elsevier, 1985); and Methods in Enzymology, Vol. 42, pp. 309–396, edited by K. Widder et al., (Academic Press, 1985);

(b) A Textbook of Drug Design and Development, edited by Krosgaard-Larsen and H. Bundgaard, Chapter 5, "Design and Application of Prodrugs," by H. Bundgaard, pp. 113–191 (1991);

(c) H. Bundgaard, Advanced Drug Deliver Reviews, 8, pp. 1–38 (1992);

(d) H. Bundgaard et al., Journal of Pharmaceutical Sciences, 77, 285 (1988); and (e) N. Kayeka et al., Chem. Phar. Bull., 32, 692 (1984).

The invention also provides a pharmaceutical composition comprising a compound of formula I, as defined above, and a pharmaceutically acceptable carrier and at least one other anti-cancer agent formulated as a fixed dose. Preferred anti-cancer agents are selected from the group consisting of: tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone; a tyrosine kinase inhibitor such as Iressa or OSI-774; an angiogenesis inhibitor; an EGF inhibitor; a VEGF inhibitor; a CDK inhibitor; a Her1/2 inhibitor and monoclonal antibodies directed against growth factor receptors such as erbitux (EGF) and herceptin (Her2).

The invention further provides a method of treating a condition via modulation of at least one tyrosine kinase enzyme comprising administering to a mammalian species in need of such treatment an effective amount of a compound of formula I, as defined above.

Additionally, the invention provides a method of treating a condition via modulation of at least one tyrosine kinase enzyme comprising administering to a mammalian species in need of such treatment an effective amount of a compound of formula I, as defined above, in combination (simultaneously or sequentially) with at least one other anti-cancer agent.

A preferred condition, treated by said methods of the instant invention, is cancer. Additionally, the tyrosine kinase enzyme may include (but is not limited to): Abl, CDK's, EGF, EMT, FGF, FAK, Flk-1/KDR, HER-2, IGF-1R, IR, LCK, MET, PDGF, Src, and VEGF.

The invention also provides a method for treating cancer, comprising administering to a mammalian species in need of such treatment, a therapeutically effective amount of at least one of the pharmaceutical compositions defined above.

The invention further provides a method for treating proliferative diseases, comprising administering to a mammalian species in need of such treatment a therapeutically effective amount of at least one of the pharmaceutical compositions defined above.

Certain compounds of formula I may generally be prepared according to the following schemes and the knowledge of one skilled in the art. Solvates (e.g., hydrates) of the compounds of formula I are also within the scope of the present invention. Methods of solvation are generally known in the art. Accordingly, the compounds of the instant invention may be in the free or hydrate form, and may be obtained by methods exemplified by the following schemes below.

More specifically, Schemes I–VII illustrate the preparation of compounds claimed in this invention. The examples, which follow, illustrate the compounds that can be synthesized by these schemes. The schemes are not limited by the examples listed or by any substituents employed for illustrative purposes.

Scheme I describes the preparation of the benzimidazoles. The starting diamines 1 are readily available using literature methods or are obtained commercially. The diamine is then condensed with an aldehyde 2 to provide the benzimidazole 3. Further modification of the functional groups on the aryl group of the benzimidazole or heterocycle of 3 are then envisioned.

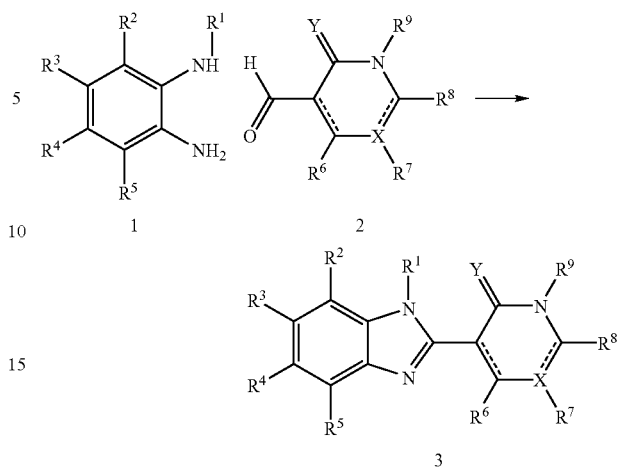

Scheme I.

Alternatively, the benzimidazole could be formed in a step-wise manner (see Scheme II) by amide formation using the acid chloride of 5 or any of the commonly used peptide coupling reagents such as DCC (dicyclohexylcarbodiimide), EDCI (1-(3-dimethylaminopropyl)-3-ethylcarbodiimide hydrochloride), etc. Once the amide 6 was formed the nitro group could be reduced using catalytic hydrogenation, transfer hydrogenation or chemical reduction such as $SnCl_2$ or iron powder or other methods known in the art for reduction of aryl nitro groups. Treatment of the aniline with acid would then form the benzimidazole.

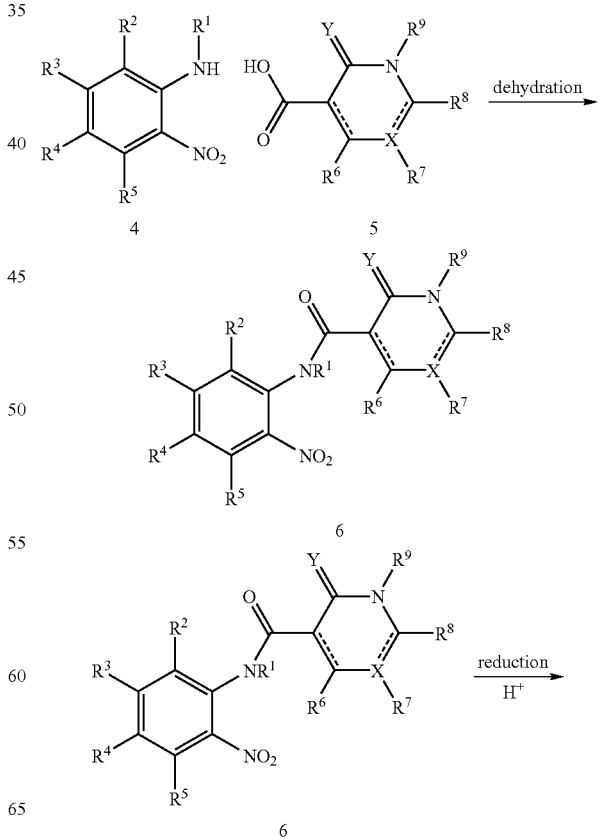

Scheme II.

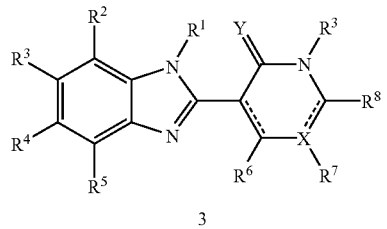
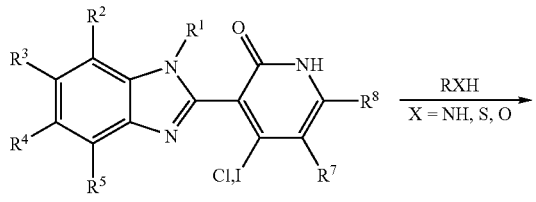

For example, Scheme III illustrates the use of 4-iodo-2-methoxy-pyridine-3-carbaldehyde 7 to provide the functionalized benzimidazole 8. Hydrolysis of the methoxy group using protic acid conditions, TMSI (trimethylsilyl iodide), BBr$_3$, or other conditions known in the art for cleaving a methyl ether would provide the halopyridone 9. Addition of heteroatom nucleophiles using amines, alcohols or thiols would then provide the substituted pyridones 10. Other functionality could be incorporated into the aldehyde and the above example is included for illustrative purposes only.

Scheme III

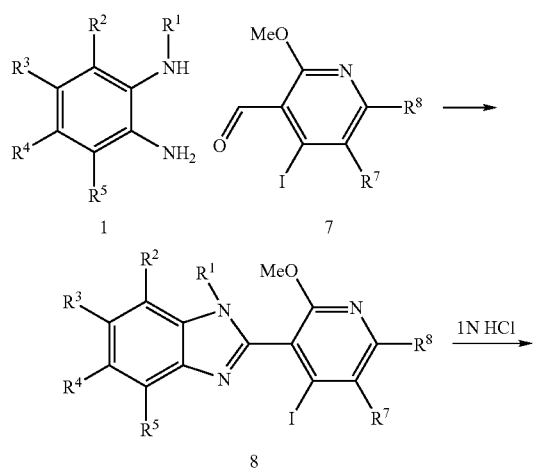

Likewise the aryl ring of the benzimidazole prepared using Schemes I or II can be modified. For example introduction of a cyano group for R$^3$ on the benzimidazole allows for the formation of heterocycles such as imidazole, imidazolines, oxazolines, thiazolines, amides, or amidines. Scheme IV illustrates such transformations. Starting from the cyano-substituted benzimidazole 11 the heterocycle can be modified as illustrated in Scheme IV to provide 12. Imidate formation preferably using ethanol and acid provides intermediate 13. Imidate 13 can be transformed using diamines to form imidazolines, amino alcohols to form oxazolines, amino acetals to form imidazoles, and amino thiols to form thiazolines 14. Alternatively the imidate can be hydrolyzed to the acid and coupled with amines using any of the standard amide formation reagents (DCC, EDCI, etc.) to form amides 15. Imidate 13 is also a useful intermediate for the preparation of amidines 16 by reacting with amines.

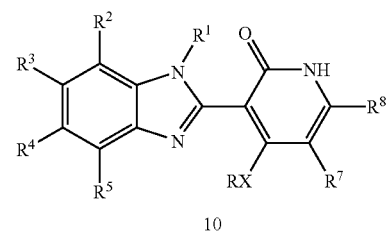

Scheme IV

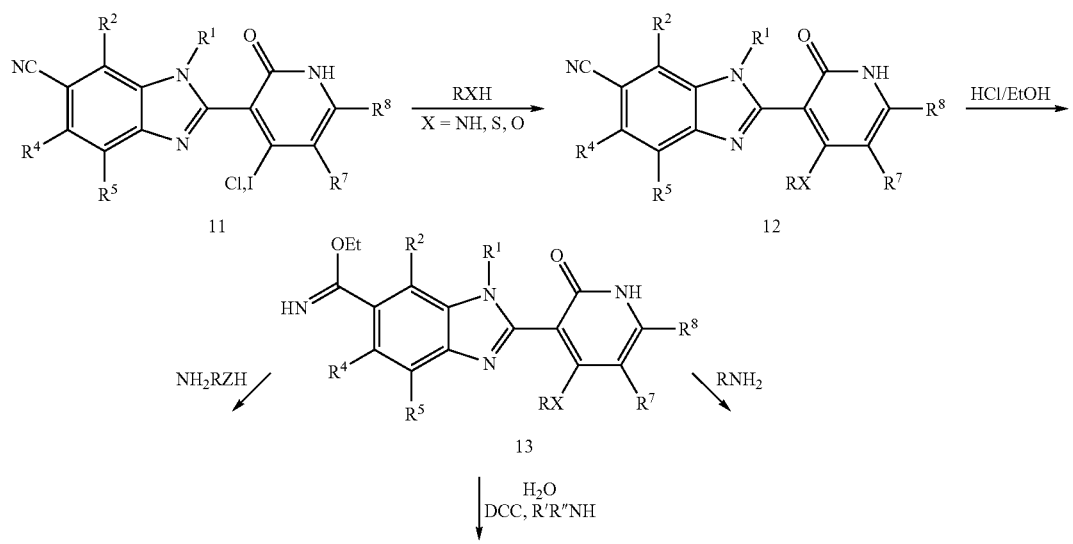

-continued

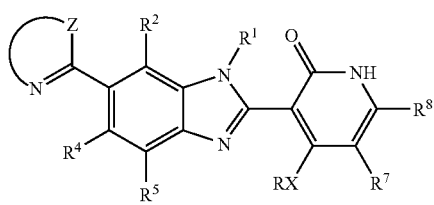
14

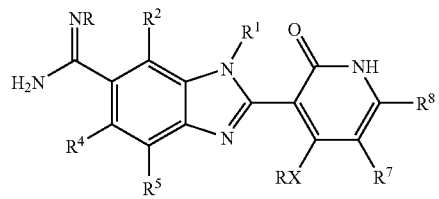
16

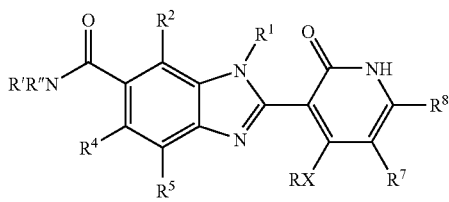
15

X = NH, S, O

Scheme V illustrates further transformation of benzimidazoles that bear a halogen atom using palladium catalysis using conditions developed by Suzuki [Yang et al. *Acta Chem. Scand.* (1993) 221; Suzuki et al. *Synth. Commun.* (1981) 11: 513] or Buchwald/Hartwig [Buchwald et al. *J. Am. Chem. Soc.* (1994) 116: 7901; Hartwig et al. *J. Am. Chem. Soc.* (1994) 116: 5969; Hartwig. *Angew. Chem., Int. Ed. Engl.* (1998) 37: 2046] and variations of these methods.

Preparation of a bromide substituted benzimidazole 17 could be envisioned to provide a substrate for Suzuki coupling with aryl, vinyl, and heterocyclic boronic acids to provide benzimidazoles 18. Likewise, amines and heterocycles such as piperazine or morpholine derivatives 19 can be prepared from the same bromide using amines under conditions described by Buchwald and Hartwig or variations thereof.

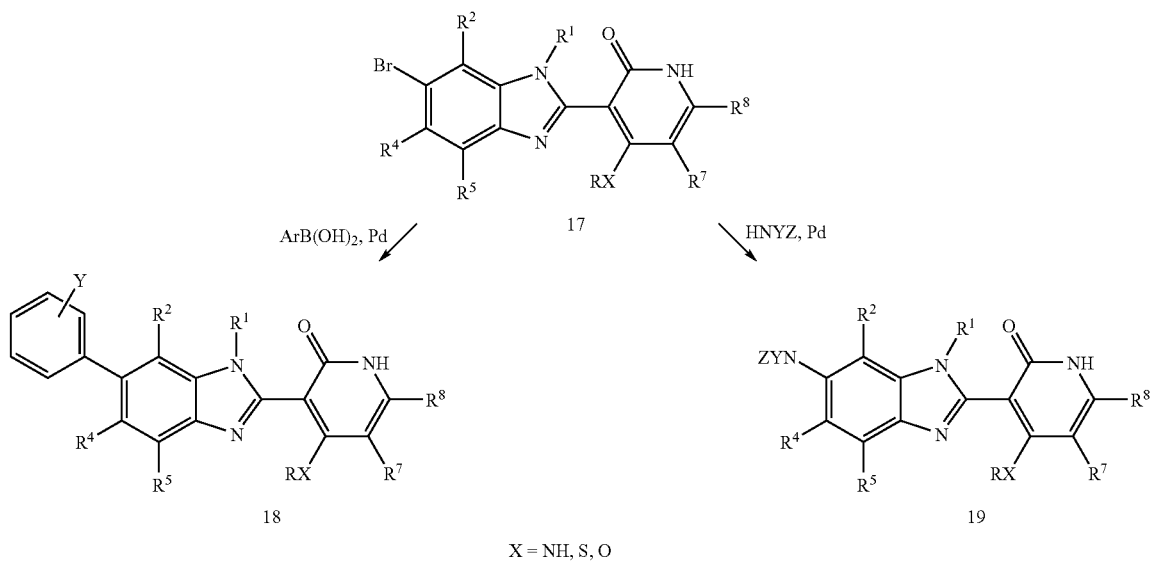

X = NH, S, O

Alternatively amine and heterocyclic derivatives such as 19 can be prepared using intermediate 6 described in Scheme II. When the $R^3$ of 6 is a halogen, preferably F, the halogen can be displaced with amines, alcohols, heterocyclic amines and other nitrogen containing heterocycles such as piperazine, piperidine, 4-amino piperidine, morpholine, imidazole, etc (Scheme VI). The terminal nitrogen of piperazine or 4-amino piperidine can then be alkylated using standard alkylation conditions or reacted with aldehydes in a reductive amination reaction to provide alkylated derivatives. Alternatively the terminal nitrogen atom of piperazine or 4-amino piperidine can be acylated or carbamoylated using any number of conditions that are routine for someone skilled in the art of organic synthesis. Following the example illustrated in Scheme II compounds such as 19 could be prepared.

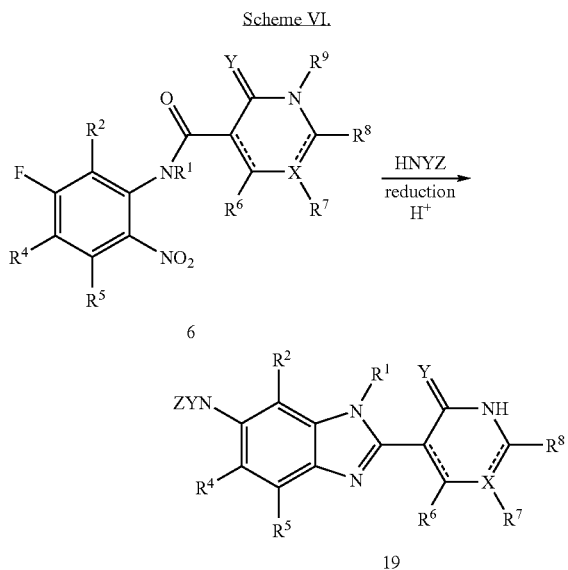

Alternatively amines, heterocycles, and alcohols can be introduced at $R_3$ using a nucleophilic aromatic substitution reaction started from an intermediate 20 were $R_3$ is halogen, preferably F, the halogen can be displaced with amines, alcohols, heterocyclic amines and other nitrogen containing heterocycles such as piperazine, piperidine, 4-amino piperidine, morpholine, imidazole, etc (Scheme VII). The terminal nitrogen of piperazine or 4-amino piperidine can then be alkylated using standard alkylation conditions or reacted with aldehydes in a reductive amination reaction to provide alkylated derivatives. Alternatively the terminal nitrogen atom of piperazine or 4-amino piperidine can be acylated or carbamoylated using any number of conditions that are routine for someone skilled in the art of organic synthesis. The resulting nitro aniline could be reduced to the diamine 21 and processed as illustrated in Scheme III.

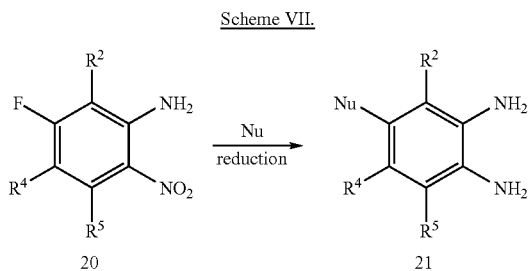

Utility

The compounds according to the invention have pharmacological properties; in particular, the compounds of formula I are tyrosine kinase enzyme inhibitors. The novel compounds of formula I are thus useful in the therapy of a variety of proliferative diseases (including but not limited to diseases associated with tyrosine kinase enzymes) such as cancer, autoimmune diseases, viral diseases, fungal diseases, neurodegenerative disorders and cardiovascular disease.

More specifically, the compounds of formula I are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including sacroma, melanoma, seminoma, teratocarcinoma, osteosarcoma, xenoderoma pigmentosum, keratoctanthoma, thyroid follicular cancer and Kaposi's sarcoma.

Due to the key role of tyrosine kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce apoptosis. The apoptotic response is aberrant in a variety of human diseases. Compounds of formula I, as modulators of apoptosis, will be useful in the treatment of cancer (including but not limited to those types mentioned herein above), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of formula I may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of formula I may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of formula I may also be useful in inhibiting tumor angiogenesis and metastasis.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methotrexate; tyrosine kinase inhibitors such as Iressa and OSI-774 (Tarceva™); Avastin, Herceptin, angiogenesis inhibitors; EGF inhibitors; VEGF inhibitors; CDK inhibitors; Her1/2 inhibitors and monoclonal antibodies directed against growth factor receptors such as erbitux (EGF) and herceptin (Her2).

If formulated as a fixed dose, such combination products employ the compounds of this invention within the dosage range described below and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

Further subject matter of the invention also includes pharmaceuticals for use, as described above, including controlling cancer, inflammation and arthritis, which contain at least one compound of the formula I as defined above or at least one of its pharmacologically acceptable acid addition salts, and the use of a compound of the formula I as defined above for the preparation of a pharmaceutical having activity against proliferative diseases as described previously including against cancer, inflammation and/or arthritis.

The pharmacological properties of the compounds of this invention may be confirmed by a number of pharmacological assays. The exemplified pharmacological assays which follow have been carried out with the compounds according to the invention and their salts.

Biological Assays

A. CDK 2/Cyclin E Kinase Assay

Kinase reactions consisted of 5 ng of baculovirus expressed GST-CDK2/cyclin E complex, 0.5 µg GST-RB fusion protein (amino acids 776–928 of retinoblastoma protein), 0.2 µCi $^{33}$P γ-ATP, 25 µM ATP in 50 µl kinase buffer (50 mM Hepes, pH 8.0, 10 mM $MgCl_2$, 1 mM EGTA, 2 mM DTT). Reactions were incubated for 45 minutes at 30° C. and stopped by the addition of cold trichloroacetic acid (TCA) to a final concentration of 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required inhibiting 50% of kinase activity ($IC_{50}$). Compounds were dissolved at 10 mM in dimethylsulfoxide (DMSO) and evaluated at six concentrations, each in triplicate. The final concentration of DMSO in the assay equaled 2%. $IC_{50}$ values were derived by non-linear regression analysis and have a coefficient of variance (SD/mean, n=6)=14%.

B. EMT Kinase Assay

A filter-based kinase assay, measuring the phosphorylation of Gst-SLP76 by Gst-Emtk, was employed to determine the compound inhibitory activity against Emt. The kinase reaction was performed in a 96-well plate at room temperature for 15 min before being terminated by adding 100 µl of 20% trichloroacetic acid (TCA) containing 0.1 M sodium pyrophosphate. The kinase reaction mixture (60 µl) contained 25 mM HEPES, pH 7.0, 0.1 mg/ml BSA, 5 mM $MgCl_2$, 5 mM $MnCl_2$, 8 ng of enzyme (Gst-Emtk), 5 µg of the substrate protein (Gst-SLP76), 1 µM ATP, 0.4 µCi of [γ-$P^{33}$]ATP and the tested compound (at various concentrations). After termination, the proteins were allowed to precipitate in the presence of TCA for 1 hr at 4° C. The precipitated proteins were then harvested on a filter plate (UniFilter-96, GF/C, Packard Instrument) and washed to remove excess [γ-$P^{33}$]ATP. The radioactivity was determined using a TopCount NXT (Packard Instrument) after adding 35 µl of Microscint 20 (Packard Instrument).

C. FAK Tyrosine Kinase Assay

The Focal Adhesion kinase was assayed using the synthetic polymer poly(Glu/Tyr) (Sigma Chemicals) as a phosphoacceptor substrate. Each reaction mixture consisted of a total volume of 50 ul and contained 100 ng of baculovirus-expressed enzyme, 2 µg of poly(Glu/Tyr), 1 µM of ATP, and 0.2 µCi of [γ-$^{33}$P]ATP. The mixtures also contained 40 mM Tris.HCl, pH 7.4, 1 mM $MnCl_2$, 0.5 mM DTT, and 0.1 mg/ml bovine serum albumin. The reaction mixtures were incubated at 26° C. for 1 hour and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived non-linear regression analysis and have a coefficient of variance (SD/mean, n=6)=16%.

D. HER-1/HER-2 Kinase Assay

Kinase reactions consisted of 10 ng of baculovirus expressed GST-HER1, 100 ng of HER2, 100 ng/ml poly (Glu/Tyr) (Sigma), 0.2 µCi 33P γ-ATP, 1 µM ATP in 50 µl kinase buffer (50 mM Tris, pH 7.5, 10 mM $MnCl_2$, 0.5 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at six concentrations, each in triplicate. The final concentration of DMSO in the assay equaled 1%. $IC_{50}$ values were derived by non-linear regression analysis and have a coefficient of variance (SD/mean, n=6)=16%.

E. IGF-Receptor Tyrosine Kinase Assay

The IGF-1 receptor tyrosine kinase was assayed using the synthetic polymer poly(Glu/Tyr) (Sigma Chemicals) as a phosphoacceptor substrate. Each reaction mixture consisted of a total volume of 50 ul and contained 125 ng of baculovirus expressed enzyme, 2.5 µg of poly(Glu/Tyr), 25 µM of ATP, and 0.1 µCi of [γ-$P^{33}$]ATP. The mixtures also contained 20 mM MOPS, pH 7.0, 5 mM $MnCl_2$, 0.5 mM. DDT, and 0.1 mg/ml bovine serum albumin. The reaction mixtures were incubated at 30° C. for 45 minutes and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived by non-linear regression analysis and have a coefficient of variance (SD/mean, n=6)=16%.

F. Insulin Receptor Tyrosine Kinase Assay

The Insulin Receptor Tryrosine kinase was assayed using the synthetic polymer poly(Glu/Tyr) (Sigma Chemicals) as a phosphoacceptor substrate. Each reaction mixture consisted of a total volume of 50 ul and contained 90 ng of baculovirus-expressed enzyme, 2.5 µg of poly(Glu/Tyr), 25 µM of ATP, and 0.1 µCi of [γ-$^{33}$P]ATP. The mixtures contained also 20 mM Tris.HCl, pH 7.4, 5 mM $MnCl_2$, 0.5 mM DTT, and 0.1 mg/ml bovine serum. The reaction mixtures were incubated at 26° C. for 1 hour and kinase activity was determined by quantitation of the amount of radioactive phosphate transferred to the poly(Glu/Tyr) substrate. Incorporation was measured by the addition of cold trichloroacetic acid (TCA) precipitation of the proteins which were collected onto GF/C unifilter plates (Packard Instrument Co., Meriden, Conn.) using a Filtermate universal harvester and the filters were quantitated using a TopCount 96-well liquid scintillation counter (Packard Instrument Co., Meriden, Conn.). Compounds were dissolved in dimethyl sulfoxide to a concentration of 10 mM and were evaluated at six concentrations, each in triplicate. The final concentration of DMSO added to the kinase assays was 0.5%, which has been shown to have no effect on kinase activity. IC50 values were derived non-linear regression analysis and have a coefficient of variance (SD/mean, n=6)=16%.

G. LCK Kinase Assay

Kinase reactions consisted of 10 ng of baculovirus expressed 10 ng GST-Lck, 100 ng/ml poly(Glu/Tyr) (Sigma), 0.2 µCi 33P γ-ATP, 1 µM ATP in 50 µl kinase buffer (50 mM Tris, pH 7.5, 10 mM MnCl2, 0.5 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at six concentrations, each in triplicate. The final concentration of DMSO in the assay equaled 1%. $IC_{50}$ values were derived by non-linear regression analysis and have a coefficient of variance (SD/mean, n=6)=16%.

H. MET Kinase Assay

Kinase reactions consisted of 10 ng of baculovirus expressed GST-Met, 2.5 ug poly(Glu/Tyr) (Sigma), 0.2 µCi 33P γ-ATP, 10 µM ATP in 50 µl kinase buffer (40 mM Tris, pH 7.5, 1 mM MnCl2, 0.50 mM DTT). Reactions were incubated for 1 h at 27 C and stopped by the addition of cold trichloroacetic acid (TCA) to a final concentration 3.5%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate. The final concentration of DMSO in the assay equaled 1%. $IC_{50}$ values were derived by non-linear regression analysis and have a coefficient of variance (SD/mean, n=6)=16%.

I. PDGF Receptor Kinase Assay

Kinase reactions consisted of 70 ng of baculovirus expressed GST-PDGFbR, 0.3 ug biotinylated poly(Glu/Tyr) (Sigma), in 50 µl kinase buffer (20 mM Hepes, pH 7.5, 0.7 uM ATP, 10 mM MnCl2, 0.5 mM DTT, 0.15 mM NaCl, 0.1 mg/ml BSA). Reactions were incubated for 30 minutes at room temperature with shaking and stopped by the addition of 10 ul of 0.2M EDTA, pH8.0. 150 ul of HTRF detection buffer was added and incubated for 1 hour and 30 minutes at room temperature. Counts were quantitated on Discovery HTRF Packard Instrument.

J. VEGFR-2 (KDR) Kinase Assay

Kinase reactions consisted of 7.5 ng of baculovirus expressed GST-KDR, 1.5 ug poly(Glu/Tyr) (Sigma), 0.04 µCi 33P γ-ATP, 2.5 µM ATP in 50 µl kinase buffer (25 mM Tris, pH 7.5, 1.8 mM MnCl2, 0.0.625 mM DTT). Reactions were incubated for 1 h at 27 C and stopped by the addition of cold trichloroacetic acid (TCA) to a final concentration 15%. TCA precipitates were collected onto GF/C unifilter plates (Packard Instrument Co., Meriden, Conn.) using a Filtermate universal harvester (Packard Instrument Co., Meriden, Conn.) and the filters were quantitated using a TopCount 96-well liquid scintillation counter (Packard Instrument Co., Meriden, Conn.). Dose response curves were generated to determine the concentration required to inhibit 50% of kinase activity ($IC_{50}$). Compounds were dissolved at 10 mM in dimethylsulfoxide (DMSO) and evaluated at six concentrations, each in triplicate. The final concentration of DMSO in the assay equaled 1%. $IC_{50}$ values were derived by non-linear regression analysis and have a coefficient of variance (SD/mean, n=6)=16%.

K. Cytotoxicity Assay (HT-29-colon; Colo205, MCF-7-breast)

Tumor cell lines are maintained in McCoy's 5A medium (GIBCO) and 10% heat inactivated fetal bovine serum (GIBCO). The in vitro cytotoxicity is assessed in tumor cells by a tetrazolium-based colorimetric assay which takes advantage of the metabolic conversion of MTS (3-(4,5-dimethylthiazol-2-yl)-5-(3-carboxymethoxyphenyl)-2-(4-sulphenyl)-2H-tetrazolium, inner salt) (Promega) to a reduced form that absorbs light at 492 nm (1). Cells are seeded 24 hr prior to drug addition. Following a 72 hour incubation at 37° C. with serially diluted test compound, MTS (Riss, T. L, et al., Comparison of MTT, XTT, and a novel tetrazolium compound MTS for in vitro proliferation and chemosensitivity assays.," *Mol. Biol. Cell* 3 (Suppl.): 184a, 1992), in combination with the electron coupling agent phenazine methosulfate, is added to the cells. The incubation is continued for 3 hours, then the absorbency of the medium at 492 nm is measured with a spectrophotometer to obtain the number of surviving cells relative to control populations. The results are expressed as median cytotoxic concentrations ($IC_{50}$ values).

Biological Activity (uM); compounds of the present invention had kinase activity of <25 uM against one or more of the following kinases CDK, EMT, FAK, Her1, Her2, IGF, IR, LCK, MEK, MET, PDGF, VEGF. HT-29 and Colo205 are human colon tumor cell lines, and MCF-7 is a human breast tumor cell line.

General Procedure for the Preparation of 2-Hydroxy-2-(substituted-phenyl)-ethylamines:

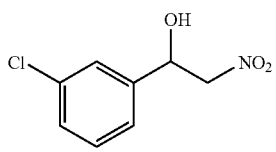

1-(3-Chloro-phenyl)-2-nitro-ethanol: To a solution of 3-chloro-benzaldehyde (20 g, 0.142 mol) in nitromethane (100 mL) were added magnesium sulfate (37.6 g, 0.312 mol) and phosphazene base $P_1$-t-bu-tris(tetramethylene) (4.43 g, 0.014 mol). The reaction mixture was stirred at room temperature for 2 h. After concentration in vacuo, the residue was purified by flash chromatography (25% EtOAc/hexane) to yield the title compound (26.4 g, 100%) as a green-yellow oil. $^1$H NMR (300 MHz, DMSO-$d_6$) δ 7.53 (1H, s), 7.35–7.42 (3H, m), 6.23 (1H, broad s), 5.32–5.33 (1H, m), 4.90 (1H, dd, J=3.2, 12.4 Hz), 4.60 (1H, dd, J=1.2, 12.4 Hz).

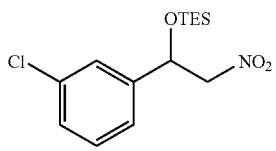

[1-(3-Chloro-phenyl)-2-nitro-ethoxy]-triethyl-silane: To a solution of 1-(3-chloro-phenyl)-2-nitro-ethanol (26 g, 0.14 mol) in DMF (50 mL) were added imidazole (28.6 g, 0.42 mol) and chlorotriethylsilane (25.3 g, 0.17 mol). The reaction mixture was stirred at room temperature for 2 h. After quenching with water, the mixture was extracted with ethyl acetate. The combined organic layers were washed with water and brine, dried over $Na_2SO_4$, and filtered. After removal of solvent, the crude product was purified by flash chromatography (2% EtOAc/hexane) to yield the title compound (37 g, 91%) as a colorless oil. $^1$H NMR (300 MHz, CDCl$_3$) δ 7.40 (1H, s), 7.27–7.32 (3H, m), 5.40 (1H, dd, J=3.2, 9.5 Hz), 4.51 (1H, dd, J=9.5, 12.1 Hz), 4.36 (1H, dd, J=3.3, 12.1 Hz), 0.85 (9H, t, J=7.5 Hz), 0.54 (6H, q, J=7.5 Hz).

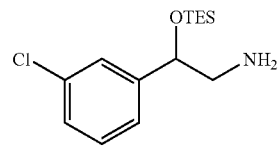

2-(3-Chloro-phenyl)-2-triethylsilanyloxy-ethylamine: Raney nickel (1 g) was washed with distilled water five times and methanol three times. [1-(3-Chloro-phenyl)-2-nitro-ethoxy]-triethyl-silane (10 g, 0.032 mol) and Raney nickel in methanol (100 mL) was hydrogenated (35 psi) at room temperature for 14 h. The reaction mixture was filtered through a pad of celite and rinsed with methanol. Concentration of the filtrate to dryness gave the title compound (5.6 g, 62%) as a colorless oil which was used for the next step without purification. $^1$H NMR (300 MHz, CDCl$_3$) δ 7.32 (1H, s), 7.18–7.26 (3H, m), 4.70 (1H, t, J=5.8 Hz), 2.86 (2H, m), 0.89 (9H, t, J=7.9 Hz), 0.56 (6H, q, J=7.8 Hz). LRMS (M+H)$^+$ m/z 286.

General Procedure for the Preparation of 2-Hydroxy-2-(substituted-phenyl)-ethylamines:

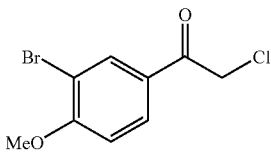

4-methoxy-3-bromophenyl chloroacetophenone: To a suspension of AlCl$_3$ (13.4 g, 0.10 mol) in methylene chloride (40 mL) was added a solution of 2-bromoanisole (12.5 mL, 0.10 mol) and chloroacetyl chloride (8 mL, 0.10 mol) at 0° C. The solution was warmed to ambient temperature for two hours and poured onto ice and extracted with methylene chloride, washed with saturated sodium bicarbonate solution, brine, and dried over MgSO$_4$. The solution was filtered, concentrated and crystalized from EtOH to give 15.37 g of white solid. LRMS [M–H]–260.8; IR (KBr) 1697, 1048, 1255 cm$^{-1}$; $^1$H NMR (300 MHz, CDCl$_3$) δ 8.18 (s, 1H), 7.94 (dd, J=8.67 Hz, 1H), 6.96 (d, J=8.67 Hz, 1H), 4.62 (s, 2H), 3.98 (s, 3H); $^{13}$C NMR (CDCl$_3$, 75.5 Hz) δ 188.8, 160.3, 134.1, 129.9, 128.2, 112.4, 111.3, 56.6, 45.3.

General Procedure for Chiral Reduction of Chloroketones and Ammonolysis:

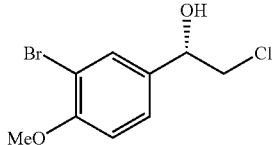

(S)-1-[4-methoxy-3-bromophenyl]-2-chloro ethanol: To a solution of (S)-Methyl-CBS-oxazaborolidine (1M in toluene, 0.745 mL, 0.745 mmol) and $BH_3$-THF (8 mL, 8 mmol) was added at the same time a solution of $BH_3$-THF (19 mL, 19 mmol) and a solution of the chloroketone (10.03 g, 37.98 mmol) in 19 mL of THF. Both solutions were added dropwise over 30 minutes. The solution was stirred for 1 hour and quenched with the slow addition of methanol (50 mL). The solution was concentrated and the residue chromatographed over a short silica gel column (1:1 hexane/ethyl acetate) to give a quantitative yield (10.0 g) of chlorohydrin as a clear oil. IR (KBr) 1053, 1258, 3406 cm$^{-1}$; $^1$H NMR (300 MHz, CDCl$_3$) δ 7.59 (s, 1H), 7.30 (dd, J=2.16 Hz, 1H), 6.90 (d, J=8.46 Hz, 1H), 4.83 (dd, J=3.57 Hz, 1H), 3.90 (s, 3H), 3.64 (ddd, J=3.6, 11.1, 8.7, 2H), 2.04 (b s, 1H). $^{13}$C NMR (CDCl$_3$, 75.5 MHz) δ 155.9, 133.5, 131.1, 126.3, 111.9, 73.1, 60.4, 56.3, 50.7.

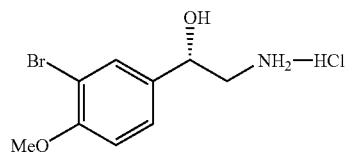

(S) 2-Amino-1-[3-chloro-4-methoxyphenyl]ethanol Hydrochloride: To a solution of the chlorohydrin (10.0 g, 37.9 mmol) in 120 mL of methanol at −40° C. was added 100 grams of ammonia. The solution was sealed in a pressure bottle and warmed to ambient temperature and stirred for 48 hours. The solution was cooled and opened. The ammonia was allowed to evaporate and solution concentrated. The residue was crystalized from ethanol/ethyl acetate to give 3.83 g of white solid (35%). The material was reacted with Boc$_2$O in ethyl acetate and saturated sodium bicarbonate and analyzed by chiral HPLC using a chiralcel OJ column using 95% hexane/ethanol as elutant and determined to by 98% ee. Additional crops were collected −2.96 g and 1.41 g for a total of 75% yield. LRMS [M+H]+246; IR (cm$^{-1}$, KBr) 1055, 1261, 3001, 2948, 3356; $^1$H NMR (500 MHz, DMSO) δ 8.09 (b s, 2H), 7.58 (s, 1H), 7.36 (dd, J=2.05, 6.45 Hz, 1H), 7.11 (d, J=8.5 Hz, 1H) 6.10 (s, 1H), 4.80 (m, 1H), 3.84 (s, 3H), 3.00 (ddd, J=2.7, 12.6, 9.5 Hz, 2H); $^{13}$C NMR (DMSO, 75.5 MHz) δ 154.8, 135.4, 130.4, 126.6, 112.4, 110.4, 67.9, 56.2, 45.4.

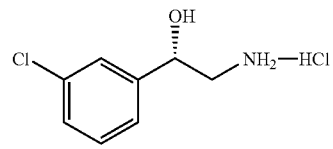

(S) 2-Amino-1-[3-chlorophenyl]ethanol Hydrochloride: was prepared according to the general procedure outlined above. LRMS [M+H]+172; IR (KBr, cm−1) 3048, 3351, 2952; $^1$H NMR (300 MHz, MeOD) δ 7.48 (s, 1H), 7.35 (m, 3H), 3.31 (ddd, J=1.5, 3.12, 9.15 Hz 2H).

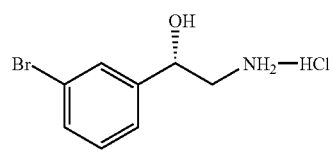

(S)-2-Amino-1-[3-bromophenyl]ethanol Hydrochloride: was prepared according to the general procedure outlined above. LRMS [MH]+217.9; IR (KBr, cm−1) 3025, 3443, 2891; $^1$H NMR (500 MHz, DMSO) δ 7.93 (b s, 2H), 7.60 (s, 1H), 7.52 (d, 1H), 7.41 (s, 1H), 7.35 (d, J=7.7 Hz, 1H) 6.17 (s, 1H), 4.82 (m, 1H), 3.08 (ddd, J=2.6, 12.7, 9.6 Hz, 2H); $^{13}$C NMR (DMSO, 75.5 MHz) δ 144.4, 130.5, 128.7, 125.0, 121.6, 68.3, 45.1.

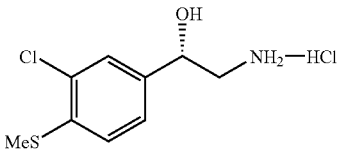

(S)-2-Amino-1-[3-chloro-4-methylthiophenyl]ethanol Hydrochloride: was prepared according to the general procedure outlined above. LRMS [M+H]+217.9; IR (KBr, cm−1) 3007, 3358; $^1$H NMR (500 MHz, DMSO) δ 8.12 (b s, 2H), 7.46 (s, 1H), 7.37 (s, 1H), 7.35 (d, 1H) 6.19 (d, 1H), 4.83 (m, 1H), 3.01 (ddd, J=3.2, 12.8, 9.3 Hz, 2H); $^{13}$C NMR (DMSO, 75.5 MHz) δ 139.6, 136.5, 129.8, 126.6, 125.4, 68.0, 45.2, 14.2.

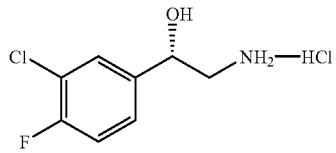

(S)-2-Amino-1-[3-chloro-4-fluoro-phenyl]ethanol Hydrochloride: was prepared according to the general procedure outlined above. LRMS [M+H]+189.9; IR (KBr, cm−1) 1509, 3008, 3359; $^1$H NMR (500 MHz, DMSO) δ 8.21 (b s, 2H), 7.61 (d, J=7.85 Hz, 1H), 7.42 (m, 2H), 6.29 (s, 1H), 4.88 (m, 1H), 3.03 (ddd, J=3.4, 12.8, 9.2 Hz, 2H); $^{13}$C NMR (DMSO, 75.5 MHz) δ 157.5, 155.5, 139.7, 128.1, 126.7, 119.3, 116.7, 109.0, 67.8, 45.2.

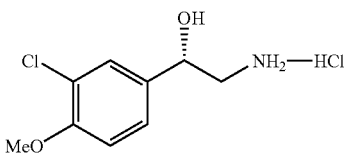

(S)-2-Amino-1-[3-chloro-4-methoxyphenyl]ethanol Hydrochloride: was prepared according to the general procedure outlined above. LRMS [M+H]+202; IR (KBr, cm−1) 3354, 3003, 2949, 1288, 1064; $^1$NMR (500 MHz, DMSO) δ 8.18 (brs, 3H), 7.43 (d, J=2.0 Hz, 1H), 7.31 (dd, J=8.5, 2.0 Hz, 1H), 7.14 (d, J=5.1 Hz, 1H), 6.11 (s, 1H), 4.81 (m, 1H), 3.84 (s, 3H), 2.99 (dd, J=13, 3.5 Hz, 1H), 2.83 (dd, J=12.5, 9 Hz, 1H); $^{13}$C NMR (DMSO, 125 MHz) δ 153.9, 135.0, 127.3, 125.8, 120.8, 112.6, 68.0, 56.1, 45.5; Elemental Analysis Calcd for $C_9H_{12}ClNO_2$—HCl: C, 45.39; H, 5.50; N, 5.88. Found: C, 45.38; H, 5.43; N, 5.70.

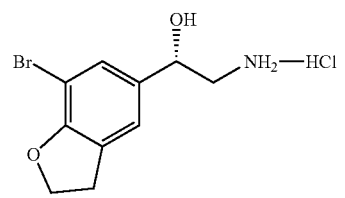

(S)-2-Amino-1-(7-bromo-2,3-dihydrobenzfuran-5-yl)-2-aminoethanol Hydrochloride : was prepared according to the general procedure outlined above. LRMS [M+H]+258; IR (KBr, cm−1) 3349, 3006, 2928, 1485, 1045, 983; $^1$H NMR (500 MHz, DMSO) δ 8.13 (brs, 3H), 7.29 (s, 1H), 7.23 (s, 1H), 6.08 (d, J=4 Hz, 1H), 4.76 (m, 1H), 4.61 (t, J=9 Hz, 2H), 3.29 (t, J=9 Hz, 2H), 2.96 (dd, J=13, 3.5 Hz, 1H), 2.82 (dd, J=13, 9.5 Hz, 1H); $^{13}$C NMR (DMSO, 125 MHz) δ 156.3, 135.9, 129.1, 128.1, 122.1, 100.9, 71.5, 68.2, 45.6, 29.9; Elemental Analysis Calcd for $C_{10}H_{12}BrNO_2$—HCl: C, 40.77; H, 4.44; N, 4.75. Found: C, 40.77; H, 4.63; N, 4.63.

General Procedure for the Preparation of 2-Amino-3-(substituted-phenyl)-propanol

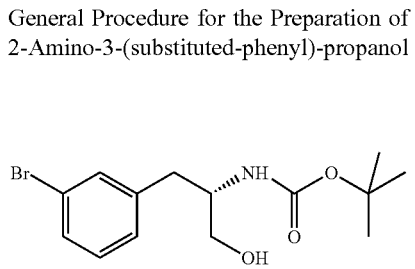

(S)-[2-(3-Bromo-phenyl)-1-hydroxymethyl-ethyl]-carbamic acid tert-butyl ester: To a solution of (S)-3-(3-bromo-phenyl)-2-tert-butoxycarbonylamino-propinic acid (500 mg, 1.45 mmol) in THF (30 mL) was added borane-tetrahydrofuran complex (1.0 M solution) (4.35 mL, 4.35 mmol). The reaction mixture was stirred at room temperature for 14 h and quenched with acetic acid (1 mL). After removal of most solvent, the residue was extracted with EtOAc, washed with brine, dried over $Na_2SO_4$. After concentration, the crude product (400 mg, 83%) was used for the next step without purification. LCMS (M+H)$^+$ m/z 330 (t=1.61 min

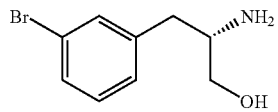

(S)-2-Amino-3-(3-bromo-phenyl)-propan-1-ol: To a solution of (S)-[2-(3-bromo-phenyl)-1-hydroxymethyl-ethyl]-carbamic acid tert-butyl ester (400 mg, 1.21 mmol) in methanol (30 mL) was added 4 M HCl in dioxane (2 mL, excess). The reaction mixture was stirred at room temperature for 14 h. After concentration in vacuo, the residue was used for the next step without purification. LCMS (M+H)$^+$ m/z 230 (t=0.78 min.)

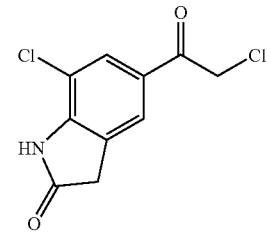

5-Chloroacetyl-7-chlorooxindole: To a suspension of $AlCl_3$ (13.4 g, 0.10 mol) in methylene chloride (40 mL) is added a solution of 7-Chlorooxindole (0.10 mol) and chloroacetyl chloride (8 mL, 0.10 mol) at 0° C. The solution is warmed to ambient temperature for two hours and poured onto ice and extracted with methylene chloride, washing with saturated bicarbonate solution, brine, and drying over $MgSO_4$ would provide the desired chloroketone.

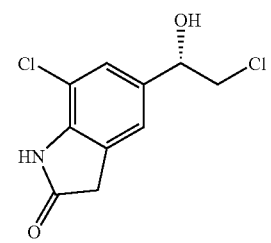

(S)-7-Chloro-5-(2-chloro-1-hydroxy-ethyl)-2-oxoindole: To a solution of (S)-Methyl-CBS-oxazaborolidine (1M in toluene, 0.745 mL, 0.745 mmol) and $BH_3$-THF (8 mL, 8 mmol) is added at the same time a solution of $BH_3$-THF (19 mL, 19 mmol) and a solution of the 5-Chloroacetyl-7-chlorooxindole (37.98 mmol) in 19 mL of THF. Both solutions are added dropwise over 30 minutes. The solution is stirred for 1 hour and quenched with the slow addition of methanol (50 mL). The solution is concentrated and the residue chromatographed over a short silica gel column (1:1 hexane/ethyl acetate).

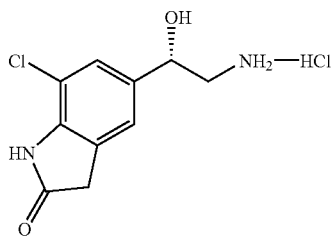

(S)-2-Amino-1-(7-chlorooxindole-5-yl)-ethanol Hydrochloride: To a solution of the chlorohydrin (37.9 mmol) in 120 mL of methanol at −40° C. is added 100 grams of ammonia. The solution is sealed in a pressure bottle and warmed to ambient temperature and stirred for 48 hours. The solution is cooled and opened. The ammonia is allowed to evaporate and solution concentrated to provide the hydrochloride salt, which can be crystallized from ethanol/ethyl acetate.

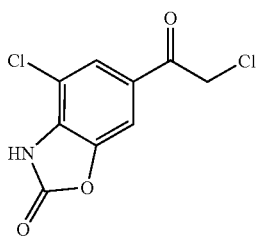

6-Chloroacetyl-4-chloro-2-benzooxazolinone: To a suspension of AlCl₃ (13.4 g, 0.10 mol) in methylene chloride (40 mL) is added a solution of 4-chloro-2-benzooxazolinone (0.10 mol) and chloroacetyl chloride (8 mL, 0.10 mol) at 0° C. The solution is warmed to ambient temperature for two hours and poured onto ice and extracted with methylene chloride, washing with saturated bicarbonate solution, brine, and drying over MgSO₄ would provide the desired chloroketone.

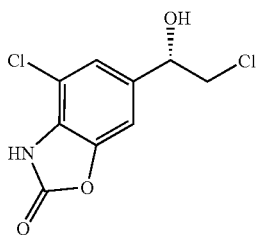

(S)-6-(2-Chloro-1-hydroxy-ethyl)-4-chloro-2-benzooxazolinone: To a solution of (S)-Methyl-CBS-oxazaborolidine (1M in toluene, 0.745 mL, 0.745 mmol) and BH₃-THF (8 mL, 8 mmol) is added at the same time a solution of BH₃-THF (19 mL, 19 mmol) and a solution of the 6-Chloroacetyl-4-chloro-2-benzooxazolinone (37.98 mmol) in 19 mL of THF. Both solutions are added dropwise over 30 minutes. The solution is stirred for 1 hour and quenched with the slow addition of methanol (50 mL). The solution is concentrated and the residue chromatographed over a short silica gel column (1:1 hexane/ethyl acetate).

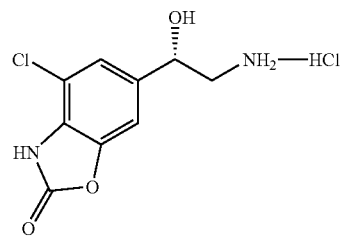

(S)-2-Amino-1-(4-chloro-2-benzooxazolinone-6-yl)-ethanol Hydrochloride: To a solution of the chlorohydrin (37.9 mmol) in 120 mL of methanol at −40° C. is added 100 grams of ammonia. The solution is sealed in a pressure bottle and warmed to ambient temperature and stirred for 48 hours. The solution is cooled and opened. The ammonia is allowed to evaporate and solution concentrated to provide the hydrochloride salt, which can be crystallized from ethanol/ethyl acetate.

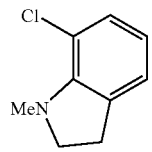

N-Methyl-7-chloroindoline: To a solution of the 7-Chloroindoline (0.10 mol) in 500 mL of acetone is added K₂CO₃ (0.15 mol) and MeI (0.15 mol) and refluxed until the starting material is consumed. The reaction is filtered and washed with water and saturated bicarbonate solution, drying over MgSO₄ would provide the N-Me-7-chloroindoline

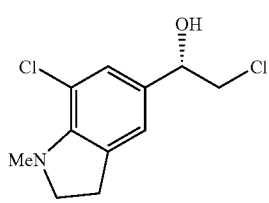

N-Methyl-5-chloroacetyl-7-chloro-indoline: To a suspension of AlCl₃ (13.4 g, 0.10 mol) in methylene chloride (40 mL) is added a solution of N-Me-7-Chloroindoline (0.10 mol) and chloroacetyl chloride (8 mL, 0.10 mol) at 0° C. The solution is warmed to ambient temperature for two hours and poured onto ice and extracted with methylene chloride, washing with saturated bicarbonate solution, brine, and drying over MgSO₄ provides the desired chloroketone.

(S)-N-Methyl-5-(2-chloro-1-hydroxylethyl)-7-chloro-indoline: To a solution of (S)-Methyl-CBS-oxazaborolidine (1M in toluene, 0.745 mL, 0.745 mmol) and BH$_3$-THF (8 mL, 8 mmol) is added at the same time a solution of BH$_3$-THF (19 mL, 19 mmol) and a solution of N-Methyl-5-chloroacetyl-7-chloro-indoline (37.98 mmol) in 19 mL of THF. Both solutions are added dropwise over 30 minutes. The solution is stirred for 1 hour and quenched with the slow addition of methanol (50 mL). The solution is concentrated and the residue chromatographed over a short silica gel column (1:1 hexane/ethyl acetate).

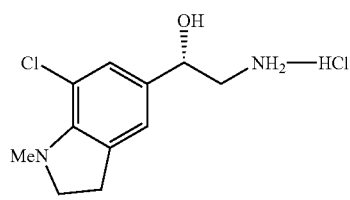

(S)-2-Amino-1-(7-chloro-N-methyl-indoline-5-yl)-ethanol Hydrochloride: To a solution of the chlorohydrin (37.9 mmol) in 120 mL of methanol at 40° C. is added 100 grams of ammonia. The solution is sealed in a pressure bottle and warmed to ambient temperature and stirred for 48 hours. The solution is cooled and opened. The ammonia is allowed to evaporate and solution concentrated to provide the hydrochloride salt, which can be crystallized from ethanol/ethyl acetate.

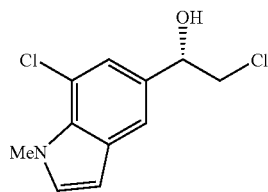

(S)-2-Chloro-1-(7-chloro-N-methyl-indol-5-yl)-ethanol: A solution (S)-N-Methyl-5-(2-chloro-1-hydroxylethyl)-7-chloro-indoline (0.10 mmol) in 100 mL of t-butyl methyl ether is treated with o-chloroanil (0.10 mmol) at ambient temperature. The solution is concentrated and the residue chromatographed over silica gel (1:1 hexane/ethyl acetate) to provide the corresponding indole.

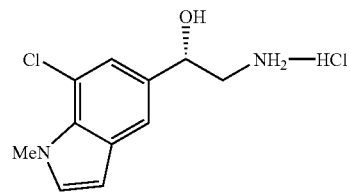

(S)-2-Amino-1-(7-chloro-N-methyl-indol-5-yl)-ethanol Hydrochloride: To a solution of the chlorohydrin (37.9 mmol) in 120 mL of methanol at −40° C. is added 100 grams of ammonia. The solution is sealed in a pressure bottle and warmed to ambient temperature and stirred for 48 hours. The solution is cooled and opened. The ammonia is allowed to evaporate and solution concentrated to provide the hydrochloride salt, which can be crystallized from ethanol/ethyl acetate.

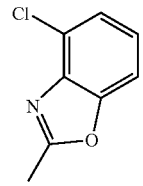

4-Chloro-2-methyl-benzooxazole: To a solution of the 4-chloro-2-benzooxazolinone (0.10 mol) in 200 mL ethanol is added LiOH (0.20 mol) in 100 mL of water. The solution is refluxed for 8 hr and cooled. The solution is neutralized with 1N HCl and extracted with ethyl acetate followed by drying over MgSO$_4$. The solution is concentrated and taken up in 200 mL of toluene and 0.10 mol of acetic acid. The solution is refluxed in a Dean Stark trap for 12 hours, concentrated and purified by flash chromatography.

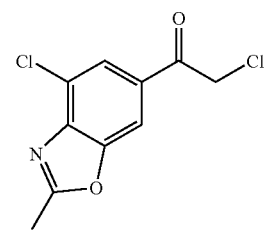

6-Chloroacetyl-4-chloro-2-methyl-benzooxazole: To a suspension of AlCl$_3$ (13.4 g, 0.10 mol) in methylene chloride (40 mL) is added a solution of 2-Methyl-4-chloro-benzooxale (0.10 mol) and chloroacetyl chloride (8 mL, 0.10 mol) at 0° C. The solution is warmed to ambient temperature for two hours and poured onto ice and extracted with methylene chloride, washing with saturated bicarbonate solution, brine, and drying over MgSO$_4$ would provide the desired chloroketone.

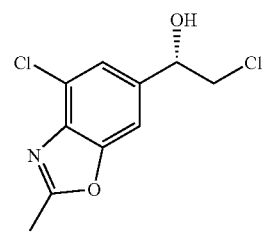

(S)-6-(2-chloro-1-hydroxy-ethyl)-4-chloro-2-methyl-benzooxazole: To a solution of (S)-Methyl-CBS-oxazaborolidine (1M in toluene, 0.745 mL, 0.745 mmol) and BH$_3$-THF (8 mL, 8 mmol) is added at the same time a solution of BH$_3$-THF (19 mL, 19 mmol) and a solution of 6-Chloroacetyl-4-chloro-2-methyl-benzooxazole (37.98 mmol) in 19 mL of THF. Both solutions are added dropwise over 30 minutes. The solution is stirred for 1 hour and quenched with the slow addition of methanol (50 mL). The solution is concentrated and the residue chromatographed over a short silica gel column (1:1 hexane/ethyl acetate).

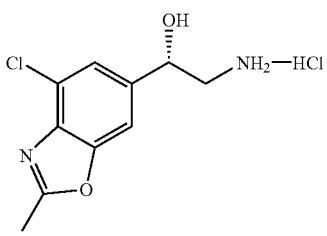

(S)-2-Amino-1-(4-chloro-2-methyl-benzooxazol-6-yl)-ethanol Hydrochloride: To a solution of the chlorohydrin (37.9 mmol) in 120 mL of methanol at −40° C. is added 100 grams of ammonia. The solution is sealed in a pressure bottle and warmed to ambient temperature and stirred for 48 hours. The solution is cooled and opened. The ammonia is allowed to evaporate and solution concentrated to provide the hydrochloride salt, which can be crystallized from ethanol/ethyl acetate.

Preparation of 3-(6-Imidazol-1-yl-4-methyl-1H-benzimidazol-2-yl)-4-iodo-1H-pyridin-2-one

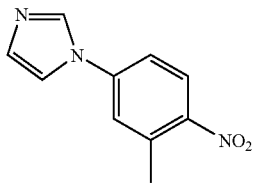

1-(3-Methyl-4-nitro-phenyl)-1H-imidazole: To a solution of 4-fluoro-2-methyl-1-nitro-benzene (300 mg, 1.84 mmol) in DMSO (2 mL) were added KOH (20 mg, 3.87 mmol) and imidazole (263 mg, 3.88 mmol). The reaction mixture was heated to 100° C. for 3.5 h, cooled to room temperature, and diluted with ice-cold water. The resulting precipitate was filtered, washed with ice-cold water, and dried under vacuum to give the title compound (310 mg, 80%) as a yellow powder. $^1$H NMR (300 MHz, DMSO-$d_6$) δ 8.46 (1H, s), 8.16 (1H, d, J=8.9 Hz), 7.90–7.92 (2H, m), 7.78 (1H, dd, J=2.5, 8.9 Hz), 7.17 (1H, s), 2.61 (3H, s). LRMS (M+H)$^+$ m/z 204.

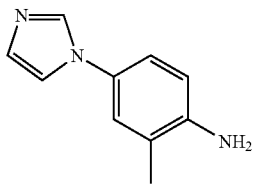

4-Imidazol-1-yl-2-methyl-phenylamine: To 1-(3-methyl-4-nitro-phenyl)-1H-imidazole (200 mg, 0.98 mmol) and 10% Palladium on carbon (35 mg) was added degassed methanol (3 mL). The suspension was flushed and evacuated with hydrogen/vacuum line. The suspension was allowed to stir at room temperature for 14 h under hydrogen atmosphere (hydrogen balloon). The dark reaction mixture was filtered through a pad of celite and rinsed with methanol. Concentration of the filtrate gave the title compound (166 mg, 98%) which was used for the next step without purification. $^1$H NMR (300 MHz, DMSO-$d_6$) δ 7.95 (1H, s), 7.48 (1H, s), 7.16 (1H, narrow d, J=2.5 Hz), 7.09 (1H, dd, J=2.5, 8.4 Hz), 7.01 (1H, s), 6.67 (1H, d, J=8.4 Hz), 5.03 (2H, broad s), 2.10 (3H, s).

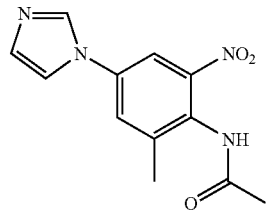

N-(4-Imidazol-1-yl-2-methyl-6-nitro-phenyl)-acetamide: To a solution of 4-imidazol-1-yl-2-methyl-phenylamine (1 g, 5.78 mmol) in CH$_2$Cl$_2$ (20 mL) was added Ac$_2$O (0.7 mL, 7.28 mmol) at 0° C. The reaction mixture was stir at room temperature for 14 h and diluted with water. The aqueous layer was extracted with CH$_2$Cl$_2$ and the combined organic layers were washed with saturated NaHCO$_3$ and brine, dried over Na$_2$SO$_4$, and concentrated in vacuo to give a white solid. The white solid was suspended in H$_2$SO$_4$ (conc.) (15 mL). Then HNO$_3$ (conc.) (0.312 mL) was added to the suspension at 0° C. The reaction mixture was slowly warmed to room temperature and stirred at room temperature for 4 h. After cooling to −10° C., the reaction mixture was neutralized with ammonium hydroxide and extracted with ethyl acetate. The combined organic layers were washed with brine, dried over Na$_2$SO$_4$, and concentrated. The residue was purified by flash chromatography (1:9:5 MeOH/THF/hexane) to yield the title compound (0.61 g, 41%). $^1$H NMR (300 MHz, CD$_3$OD) δ 8.11 (1H, s), 7.45–7.56 (2H, m), 7.38 (1H, dd, J=2.4, 8.4 Hz), 7.14 (1H, s), 2.33 (3H, s), 2.18 (3H, s).

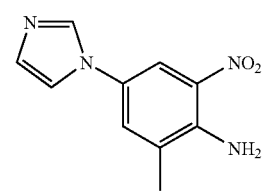

4-Imidazol-1-yl-2-methyl-6-nitro-phenylamine: To a suspension of N-(4-imidazol-1-yl-2-methyl-6-nitro-phenyl)-acetamide (279 mg, 1.07 mmol) in ethanol (3 mL) was added 2 N HCl (2 mL). The reaction mixture was heated to reflux for 14 h, cooled to room temperature, and neutralized with saturated NaHCO$_3$. The resulting bright orange solid was filtered and dried under vacuum. The title compound (179 mg, 76%) was obtained as an orange solid. $^1$H NMR (300 MHz, CD$_3$OD) δ 8.78 (1H, s), 8.24 (1H, s), 7.78 (1H, s), 7.64 (1H, s), 7.46 (1H, s), 2.36 (3H, s).

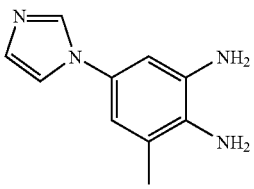

5-Imidazol-1-yl-3-methyl-benzene-1,2-diamine: To 4-imidazol-1-yl-2-methyl-6-nitro-phenylamine (350 mg, 1.61 mmol) and 10% Palladium on carbon (40 mg) were added degassed methanol (5 mL) and TFA (5 drops). The reaction mixture was flushed and evacuated with hydrogen/vacuum line, stirred at room temperature for 14 h under hydrogen atmosphere (hydrogen balloon). The dark reaction mixture was filtered through a pad of celite and rinsed with methanol. Concentration of the filtrate gave the residue, which was diluted with water, extracted with ethyl acetate. The combined organic layers were washed with saturated NaHCO$_3$, brine, dried over Na$_2$SO$_4$. Concentration to dryness gave the title compound (275 mg, 91%) as a solid. $^1$H NMR (300 MHz, CD$_3$OD) δ 7.87 (1H, s), 7.34 (1H, s), 7.05 (1H, s), 6.72 (1H, d, J=2.4 Hz), 6.65 (1H, d, J=2.4 Hz) 2.21 (3H, s). LCMS (M+H)$^+$ m/z 189 (t=0.23 min.).

4-Iodo-2-methoxy-pyridine-3-carbaldehyde (WO 95/29917): A 5-liter three-necked round bottom flask was equipped with an overhead mechanical stirrer under nitrogen, the flask was charged with THF (1 L) and cooled to −78° C. To this stirred solution was added tert-butyllithium (1.7 M solution in pentane) (800 mL, 1.36 mol) via canula followed by 2-methoxypyridine (132.2 g, 1.21 mol) at −78° C. The mixture was stirred for 1 h at −78° C. To the mixture was added N-formyl-N,N',N'-trimethylethylenediamine (176 mL, 1.37 mol) dropwise at −78° C. The reaction mixture was stirred for ca. 30 min at −78° C. before warming to −23° C. over ca. 30 min. To the mixture at −23° C. was added ethylene glycol dimethyl ether (1 L) followed by n-butyllithium (2.5 M solution in hexane) (800 mL, 2.0 mol). The resulting mixture was stirred for ca. 2 h during which time the reaction mixture turned deep green. A 12-L 4-necked round flask was charged with iodine (571 g, 2.25 mol) and ethylene glycol dimethyl ether (2 L) and the resultant solution was cooled to −78° C. The contents of the 5-L flask were transferred via canula to the mixture of iodine and ethylene glycol dimethyl ether in the 12-L flask at −78° C. After the addition was complete, the reaction mixture was stirred for an additional 1 h at −78° C. The cooling bath was removed and the mixture was allowed to warm to about 0° C. and treated with 2 L of water and 2 L of 1 N hydrochloric acid. Methyl t-butyl ether (2L) was added and the layers were separated. The aqueous layer was extracted with 2×1 L of methyl t-butyl ether. The combined organic layers were washed with saturated Na$_2$S$_2$O$_3$ (1.2 L), brine (1.2 L), dried over Na$_2$SO$_4$. After concentration in vacuo, the thick slurry was diluted with hexane (1 L). The mixture was cooled with an ice/water bath for ca. 30 min. The precipitate was filtered and dried in vacuum to yield the title compound as a light yellow solid. $^1$H NMR (300 MHz, CDCl$_3$) δ 10.22 (s, 1H), 7.86 (1H, d, J=5.3 Hz), 7.54 (1H, d, J=5.3 Hz), 4.06 (3H, s). LCMS (M+H)$^+$ m/z 364 (t=2.26 min.).

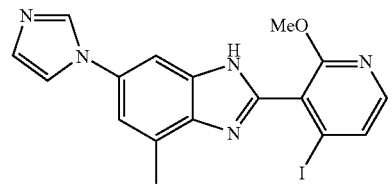

6-Imidazol-1-yl-2-(4-iodo-2-methoxy-pyridin-3-yl)-4-methyl-1H-benzimidazole: To a solution of 5-imidazol-1-yl-3-methyl-benzene-1,2-diamine (175 mg, 0.93 mmol) in methanol (8 mL) was added a solution of 4-iodo-2-methoxy-pyridine-3-carbaldehyde (245 mg, 0.93 mmol) in methanol (5 mL) at 0° C. The reaction mixture was stirred at 0° C. for 1.5 h and then at room temperature for 2 h. After concentration, the residue was purified by flash column chromatography (10% MeOH/CH$_2$Cl$_2$) to give the title compound (291 mg, 60%). $^1$H NMR (300 MHz, CD$_3$OD) δ 8.13 (1H, s), 7.98 (1H, d, J=5.4 Hz), 7.62 (1H, d, J=5.4 Hz), 7.59 (2H, s), 7.33 (1H, s), 7.16 (1H, s), 3.90 (3H, s), 2.67 (3H, s). LCMS (M+H)$^+$ m/z 432 (t=0.99 min.).

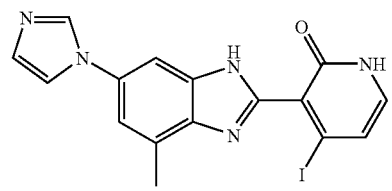

3-(6-Imidazol-1-yl-4-methyl-1H-benzimidazol-2-yl)-4-iodo-1H-pyridin-2-one: The suspension of 6-imidazol-1-yl-2-(4-iodo-2-methoxy-pyridin-3-yl)-4-methyl-1H-benzimidazole in 1 N HCl (6 mL) was heated to 70° C. for 3 days, cooled to room temperature, and diluted with ethyl acetate. After extraction, the combined organic layers were washed with brine, dried over Na$_2$SO$_4$ and concentrated. The residue was purified by flash chromatography (1% NH$_4$OH/10% MeOH/CH$_2$Cl$_2$) to yield the title compound (78 mg, 81%) as a solid. $^1$H NMR (300 MHz, CD$_3$OD) δ 8.12 (1H, s), 7.58 (2H, s), 7.29–7.31 (2H, m), 7.16 (1H, s), 7.01 (1H, J=6.8 Hz), 2.66 (3H, s). LCMS (M+H)$^+$ m/z 418 (t=0.75 min.)

Preparation of 2-(4-Chloro-2-oxo-1,2-dihydro-pyridin-3-yl)-7-methyl-3H-benzimidazole-5-carbonitrile

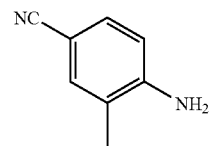

4-Amino-3-methyl-benzonitrile: To a solution of 3-methyl-4-nitro-benzonitrile (20 g, 0.123 mol) in HOAc (200 mL) was added iron powder (17.55 g, 0.309 mol). After 10 min, the reaction was exothermic and turned to dark color. The reaction mixture was allowed to stir at room temperature for 14 h and then diluted with EtOAc (200 mL). The brown precipitate was filtered through a pad of celite and the filtercake was rinsed with EtOAc. The filtrate was concentrated in vacuo and the residue was purified by flash chromatography (40% EtOAc/hexane) to yield the title compound (15.3 g, 92%). $^1$H NMR (300 MHz, CDCl$_3$) δ 7.30–7.34 (2H, m), 6.64 (1H, d, J=8.7 Hz), 2.16 (3H, s). LCMS (M+H)$^+$ m/z 133 (t=0.93 min).

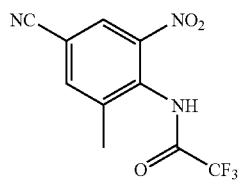

N-(4-Cyano-2-methyl-6-nitro-phenyl)-2,2,2-trifluoro-acetamide: To the ice-cold trifluoroacetic anhydride (60 mL) was added 4-amino-3-methyl-benzonitrile (14.33 g, 0.108 mol) in portion. The resulting white slurry was stirred at 0° C. for 30 min. Then ammonium nitrate (17.28 g, 0.216 mol) was added. The reaction mixture was allowed to stir at 0° C. for 1 h and at room temperature for 14 h. After removal of most solvent, the reaction mixture was cooled with ice and quenched with ice. The yellow precipitate was filtered, washed with cold water, and dried under vacuum. The crude product (15.5 g, 52% yield, and ca. 80% pure) was used for the next step without purification. $^1$H NMR (300 MHz, CD$_3$OD) δ 8.05 (1H, s), 7.74 (1H, s), 2.30 (3H, s). LRMS (neg. ESI, (M–H)$^-$) m/z 272.

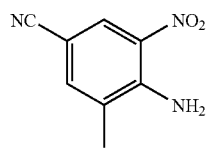

4-Amino-3-methyl-5-nitro-benzonitrile: A mixture of N-(4-cyano-2-methyl-6-nitro-phenyl)-2,2,2-trifluoro-acetamide (5 g, 18.3 mmol) and 2 M ammonia in methanol (80 mL) was heated to reflux for 14 h and then cooled to room temperature. After concentration in vacuo, the residue was purified by flash chromatography (20% EtOAc/hexane) to yield the title compound (3.24 g, 100%, ca 80% pure). $^1$H NMR (300 MHz, CDCl$_3$) δ 8.40 (1H, s), 7.47 (1H, s), 6.6–6.8 (2H, broad s), 2.89 (3H, s).

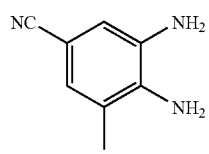

3,4-Diamino-5-methyl-benzonitrile: To a solution of 4-amino-3-methyl-5-nitro-benzonitrile (3.24 g, 18.3 mmol) in ethanol (80 mL) was added tin chloride dihydrate (8.67 g, 49.75 mmol). The reaction mixture was heated to reflux for 14 h, then cooled to room temperature, and concentrated in vacuum. The residue was diluted with ethyl acetate (100 mL) and treated with triethylamine (20 mL). The resulting slurry was filtered through a pad of celite and the filtercake was rinsed with three-portion ethyl acetate (50 mL). The filtrate was washed with saturated NaHCO$_3$, water, and brine, then dried over Na$_2$SO$_4$ and filtered. After removal of solvent, the residue was purified by flash chromatography on silica gel (30%–50% EtOAc/hexane) to yield the title compound (2.17 g, 81%) as a light yellow solid. $^1$H NMR (300 MHz, CDCl$_3$) δ 6.94 (1H, s), 6.85 (1H, s), 2.16 (3H, s). LCMS (M+H)$^+$ m/z 148 (t=0.67 min.).

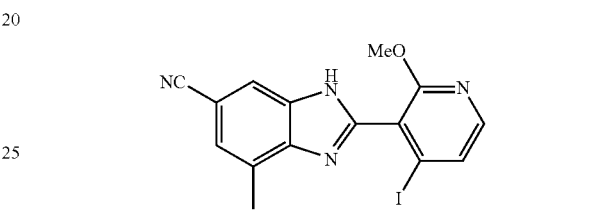

2-(4-Iodo-2-methoxy-pyridin-3-yl)-7-methyl-3H-benzimidazole-5-carbonitrile: To a solution of 3,4-diamino-5-methyl-benzonitrile (2.00 g, 13.6 mmol) in MeOH (40 mL) was added 4-iodo-2-methoxy-pyridine-3-carbaldehyde (3.6 g, 13.6 mmol) in MeOH (20 mL) at 0° C. The resulting slurry was stirred at 0° C. for 1 h. Iodine (1.73 g, 8.8 mmol) in MeOH (10 mL) was added dropwise via a dropping funnel to the reaction mixture at 0° C. The reaction mixture was stirred at room temperature for 14 h. After removal of MeOH, the residue was diluted with saturated Na$_2$S$_2$O$_3$ and extracted with EtOAc. The combined organic layers were washed with water and brine, dried over Na$_2$SO$_4$. The crude product was purified by flash column chromatography (3% MeOH/CH$_2$Cl$_2$) to yield the title compound (1.81 g, 46%). $^1$H NMR (300 MHz, CDCl$_3$) δ 7.90 (1H, s), 7.49 (1H, d, J=5.4 Hz), 7.46 (1H, s), 7.41 (1H, d, J=5.3 Hz), 3.78 (3H, s), 2.68 (3H, s). LCMS (M+H)$^+$ m/z 391 (t=1.27 min.).

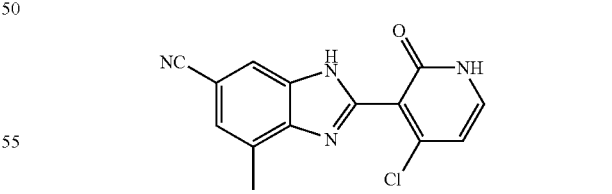

2-(4-Chloro-2-oxo-1,2-dihydro-pyridin-3-yl)-7-methyl-3H-benzimidazole-5-carbonitrile: A suspension of 2-(4-iodo-2-methoxy-pyridin-3-yl)-7-methyl-3H-benzimidazole-5-carbonitrile (1.8 g, 4.63 mmol) in 4 M HCl dioxane (40 mL) was heated to 80° C. for 6 h and cooled to room temperature. The precipitate was filtered and dried. The crude product (1.08 g, 82%) was used for the next step without purification. LRMS (neg. ESI, (M–H)$^-$) m/z 283.

Preparation of (S)-4-(1-Benzyl-2-trityloxy-ethylamino)-3-(6-bromo-4-methyl-1H-benzimidazol-2-yl)-1H-pyridin-2-one

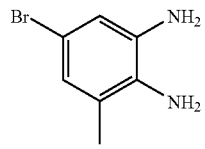

5-Bromo-3-methyl-benzene-1,2-diamine: To a suspension of 4-bromo-2-methyl-6-nitro-phenylamine (20 g, 0.086 mol) in ethanol (200 mL) was added tin chloride dihydrate (49.2 g, 0.258 mol). The reaction mixture was heated to reflux for 14 h, cooled to room temperature, and concentrated in vacuo. The residue was diluted with ethyl acetate (150 mL) and treated with triethylamine (40 mL). The resulting slurry was filtered through a pad of celite, and the filtercake was rinsed with three portions ethyl acetate (50 mL). The filtrate was washed with saturated NaHCO$_3$, water, and brine, then dried over Na$_2$SO$_4$ and filtered. After removal of the solvent, the residue was purified by flash chromatography on silica gel (30% EtOAc/hexane, then 5% MeOH/CH$_2$Cl$_2$) to yield the title compound (10.26 g, 59%) as a yellow oil. $^1$H NMR (300 MHz, CDCl$_3$) δ 6.77 (1H, d, J=2.0 Hz), 6.74 (1H, d, J=2.0 Hz), 2.16 (3H, s). LCMS (M+H)$^+$ m/z 201. (t=0.83 min.).

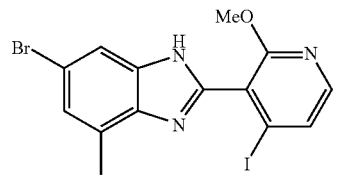

6-Bromo-2-(4-iodo-2-methoxy-pyridin-3-yl)-4-methyl-1H-benzimidazole: To a solution of 5-bromo-3-methyl-1,2-phenylenediamine (4 g, 19.9 mmol) in methanol (80 mL) was added 4-iodo-2-methoxy-pyridine-3-carbaldehyde (5.23 g, 19.9 mmol) in methanol (20 mL) dropwise at 0° C. The resulting slurry was stirred for 30 min at room temperature. Then iodine (2.53 g, 9.95 mmol) in methanol (20 mL) was added via a dropping funnel. After 14 h, the reaction mixture was concentrated in vacuo, diluted with 5% Na$_2$S$_2$O$_3$, and extracted with ethyl acetate. The combined organic layers were washed with water, brine, and dried over Na$_2$SO$_4$. After removal of solvent, the residue was purified by careful flash chromatography (20% EtOAc/hexane) to yield the title compound (4.05 g, 46%) as a yellow foam. $^1$H NMR (300 MHz, CDCl$_3$) δ 7.86 (1H, d, J=5.31 Hz), 7.53 (1H, d, J=5.3 Hz), 7.26 (2H, broad s), 3.91 (3H, s), 2.63 (3H, s). LCMS (M+H)$^+$ m/z 444 (t=1.39 min.).

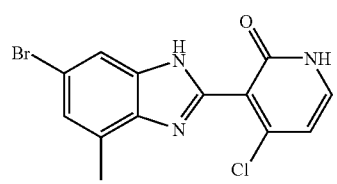

3-(6-Bromo-4-methyl-1H-benzimidazol-2-yl)-4-chloro-1H-pyridin-2-one: The suspension of 6-bromo-2-(4-iodo-2-methoxy-pyridin-3-yl)-4-methyl-1H-benzimidazole (4 g, 9.03 mmol) and 60 mL of 4 M HCl in dioxane was heated to 80° C. for 6 h and cooled to room temperature. The precipitate was filtered and dried to yield the title compound (3.0 g, 100%) as a brown powder. The crude product was used for the next step without purification. $^1$H NMR (300 MHz, CD$_3$OD) δ 7.55 (1H, s), 7.42 (1H, d, J=6.0 Hz), 7.17 (1H, s), 6.91 (1H, d, J=6.0 Hz), 2.55 (3H, s). LCMS (M+H)$^+$ m/z 338 (t=1.33 min.).

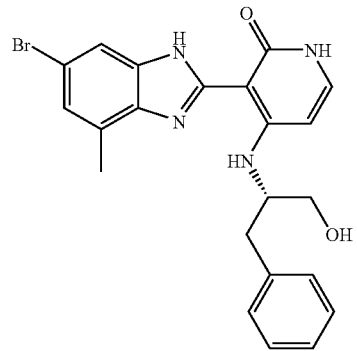

(S)-4-(1-Benzyl-2-hydroxy-ethylamino)-3-(6-bromo-4-methyl-1H-benzimidazol-2-yl)-1H-pyridin-2-one: To a solution of 3-(6-bromo-4-methyl-1H-benzimidazol-2-yl)-4-chloro-1H-pyridin-2-one (1.42 g, 3.78 mmol) in DMF (15 mL) were added (S)-(−)-2-amino-3-phenyl-1-propanol (1.43 g, 9.45 mmol) and N-methyl morpholine (1.5 mL). The reaction mixture was heated to 80° C. for 6 h and cooled to room temperature. The solvent was removed with high vacuum and the residue was purified by flash chromatography (5% MeOH/CH$_2$Cl$_2$) to yield the title compound (1.26 g, 74%) as a yellow foam. $^1$H NMR (300 MHz, CDCl$_3$) δ 6.9–7.2 (8H, m), 5.86 (1H, d, J=7.1 Hz), 3.7–3.9 (3H, m), 2.9–3.1(2H, m), 2.57 (3H, s). LCMS (M+H)$^+$ m/z 453 (t=2.03 min.).

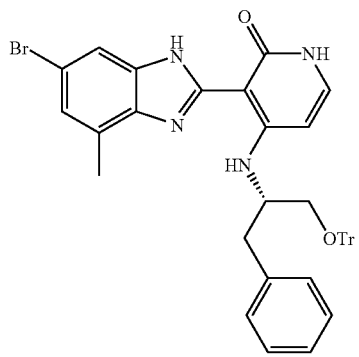

(S)-4-(1-Benzyl-2-trityloxy-ethylamino)-3-(6-bromo-4-methyl-1H-benzimidazol-2-yl)-1H-pyridin-2-one: To a solution of (S)-4-(1-benzyl-2-hydroxy-ethylamino)-3-(6-bromo-4-methyl-1H-benzimidazol-2-yl)-1H-pyridin-2-one (0.9 g, 1.98 mmol) in THF (30 mL), was added Cs$_2$CO$_3$ (1.29 g, 3.96 mmol) followed by triphenylmethyl chloride (1.10 g, 3.96 mmol). The reaction mixture was heated to reflux for 14 h under nitrogen and then cooled to room temperature. After removal of the solvent, the residue was diluted with ethyl acetate and washed with water. The aqueous fraction was extracted with ethyl acetate and the combined organic layers were washed with water and brine, dried over Na$_2$SO$_4$. After concentration in vacuo, the residue was purified by flash column chromatography (30% EtOAc/hexane) to yield the title compound (1 g, 73%) as a white solid. $^1$N NMR (300 MHz, DMSO-d$_6$) δ 11.77 (1H, broad s), 11.73 (1H, d, J=5.2 Hz), 11.46 (1H, broad s), 7.13–7.54 (23H, m), 5.87 (1H, d, J=4.5 Hz), 4.09–4.14 (1H, m), 3.07–3.42 (4H, m), 2.54 (3H, s). LCMS (M+H)$^+$ m/z 695 (t=2.79 min.).

Preparation of 3-[6-(4-Acetyl-piperazin-1-yl)-4-methyl-1H-benzimidazol-2-yl]-4-chloro-1H-pyridin-2-one

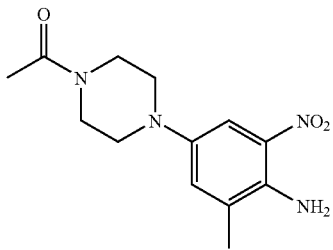

1-[4-(4-Amino-3-methyl-5-nitro-phenyl)-piperazin-1-yl]-ethanone: A mixture of 4-bromo-2-methyl-6-nitro-phenylamine (5 g, 21.64 mmol), 1-acetylpiperazine (4.2 g, 32.46 mmol), palladium acetate (244 mg, 1.08 mmol), tri-tert-butylphosphine (440 mg, 2.16 mmol) and sodium tert-butoxide (4.2 g, 43.29 mmol) in toluene (70 mL) was heated to 100° C. for 14 h under nitrogen. The reaction mixture was cooled to room temperature and diluted with EtOAc. After extraction, the combined organic layers were washed with water, brine, dried over Na$_2$SO$_4$. Concentration gave a brownish residue which was purified by flash column chromatography (10% MeOH/CH$_2$Cl$_2$) to yield the title compound (4.21 g, 70%). $^1$H NMR (400 MHz, CD$_3$OD) δ 7.42 (1H, d, J=2.8 Hz), 7.23 (1H, d, J=2.8 Hz), 3.71 (2H, t, J=5.1 Hz), 3.67 (2H, t, J=5.1 Hz), 3.04 (2H, t, J=5.2 Hz), 2.98 (2H, t, J=5.2 Hz), 2.24 (3H, s), 2.13 (3H, s). LCMS (M+H)$^+$ m/z 279 (t=1.46 min.).

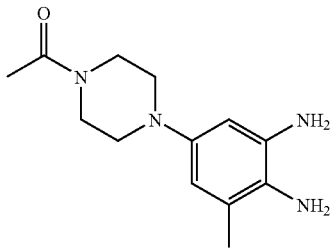

1-[4-(3,4-Diamino-5-methyl-phenyl)-piperazin-1-yl]-ethanone: To 1-[4-(4-amino-3-methyl-5-nitro-phenyl)-piperazin-1-yl]-ethanone (4.5 g, 16.2 mmol) and 10% palladium on carbon (400 mg) were added methanol (50 mL) and acetic acid (5 mL) under nitrogen. The reaction mixture was stirred under hydrogen atmosphere (hydrogen balloon) for 14 h. The dark solution was filtered through a pad of celite and the filtercake was washed with methanol. Concentration of the filtrate gave the title compound (4.00 g, 100%) which was used for the next step without purification. LCMS (M+H)$^+$ m/z 207 (t=0.41 min.).

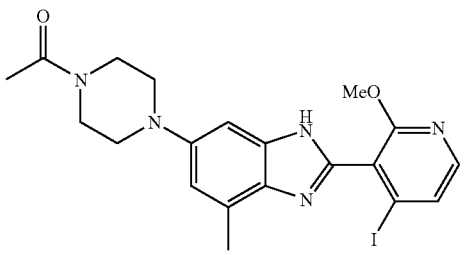

1-{4-[2-(4-Iodo-2-methoxy-pyridin-3-yl)-7-methyl-3H-benzimidazol-5-yl]-piperazin-1-yl}-ethanone: To a solution of 1-[4-(3,4-diamino-5-methyl-phenyl)-piperazin-1-yl]-ethanone (4.00 g, 16.18 mmol) in methanol (100 mL) was added 4-iodo-2-methoxy-pyridine-3-carbaldehyde (4.25 g, 16.18 mmol). The reaction mixture was stirred at room temperature for 14 h. After concentration, the residue was purified by flash column chromatography (10% MeOH/CH$_2$Cl$_2$) to yield the title compound (5.25 g, 66%). $^1$H NMR (400 MHz, CD$_3$OD) δ 7.81 (1H, d, J=5.4 Hz), 7.48 (1H, d, J=5.4 Hz), 7.26 (1H, s), 6.85 (1H, s), 3.85 (3H, s), 3.78 (2H, t, J=5.0 Hz), 3.64 (2H, t, J=5.0 Hz), 3.16 (2H, t, J=5.2 Hz), 3.11 (2H, t, J=5.2 Hz), 2.62 (3H, s), 2.13 (3H, s). LCMS (M+H)$^+$ m/z 492 (t=1.71 min.).

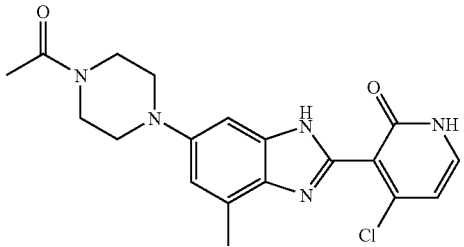

3-[6-(4-Acetyl-piperazin-1-yl)-4-methyl-1H-benzimidazol-2-yl]-4-chloro-1H-pyridin-2-one: To a solution of 1-{4-[2-(4-Iodo-2-methoxy-pyridin-3-yl)-7-methyl-3H-benzimidazol-5-yl]-piperazin-1-yl}-ethanone (5.2 g, 10.6 mmol) in 4 M HCl in dioxane (60 mL) was added water (5 mL). The reaction mixture was stirred at room temperature for 14 h. Concentration of the reaction mixture gave the title compound (4.02 g, 100%) which was used for the next step without purification. LCMS (M+H)$^+$ m/z 486 (t=1.55 min.).

Preparation of (S)-4-(1-Hydroxymethyl-2-phenyl-ethylamino)-3-(4-methyl-6-piperazin-1-yl-1H-benzimidazol-2-yl)-1H-pyridin-2-one

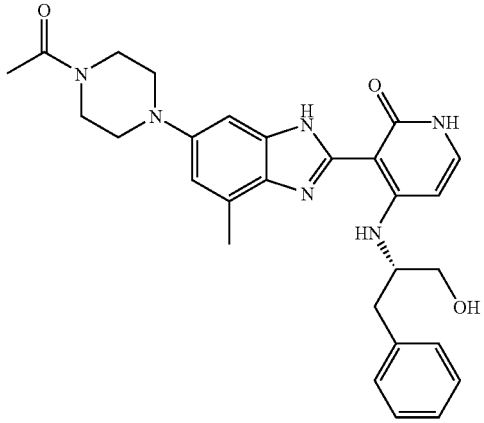

(S)-3-[6-(4-Acetyl-piperazin-1-yl)-4-methyl-1H-benzimidazol-2-yl]-4-(1-hydroxymethyl-2-phenyl-ethylamino)-1H-pyridin-2-one: To a solution of 3-[6-(4-acetyl-piperazin-1-yl)-4-methyl-1H-benzimidazol-2-yl]-4-chloro-1 H-pyridin-2-one (1 g, 2.6 mmol) in DMF (10 mL) was added (S)-(−)-2-amino-3-phenyl-propanol (0.78 mg, 5.2 mmol) and N-methyl morpholine (2 mL). The reaction mixture was heated to 80° C. for 12 h, cooled to room temperature and concentrated with high vacuum. The residue was purified by flash column chromatography (10% MeOH/CH$_2$Cl$_2$) to yield the title compound (0.90 g, 69%). $^1$H NMR (400 MHz, CD$_3$OD) δ 7.36 (1H, s), 7.02–7.23 (6H, m), 6.80 (1H, s), 5.98 (1H, d, J=7.5 Hz), 4.10–4.12 (3H, m), 3.67–3.78 (6H, m), 3.06–3.11 (3H, m), 2.90 (1H, dd, J=7.8, 13.6 Hz), 2.54 (3H, s), 2.12 (3H, s). LCMS (M+H)$^+$ m/z 501 (t=1.30 min.).

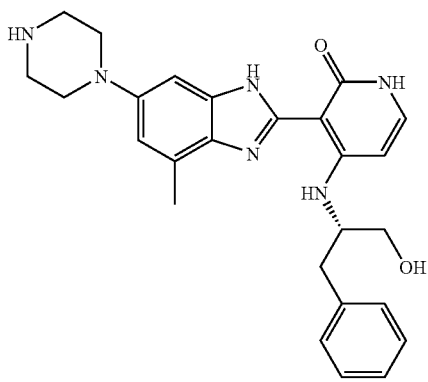

(S)-4-(1-Hydroxymethyl-2-phenyl-ethylamino)-3-(4-methyl-6-piperazin-1-yl-1H-benzimidazol-2-yl)-1H-pyridin-2-one: To a solution of (S)-3-[6-(4-acetyl-piperazin-1-yl)-4-methyl-1H-benzimidazol-2-yl]-4-(1-hydroxymethyl-2-phenyl-ethylamino)-1H-pyridin-2-one (900 mg, 18 mmol) in 4 M HCl in dioxane (10 mL) was added water (1 mL). The reaction mixture was heated to 80° C. for 14 h and cooled to room temperature. Concentration with high vacuum gave the title compound (0.83 g, 100%) which was used for the next step without purification. LCMS (M+H)$^+$ m/z 459 (t=1.13 min.).

Preparation of 2-(4,6-Dichloro-pyrimidin-5-yl)-6-imidazol-1-yl-4-methyl-1H-benzimidazole

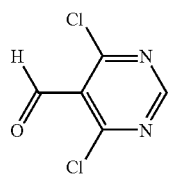

4,6-Dichloro-pyrimidine-5-carbaldehyde: DMF (7 mL, 0.09 mol) was added to POCl$_3$ (21 mL, 0.23 mol) at 0° C. The reaction mixture was stirred at room temperature for 0.5 h. 4,6-Dihydroxy-pyrimidine-5-carbaldehyde (5 g, 0.045 mol) was added in small portions. The reaction mixture was heated to 90° C. for 6 h and cooled to room temperature. A large excess of crushed ice was added to the reaction mixture very slowly under ice-bath. The mixture was extracted with CH$_2$Cl$_2$. The combined organic layers were washed with water, brine, and dried over Na$_2$SO$_4$. After concentration, the residue was purified by column chromatography (20% EtOAc/hexane) to yield the title compound (4 g, 50%). $^1$H NMR (400 MHz, CDCl$_3$) δ 8.91 (1H, s), 7.87 (1H, s). LRMS (M+H)$^+$ m/z 177.

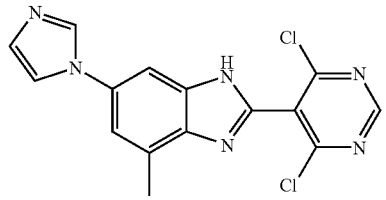

2-(4,6-Dichloro-pyrimidin-5-yl)-6-imidazol-1-yl-4-methyl-1H-benzimidazole: To a solution of 5-imidazol-1-yl-3-methyl-benzene-1,2-diamine (180 mg, 0.96 mmol) in methanol (4 mL) was added a solution of 4,6-dichloro-pyrimidine-5-carbaldehyde (183 mg, 0.96 mmol) in methanol (1 mL). The reaction mixture was stirred at room temperature for 14 h. After concentration, the residue was purified by flash column chromatography (5% methanol/CH$_2$Cl$_2$) to yield the title compound (180 mg, 55%). LCMS (M+H)$^+$ m/z 344 (t=1.31 min.).

Procedure for the Preparation of 2-Amino-4-Fluoro-6-Methyl Nitrobenzene

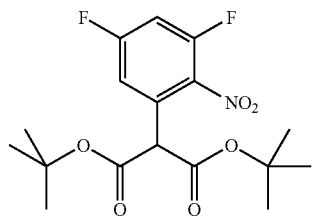

2-(3,5-Difluoro-2-nitro-phenyl)-malonic acid di-tert-butyl ester: To a suspension of NaH (54.6 g, 60%, 1.365 mol) in 600 mL of DMF was added di-t-Butyl malonate (118 g, 0.546 mol) at 0° C. and stirred for 30 min. 2,4,6 trifluoronitrobenzene was added as a solution in 400 mL of DMF (75 g, 0.42 mol) over 3 hours and the solution stirred at ambient temperature for 12 hours. The reaction mixture was extracted with ethyl acetate (3×'s). The ethyl acetate was washed with water (3×'s) and with brine and dried over MgSO$_4$ and concentrated to give 62 g of crude product. LCMS [M+Na]−396; $^1$H NMR (500 MHz, DMSO) δ 7.81 (m, 1H), 7.27 (m, 1H), 5.00 (s, 1H), 1.41 (m, 18H).

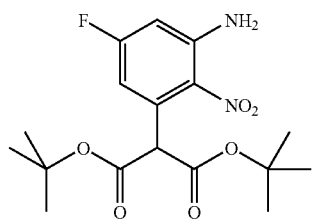

2-(3-Amino-5-fluoro-2-nitro-phenyl)-malonic acid di-tert-butyl ester: To the crude 2-(3,5-Difluoro-2-nitrophenyl)-malonic acid di-tert-butyl ester (62 g, 0.42 mol) was added 700 mL of 2M ammonia in methanol in a pressure bottle. The vessel was sealed and heated to 85° C. for 18 hours. The reaction mixture was cooled and the vessel opened carefully and the methanol solution concentrated to provide 140 g of crude material. LCMS [M+Na]–393; $^1$H NMR (500 MHz, DMSO) δ 6.76 (dd, J=10.8 2.8 Hz, 1H), 6.29 (dd, J=10.8, 2.8 Hz, 1H), 4.99 (brs, 2H), 4.80 (s, 1H), 1.40 (m, 18H).

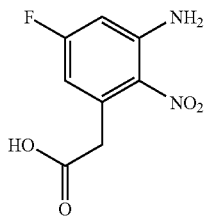

3-Amino-5-fluoro-2-nitro phenyl acetic acid: To the 2-(3-Amino-5-fluoro-2-nitro-phenyl)-malonic acid di-tert-butyl ester (140 g) in 500 mL of 4N HCl in dioxane was added 50 mL of water and heated to 40° C. for 2 days. The solution was extracted with ethyl acetate (3×'s) and the ethyl acetate washed with water (3×'s) and brine. The organic fraction was dried over MgSO$_4$ and was concentrated to give 78 g of crude (66% pure by LC/MS); $^1$H NMR (500 MHz, DMSO) δ 12.40 (brs, 1H), 7.04 (s, 2H), 6.68 (dd, J=10.9 2.8 Hz, 1H), 6.47 (dd, J=10.9, 2.8 Hz, 1H), 3.80 (s, 2H).

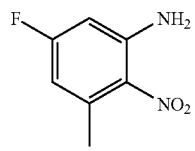

2-Amino-4-fluoro-6-methyl nitrobenzene: To the crude 3-Amino-5-fluoro-2-nitro phenyl acetic acid (3.6 g, 16.8 mmol) was added Cu$_2$O (10.1 g, 70.6 mmol) in 120 mL of acetonitrile along with 50 uL of methanol and the suspension was refluxed for 12 hours. The reaction mixture was filtered through Celite and the Celite pad washed with water and ethyl acetate. The filtrate was extracted with ethyl acetate, washed with water and brine, dried over Na$_2$SO$_4$ and concentrated to give 2.95 g of material which by $^1$H NMR was 80% pure. ESIMS [M+Na]–193; $^1$H NMR (500 MHz, DMSO) δ 6.67 (s, 2H), 6.56 (dd, J=11, 2.8 Hz, 1H), 6.39 (dd, J=11, 2.8 Hz, 1H), 2.50 (s, 3H).

Procedure for the preparation of 4-Chloro-3-(4-methyl-6-morpholin-4-yl-1H-benzoimidazol-2-yl)-1H-pyridin-2-one and 4-Iodo-3-(4-methyl-6-morpholin-4-yl-1H-benzoimidazol-2-yl)-1H-pyridin-2-one

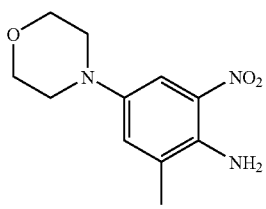

2-Methyl-4-morpholin-4-yl-6-nitro-phenylamine: To a 800 ml pressure flask was added Tris(dibenzylideneacetone)dipalladium (2.64 g, 2.88 mmol), 2-(Di-t-butylphosphino)biphenyl (1.42 g, 4.75 mmol) and sodium tert-butoxide (17.5 g, 182 mmol). Then dry THF (500 mL), 4-bromo-2-methyl-6-nitroaniline (30.0 g, 130 mmol) and morpholine (34 ml, 390 mmol) were added. Argon was bubbled through the solution for 1 minute and the flask was sealed. The reaction mixture was stirred at 85° C. for 3 days. THF was evaporated in vacuo and the crude product was preabsorbed on silica and this then transferred on top of a silica gel column. Elution with hexane-ethyl acetate (6:4 to 4:6 to 0:1 gradient) gave, after evaporation of solvents, the title compound (15.2 g red-brown solid, 49.3%). LCMS (M+H)$^+$ m/z 238 (t=0.64 min.) $^1$H NMR (500 MHz, DMSO-d$_6$) δ 7.32 (1H, s), 7.22 (1H, s), 6.96 (2H, s), 3.72 (4H, broad s), 2.96 (4H, broad s), 2.21 (3H, s).

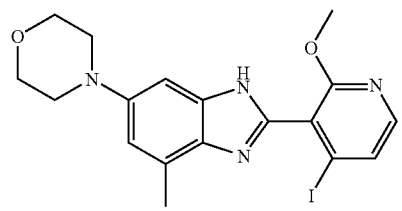

2-(4-Iodo-2-methoxy-pyridin-3-yl)-4-methyl-6-morpholin-4-yl-1H-benzoimidazole: 2-Methyl-4-morpholin-4-yl-6-nitro-phenylamine (15.2 g, 64 mmol) was suspended in methanol (200 ml) in a PARR flask. Palladium on carbon (1.0 g, 10% Pd) was added and the suspension shaken under 60 psi of hydrogen overnight. The mixture was filtered through a pad of celite (under argon) into a 3-neck flask, the celite rinsed with methanol and the filtrate diluted with methanol to a total volume of 500 ml and cooled to 0° C. A solution of 4-Iodo-2-methoxy-pyridine-3-carbaldehyde (14.6 g, 55.5 mmol) in methanol (500 ml) was added slowly (during 3 hours). After addition of ~¼ of the solution the system was opened to air and stirred over the weekend, thereby reaching room temperature. The reaction mixture was concentrated in vacuo, filtered through a pad of silica (eluent: methylenechloride-ethyl acetate-methanol 55-40-5) then crystallized from ethyl acetate. The title compound was isolated as brown solid (12.68 g, 51%). Flash column chromatography of the mother liquor (gave additional 2.90 g (12%). [pack column with methylene chloride, elute compound with methylene chloride-ethyl acetate 6-4, then methylenechloride-ethyl acetate-methanol 58-40-2]. LCMS (M+H)$^+$ m/z 451 (t=1.03 min.). $^1$H NMR (500 MHz, CDCl$_3$) δ 7.76 (1H, d, J=5.3 Hz),), 7.42 (1H, d, J=5.3 Hz), 6.85 (1H, broad s), 6.82 (1H, s), 3.86 (4H, t, J=4.5 Hz), 3.79 (3H, s), 3.12 (4H, t, J=4.5 Hz), 2.60 (3H, s), 2.21 (3H, s).

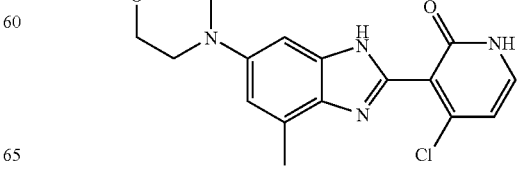

4-Chloro-3-(4-methyl-6-morpholin-4-yl-1H-benzoimidazole-2-yl)-1H-pyridin-2-one and 4-Iodo-3-(4-methyl-6-morpholin-4-yl-1H-benzoimidazol-2-yl)-1H-pyridin-2-one: 2-(4-Iodo-2-methoxy-pyridin-3-yl)-4-methyl-6-morpholin-4-yl-1H-benzoimidazole (15.58 g, 34.6 mmol) was suspended in 1,4-dioxane (300 ml) and conc. aqueous HCl (50 ml) was added. The mixture was stirred at ambient temperature overnight, then 3 hours at 50° C. The mixture was cooled to room temperature and poured into an ice cold solution of NaHCO$_3$ (67 g, 0.8 mol) and filtered. The aqueous phase was extracted with ethyl acetate. The solid material was dissolved in CH$_2$Cl$_2$ with some methanol, then extracted between water and CH$_2$Cl$_2$. The combined organic layers were dried over Na$_2$SO$_4$, and concentrated in vacuo to give an inseparable mixture of the 4-Chloro- and 4-Iodo- title compounds. The product was used without further purification. LCMS (M+H)$^+$ m/z 437 and m/z 345 (both t=0.92 min.).

Procedure for the preparation of 4-[2-(4-Chloro-2-oxo-1,2-dihydro-pyridin-3-yl)-7-methyl-3H-benzoimidazol-5-yl]-piperazine-1-carboxylic acid tert-butyl ester and 4-[2-(4-Iodo-2-oxo-1,2-dihydro-pyridin-3-yl)-7-methyl-3H-benzoimidazol-5-yl]-piperazine-1-carboxylic acid tert-butyl ester

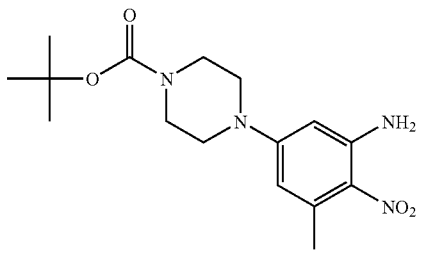

4-(3-Amino-5-methyl-4-nitro-phenyl)-piperazine-1-carboxylic acid tert-butyl ester: To a stirred solution of 3-fluoro-5-amino-6-nitrotoluene (10 g, 58.79 mmol) in anhydrous NMP (160 mL) under nitrogen was added BOC-piperazine (39 g, 209.4 mmol) and 4-methylmorpholine (25.9 mL). The resulting dark solution was heated to reflux for 72 h, cooled to room temperature and diluted with ethyl acetate (4000 mL). The organic layer was washed with water (8×1500 mL), brine (1×1500 mL), dried over sodium sulfate and evaporated in vacuo. The resulting dark oil was dissolved in boiling absolute ethanol (800 mL) and concentrated to a total volume of 400 mL and left to stand overnight at room temperature. The solution was further cooled to −20° C. for 5 h and the resulting solid was filtered off and dried in vacuo to give 16.3 g (83%) of a light yellow solid. $^1$H NMR (500 MHz, CDCl$_3$) δ 6.16 (brs, 1H), 6.04 (brs, 1H), 3.70–3.60 (m,4H), 3.38–3.25 (m, 4H), 2.53 (s, 3H), 1.48 (s, 9H); LCMS (M+H)$^+$ m/z 337.

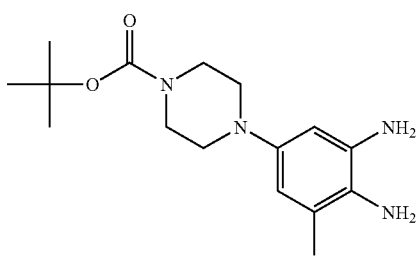

4-(3,4-Diamino-5-methyl-phenyl)-piperazine-1-carboxylic acid tert-butyl ester: To a stirred solution of 4-(3-Amino-5-methyl-4-nitro-phenyl)-piperazine-1-carboxylic acid tert-butyl ester (15 g, 44.6 mmol) in methanol (2200 mL) was added 20% Pd(OH)2/C (1.6 g) and the suspension flushed well with nitrogen, followed by hydrogen. The resulting suspension was stirred overnight at room temperature under an atmosphere of hydrogen (ca. 1 atm). The resulting suspension was filtered under nitrogen through a pad of Celite and washed with methanol (400–500 mL). The resulting material was used immediately. LCMS (M+H)$^+$ m/z 307.

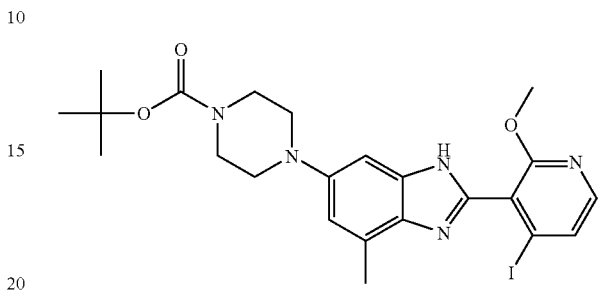

4-[2-(4-Iodo-2-methoxy-pyridin-3-yl)-7-methyl-3H-benzoimidazol-5-yl]-piperazine-1-carboxylic acid tert-butyl ester: To a stirred solution of 4-(3,4-Diamino-5-methyl-phenyl)-piperazine-1-carboxylic acid tert-butyl ester (44.6 mmol—assuming 100% conversion in previous step) in methanol (ca 2700 mL) at 0° C under a nitrogen atmosphere was slowly added (2 h) via addition funnel, a solution of 4-iodo-2-methoxy-pyridine-3-carbaldehyde (15.0 g, 57.1 mmol) in anhydrous methanol (225 mL). The resulting solution was then stirred at 0° C. for an additional 30 min, the cooling bath was removed, and the reaction mixture was allowed to stir at room temperature in the presence of air for 72 h. The resulting solution was concentrated in vacuo and the residue was dissolved in dichloromethane (1500 mL) and the solvent removed in vacuo (repeated 3×). The resulting dark foamy solid was dried under high vacuum. $^1$H NMR (500 MHz, CDCl3) δ 7.82 (d, 1H, J=5.4 Hz), 7.50 (d, 1H, J=5.4 Hz), 6.98 (brs, 1H), 6.90 (brs, 1H), 4.05 (s, 3H), 3.67–3.58 (m, 4H), 3.18–3.09 (m, 4H), 2.63 (s, 3H), 1.49 (s, 9H); LCMS (M+H)$^+$ m/z 550.

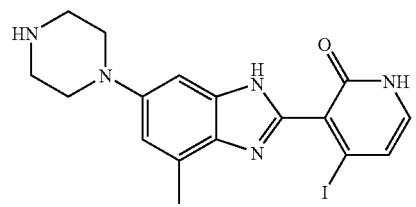

4-(3,4-Diamino-5-methyl-phenyl)-piperazine-1-carboxylid besteresteresterster: To a stirred solution of 4-(3-Amino-5-methyl-4-nitro-pheny)eeboxyboxyboxyboxylic acid tert-butyl ester (15 g, 44.6 mmol) in methanol (2200 mased Pd(OH)2/C (1.6 g) and the suspension flushed well with nitn, tw hydrogen. The resulting suspension was stirred overnight atn er und und und under an atmosphere of hydrogen (ca. 1 atm). The resulting suspe wiltundeundeundeunder nitrogen through a pad of Celite and washed with methanol—mThe he he he resulting material was used immediately. LCMS (M+H)$^+$ m/7.

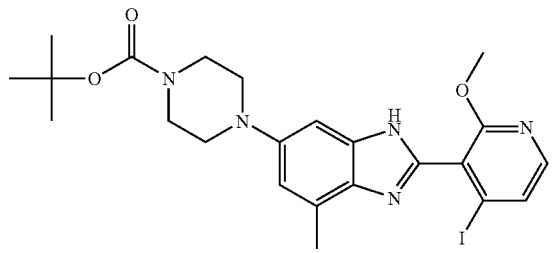
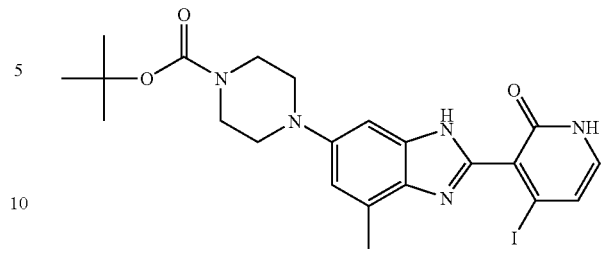

4-[2-(4-Iodo-2-methoxy-pyridin-3-yl)-7-methyl-3H-benzda-y piperazine-1-carboxylic acid tert-butyl ester: To a stirredt (4-Diamino-5-methyl-phenyl)-piperazine-1-carboxylic acid teryl (mmommommommol—assuming 100% conversion in previous step) in methanol (c)0 aC unC uncf uncf under a nitrogen atmosphere was slowly added (2 h) via addition fl, utf 4- f4- f4- f4-iodo-2-methoxy-pyridine-3-carbaldehyde (15.0 g, 57.1 mmoanoethanethanethanethanol (225 mL). The resulting solution was then stirred at 0° C. foadnamin,. min, .min, .min,. the cooling bath was removed, and the reaction mixture waswestroomoomoomoom temperature in the presence of air for 72 h. The resulting son cotratecratecratecrated in vacuo and the residue was dissolved in dichloromethane (15L tlventlventlventlvent removed in vacuo (repeated 3×). The resulting dark foamy swieder hier hier hier high vacuum. $^1$H NMR (500 MHz, CDCl3) δ 7.82 (d, 1H, J=5.4, (d, J=5J=5J=5J=5.4 Hz), 6.98 (brs, 1H), 6.90 (brs, 1H), 4.05 (s, 3H), 3.67–3.584H 8.09 (n09 (n09 (n09 (m, 4H), 2.63 (s, 3H), 1.49 (s, 9H);. LCMS (M+H)$^+$ m/z 550.

4-[2-(4-Chloro-2-oxo-1,2-dihydro-pyridin-3-yl)-7-methyl-3H-benzoimidazol-5-yl]-piperazine-1-carboxylic acid tert-butyl ester and 4-[2-(4-Iodo-2-oxo-1,2-dihydro-pyridin-3-yl)-7-methyl-3H-benzoimidazol-5-yl]-piperazine-1-carboxylic acid tert-butyl ester: To a stirred suspension of 4-Iodo-3-(4-methyl-6-piperazin-1-yl-1H-benzoimidazol-2-yl)-1H-pyridin-2-one (17.7 g, 40.7 mmol) in dichloromethane (750 mL) was added di-tert-butyl dicarbonate (9.8 g, 44.8 mmol) and triethylamine (67.4 mL, 483.6 mmol). The mixture was stirred at room temperature for 30 min. and purified via flash chromatography on silica gel. After elution with dichloromethane followed by 2.5% methanol/ethyl acetate, homogeneous fractions were combined and partially evaporated in vacuo to give the product as a yellow solid, following filtration (8.9 g, ca 41%, 2 crops). $^1$H NMR (500 MHz, CD$_3$OD) δ 7.25 (d, 1H, J=6.9 Hz), 6.97 (d, 1H, J=6.9 Hz), 6.97 (brs, 1H), 6.89 (brs, 1H), 3.65–3.56 (m, 4H), 3.16–3.07 (m, 4H), 2.55 (s, 3H), 1.49 (s, 9H); LCMS (M+H)$^+$ m/z 536. (Note: A small peak (4-chloro-pyridin-2-one) in the LC/MS shows m/z 444, 446).

Procedure for the preparation of 3-[6-(4-Amino-piperidin-1-yl)-4-methyl-1H-benzoimidazol-2-yl]-4-iodo-1H-pyridin-2-one and 3-16-(4-Amino-piperidin-1-yl)-4-methyl-1H-benzoimidazol-2-yl]-4-chloro-1H-pyridin-2-one

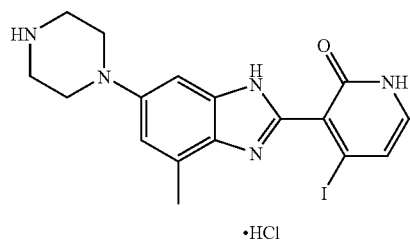

·HCl

4-Iodo-3-(4-methyl-6-piperazin-1-yl-1H-benzoimidazol-2-yl)-1H-pyridin-2-one: To a stirred solution of 4-[2-(4-Iodo-2-methoxy-pyridin-3-yl)-7-methyl-3H-benzoimidazol-5-yl]-piperazine-1-carboxylic acid tert-butyl ester (24 g, 43.7 mmol) was added 1,4-dioxane (750 mL) and 6 N aqueous HCl (30 mL) and the mixture was heated to 75° C. overnight. The solution was cooled to room temperature, the supernatent was poured off, and the resulting dark gummy solid was washed with anhydrous diethyl ether (3×500 mL) and dried in vacuo to give 17.7 g (93%) of the title compound as a dark solid that was used as described to prepare 4-[2-(4-Chloro-2-oxo-1,2-dihydro-pyridin-3-yl)-7-methyl-3H-benzoimidazol-5-yl]-piperazine-1-carboxylic acid tert-butyl ester and 4-[2-(4-Iodo-2-oxo-1,2-dihydro-pyridin-3-yl)-7-methyl-3H-benzoimidazol-5-yl]-piperazine-1-carboxylic acid tert-butyl ester; LCMS (M+H)$^+$ m/z 436. (Note: A small peak (4-chloro-pyridin-2-one) in the LC/MS shows m/z 344, 346).

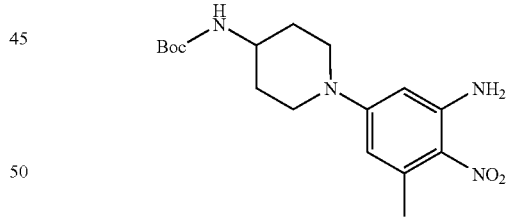

[1-(3-Amino-5-methyl-4-nitro-phenyl)-piperidin-4-yl]-carbamic acid tert-butyl ester: 5-Fluoro-3-methyl-2-nitro-phenylamine (0.97 g, 5.7 mmol), 4-N-BOC-aminopiperidine (1.60 g, 8.0 mmol), diusopropylethylamine (2.5 ml, 14 mmol) and DMSO (10 ml) are combined and stirred at 85° C. for 3 hours. The reaction mixture was poured on saturated aqueous NaHCO$_3$ solution and extracted with ethyl acetate. The organic layers were washed with water (3×) and brine, dried over Na$_2$SO$_4$ and concentrated. Flash column chromatography on silica (eluent hexanes-ethyl acetate-triethylamine 50-50-1, then 33-66-1) gave the title compound as a yellow solid. (1.57 g, 79%). LCMS (M+H)$^+$ m/z 351 (t=1.55 min.). $^1$H NMR (500 MHz, CD$_3$OD) δ 6.70 (1H, broad s), 6.22 (1H, d, J=2.5 Hz)), 6.13 (1H, d, J=2.5 Hz), 3.88 (2H, d, J=13.3 Hz), 3.58 (1H, broad s), 2.98 (2H, t, J=11.8 Hz), 2.48 (3H, s), 1.92 (2H, d, J=11.3 Hz), 1.48 (2H, m), 1.45 (9H, s).

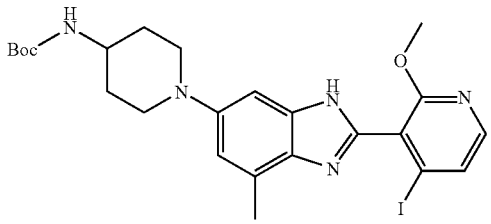

{1-[2-(4-Iodo-2-methoxy-pyridin-3-yl)-7-methyl-3H-benzoimidazol-5-yl]-piperidin-4-yl}-carbamic acid tert-butyl ester: [1-(3-Amino-5-methyl-4-nitro-phenyl)-piperidin-4-yl]-carbamic acid tert-butyl ester (1.54 g, 4.4 mmol) was dissolved in methanol (100 ml). Palladium on carbon (0.3 g, 10% Pd) was added and the suspension stirred vigorously under a balloon pressure of hydrogen overnight. The mixture was filtered through a pad of celite (under argon) into a 3-neck flask, the celite rinsed with methanol and the filtrate cooled to 0° C. A solution of 4-Iodo-2-methoxy-pyridine-3-carbaldehyde (1.21 g, 4.6 mmol) in methanol (50 ml) was added slowly (during 2 hours). The mixture was stirred overnight under air at ambient temperature, then concentrated in vacuo. Flash column chromatography on silica (eluent hexanes-ethyl acetate -methanol 5-4-1 gave the title compound. (0.79 g, 32%). LCMS (M+H)+ m/z 564 (t=1.31 min.).

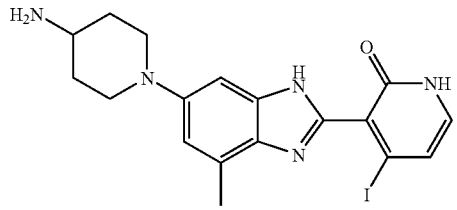

3-[6-(4-Amino-piperidin-1-yl)-4-methyl-1H-benzoimidazol-2-yl]-4-iodo-1H-pyridin-2-one and 3-[6-(4-Amino-piperidin-1-yl)-4-methyl-1H-benzoimidazol-2-yl]-4-chloro-1H-pyridin-2-one: {1-[2-(4-Iodo-2-methoxy-pyridin-3-yl)-7-methyl-3H-benzoimidazol-5-yl]-piperidin-4-yl}-carbamic acid tert-butyl ester (330 mg, 0.59 mmol) was suspended in 4M HCl in 1,4-dioxane (20 ml) and water (3 ml) was added. (exothermic reaction). The mixture was stirred at ambient temperature overnight, then concentrated in vacuo to give an inseparable mixture of the 4-Chloro- and 4-Iodo-title compounds. The product was used without further purification. LCMS (M+H)+ m/z 450 and m/z 358 (both t=0.69 min.).

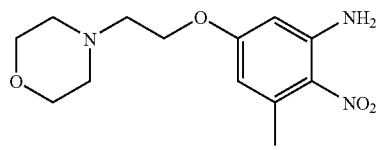

3-Methyl-5-(2-morpholin-4-ethoxy)-2-nitro-phenylamine: To a solution of 2-morpholin-4-yl-ethanol (5 g, excess) in THF (30 mL) was added NaH (0.21 g, 8.82 mmol) in portion under ice bath. The reaction mixture was stirred at room temperature for 30 min. Then 5-fluoro-3-methyl-2-nitro-phenylamine was added. The reaction mixture was heated to reflux for 6 h, cooled to room temperature, and concentrated. The residue was diluted with water and extracted with EtOAc. The combined organic layers were washed with water, brine, and dried over Na2SO4. After concentration, the residue was purified by column chromatography (20% EtOAc/hexane) to yield the title compound (0.70 g, 85%). 1H NMR (400 MHz, CD3OD) δ 6.10 (1H, s), 6.09 (1H, s), 4.38–4.42 (2H, m), 3.92–4.08 (4H, m), 3.72 (1H, d, J=12 Hz), 3.53–3.56 (2H, m), 3.05–3.10 (2H, m), 2.48 (3H, s). LCMS (M+H)+ m/z 282 (t=0.73 min.).

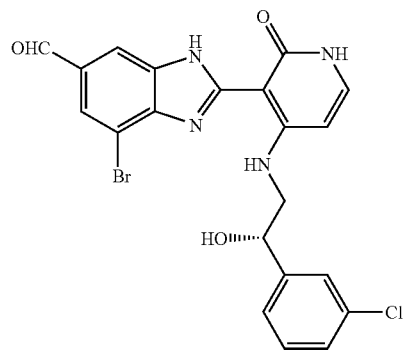

(S)-7-Bromo-2-{4-[2-(3-chloro-phenyl)-2-hydroxy-ethylamino]-2-oxo-1,2-dihydro-pyridin-3-yl}-3H-benzimidazole-5-carbaldehyde: To a solution of (S)-7-Bromo-2-{4-[2-(3-chloro-phenyl)-2-hydroxy-ethylamino]-2-oxo-1,2-dihydro-pyridin-3-yl}-3H-benzimidazole-5-carbonitrile (150 mg, 0.31 mmol) in THF (50 mL) was added DIBAL-H (1 M toluene solution, 1.55 mL, 1.55 mmol) at –78° C. The reaction mixture was stirred at –40° C. for 10 h and cooled to –78° C. EtOAc (0.5 mL) was added. The reaction mixture was stirred for 30 min at –78° C. before water (1 mL) was added. The reaction mixture was warmed to room temperature and concentrated. The residue was passed through a small pad of celite. The filtrate was concentrated and purified by prep. HPLC to give the titled compound (67 mg, 43%). 1H NMR (400 MHz, CD3OD) δ 9.45 (1H, s), 7.62 (1H, s), 7.56 (1H, narrow d, J=1.6 Hz), 7.44 (1H, narrow d, J=1.0 Hz), 7.32–7.42 (2H, m), 7.24–7.30 (3H, m), 6.24 (1H, d, J=7.6 Hz), 5.01 (1H, m), 3.65–3.76 (2H, m). LCMS (M+H)+ m/z 487 (t=1.76 min.).

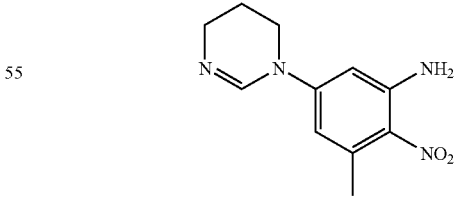

5-(1,4,5,6-Tetrahydropyrimidin-1-yl)-3-methyl-2-nitro aniline: To a stirred solution of 2.0 g (11.76 mmol) of the 5-Flouro-3-methyl-2-nitro aniline in 10 mL of DMSO was added 1.2 g (14.11 mmol) of 1,4,5,6-Tetrahydropyrimidine, and 2.43 g (17.64 mmol) of potassium carbonate, and the mixture was heated at 100° C. for 10 hrs, cooled, diluted with water, and extracted with Ethylacetate containing 5% methanol. The combined organic extract was washed with water, brine and dried (Na₂SO₄). Evaporation of the solvent furnished the residue, which was chromatographed (20% of 2M ammonia in methanol and dichloromethane) to produce 1.85 g (67%) of the product as red solid. $^1$H NMR (400 MHz, CD₃OD) δ 7.89 (1H,s), 6.53 (1H,d, J=2.57 Hz), 6.44 ((1H, d, J=2.1 Hz), 7.04 (1H, d, J=2.1 Hz), 3.70 (2H, t, J=6.0 Hz), 3.41 (2H, t, J=5.65 Hz, 2.43 (3H, s), 2.05 (2H, m) LCMS (M+H)⁺ m/z 235 (t=0.78 min).

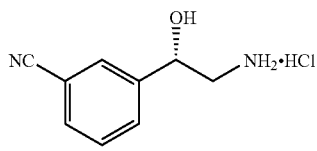

(S)-2-Amino-1-[3-cynaophenyl]ethanol Hydrochloride: was prepared according to the general procedure outlined above. LRMS [M+H]+163; 1H NMR (500 MHz) δ 7.64 (brs, 1H), 7.47 (d, 1H), 7.37 (d, 1H), 7.25 (t, 1H), 4.85 (dd, 1H), 3.05 (dd, 1H), 2.75 (dd, 1H).

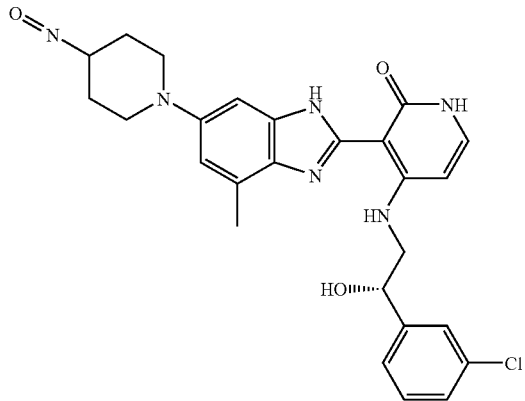

4-[2-(3-Chloro-phenyl)-2-hydroxy-ethylamino]-3-[6-(4-isocyanato-piperidin-1-yl)-4-methyl-1H-benzoimidazol-2-yl]-1H-pyridin-2-one: To a solution of the 4-amino-piperidine compound (1.5 g) in THF (15 ml) was added Di-t-butyltricarbonate [Dean, C. S. et al. *J. Org. Chem.*, 35; 1970; 3393–3397] (1.04 g, 1.3 eq) in THF (15 ml) at room temperature. The reaction mixture was stirred at r.t. for 1 hr and concentrated and was used as it is. LCMS (M+H)⁺ m/z 519 (t=1.84 min, YMC Xterra C18 S7 3.0×50 mm; 0–100% gradient over 2 min; 5 mL/min flow rate).

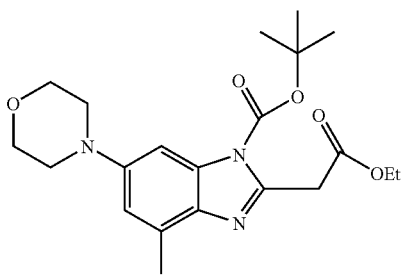

(1-Tert-butyloxycarbonyl-4-methyl-6-morpholin-4-yl-1H-benzoimidazol-2-yl)-acetic acid ethyl ester: A solution of 2-methyl-4-morpholin-4-yl-6-nitro-phenylamine (1.84 g, 7.75 mmol) in methanol (115 mL) was hydrogenated (15 psi) in presence of palladium(II) hydroxide for 12 hours. The reaction was filtered and the filtrate was evaporated. The crude amine was dissolved in N,N-dimethylformamide (70 mL) and treated with the hydrochloride salt of ethyl mono-imido malonate (3.04 g, 15.48 mmol) and this mixture was stirred at 70° C. for 2 hours. The solvent was evaporated and the residue was dissolved in dichloromethane (100 mL) and treated with triethylamine (2.16 mL, 15.48 mmol), di-tert-butyl dicarbonate (3.38 g, 15.48 mmol) and dimethylaminopyridine (2 crystals). The reaction was stirred at RT for 1.5 hours, then saturated ammonium chloride was added and the mixture was extracted with ethyl acetate (3×). The combined organic layers were dried over anhydrous magnesium sulfate, filtered and concentrated. The residue was purified by silica gel column chromatography (50% ethyl acetate in hexane) to give the title material (1.955 g, 63%) as a brown solid. LCMS (⁺ESI, M+H⁺) m/z 404; $^1$H NMR (400 MHz, DMSO-d₆) δ (ppm): 1.26 (3H, t, J=7.1 Hz), 1.70 (9H, s), 2.56 (3H, s), 3.21 (4H, br dd), 3.85 (4H, br dd), 4.18 (2H, qa, J=7.1 Hz), 4.27 (2H, s), 7.02 (1H, d, J~1.5 Hz), 7.33 (1H, d, J=2.0 Hz).

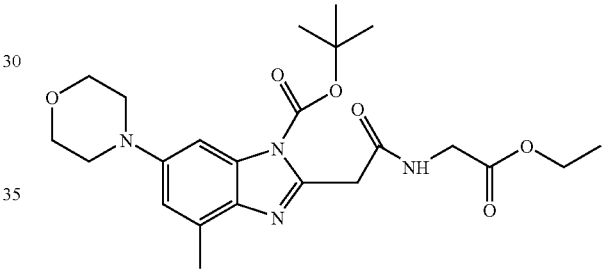

[2-(1-Tert-butyloxycarbonyl-4-methyl-6-morpholin-4-yl-1H-benzoimidazol-2-yl)-acetylamino]-acetic acid ethyl ester: To a stirred solution of (1-tert-butyloxycarbonyl-4-methyl-6-morpholin-4-yl-1H-benzoimidazol-2-yl)-acetic acid ethyl ester (0.400 g, 0.99 mmol) in ethanol (15 mL) at 0° C. was added aqueous sodium hydroxide (5N, 1 mL). The mixture was stirred at RT for ~1 hour, then cooled down to 0° C. and neutralized with aqueous hydrochloric acid (1N) until the pH reaches ~7. Ethyl acetate was added and the aqueous phase was washed with ethyl acetate (3×). The aqueous phase was evaporated to remove the last traces of ethanol and was then lyophilized.

The resulting solid (0.499 g) was suspended in N,N-dimethylformamide (15 mL) and treated with triethylamine (0.553 mL, 3.96 mmol), the hydrochloric acid salt of glycine ethyl ester (0.207 g, 1.49 mmol) and benzotriazole-1-yl-oxy-tris-pyrrolidino-phosphonium hexafluorophosphate (PyBOP) (1.03 g, 1.98 mmol). The mixture was stirred at RT for 5 minutes then the solvent was evaporated. The residue was dissolved in ethyl acetate and washed with water (3×). The organic layer was dried over anhydrous magnesium sulfate, filtered and concentrated.

The residue was dissolved in dichloromethane (12 mL) and treated with triethylamine (0.250 mL), di-tert-butyl dicarbonate (0.325 g, 1.49 mmol) and 2,4-dimethylamino pyridine (1 crystal). The reaction was stirred at RT during the week-end. Saturated ammonium chloride solution was added and the aqueous phase was extracted with dichloromethane (3×). The combined organic layers were dried over anhydrous magnesium sulfate, filtered and concentrated. The residue was purified by chromatography (ethyl acetate) to give the title material (0.481 g, 83%). HPLC: 89% (220 nm), LCMS ($^+$ESI, M+H$^+$) m/z 461; $^1$H NMR (400 MHz, DMSO-d$_6$) δ (ppm): 1.17 (3H, t, J=7.2 Hz), 1.58 (9H, s), 2.45 (3H, s), 3.09 (4H, br dd), 3.75 (4H, br dd), 3.83 (2H, d, J=5.8 Hz), 4.07 (2H, qa, J=7.2 Hz), 4.09 (2H, br s), 6.88 (1H, br dd), 7.23 (1H, d J=2.3 Hz), 8.50 (1H, t, J=5.8 Hz).

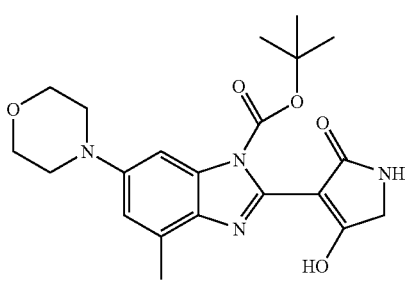

4-Hydroxy-3-(1-tert-butyloxycarbonyl-4-methyl-6-morpholin-4-yl-1H-benzoimidazol-2-yl)-1,5-dihydro-pyrrol-2-one: To a stirred suspension of sodium hydride (60% in oil, 0.014 g, 0.352 mmol) in toluene (5 mL) was added [2-(1-tert-butyloxycarbonyl-4-methyl-6-morpholin-4-yl-1H-benzoimidazol-2-yl)-acetylamino]-acetic acid ethyl ester (0.135 g, 0.293 mmol) in tetrahydrofuran (5 mL) over 5 minutes. The mixture was stirred at 90–100° C. for 2.5 hours, then cooled down to ~0° C. and ethyl acetate followed by aqueous ammonium chloride (~3 mL) were added. The aqueous phase was extracted with ethyl acetate (3×). The combined organic layers were dried over anhydrous magnesium sulfate, filtered and concentrated. The residue was quickly purified by silica gel chromatography to give the title material (0.072 g, 59%) as a white solid. LCMS ($^+$ESI, M+H$^+$) m/z 415, ($^-$ESI, M–H$^-$) m/z 413; $^1$H NMR (400 MHz, DMSO-d$_6$) δ (ppm): 1.47 (9H, s), 3.06 (4H, br s), 3.74 (4H, br s), 3.94 (2H, br s), 6.83 (1H, s), 6.97 (1H, s), 12.1 (1H, m), 12.56 (1H, s).

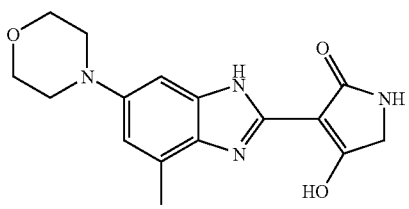

4-Hydroxy-3-(4-methyl-6-morpholin-4-yl-1H-benzoimidazol-2-yl)-1,5-dihydro-pyrrol-2-one: To a stirred suspension of sodium hydride (60% in oil, 0.003 g, 0.044 mmol) in toluene (1 mL) was added [2-(1-tert-butyloxycarbonyl-4-methyl-6-morpholin-4-yl-1H-benzoimidazol-2-yl)-acetylamino]-acetic acid ethyl ester (0.135 g, 0.293 mmol) in tetrahydrofuran (2 mL) over 5 minutes. The mixture was stirred at 90–100° C. for 5 hours, then cooled down to ~0° C. and ethyl acetate followed by aqueous hydrochloric acid (1N, ~0.5 mL) were added. The aqueous phase was washed with ethyl acetate (3×) and this was submitted to Prep HPLC (acetonitrile/ammonium acetate/water) to give the title material (0.008 g, 69%) as a white solid. HPLC 100% (220 nm); LCMS ($^+$ESI, M+H$^+$) m/z 315; $^1$H NMR (400 MHz, methanol-d$_4$) δ (ppm): 2.55 (3H, s), 3.18 (4H, br dd), 3.81 (2H, s), 3.88 (4H, br dd), 6.92 (1H, br s), 6.99 (11H, d, J=2.0 Hz).

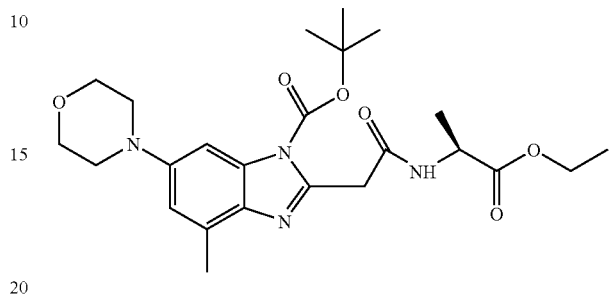

(S)-2-[2-(1-tert-butyloxycarbonyl-4-methyl-6-morpholin-4-yl-1H-benzoimidazol-2-yl)-acetylamino]-propionic acid ethyl ester: (4-Methyl-6-morpholin-4-yl-1H-benzoimidazol-2-yl)-acetic acid (0.250 g, 0.574 mmol, prepared as described in the procedure to synthesize [2-(1-tert-butyloxycarbonyl-4-methyl-6-morpholin-4-yl-1H-benzoimidazol-2-yl)-acetylamino]-acetic acid ethyl ester) was reacted as described in the same procedure using L-alanine ethyl ester instead of glycine ethyl ester to give the title material (0.197 g, 72%). LCMS ($^+$ESI, M+H$^+$) m/z 475; $^1$H NMR (400 MHz, DMSO-d$_6$) δ (ppm): 1.16 (3H, t, J=7.1 Hz), 1.28 (3H, d, J=7.3 Hz), 1.58 (9H, s), 2.44 (3H, s), 3.09 (4H, br dd), 3.75 (4H, br dd), 4.02 (2H, qa, J=7.1 Hz), 4.05 (2H, m), 4.23 (1H, m), 6.88 (1H, br s), 7.23 (1H, d, J=2.0 Hz), 8.57 (1H, d, J=6.8 Hz).

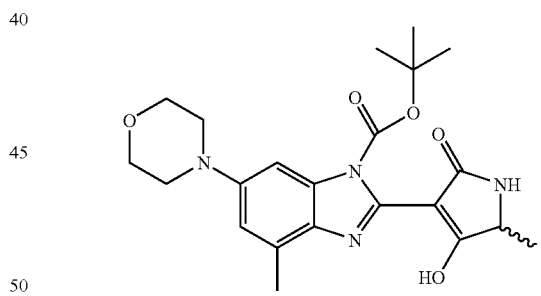

(S and R)-4-Hydroxy-5-methyl-3-(1-tert-butyloxycarbonyl-4-methyl-6-morpholin-4-yl-1H-benzoimidazol-2-yl)-1,5-dihydro-pyrrol-2-one: (S)-2-[2-(1-tert-butyloxycarbonyl-4-methyl-6-morpholin-4-yl-1H-benzoimidazol-2-yl)-acetylamino]-propionic acid ethyl ester (0.195 g, 0.411 mmol) was reacted as described in the procedure used to synthesize 4-hydroxy-3-(1-tert-butyloxycarbonyl-4-methyl-6-morpholin-4-yl-1H-benzoimidazol-2-yl)-1,5-dihydro-pyrrol-2-one and gave the title material (0.031 g, 18% precipitated from ethyl acetate and 0.129 g crude, 73%). HPLC 91% (220 nm), LCMS ($^+$ESI, M+H$^+$) m/z 429; $^1$H NMR (400 MHz, methanol-d$_4$) δ (ppm): 1.50 (3H, d, J=6.9 Hz), 1.57 (9H, s), 2.54 (3H, s)3.16 (4H, br dd), 3.85(4H, br dd), 4.17(1H, m), 6.15 (1H, s), 6.93(1H, s).

EXAMPLE 1

General Procedure for Examples 1–21

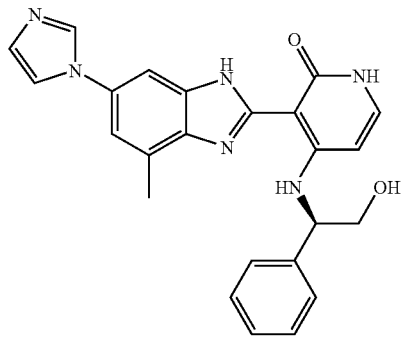

(S)-4-(2-Hydroxy-1-phenyl-ethylamino)-3-(6-imidazol-1-yl-4-methyl-1H-benzimidazol-2-yl)-1H-pyridin-2-one: To a solution of 3-(6-imidazol-1-yl-4-methyl-1H-benzimidazol-2-yl)-4-iodo-1H-pyridin-2-one (30 mg, 0.072 mmol) in DMF (1 mL) were added (S)-(−)-2-phenylglycinol (26 mg, 0.18 mmol) and N-methylmorpholine (0.1 mL). The reaction mixture was heated to 80° C. for 6 h and cooled to room temperature. The solvent was removed under vacuum and the residue was purified by prep. HPLC to yield the title compound (16 mg, 52%). $^1$H NMR (300 MHz, CD$_3$OD) δ 8.07 (1H, narrow t, J=1.7 Hz), 7.76 (2H, s), 7.27–7.48 (7H, m), 7.21 (1H, d, J=7.5 Hz), 6.11 (1H, d, J=7.5 Hz), 4.92 (1H, m), 4.03 (1H, dd, J=4.5, 11.2 Hz), 3.95 (1H, dd, J=6.2, 11.2 Hz), 2.75 (3H, s). LCMS (M+H)$^+$ m/z 427 (t=1.44 min.)

EXAMPLE 2

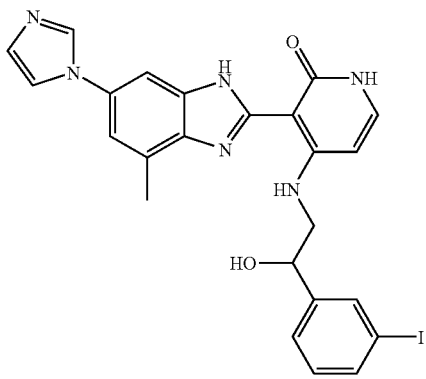

(±)-4-[2-Hydroxy-2-(3-iodo-phenyl)-ethylamino]-3-(6-imidazol-1-yl-4-methyl-1H-benzimidazol-2-yl)-1H-pyridin-2-one: $^1$H NMR (300 MHz, CD$_3$OD) δ 9.41 (1H, s), 8.06 (1H, s), 7.88 (1H, s), 7.76 (1H, s), 7.71 (1H, s), 7.59 (1H, d, J=7.8 Hz), 7.47 (1H, d, J=7.8 Hz) 7.32 (1H, s) 7.29 (1H, d, J=7.6 Hz) 7.09 (1H, t, J=7.8 Hz), (6.24 (1H, d, J=7.6 Hz), 4.97 (1H, dd, J=5.0, 6.0 Hz), 3.75 (1H, dd, J=5.0, 13.5 Hz), 3.67 (1H, dd, J=6.0, 13.5 Hz), 2.68 (3H, s). LCMS (M+H)$^+$ m/z 553 (t=1.43 min.).

EXAMPLE 3

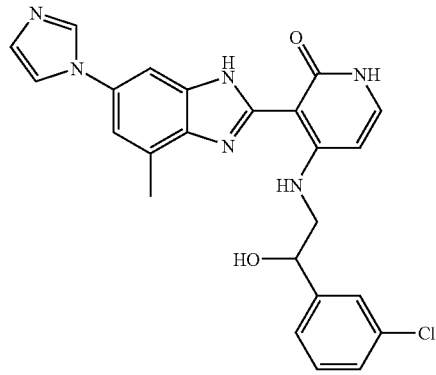

(±)-4-[2-(3-Chloro-phenyl)-2-hydroxy-ethylamino]-3-(6-imidazol-1-yl-4-methyl-1H-benzimidazol-2-yl)-1H-pyridin-2-one: $^1$H NMR (300 MHz, CD$_3$OD) δ 9.39 (1H, narrow t, J=1.4 Hz), 8.04 (1H, narrow t, J=1.7 Hz), 7.76 (1H, narrow t, J=1.7 Hz), 7.69 (1H, narrow d, J=1.9 Hz), 7.55 (1H, s), 7.23–7.42 (5H, m), 6.25 (1H, d, J=7.6 Hz), 5.01 (1H, dd, J=4.8, 6.4 Hz), 3.76 (1H, dd, J=4.8, 13.4 Hz), 3.66 (1H, dd, J=6.4, 13.4 Hz), 2.67 (3H, s). LCMS (M+H)$^+$ m/z 461 (t=1.46 min.).

EXAMPLE 4

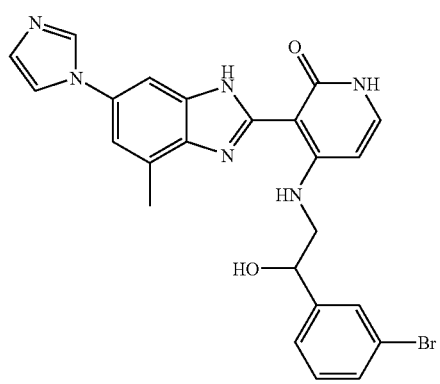

(±)-4-[2-(3-Bromo-phenyl)-2-hydroxy-ethylamino]-3-(6-imidazol-1-yl-4-methyl-1H-benzimidazol-2-yl)-1H-pyridin-2-one: $^1$H NMR (300 MHz, CD$_3$OD) δ 9.38 (1H, s), 8.02 (1H, s), 7.74 (1H, s), 7.69 (1H, s), 7.66 (1H, narrow d, J=1.4 Hz), 7.20–7.48 (5H, m), 6.21 (1H, d, J=7.6 Hz), 4.99 (1H, dd, J=4.8, 6.3 Hz), 3.73 (1H, dd, J=4.8, 13.5 Hz), 3.64 (1H, dd, J=6.3, 13.5 Hz), 2.65 (3H, s). LCMS (M+H)$^+$ m/z 505 (t=1.47 min.).

EXAMPLE 5

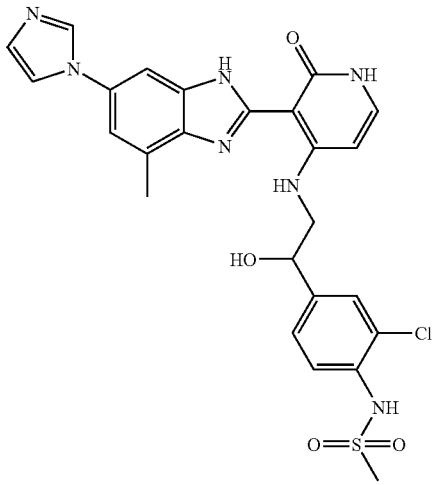

(±)-N-(2-Chloro-4-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-methanesulfonamide: $^1$H NMR (300 MHz, CD$_3$OD) δ 9.39 (1H, s), 8.05 (1H, s), 7.76 (1H, s), 7.68 (1H, s), 7.62 (1H, narrow d, J=1.5 Hz), 7.52 (1H, s), 7.42–7.49 (2H, m), 7.31 (1H, s), 7.30 (1H, d, J=7.6 Hz), 6.26 (1H, d, J=7.6 Hz), 5.01 (1H, dd, J=5.0, 5.6 Hz), 3.76 (1H, d, J=5.0, 13.4 Hz), 3.74 (1H, dd, J=5.6, 13.4 Hz), 2.98 (3H, s), 2.68 (3H, s). LCMS (M+H)$^+$ m/z 554 (t=1.11 min.).

EXAMPLE 6

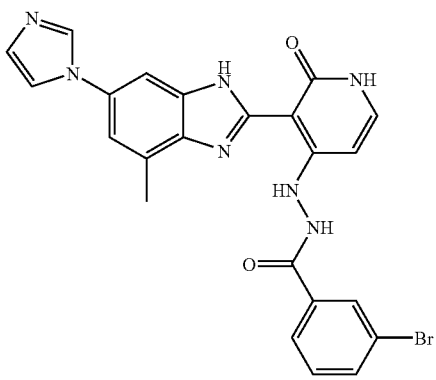

3-Bromo-benzoic-acid N'-[3-(6-imidazol-1-yl-4-methyl-1H-benzimidazol-2-yl)-2-oxo-1,2-dihydro-pyridin-4-yl]-hydrazide: $^1$H NMR (300 MHz, CD$_3$OD) δ 9.40 (1H, narrow t, J=1.4 Hz), 8.14 (1H, narrow t, J=1.7 Hz), 8.05 (1H, narrow t, J=1.7 Hz), 7.95 (1H, d, J=7.9 Hz), 7.81 (1H, d, J=7.9 Hz), 7.74–7.77 (2H, m), 7.49 (1H, t, J=7.9 Hz), 7.41 (1H, d, J=7.4 Hz), 7.34 (1H, s), 6.38 (1H, d, J=7.4 Hz), 2.70 (3H, s). LCMS (M+H)$^+$ m/z 504 (t=1.44 min.).

EXAMPLE 7

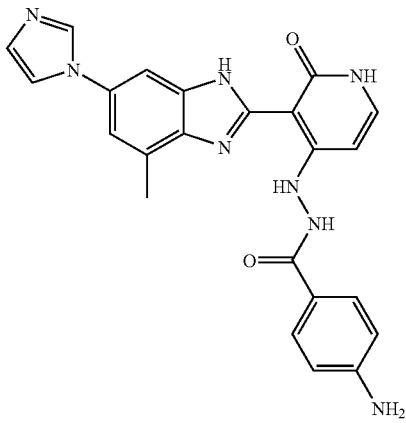

4-Amino-benzoic-acid N'-[3-(6-imidazol-1-yl-4-methyl-1H-benzimidazol-2-yl)-2-oxo-1,2-dihydro-pyridin-4-yl]-hydrazide: $^1$H NMR (300 MHz, CD$_3$OD) δ 9.41 (1H, s), 8.06 (1H, s), 7.76–7.79 (4H, m), 7.39 (1H, d, J=7.4 Hz), 7.36 (1H, s), 6.81 (2H, d, J=8.6 Hz), 6.36 (1H, d, J=7.4 Hz), 2.70 (3H, s). LCMS (M+H)$^+$ m/z 441 (t=0.96 min.).

EXAMPLE 8

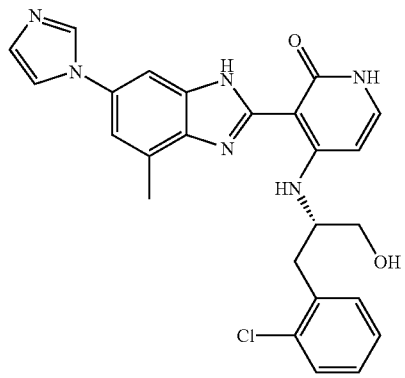

(S)-4-[2-(2-Chloro-phenyl)-1-hydroxymethyl-ethylamino]-3-(6-imidazol-1-yl-4-methyl-1H-benzimidazol-2-yl)-1H-pyridin-2-one: $^1$H NMR (300 MHz, CD$_3$OD) δ 9.41 (1H, s), 8.05 (1H, narrow t, J=1.7 Hz), 7.76 (1H, narrow t, J=1.7 Hz), 7.72 (1H, narrow d, J=1.9 Hz), 7.08–7.36 (6H, m), 6.10 (1H, d, J=7.7 Hz), 3.98–4.24 (1H, m), 3.84 (1H, dd, J=4.4, 11.2 Hz), 3.79 (1H, dd, J=4.8, 11.2 Hz), 3.35 (1H, dd, J=5.4, 13.6 Hz), 3.09 (1H, dd, J=7.8, 13.6 Hz), 2.72 (3H, s). LCMS (M+H)$^+$ m/z 475 (t=1.56 min.).

EXAMPLE 9

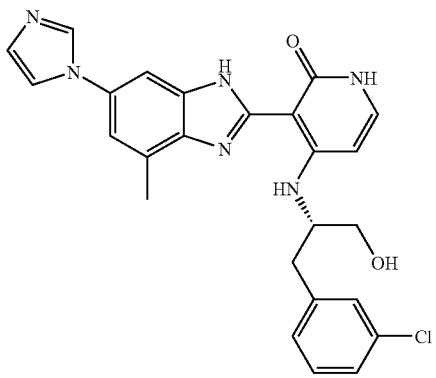

(S)-4-[2-(3-Chloro-phenyl)-1-hydroxymethyl-ethylamino]-3-(6-imidazol-1-yl-4-methyl-1H-benzimidazol-2-yl)-1H-pyridin-2-one: $^1$H NMR (300 MHz, CD$_3$OD) δ 9.42 (1H, s), 8.07 (1H, narrow t, J=1.7 Hz), 7.75–7.78 (2H, m), 7.14–7.37 (6H, m), 6.18 (1H, d, J=7.7 Hz), 4.07–4.11 (1H, m), 3.76–3.77 (2H, m), 3.17 (1H, dd, J=5.1, 13.7 Hz), 2.98 (1H, dd, J=8.2, 13.7 Hz), 2.71 (3H, s). LCMS (M+H)$^+$ m/z 475 (t=1.57 min.).

EXAMPLE 10

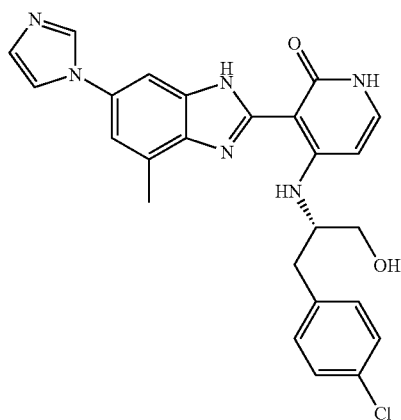

(S)-4-[2-(4-Chloro-phenyl)-1-hydroxymethyl-ethylamino]-3-(6-imidazol-1-yl-4-methyl-1H-benzimidazol-2-yl)-1H-pyridin-2-one: $^1$H NMR (300 MHz, CD$_3$OD) δ 9.42 (1H, s), 8.07 (1H, narrow t, J=1.6 Hz), 7.77 (1H, narrow t, J=1.6 Hz), 7.73 (1H, narrow d, J=1.9 Hz), 7.16–7.37 (6H, m), 6.19 (1H, d, J=7.7 Hz), 4.06–4.10 (1H, m), 3.72–3.77 (2H, m), 3.14 (1H, dd, J=5.3, 13.8 Hz), 2.98 (1H, dd, J=7.8, 13.8 Hz), 2.69 (3H, s). LCMS (M+H)$^+$ m/z 475 (t=1.61 min.).

EXAMPLE 11

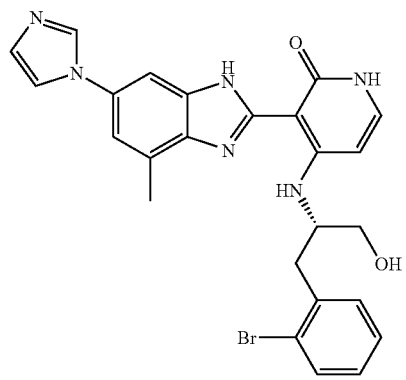

(S)-4-[2-(2-Bromo-phenyl)-1-hydroxymethyl-ethylamino]-3-(6-imidazol-1-yl-4-methyl-1H-benzimidazol-2-yl)-1H-pyridin-2-one: $^1$H NMR (300 MHz, CD$_3$OD) δ 9.41 (1H, s), 8.06 (1H, s), 7.75–7.77 (2H, m), 7.52 (1H, dd, J=1.5, 7.5 Hz), 7.36 (1H, d, J=1.9 Hz), 7.34 (1H, s), 7.03–7.16 (3H, m), 6.09 (1H, d, J=7.7 Hz), 4.15–4.27 (1H, m), 3.82 (2H, m), 3.35 (1H, dd, J=5.0, 13.6 Hz), 3.10 (1H, dd, J=9.0, 13.6 Hz), 2.74 (3H, s). LCMS (M+H)$^+$ m/z 519 (t=1.56 min.).

EXAMPLE 12

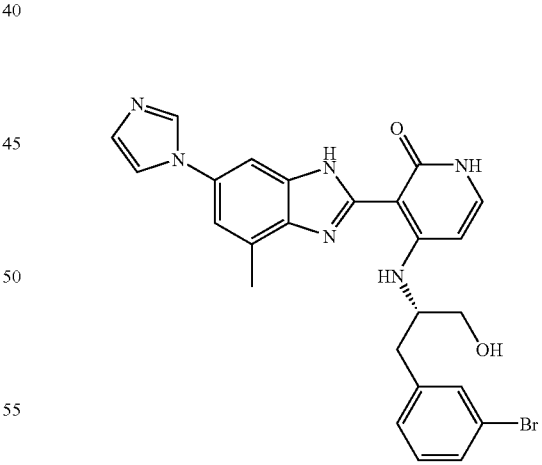

(S)-4-[2-(3-Bromo-phenyl)-1-hydroxymethyl-ethylamino]-3-(6-imidazol-1-yl-4-methyl-1H-benzimidazol-2-yl)-1H-pyridin-2-one: $^1$H NMR (300 MHz, CD$_3$OD) δ 9.41 (1H, s), 8.06 (1H, s), 7.74–7.77 (2H, m), 7.47 (1H, s), 7.24–7.31 (4H, m), 7.11 (1H, d, J=7.7 Hz), 6.16 (1H, d, J=7.7 Hz), 4.05–4.11 (1H, m), 3.76 (2H, m), 3.15 (1H, dd, J=5.0, 13.6 Hz), 2.96 (1H, dd, J=8.3, 13.6 Hz), 2.70 (3H, s). LCMS (M+H)$^+$ m/z 519 (t=1.54 min.).

EXAMPLE 13

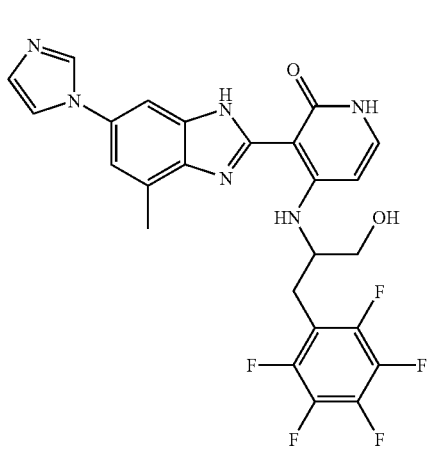

(±)-4-(1-Hydroxymethyl-2-pentafluorophenyl-ethylamino)-3-(6-imidazol-1-yl-4-methyl-1H-benzimidazol-2-yl)-1H-pyridin-2-one: $^1$H NMR (300 MHz, CD$_3$OD) δ 9.40 (1H, s), 8.06 (1H, narrow t, J=1.8 Hz), 7.77 (1H, narrow t, J=1.7 Hz), 7.74 (1H, narrow d, J=1.8 Hz), 7.35 (1H, s), 7.29 (1H, d, J=7.6 Hz), 6.22 (1H, d, J=7.6 Hz), 4.24 (1H, m), 3.82 (2H, dd, J=2.6, 4.5 Hz), 3.23 (2H, t, J=6.5 Hz), 2.70 (3H, s). LCMS (M+H)$^+$ m/z 531 (t=1.61 min.).

EXAMPLE 14

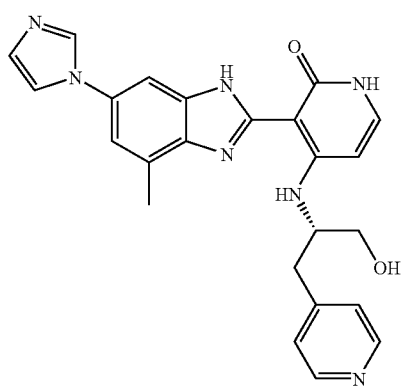

(S)-4-(1-Hydroxymethyl-2-pyridin-4-yl-ethylamino)-3-(6-imidazol-1-yl-4-methyl-1H-benzimidazol-2-yl)-1H-pyridin-2-one: $^1$H NMR (400 MHz, CD$_3$OD) δ 9.42 (1H, s), 8.67 (2H, d, J=6.6 Hz), 8.07 (2H, d, J=6.6 Hz), 8.06 (1H, s), 7.77 (2H, s), 7.36 (1H, s), 7.28 (1H, d, J=7.6 Hz), 6.24 (1H, d, J=7.6 Hz), 4.35 (1H, m), 3.82 (2H, d, J=4.4 Hz), 3.50 (1H, dd, J=4.4, 13.6 Hz), 3.40 (1H, dd, J=8.7, 13.6 Hz), 2.71 (3H, s). LCMS (M+H)$^+$ m/z 442 (t=0.96 min.).

EXAMPLE 15

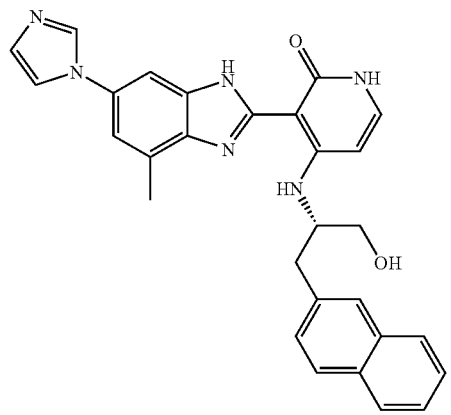

(S)-4-(1-Hydroxymethyl-2-naphthalen-2-yl-ethylamino)-3-(6-imidazol-1-yl-4-methyl-1H-benzimidazol-2-yl)-1H-pyridin-2-one: $^1$H NMR (300 MHz, CD$_3$OD) δ 7.99 (1H, narrow t, J=1.7 Hz), 7.26–7.75 (11H, m), 7.15 (1H, d, J=7.6 Hz), 6.19 (1H, d, J=7.6 Hz), 4.16–4.20 (1H, m), 3.75–3.86 (2H, m), 3.30 (1H, dd, J=5.4, 13.6 Hz), 3.15 (1H, dd, J=7.6, 13.6 Hz), 2.60 (3H, s). LCMS (M+H)$^+$ m/z 491 (t=1.71 min.).

EXAMPLE 16

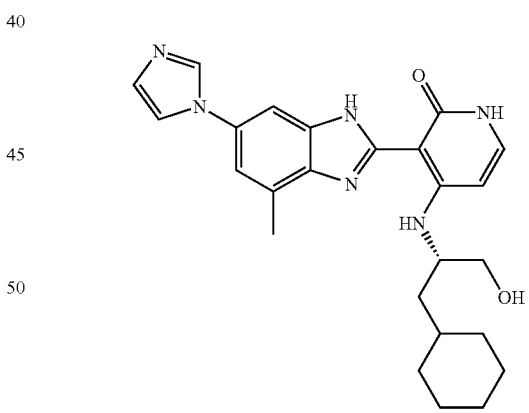

(S)-4-(2-Cyclohexyl-1-hydroxymethyl-ethylamino)-3-(6-imidazol-1-yl-4-methyl-1H-benzimidazol-2-yl)-1H-pyridin-2-one: $^1$H NMR (300 MHz, CD$_3$OD) δ 9.40 (1H, s), 8.06 (1H, narrow t, J=1.7 Hz), 7.76 (1H, narrow t, J=1.7 Hz), 7.73 (1H, narrow d, J=1.7 Hz), 7.34 (1H, d, J=7.6 Hz), 7.33 (1H, s), 6.34 (1H, d, J=7.6 Hz), 3.89–3.94 (1H, m), 3.68 (2H, d, J=4.9 Hz), 2.68 (3H, s), 1.62–1.83 (7H, m), 0.95–1.26 (6H, m). LCMS (M+H)$^+$ m/z 447 (t=1.71 min.).

EXAMPLE 17

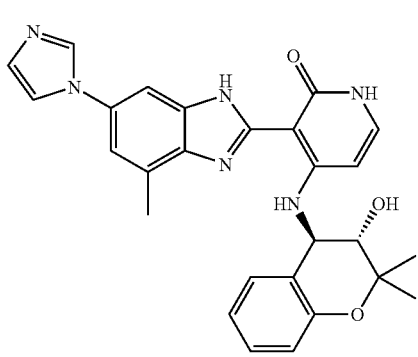

(3S,4R)-4-(3-Hydroxy-2,2-dimethyl-chroman-4-ylamino)-3-(6-imidazol-1-yl-4-methyl-1H-benzimidazol-2-yl)-1H-pyridin-2-one: $^1$H NMR (300 MHz, CD$_3$OD) δ 9.36 (1H, s), 8.02 (1H, narrow t, J=1.7 Hz), 7.73 (1H, narrow t, J=1.7 Hz), 7.69 (1H, narrow d, J=2.0 Hz), 7.37 (1H, d, J=7.6 Hz), 7.18–7.30 (3H, m), 6.89 (1H, t, J=7.6 Hz), 6.85 (1H, d, J=8.4 Hz), 6.61 (1H, d, J=7.6 Hz), 4.93 (1H, d, J=8.2 Hz), 3.80 (1H, d, J=8.2 Hz), 2.46 (3H, s), 1.48 (3H, s), 1.35 (3H, s). LCMS (M+H)$^+$ m/z 483 (t=1.70 min.).

EXAMPLE 18

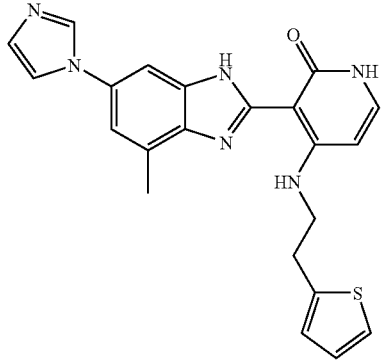

3-(6-Imidazol-1-yl-4-methyl-1H-benzimidazol-2-yl)-4-(2-thiophen-2-yl-ethylamino)-1H-pyridin-2-one: $^1$H NMR (500 MHz, DMSO-d$_6$) δ 13.17 (1H, broad s), 11.32 (1H, broad s), 11.03 (1H, broad s), 9.59 (1H, broad s), 8.22 (1H, broad s), 7.91 (1H, s), 7.82 (1H, d, J=2.0 Hz), 7.41 (1H, t, J=6.9 Hz), 7.36 (1H, dd, J=1.0, 5.1 Hz), 7.30–7.40 (1H, m), 7.05 (1H, broad s), 7.01 (1H, t, J=4.2 Hz), 6.23 (1H, d, J=7.5 Hz), 3.74 (2H, t, J=6.5 Hz), 3.25 (2H, t, J=6.5 Hz), 2.58 (3H, s).

EXAMPLE 19

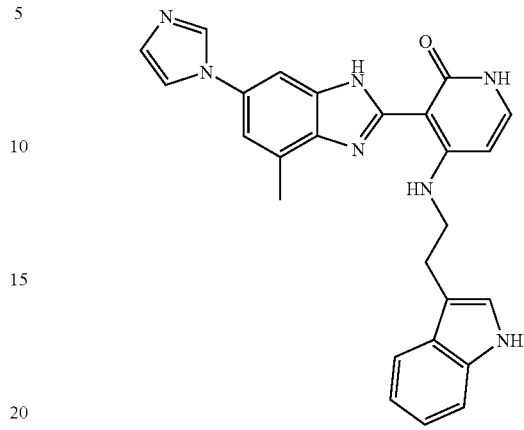

3-(6-Imidazol-1-yl-4-methyl-1H-benzimidazol-2-yl)-4-[2-(1H-indol-3-yl)-ethylamino]-1H-pyridin-2-one: $^1$H NMR (500 MHz, DMSO-d$_6$) δ 13.17 (1H, broad s), 11.27 (broad s, 1H), 11.00 (1H, broad s), 10.89 (1H, s), 9.58 (1H, broad s), 8.30 (1H, broad s), 7.91 (1H, s), 7.80 (1H, s), 7.63 (1H, d, J=7.9 Hz), 7.40 (1H, t, J=6.9 Hz), 7.34 (1H, d, J=8.0 Hz), 7.30–7.40 (2H, m), 7.07 (1H, t, J=7.5 Hz), 6.99 (1H, t, J=7.6 Hz), 6.23 (1H, dd, J=0.8, 7.2 Hz), 3.76 (2H, broad s), 3.17 (2H, t, J=6.7 Hz), 2.50 (3H, s).

EXAMPLE 20

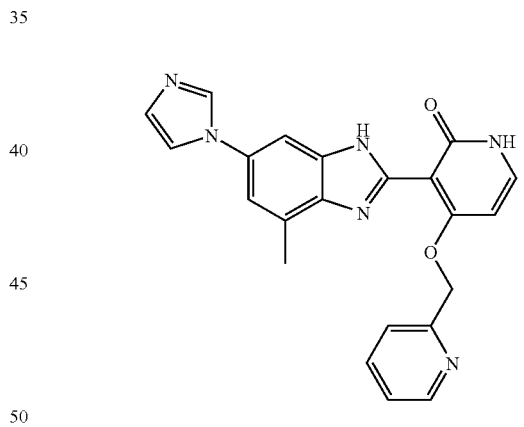

3-(6-Imidazol-1-yl-4-methyl-1H-benzimidazol-2-yl)-4-(pyridin-2-ylmethoxy)-1H-pyridin-2-one: To a solution of 3-(6-imidazol-1-yl-4-methyl-1H-benzimidazol-2-yl)-4-iodo-1H-pyridin-2-one (25 mg, 0.06 mmol) in DMF (2 mL) were added pyridine carbinol (26 mg, 0.24 mmol) and cesium fluoride (36 mg, 0.24 mmol). The reaction mixture was heated to 130° C. for 14 h and cooled to room temperature. After concentration in vacuo, the residue was purified by prep. HPLC to yield the title compound (8.2 mg, 34%). $^1$H NMR (300 MHz, CD$_3$OD) δ 9.58 (1H, narrow d, J=1.2 Hz), 8.92 (1H, d, J=4.9 Hz), 8.19 (1H, narrow t, J=1.2 Hz), 8.12 (1H, s), 7.97–8.02 (2H, m), 7.85 (1H, narrow t, J=1.8 Hz), 7.81 (1H, narrow t, J=1.0 Hz), 7.63 (1H, d, J=7.9 Hz), 7.54 (1H, t, J=6.2 Hz), 6.81 (1H, J=7.5 Hz), 5.86 (2H, s), 2.86 (3H, s). LCMS (M+H)$^+$ m/z 399 (t=1.07 min.).

EXAMPLE 21

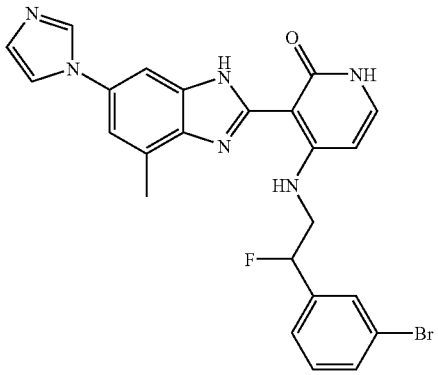

(±)-4-[2-(3-Bromo-phenyl)-2-fluoro-ethylamino]-3-(6-imidazol-1-yl-4-methyl-1H-benzimidazol-2-yl)-1H-pyridin-2-one: $^1$H NMR (300 MHz, CD$_3$OD) δ 9.40 (1H, t, J=1.4 Hz), 8.06 (1H, t, J=1.9 Hz), 7.76 (1H, t, J=1.7 Hz), 7.72 (1H, d, J=1.9 Hz), 7.66 (1H, s), 7.27–7.50 (5H, m), 6.29 (1H, d, J=7.6 Hz), 5.75–5.94 (1H, m), 3.86–4.06 (2H, m), 2.64 (3H, s). LCMS (M+H)$^+$ m/z 507 (t=1.70 min.).

EXAMPLE 22

General Procedure for Examples 22–28

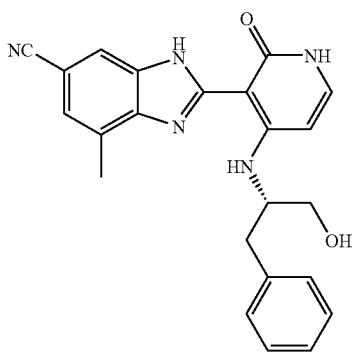

(S)-2-[4-(1-Hydroxymethyl-2-phenyl-ethylamino)-2-oxo-1,2-dihydro-pyridin-3-yl]-7-methyl-3H-benzimidazole-5-carbonitrile: To a solution of 2-(4-chloro-2-oxo-1,2-dihydro-pyridin-3-yl)-7-methyl-3H-benzimidazole-5-carbonitrile (0.7 g, 2.19 mmol) in DMF (15 mL) were added N-methylmorpholine (0.66 g, 6.57 mmol) and (S)-(–)-2-amino-3-phenyl-1-propanol (0.40 g, 2.63 mmol). The reaction mixture was heated to 80° C. for 6 h and then cooled to room temperature. After concentration in vacuo, the residue was purified by flash chromatography (3% MeOH/CH$_2$Cl$_2$) to yield the title compound (0.59 g, 68%) as a yellow foam. $^1$H NMR (400 MHz, CD$_3$OD) δ 7.74 (1H, s), 7.63 (1H, s), 7.12–7.27 (6H, m), 6.07 (1H, d, J=7.5 Hz), 3.97 (1H, m), 3.74 (2H, t, J=5 Hz), 3.14 (1H, dd, J=5.5, 14.0 Hz), 2.94 (1H, dd, J=7.9, 14.0 Hz), 2.60 (3H, s). LCMS (M+H)$^+$ m/z 400 (t=1.71 min.).

EXAMPLE 23

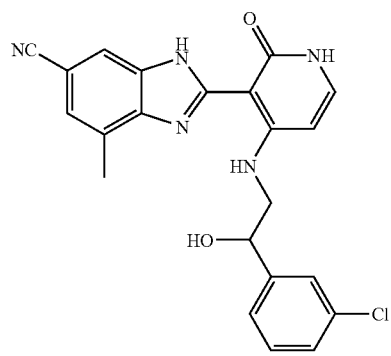

(±)-2-{4-[2-(3-Chloro-phenyl)-2-hydroxy-ethylamino[-2-oxo-1,2-dihydro-pyridin-3-yl}-7-methyl-3H-benzimidazole-5-carbonitrile: $^1$H NMR (300 MHz, DMSO-d$_6$) δ 7.92 (1H, s), 7.59 (1H, s), 7.28–7.47 (5H, m), 6.19 (1H, d, J=7.3 Hz), 4.92–4.96 (1H, m), 3.53–3.73 (2H, m), 2.58 (3H, s). LCMS (M+H)$^+$ m/z 420 (t=1.99 min.).

EXAMPLE 24

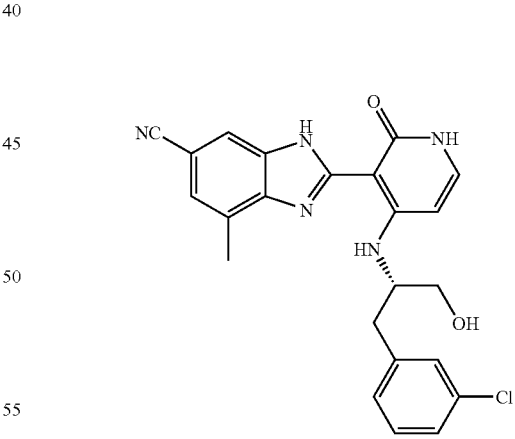

(S)-2-{4-[2-(3-Chloro-phenyl)-1-hydroxymethyl-ethylamino]-2-oxo-1,2-dihydro-pyridin-3-yl}-7-methyl-3H-benzimidazole-5-carbonitrile: $^1$H NMR (400 MHz, CD$_3$OD) δ 7.86 (1H, s), 7.10–7.33 (6H, m), 6.12 (1H, d, J=7.6 Hz), 4.01–4.05 (1H, m), 3.75 (2H, d, J=4.9 Hz), 3.15 (1H, dd, J=4.9, 13.5 Hz), 2.86–3.00 (1H, m), 2.63 (3H, s). LCMS (M+H)$^+$ m/z 434 (t=1.81 min.).

EXAMPLE 25

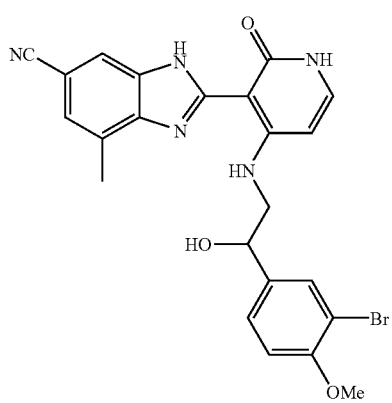

(±)-2-{4-[2-(3-Bromo-4-methoxy-phenyl)-2-hydroxy-ethylamino]-2-oxo-1,2-dihydro-pyridin-3-yl}-7-methyl-3H-benzimidazole-5-carbonitrile: $^1$H NMR (300 MHz, CD$_3$OD) δ 7.86 (1H, s), 7.75 (1H, s), 7.67 (1H, s), 7.28–7.40 (2H, m), 6.95 (1H, d, J=8.5 Hz), 6.24 (1H, d, J=7.4 Hz), 4.93 (1H, m), 3.65–3.97 (2H, m), 3.82 (3H, s), 2.57 (3H, s). LCMS (M+H)$^+$ m/z 494 (t=2.10 min.).

EXAMPLE 26

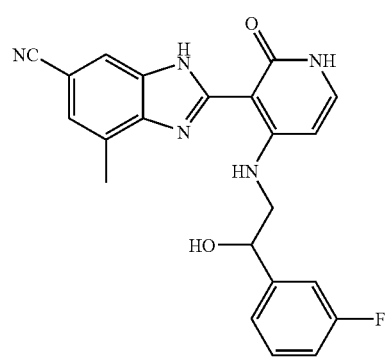

(±)-2-{4-[2-(3-Fluoro-phenyl)-2-hydroxy-ethylamino]-2-oxo-1,2-dihydro-pyridin-3-yl}-7-methyl-3H-benzimidazole-5-carbonitrile: $^1$H NMR (400 MHz, CD$_3$OD) δ 7.70 (1H, s), 7.49 (1H, s), 7.22–7.32 (4H, m), 6.92 (1H, d, J=8.9 Hz), 6.17 (1H, d, J=7.2 Hz), 4.92 (1H, t, J=6.3 Hz), 3.66 (2H, d, J=5.9 Hz), 2.56 (3H, s). LCMS (M+H)$^+$ m/z 404 (t=1.65 min.).

EXAMPLE 27

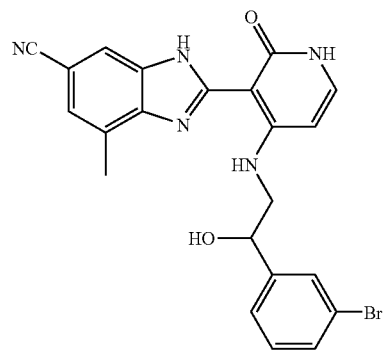

(±)-2-{4-[2-(3-Bromo-phenyl)-2-hydroxy-ethylamino]-2-oxo-1,2-dihydro-pyridin-3-yl}-7-methyl-3H-benzimidazole-5-carbonitrile: $^1$H NMR (300 MHz, CD$_3$OD) δ 7.92 (1H, s), 7.72 (1H, s), 7.26–7.50 (5H, m), 6.19 (1H, d, J=7.1 Hz), 4.93 (1H, t, J=4.3 Hz), 3.47–3.73 (2H, m), 2.58 (3H, s). LCMS (M+H)$^+$ m/z 464 (t=2.00 min.).

EXAMPLE 28

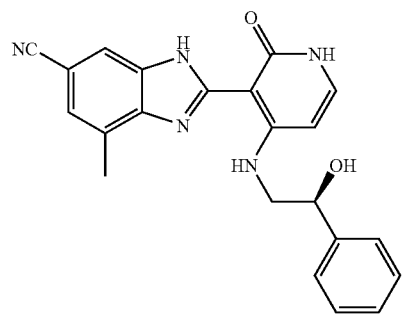

(S)-2-[4-(2-Hydroxy-2-phenyl-ethylamino)-2-oxo-1,2-dihydro-pyridin-3-yl]-7-methyl-3H-benzimidazole-5-carbonitrile: $^1$H NMR (400 MHz, CD$_3$OD) δ 8.04 (1H, s), 7.74 (1H, s), 7.24–14 7.51 (6H, m), 6.22 (1H, d, J=7.5 Hz), 5.00 (1H, m), 3.64–3.74 (2H, m), 2.60 (3H, s). LCMS (M+H)$^+$ m/z 386 (t=1.65 min.).

Examples 29–35 were prepared from commercially or readily available diamines which were prepared and condensed with 4-iodo-2-methoxy-pyridine-3-carbaldehyde as described in Scheme III.

EXAMPLE 29

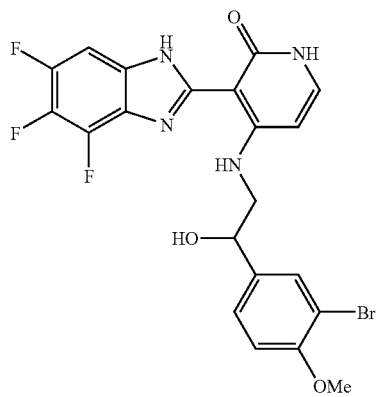

(±)-4-[2-(3-Bromo-4-methoxy-phenyl)-2-hydroxy-ethylamino]-3-(4,5,6-trifluoro-1H-benzimidazol-2-yl)-1H-pyridin-2-one: $^1$H NMR (500 MHz, CD$_3$COCD$_3$) δ 13.26 (1H, broad s), 10.93 (1H, broad s), 10.27 (1H, broad s), 7.76 (1H, s), 7.54–7.56 (2H, m), 7.41–7.42 (1H, m), 7.06 (1H, d, J=8.2 Hz), 6.29 (1H, d, J=7.5 Hz), 5.05–5.07 (1H, m), 3.87 (3H, s), 3.74–3.79 (1H, m), 3.65–3.69 (1H, m).

EXAMPLE 30

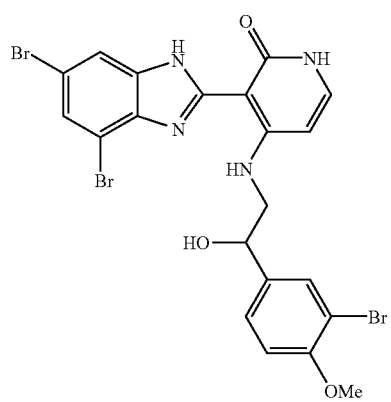

(±)-4-[2-(3-Bromo-4-methoxy-phenyl)-2-hydroxy-ethylamino]-3-(4,6-dibromo-1H-benzimidazol-2-yl)-1H-pyridin-2-one: $^1$H NMR (500 MHz, CD$_3$COCD$_3$) δ 13.18 (1H, broad s), 11.18 (1H, broad s), 10.20 (1H, broad s), 7.92 (1H, s), 7.78 (1H, s), 7.52–7.55 (3H, m), 7.03 (1H, d, J=8.5 Hz), 6.28 (1H, d, J=7.4 Hz), 5.06–5.08 (1H, m), 3.86 (3H, s), 3.73–3.77 (1H, m), 3.66–3.70 (1H, m).

EXAMPLE 31

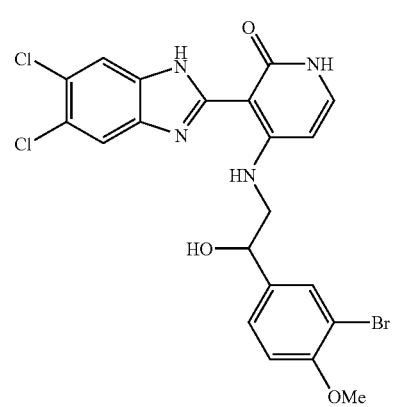

(±)-4-[2-(3-Bromo-4-methoxy-phenyl)-2-hydroxy-ethylamino]-3-(5,6-dichloro-1H-benzimidazol-2-yl)-1H-pyridin-2-one: $^1$H NMR (500 MHz, CD$_3$COCD$_3$) δ 7.79 (3H, m), 7.53 (1H, dd, J=2.0, 8.4 Hz), 7.41–7.44 (1H, m), 7.08 (1H, d, J=8.4 Hz), 6.29 (1H, d, J=7.5 Hz), 5.05–5.08 (1H, m), 3.89 (3H, s), 3.74–3.78 (1H, m), 3.70–3.72 (1H, m).

EXAMPLE 32

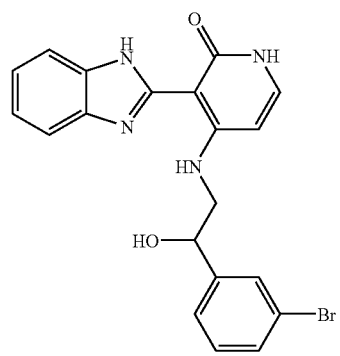

(±)-3-(1H-Benzimidazol-2-yl)-4-[2-(3-bromo-phenyl)-2-hydroxy-ethylamino]-1H-pyridin-2-one: $^1$H NMR (500 MHz, CD$_3$COCD$_3$) δ 7.80 (1H, s), 7.64–7.69 (2H, m), 7.60 (1H, d, J=7.7 Hz), 7.46–7.48 (2H, m), 7.33 (1H, t, J=7.8 Hz), 7.19–7.22 (2H, m), 6.59 (1H, d, J=4.5 Hz), 5.12–5.14 (1H, m), 5.13 (1H, dd, J=4.5, 7.2 Hz), 3.82 (1H, dd, J=4.5, 13.6 Hz), 3.71 (1H, dd, J=7.2, 13.6 Hz).

EXAMPLE 33

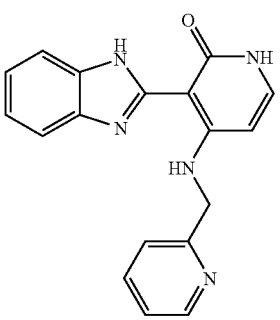

3-(1H-Benzimidazol-2-yl)-4-[(pyridin-2-ylmethyl)-amino]-1H-pyridin-2-one: $^1$H NMR (500 MHz, CD$_3$COCD$_3$) δ 8.96–8.98 (1H, m), 8.46–8.49 (1H, m), 8.03 (1H, d, J=8.0 Hz), 7.93 (1H, t, J=6.4 Hz), 7.69–7.73 (2H, m), 7.53 (1H, d, J=7.5 Hz), 7.28–7.32 (2H, s), 6.34 (1H, d, J=7.5 Hz), 5.29 (2H, m).

EXAMPLE 34

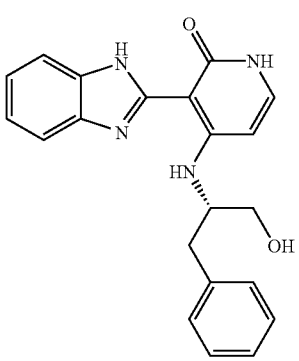

(S)-3-(1H-Benzimidazol-2-yl)-4-(1-hydroxymethyl-2-phenyl-ethylamino)-1H-pyridin-2-one: $^1$H NMR (500 MHz, CD$_3$COCD$_3$) δ 7.67–7.69 (2H, m), 7.15–7.44 (8H, m), 6.31 (1H, d, J=7.5 Hz), 4.10–4.13 (1H, m), 3.76–3.82 (2H, m), 3.23 (1H, dd, J=5.6, 13.7 Hz), 3.04 (1H, dd, J=8.1, 13.7 Hz).

EXAMPLE 35

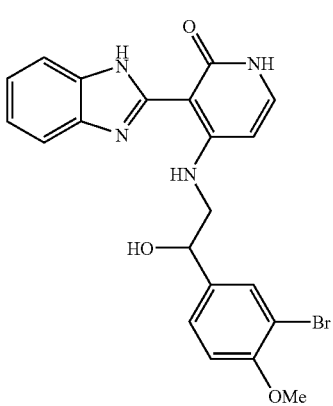

(±)-3-(1H-Benzimidazol-2-yl)-4-[2-(3-bromo-4-methoxy-phenyl)-2-hydroxy-ethylamino]-1H-pyridin-2-one: $^1$H NMR (500 MHz, CD$_3$COCD$_3$) δ 7.78 (1H, s), 7.68 (2H, s), 7.50–7.55 (2H, m), 7.21–7.24 (2H, m), 7.06 (1H, d, J=8.4 Hz), 6.44 (1H, d, J=7.5 Hz), 5.08 (1H, dd, J=4.6, 7.2 Hz), 3.87 (3H, s), 3.79 (1H, dd, J=4.6, 13.4 Hz), 3.71 (1H, dd, J=7.2, 13.4 Hz).

Examples 36–43 were prepared according to Scheme V.

EXAMPLE 36

General Procedure for Examples 36–43

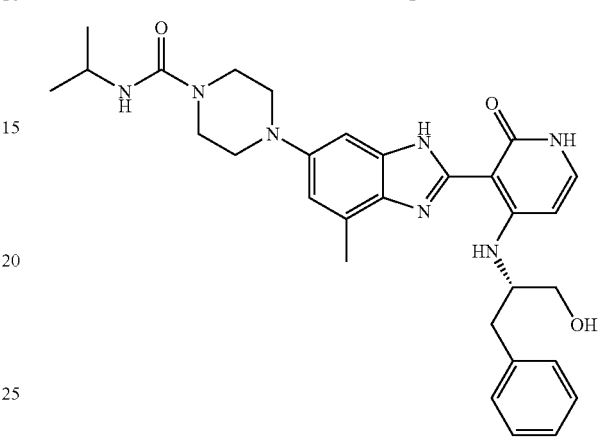

(S)-4-{2-[4-(1-Hydroxymethyl-2-phenyl-ethylamino)-2-oxo-1,2-dihydro-pyridin-3-yl]-7-methyl-3H-benzimidazol-5-yl}-piperazine-1-carboxylic acid isopropylamide: To a solution of (S)-4-(1-hydroxymethyl-2-phenyl-ethylamino)-3-(4-methyl-6-piperazin-1-yl-1 H-henzimidazol-2-yl)-1H-pyridin-2-one (30 mg, 0.063 mmol) in methanol (2 mL) was added isopropyl isocyanate (2 drops). The reaction mixture was stirred at room temperature for 5 min. Concentration gave the residue, which was purified by prep. HPLC to yield the title compound (23.8 mg, 69%). $^1$H NMR (400 MHz, CD$_3$OD) δ 7.55 (1H, s), 7.14–7.28 (7H, m), 6.12 (1H, d, J=7.8 Hz), 4.01–4.03 (1H, m), 3.92 (quintet, J=6.6 Hz), 3.80 (4H, m), 3.76 (1H, dd, J=4.8, 11.2 Hz), 3.70 (1H, dd, J=5.2, 11.2 Hz), 3.61 –3.64 (4H, m), 3.09 (1H, dd, J=5.6, 13.7 Hz), 2.91 (1H, dd, J=8.0, 13.7 Hz), 2.64 (3H, s), 1.19 (6H, d, J=6.8 Hz). LCMS (M+H)$^+$ m/z 545 (t=1.99 min.).

EXAMPLE 37

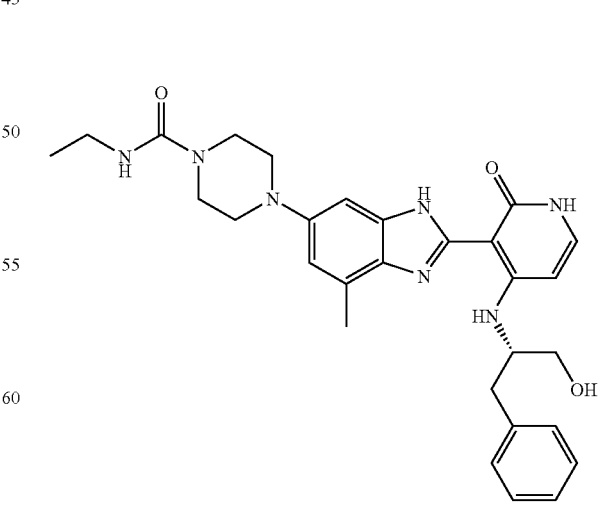

(S)-4-{2-[4-(1-Hydroxymethyl-2-phenyl-ethylamino)-2-oxo-1,2-dihydro-pyridin-3-yl]-7-methyl-3H-benzimidazol- 5-yl}-piperazine-1-carboxylic acid ethylamide: $^1$H NMR (400 MHz, CD$_3$OD) δ 7.55 (1H, s), 7.12–7.28 (7H, m), 6.12 (1H, d, J=7.8 Hz), 4.01–4.05 (1H, m), 3.62–3.81 (10H, m), 3.24 (2H, q, J=7.2 Hz), 3.08 (1H, dd, J=5.6, 13.7 Hz), 2.91 (1H, dd, J=8.0, 13.7 Hz), 2.65 (3H, s), 1.14 (3H, t, J=7.2 Hz). LCMS (M+H)$^+$ m/z 531 (t=1.93 min.).

EXAMPLE 38

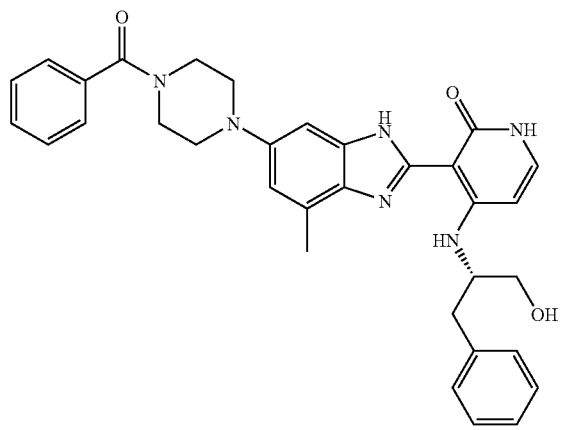

(S)-4-(1-Hydroxymethyl-2-phenyl-ethylamino)-3-{4-methyl-6-[4-(1-phenyl-methanoyl)-piperazin-1-yl]-1H-benzimidazol-2-yl}-1H-pyridin-2-one: To a solution of (S)-4-(1-hydroxymethyl-2-phenyl-ethylamino)-3-(4-methyl-6-piperazin-1-yl-1H-benzimidazol-2-yl)-1H-pyridin-2-one (30 mg, 0.063 mmol) in methanol (2 mL) was added benzoyl chloride (1 drop). The reaction mixture was stirred for 5 min. and concentrated. The residue was purified by prep. HPLC to yield the title compound (11 mg, 33%). $^1$H NMR (400 MHz, CD$_3$OD) δ 7.48–7.54 (5H, m), 7.37 (1H, s), 7.13–7.26 (7H, m), 6.08 (1H, d, J=7.7 Hz), 3.79–4.02 (5H, m), 3.76 (1H, dd, J=4.7, 11.2 Hz), 3.67 (1H, dd, J=5.7, 11.2 Hz), 3.54 (4H, m), 3.03 (1H, dd, J=5.7, 13.7 Hz), 2.89 (1H, dd, J=8.0, 13.7 Hz), 2.62 (3H, s). LCMS (M+H)$^+$ m/z 563 (t=2.19 min.).

EXAMPLE 39

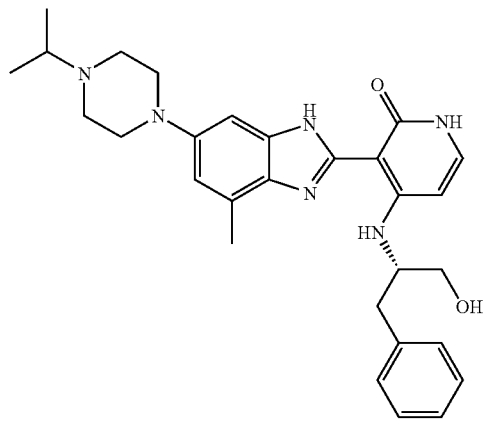

(S)-4-(1-Hydroxymethyl-2-phenyl-ethylamino)-3-[6-(4-isopropyl-piperazin-1-yl)-4-methyl-1H-benzimidazol-2-yl]-1H-pyridin-2-one: To a solution of (S)-4-(1-hydroxymethyl-2-phenyl-ethylamino)-3-(4-methyl-6-piperazin-1-yl-1H-benzimidazol-2-yl)-1H-pyridin-2-one (25 mg, 0.054 mmol) in methanol (0.5 mL) was added acetone (0.25 mL) and 1 M THF solution of NaCNBH$_3$ (0.2 mL). The reaction mixture was stirred at room temperature for 1 h and concentrated in vacuo. The residue was purified by prep. HPLC to yield the title compound (12 mg, 44%). $^1$H NMR (400 MHz, CD$_3$OD) δ 7.10–7.24 (6H, m), 7.08 (1H, s), 7.06 (1H, s), 6.06 (1H, d, J=7.9 Hz), 3.58–4.01 (10H, m), 3.34 (1H, m), 3.14 (1H, m), 2.98 (1H, dd, J=5.9, 13.7 Hz), 2.83 (1H, dd, J=7.9, 13.7 Hz), 2.60 (3H, s), 1.44 (6H, d, J=6.7 Hz). LCMS (M+H)$^+$ m/z 501 (t=1.80 min.).

EXAMPLE 40

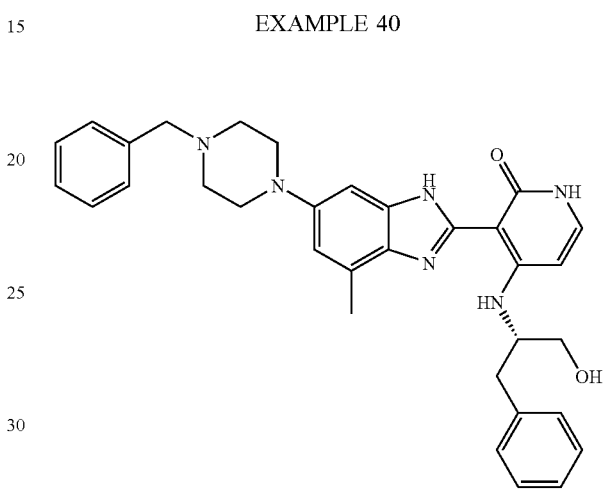

(S)-3-[6-(4-Benzyl-piperazine-1-yl)-4-methyl-1H-benzimidazol-2-yl]-4-(1-hydroxymethyl-2-phenyl-ethylamino)-1H-pyridin-2-one: $^1$H NMR (400 MHz, CD$_3$OD) δ 7.50–7.57 (6H, m), 7.04–7.27 (7H, m), 6.07 (1H, d, J=7.8 Hz), 4.22 (2H, s), 3.97–4.00 (1H, m), 3.34–3.77 (2H, m), 2.82–3.04 (10H, m), 2.58 (3H, s). LCMS (M+H)$^+$ m/z 549 (t=1.93 min.).

EXAMPLE 41

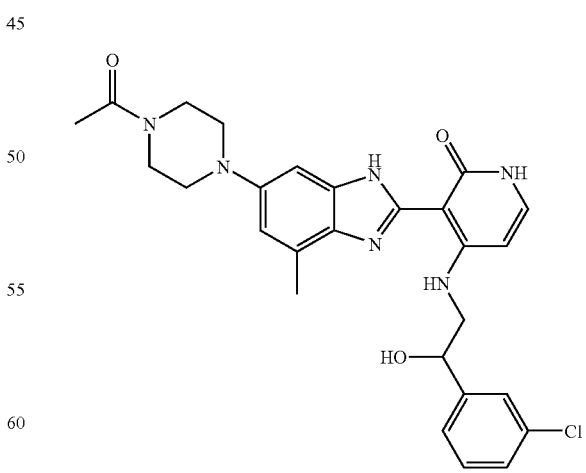

(±)-3-[6-(4-Acetyl-piperazine-1-yl)-4-methyl-1H-benzimidazol-2-yl]-4-[2-(3-chloro-phenyl)-2-hydroxy-ethylamino]-1H-pyridin-2-one: $^1$H NMR (400 MHz, CD$_3$OD) δ 7.50 (1H, s), 7.25–7.49 (5H, m), 7.20 (1H, s), 6.25 (1H, d, J=8.0 Hz), 4.94 (1H, dd, J=4.6, 7.1 Hz), 3.88–3.92 (4H, m), 3.50–3.65 (6H, m), 2.62 (3H, s), 2.20 (3H, s). LCMS (M+H)+ m/z 521 (t=2.13 min.).

EXAMPLE 42

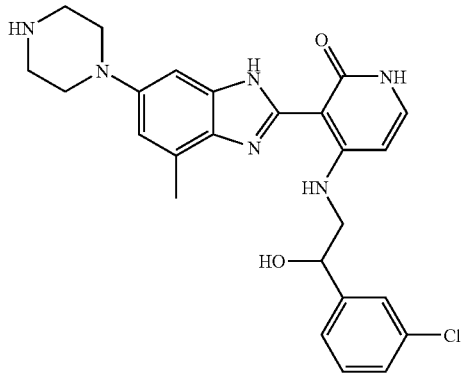

(±)-4-[2-(3-Chloro-phenyl)-2-hydroxy-ethylamino]-3-(4-methyl-6-piperazin-1-yl-1H-benzimidazol-2-yl)-1H-pyridin-2-one: ¹H NMR (400 MHz, CD₃OD) δ 7.47 (1H, s), 7.25–7.38 (4H, m), 7.07 (2H, s), 6.25 (1H, d, J=7.6 Hz), 4.90 (1H, m), 3.42–3.66 (10 H, m), 2.59 (3H, s). LCMS (M+H)+ m/z 479 (t=1.90 min.).

EXAMPLE 43

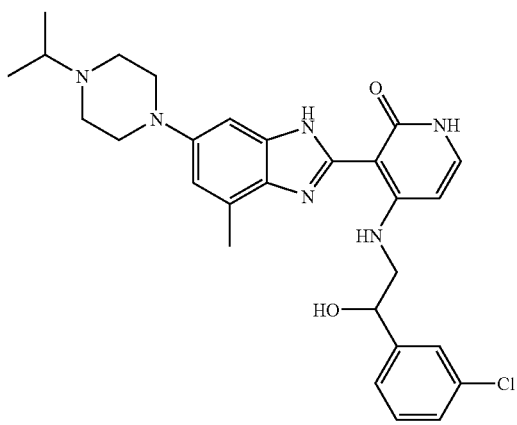

(±)-4-[2-(3-Chloro-phenyl)-2-hydroxy-ethylamino]-3-[6-(4-isopropyl-piperazine-1-yl)-4-methyl-1H-benzimidazol-2-yl]-1H-pyridin-2-one: ¹H NMR (400 MHz, CD₃OD) δ 7.47 (1H, s), 7.25–7.38 (4H, m), 7.06 (2H, s), 6.26 (1H, d, J=7.6 Hz), 4.91–4.93 (1H, m), 3.89–3.92 (2H, m), 3.51–3.64 (5H, m), 3.31–3.37 (2H, m), 3.09–3.30 (2H, m), 2.59 (3H, s), 1.44 (6H, d, J=6.6 Hz). LCMS (M+H)+ m/z 521 (t=1.95 min.).

EXAMPLE 44

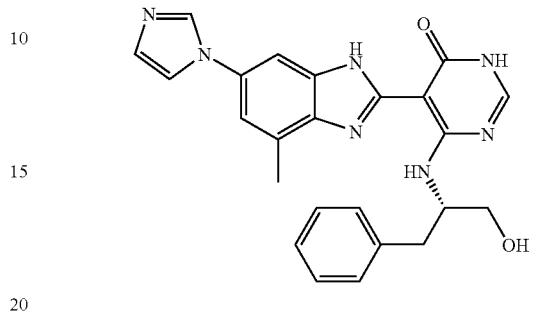

(S)-6-(1-Hydroxymethyl-2-phenyl-ethylamino)-5-(6-imidazol-1-yl-4-methyl-1H-benzimidazol-2-yl)-3H-pyrimidin-4-one:

(S)-2-[6-Chloro-5-(6-imidazol-1-yl-4-methyl-1H-benzimidazol-2-yl)-pyrimidin-4-ylamino]-3-phenyl-propan-1-ol: To a solution of 2-(4,6-dichloro-pyrimidin-5-yl)-6-imidazol-1-yl-4-methyl-1H-benzimidazole (40 mg, 0.16 mmol) in isopropanol (5 mL) was added (S)-(−)-2-amino-3-phenyl-propanol (35 mg, 0.23 mmol) and triethylamine (0.5 mL). The reaction mixture was heated to 80° C. for 4 h, cooled to room temperature and concentrated with high vacuum. The crude product was used for the next step without purification. LCMS (M+H)+ m/z 460 (t=2.13 min.).

(S)-6-(1-Hydroxymethyl-2-phenyl-ethylamino)-5-(6-imidazol-1-yl-4-methyl-1H-benzimidazol-2-yl)-3H-pyrimidin-4-one: To a solution of (S)-2-[6-chloro-5-(6-imidazol-1-yl-4-methyl-1H-benzimidazol-2-yl)-pyrimidin-4-ylamino]-3-phenyl-propan-1-ol in 4 N HCl (0.5 mL) and acetic acid (0.5 mL) was added two drops of water. The reaction mixture was heated to 100° C. for 8 h, cooled to room temperature, and neutralized with ammonia in methanol. After concentration, the residue was purified by prep. HPLC to yield the title compound (26 mg, 37% for two steps). ¹H NMR (400 MHz, CD₃OD) δ 9.41 (1H, narrow t, J=1.5 Hz), 8.06 (1H, narrow dd, J=1.6, 1.9 Hz), 7.93 91H, s), 7.77 (1H, narrow dd, J=1.6, 1.8 Hz), 7.73 (1H, narrow d, J=1.9 Hz), 7.11–7.21 (6H, m), 4.70–4.74 (1H, m), 3.74 (2H, d, J=4.7 Hz), 3.11 (1H, dd, J=6.1, 13.5 Hz), 3.00 (1H, dd, J=7.8, 13.5 Hz), 2.70 (3H, s). LCMS (M+H)+ m/z 442 (t=2.17 min.).

Examples 45–383 were prepared according to the general methods described above (Scheme III)

LCMS conditions:
a) YMC C18 S5 4.6×50 mm; 0–100% gradient over 4 min*; 4 mL/min flow rate
b) YMC ODS-A C18 S7 3.0×50 mm; 0–100% gradient over 2 min*; 5 mL/min flow rate
c) YMC C18 S5 4.5×50 mm; 0–100% gradient over 8 min*; 2.5 mL/min flow rate
d) YMC C18 S7 3.0×50 mm; 0–100% gradient over 3 min*; 5 mL/min flow rate
e) YMC ODSA S3 6.0×150 mm; 0–100% gradient over 5 min*; 1.5 mL/min flow rate
f) PHS-PRIMESPHERE C18 4.6×30 mm; 0–100% gradient over 2 min*; 5 mL/min flow rate
g) YMC C18 S7 3.0×50 mm; 0–100% gradient over 4 min*; 5 mL/min flow rate h) YMC ODS-A C18 S7 3.0×50 mm; 0–100% gradient over 2 min*; 5 mL/min flow rate
i) YMC ODS-A C18 S7 3.0×50 mm; 0–100% gradient over 1.5 min*; 5 mL/min flow rate
j) YMC Xterra C18 S7 3.0×50 mm; 0–100% gradient over 2 min*; 5 mL/min flow rate
k) YMC Pro-ODS C18 S5 4.6×33 mm; 0–100% gradient over 3 min*; 4 mL/min flow rate
l) YMC ODS-A C18 S7 3.0×50 mm; 0–100% gradient over 4 min*; 4 mL/min flow rate

*Gradient begin with 10% methanol/90% water (0.1% TFA) and end with 90% methanol/10% water (0.1% TFA)

| Example # | Name | structure | T (min.) | Mass (M + H)+ m/z |
|---|---|---|---|---|
| 45 | 4-(2-Fluoro-benzylamino)-3-(6-imidazol-1-yl-4-methyl-1H-benzimidazol-2-yl)-1H-pyridin-2-one | 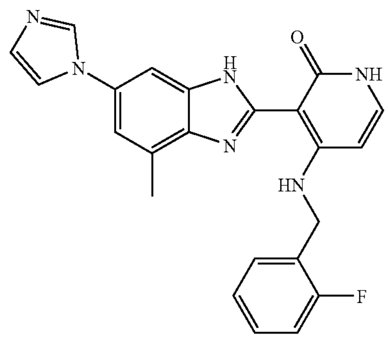 | 1.43 (l) | 415 |
| 46 | 4-(3,4-Dimethoxy-benzylamino)-3-(6-imidazol-1-yl-4-methyl-1H-benzimidazol-2-yl)-1H-pyridin-2-one | 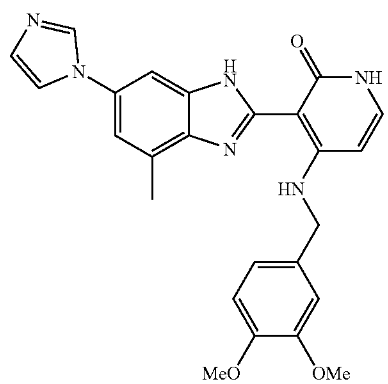 | 1.37 (l) | 457 |
| 47 | 3-(6-Imidazol-1yl-4-methyl-1H-benzimidazol-2-yl)-4-[(pyridin-2-ylmethyl)-amino]-1H-pyridin-2-one | 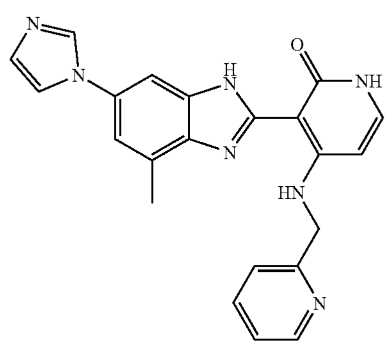 | 2.17 (a) | 398 |

-continued

| Example # | Name | structure | T (min.) | Mass (M + H)+ m/z |
|---|---|---|---|---|
| 48 | (S)-4-(1-Hydroxymethyl-2-phenyl-ethylamino)-3-(6-imidazol-1-yl-4-methyl-1H-benzimidazol-2-yl)-1H-pyridin-2-one | 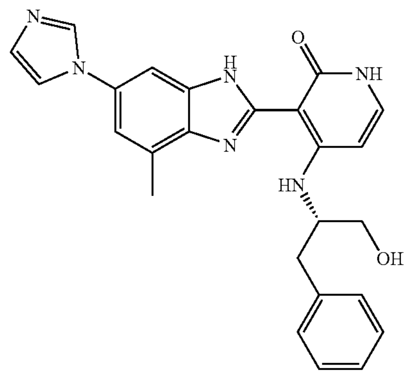 | 1.48 (b) | 441 |
| 49 | (R)-4-(1-Hydroxymethyl-2-phenyl-ethylamino)-3-(6-imidazol-1-yl-4-methyl-1H-benzimidazol-2-yl)-1H-pyridin-2-one | 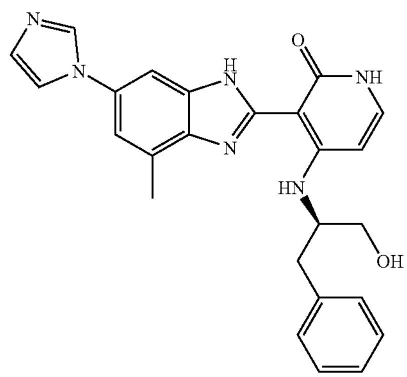 | 1.48 (b) | 441 |
| 50 | N-{2-[3-(6-Imidazol-1-yl-4-methyl-1H-benzimidazol-2-yl)-2-oxo-1,2-dihydro-pyridin-4-ylamino]-ethyl}-acetamide | 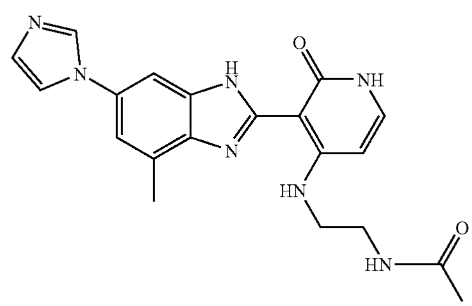 | 1.55 (l) | 392 |
| 51 | 4-(3,4-Dihydroxy-benzylamino)-3-(6-imidazol-1-yl-4-methyl-1H-benzimidazol-2-yl)-1H-pyridin-2-one | 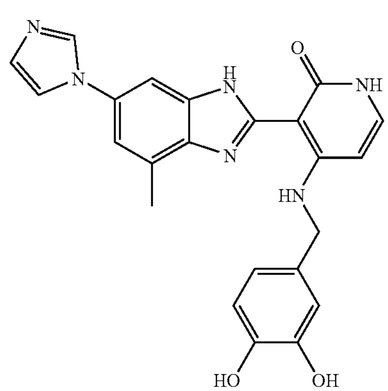 | 1.97 (l) | 429 |

-continued

| Example # | Name | structure | T (min.) | Mass (M + H)+ m/z |
|---|---|---|---|---|
| 52 | 4-[2-(3H-Imidazol-4-yl)-ethylamino]-3-(6-imidazol-1-yl-4-methyl-1H-benzimidazol-2-yl)-1H-pyridin-2-one | 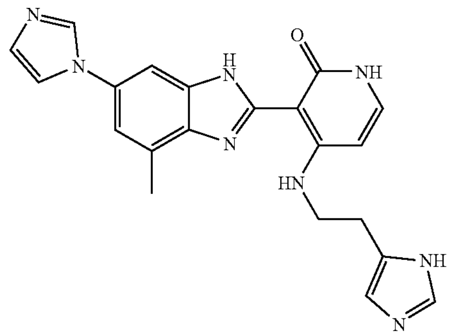 | 1.91 (a) | 401 |
| 53 | 4-(3,4-Dihydro-2H-quinolin-1-yl)-3-(6-imidazol-1-yl-4-methyl-1H-benzimidazol-2-yl)-1H-pyridin-2-one | 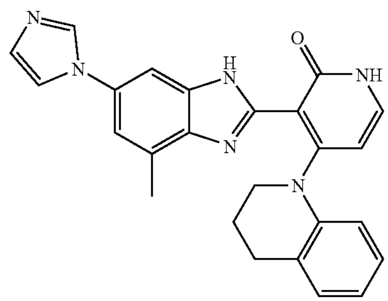 | 1.88 (a) | 423 |
| 54 | 3-(6-Imidazol-1-yl-4-methyl-1H-benzimidazol-2-yl)-4-[(pyridin-3-ylmethyl)-amino]-1H-pyridin-2-one | 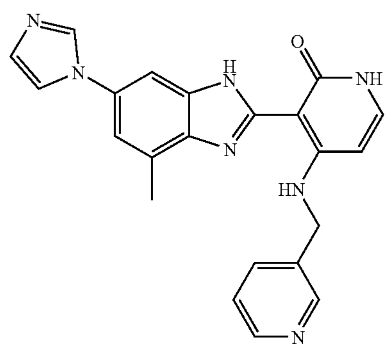 | 1.83 (a) | 398 |
| 55 | 3-(6-Imidazol-1-yl-4-methyl-1H-benzimidazol-2-yl)-4-[(pyridin-4-ylmethyl)-amino]-1H-pyridin-2-one | 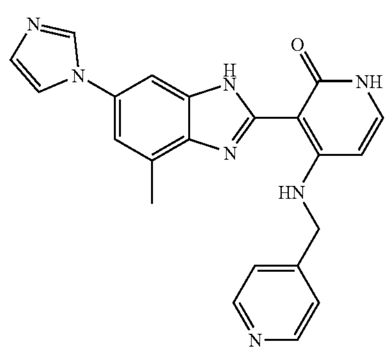 | 1.74 (a) | 398 |

-continued

| Example # | Name | structure | T (min.) | Mass (M + H)+ m/z |
|---|---|---|---|---|
| 56 | 3-(6-Imidazol-1-yl-4-methyl-1H-benzimidazol-2-yl)-4-(2-pyridin-2-yl-ethylamino)-1H-pyridin-2-one | 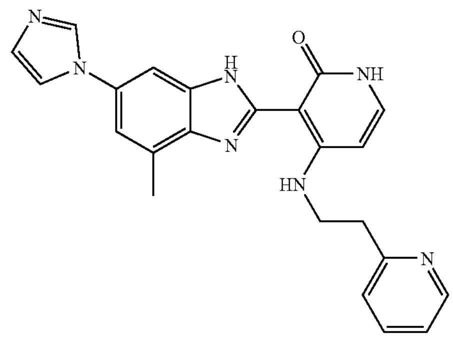 | 1.99 (a) | 412 |
| 57 | 4-[Benzyl-(2-hydroxy-ethyl)-amino]-3-(6-imidazol-1-yl-4-methyl-1H-benzimidazol-2-yl)-1H-pyridin-2-one | 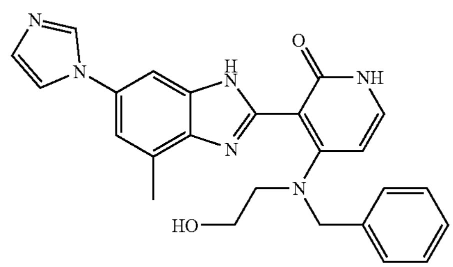 | 1.86 (a) | 441 |
| 58 | (±)-4-[1-(4-Chloro-phenyl)-2-hydroxy-ethylamino]-3-(6-imidazol-1-yl-4-methyl-1H-benzimidazol-2-yl)-1H-pyridin-2-one | 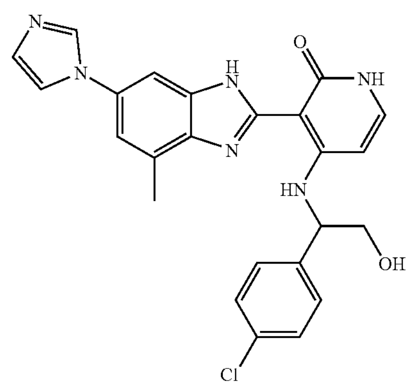 | 3.3 (a) | 461 |
| 59 | (±)-4-[(1-Ethyl-pyrrolidin-2-ylmethyl)-amino]-3-(6-imidazol-1-yl-4-methyl-1H-benzimidazol-2-yl)-1H-pyridin-2-one | 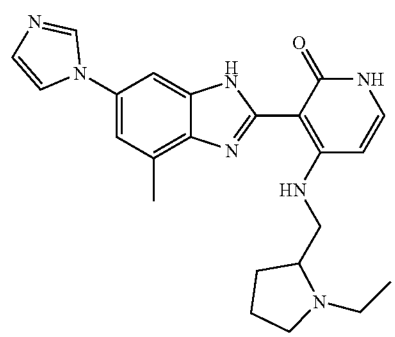 | 1.88 (a) | 418 |

-continued

| Example # | Name | structure | T (min.) | Mass (M + H)+ m/z |
|---|---|---|---|---|
| 60 | (1R,2S)-4-(2-Hydroxy-1-methyl-2-phenyl-ethylamino)-3-(6-imidazol-1-yl-4-methyl-1H-benzimidazol-2-yl)-1H-pyridin-2-one | 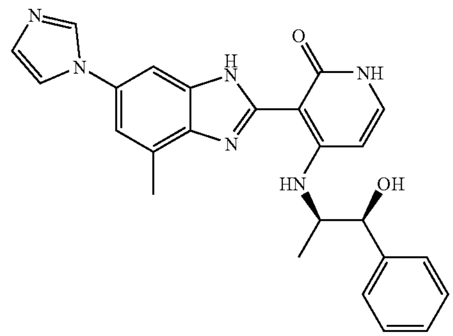 | 3.01 (a) | 441 |
| 61 | (±)-4-(2-Hydroxy-2-phenyl-ethylamino)-3-(6-imidazol-1-yl-4-methyl-1H-benzimidazol-2-yl)-1H-pyridin-2-one | 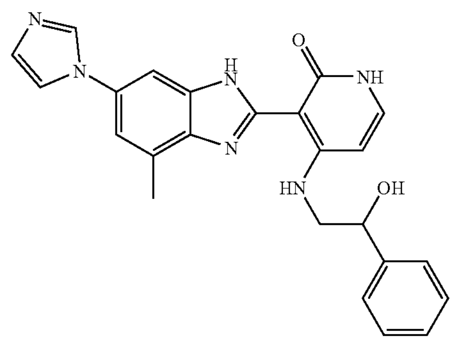 | 2.96 (a) | 427 |
| 62 | 3-(6-Imidazol-1-yl-4-methyl-1H-benzimidazol-2-yl)-4-(3-imidazol-1-yl-propylamino)-1H-pyridin-2-one | 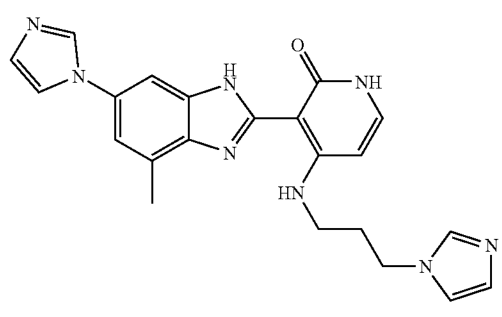 | 1.94 (a) | 415 |
| 63 | (S)-4-(2-Hydroxy-2-phenyl-ethylamino)-3-(6-imidazol-1-yl-4-methyl-1H-benzimidazol-2-yl)-1H-pyridin-2-one | 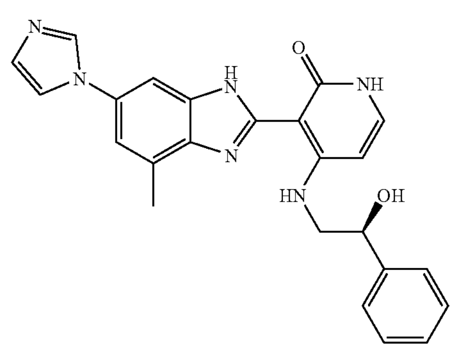 | 1.27 (b) | 427 |

-continued

| Example # | Name | structure | T (min.) | Mass (M + H)+ m/z |
|---|---|---|---|---|
| 64 | (R)-4-(2-Hydroxy-2-phenyl-ethylamino)-3-(6-imidazol-1-yl-4-methyl-1H-benzimidazol-2-yl)-1H-pyridin-2-one | 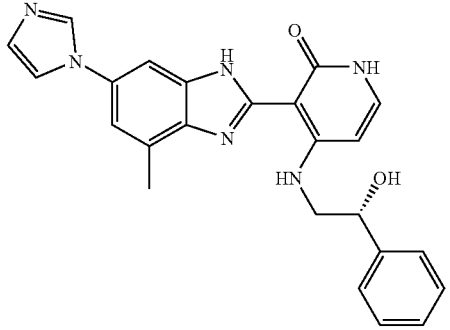 | 1.27 (b) | 427 |
| 65 | (±)-4-(1-Benzyl-pyrrolidin-3-ylamino)-3-(6-imidazol-1-yl-4-methyl-1H-benzimidazol-2-yl)-1H-pyridin-2-one | 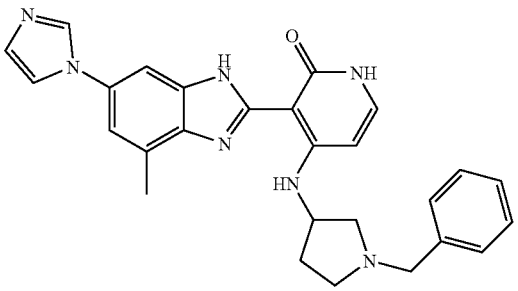 | 1.19 (b) | 466 |
| 66 | 3-(6-Imidazol-1-yl-4-methyl-1H-benzimidazol-2-yl)-4-[2-(5-nitro-pyridin-2-ylamino)-ethylamino]-1H-pyridin-2-one | 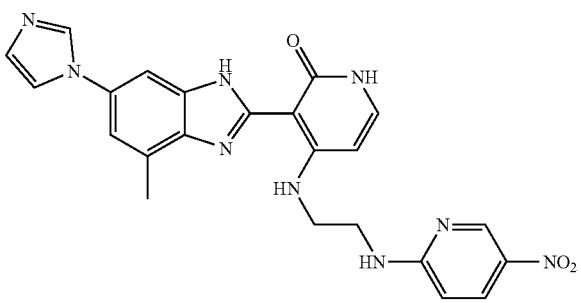 | 1.37 (b) | 472 |
| 67 | 3-(6-Imidazol-1-yl-4-methyl-1H-benzimidazol-2-yl)-4-(2-morpholin-4-yl-ethylamino)-1H-pyridin-2-one | 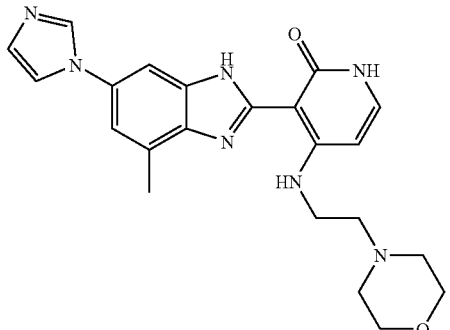 | 0.98 (b) | 420 |

-continued

| Example # | Name | structure | T (min.) | Mass (M + H)+ m/z |
|---|---|---|---|---|
| 68 | 3-(6-Imidazol-1-yl-4-methyl-1H-benzimidazol-2-yl)-4-[2-(2-methyl-5-nitro-1H-imidazol-1-yl)-ethylamino]-1H-pyridin-2-one | 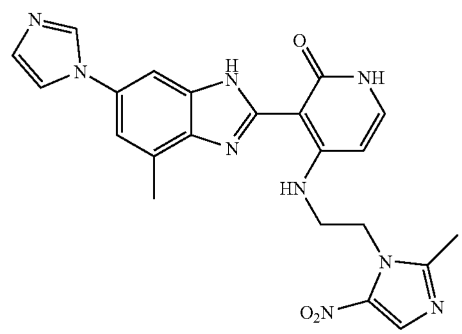 | 1.31 (b) | 460 |
| 69 | 3-(6-Imidazol-1-yl-4-methyl-1H-benzimidazol-2-yl)-4-[2-(3-methyl-3H-imidazol-4-yl)-ethylamino]-1H-pyridin-2-one | 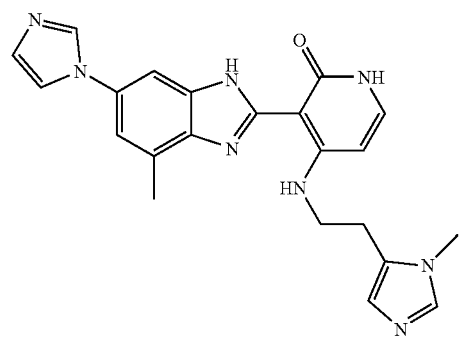 | 0.97 (b) | 415 |
| 70 | (±)-4-(4-Diethylamino-1-methyl-butylamino)-3-(6-imidazol-1-yl-4-methyl-1H-benzimidazol-2-yl)-1H-pyridin-2-one | 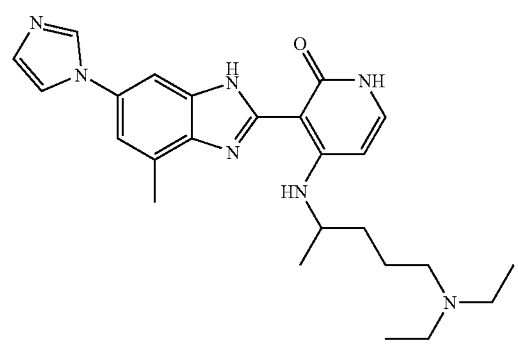 | 1.13 (b) | 448 |
| 71 | 3-(6-Imidazol-1-yl-4-methyl-1H-benzimidazol-2-yl)-4-(2-pyrrolidin-1-yl-ethylamino)-1H-pyridin-2-one | 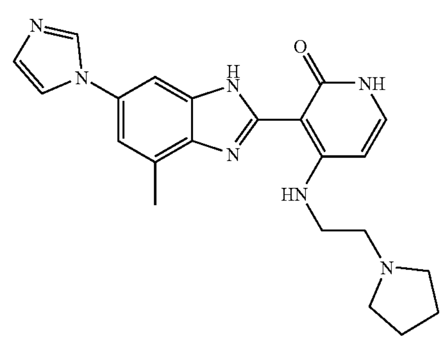 | 0.87 (b) | 404 |

-continued

| Example # | Name | structure | T (min.) | Mass (M + H)+ m/z |
|---|---|---|---|---|
| 72 | (±)-4-(1,2-Diphenyl-ethylamino)-3-(6-imidazol-1-yl-4-methyl-1H-benzimidazol-2-yl)-1H-pyridin-2-one | 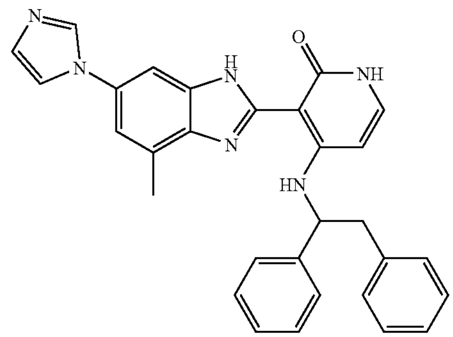 | 1.72 (b) | 487 |
| 73 | 4-Benzylamino-3-(6-imidazol-1-yl-4-methyl-1H-benzimidazol-2-yl)-1H-pyridin-2-one | 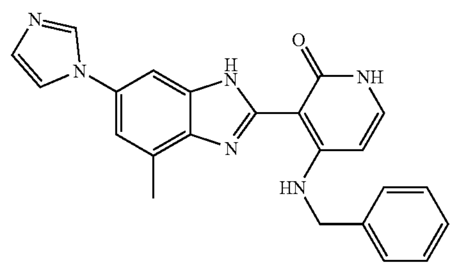 | 1.49 (b) | 397 |
| 74 | 4-(3-Dimethylamino-propylamino)-3-(6-imidazol-1-yl-4-methyl-1H-benzimidazol-2-yl)-1H-pyridin-2-one | 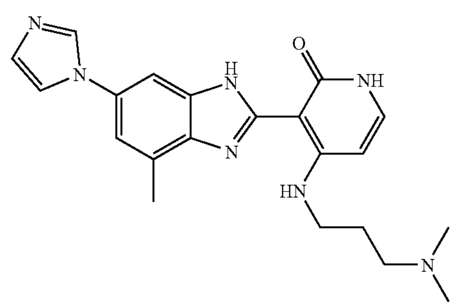 | 1.03 (b) | 392 |
| 75 | 4[(Adamantan-1-ylmethyl)-amino]-3-(6-imidazol-1-yl-4-methyl-1H-benzimidazol-2-yl)-1H-pyridin-2-one | 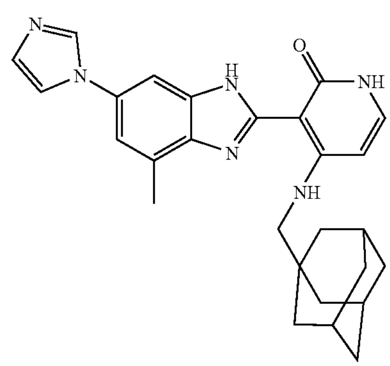 | 1.87 (b) | 455 |

| Example # | Name | structure | T (min.) | Mass (M + H)+ m/z |
|---|---|---|---|---|
| 76 | 3-(6-Imidazol-1-yl-4-methyl-1H-benzoimidazol-2-yl)-4-(indan-2-ylamino)-1H-pyridin-2-one | 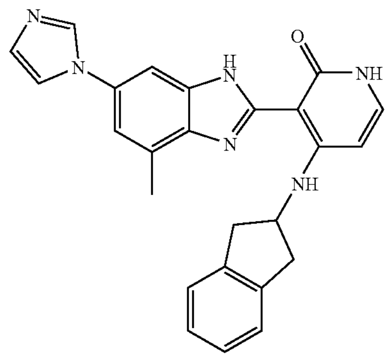 | 1.57 (b) | 423 |
| 77 | 4-(3,5-Bis-trifluoromethyl-benzylamino)-3-(6-imidazol-1-yl-4-methyl-1H-benzimidazol-2-yl)-1H-pyridin-2-one | 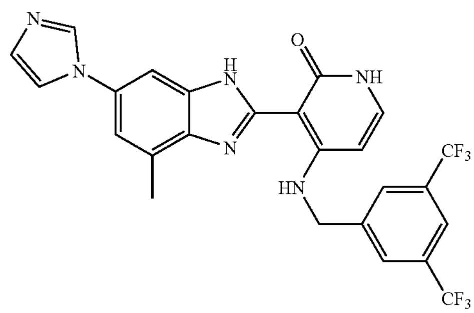 | 1.68 (b) | 533 |
| 78 | (±)-4-(1,1-Dioxo-tetrahydro-1λ⁶-thiophene-3-ylamino)-3-(6-imidazol-1-yl-4-methyl-1H-benzimidazol-2-yl)-1H-pyridin-2-one | 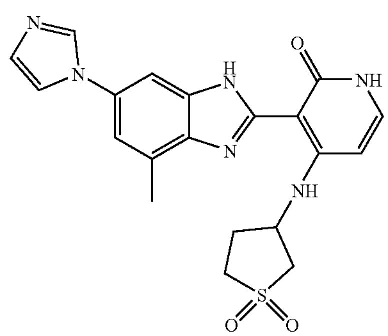 | 1.03 (b) | 425 |
| 79 | 3-(6-Imidazol-1-yl-4-methyl-1H-benzoimidazol-2-yl)-4-(3,4,5-trimethoxy-benzylamino)-1H-pyridin-2-one | 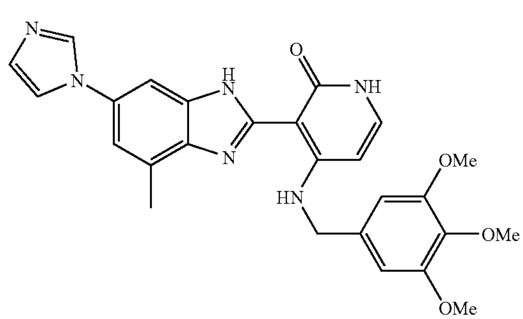 | 1.33 (b) | 487 |

| Example # | Name | structure | T (min.) | Mass (M + H)+ m/z |
|---|---|---|---|---|
| 80 | 4-[(Furan-2-ylmethyl)-amino]-3-(6-imidazol-1-yl-4-methyl-1H-benzimidazol-2-yl)-1H-pyridin-2-one | 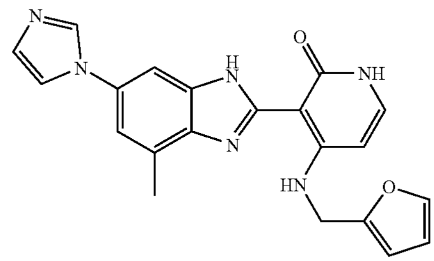 | 1.34 (b) | 387 |
| 81 | 3-(6-Imidazol-1-yl-4-methyl-1H-benzimidazol-2-yl)-4-[(thiophen-2-ylmethyl)-amino]-1H-pyridin-2-one | 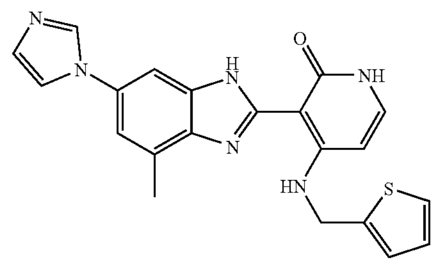 | 1.42 (b) | 403 |
| 82 | 3-(6-Imidazol-1-yl-4-methyl-1H-benzimidazol-2-yl)-4-[3-(2-oxo-pyrrolidin-1-yl)-propylamino]-1H-pyridin-2-one | 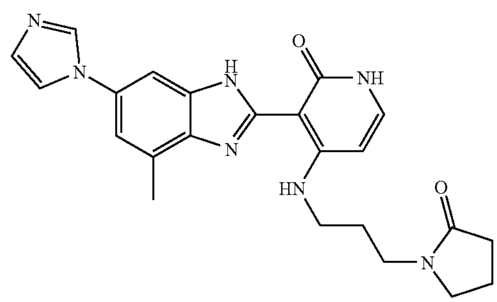 | 1.15 (b) | 432 |
| 83 | 4-[(1H-Benzimidazol-2-ylmethyl)-amino]-3-(6-imidazol-1-yl-4-methyl-1H-benzimidazol-2-yl)-1H-pyridin-2-one | 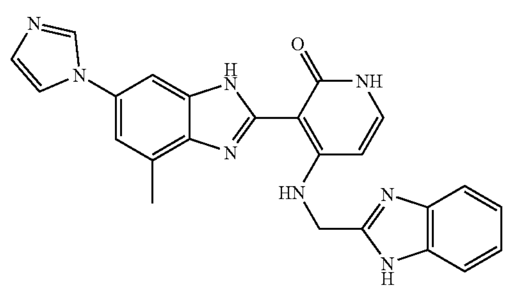 | 0.98 (b) | 437 |
| 84 | 4-[2-(6-Fluoro-1H-indol-2-yl)-ethylamino]-3-(6-imidazol-1-yl-4-methyl-1H-benzimidazol-2-yl)-1H-pyridin-2-one | 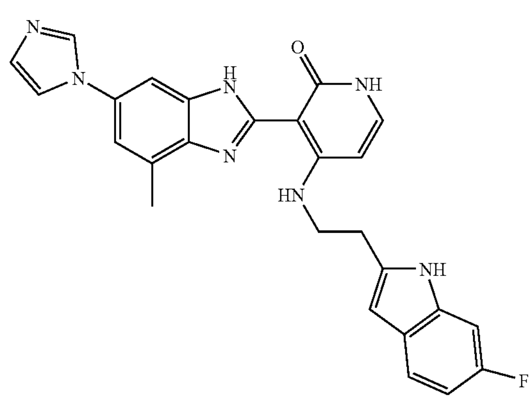 | 1.53 (b) | 468 |

-continued

| Example # | Name | structure | T (min.) | Mass (M + H)+ m/z |
|---|---|---|---|---|
| 85 | {2-[3-(6-Imidazol-1-yl-4-methyl-1H-benzimidazol-2-yl)-2-oxo-1,2-dihydro-pyridin-4-ylamino]-ethyl}-carbamic acid benzyl ester | 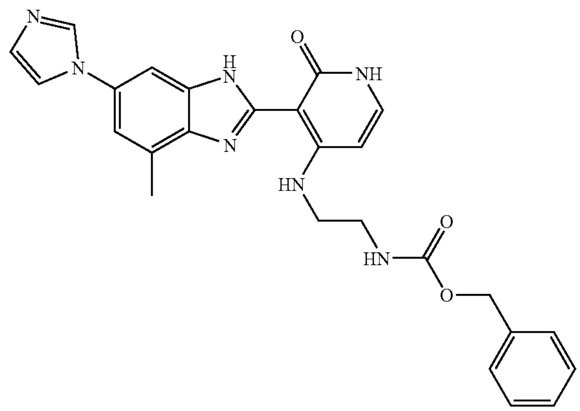 | 1.31 (b) | 484 |
| 86 | (1S,2R)-4-(2-Hydroxy-1,2-diphenyl-ethylamino)-3-(6-imidazol-1-yl-4-methyl-1H-benzimidazol-2-yl)-1H-pyridin-2-one | 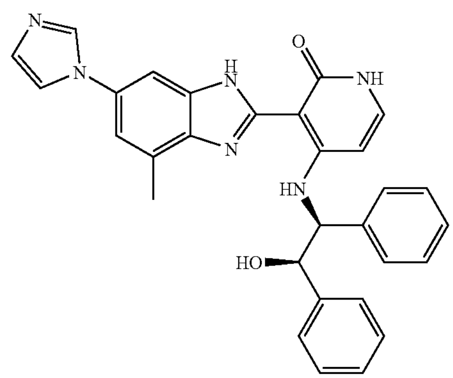 | 1.42 (b) | 503 |
| 87 | (±)-4-(2-[1,3]Dioxolan-2-yl-ethylamino)-3-(6-imidazol-1-yl-4-methyl-1H-benzimidazol-2-yl)-1H-pyridin-2-one | 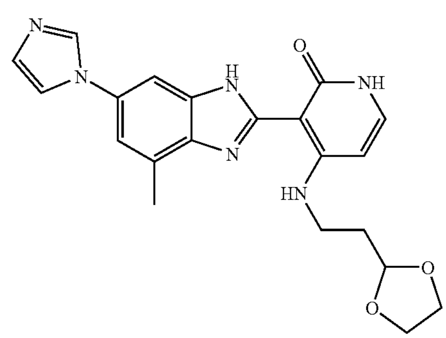 | 1.24 (b) | 407 |
| 88 | (±)-2-[3-(6-Imidazol-1-yl-4-methyl-1H-benzimidazol-2-yl)-2-oxo-1,2-dihydro-pyridin-4-ylamino]-3-phenyl-propionic acid methyl ester | 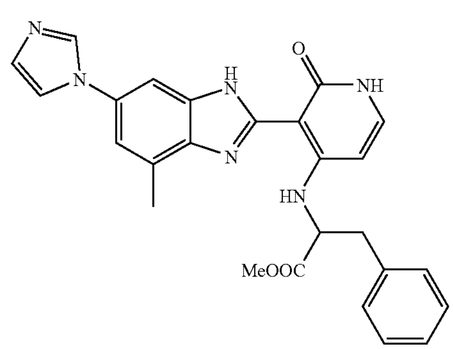 | 1.44 (b) | 469 |

-continued

| Example # | Name | structure | T (min.) | Mass (M + H)+ m/z |
|---|---|---|---|---|
| 89 | 3-(6-Imidazol-1-yl-4-methyl-1H-benzimidazol-2-yl)-4-(2-2H-[1,2,3]triazol-2-yl-ethylamino)-1H-pyridin-2-one | 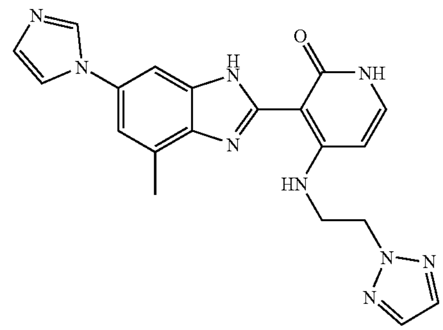 | 1.05 (b) | 402 |
| 90 | (±)-3-(6-Imidazol-1-yl-4-methyl-1H-benzimidazol-2-yl)-4-[(1-phenyl-1-pyridin-2-yl-methyl)-amino]-1H-pyridin-2-one | 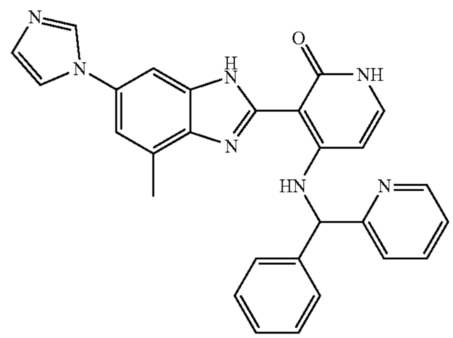 | 1.35 (b) | 474 |
| 91 | (1R,2S)-4-(1-Hydroxy-indan-2-ylamino)-3-(6-imidazol-1-yl-4-methyl-1H-benzimidazol-2-yl)-1H-pyridin-2-one | 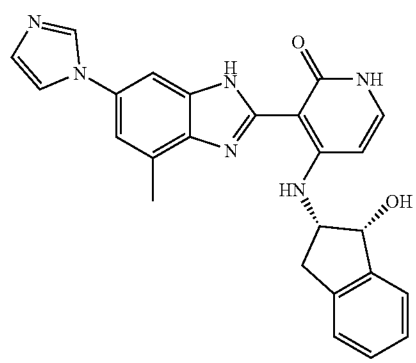 | 1.35 (b) | 439 |
| 92 | 3-(6-Imidazol-1-yl-4-methyl-1H-benzimidazol-2-yl)-4-phenethylamino-1H-pyridin-2-one | 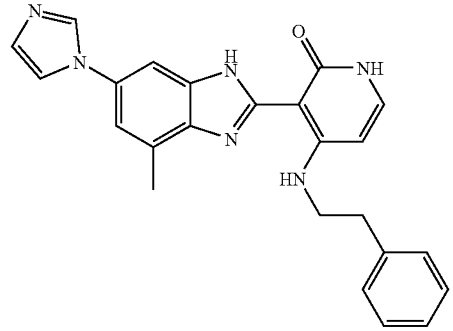 | 1.51 (b) | 411 |

| Example # | Name | structure | T (min.) | Mass (M + H)+ m/z |
|---|---|---|---|---|
| 93 | (±)-4-[2-Hydroxy-2-(3-hydroxy-phenyl)-ethylamino]-3-(6-imidazol-1-yl-4-methyl-1H-benzimidazol-2-yl)-1H-pyridin-2-one | 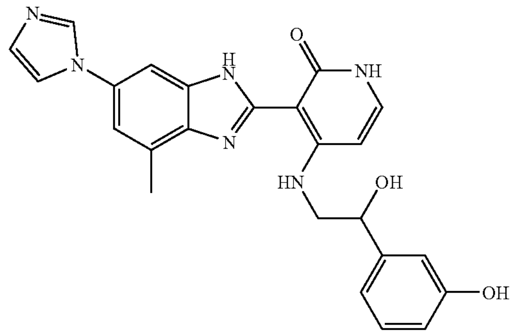 | 1.15 (a) | 443 |
| 94 | (S)-4-[1-Hydroxymethyl-2-(4-hydroxy-phenyl)-ethylamino]-3-(6-imidazol-1-yl-4-methyl-1H-benzimidazol-2-yl)-1H-pyridin-2-one | 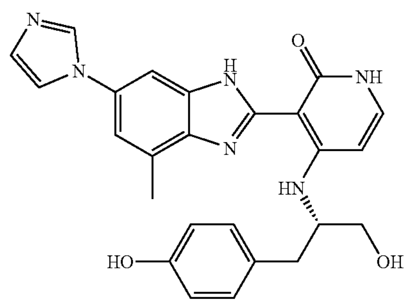 | 1.1 (b) | 457 |
| 95 | (R)-4-(2-Hydroxy-2-pyridin-2-yl-ethylamino)-3-(6-imidazol-1-yl-4-methyl-1H-benzimidazol-2-yl)-1H-pyridin-2-one | 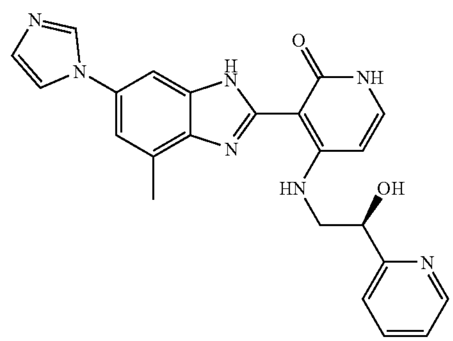 | 1.09 (a) | 428 |
| 96 | (S)-4-(2-Hydroxy-2-pyridin-2-yl-ethylamino)-3-(6-imidazol-1-yl-4-methyl-1H-benzimidazol-2-yl)-1H-pyridin-2-one | 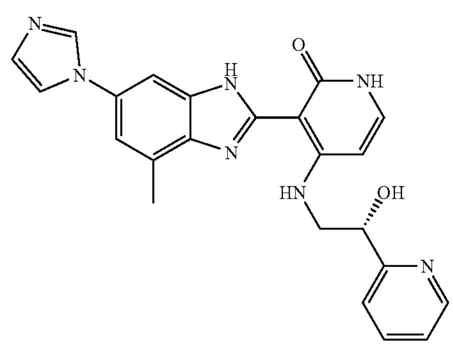 | 1.09 (a) | 428 |

-continued

| Example # | Name | structure | T (min.) | Mass (M + H)+ m/z |
|---|---|---|---|---|
| 97 | (S)-4-(2-Benzylsulfanyl-1-hydroxymethyl-ethylamino)-3-(6-imidazol-1-yl-4-methyl-1H-benzimidazol-2-yl)-1H-pyridin-2-one | 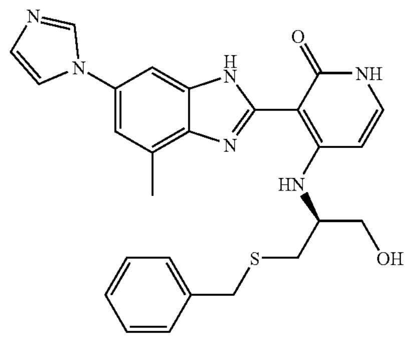 | 1.4 (b) | 487 |
| 98 | 4-(2-Hydroxy-ethylamino)-3-(6-imidazol-1-yl-4-methyl-1H-benzimidazol-2-yl)-1H-pyridin-2-one | 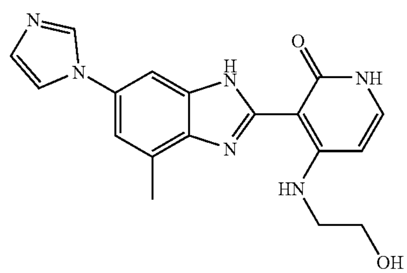 | 0.93 (b) | 351 |
| 99 | 3-(6-Imidazol-1-yl-4-methyl-1H-benzimidazol-2-yl)-[methyl-(2-pyridin-2-yl-ethylamino]-1H-pyridin-2-one | 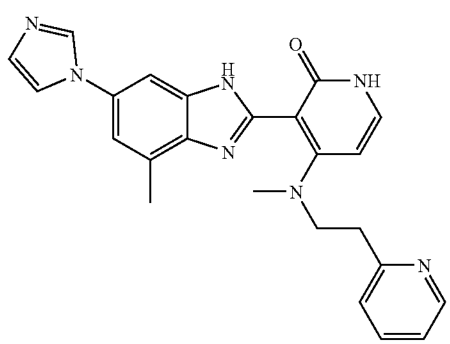 | 0.43 (b) | 426 |
| 100 | (S)-4-(1-Hydroxymethyl-2-pyridin-2-yl-ethylamino)-3-(6-imidazol-1-yl-4-methyl-1H-benzimidazol-2-yl)-1H-pyridin-2-one | 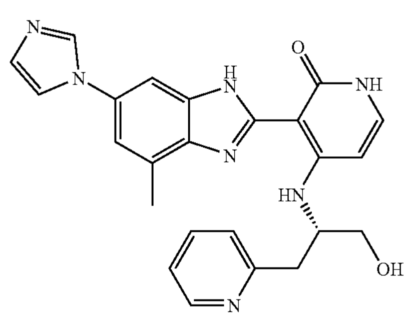 | 0.93 (f) | 442 |

-continued

| Example # | Name | structure | T (min.) | Mass (M + H)+ m/z |
|---|---|---|---|---|
| 101 | (R)-4-(1-Hydroxymethyl-2-pyridin-2-yl-ethylamino)-3-(6-imidazol-1-yl-4-methyl-1H-benzimidazol-2-yl)-1H-pyridin-2-one | 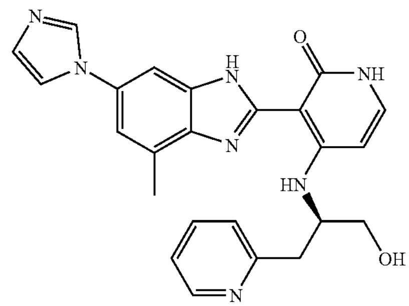 | 0.94 (f) | 442 |
| 102 | Dimethylamino-(6-imidazol-1-yl-4-methyl-1H-benzimidazol-2-yl)-1H-pyridin-2-one | 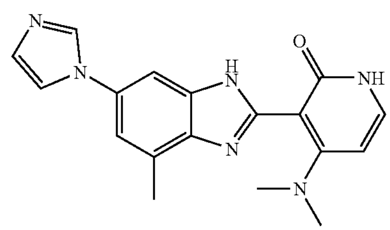 | 0.70 (f) | 335 |
| 103 | (1S,2S)-4-(2-Hydroxy-1-hydroxymethyl-2-phenyl-ethylamino)-3-(6-imidazol-1-yl-4-methyl-1H-benzimidazol-2-yl)-1H-pyridin-2-one | 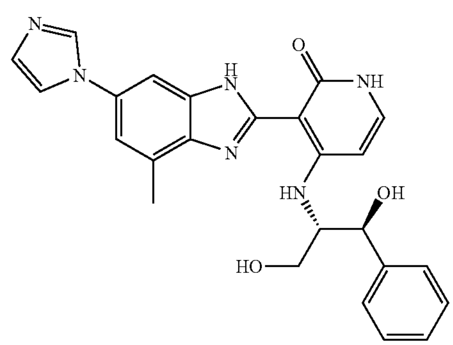 | 1.10 (b) | 457 |
| 104 | (±)-4-[2-Hydroxy-3-(naphthalen-1-yloxy)-propylamino]-3-(6-imidazol-1-yl-4-methyl-1H-benzimidazol-2-yl)-1H-pyridin-2-one | 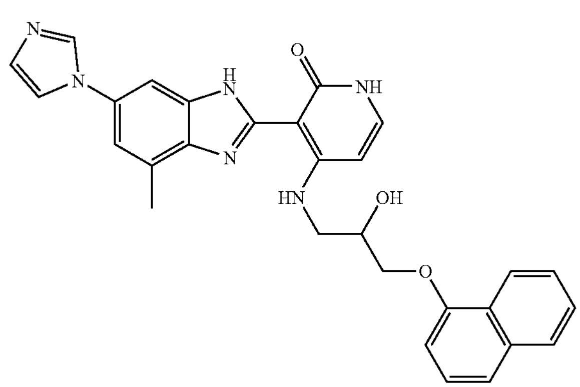 | 1.53 (b) | 507 |

-continued

| Example # | Name | structure | T (min.) | Mass (M + H)+ m/z |
|---|---|---|---|---|
| 105 | (1R,2R)-4-(2-Benzyloxy-1-hydroxymethyl-propylamino)-3-(6-imidazol-1-yl-4-methyl-1H-benzoimidazol-2-yl)-1H-pyridin-2-one | 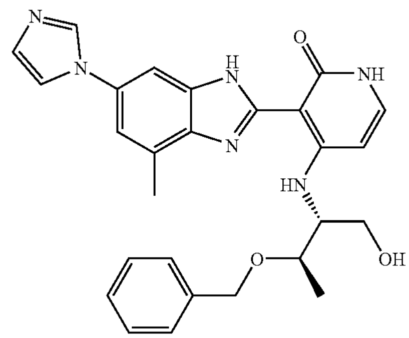 | 3.14 (a) | 485 |
| 106 | (S)-3-Hydroxy-2-[3-(6-imidazol-1-yl-4-methyl-1H-benzimidazol-2-yl)-2-oxo-1,2-dihydro-pyridin-4-ylamino]-propionic acid benzyl ester | 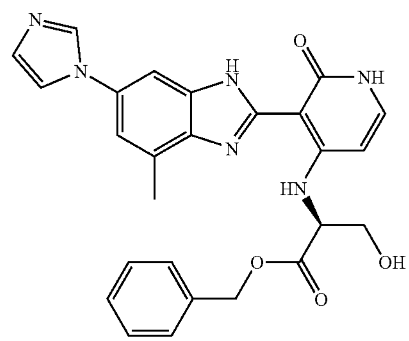 | 2.95 (a) | 485 |
| 107 | (S)-3-Hydroxy-2-[3-(6-imidazol-1-yl-4-methyl-1H-benzimidazol-2-yl)-2-oxo-1,2-dihydro-pyridin-4-ylamino]-propionic acid methyl ester | 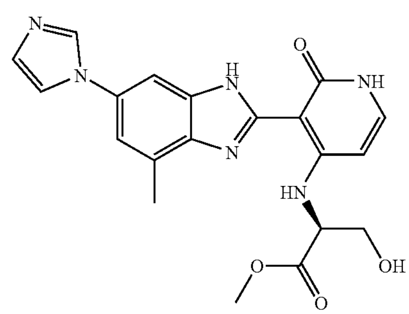 | 2.29 (a) | 409 |
| 108 | (S)-2-[3-(6-Imidazol-1-yl-4-methyl-1H-benzimidazol-2-yl)-2-oxo-1,2-dihydro-pyridin-4-ylamino]-3-pyridin-2-yl-propionic acid | 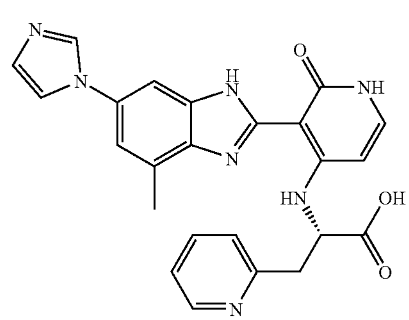 | 0.94 (f) | 456 |

-continued

| Example # | Name | structure | T (min.) | Mass (M + H)+ m/z |
|---|---|---|---|---|
| 109 | 3-(6-Imidazol-1-yl-4-methyl-1H-benzimidazol-2-yl)-4-(pyridin-3-ylamino)-1H-pyridin-2-one | 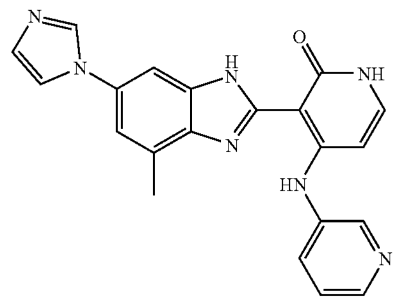 | 1.15 (a) | 384 |
| 110 | 3-(6-Imidazol-1-yl-4-methyl-1H-benzimidazol-2-yl)-4-(pyridin-4-ylamino)-1H-pyridin-2-one | 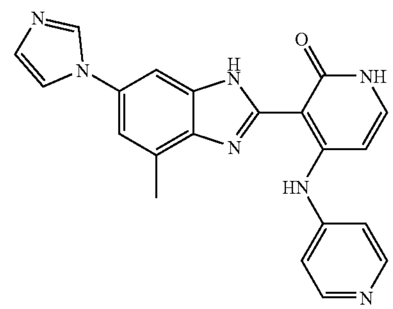 | 0.65 (f) | 384 |
| 111 | (S)-4-[2-(3,4-Dihydroxy-phenyl)-2-hydroxy-ethylamino]-3-(6-imidazol-1-yl-4-methyl-1H-benzimidazol-2-yl)-1H-pyridin-2-one | 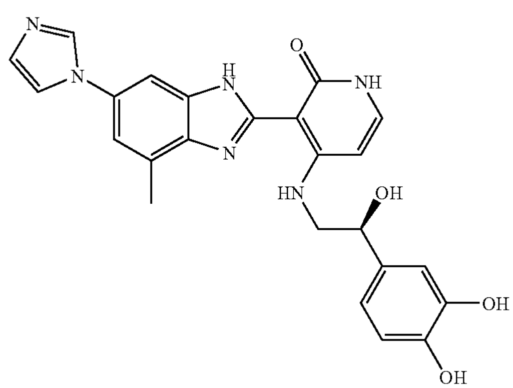 | 1.04 (b) | 459 |
| 112 | (S)-4-[1-Hydroxymethyl-2-(3-methyl-benzylsulfanyl)-ethylamino]-3-(6-imidazol-1-yl-4-methyl-1H-benzimidazol-2-yl)-1H-pyridin-2-one | 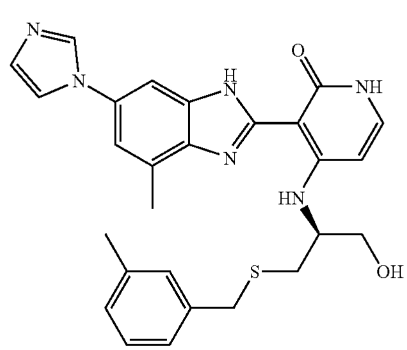 | 1.49 (b) | 501 |

| Example # | Name | structure | T (min.) | Mass (M + H)+ m/z |
|---|---|---|---|---|
| 113 | (S)-4-[1-Hydroxymethyl-2-(4-methyl-benzylsulfanyl)-ethylamino]-3-(6-imidazol-1-yl-4-methyl-1H-benzimidazol-2-yl)-1H-pyridin-2-one | 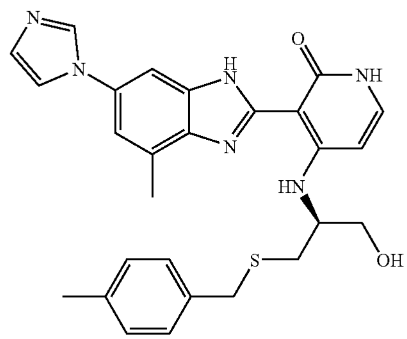 | 1.49 (b) | 501 |
| 114 | (±)-4-[2-Hydroxy-2-(4-hydroxy-3-methoxy-phenyl)-ethylamino]-3-(6-imidazol-1-yl-4-methyl-1H-benzimidazol-2-yl)-1H-pyridin-2-one | 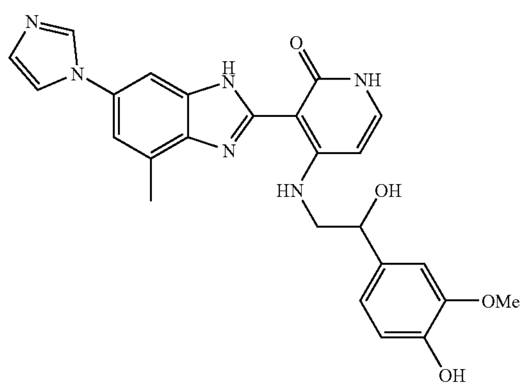 | 1.10 (b) | 473 |
| 115 | 4-(2-Hydroxy-2-naphthalen-1-yl-ethylamino)-3-(6-imidazol-1-yl-4-methyl-1H-benzimidazol-2-yl)-1H-pyridin-2-one | 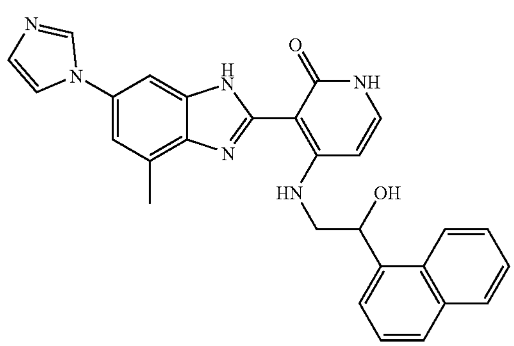 | 1.49 (b) | 477 |
| 116 | (S)-N-(1-Carbamoyl-2-phenyl-ethyl)-3-hydroxy-2-[3-(6-imidazol-1-yl-4-methyl-1H-benzimidazol-2-yl)-2-oxo-1,2-dihydro-pyridin-4-ylamino]-propionamide | 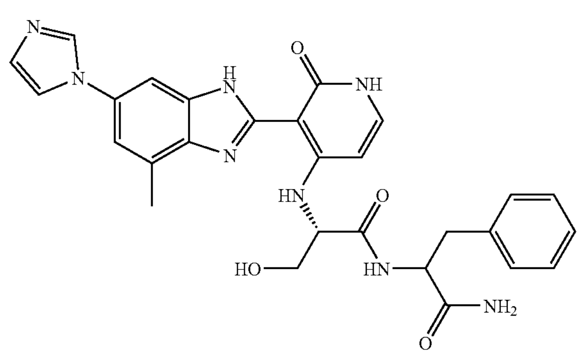 | 1.07 (b) | 541 |

-continued

| Example # | Name | structure | T (min.) | Mass (M + H)+ m/z |
|---|---|---|---|---|
| 117 | (±)-N-(4'-{1-Hydroxy-2-[3-(6-imidazol-1-yl-4-methyl-1H-benzimidazol-2-yl)-2-oxo-1,2-dihydro-pyridin-4-ylamino]-ethyl}-biphenyl-2-yl)-methanesulfonamide | 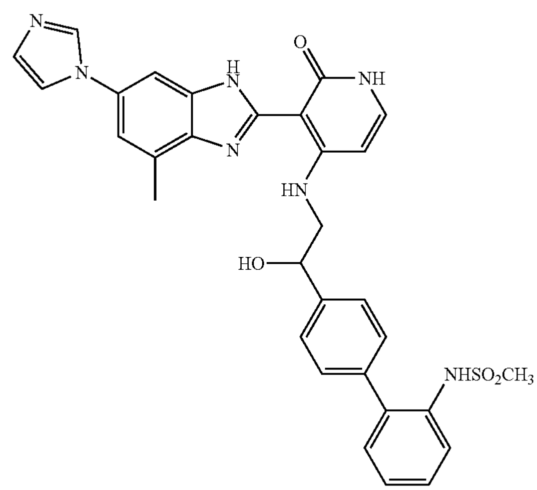 | 1.34 (b) | 596 |
| 118 | (±)-N-(4-{1-Hydroxy-2-[3-(6-imidazol-1-yl-4-methyl-1H-benzimidazol-2-yl)-2-oxo-1,2-dihydro-pyridin-4-ylamino]-ethyl}-phenyl)-methanesulfonamide | 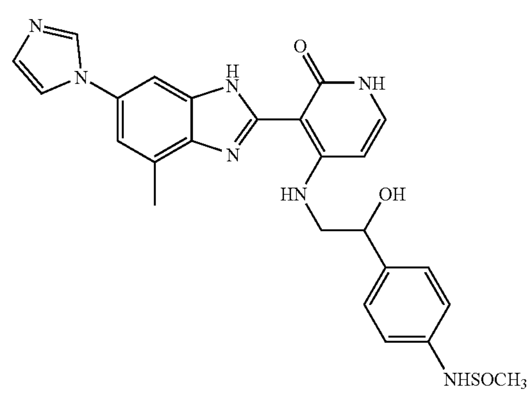 | 1.11 (b) | 520 |
| 119 | (±)-N-(3-{1-Hydroxy-2-[3-(6-imidazol-1-yl-4-methyl-1H-benzimidazol-2-yl)-2-oxo-1,2-dihydro-pyridin-4-ylamino]-ethyl}-phenyl)-methanesulfonamide | 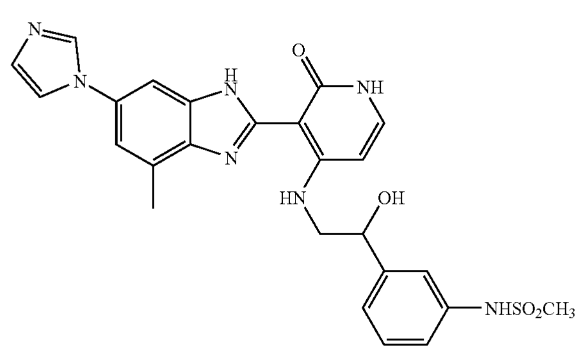 | 1.14 (b) | 520 |

-continued

| Example # | Name | structure | T (min.) | Mass (M + H)+ m/z |
|---|---|---|---|---|
| 120 | (±)-N-(5-{1-Hydroxy-2-[3-(6-imidazol-1-yl-4-methyl-1H-benzimidazol-2-yl)-2-oxo-1,2-dihydro-pyridin-4-ylamino]-ethyl}-2-methoxy-phenyl)-methanesulfonamide | 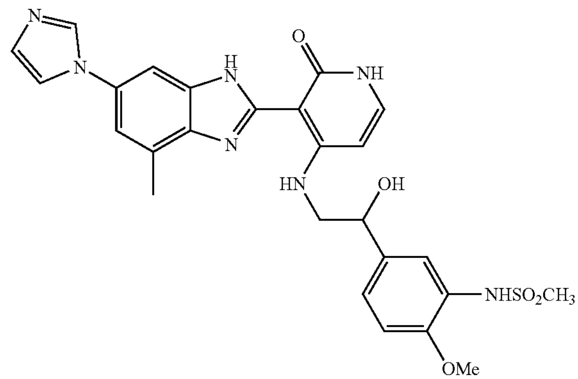 | 1.12 (b) | 550 |
| 121 | (±)-N-(2-{1-Hydroxy-2-[3-(6-imidazol-1-yl-4-methyl-1H-benzimidazol-2-yl)-2-oxo-1,2-dihydro-pyridin-4-ylamino]-ethyl}-phenyl)-methanesulfonamide | 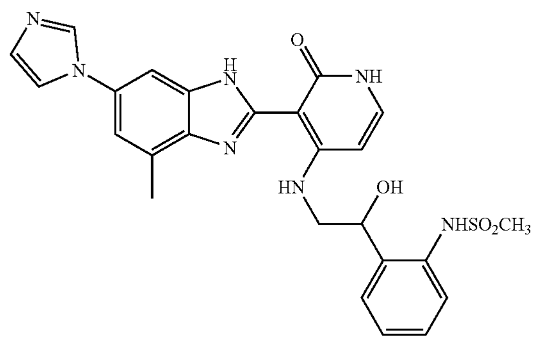 | 1.19 (b) | 520 |
| 122 | (±)-N-(3-{1-Hydroxy-2-[3-(6-imidazol-1-yl-4-methyl-1H-benzimidazol-2-yl)-2-oxo-1,2-dihydro-pyridin-4-ylamino]-ethyl}-phenyl)-4-methyl-benzenesulfonamide | 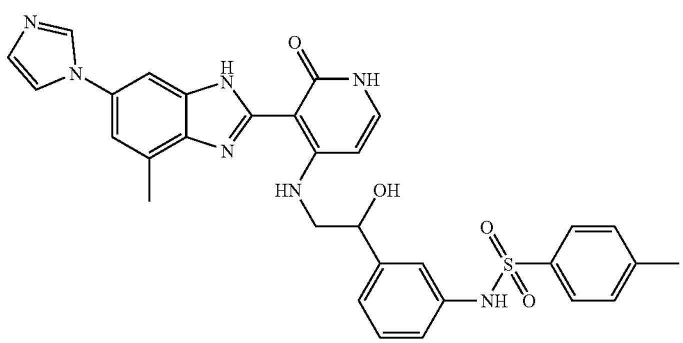 | 1.33 (b) | 596 |
| 123 | (±)-2,2,2-Trifluoro-N-(3-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-acetamide | 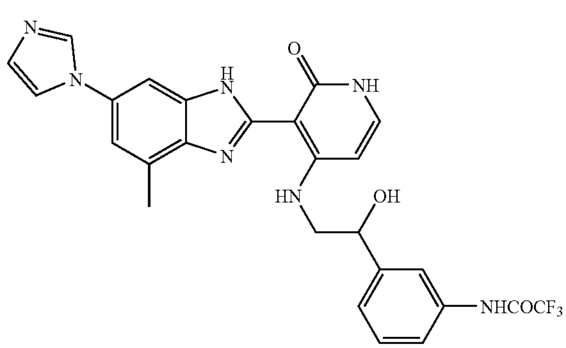 | 2.97 (a) | 538 |

-continued

| Example # | Name | structure | T (min.) | Mass (M + H)+ m/z |
|---|---|---|---|---|
| 124 | (±)-N-(2-Chloro-5-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-methanesulfonamide | 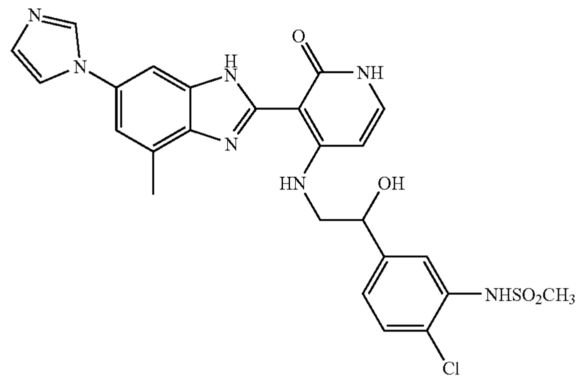 | 2.75 (a) | 554 |
| 125 | (±)-N-(5-{1-Hydroxy-2-[3-(6-imidazol-1-yl-4-methyl-1H-benzimidazol-2-yl)-2-oxo-1,2-dihydro-pyridin-4-ylamino]-ethyl}-2-methyl-phenyl)-methanesulfonamide | 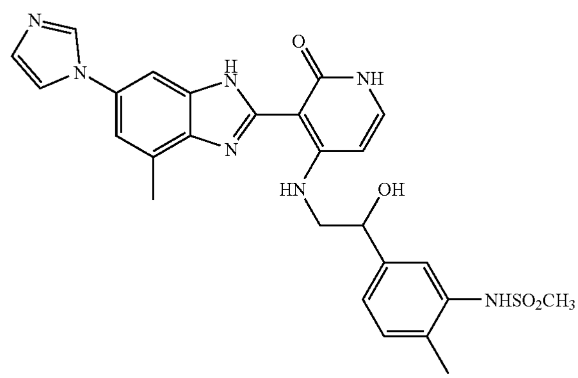 | 2.73 (a) | 534 |
| 126 | (S)-2-[3-(6-Imidazol-1-yl-4-methyl-1H-benzimidazol-2-yl)-2-oxo-1,2-dihydro-pyridin-4-ylamino]-3-phenyl-propionic acid | 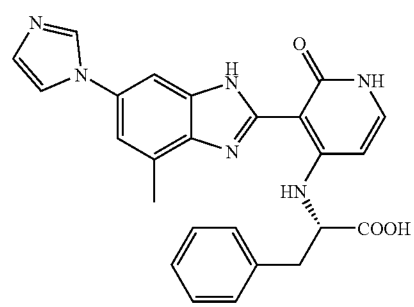 | 1.50 (f) | 455 |
| 127 | (S)-2-[3-(6-Imidazol-1-yl-4-methyl-1H-benzimidazol-2-yl)-2-oxo-1,2-dihydro-pyridin-4-ylamino]-N-methyl-3-phenyl-propionamide | 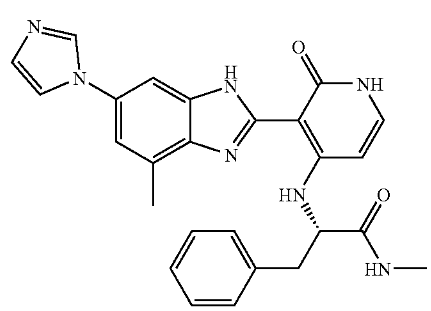 | 1.43 (f) | 468 |

-continued

| Example # | Name | structure | T (min.) | Mass (M + H)+ m/z |
|---|---|---|---|---|
| 128 | (S)-2-[3-(6-Imidazol-1-yl-4-methyl-1H-benzimidazol-2-yl)-2-oxo-1,2-dihydro-pyridin-4-ylamino]-3-phenyl-propionamide | 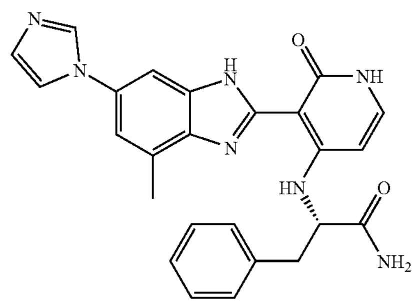 | 1.39 (f) | 454 |
| 129 | (S)-2-[3-(6-Imidazol-1-yl-4-methyl-1H-benzimidazol-2-yl)-2-oxo-1,2-dihydro-pyridin-4-ylamino]-N,N-dimethyl-3-phenyl-propionamide | 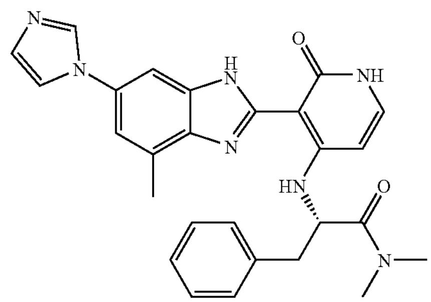 | 1.48 (f) | 482 |
| 130 | (R)-4-(2-Hydroxy-1-phenyl-ethylamino)-3-(6-imidazol-1-yl-4-methyl-1H-benzimidazol-2-yl)-1H-pyridin-2-one | 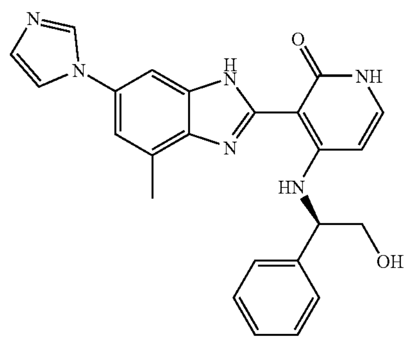 | 1.44 (f) | 427 |
| 131 | 3-(6-Imidazol-1-yl-4-methyl-1H-benzimidazol-2-yl)-4-(3-pyridin-2-yl-propylamino)-1H-pyridin-2-one | 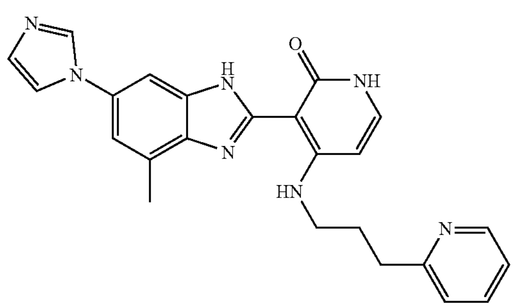 | 1.0 (b) | 426 |
| 132 | (S)-4-(1-Benzyl-4-hydroxy-2-oxo-butylamino)-3-(6-imidazol-1-yl-4-methyl-1H-benzimidazol-2-yl)-1H-pyridin-2-one | 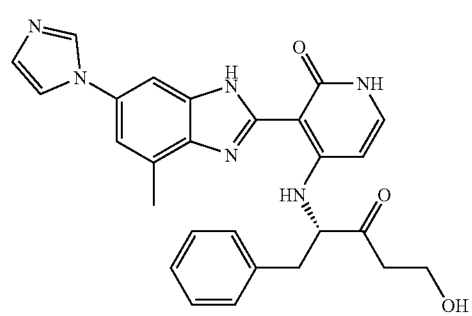 | 1.41 (f) | 483 |

-continued

| Example # | Name | structure | T (min.) | Mass (M + H)+ m/z |
|---|---|---|---|---|
| 133 | 3-(6-Imidazol-1-yl-4-methyl-1H-benzimidazol-2-yl)-4-(4-pyridin-2-yl-n-butylamino)-1H-pyridin-2-one | 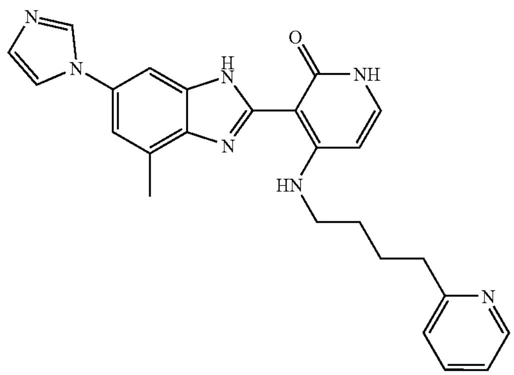 | 1.06 (d) | 440 |
| 134 | (S)-4-(1-Aminomethyl-2-phenyl-ethylamino)-3-(6-imidazol-1-yl-4-methyl-1H-benzimidazol-2-yl)-1H-pyridin-2-one | 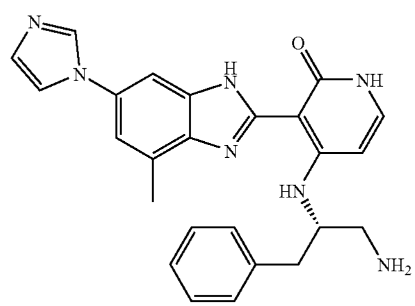 | 1.27 (f) | 440 |
| 135 | (S)-3-(6-Imidazol-1-yl-4-methyl-1H-benzimidazol-2-yl)-4-(1-methylaminomethyl-2-phenyl-ethylamino)-1H-pyridin-2-one | 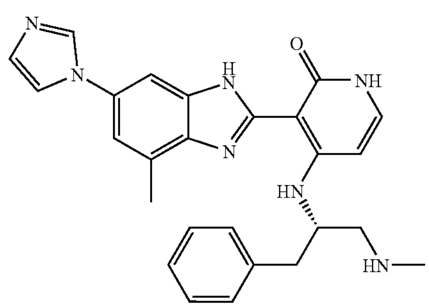 | 1.27 (f) | 454 |
| 136 | (S)-4-(1-Dimethylaminomethyl-2-phenyl-ethylamino)-3-(6-imidazol-1-yl-4-methyl-1H-benzimidazol-2-yl)-1H-pyridin-2-one | 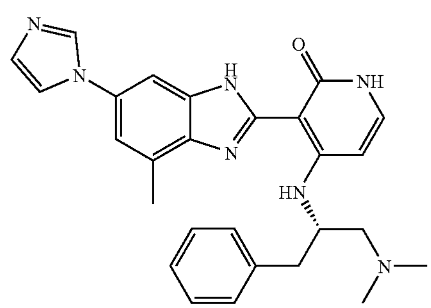 | 1.25 (f) | 468 |

-continued

| Example # | Name | structure | T (min.) | Mass (M + H)+ m/z |
|---|---|---|---|---|
| 137 | 4-(4-Hydroxy-butylamino)-3-(6-imidazol-1-yl-4-methyl-1H-benzimidazol-2-yl)-1H-pyridin-2-one | 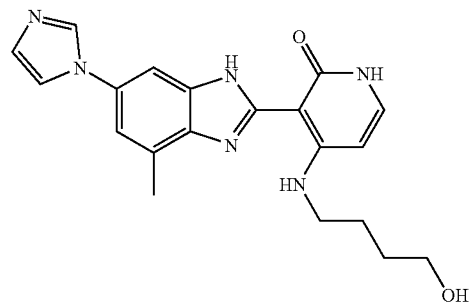 | 1.19 (f) | 379 |
| 138 | (±)-4-[2-Hydroxy-2-(3-trifluoromethyl-phenyl)-ethylamino]-3-(6-imidazol-1-yl-4-methyl-1H-benzimidazol-2-yl)-1H-pyridin-2-one | 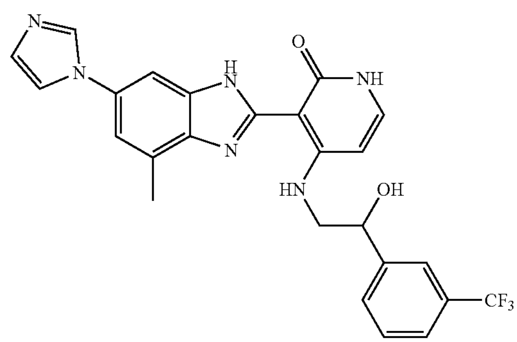 | 1.40 (b) | 495 |
| 139 | (±)-4-[2-Hydroxy-2-(3,4,5-trimethoxy-phenyl)-ethylamino]-3-(6-imidazol-1-yl-4-methyl-1H-benzimidazol-2-yl)-1H-pyridin-2-one | 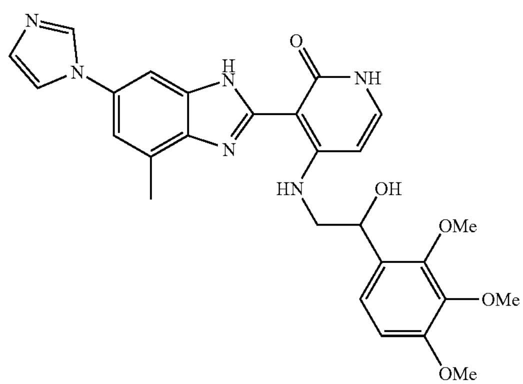 | 1.18 (b) | 517 |
| 140 | (S)-4-(1-Benzyl-2-methoxy-ethylamino)-3-(6-imidazol-1-yl-4-methyl-1H-benzimidazol-2-yl)-1H-pyridin-2-one | 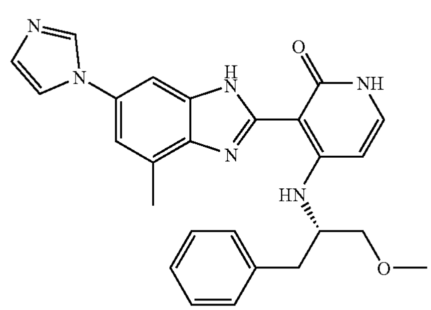 | 1.67 (f) | 455 |

-continued

| Example # | Name | structure | T (min.) | Mass (M + H)+ m/z |
|---|---|---|---|---|
| 141 | 4-(3-Hydroxy-propylamino)-3-(6-imidazol-1-yl-4-methyl-1H-benzimidazol-2-yl)-1H-pyridin-2-one | 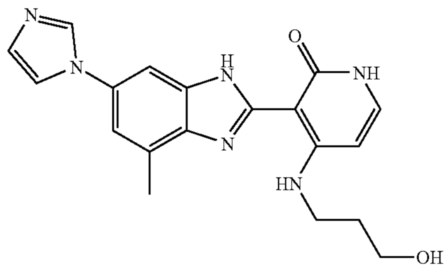 | 0.95 (f) | 365 |
| 142 | (±)-4-[2-Hydroxy-1-(4-nitro-benzyl)-ethylamino]-3-(6-imidazol-1-yl-4-methyl-1H-benzimidazol-2-yl)-1H-pyridin-2-one | 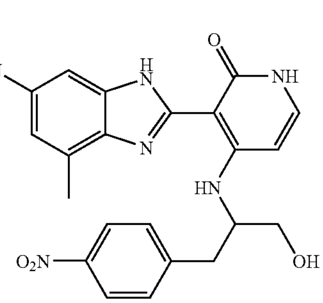 | 1.51 (a) | 486 |
| 143 | (±)-4-[1-(2-Fluoro-benzyl)-2-hydroxy-ethylamino]-3-(6-imidazol-1-yl-4-methyl-1H-benzimidazol-2-yl)-1H-pyridin-2-one | 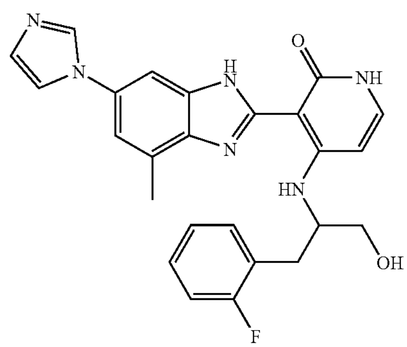 | 1.57 (a) | 459 |
| 144 | (±)-4-[1-(3-Fluoro-benzyl)-2-hydroxy-ethylamino]-3-(6-imidazol-1-yl-4-methyl-1H-benzimidazol-2-yl)-1H-pyridin-2-one | 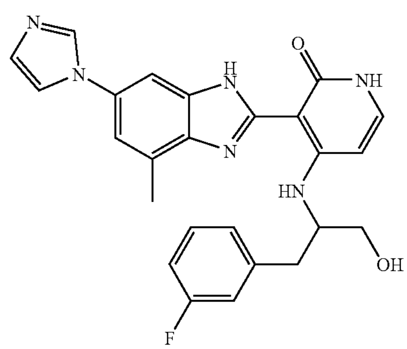 | 1.57 (a) | 459 |
| 145 | (S)-4-[2-Hydroxy-1-(4-methoxy-benzyl)-ethylamino]-3-(6-imidazol-1-yl-4-methyl-1H-benzimidazol-2-yl)-1H-pyridin-2-one | 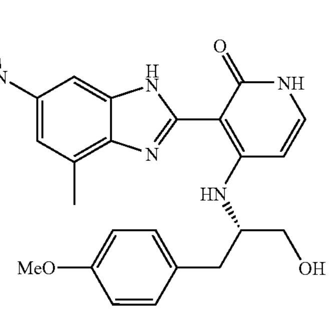 | 1.54 (a) | 471 |

-continued

| Example # | Name | structure | T (min.) | Mass (M + H)+ m/z |
|---|---|---|---|---|
| 146 | (±)-4-[2-Hydroxy-1-(3-hydroxy-benzyl)-ethylamino]-3-(6-imidazol-1-yl-4-methyl-1H-benzimidazol-2-yl)-1H-pyridin-2-one | 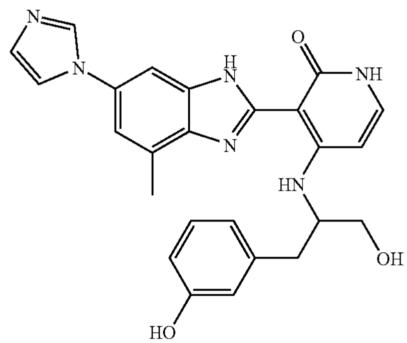 | 1.38 (a) | 457 |
| 147 | 3-(6-Imidazol-1-yl-4-methyl-1H-benzimidazol-2-yl)-4-[(isoquinolin-3-ylmethyl)-amino]-1H-pyridin-2-one | 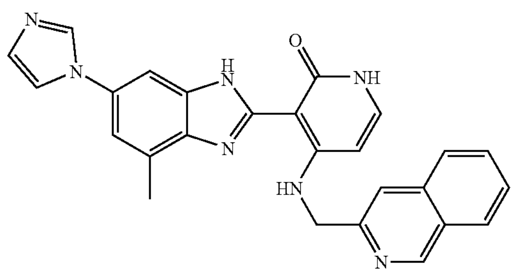 | 1.15 (d) | 448 |
| 148 | 3-(6-Imidazol-1-yl-4-methyl-1H-benzimidazol-2-yl)-4-{[4-(3-phenyl-propyl)-pyridin-2-ylmethyl]-amino}-1H-pyridin-2-one | 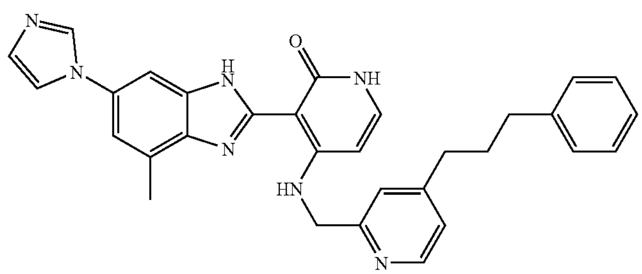 | 1.31 (d) | 516 |
| 149 | 3-(6-Imidazol-1-yl-4-methyl-1H-benzimidazol-2-yl)-4-[(3-methyl-pyridin-2-ylmethyl)-amino]-1H-pyridin-2-one | 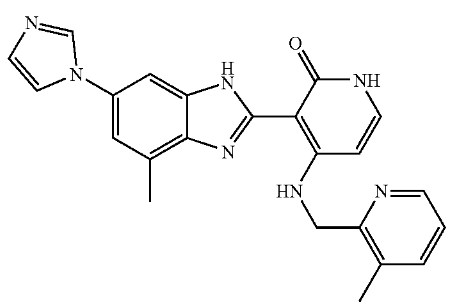 | 1.00 (d) | 412 |
| 150 | 4-[(3,5-Dimethyl-pyridin-2-ylmethyl)-amino]-3-(6-imidazol-1-yl-4-methyl-1H-benzimidazol-2-yl)-1H-pyridin-2-one | 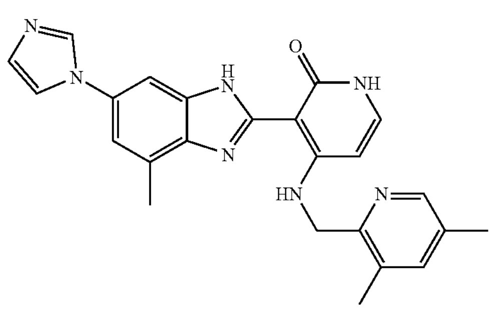 | 1.00 (d) | 426 |

-continued

| Example # | Name | structure | T (min.) | Mass (M + H)+ m/z |
|---|---|---|---|---|
| 151 | 4-[(3-Hydroxymethyl-pyridin-2-ylmethyl)-amino]-3-(6-imidazol-1-yl-4-methyl-1H-benzimidazol-2-yl)-1H-pyridin-2-one | 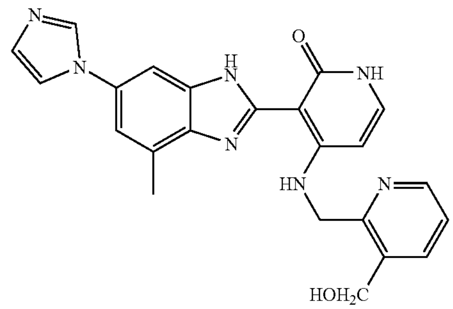 | 0.93 (d) | 428 |
| 152 | (S)-4-[2-Hydroxy-1-(4-hydroxy-3-nitro-benzyl)-ethylamino]-3-(6-imidazol-1-yl-4-methyl-1H-benzimidazol-2-yl)-1H-pyridin-2-one | 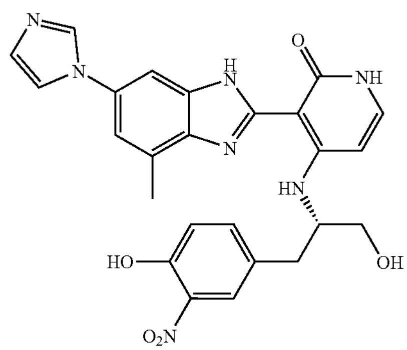 | 1.47 (a) | 486 |
| 153 | (S)-4-[2-Hydroxy-1-(4-iodo-benzyl)-ethylamino]-3-(6-imidazol-1-yl-4-methyl-1H-benzimidazol-2-yl)-1H-pyridin-2-one | 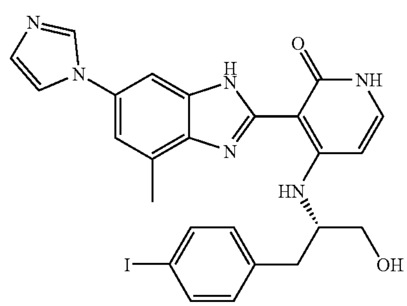 | 1.73 (a) | 567 |
| 154 | (S)-4-[2-Hydroxy-1-(4-hydroxy-3-iodo-benzyl)-ethylamino]-3-(6-imidazol-1-yl-4-methyl-1H-benzimidazol-2-yl)-1H-pyridin-2-one | 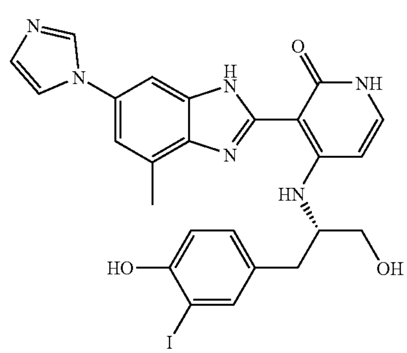 | 1.44 (a) | 583 |
| 155 | 3-(6-Imidazol-1-yl-4-methyl-1H-benzimidazol-2-yl)-4-[(6-methyl-pyridin-2-ylmethyl)-amino]-1H-pyridin-2-one | 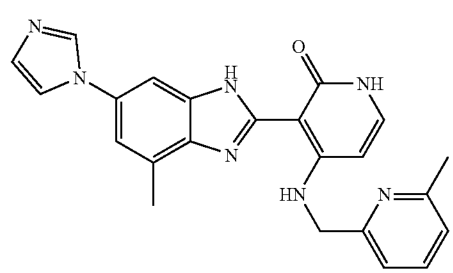 | 0.71 (b) | 412 |

-continued

| Example # | Name | structure | T (min.) | Mass (M + H)+ m/z |
|---|---|---|---|---|
| 156 | 4-[2-(5-Ethyl-pyridin-2-yl)-ethylamino]-3-(6-imidazol-1-yl-4-methyl-1H-benzimidazol-2-yl)-1H-pyridin-2-one | 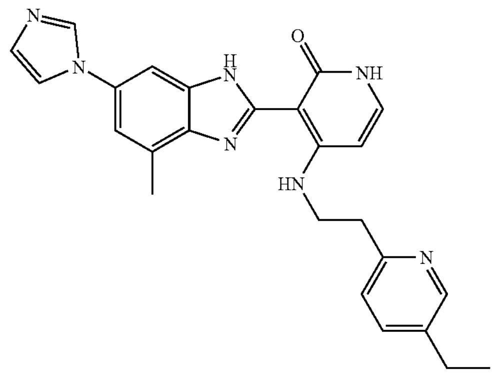 | 1.01 (b) | 440 |
| 157 | (±)-4-(2,3-Dihydroxy-propylamino)-3-(6-imidazol-1-yl-4-methyl-1H-benzimidazol-2-yl)-1H-pyridin-2-one | 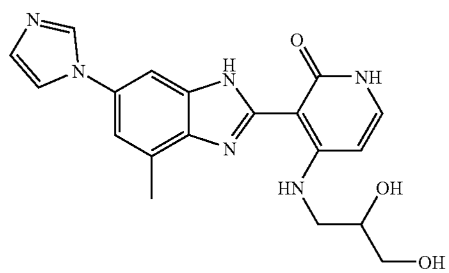 | 1.11 (a) | 381 |
| 158 | (S)-4-[2-Hydroxy-1-(4-hydroxy-3-methoxy-benzyl)-ethylamino]-3-(6-imidazol-1-yl-4-methyl-1H-benzimidazol-2-yl)-1H-pyridin-2-one | 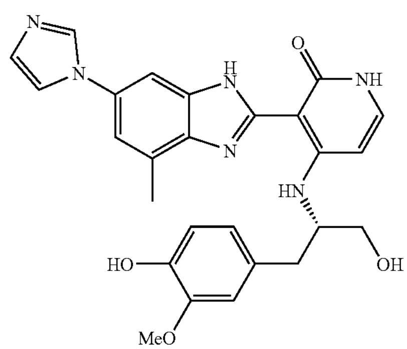 | 1.29 (f) | 491 |
| 159 | (S)-4-[1-(4-Fluoro-benzyl)-2-hydroxy-ethylamino]-3-(6-imidazol-1-yl-4-methyl-1H-benzimidazol-2-yl)-1H-pyridin-2-one | 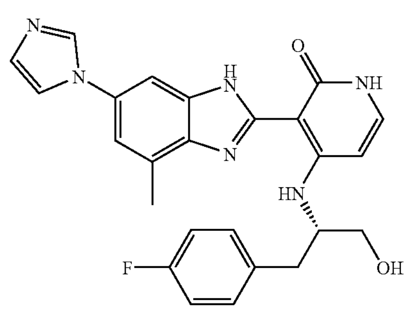 | 1.57 (a) | 459 |

-continued

| Example # | Name | structure | T (min.) | Mass (M + H)+ m/z |
|---|---|---|---|---|
| 160 | (S)-4-[2-Hydroxy-1-(naphthalen-1-yl-methyl)-ethylamino]-3-(6-imidazol-1-yl-4-methyl-1H-benzimidazol-2-yl)-1H-pyridin-2-one | 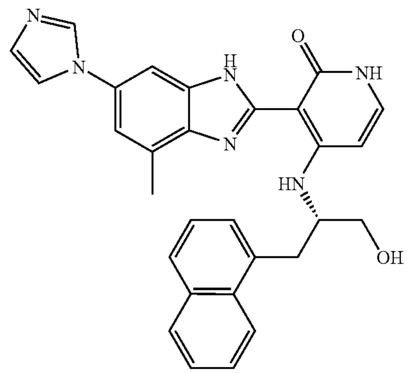 | 1.71 (a) | 491 |
| 161 | 4-(2-Hydroxy-1-hydroxymethyl-ethylamino)-3-(6-imidazol-1-yl-4-methyl-1H-benzimidazol-2-yl)-1H-pyridin-2-one | 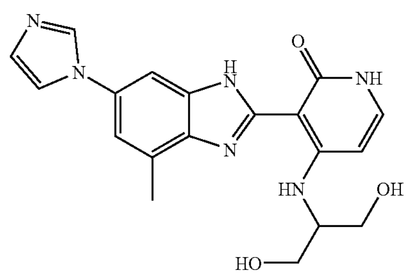 | 1.00 (f) | 381 |
| 162 | 4-[2-Hydroxy-1,1-bis-hydroxymethyl-ethylamino)-3-(6-imidazol-1-yl-4-methyl-1H-benzimidazol-2-yl)-1H-pyridin-2-one | 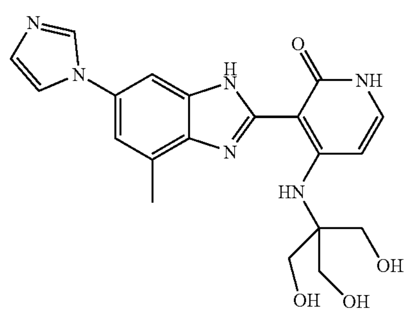 | 0.89 (f) | 411 |
| 163 | (±)-4-[2-(3-Fluoro-phenyl)-2-hydroxy-ethylamino]-3-(6-imidazol-1-yl-4-methyl-1H-benzimidazol-2-yl)-1H-pyridin-2-one | 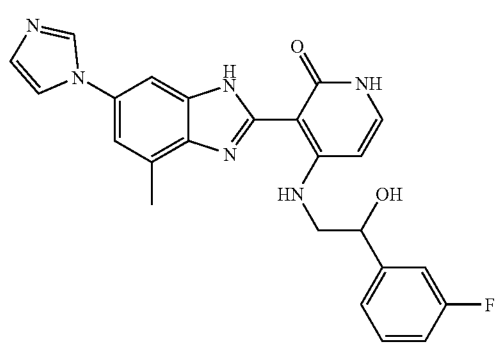 | 1.38 (b) | 445 |

| Example # | Name | structure | T (min.) | Mass (M + H)+ m/z |
|---|---|---|---|---|
| 164 | (±)-4-[2-Hydroxy-2-(3-methoxy-phenyl)-ethylamino]-3-(6-imidazol-1-yl-4-methyl-1H-benzimidazol-2-yl)-1H-pyridin-2-one | 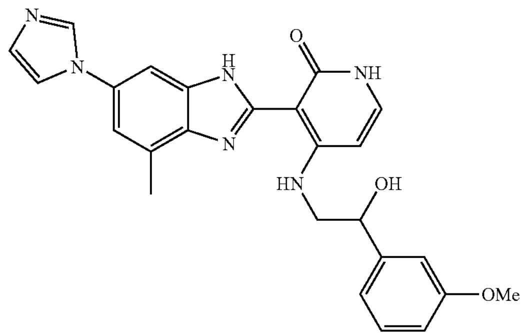 | 1.35 (b) | 457 |
| 165 | (±)-4-[2-Hydroxy-2-(4-methoxy-phenyl)-ethylamino]-3-(6-imidazol-1-yl-4-methyl-1H-benzimidazol-2-yl)-1H-pyridin-2-one | 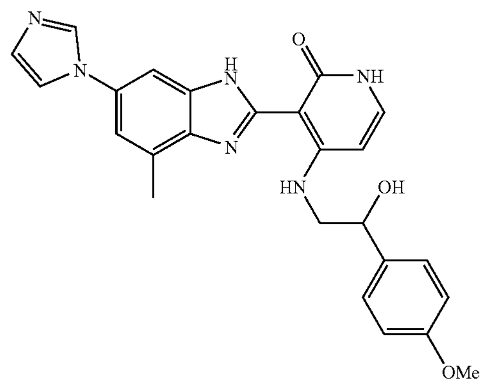 | 1.35 (b) | 457 |
| 166 | (±)-4-(2-Hydroxy-3-phenyl-propylamino)-3-(6-imidazol-1-yl-4-methyl-1H-benzimidazol-2-yl)-1H-pyridin-2-one | 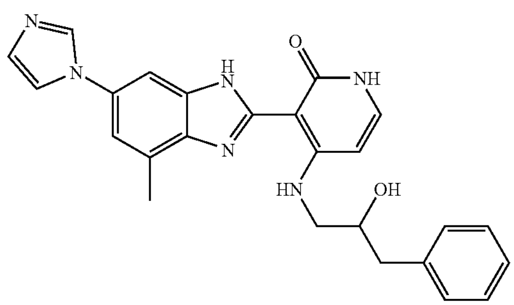 | 1.44 (b) | 441 |
| 167 | 3-(6-Imidazol-1-yl-4-methyl-1H-benzimidazol-2-yl)-4-[(3-trifluoromethyl-pyridin-2-ylmethyl)-amino]-1H-pyridin-2-one | 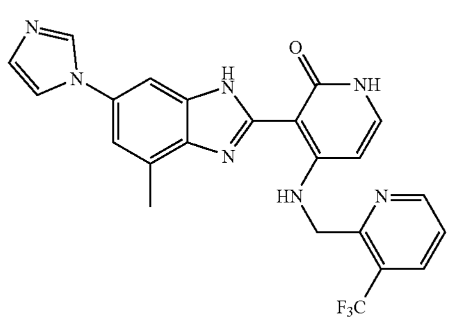 | 1.53 (d) | 466 |

| Example # | Name | structure | T (min.) | Mass (M + H)+ m/z |
|---|---|---|---|---|
| 168 | 4-[(6-Ethoxy-pyridin-2-ylmethyl)-amino]-3-(6-imidazol-1-yl-4-methyl-1H-benzimidazol-2-yl)-1H-pyridin-2-one | 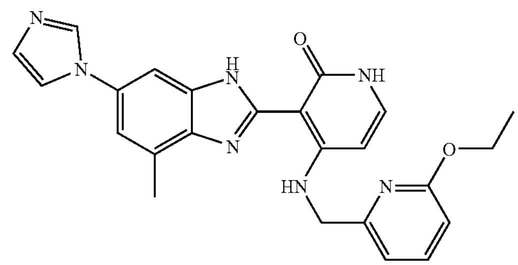 | 1.51 (d) | 442 |
| 169 | 4-[(4-Chloro-pyridin-2-ylmethyl)-amino]-3-(6-imidazol-1-yl-4-methyl-1H-benzimidazol-2-yl)-1H-pyridin-2-one | 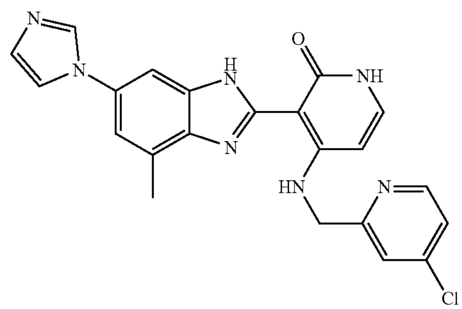 | 1.38 (d) | 432 |
| 170 | 3-(6-Imidazol-1-yl-4-methyl-1H-benzimidazol-2-yl)-4-[(4-phenyl-pyridin-2-ylmethyl)-amino]-1H-pyridin-2-one | 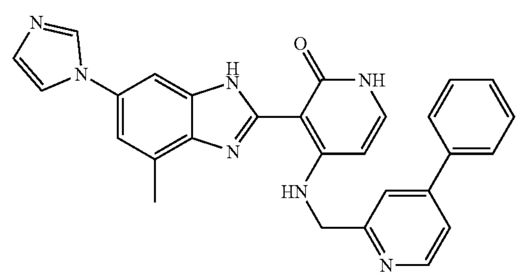 | 1.24 (d) | 474 |
| 171 | 3-(6-Imidazol-1-yl-4-methyl-1H-benzimidazol-2-yl)-4-[(4-benzyloxy-pyridin-2-ylmethyl)-amino]-1H-pyridin-2-one | 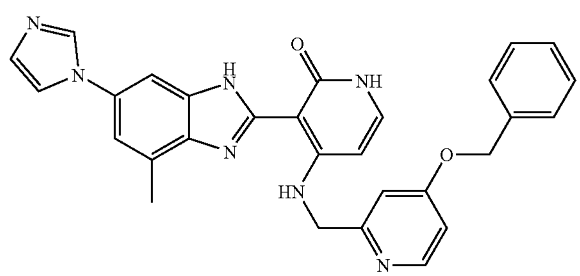 | 1.14 (d) | 504 |
| 172 | (2S,3S)-{2-Hydroxy-3-[3-(6-imidazol-1-yl-4-methyl-1H-benzimidazol-2-yl)-2-oxo-1,2-dihydro-pyridin-4-ylamino]-4-phenyl-butyl}-carbamic acid benzyl ester | 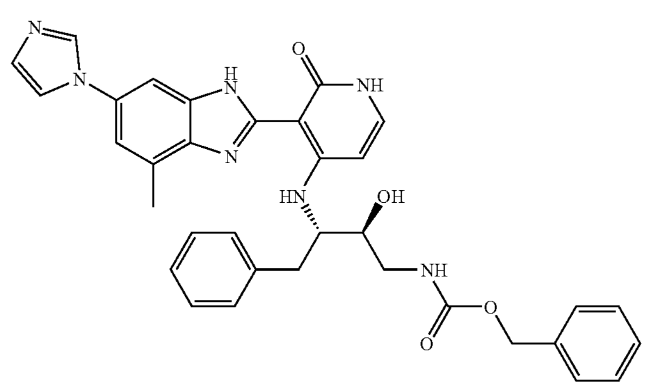 | 1.59 (f) | 604 |

-continued

| Example # | Name | structure | T (min.) | Mass (M + H)+ m/z |
|---|---|---|---|---|
| 173 | (S)-4-[1-(4-Benzyloxy-benzyl)-2-hydroxy-ethylamino]-3-(6-imidazol-1-yl-4-methyl-1H-benzimidazol-2-yl)-1H-pyridin-2-one | 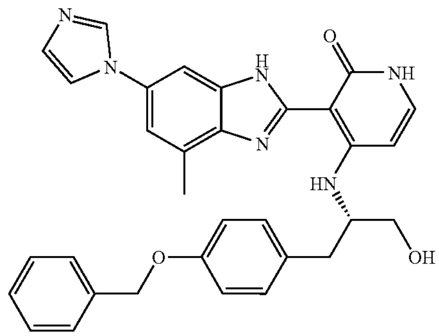 | 1.74 (f) | 547 |
| 174 | 3-(6-Imidazol-1-yl-4-methyl-1H-benzimidazol-2-yl)-4-[(4-methyl-pyridin-2-ylmethyl)-amino]-1H-pyridin-2-one | 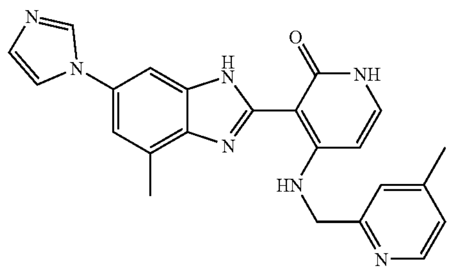 | 0.95 (d) | 412 |
| 175 | 3-(6-Imidazol-1-yl-4-methyl-1H-benzimidazol-2-yl)-4-[(4-methoxy-pyridin-2-ylmethyl)-amino]-1H-pyridin-2-one | 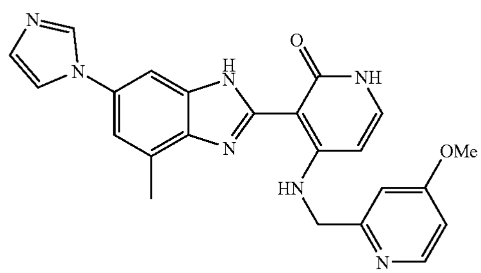 | 0.92 (d) | 428 |
| 176 | 4-{[6-(3-Hydroxy-propyl)-pyridin-2-ylmethyl]-amino}-3-(6-imidazol-1-yl-4-methyl-1H-benzimidazol-2-yl)-1H-pyridin-2-one | 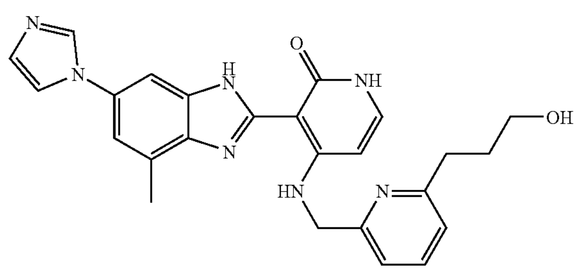 | 0.96 (d) | 456 |
| 177 | 4-[(6-Aminomethyl-pyridin-2-ylmethyl)-amino]-3-(6-imidazol-1-yl-4-methyl-1H-benzimidazol-2-yl)-1H-pyridin-2-one | 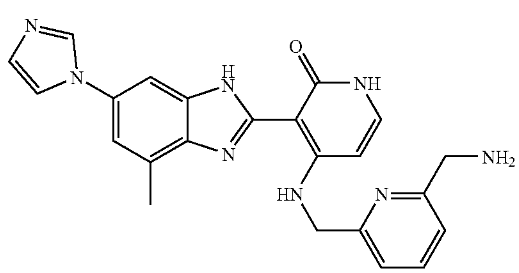 | 0.99 (b) | 427 |

-continued

| Example # | Name | structure | T (min.) | Mass (M + H)+ m/z |
|---|---|---|---|---|
| 178 | N-(6-{[3-(6-imidazol-1-yl-4-methyl-1H-benzimidazol-2-yl)-2-oxo-1,2-dihydro-pyridin-4-ylamino]-methyl}-pyridin-2-ylmethyl)-formamide | 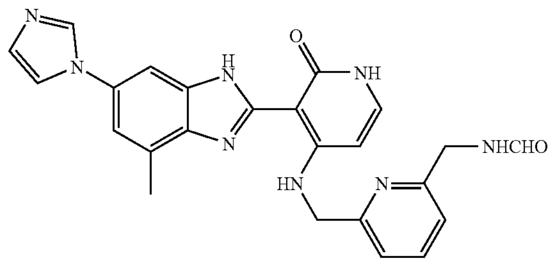 | 1.02 (b) | 455 |
| 179 | 3-(6-Imidazol-1-yl-4-methyl-1H-benzimidazol-2-yl)-4-[(quinolin-2-ylmethyl)-amino]-1H-pyridin-2-one | 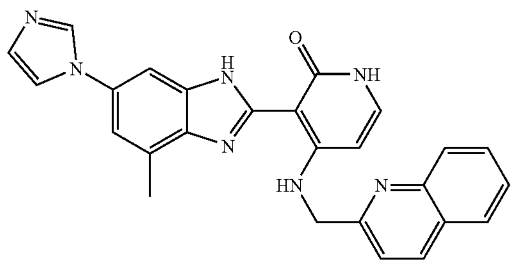 | 1.16 (b) | 448 |
| 180 | 4-(2-Cyclohex-1-enyl-ethylamino)-3-(6-imidazol-1-yl-4-methyl-1H-benzimidazol-2-yl)-1H-pyridin-2-one | 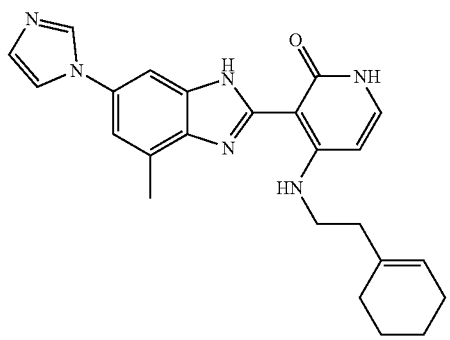 | 1.61 (b) | 415 |
| 181 | (S)-4-[2-(4-tert-Butoxy-phenyl)-1-hydroxymethyl-ethylamino]-3-(6-imidazol-1-yl-4-methyl-1H-benzimidazol-2-yl)-1H-pyridin-2-one | 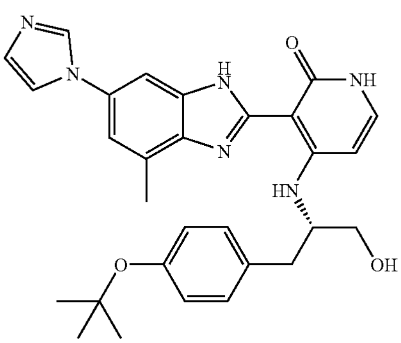 | 1.61 (f) | 513 |
| 182 | (±)-4-[2-(2,3-Dichloro-phenyl)-2-hydroxy-ethylamino]-3-(6-imidazol-1-yl-4-methyl-1H-benzimidazol-2-yl)-1H-pyridin-2-one | 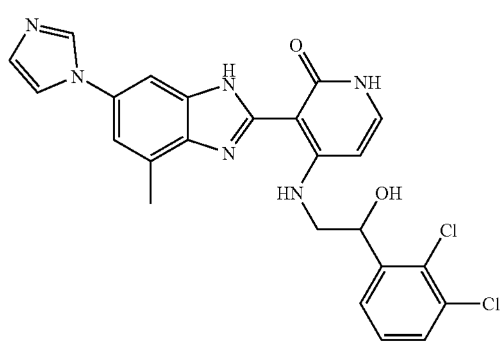 | 1.52 (b) | 495 |

-continued

| Example # | Name | structure | T (min.) | Mass (M + H)+ m/z |
|---|---|---|---|---|
| 183 | (±)-4-[2-(3,4-Difluoro-phenyl)-2-hydroxy-ethylamino]-3-(6-imidazol-1-yl-4-methyl-1H-benzimidazol-2-yl)-1H-pyridin-2-one | 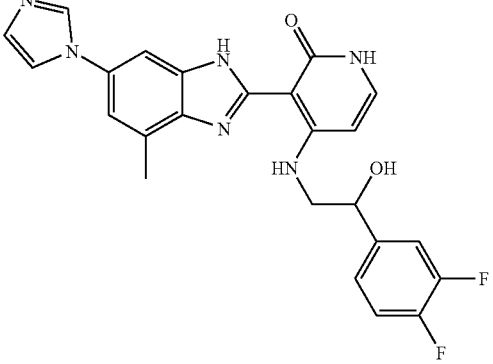 | 1.34 (b) | 463 |
| 184 | (S)-4-[2-(3,4-Dichloro-phenyl)-1-hydroxymethyl-ethylamino]-3-(6-imidazol-1-yl-4-methyl-1H-benzimidazol-2-yl)-1H-pyridin-2-one | 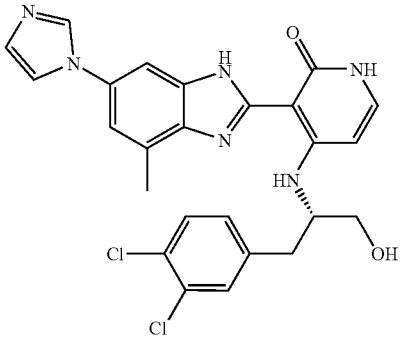 | 1.67 (f) | 509 |
| 185 | (S)-4-[1-Hydroxymethyl-2-(4-hydroxy-2-trifluoromethyl-phenyl)-ethylamino]-3-(6-imidazol-1-yl-4-methyl-1H-benzimidazol-2-yl)-1H-pyridin-2-one | 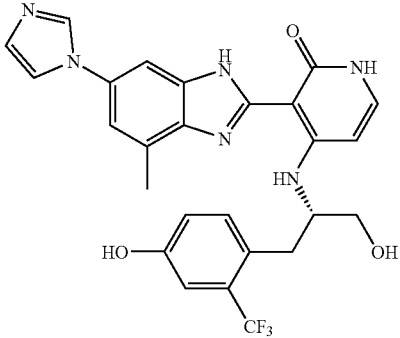 | 1.46 (f) | 525 |
| 186 | 3-(6-Imidazol-1-yl-4-methyl-1H-benzimidazol-2-yl)-4-[(isoquinolin-1-ylmethyl)-amino]-1H-pyridin-2-one | 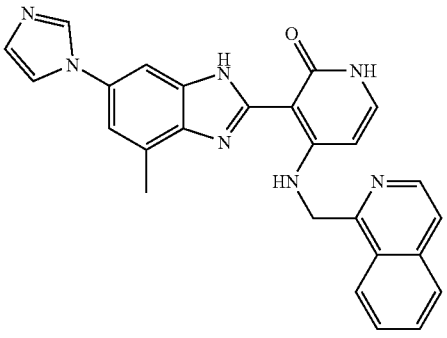 | 1.14 (d) | 448 |

| Example # | Name | structure | T (min.) | Mass (M + H)+ m/z |
|---|---|---|---|---|
| 187 | (S)-4-[2-(3,4-Difluoro-phenyl)-1-hydroxymethyl-ethylamino]-3-(6-imidazol-1-yl-4-methyl-1H-benzimidazol-2-yl)-1H-pyridin-2-one | 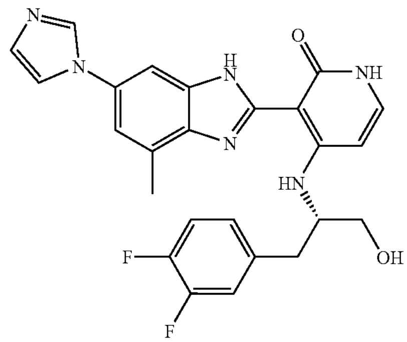 | 1.52 (f) | 477 |
| 188 | 4-[(4-Hydroxy-pyridin-2-ylmethyl)-amino]-3-(6-imidazol-1-yl-4-methyl-1H-benzimidazol-2-yl)-1H-pyridin-2-one | 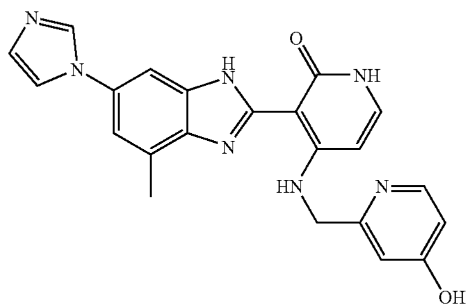 | 0.91 (d) | 414 |
| 189 | 3-(6-Imidazol-1-yl-4-methyl-1H-benzimidazol-2-yl)-4-(2-piperidin-1-yl-ethylamino)-1H-pyridin-2-one | 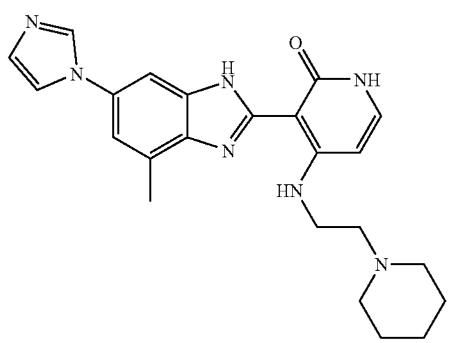 | 0.92 (b) | 418 |
| 190 | (±)-4-(2-Hydroxy-2-p-tolyl-ethylamino)-3-(6-imidazol-1-yl-4-methyl-1H-benzimidazol-2-yl)-1H-pyridin-2-one | 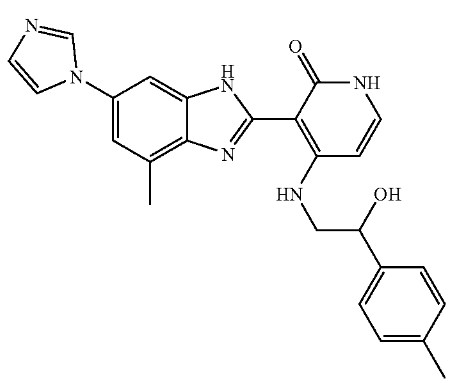 | 5.74 (c) | 441 |

-continued

| Example # | Name | structure | T (min.) | Mass (M + H)+ m/z |
|---|---|---|---|---|
| 191 | 4-[2-(3,5-Bis-trifluoromethyl-phenyl)-2-hydroxy-ethylamino]-3-(6-imidazol-1-yl-4-methyl-1H-benzoimidazol-2-yl)-1H-pyridin-2-one | 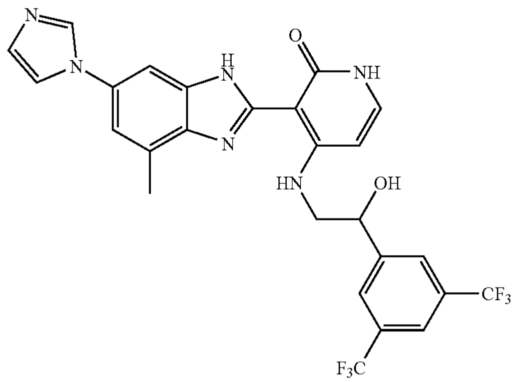 | 6.40 (c) | 563 |
| 192 | (±)-4-[2-(3-Chloro-phenyl)-2-methoxy-ethylamino]-3-(6-imidazol-1-yl-4-methyl-1H-benzimidazol-2-yl)-1H-pyridin-2-one | 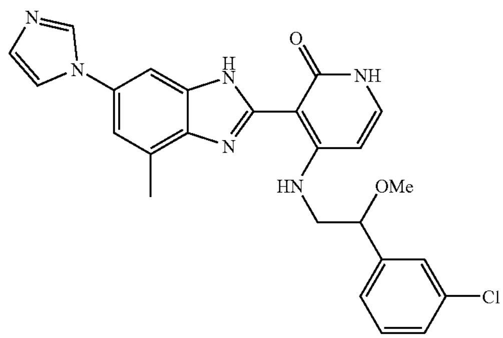 | 6.5 (c) | 475 |
| 193 | 4-[(4-Hydroxymethyl-pyridin-2-ylmethyl)-amino]-3-(6-imidazol-1-yl-4-methyl-1H-benzimidazol-2-yl)-1H-pyridin-2-one | 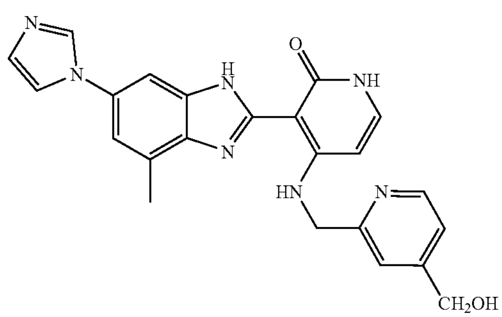 | 0.9 (b) | 428 |
| 194 | (±)-4-[2-(3,5-Dichloro-phenyl)-2-hydroxy-ethylamino]-3-(6-imidazol-1-yl-4-methyl-1H-benzimidazol-2-yl)-1H-pyridin-2-one | 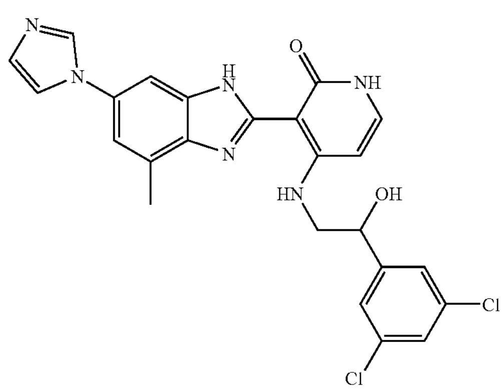 | 1.54 (b) | 495 |

-continued

| Example # | Name | structure | T (min.) | Mass (M + H)+ m/z |
|---|---|---|---|---|
| 195 | (±)-4-[(4-tert-Butyl-1-hydroxy-cyclohexylmethyl)-amino]-3-(6-imidazol-1-yl-4-methyl-1H-benzimidazol-2-yl)-1H-pyridin-2-one | 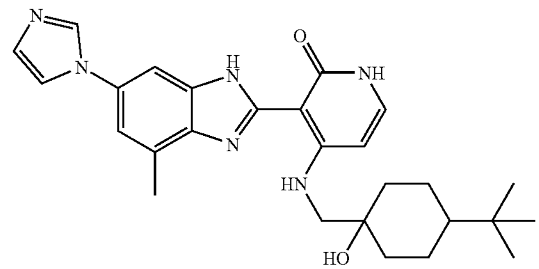 | 3.82 (a) | 475 |
| 196 | (±)-{2-Hydroxy-3-[3-(6-imidazol-1-yl-4-methyl-1H-benzimidazol-2-yl)-2-oxo-1,2-dihydro-pyridin-4-ylamino]-propyl}-carbamic acid tert-butyl ester | 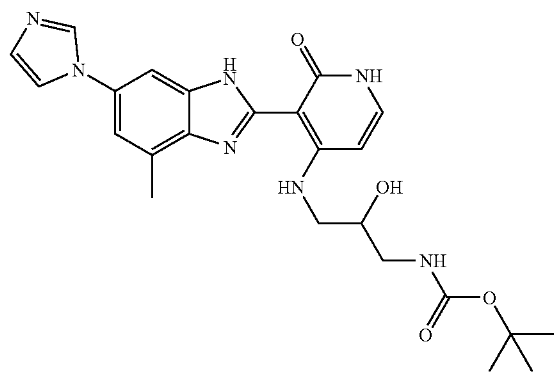 | 1.23 (b) | 480 |
| 197 | (±)-3-(6-Imidazol-1-yl-4-methyl-1H-benzimidazol-2-yl)-4-(3,3,3-trifluoro-2-hydroxy-propylamino)-1H-pyridin-2-one | 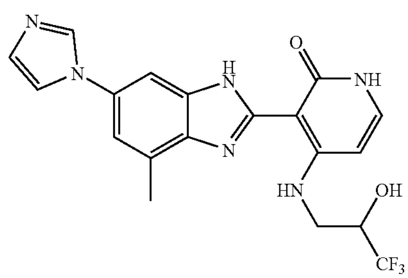 | 1.17 (b) | 419 |
| 198 | (±)-4-[2-(3-Chloro-4-fluoro-phenyl)-2-hydroxy-ethylamino]-3-(6-imidazol-1-yl-4-methyl-1H-benzimidazol-2-yl)-1H-pyridin-2-one | 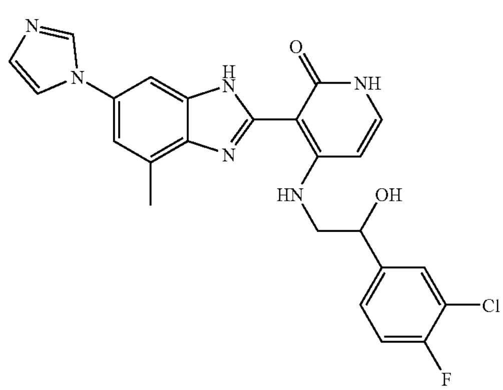 | 1.40 (b) | 479 |

-continued

| Example # | Name | structure | T (min.) | Mass (M + H)+ m/z |
|---|---|---|---|---|
| 199 | (±)-4-(2-Hydroxy-2-m-tolyl-ethylamino)-3-(6-imidazol-1-yl-4-methyl-1H-benzimidazol-2-yl)-1H-pyridin-2-one | 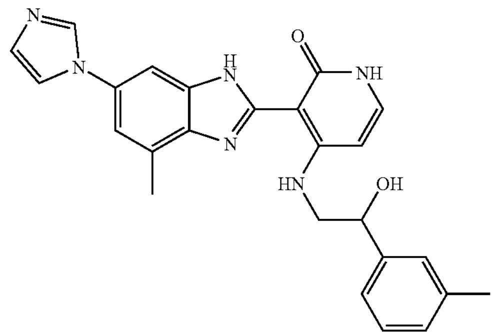 | 1.37 (b) | 441 |
| 200 | (S)-4-(1-Hydroxymethyl-3-phenyl-propylamino)-3-(6-imidazol-1-yl-4-methyl-1H-benzimidazol-2-yl)-1H-pyridin-2-one | 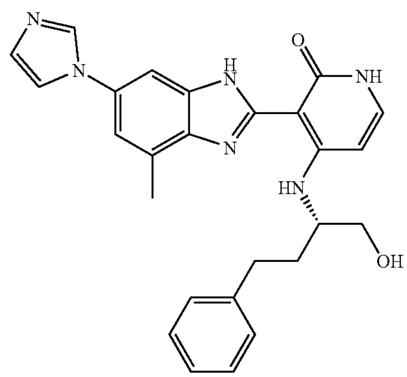 | 1.56 (f) | 455 |
| 201 | (S)-4-(1-Hydroxymethyl-2-p-tolyl-ethylamino)-3-(6-imidazol-1-yl-4-methyl-1H-benzimidazol-2-yl)-1H-pyridin-2-one | 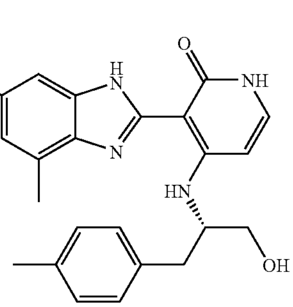 | 1.57 (f) | 455 |
| 202 | (S)-4-[2-(3-Fluoro-phenyl)-1-hydroxymethyl-ethylamino]-3-(6-imidazol-1-yl-4-methyl-1H-benzimidazol-2-yl)-1H-pyridin-2-one | 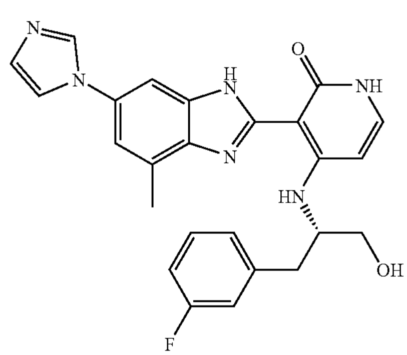 | 1.48 (f) | 459 |

-continued

| Example # | Name | structure | T (min.) | Mass (M + H)+ m/z |
|---|---|---|---|---|
| 203 | (1S,2R)-4-(1-Benzyl-2,4-dihydroxy-butylamino)-3-(6-imidazol-1-yl-4-methyl-1H-benzimidazol-2-yl)-1H-pyridin-2-one | 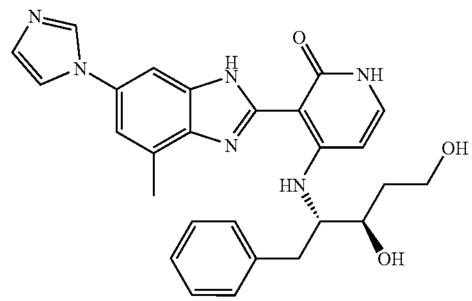 | 1.39 (f) | 485 |
| 204 | (S)-4-[1-Hydroxymethyl-2-(3-trifluoromethyl-phenyl)-ethylamino]-3-(6-imidazol-1-yl-4-methyl-1H-benzimidazol-2-yl)-1H-pyridin-2-one | 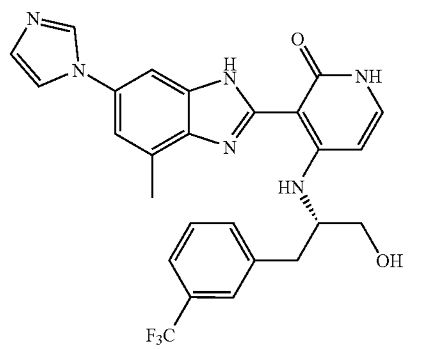 | 1.56 (f) | 509 |
| 205 | 3-(6-Imidazol-1-yl-4-methyl-1H-benzimidazol-2-yl)-4-[(pyrimidin-2-ylmethyl)-amino]-1H-pyridin-2-one | 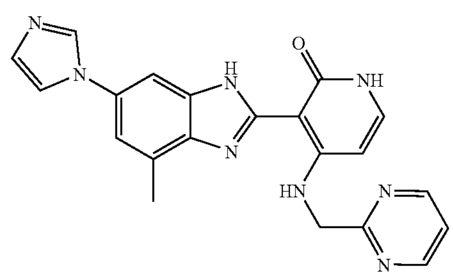 | 1.16 (b) | 399 |
| 206 | 3-(6-Imidazol-1-yl-4-methyl-1H-benzimidazol-2-yl)-4-[(pyrazin-2-ylmethyl)-amino]-1H-pyridin-2-one | 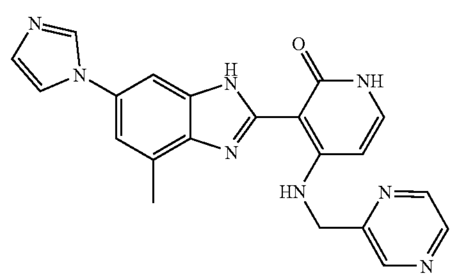 | 1.14 (b) | 399 |
| 207 | (±)-3-(6-Imidazol-1-yl-4-methyl-1H-benzimidazol-2-yl)-4-(2-phenyl-1-pyridin-2-yl-ethylamino)-1H-pyridin-2-one | 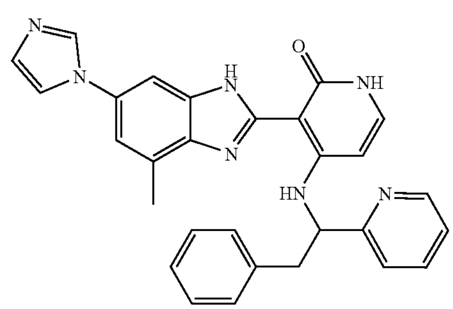 | 1.26 (b) | 488 |

-continued

| Example # | Name | structure | T (min.) | Mass (M + H)+ m/z |
|---|---|---|---|---|
| 208 | (±)-3-(6-Imidazol-1-yl-4-methyl-1H-benzimidazol-2-yl)-4-(3-phenyl-1-pyridin-2-yl-propylamino)-1H-pyridin-2-one | 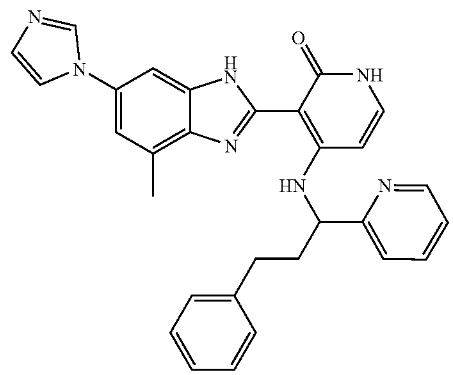 | 1.34 (d) | 502 |
| 209 | (±)-4-[2-(3-Fluoro-phenyl)-1-pyridin-2-yl-ethylamino]-3-(6-imidazol-1-yl-4-methyl-1H-benzimidazol-2-yl)-1H-pyridin-2-one | 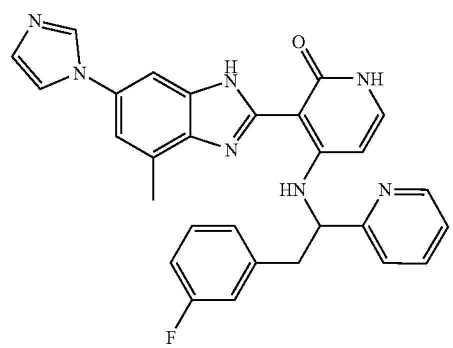 | 1.31 (d) | 506 |
| 210 | (±)-4-[2-(3-Chloro-phenyl)-1-pyridin-2-yl-ethylamino]-3-(6-imidazol-1-yl-4-methyl-1H-benzimidazol-2-yl)-1H-pyridin-2-one | 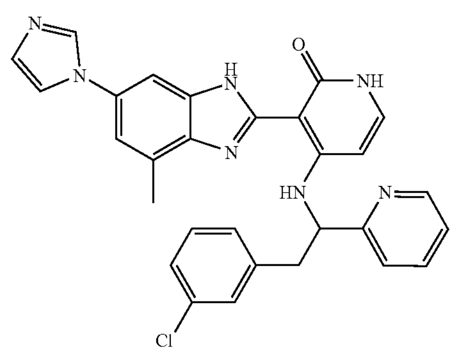 | 1.39 (d) | 522 |
| 211 | 4-[2-(2-Fluoro-phenyl)-1-pyridin-2-yl-ethylamino]-3-(6-imidazol-1-yl-4-methyl-1H-benzimidazol-2-yl)-1H-pyridin-2-one | 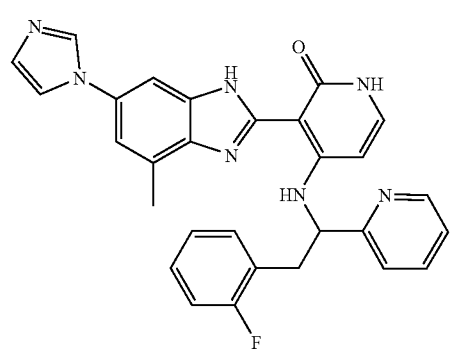 | 1.33 (d) | 506 |

-continued

| Example # | Name | structure | T (min.) | Mass (M + H)+ m/z |
|---|---|---|---|---|
| 212 | (±)-4-[2-(3-Bromo-phenyl)-1-pyridin-2-yl-ethylamino]-3-(6-imidazol-1-yl-4-methyl-1H-benzimidazol-2-yl)-1H-pyridin-2-one | 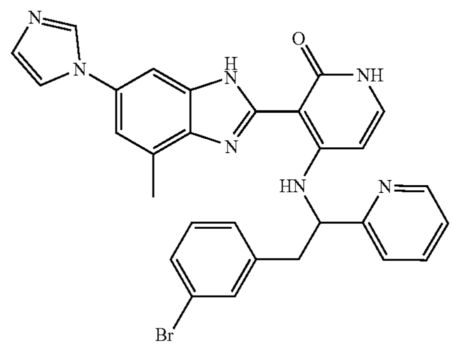 | 1.40 (d) | 566 |
| 213 | (±)-4-[2-(2-Bromo-phenyl)-1-pyridin-2-yl-ethylamino]-3-(6-imidazol-1-yl-4-methyl-1H-benzimidazol-2-yl)-1H-pyridin-2-one | 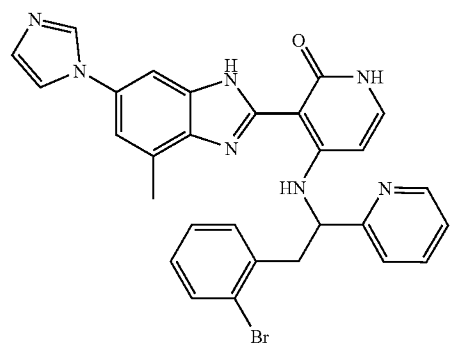 | 1.45 (d) | 566 |
| 214 | (±)-3-(6-Imidazol-1-yl-4-methyl-1H-benzimidazol-2-yl)-4-[2-(2-iodo-phenyl)-1-pyridin-2-yl-ethylamino]-1H-pyridin-2-one | 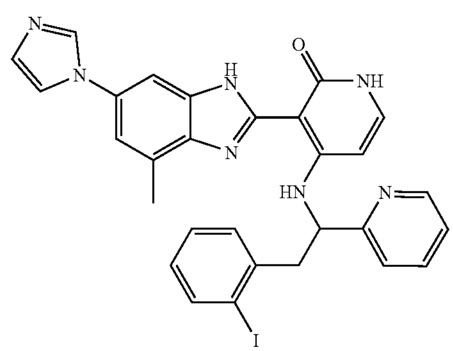 | 1.47 (d) | 614 |
| 215 | (±)-4-[2-(2-Chloro-phenyl)-2-hydroxy)-ethylamino]-3-(6-imidazol-1-yl-4-methyl-1H-benzimidazol-2-yl)-1H-pyridin-2-one | 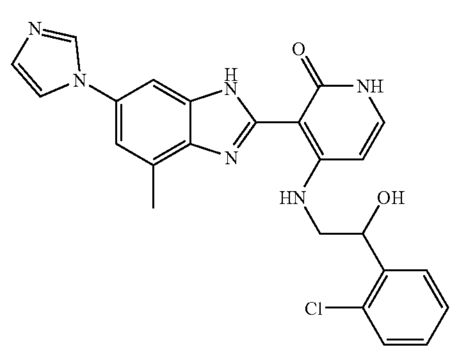 | 1.21 (i) | 461 |

-continued

| Example # | Name | structure | T (min.) | Mass (M + H)+ m/z |
|---|---|---|---|---|
| 216 | 4-[3-(4-Cyclopentylamino-6-propoxy-[1,3,5]triazin-2-yloxy)-propylamino]-3-(6-imidazol-1-yl-4-methyl-1H-benzimidazol-2-yl)-1H-pyridin-2-one | 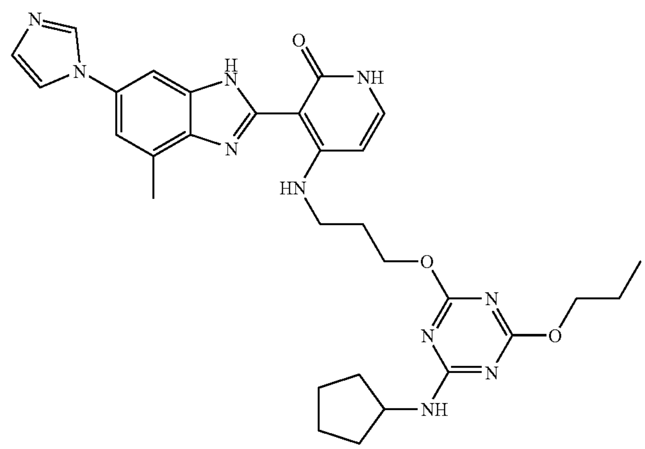 | 1.67 (b) | 585 |
| 217 | (±)-3-{1-Hydroxy-2-[3-(6-imidazol-yl-4-methyl-1H-benzimidazol-2-yl)-2-oxo-1,2-dihydro-pyridin-4-ylamino]-ethyl}-benzonitrile | 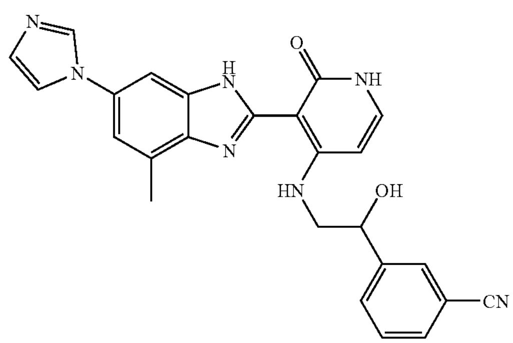 | 1.20 (b) | 452 |
| 218 | (±)-4-(2-Biphenyl-3-yl-2-hydroxy-ethylamino)-3-(6-imidazol-1-yl-4-methyl-1H-benzimidazol-2-yl)-1H-pyridin-2-one | 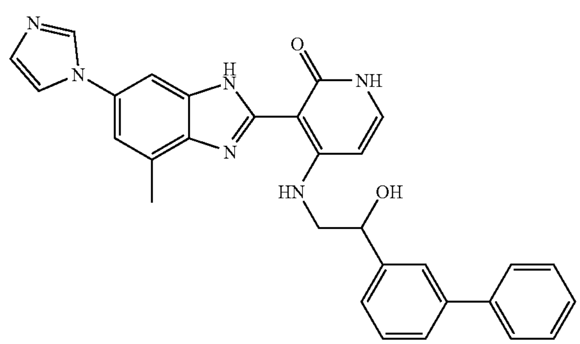 | 1.51 (b) | 503 |
| 219 | (±)-4-[2-(3-Chloro-phenyl)-2-hydroxy-ethylamino]-3-(6-imidazol-1-yl-1H-benzimidazol-2-yl)-1H-pyridin-2-one | 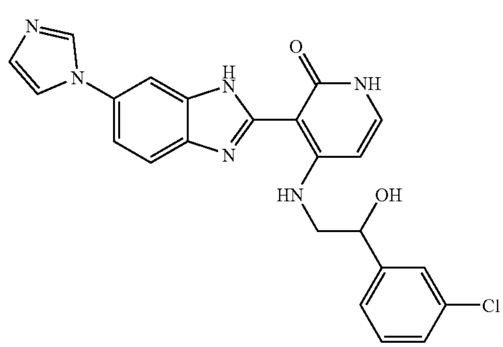 | 1.35 (f) | 447 |

-continued

| Example # | Name | structure | T (min.) | Mass (M + H)+ m/z |
|---|---|---|---|---|
| 220 | (S)-4-[1-Hydroxymethyl-2-(2-methoxy-phenyl)-ethylamino]-3-(6-imidazol-1-yl-4-methyl-1H-benzimidazol-2-yl)-1H-pyridin-2-one | 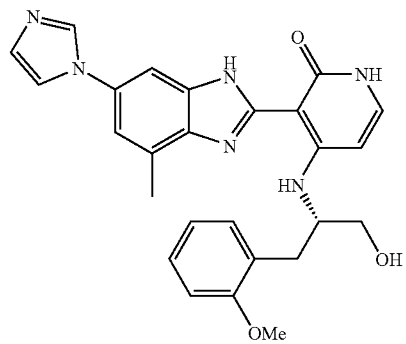 | 1.52 (f) | 471 |
| 221 | (S)-4-[1-Hydroxymethyl-2-(3-methoxy-phenyl)-ethylamino]-3-(6-imidazol-1-yl-4-methyl-1H-benzimidazol-2-yl)-1H-pyridin-2-one | 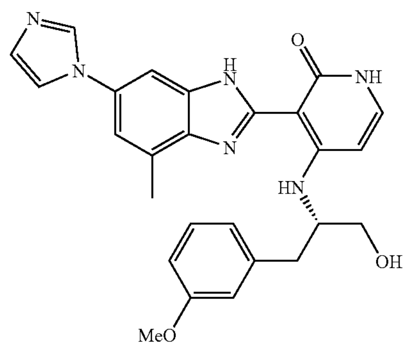 | 1.42 (f) | 471 |
| 222 | (S)-4-[1-Hydroxymethyl-2-(3-nitro-phenyl)-ethylamino]-3-(6-imidazol-1-yl-4-methyl-1H-benzimidazol-2-yl)-1H-pyridin-2-one | 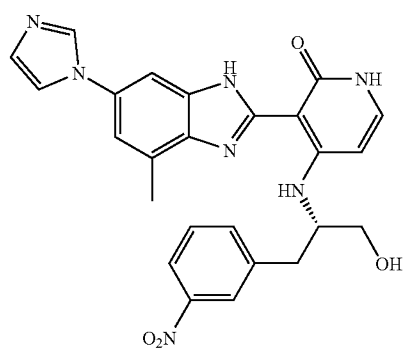 | 1.27 (f) | 486 |
| 223 | (S)-4-[3-(2-Benzothiazol-2-yl-phenoxy)-2-hydroxy-propylamino]-3-(6-imidazol-1-yl-4-methyl-1H-benzoimidazol-2-yl)-1H-pyridin-2-one | 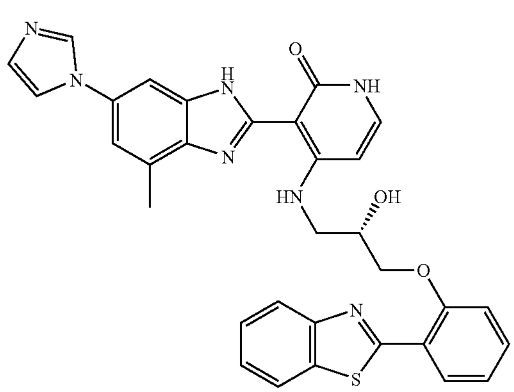 | 1.47 (j) | 590 |

-continued

| Example # | Name | structure | T (min.) | Mass (M + H)+ m/z |
|---|---|---|---|---|
| 224 | (±)-4-[2-(3-Bromo-4-methoxy-phenyl)-2-hydroxy-ethylamino]-3-(6-imidazol-1-yl-4-methyl-1H-benzimidazol-2-yl)-1H-pyridin-2-one | 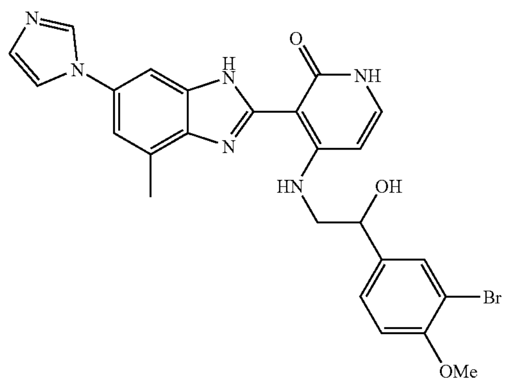 | 1.35 (j) | 535 |
| 225 | (S)-4-(1-Benzyl-2-hydroxy-2-methyl-propylamino)-3-(6-imidazol-1-yl-4-methyl-1H-benzoimidazol-2-yl)-1H-pyridin-2-one | 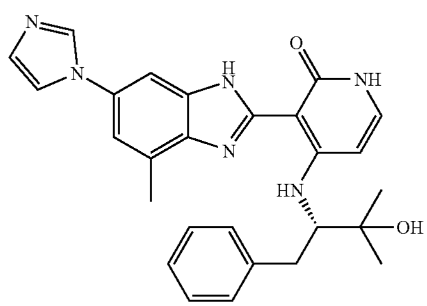 | 22.07 | HPLC |
| 226 | (R)-4-(1-Benzyl-2-hydroxy-2-methyl-propylamino)-3-(6-imidazol-1-yl-4-methyl-1H-benzoimidazol-2-yl)-1H-pyridin-2-one | 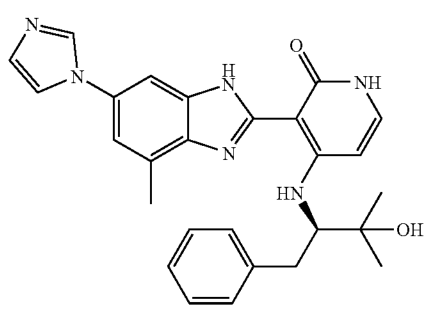 | 22.09 | HPLC |
| 227 | 3-(6-Imidazol-1-yl-4-methyl-1H-benzimidazol-2-yl)-4-[(5-methyl-pyridin-2-ylmethyl)-amino]-1H-pyridin-2-one | 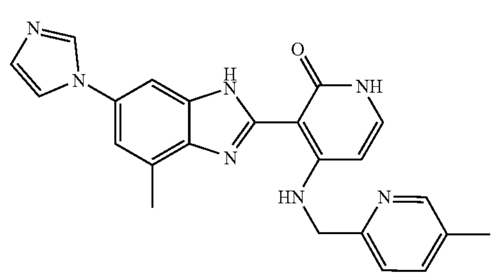 | 0.99 (d) | 412 |

-continued

| Example # | Name | structure | T (min.) | Mass (M + H)+ m/z |
|---|---|---|---|---|
| 228 | (±)-3-(6-Imidazol-1-yl-4-methyl-1H-benzimidazol-2-yl)-4-(2-phenyl-2-pyridin-2-yl-pent-4-enylamino)-1H-pyridin-2-one | 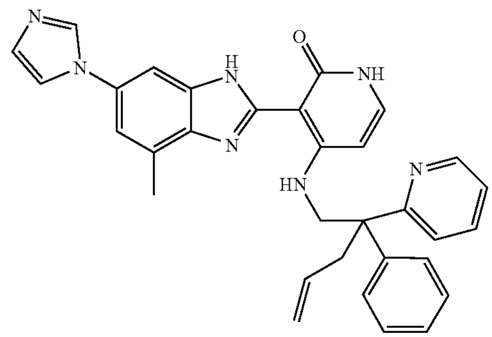 | 1.41 (d) | 528 |
| 229 | (±)-3-(6-Imidazol-1-yl-4-methyl-1H-benzimidazol-2-yl)-4-(2-phenyl-2-pyridin-2-yl-ethylamino)-1H-pyridin-2-one | 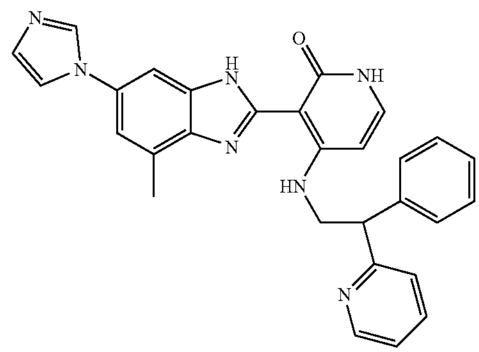 | 1.22 (d) | 488 |
| 230 | 6-{[3-(6-Imidazol-1-yl-4-methyl-1H-benzimidazol-2-yl)-2-oxo-1,2-dihydro-pyridin-4-ylamino]-methyl}-nicotinonitrile | 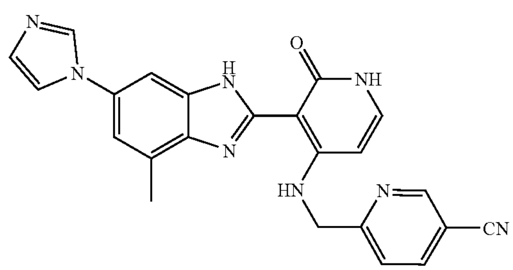 | 1.22 (d) | 423 |
| 231 | (±)-4-[2-(5-Bromo-2-methoxy-phenyl)-2-hydroxy-ethylamino]-3-(6-imidazol-1-yl-4-methyl-1H-benzimidazol-2-yl)-1H-pyridin-2-one | 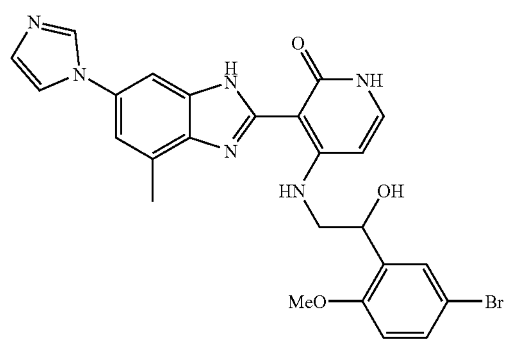 | 1.27 (i) | 535 |
| 232 | (±)-3-(6-Imidazol-1-yl-4-methyl-1H-benzimidazol-2-yl)-4-(1-pyridin-2-yl-ethylamino)-1H-pyridin-2-one | 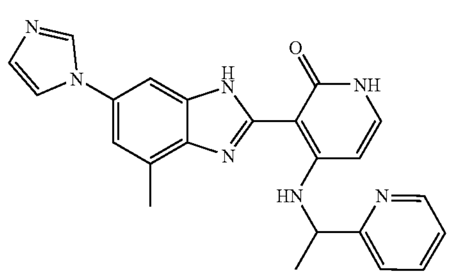 | 1.12 (d) | 412 |

-continued

| Example # | Name | structure | T (min.) | Mass (M + H)+ m/z |
|---|---|---|---|---|
| 233 | (±)-3-(6-Imidazol-1-yl-4-methyl-1H-benzimidazol-2-yl)-4-(1-pyridin-2-yl-propylamino)-1H-pyridin-2-one | 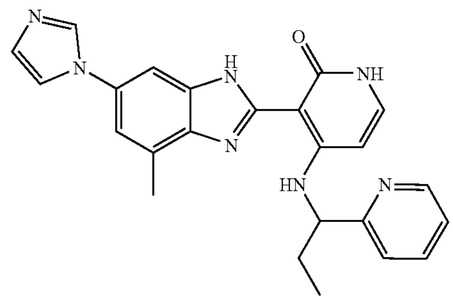 | 1.17 (d) | 426 |
| 234 | (±)-4-[2-(3-Bromo-4-fluoro-phenyl)-2-hydroxy-ethylamino]-3-(6-imidazol-1-yl-4-methyl-1H-benzimidazol-2-yl)-1H-pyridin-2-one | 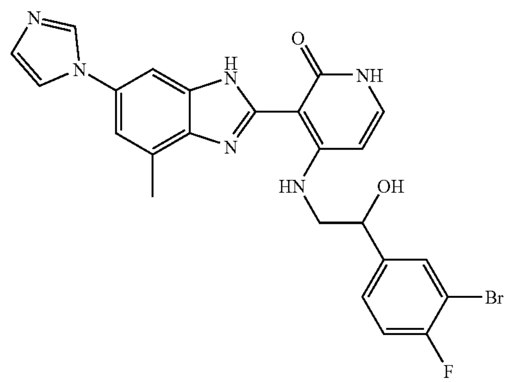 | 1.24 (i) | 523 |
| 235 | (±)-4-[2-(5-Bromo-2-fluoro-phenyl)-2-hydroxy-ethylamino]-3-(6-imidazol-1-yl-4-methyl-1H-benzimidazol-2-yl)-1H-pyridin-2-one | 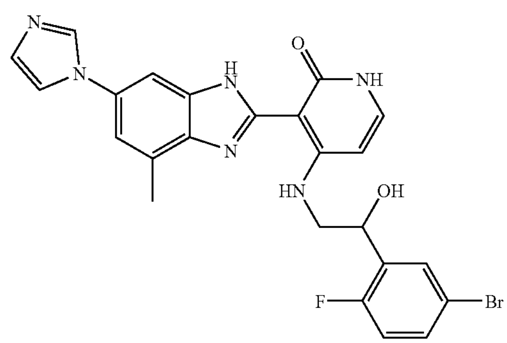 | 1.15 (i) | 523 |
| 236 | (±)-4-[2-(3,5-Dibromo-phenyl)-2-hydroxy-ethylamino]-3-(6-imidazol-1-yl-4-methyl-1H-benzimidazol-2-yl)-1H-pyridin-2-one | 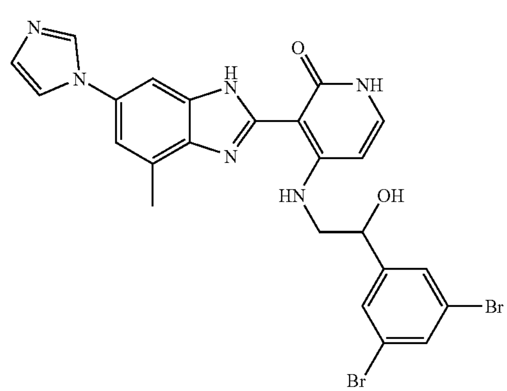 | 1.30 (i) | 583 |

-continued

| Example # | Name | structure | T (min.) | Mass (M + H)+ m/z |
|---|---|---|---|---|
| 237 | (±)-4-[2-(3-Bromo-phenyl)-2-hydroxy-propylamino]-3-(6-imidazol-1-yl-4-methyl-1H-benzimidazol-2-yl)-1H-pyridin-2-one | 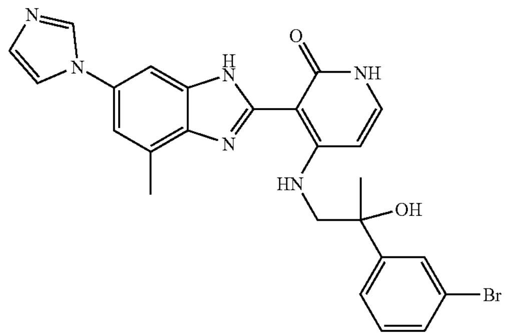 | 1.90 (d) | 519 |
| 238 | (E)-4-[2-(3-Bromo-phenyl)-2-hydroxyimino-ethylamino]-3-(6-imidazol-1-yl-4-methyl-1H-benzimidazol-2-yl)-1H-pyridin-2-one | 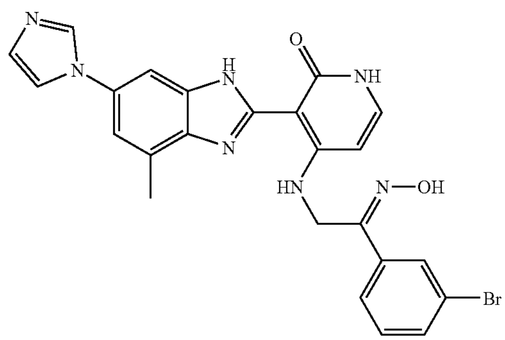 | 7.81 (e) | 518 |
| 239 | (Z)-4-[2-(3-Bromo-phenyl)-2-hydroxyimino-ethylamino]-3-(6-imidazol-1-yl-4-methyl-1H-benzimidazol-2-yl)-1H-pyridin-2-one | 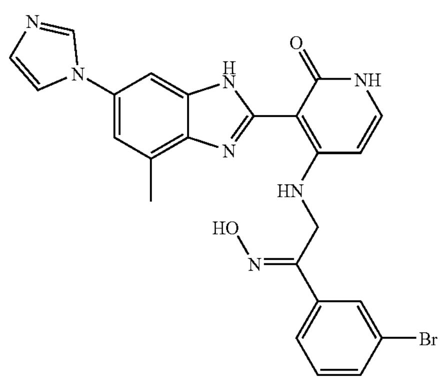 | 7.91 (e) | 518 |
| 240 | (R)-4-(3-Hydroxy-1-phenyl-propylamino)-3-(6-imidazol-1-yl-4-methyl-1H-benzimidazol-2-yl)-1H-pyridin-2-one | 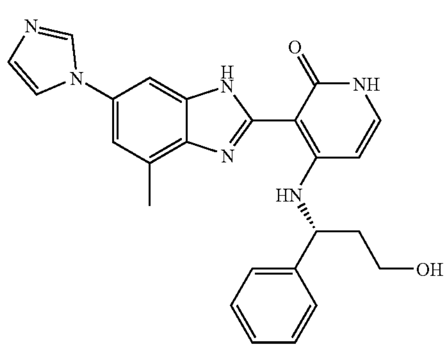 | 1.48 (f) | 441 |

-continued

| Example # | Name | structure | T (min.) | Mass (M + H)+ m/z |
|---|---|---|---|---|
| 241 | (S)-4-(3-Hydroxy-1-phenyl-propylamino)-3-(6-imidazol-1-yl-4-methyl-1H-benzimidazol-2-yl)-1H-pyridin-2-one | 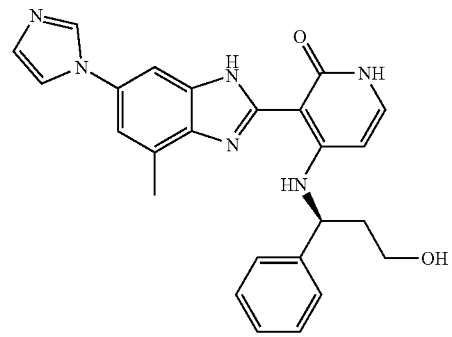 | 1.48 (f) | 441 |
| 242 | (S)-4-[3-Hydroxy-1-(2-iodo-phenyl)-propylamino]-3-(6-imidazol-1-yl-4-methyl-1H-benzimidazol-2-yl)-1H-pyridin-2-one | 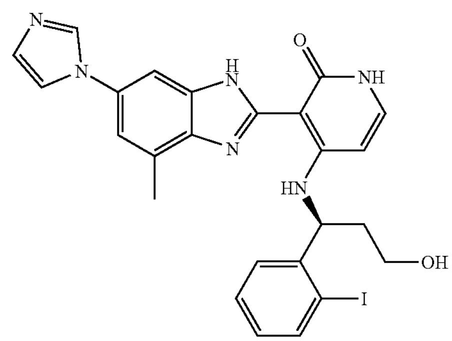 | 1.61 (f) | 567 |
| 243 | (S)-4-[2-(3-Bromo-phenyl)-2-hydroxy-ethylamino]-3-(6-imidazol-1-yl-4-methyl-1H-benzimidazol-2-yl)-1H-pyridin-2-one | 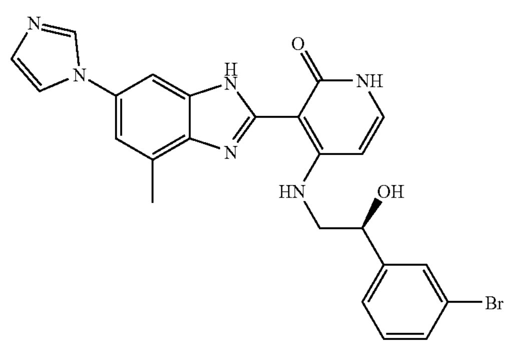 | 1.35 (b) | 505 |
| 244 | (S)-4-[2-(3-Chloro-phenyl)-2-hydroxy-ethylamino]-3-(6-imidazol-1-yl-4-methyl-1H-benzimidazol-2-yl)-1H-pyridin-2-one | 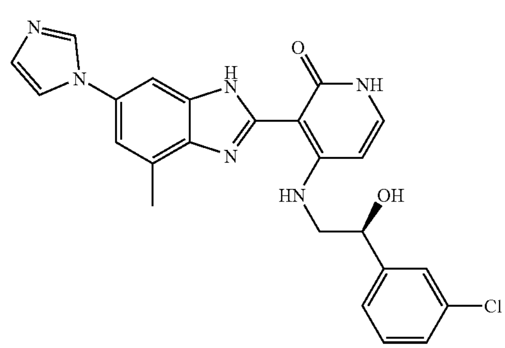 | 1.30 (b) | 461 |

-continued

| Example # | Name | structure | T (min.) | Mass (M + H)+ m/z |
|---|---|---|---|---|
| 245 | (R)-4-[2-(3-Chloro-phenyl)-2-hydroxy-ethylamino]-3-(6-imidazol-1-yl-4-methyl-1H-benzimidazol-2-yl)-1H-pyridin-2-one | 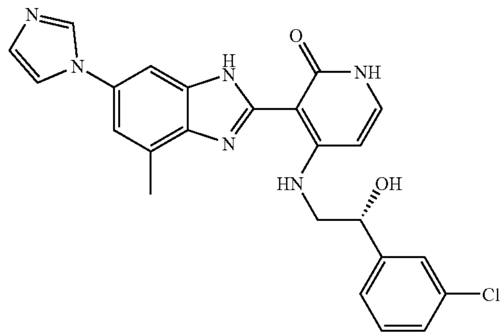 | 1.37 (b) | 461 |
| 246 | (R)-4-[2-(3-Bromo-phenyl)-2-hydroxy-ethylamino]-3-(6-imidazol-1-yl-4-methyl-1H-benzimidazol-2-yl)-1H-pyridin-2-one | 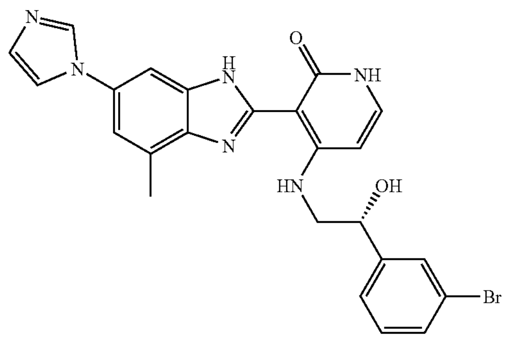 | 1.35 (b) | 505 |
| 247 | 4-[2-(3-Chloro-phenyl)-ethylamino]-3-(6-imidazol-1-yl-4-methyl-1H-benzimidazol-2-yl)-1H-pyridin-2-one | 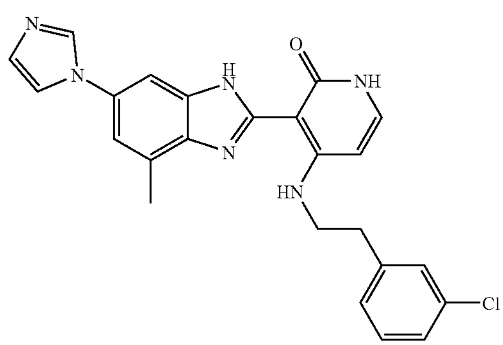 | 1.53 (b) | 445 |
| 248 | (±)-4-[2-(3-Chloro-4-hydroxy-phenyl)-2-hydroxy-ethylamino]-3-(6-imidazol-1-yl-4-methyl-1H-benzimidazol-2-yl)-1H-pyridin-2-one | 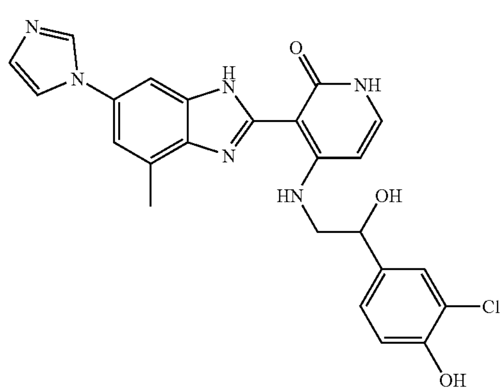 | 1.15 (b) | 477 |

-continued

| Example # | Name | structure | T (min.) | Mass (M + H)+ m/z |
|---|---|---|---|---|
| 249 | (±)-4-[2-(3-Chloro-4-methoxy-phenyl)-2-hydroxy-ethylamino]-3-(6-imidazol-1-yl-4-methyl-1H-benzimidazol-2-yl)-1H-pyridin-2-one | 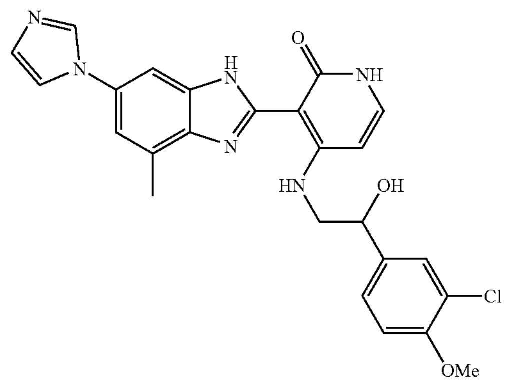 | 1.24 (b) | 491 |
| 250 | (±)-4-{2-[3-Chloro-4-(2-methyl-allyloxy)-phenyl]-2-hydroxy-ethylamino}-3-(6-imidazol-1-yl-4-methyl-1H-benzimidazol-2-yl)-1H-pyridin-2-one | 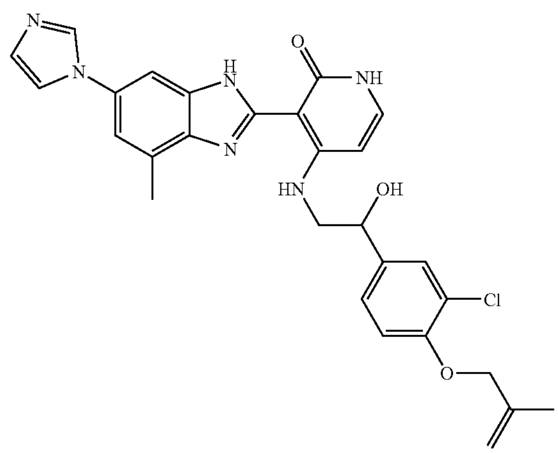 | 1.46 (b) | 531 |
| 251 | (±)-[2-(5-Bromo-biphenyl-3-yl)-2-hydroxy-ethylamino]-3-(6-imidazol-1-yl-4-methyl-1H-benzimidazol-2-yl)-1H-pyridin-2-one | 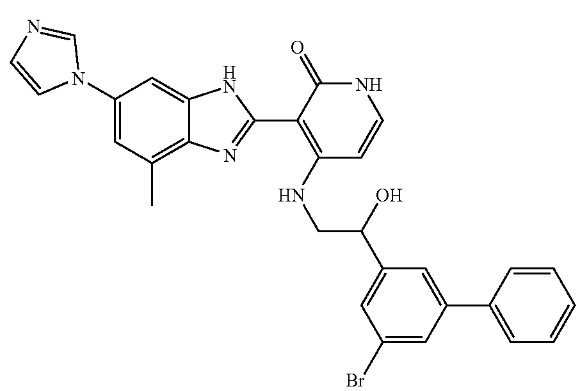 | 1.44 (i) | 581 |

| Example # | Name | structure | T (min.) | Mass (M + H)+ m/z |
|---|---|---|---|---|
| 252 | (±)-4-(2-Hydroxy-2-[1,1',3',1'']terphenyl-5'-yl-ethylamino)-3-(6-imidazol-1-yl-4-methyl-1H-benzimidazol-2-yl)-1H-pyridin-2-one | 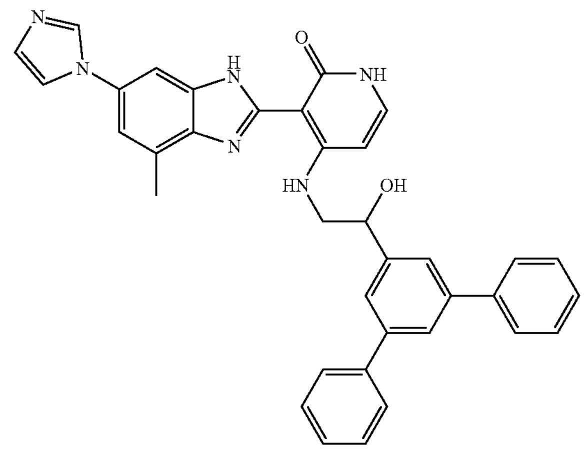 | 1.48 (i) | 579 |
| 253 | (±)-4-[2-(3-Chloro-4-propoxy-phenyl)-2-hydroxy-ethylamino]-3-(6-imidazol-1-yl-4-methyl-1H-benzimidazol-2-yl)-1H-pyridin-2-one | 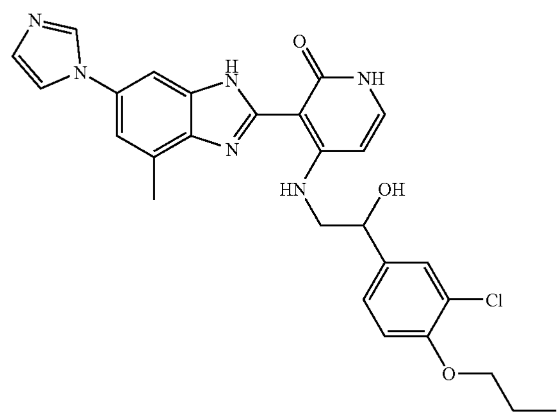 | 1.76 (b) | 519 |
| 254 | 3-[3-(6-Imidazol-1-yl-4-methyl-1H-benzimidazol-2-yl)-2-oxo-1,2-dihydro-pyridin-4-ylamino]-N-phenyl-propionamide | 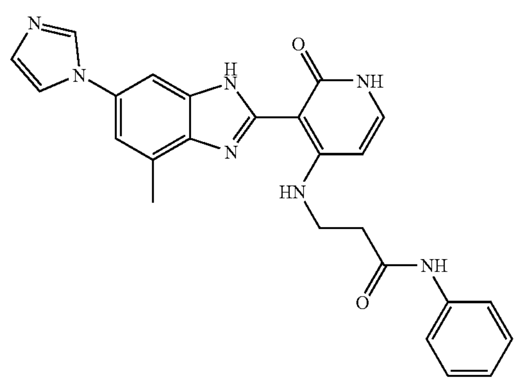 | 1.13 (i) | 454 |
| 255 | (±)-4-[2-Hydroxy-2-(3-nitro-phenyl)-ethylamino]-3-(6-imidazol-1-yl-4-methyl-1H-benzimidazol-2-yl)-1H-pyridin-2-one | 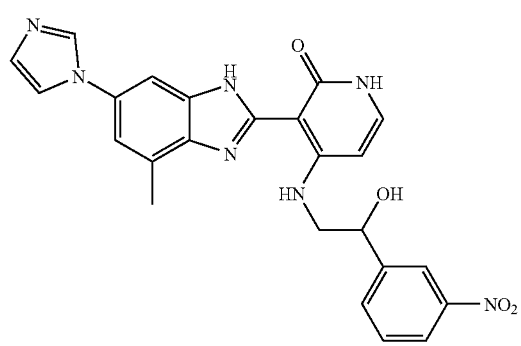 | 1.20 (i) | 472 |

-continued

| Example # | Name | structure | T (min.) | Mass (M + H)+ m/z |
|---|---|---|---|---|
| 256 | 4-[2-(5-Bromo-2-methoxy-phenyl)-ethylamino]-3-(6-imidazol-1-yl-4-methyl-1H-benzimidazol-2-yl)-1H-pyridin-2-one | 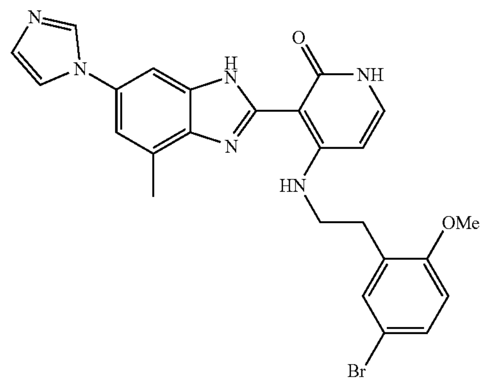 | 1.51 (i) | 519 |
| 257 | 2-[3-(6-Imidazol-1-yl-4-methyl-1H-benzimidazol-2-yl)-2-oxo-1,2-dihydro-pyridin-4-ylamino]-N-phenyl-acetamide | 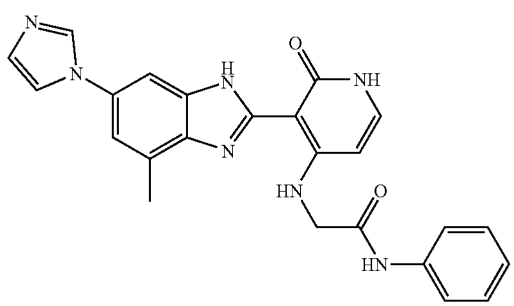 | 1.25 (i) | 440 |
| 258 | (R)-N-{2-[3-(6-Imidazol-1-yl-4-methyl-1H-benzimidazol-2-yl)-2-oxo-1,2-dihydro-pyridin-4-ylamino]-2-phenyl-ethyl}-methanesulfonamide | 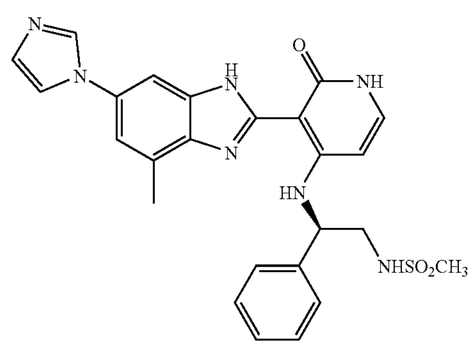 | 1.35 (h) | 504 |
| 259 | (S)-N-{2-[3-(6-Imidazol-1-yl-4-methyl-1H-benzimidazol-2-yl)-2-oxo-1,2-dihydro-pyridin-4-ylamino]-1-phenyl-ethyl}-methanesulfonamide | 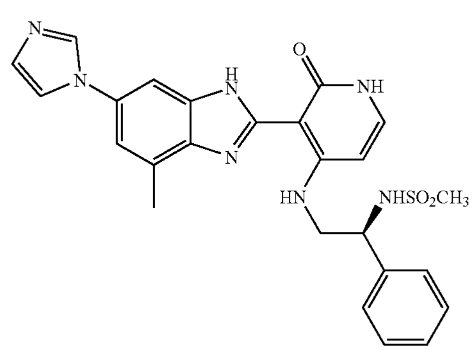 | 1.32 (h) | 504 |

| Example # | Name | structure | T (min.) | Mass (M + H)+ m/z |
|---|---|---|---|---|
| 260 | (±)-N-(2-Chloro-4-{1-fluoro-2-[3-(6-imidazol-1-yl-4-methyl-1H-benzimidazol-2-yl)-2-oxo-1,2-dihydro-pyridin-4-ylamino]-ethyl}-phenyl)-2,2,2-trifluoro-acetamide | 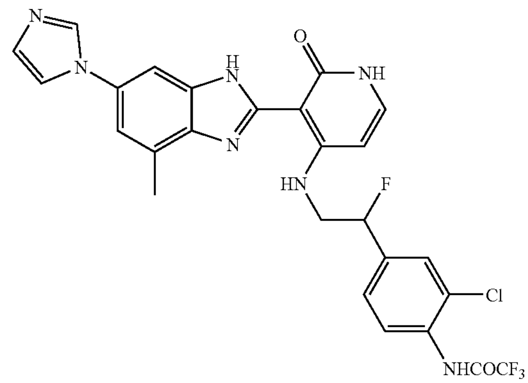 | 1.30 (b) | 574 |
| 261 | 3-(6-Imidazol-1-yl-4-methyl-1H-benzimidazol-2-yl)-4-[(piperidin-4-ylmethyl)-amino]-1H-pyridin-2-one | 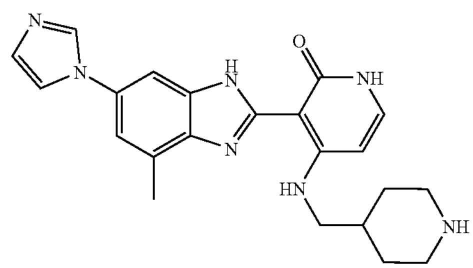 | 0.90 (b) | 404 |
| 262 | (±)-4-[2-(3-Bromo-5-pyridin-3-yl-phenyl)-2-hydroxy-ethylamino]-3-(6-imidazol-1-yl-4-methyl-1H-benzimidazol-2-yl)-1H-pyridin-2-one | 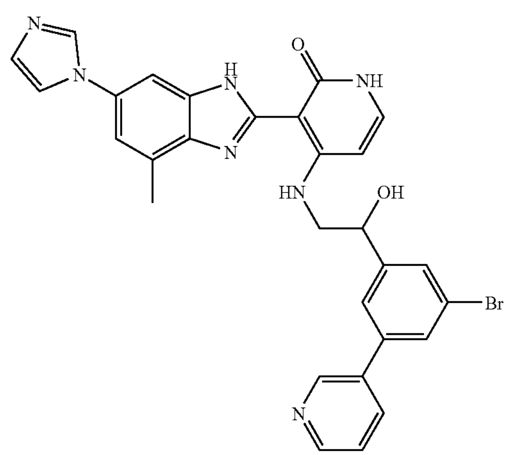 | 1.18 (a) | 582 |
| 263 | (±)-(2-Chloro-4-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-carbamic acid ethyl ester | 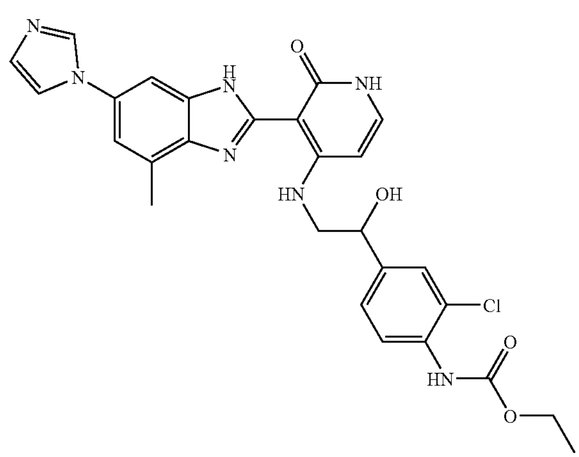 | 1.36 (b) | 548 |

-continued

| Example # | Name | structure | T (min.) | Mass (M + H)+ m/z |
|---|---|---|---|---|
| 264 | (±)-N-(2-Chloro-4-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-2,2-dimethyl-propionamide | 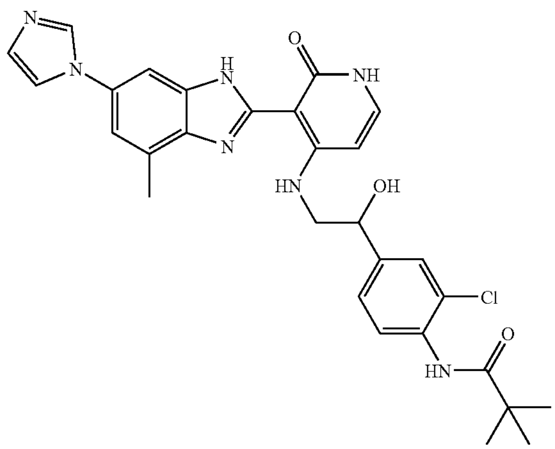 | 1.42 (b) | 560 |
| 265 | (S)-3-(6-Imidazol-1-yl-4-methyl-1H-benzimidazol-2-yl)-4-(1-hydroxymethyl-2-pyridin-3-yl-ethylamino)-1H-pyridin-2-one | 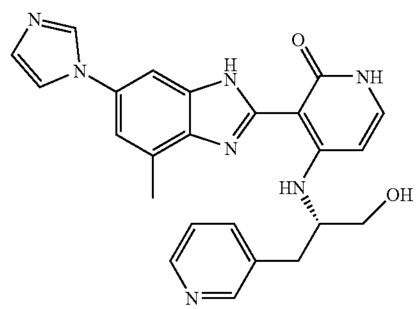 | 0.78 (b) | 442 |
| 266 | (S)-3-Hydroxy-2-[3-(6-imidazol-1-yl-4-methyl-1H-benzimidazol-2-yl)-2-oxo-1,2-dihydro-pyridin-4-ylamino]-N-naphthalen-1-yl-propionamide | 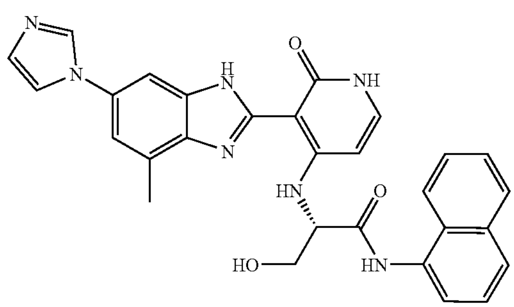 | 1.41 (b) | 520 |
| 267 | (S)-3-(6-Imidazol-1-yl-4-methyl-1H-benzimidazol-2-yl)-4-[1-(1H-indol-3-ylmethyl)-2-hydroxy-ethylamino]-1H-pyridin-2-one | 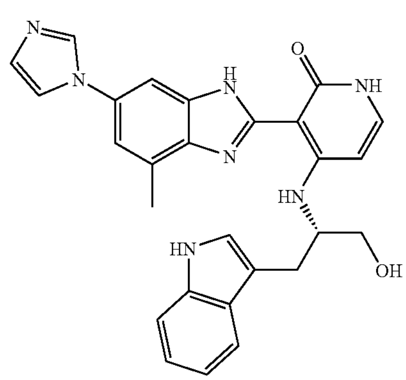 | 1.22 (b) | 480 |

-continued

| Example # | Name | structure | T (min.) | Mass (M + H)+ m/z |
|---|---|---|---|---|
| 268 | (S)-4-[3-Hydroxy-1-(1H-imidazol-4-yl)-propylamino]-3-(6-imidazol-1-yl-4-methyl-1H-benzimidazol-2-yl)-1H-pyridin-2-one | 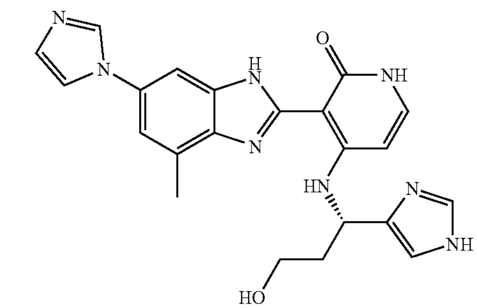 | 0.75 (b) | 431 |
| 269 | (±)-4-[2-(3,4-Dichloro-phenyl)-2-hydroxy-ethylamino]-3-(6-imidazol-1-yl-4-methyl-1H-benzimidazol-2-yl)-1H-pyridin-2-one | 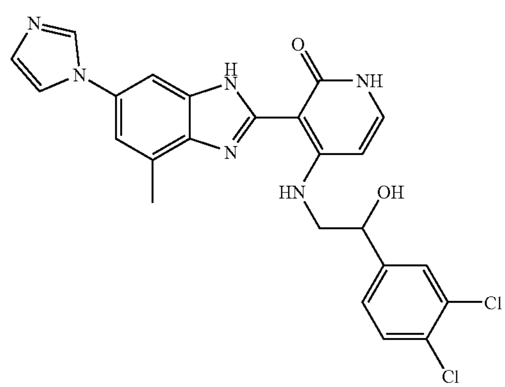 | 1.48 (b) | 495 |
| 270 | (±)-1-(2-Chloro-ethyl)-3-(2-chloro-4-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-urea | 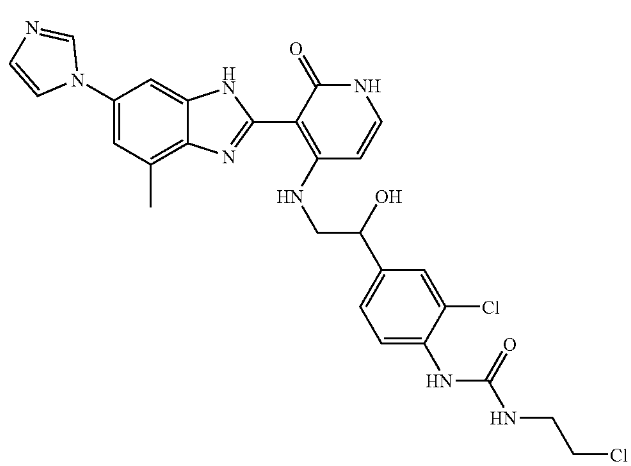 | 1.26 (b) | 581 |

-continued

| Example # | Name | structure | T (min.) | Mass (M + H)+ m/z |
|---|---|---|---|---|
| 271 | (±)-(2-Chloro-4-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-carbamic acid isopropyl ester | 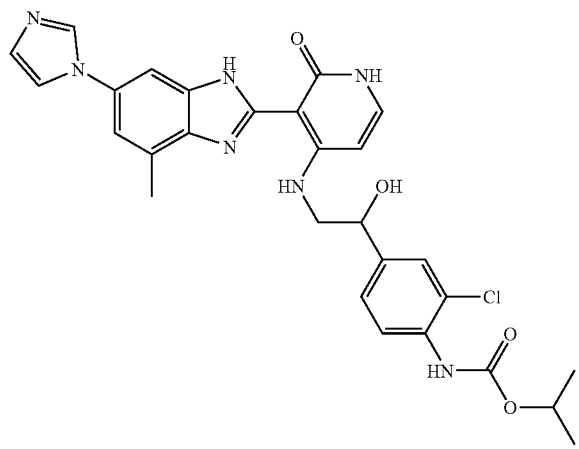 | 1.41 (b) | 562 |
| 272 | (±)-(2-Chloro-4-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-carbamic acid isobutyl ester | 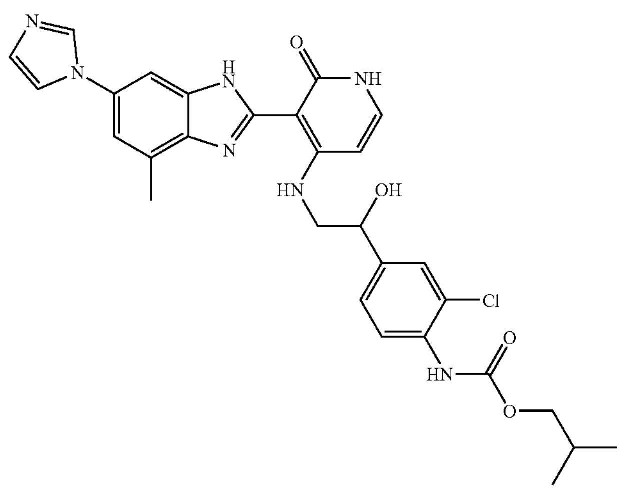 | 1.49 (b) | 576 |
| 273 | (S)-3-Hydroxy-2-[3-(6-imidazol-1-yl-4-methyl-1H-benzimidazol-2-yl)-2-oxo-1,2-dihydro-pyridin-4-ylamino]-N-naphthalen-2-yl-propionamide | 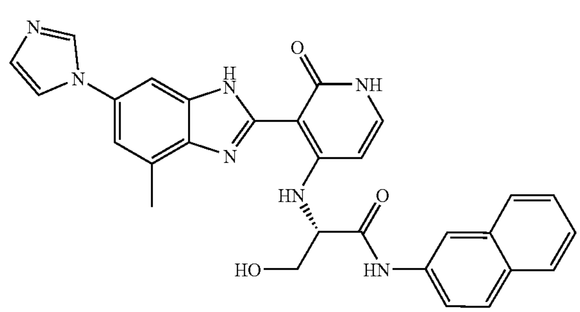 | 1.36 (b) | 520 |

-continued

| Example # | Name | structure | T (min.) | Mass (M + H)+ m/z |
|---|---|---|---|---|
| 274 | (S)-3-Hydroxy-2-[3-(6-imidazol-1-yl-4-methyl-1H-benzimidazol-2-yl)-2-oxo-1,2-dihydro-pyridin-4-ylamino]-N-(4-methoxy-naphthalen-2-yl)-propionamide | 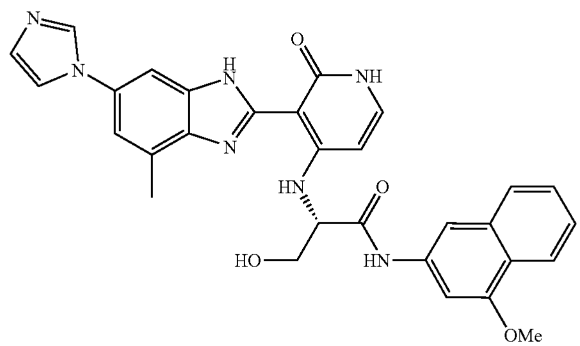 | 1.45 (b) | 550 |
| 275 | (S)-Ethanesulfonic acid {2-[3-(6-imidazol-1-yl-4-methyl-1H-benzimidazol-2-yl)-2-oxo-1,2-dihydro-pyridin-4-ylamino]-1-phenyl-ethyl}-amide | 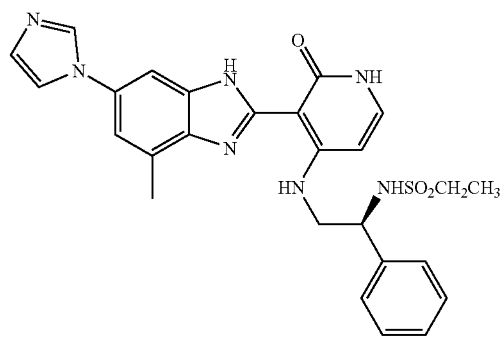 | 1.47 (b) | 518 |
| 276 | (±)-(2-Chloro-4-{1-hydroxy-2-[3-(6-imidazol-1-yl-4-methyl-1H-benzimidazol-2-yl)-2-oxo-1,2-dihydro-pyridin-4-ylamino]-ethyl}-phenyl)-carbamic acid methyl ester | 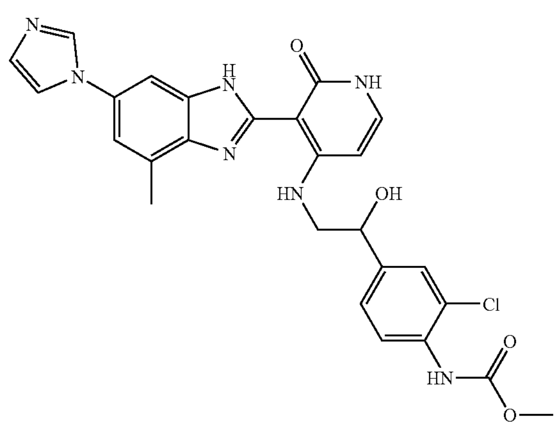 | 1.23 (b) | 534 |
| 277 | (±)-4-[1-Hydroxymethyl-2-(2-hydroxy-3-methyl-phenyl)-ethylamino]-3-(6-imidazol-1-yl-4-methyl-1H-benzimidazol-2-yl)-1H-pyridin-2-one | 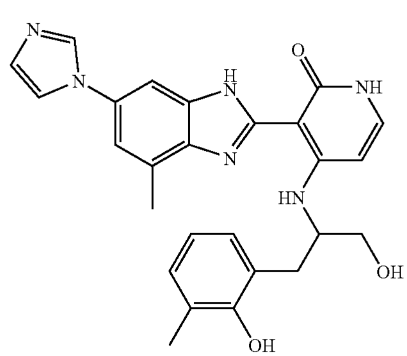 | 1.29 (b) | 471 |

-continued

| Example # | Name | structure | T (min.) | Mass (M + H)+ m/z |
|---|---|---|---|---|
| 278 | (S)-4-[2-(5-Bromo-2-methoxy-phenyl)-1-hydroxymethyl-ethylamino]-3-(6-imidazol-1-yl-4-methyl-1H-benzimidazol-2-yl)-1H-pyridin-2-one | 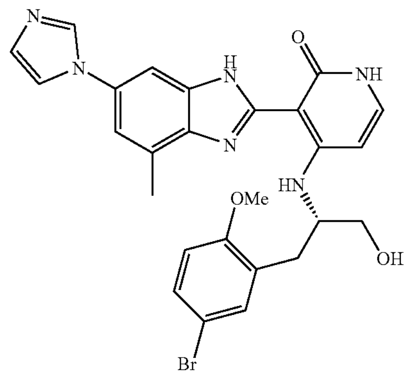 | 1.48 (b) | 549 |
| 279 | 4-(2S-Hydroxy-1-indan-1-yl-ethylamino)-3-(6-imidazol-1-yl-4-methyl-1H-benzoimidazol-2-yl)-1H-pyridin-2-one | 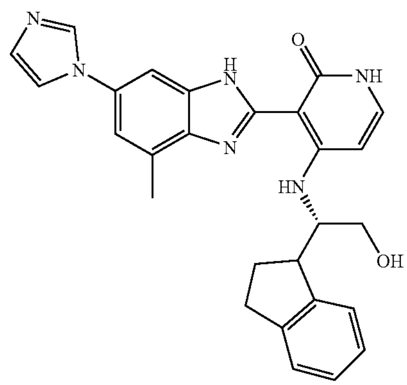 | 1.42 (b) | 467 |
| 280 | (±)-4-[2-(3-Bromo-4-methyl-phenyl)-2-hydroxy-ethylamino]-3-(6-imidazol-1-yl-4-methyl-1H-benzimidazol-2-yl)-1H-pyridin-2-one | 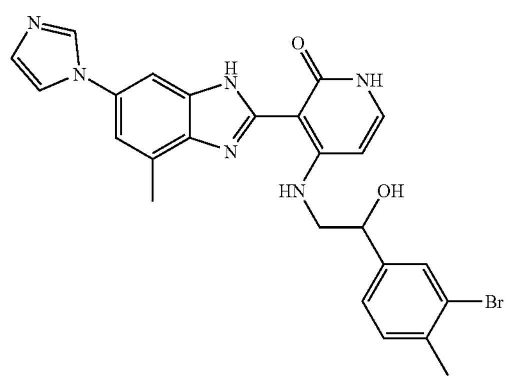 | 1.43 (b) | 519 |
| 281 | 3-(6-Imidazol-1-yl-4-methyl-1H-benzimidazol-2-yl)-4-[2-(1H-indol-5-yl)-ethylamino]-1H-pyridin-2-one | 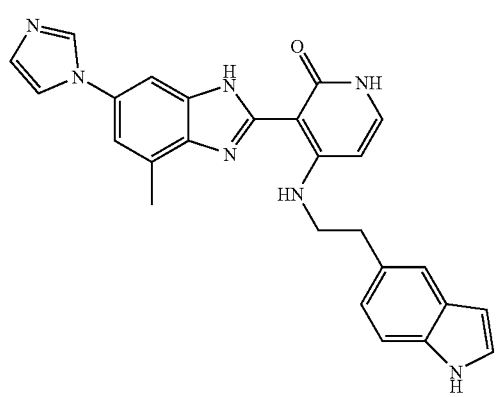 | 1.54 (b) | 450 |

| Example # | Name | structure | T (min.) | Mass (M + H)+ m/z |
|---|---|---|---|---|
| 282 | (S)-3-(5-Bromo-2-methoxy-phenyl)-2-[3-(6-imidazol-1-yl-4-methyl-1H-benzimidazol-2-yl)-2-oxo-1,2-dihydro-pyridin-4-ylamino]-propionic acid | 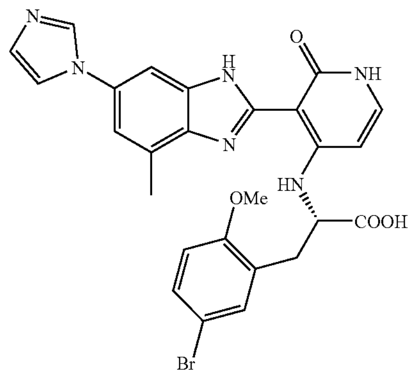 | 1.09 (b) | 563 |
| 283 | (S)-Propane-2-sulfonic acid {2-[3-(6-imidazol-1-yl-4-methyl-1H-benzimidazol-2-yl)-2-oxo-1,2-dihydro-pyridin-4-ylamino]-1-phenyl-ethyl}-amide | 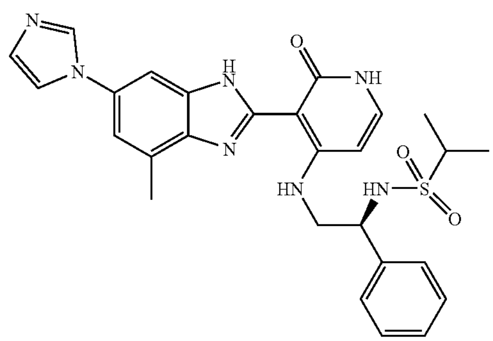 | 1.34 (b) | 532 |
| 284 | (S)-Thiophen-2-sulfonic acid {2-[3-(6-imidazol-1-yl-4-methyl-1H-benzimidazol-2-yl)-2-oxo-1,2-dihydro-pyridin-4-ylamino]-1-phenyl-ethyl}-amide | 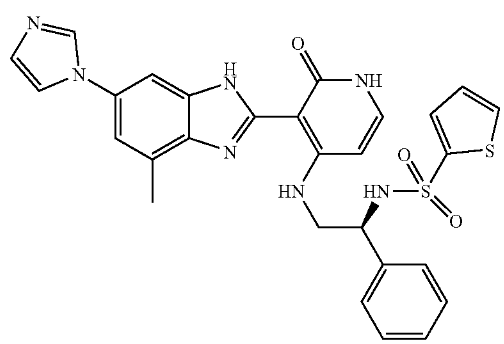 | 2.45 (a) | 572 |
| 285 | (S)-N-{2-[3-(6-Imidazol-1-yl-4-methyl-1H-benzimidazol-2-yl)-2-oxo-1,2-dihydro-pyridin-4-ylamino]-1-phenyl-ethyl}-4-methanesulfonyl-benzenesulfonamide | 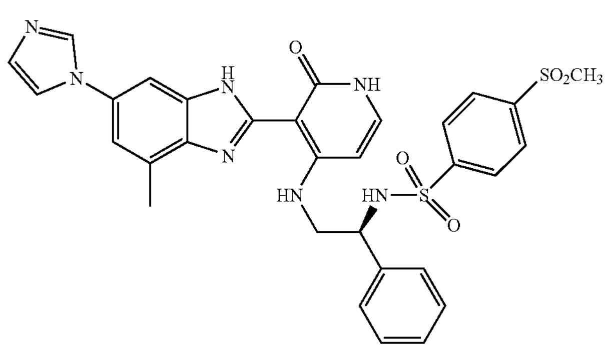 | 1.34 (b) | 644 |

-continued

| Example # | Name | structure | T (min.) | Mass (M + H)+ m/z |
|---|---|---|---|---|
| 286 | (S)-N-{2-[3-(6-Imidazol-1-yl-4-methyl-1H-benzimidazol-2-yl)-2-oxo-1,2-dihydro-pyridin-4-ylamino]-1-phenyl-ethyl}-benzenesulfonamide | 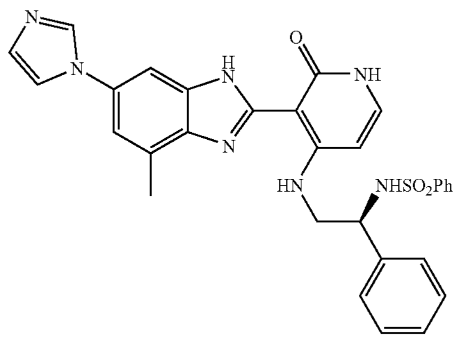 | 1.60 (b) | 566 |
| 287 | (S)-2-{3-Hydroxy-2-[3-(6-imidazol-1-yl-4-methyl-1H-benzoimidazol-2-yl)-2-oxo-1,2-dihydro-pyridin-4-ylamino]-propyl}-benzonitrile | 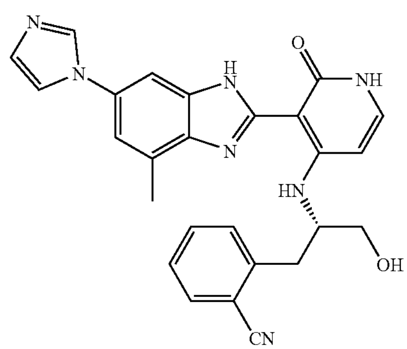 | 1.16 (b) | 466 |
| 288 | (S)-4-(1-Hydroxymethyl-2-o-tolyl-ethylamino)-3-(6-imidazol-1-yl-4-methyl-1H-benzimidazol-2-yl)-1H-pyridin-2-one | 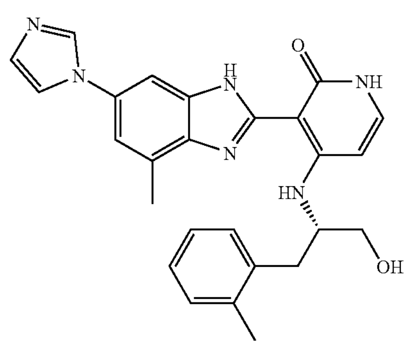 | 1.33 (b) | 455 |
| 289 | (S)-5-Bromo-3-[6-(2-bromo-imidazol-1-yl)-4-methyl-1H-benzimidazol-2-yl]-4-(1-hydroxymethyl-2-phenyl-ethylamino)-1H-pyridin-2-one | 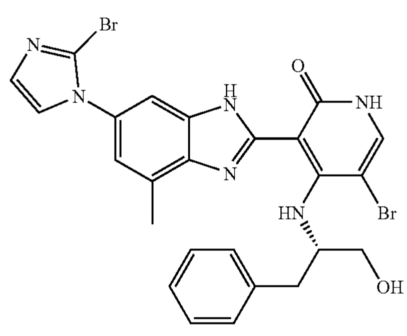 | 1.36 (b) | 597 |

-continued

| Example # | Name | structure | T (min.) | Mass (M + H)+ m/z |
|---|---|---|---|---|
| 290 | (S)-4-[2-(2-Chloro-6-fluoro-phenyl)-1-hydroxymethyl-ethylamino]-3-(6-imidazol-1-yl-4-methyl-1H-benzimidazol-2-yl)-1H-pyridin-2-one | 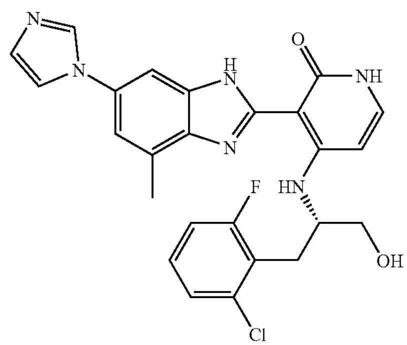 | 1.40 (a) | 493 |
| 291 | (S)-4-[2-(2,5-Difluoro-phenyl)-1-hydroxymethyl-ethylamino]-3-(6-imidazol-1-yl-4-methyl-1H-benzimidazol-2-yl)-1H-pyridin-2-one | 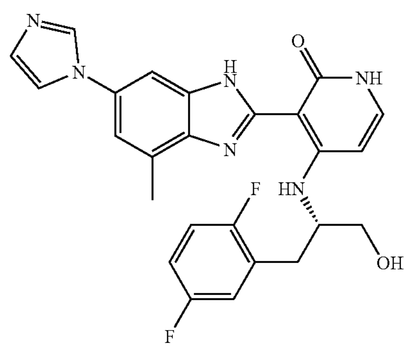 | 1.44 (a) | 477 |
| 292 | (S)-4-[1-hydroxymethyl-2-(2-methoxy-phenyl)-ethylamino]-3-(6-imidazol-1-yl-4-methyl-1H-benzimidazol-2-yl)-1H-pyridin-2-one | 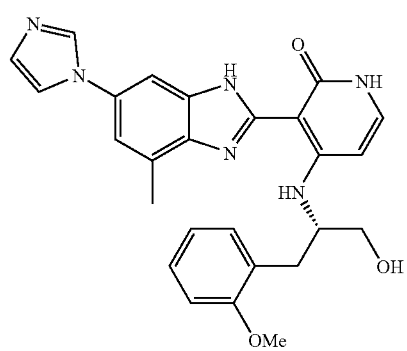 | 1.52 (f) | 471 |
| 293 | (S)-4-[2-(2,6-Difluoro-phenyl)-1-hydroxymethyl-ethylamino]-3-(6-imidazol-1-yl-4-methyl-1H-benzimidazol-2-yl)-1H-pyridin-2-one | 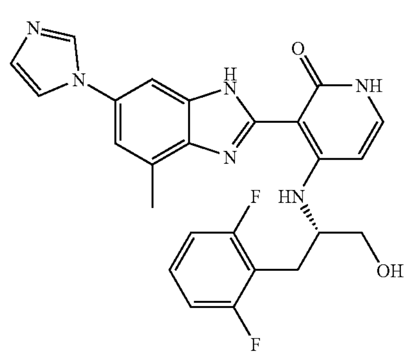 | 1.42 (a) | 477 |

-continued

| Example # | Name | structure | T (min.) | Mass (M + H)+ m/z |
|---|---|---|---|---|
| 294 | (S)-4-[2-(2,6-Dichloro-phenyl)-1-hydroxymethyl-ethylamino]-3-(6-imidazol-1-yl-4-methyl-1H-benzimidazol-2-yl)-1H-pyridin-2-one | 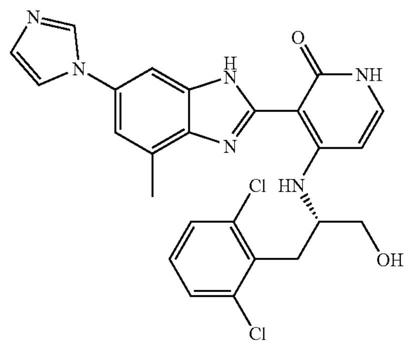 | 1.42 (a) | 509 |
| 295 | (S)-4-[1-Hydroxymethyl-2-(2-trifluoromethoxy-phenyl)-ethylamino]-3-(6-imidazol-1-yl-4-methyl-1H-benzimidazol-2-yl)-1H-pyridin-2-one | 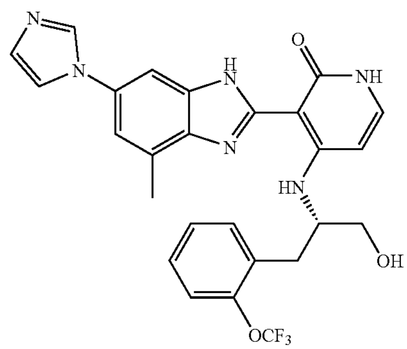 | 1.48 (a) | 525 |
| 296 | (S)-N-{2-[3-(6-Imidazol-1-yl-4-methyl-1H-benzimidazol-2-yl)-2-oxo-1,2-dihydro-pyridin-4-ylamino]-3-phenyl-propyl}-methanesulfonamide | 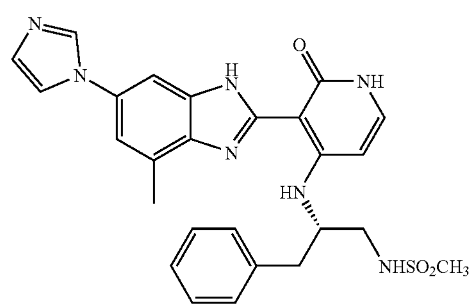 | 1.31 (a) | 518 |
| 297 | (S)-2-{4-[2-(2-Chloro-phenyl)-1-hydroxymethyl-ethylamino]-2-oxo-1,2-dihydro-pyridin-3-yl}-7-methyl-3H-benzimidazole-5-carbonitrile | 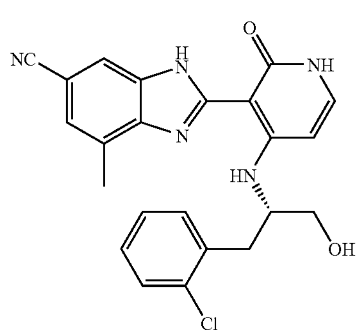 | 1.80 (b) | 434 |

-continued

| Example # | Name | structure | T (min.) | Mass (M + H)+ m/z |
|---|---|---|---|---|
| 298 | (S)-2-[4-(1-Hydroxymethyl-2-pyridin-3-yl-ethylamino)-2-oxo-1,2-dihydro-pyridin-3-yl]-7-methyl-3H-benzimidazole-5-carbonitrile | 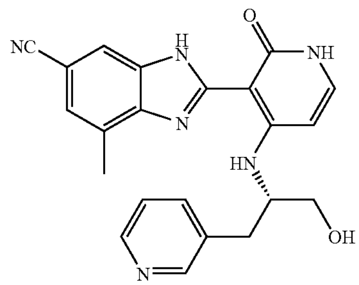 | 1.07 (b) | 401 |
| 299 | (S)-2-[4-(1-Hydroxymethyl-2-pyridin-4-yl-ethylamino)-2-oxo-1,2-dihydro-pyridin-3-yl]-7-methyl-3H-benzimidazole-5-carbonitrile | 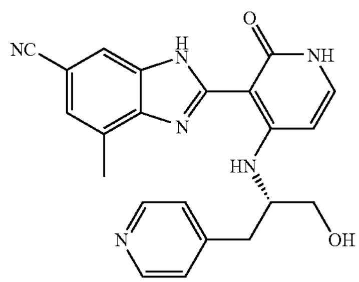 | 1.16 (b) | 401 |
| 300 | (S)-2-[4-(1-Hydroxymethyl-2-thiophen-2-yl-ethylamino)-2-oxo-1,2-dihydro-pyridin-3-yl]-7-methyl-3H-benzimidazole-5-carbonitrile | 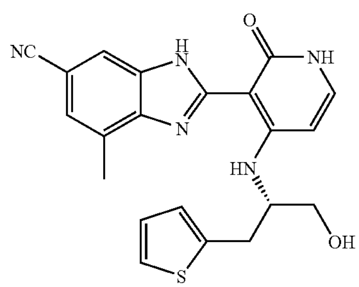 | 1.73 (b) | 406 |
| 301 | (S)-2-[4-(2-Benzo[b]thiophen-3-yl-1-hydroxymethyl-ethylamino)-2-oxo-1,2-dihydro-pyridin-3-yl]-7-methyl-3H-benzimidazole-5-carbonitrile | 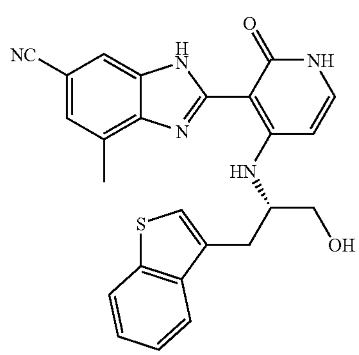 | 1.84 (b) | 456 |
| 302 | 7-Methyl-2-{2-oxo-4-[(pyridin-2-ylmethyl)-amino]-1,2-dihydro-pyridin-3-yl}-3H-benzimidazole-5-carbonitrile | 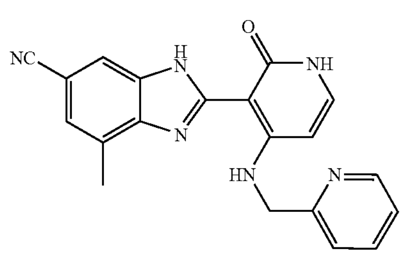 | 1.30 (b) | 357 |

-continued

| Example # | Name | structure | T (min.) | Mass (M + H)+ m/z |
|---|---|---|---|---|
| 303 | (±)-2-{4-[2-(3-Bromo-4-methoxy-phenyl)-2-hydroxy-ethylamino]-2-oxo-1,2-dihydro-pyridin-3-yl}-7-chloro-3H-benzimidazole-5-carbonitrile | 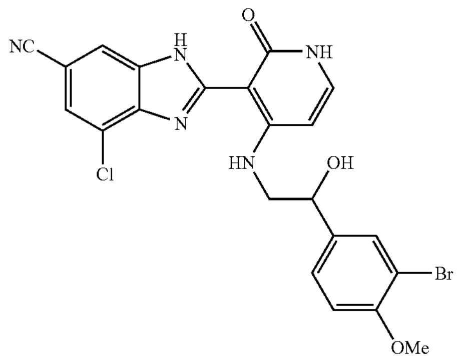 | 1.74 (d) | 514 |
| 304 | (±)-2-{4-[2-(3-Chloro-phenyl)-2-hydroxy-ethylamino]-2-oxo-1,2-dihydro-pyridin-3-yl}-7-chloro-3H-benzimidazole-5-carbonitrile | 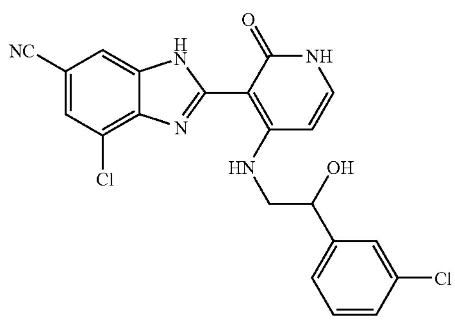 | 1.78 (d) | 440 |
| 305 | (±)-2-{4-[2-(3-Bromo-phenyl)-2-hydroxy-ethylamino]-2-oxo-1,2-dihydro-pyridin-3-yl}-7-chloro-3H-benzimidazole-5-carbonitrile | 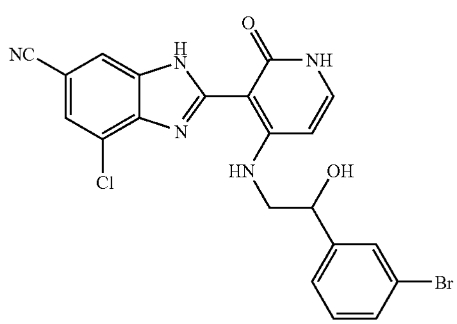 | 1.77 (d) | 484 |
| 306 | (±)-2-{4-[2-(3-Bromo-phenyl)-2-hydroxy-ethylamino]-2-oxo-1,2-dihydro-pyridin-3-yl}-7-ethyl-3H-benzimidazole-5-carbonitrile | 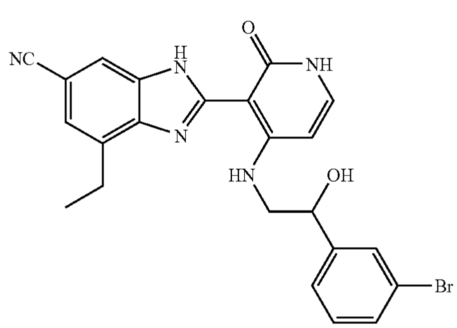 | 1.82 (d) | 478 |

-continued

| Example # | Name | structure | T (min.) | Mass (M + H)+ m/z |
|---|---|---|---|---|
| 307 | (±)-2-{4-[2-(3-Bromo-4-methoxy-phenyl)-2-hydroxy-ethylamino]-2-oxo-1,2-dihydro-pyridin-3-yl}-7-ethyl-3H-benzimidazole-5-carbonitrile | 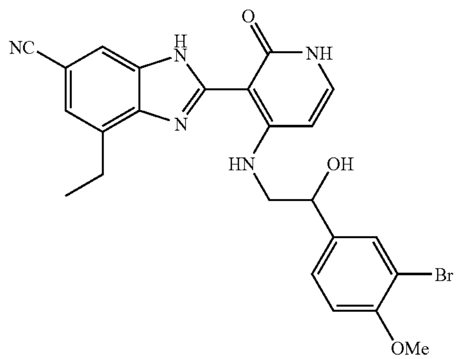 | 1.76 (d) | 508 |
| 308 | (±)-2-{4-[2-(3-Chloro-phenyl)-2-hydroxy-ethylamino]-2-oxo-1,2-dihydro-pyridin-3-yl}-7-ethyl-3H-benzimidazole-5-carbonitrile | 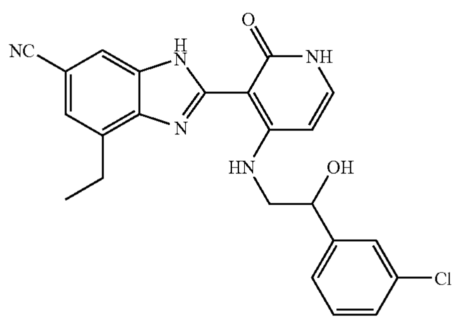 | 1.80 (d) | 434 |
| 309 | (±)-(2-Chloro-4-{2-[3-(6-cyano-4-methyl-1H-benzimidazol-2-yl)-2-oxo-1,2-dihydro-pyridin-4-ylamino]-1-hydroxy-ethyl}-phenyl)-carbamic acid isobutyl ester | 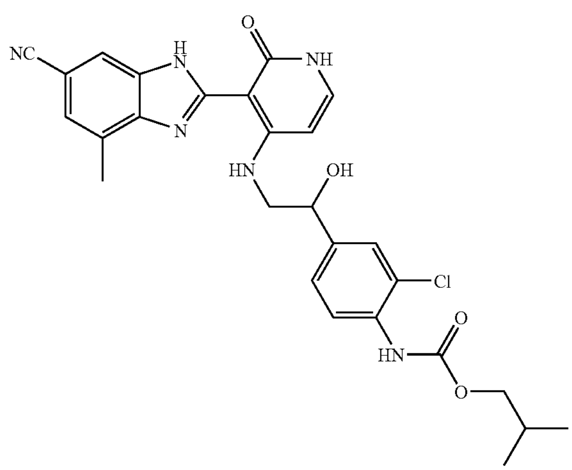 | 1.93 (b) | 535 |
| 310 | (S)-7-Ethyl-2-[4-(1-hydroxymethyl-2-phenyl-ethylamino)-2-oxo-1,2-dihydro-pyridin-3-yl]-3H-benzimidazole-5-carbonitrile | 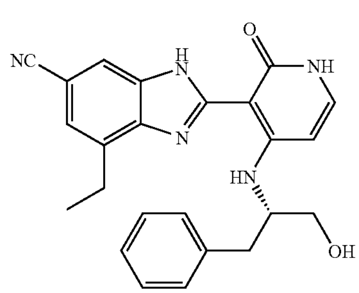 | 1.75 (d) | 414 |

-continued

| Example # | Name | structure | T (min.) | Mass (M + H)+ m/z |
|---|---|---|---|---|
| 311 | (S)-7-Bromo-2-[4-(1-hydroxymethyl-2-phenyl-ethylamino)-2-oxo-1,2-dihydro-pyridin-3-yl]-3H-benzimidazole-5-carbonitrile | 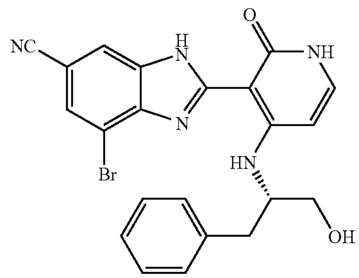 | 1.91 (b) | 464 |
| 312 | (S)-4-(1-Hydroxymethyl-2-phenyl-ethylamino)-3-[4-methyl-6-(4-methyl-piperazin-1-yl)-1H-benzimidazol-2-yl]-1H-pyridin-2-one | 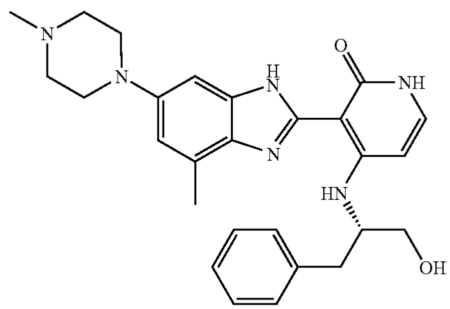 | 1.08 (f) | 473 |
| 313 | (S)-4-(1-Hydroxymethyl-2-phenyl-ethylamino)-3-[4-methyl-6-(4-n-butyl-piperazin-1-yl)-1H-benzimidazol-2-yl]-1H-pyridin-2-one | 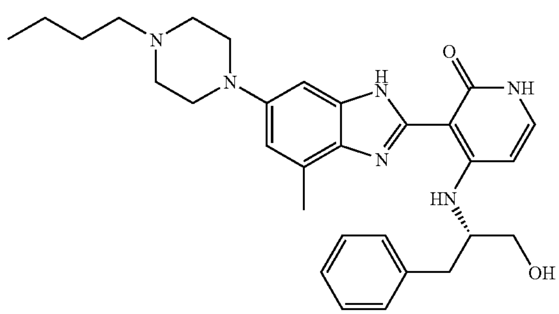 | 1.29 (k) | 515 |
| 314 | (S)-3-{6-[4-(2-Hydroxy-ethyl)-piperazin-1-yl]-4-methyl-1H-benzimidazol-2-yl}-4-(1-hydroxymethyl-2-phenyl-ethylamino)-1H-pyridin-2-one | 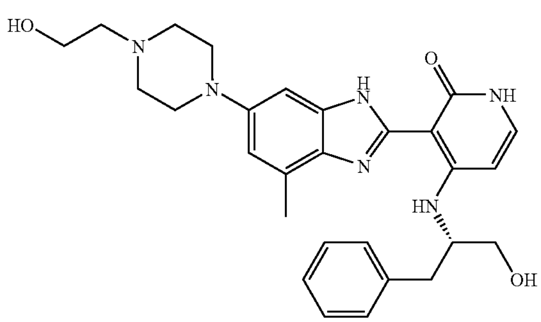 | 1.62 (k) | 503 |

-continued

| Example # | Name | structure | T (min.) | Mass (M + H)+ m/z |
|---|---|---|---|---|
| 315 | (S)-3-[6-(4-Cyclohexyl-piperazin-1-yl)-4-methyl-1H-benzimidazol-2-yl]-4-(1-hydroxymethyl-2-phenyl-ethylamino)-1H-pyridin-2-one | 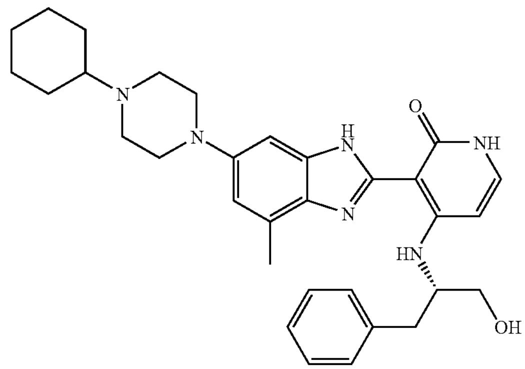 | 1.34 (f) | 541 |
| 316 | (S)-3-[6-(4-benzyl-piperazin-1-yl)-4-methyl-1H-benzimidazol-2-yl]-4-(1-hydroxymethyl-2-phenyl-ethylamino)-1H-pyridin-2-one | 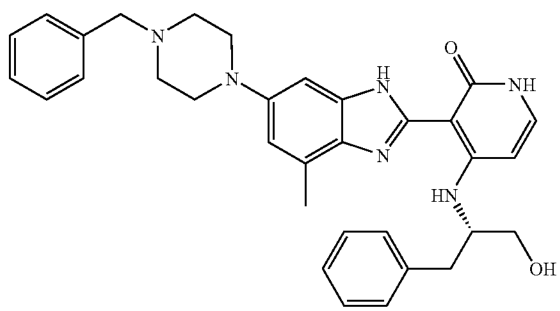 | 1.93 (f) | 549 |
| 317 | (S)-4-{2-[4-(1-Hydroxymethyl-2-phenyl-ethylamino)-2-oxo-1,2-dihydro-pyridin-3-yl]-7-methyl-3H-benzimidazol-5-yl}-piperazine-1-carboxylic acid amide | 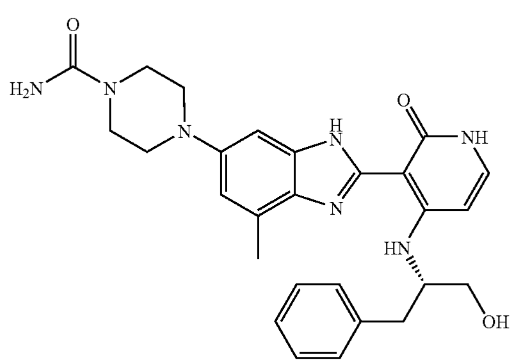 | 1.26 (f) | 502 |
| 318 | (S)-3-[6-(4-Benzenesulfonyl-piperazin-1-yl)-4-methyl-1H-benzimidazol-2-yl]-4-(1-hydroxymethyl-2-phenyl-ethylamino)-1H-pyridin-2-one | 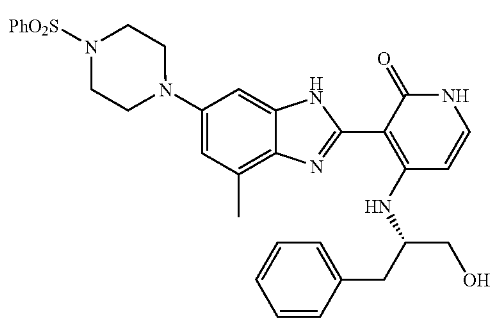 | 2.30 (k) | 599 |

-continued

| Example # | Name | structure | T (min.) | Mass (M + H)+ m/z |
|---|---|---|---|---|
| 319 | (S)-4-(1-Hydroxymethyl-2-phenyl-ethylamino)-3-[6-(4-methanesulfonyl-piperazin-1-yl)-4-methyl-1H-benzimidazol-2-yl]-1H-pyridin-2-one | 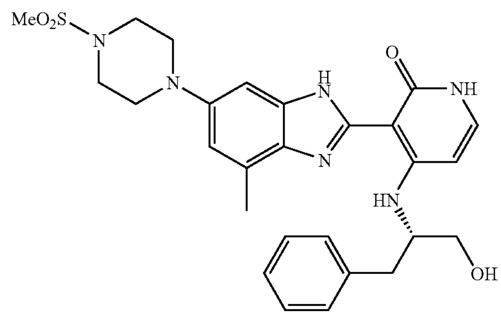 | 1.93 (k) | 537 |
| 320 | (±)-4-[2-(3-Chloro-phenyl)-2-hydroxy-ethylamino]-3-(4-methyl-6-piperazin-1-yl-1H-benzimidazol-2-yl)-1H-pyridin-2-one | 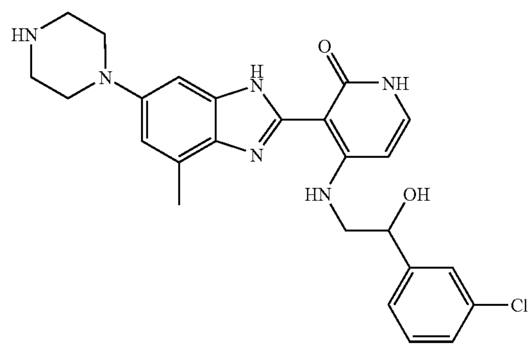 | 1.90 (f) | 479 |
| 321 | (±)-4-[2-(3-Chloro-phenyl)-2-hydroxy-ethylamino]-3-[6-(4-cyclopropylmethyl-piperazin-1-yl)-4-methyl-1H-benzimidazol-2-yl]-1H-pyridin-2-one | 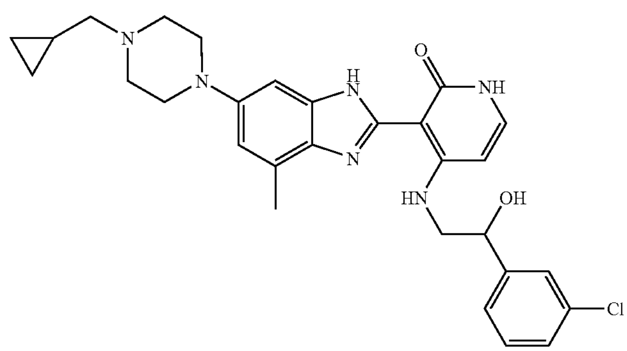 | 1.97 (k) | 533 |
| 322 | (±)-4-[2-(3-Chloro-phenyl)-2-hydroxy-ethylamino]-3-{6-[4-(2,2-dimethyl-propyl)-piperazin-1-yl]-4-methyl-1H-benzimidazol-2-yl}-1H-pyridin-2-one | 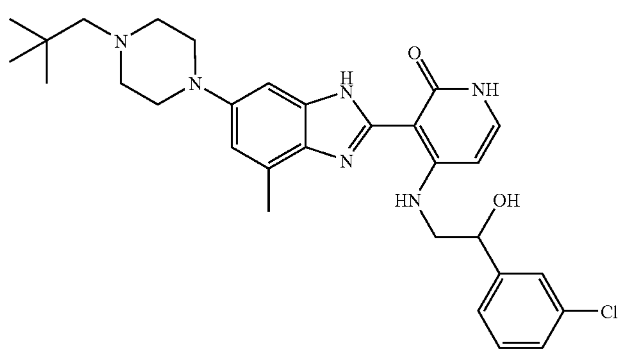 | 2.06 (k) | 549 |

-continued

| Example # | Name | structure | T (min.) | Mass (M + H)+ m/z |
|---|---|---|---|---|
| 323 | (±)-4-[2-(3-Chloro-phenyl)-2-hydroxy-ethylamino]-3-[6-(4-cyclobutyl-piperazin-1-yl)-4-methyl-1H-benzimidazol-2-yl]-1H-pyridin-2-one | 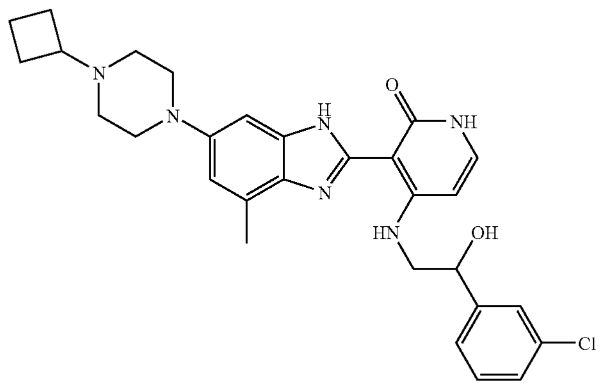 | 1.97 (k) | 533 |
| 324 | (±)-4-[2-(3-Chloro-phenyl)-2-hydroxy-ethylamino]-3-[6-(4-ethyl-piperazin-1-yl)-4-methyl-1H-benzimidazol-2-yl]-1H-pyridin-2-one | 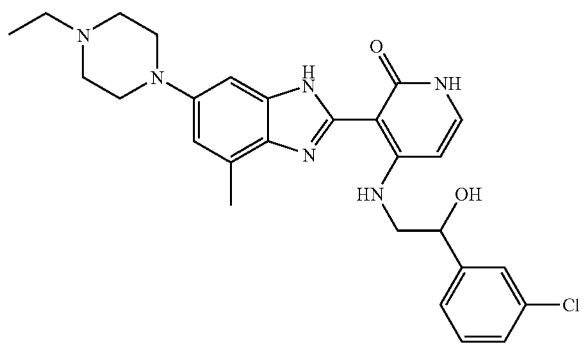 | 1.88 (k) | 507 |
| 325 | (±)-4-[2-(3-Chloro-phenyl)-2-hydroxy-ethylamino]-3-{6-[4-(2-hydroxy-ethyl)-piperazin-1-yl]-4-methyl-1H-benzimidazol-2-yl}-1H-pyridin-2-one | 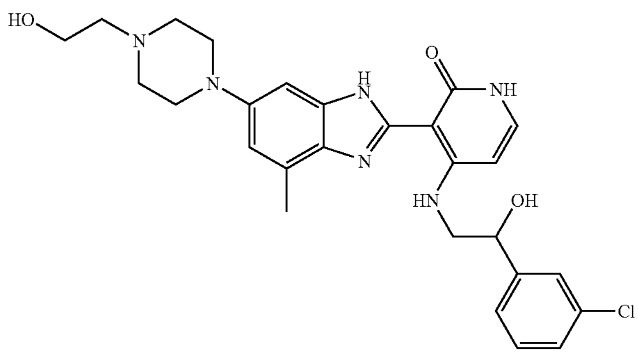 | 1.82 (k) | 524 |
| 326 | (±)-[4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazin-1-yl]-acetic acid ethyl ester | 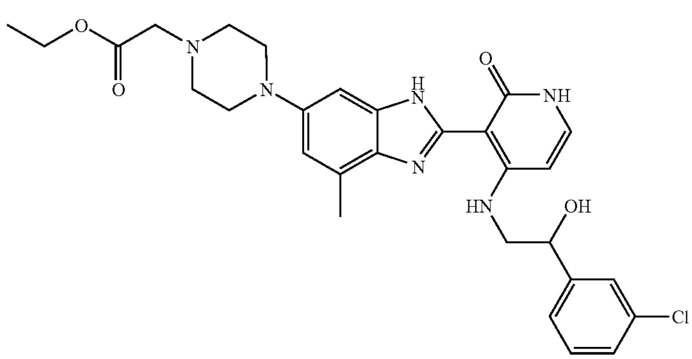 | 2.03 (k) | 565 |

-continued

| Example # | Name | structure | T (min.) | Mass (M + H)+ m/z |
|---|---|---|---|---|
| 327 | (±)-4-[2-(3-Chloro-phenyl)-2-hydroxy-ethylamino]-3-{6-[4-(3-dimethylamino-2,2-dimethyl-propyl)-piperazin-1-yl]-4-methyl-1H-benzoimidazol-2-yl}-1H-pyridin-2-one | 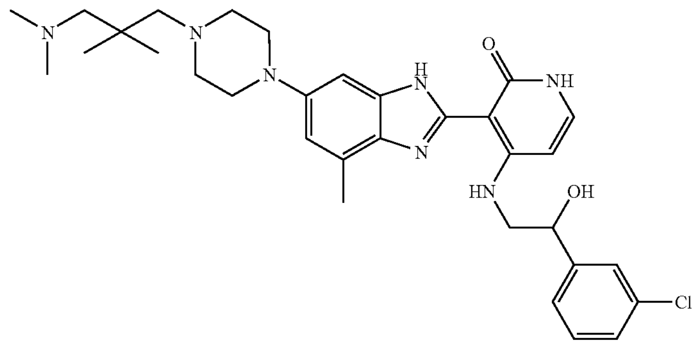 | 1.84 (k) | 592 |
| 328 | (±)-4-[2-(3-Chloro-phenyl)-2-hydroxy-ethylamino]-3-(4-methyl-6-morpholin-4-yl-1H-benzimidazol-2-yl)-1H-pyridin-2-one | 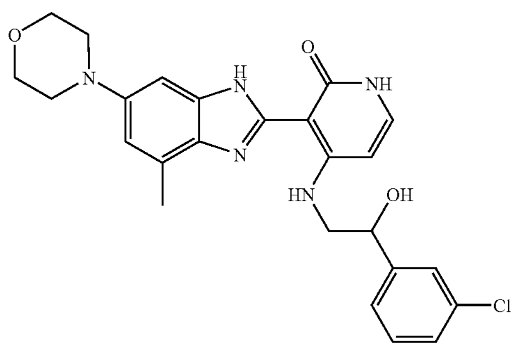 | 1.19 (a) | 480 |
| 329 | (±)-4-[2-(3-Bromo-phenyl)-2-hydroxy-ethylamino]-3-(4-methyl-6-morpholin-4-yl-1H-benzimidazol-2-yl)-1H-pyridin-2-one | 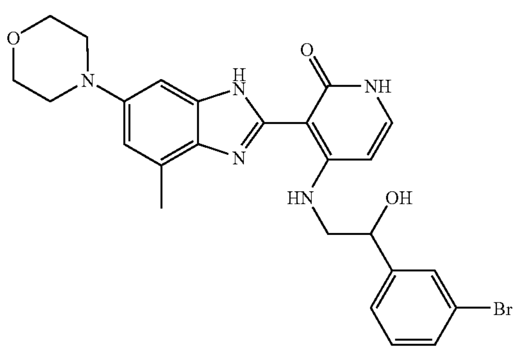 | 1.21 (a) | 524 |
| 330 | (±)-4-[2-(3-Bromo-4-methoxy-phenyl)-2-hydroxy-ethylamino]-3-(4-methyl-6-morpholin-4-yl-1H-benzimidazol-2-yl)-1H-pyridin-2-one | 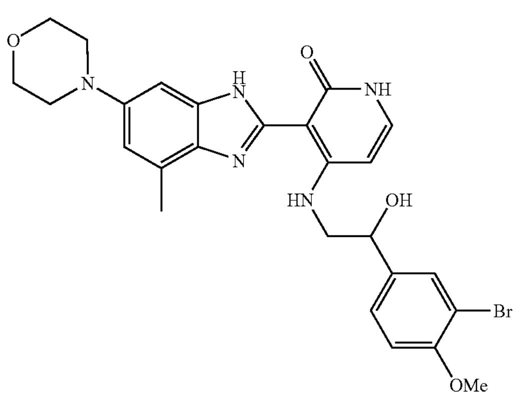 | 1.16 (a) | 554 |

| Example # | Name | structure | T (min.) | Mass (M + H)+ m/z |
|---|---|---|---|---|
| 331 | (±)-4-[2-(3-Chlorophenyl)-2-hydroxyethylamino]-3-{4-methyl-6-[4-(tetrahydropyran-4-yl)-piperazin-1-yl]-1H-benzoimidazol-2-yl}-1H-pyridin-2-one | 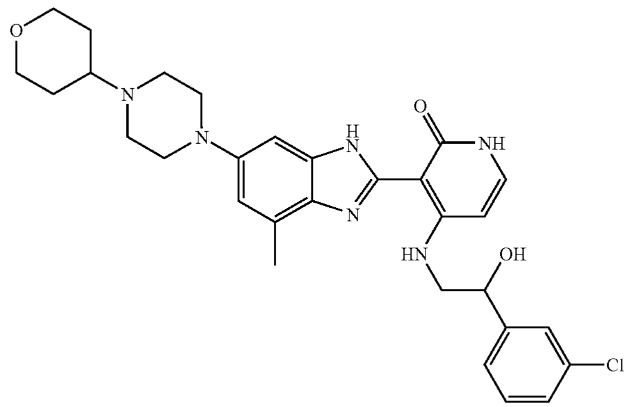 | 1.19 (f) | 563 |
| 332 | (±)-4-[2-(3-Chlorophenyl)-2-hydroxyethylamino]-3-[6-(4-imidazol-2-ylmethyl-piperazin-1-yl)-4-methyl-1H-benzimidazol-2-yl]-1H-pyridin-2-one | 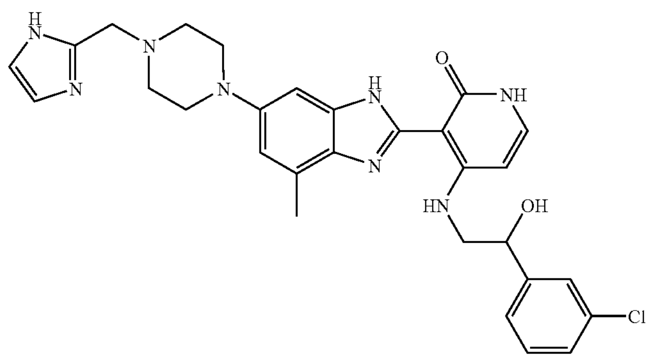 | 1.19 (f) | 559 |
| 333 | (±)-4-[2-(3-Chlorophenyl)-2-hydroxyethylamino]-3-[4-methyl-6-(4-propyl-piperazin-1-yl)-1H-benzimidazol-2-yl]-1H-pyridin-2-one | 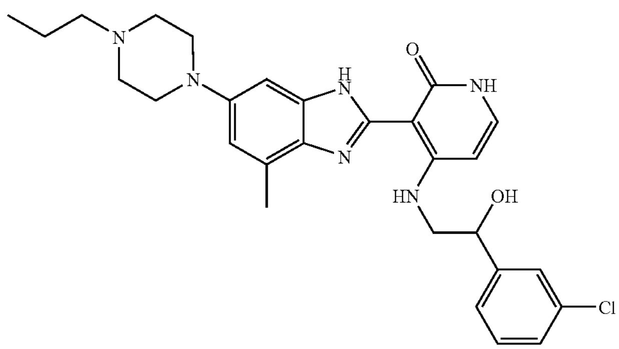 | 1.19 (f) | 521 |
| 334 | (±)-4-[2-(3-Chlorophenyl)-2-hydroxyethylamino]-3-{4-methyl-6-[4-(1-methyl-piperidin-4-yl)-piperazin-1-yl]-1H-benzimidazol-2-yl}-1H-pyridin-2-one | 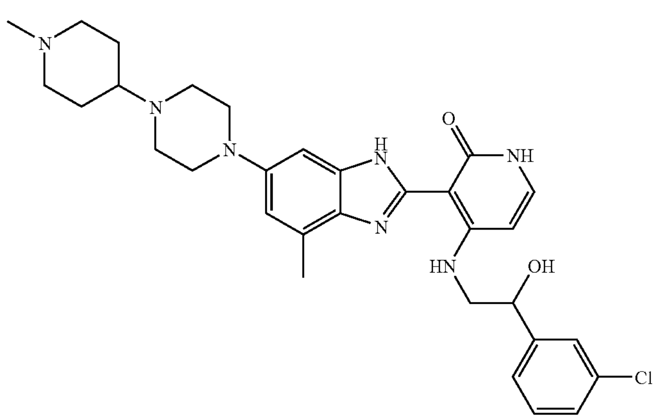 | 1.08 (f) | 576 |

-continued

| Example # | Name | structure | T (min.) | Mass (M + H)+ m/z |
|---|---|---|---|---|
| 335 | (±)-4-[2-(3-Bromo-phenyl)-2-hydroxy-ethylamino]-3-{6-[4-(2-hydroxy-ethyl)-piperazin-1-yl]-4-methyl-1H-benzimidazol-2-yl}-1H-pyridin-2-one | 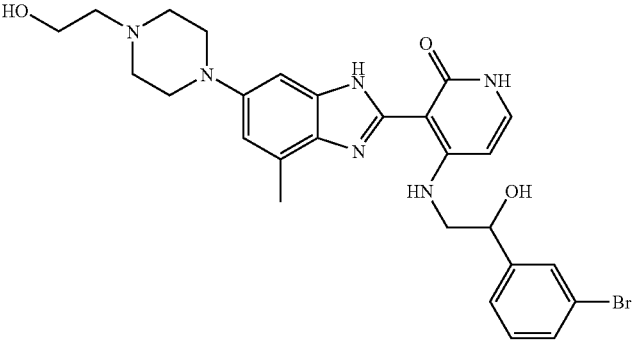 | 1.79 (f) | 567 |
| 336 | (±)-4-[2-(3-Bromo-phenyl)-2-hydroxy-ethylamino]-3-(4-methyl-6-piperazin-1-yl-1H-benzimidazol-2-yl)-1H-pyridin-2-one | 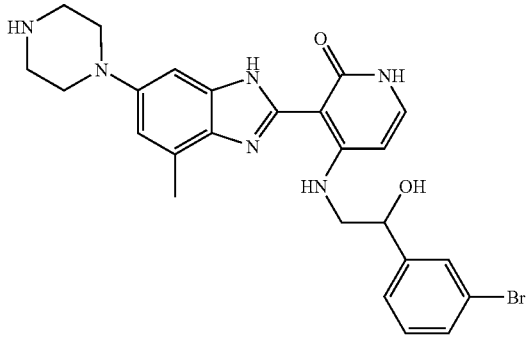 | 1.83 (f) | 523 |
| 337 | (±)-4-[2-(3-Bromo-4-methoxy-phenyl)-2-hydroxy-ethylamino]-3-(4-methyl-6-piperazin-1-yl-1H-benzimidazol-2-yl)-1H-pyridin-2-one | 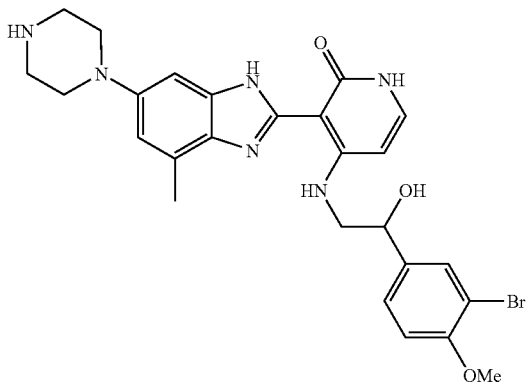 | 1.72 (f) | 553 |
| 338 | (±)-3-[6-(4-Acetyl-piperazin-1-yl)-4-methyl-1H-benzimidazol-2-yl]-4-[2-(3-bromo-phenyl)-2-hydroxy-ethylamino]-1H-pyridin-2-one | 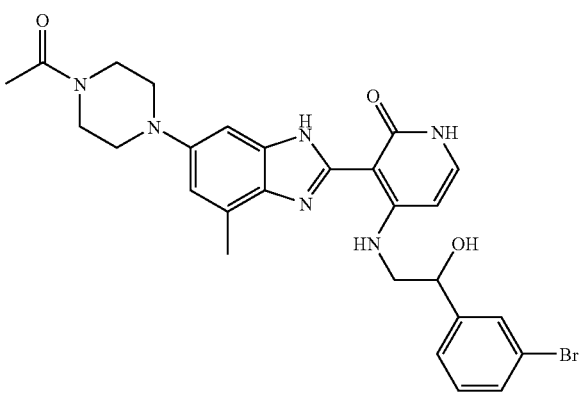 | 1.90 (f) | 565 |

| Example # | Name | structure | T (min.) | Mass (M + H)+ m/z |
|---|---|---|---|---|
| 339 | (±)-3-(6-Amino-5-methyl-1H-benzimidazol-2-yl)-4-[2-(3-bromo-phenyl)-2-hydroxy-ethylamino]-1H-pyridin-2-one | 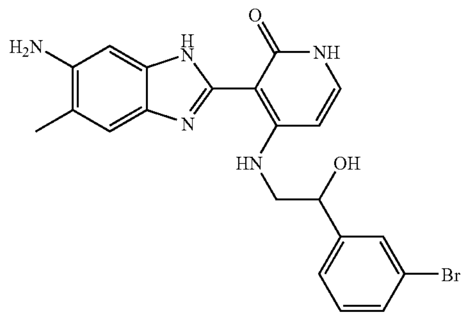 | 1.41 (j) | 454 |
| 340 | (±)-4-[2-(3-Chloro-phenyl)-2-hydroxy-ethylamino]-3-(6-pyrazol-1-yl-1H-benzimidazol-2-yl)-1H-pyridin-2-one | 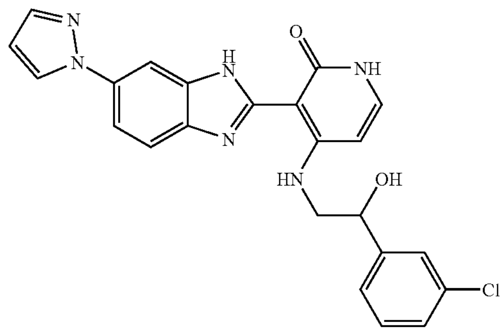 | 1.86 (f) | 447 |
| 341 | (±)-3-(6-Amino-4-methyl-1H-benzimidazol-2-yl)-4-[2-(3-chloro-phenyl)-2-hydroxy-ethylamino]-1H-pyridin-2-one | 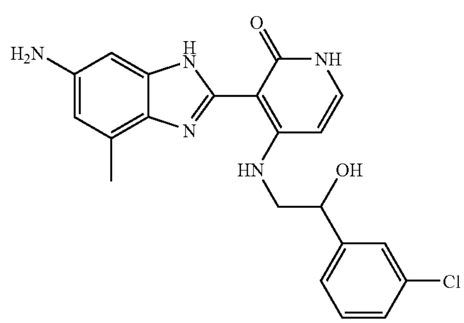 | 1.51 (f) | 410 |
| 342 | (±)-4-[2-(3-Chloro-phenyl)-2-hydroxy-ethylamino]-3-(6-[1,2,3]triazol-1-yl-1H-benzimidazol-2-yl)-1H-pyridin-2-one | 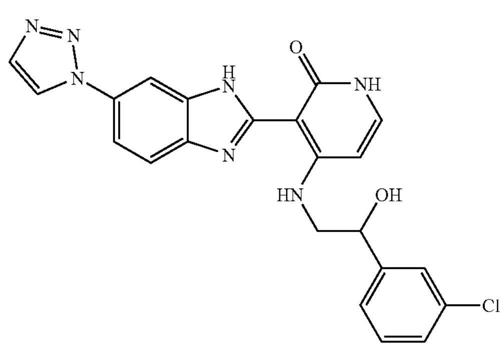 | 2.04 (f) | 448 |

-continued

| Example # | Name | structure | T (min.) | Mass (M + H)+ m/z |
|---|---|---|---|---|
| 343 | (±)-N-(2-{4-[2-(3-Chloro-Phenyl)-2-hydroxy-ethylamino]-2-oxo-1,2-dihydro-pyridin-3-yl}-7-methyl-3H-benzimidazol-5-yl)-acetamide | 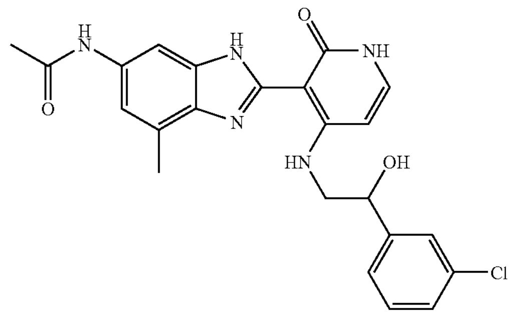 | 1.62 (f) | 452 |
| 344 | (±)-(2-{4-[2-(3-Chloro-phenyl)-2-hydroxy-ethylamino]-2-oxo-1,2-dihydro-pyridin-3-yl}-7-methyl-3H-benzimidazol-5-yl)-urea | 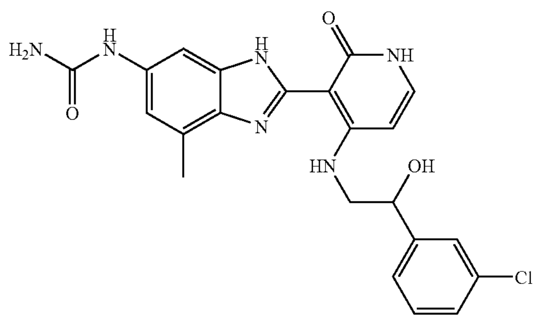 | 1.49 (f) | 453 |
| 345 | (±)-1-(2-{4-[2-(3-Chloro-phenyl)-2-hydroxy-ethylamino]-2-oxo-1,2-dihydro-pyridin-3-yl}-7-methyl-3H-benzimidazol-5-yl)-3-ethyl-urea | 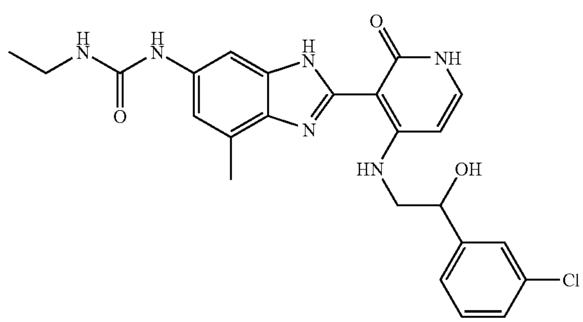 | 1.64 (f) | 481 |
| 346 | (±)-1-(2-{4-[2-(3-Chloro-phenyl)-2-hydroxy-ethylamino]-2-oxo-1,2-dihydro-pyridin-3-yl}-7-methyl-3H-benzimidazol-5-yl)-3-isopropyl-urea | 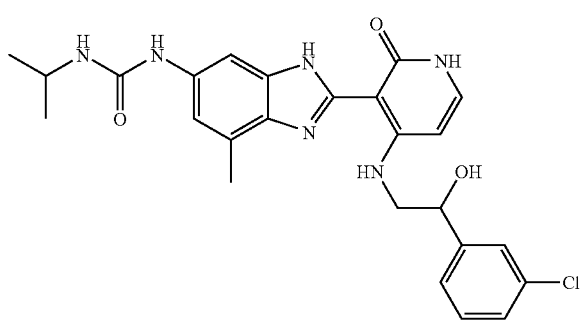 | 1.71 (f) | 495 |
| 347 | (S)-4-(1-Hydroxymethyl-2-phenyl-ethylamino)-3-[4-methyl-6-(2-morpholin-4-yl-ethylamino)-1H-benzimidazol-2-yl]-1H-pyridin-2-one | 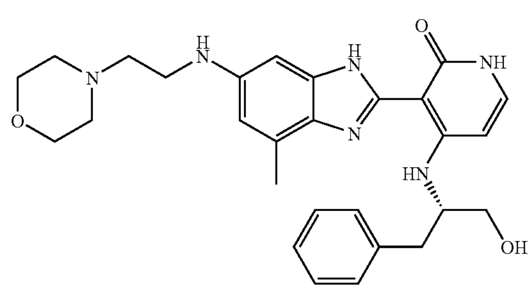 | 1.05 (f) | 503 |

-continued

| Example # | Name | structure | T (min.) | Mass (M + H)+ m/z |
|---|---|---|---|---|
| 348 | (±)-4-[2-(3-Bromo-phenyl)-2-hydroxy-ethylamino]-3-(4,5,6-trifluoro-1H-benzimidazol-2-yl)-1H-pyridin-2-one | 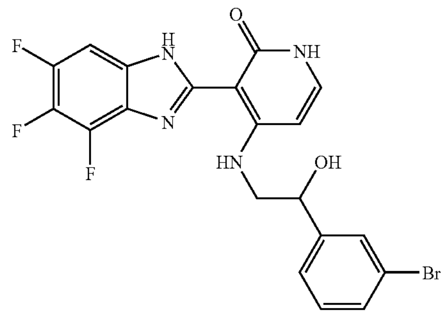 | 1.76 (d) | 479 |
| 349 | 4-[(Pyridin-2-ylmethyl)-amino]-3-(4,5,6-trifluoro-1H-benzimidazol-2-yl)-1H-pyridin-2-one | 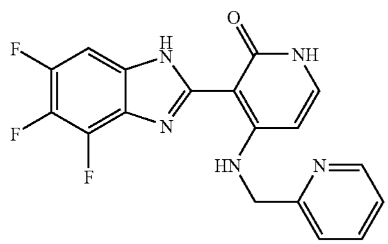 | 1.36 (d) | 372 |
| 350 | (S)-4-(1-Hydroxymethyl-2-phenyl-ethylamino)-3-(4,5,6,-trifluoro-1H-benzimidazol-2-yl)-1H-pyridin-2-one | 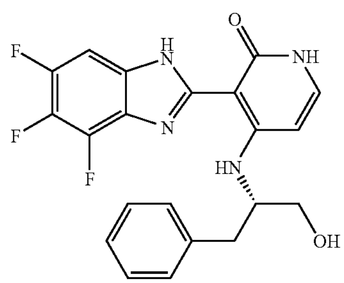 | 1.73 (d) | 415 |
| 351 | 3-(4,6-Dibromo-1H-benzimidazol-2-yl)-4-[(pyridin-2-ylmethyl)-amino]-1H-pyridin-2-one | 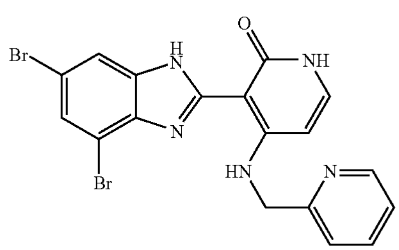 | 1.66 (d) | 474 |
| 352 | (±)-4-[2-(3-Bromo-phenyl)-2-hydroxy-ethylamino]-3-(4,6-dibromo-1H-benzimidazol-2-yl)-1H-pyridin-2-one | 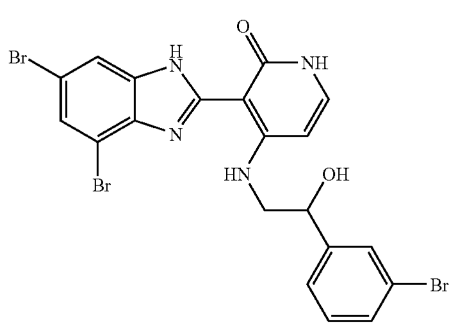 | 1.95 (d) | 581 |

-continued

| Example # | Name | structure | T (min.) | Mass (M + H)+ m/z |
|---|---|---|---|---|
| 353 | (S)-3-(4,6-Dibromo-1H-benzimidazol-2-yl)-4-(1-hydroxymethyl-2-phenyl-ethylamino)-1H-pyridin-2-one | 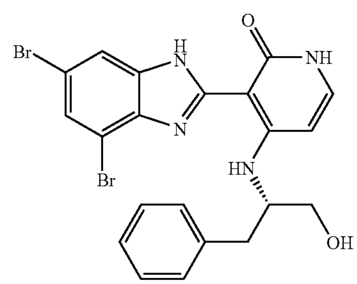 | 1.92 (d) | 517 |
| 354 | (±)-4-[2-(3-Bromo-phenyl)-2-hydroxy-ethylamino]-3-(5,6-dichloro-1H-benzimidazol-2-yl)-1H-pyridin-2-one | 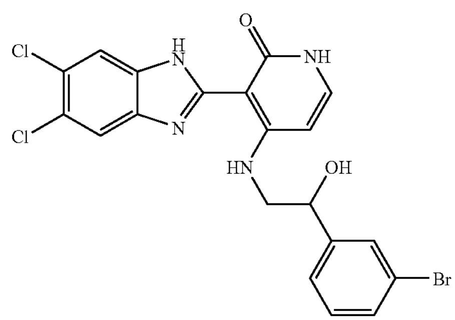 | 1.85 (d) | 493 |
| 355 | 3-(5,6-Dichloro-1H-benzimidazol-2-yl)-4-[(pyridin-2-ylmethyl)-amino]-1H-pyridin-2-one | 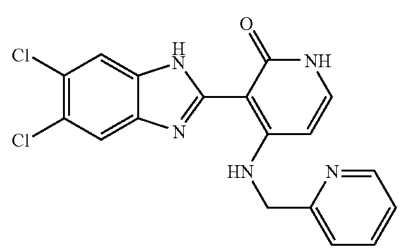 | 1.48 (d) | 386 |
| 356 | (S)-3-(5,6-Dichloro-1H-benzimidazol-2-yl)-4-(1-hydroxymethyl-2-phenyl-ethylamino)-1H-pyridin-2-one | 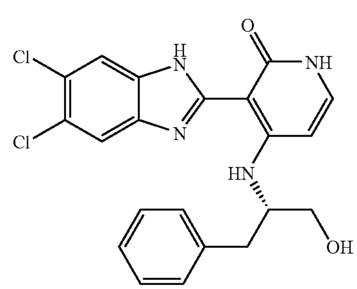 | 1.82 (d) | 429 |
| 357 | (±)-3-(4,6-Bis-trifluoromethyl-1H-benzimidazol-2-yl)-4-[2-(3-bromo-phenyl)-2-hydroxy-ethylamino]-1H-pyridin-2-one | 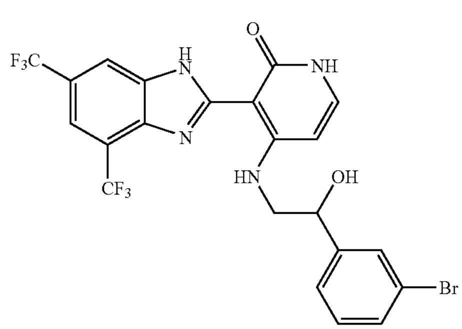 | 1.56 (b) | 561 |

-continued

| Example # | Name | structure | T (min.) | Mass (M + H)+ m/z |
|---|---|---|---|---|
| 358 | 3-(4,6-Bis-trifluoromethyl-1H-benzimidazol-2-yl)-4-[(pyridin-2-ylmethyl)-amino]-1H-pyridin-2-one | 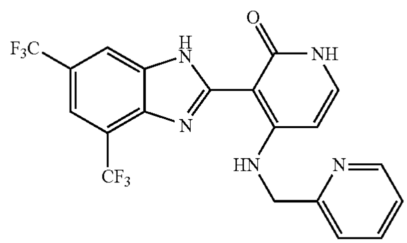 | 1.39 (b) | 454 |
| 359 | (S)-3-(4,6-Bis-trifluoromethyl-1H-benzimidazol-2-yl)-4-(1-hydroxymethyl-2-phenyl-ethylamino)-1H-pyridin-2-one | 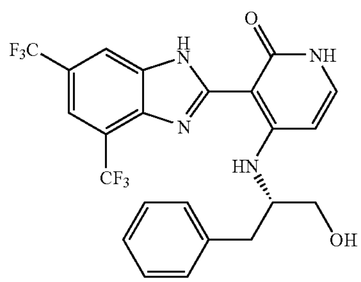 | 1.53 (b) | 497 |
| 360 | (±)-3-(4,6-Bis-trifluoromethyl-1H-benzimidazol-2-yl)-4-[2-(3-bromo-4-methoxy-phenyl)-2-hydroxy-ethylamino]-1H-pyridin-2-one | 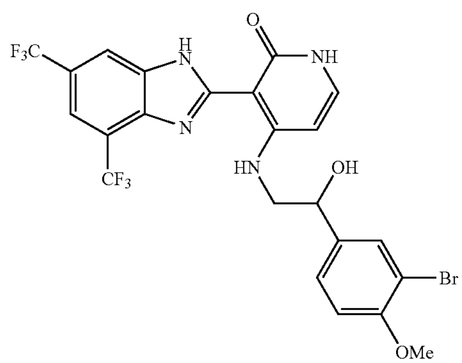 | 1.51 (b) | 591 |
| 361 | (±)-4-[2-(3-Bromo-phenyl)-2-hydroxy-ethylamino]-3-(4-chloro-6-trifluoromethyl-1H-benzimidazol-2-yl)-1H-pyridin-2-one | 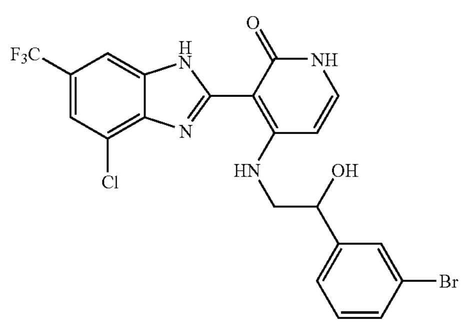 | 1.54 (b) | 527 |
| 362 | 3-(4-Chloro-6-trifluoromethyl-1H-benzimidazol-2-yl)-4-[(pyridin-2-ylmethyl)-amino]-1H-pyridin-2-one | 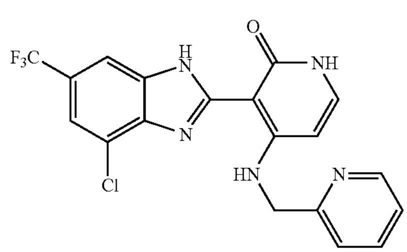 | 1.34 (b) | 420 |

-continued

| Example # | Name | structure | T (min.) | Mass (M + H)+ m/z |
|---|---|---|---|---|
| 363 | (S)-3-(4-Chloro-6-trifluoromethyl-1H-benzimidazol-2-yl)-4-(1-hydroxymethyl-2-phenyl-ethylamino)-1H-pyridin-2-one | 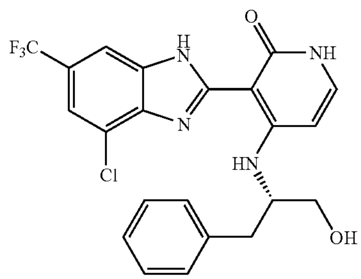 | 1.51 (b) | 463 |
| 364 | (±)-4-[2-(3-Bromo-4-methoxy-phenyl)-2-hydroxy-ethylamino]-3-(4-chloro-6-trifluoromethyl-1H-benzimidazol-2-yl)-1H-pyridin-2-one | 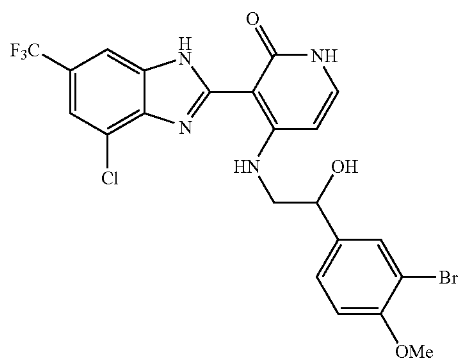 | 1.50 (b) | 557 |
| 365 | (±)-4-[2-(3-Bromo-phenyl)-2-hydroxy-ethylamino]-3-(5-trifluoromethyl-1H-benzimidazol-2-yl)-1H-pyridin-2-one | 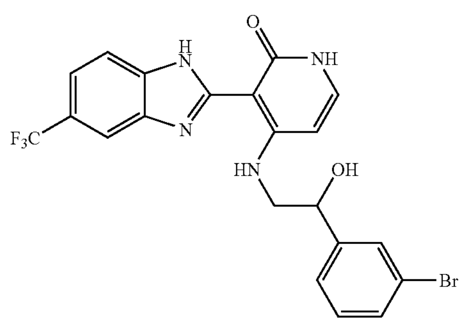 | 1.42 (b) | 493 |
| 366 | 4-[(Pyridin-2-ylmethyl)-amino]-3-(5-trifluoromethyl-1H-benzimidazol-2-yl)-1H-pyridin-2-one | 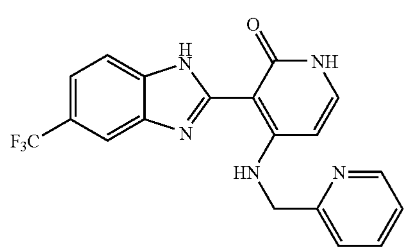 | 1.16 (b) | 386 |
| 367 | (S)-4-(1-Hydroxymethyl-2-phenyl-ethylamino)-3-(5-trifluoromethyl-1H-benzimidazol-2-yl)-1H-pyridin-2-one | 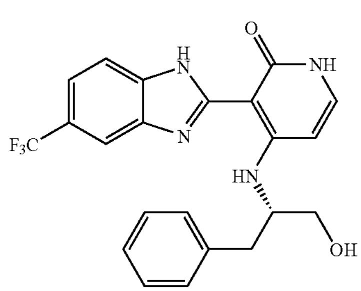 | 1.41 (b) | 429 |

-continued

| Example # | Name | structure | T (min.) | Mass (M + H)+ m/z |
|---|---|---|---|---|
| 368 | (±)-4-[2-(3-Bromo-4-methoxy-phenyl)-2-hydroxy-ethylamino]-3-(5-trifluoromethyl-1H-benzimidazol-2-yl)-1H-pyridin-2-one | 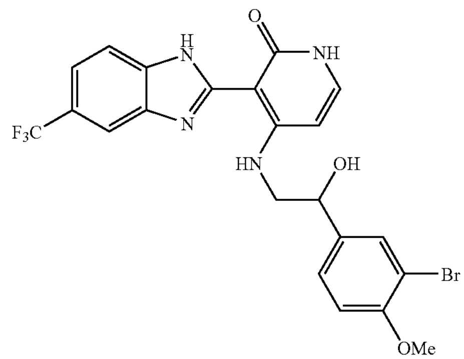 | 1.38 (b) | 523 |
| 369 | (±)-4-[2-(3-Bromo-phenyl)-2-hydroxy-ethylamino]-3-(5-fluoro-6-imidazol-1-yl-1H-benzimidazol-2-yl)-1H-pyridin-2-one | 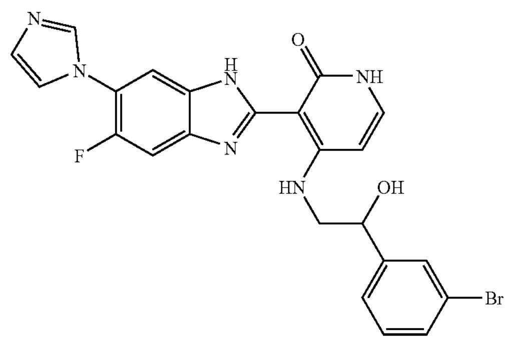 | 1.10 (b) | 509 |
| 370 | 3-(5-Fluoro-6-imidazol-1-yl-1H-benzimidazol-2-yl)-4-[(pyridin-2-ylmethyl)-amino]-1H-pyridin-2-one | 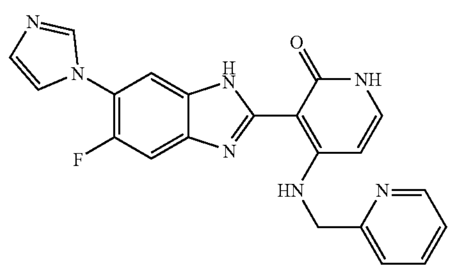 | 0.73 (b) | 402 |
| 371 | (S)-3-(5-Fluoro-6-imidazol-1-yl-1H-benzimidazol-2-yl)-4-(1-hydroxymethyl-2-phenyl-ethylamino)-1H-pyridin-2-one | 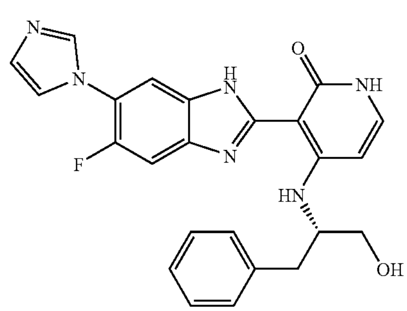 | 1.04 (b) | 445 |

| Example # | Name | structure | T (min.) | Mass (M + H)+ m/z |
|---|---|---|---|---|
| 372 | (±)-4-[2-(3-Bromo-4-methoxy-phenyl)-2-hydroxy-ethylamino]-3-(5-fluoro-6-imidazol-1-yl-1H-benzimidazol-2-yl)-1H-pyridin-2-one | 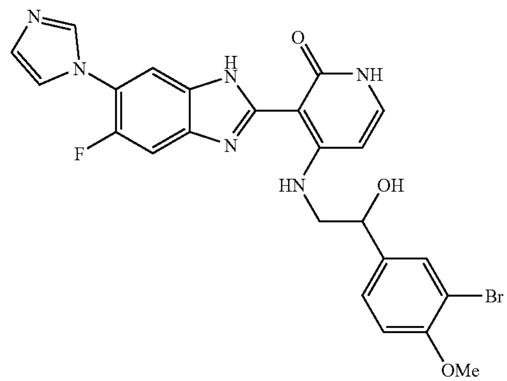 | 1.05 (b) | 539 |
| 373 | (±)-3-(4-Bromo-6-trifluoromethyl-1H-benzimidazol-2-yl)-4-[2-(3-bromo-phenyl)-2-hydroxy-ethylamino]-1H-pyridin-2-one | 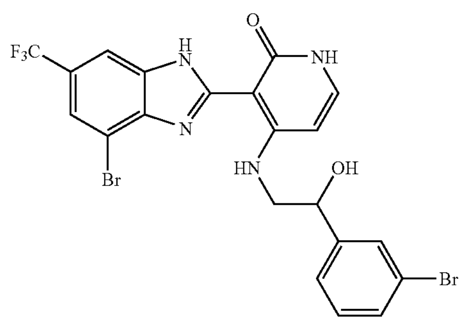 | 1.97 (d) | 571 |
| 374 | (±)-3-(4-Bromo-6-trifluoromethyl-1H-benzimidazol-2-yl)-4-[2-(3-chloro-phenyl)-2-hydroxy-ethylamino]-1H-pyridin-2-one | 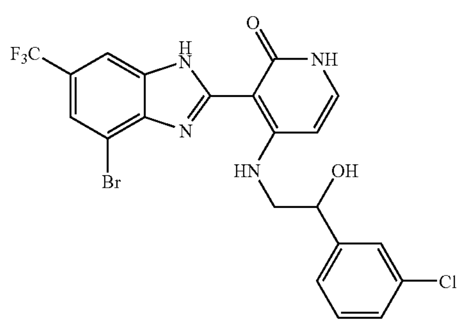 | 1.95 (d) | 527 |
| 375 | (±)-4-[2-(3-Bromo-phenyl)-2-hydroxy-ethylamino]-3-(4,6-difluoro-1H-benzimidazol-2-yl)-1H-pyridin-2-one | 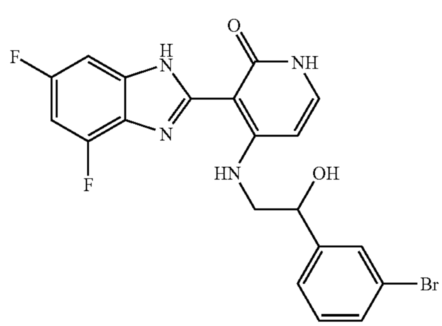 | 1.72 (d) | 461 |

| Example # | Name | structure | T (min.) | Mass (M + H)+ m/z |
|---|---|---|---|---|
| 376 | (±)-4-[2-(3-Chloro-phenyl)-2-hydroxy-ethylamino]-3-(4,6-difluoro-1H-benzimidazol-2-yl)-1H-pyridin-2-one | 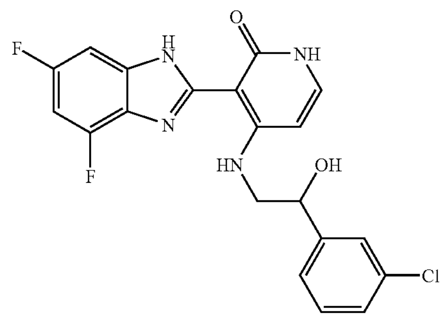 | 1.70 (d) | 417 |
| 377 | (±)-4-[2-(3-Bromo-4-methoxy-phenyl)-2-hydroxy-ethylamino]-3-(4,6-difluoro-1H-benzimidazol-2-yl)-1H-pyridin-2-one | 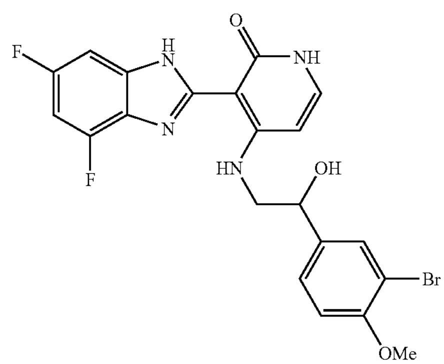 | 1.65 (d) | 491 |
| 378 | (±)-4-[2-(3-chloro-phenyl)-2-hydroxy-ethylamino]-3-[4-methyl-6-(2-methyl-imidazol-1-yl]-1H-benzimidazol-2-yl)-1H-pyridin-2-one | 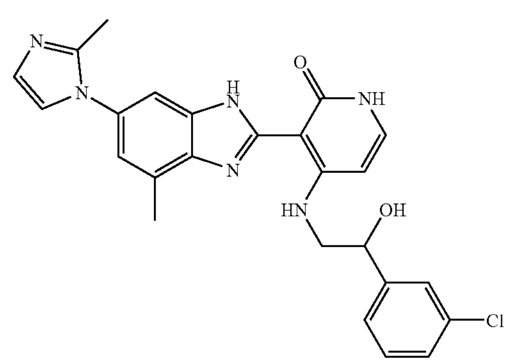 | 1.38 (d) | 475 |
| 379 | (±)-4-[2-(3-Bromo-4-methoxy-phenyl)-2-hydroxy-ethylamino]-3-[4-methyl-6-(4-methyl-imidazol-1-yl]-1H-benzimidazol-2-yl]-1H-pyridin-2-one | 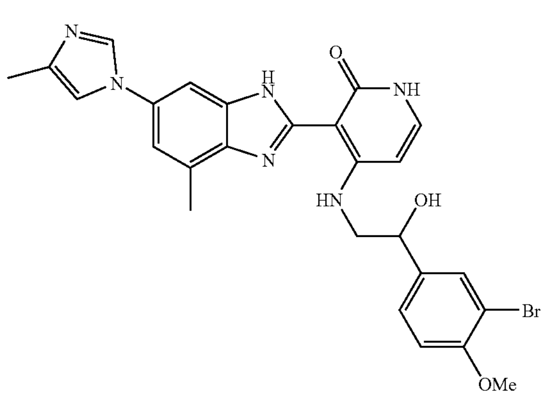 | 1.35 (d) | 549 |

-continued

| Example # | Name | structure | T (min.) | Mass (M + H)+ m/z |
|---|---|---|---|---|
| 380 | (±)-4-[2-(3-Bromo-phenyl)-2-hydroxy-ethylamino]-3-(5,6-difluoro-1H-benzimidazol-2-yl)-1H-pyridin-2-one | 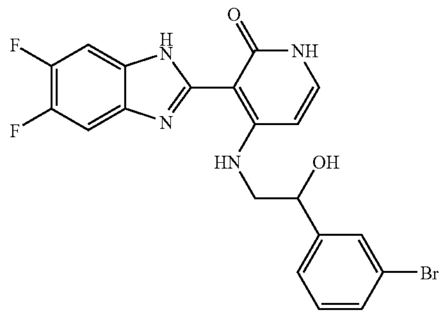 | 1.67 (b) | 461 |
| 381 | 3-(5,6-Difluoro-1H-benzimidazol-2-yl)-4-[(pyridin-2-yl-methyl)-amino]-1H-pyridin-2-one | 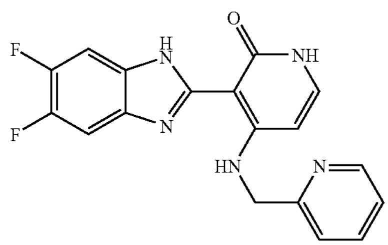 | 1.18 (b) | 354 |
| 382 | 6-Hydroxy-5-(6-imidazol-1-yl-4-methyl-1H-benzimidazol-2-yl)-3H-pyrimidin-4-one | 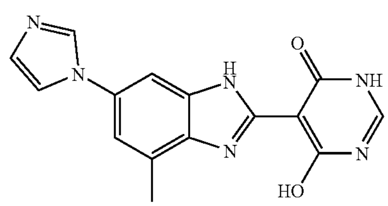 | 0.96 (f) | 309 |
| 383 | (±)-6-[2-(3-Chloro-phenyl)-2-hydroxy-ethylamino]-5-(6-imidazol-1-yl-4-methyl-1H-benzimidazol-2-yl)-3H-pyrimidin-4-one | 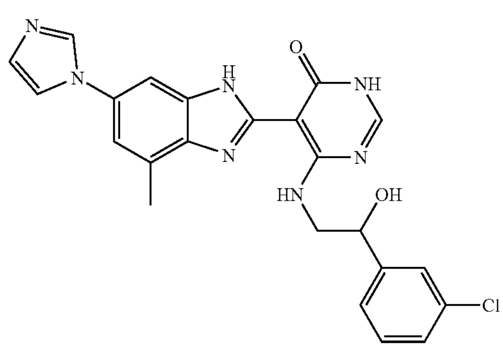 | 2.30 (f) | 462 |

Intermediate Imidate Formation (Scheme IV, 13)

General Procedure for Examples 384–397—Imidazoline Formation (Scheme IV, 14)

EXAMPLE 384

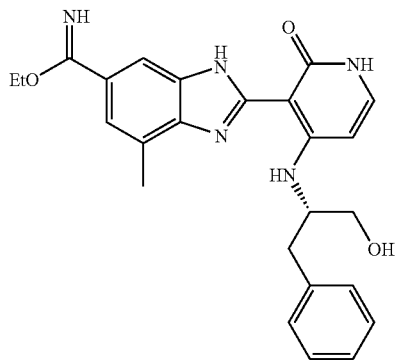

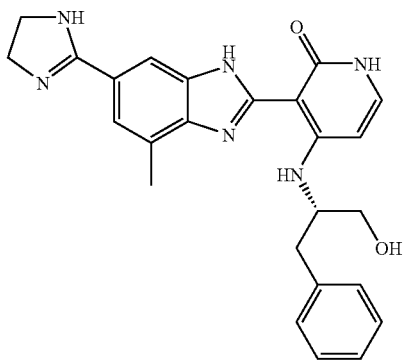

5  (S)-2-[4-(1-Hydroxymethyl-2-phenyl-ethylamino)-2-oxo-1,2-dihydro-pyridin-3-yl]-7-methyl-3H-benzimidazole-5-carboximidic ethyl ester: To a suspension of (S)-2-[4-(1-hydroxymethyl-2-phenyl-ethylamino)-2-oxo-1,2-dihydro-pyridin-3-yl]-7-methyl-3H-benzimidazole-5-carbonitrile (0.8 g, 2.0 mmol) in ethanol (anhydrous, 80 mL) was bubbled HCl (anhydrous) at 0° C. until saturation. The mixture became a clear solution after a few minutes of bubbling and the solution was stirred at room temperature for 14 h. After concentration in vacuo, the crude product (0.89 g, 100%) was directly used for the next step without purification. LCMS (M+H)$^+$ m/z 446 (t=1.55 min).

(S)-3-[6-(4,5-Dihydro-1H-imidazol-2-yl)-4-methyl-1H-benzimidazol-2-yl]-4-(1-hydroxymethyl-2-phenyl-ethylamino)-1H-pyridin-2-one: The crude imidate ester (60 mg, 0.135 mmol) was diluted with methanol followed by addition of ethylenediamine (24 mg, 0.40 mmol). The reaction mixture was heated to reflux for 6 h. After concentration in vacuo, the residue was purified by prep. HPLC to yield the title compound (37 mg, 62%). $^1$H NMR (300 MHz, CD$_3$OD) δ 7.94 (1H, s), 7.50 (1H, s), 7.12–7.30 (6H, m), 6.16 (1H, d, J=7.7 Hz), 4.04–4.10 (5H, m), 3.75–3.77 (2H, m), 3.15 (1H, dd, J=5.2, 13. 6 Hz), 2.96 (1H, dd, J=8.1, 13.6 Hz), 2.67 (3H, s). LCMS (M+H)$^+$ m/z 443 (t=1.50 min.).

EXAMPLE 385

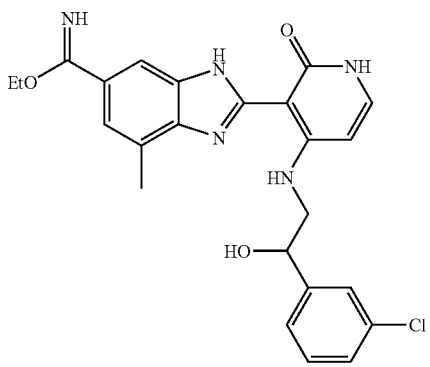

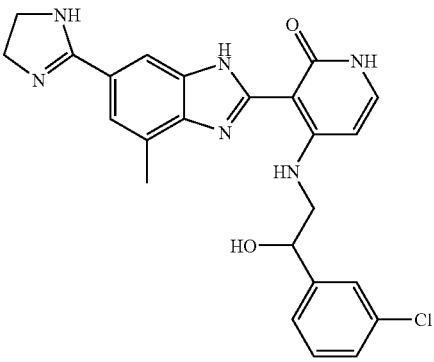

(±)-2-{4-[2-(3-Chloro-phenyl)-2-hydroxy-ethylamino]-2-oxo-1,2-dihydro-pyridin-3-yl}-7-methyl-3H-benzimidazole-5-carboximidic ethyl ester: The title compound was prepared using the General Procedure for Imidate Formation. LCMS (M+H)$^+$ m/z 466 (t=1.43 min.).

(±)-4-[2-(3-Chloro-phenyl)-2-hydroxy-ethylamino]-3-[6-(4,5-dihydro-1H-imidazol-2-yl)-4-methyl-1H-benzimidazol-2yl]-1H-pyridin-2-one: $^1$H NMR (300 MHz, CD$_3$OD) δ 7.93 (1H, s), 7.54 (1H, s), 7.23–7.45 (5H, m), 6.26 (1H, d, J=7.6 Hz), 5.01 (1H, t, J=6.3 Hz), 4.01 (4H, s), 3.78 (1H, dd, J=4.7, 13.5 Hz), 3.67 (1H, dd, J=6.6, 13.5 Hz), 2.66 (3H, s). LCMS (M+H)$^+$ m/z 463 (t=1.54 min

EXAMPLE 386

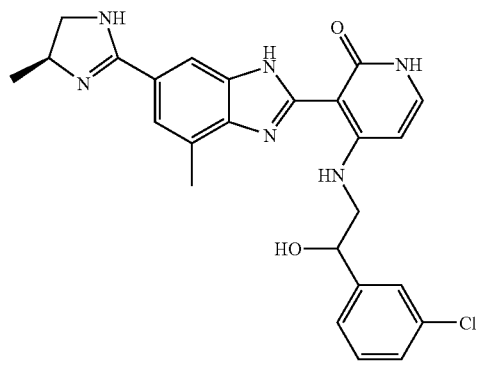

4-[2-(3-Chloro-phenyl)-2R2-hydroxy-ethylamino]-3-[4-methyl-6-(4S-methyl-4,5-dihydro-1H-imidazol-2-yl)-1H-benzoimidazol-2-yl]-1H-pyridin-2-one and 4-[2-(3-Chloro-phenyl)-2S-hydroxy-ethylamino]-3-[4-methyl-6-(4S-methyl-4,5-dihydro-1H-imidazol-2-yl)-1H-benzoimidazol-2-yl]-1H-pyridin-2-one: $^1$H NMR (300 MHz, CD$_3$OD) δ 7.90 (2H, s), 7.53 (2H, s), 7.22–7.47 (10H, m), 6.23 (2H, d, J=7.5 Hz), 5.00 (2H, t, J=6.4 Hz), 4.49–4.57 (2H, m), 4.21 (2H, t, J=11.0 Hz), 3.61–3.78 (6H, m), 2.63 (6H, s), 1.48 (6H, d, J=6.3 Hz). LCMS (M+H)$^+$ m/z 477 (t=1.71 min.).

EXAMPLE 387

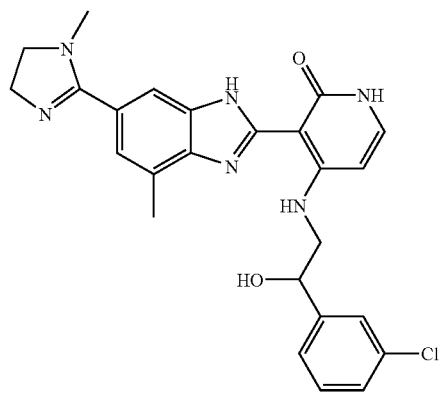

(±)-4-[2-(3-Chloro-phenyl)-2-hydroxy-ethylamino]-3-[4-methyl-6-(1-methyl-4,5-dihydro-1H-imidazol-2-yl)-1H-benzoimidazol-2yl]-1H-pyridin-2-one: $^1$H NMR (300 MHz, CD$_3$OD) δ 7.94 (1H, s), 7.57 (1H, s), 7.23–7.52 (5H, m), 6.22 (1H, d, J=7.5 Hz), 4.99 (1H, m), 4.00–4.15 (2H, m), 3.57–3.75 (4H, m), 2.77 (3H, s), 2.61 (3H, s). LCMS (M+H)$^+$ m/z 477 (t=1.60 min.).

EXAMPLE 388

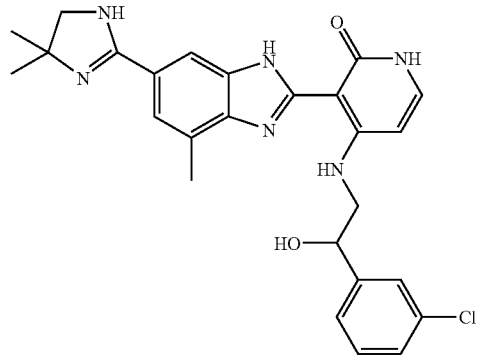

(±)-4-[2-(3-Chloro-phenyl)-2-hydroxy-ethylamino]-3-[6-(4,4-dimethyl-4,5-dihydro-1H-imidazol-2-yl)-4-methyl-1H-benzimidazol-2yl]-1H-pyridin-2-one: $^1$H NMR (300 MHz, CD$_3$OD) δ 7.89 (1H, s), 7.52 (1H, s), 7.22–7.45 (5H, m), 6.19 (1H, d, J=7.4 Hz), 4.99 (1H, t, J=6.2 Hz), 3.84 (2H, s), 3.78 (1H, dd, J=4.4, 13.4 Hz), 3.60 (1H, dd, J=6.7, 13.4 Hz), 2.61 (3H, s), 1.55 (6H, s). LCMS (M+H)$^+$ m/z 491 (t=1.73 min.).

EXAMPLE 389

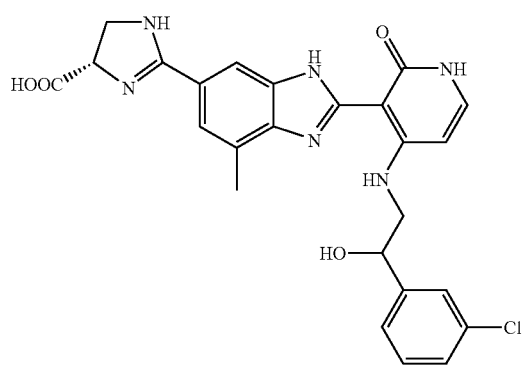

2-(2-{4-[2-(3-Chloro-phenyl)-2R-hydroxy-ethylamino]-2-oxo-1,2-dihydro-pyridin-3-yl}-7-methyl-3H-benzimidazol-5-yl)-4,5-dihydro-1H-imidazole-4S-carboxylic acid and 2-(2-{4-[2-(3-Chloro-phenyl)-2S-hydroxy-ethylamino]-2-oxo-1,2-dihydro-pyridin-3-yl}-7-methyl-3H-benzimidazol- 5-yl)-4,5-dihydro-1H-imidazole-4S-carboxylic acid: ¹H NMR (300 MHz, CD₃OD) δ 7.88 (2H, s), 7.52 (2H, s), 7.22–7.44 (10H, m), 6.17 (2H, d, J=7.4 Hz), 5.05 (2H, m), 4.23–4.38 (4H, m), 3.56–3.72 (6H, m), 2.58 (6H, s). LCMS (M+H)⁺ m/z 507 (t=1.64 min.).

EXAMPLE 390

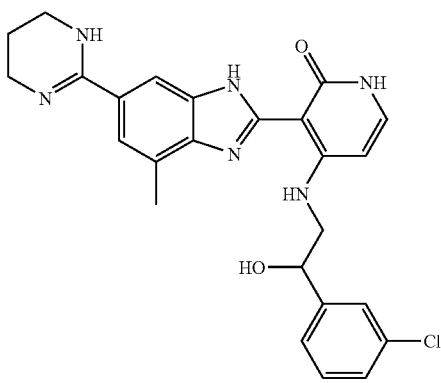

(±)-4-[2-(3-Chloro-phenyl)-2-hydroxy-ethylamino]-3-[4-methyl-6-(1,4,5,6-tetrahydro-pyrimidin-2-yl)-1H-benzimidazol-2-yl]-1H-pyridin-2-one: ¹H NMR (300 MHz, CD₃OD) δ 7.90 (1H, s), 7.53 (1H, s), 7.22–7.47 (5H, m), 6.23 (1H, d, J=7.6 Hz), 5.00 (1H, t, J=6.3 Hz), 4.49–4.57 (1H, m), 3.60–3.77 (5H, m), 3.24–3.34 (2H, m), 2.63 (3H, s). LCMS (M+H)⁺ m/z 477 (t=1.59 min.).

EXAMPLE 391

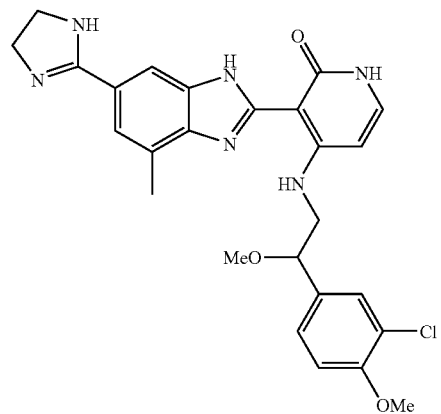

(±)-4-[2-(3-Chloro-4-methoxy-phenyl)-2-methoxy-ethylamino]-3-[6-(4,5-dihydro-1H-imidazol-2-yl)-4-methyl-1H-benzimidazol-2-yl]-1H-pyridin-2-one: ¹H NMR (300 MHz, CD₃OD) δ 7.88 (1H, s), 7.46 (1H, s), 7.44 (1H, s), 7.31 (1H, d, J=6.4 Hz), 7.28 (1H, d, J=5.6 Hz), 7.01 (1H, d, J=6.4 Hz), 6.19 (1H, d, J=5.6 Hz), 4.49 (1H, dd, J=3.4, 5.0 Hz), 4.09 (4H, s), 3.82 (3H, s), 3.36 (3H, s), 3.63–3.67 (2H, m), 2.62 (3H, s). LCMS (M+H)⁺ m/z 507 (t=1.72 min.).

EXAMPLE 392

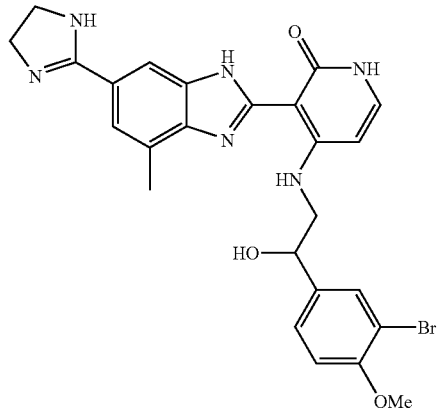

(±)-4-[2-(3-Bromo-4-methoxy-phenyl)-2-hydroxy-ethylamino]-3-[6-(4,5-dihydro-1H-imidazol-2-yl)-4-methyl-1H-benzimidazol-2-yl]-1H-pyridin-2-one: The title compound was prepared following hydrolysis of the benzylic chloride to the hydroxyl. ¹H NMR (400 MHz, CD₃OD) δ 7.90 (1H, s), 7.67 (1H, s), 7.48 (1H, s), 7.38 (1H, dd, J=2.0, 8.5 Hz), 7.31 (1H, d, J=7.6 Hz), 6.95 (1H, d, J=8.5 Hz), 6.26 (1H, d, J=7.6 Hz), 4.94 (1H, m), 4.10 (4H, s), 3.80 (3H, s), 3.62–3.74 (2H, m), 2.62 (3H, s). LCMS (M+H)⁺ m/z 537 (t=1.49 min.).

EXAMPLE 393

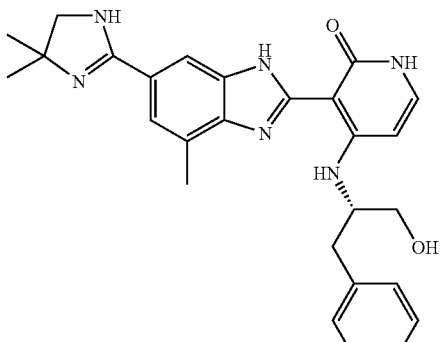

(S)-3-[6-(4,4-Dimethyl-4,5-dihydro-1H-imidazol-2-yl)-4-methyl-1H-benzimidazol-2-yl]-4-(1-hydroxymethyl-2-phenyl-ethylamino)-1H-pyridin-2-one: ¹H NMR (300 MHz, CD₃OD) δ 7.94 (1H, s), 7.50 (1H, s), 7.12–7.30 (6H, m), 6.15 (1H, dd, J=7.7 Hz), 4.02–4.10 (1H, m), 3.85 (2H, s), 3.75–3.77 (2H, m), 2.96–3.17 (2H, m), 2.67 (3H, s), 1.56 (6H, s). LCMS (M+H)$^+$ m/z 471 (t=1.62 min.).

EXAMPLE 394

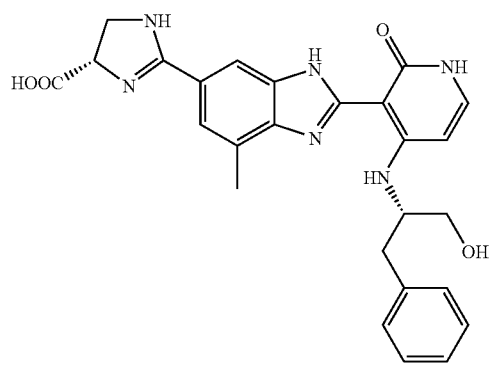

(S)-2-{2-[4-(1S-Hydroxymethyl-2-phenyl-ethylamino)-2-oxo-1,2-dihydro-pyridin-3-yl]-7-methyl-3H-benzimidazol-5-yl}-4,5-dihydro-1H-imidazole-4S-carboxylic acid. $^1$H NMR (300 MHz, CD₃OD) δ 8.03 (1H, s), 7.60 (1H, s), 7.11–7.29 (6H, m), 6.15 (1H, d, J=7.3 Hz), 5.07 (1H, dd, J=6.9, 11.8 Hz), 4.25–4.41 (2H, m), 4.05–4.07 (1H, m), 3.70–3.82 (2H, m), 3.12 (1H, dd, J=5.5, 13.6 Hz), 2.95 (1H, dd, J=8.0, 13.6 Hz), 2.69 (3H, s). LCMS (M+H)$^+$ m/z 487 (t=1.35 min.).

EXAMPLE 395

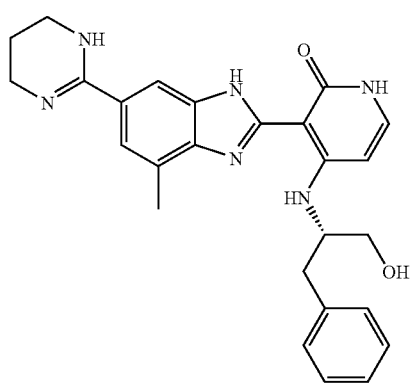

(S)-4-(1-Hydroxymethyl-2-phenyl-ethylamino)-3-[4-methyl-6(1,4,5,6-tetrahydro-pyrimidin-2-yl)-1H-benzimidazol-2-yl]-1H-pyridin-2-one: $^1$H NMR (300 MHz, CD₃OD) δ 7.76 (1H, s), 7.32 (1H, s), 7.09–7.29 (6H, m), 6.15 (1H, d, J=7.6 Hz), 4.02–4.07 (1H, m), 3.71–3.79 (2H, m), 3.61 (4H, t, J=5.6 Hz), 3.14 (1H, dd, J=5.3, 13.6 Hz), 2.95 (1H, dd, J=8.1, 13.6 Hz), 2.65 (3H, s), 2.09–2.16 (2H, m). LCMS (M+H)$^+$ m/z 457 (t=1.49 min.).

EXAMPLE 396

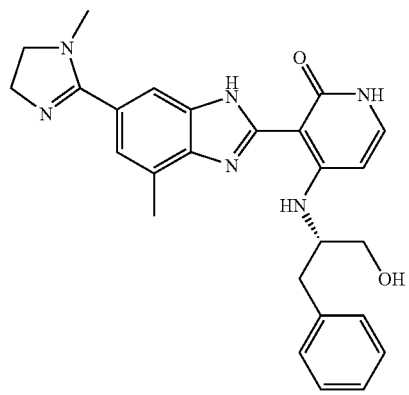

(S)-4-(1-Hydroxymethyl-2-phenyl-ethylamino)-3-[4-methyl-6-(1-methyl-4,5-dihydro-1H-imidazol-2-yl)-1H-benzoimidazo-2-yl]-1H-pyridin-2-one: $^1$H NMR (300 MHz, CD₃OD) δ 7.77 (1H, s), 7.10–7.30 (7H, m), 6.16 (1H, d, J=7.6 Hz), 3.97–4.20 (5H, m), 3.73–3.77 (2H, m), 3.26 (3H, s), 3.15 (1H, dd, J=5.3, 13.6 Hz), 2.96 (1H, dd, J=8.0, 13.6 Hz), 2.68 (3H, s). LCMS (M+H)$^+$ m/z 457 (t=1.53 min.)

EXAMPLE 397

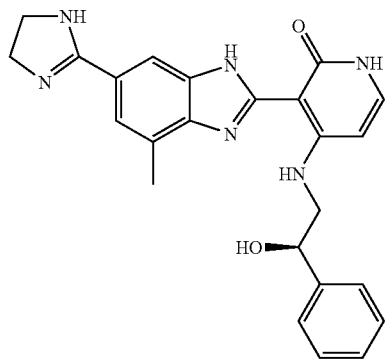

(S)-3-[6-(4,5-Dihydro-1H-imidazol-2-yl)-4-methyl-1H-benzimidazol-2-yl]-4-(2-hydroxy-2-phenyl-ethylamino)-1H-pyridin-2-one: $^1$H NMR (400 MHz, CD₃OD) δ 7.91 (1H, s), 7.50 (1H, s), 7.48 (2H, s), 7.24–7.35 (4H, m), 6.25

(1H, d, J=7.6 Hz), 5.01 (1H, dd, J=4.6, 7.0 Hz), 4.10 (4H, s), 3.65–3.76 (2H, m), 2.64 (3H, s). LCMS (M+H)+ m/z 429 (t=1.48 min.).

EXAMPLE 398

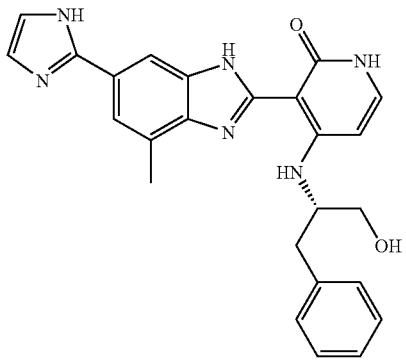

(S)-4-(1-Hydroxymethyl-2-phenyl-ethylamino)-3-[6-(1H-imidazol-2-yl)-4-methyl-1H-benzimidazol-2-yl]-1H-pyridin-2-one: To a solution of the imidate ester (150 mg, 0.31 mmol) in methanol (10 mL) was added aminoacetaldehyde diethyl acetal (97 mg, 0.93 mmol). The mixture was stirred at room temperature for 14 h. The solvent was removed in vacuo and the residue was treated with 60% HClO$_4$ (5 mL) at room temperature for 14 h. The reaction mixture was then neutralized with ammonium hydroxide (conc.). The inorganic salt was filtered. The filtrate was concentrated and purified by prep. HPLC to yield the title compound (37 mg, 27%) as a white solid. $^1$H NMR (300 MHz, CD$_3$OD) δ 7.94 (1H, narrow d, J=1.3 Hz), 7.58 (2H, s), 7.53 (1H, narrow d, J=0.6 Hz), 7.12–7.31 (6H, m), 6.16 (1H, d, J=7.7 Hz), 4.04–4.08 (1H, m), 3.76–3.79 (2H, m), 3.16 (1H, dd, J=5.4, 13.6 Hz), 3.97 (1H, dd, J=8.1, 13.6 Hz), 2.69 (3H, s). LCMS (M+H)+ m/z 441 (t=1.60 min.).

General Procedure for Amidine Formation, Examples 399–412 (Scheme IV, 16)

EXAMPLE 399

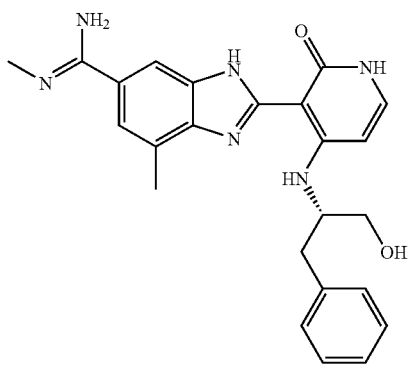

(S)-2-[4-(1-Hydroxymethyl-2-phenyl-ethylamino)-2-oxo-1,2-dihydro-pyridin-3-yl]-7,N-dimethyl-3H-benzimidazole-5-carboxamidine: The crude imidate ester (60 mg, 0.135 mmol) was diluted with methanol (10 mL), then methylamine (2.0 M methanol solution, 0.5 mL, excess) was added to the solution. After stirring for 2 h, the reaction mixture was concentrated and purified by prep. HPLC to yield the title compound (32 mg, 55%) as a white solid. $^1$H NMR (300 MHz, CD$_3$OD) δ 7.82 (1H, s), 7.38 (1H, s), 7.10–7.30 (6H, m), 6.15 (1H, J=7.7 Hz), 4.03–4.07 (1H, m), 4.72–4.76 (2H, m), 3.06–3.18 (1H, m), 3.12 (3H, s), 2.96 (1H, dd, J=8.0, 13.5 Hz), 2.67 (3H, s). LCMS (M+H)+ m/z 431 (t=1.34 min.).

EXAMPLE 400

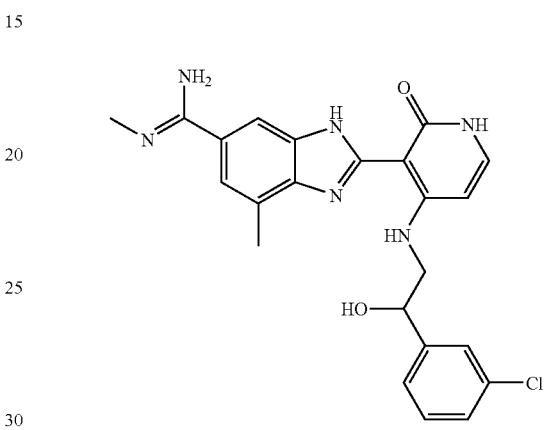

(±)-2-{4-[2-(3-Chloro-phenyl)-2-hydroxy-ethylamino]-2-oxo-1,2-dihydro-pyridin-3-yl}-7,N-dimethyl-3H-benzimidazole-5-carboxamidine: $^1$H NMR (300 MHz, CD$_3$OD) δ 7.81 (1H, s), 7.54 (1H, s), 7.23–7.54 (5H, m), 6.26 (1H, d, J=7.6 Hz), 5.01 (1H, t, J=4.8 Hz), 3.77 (1H, dd, J=4.5, 13.4 Hz), 3.67 (1H, dd, J=6.6, 13.4 Hz), 3.12 (3H, s), 2.66 (3H, s). LCMS (M+H)+ m/z 451 (t=1.32 min.).

EXAMPLE 401

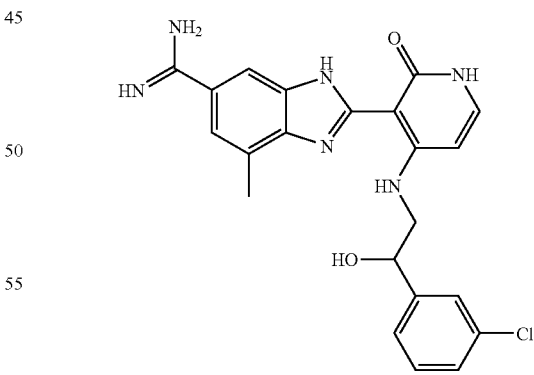

(±)-2-{4-[2-(3-Chloro-phenyl)-2-hydroxy-ethylamino]-2-oxo-1,2-dihydro-pyridin-3-yl}-7-methyl-3H-benzimidazole-5-carboxamidine: $^1$H NMR (300 MHz, CD$_3$OD) δ 7.90 (1H, s), 7.26–7.57 (6H, m), 6.25 (1H, d, J=7.6 Hz), 5.01 (1H, t, J=6.4 Hz), 3.75 (1H, dd, J=4.8, 13.4 Hz), 3.66 (1H, dd, J=6.7, 13.4 Hz), 2.62 (3H, s). LCMS (M+H)+ m/z 437 (t=1.59 min.).

EXAMPLE 402

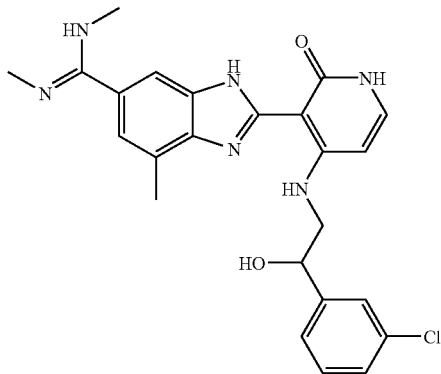

(±)-2-{4-[2-(3-Chloro-phenyl)-2-hydroxy-ethylamino]-2-oxo-1,2-dihydro-pyridin-3-yl}-7,N,N,-trimethyl-3H-benzimidazole-5-carboxamidine: $^1$H NMR (300 MHz, CD$_3$OD) δ 7.63 (1H, s), 7.54 (1H, s), 7.18–7.41 (5H, m), 6.26 (1H, d, J=7.6 Hz), 5.01 (1H, t, J=6.3 Hz), 3.77 (1H, dd, J=4.7, 13.5 Hz), 3.67 (1H, dd, J=6.6, 13.5 Hz), 3.34 (6H, s), 2.66 (3H, s). LCMS (M+H)+ m/z 465 (t=1.57 min.).

EXAMPLE 403

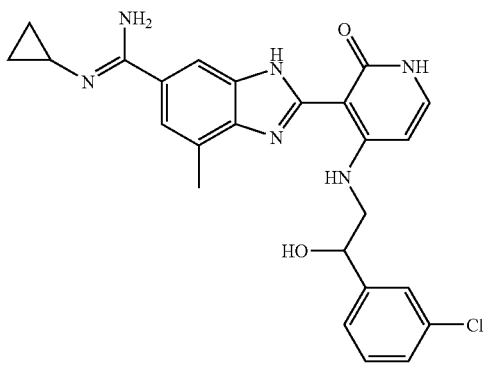

(±)-2-{4-[2-(3-Chloro-phenyl)-2-hydroxy-ethylamino]-2-oxo-1,2-dihydro-pyridin-3-yl}-N-cyclopropyl-7-methyl-3H-benzimidazole-5-carboxamidine: $^1$H NMR (300 MHz, CD$_3$OD) δ 7.78 (1H, s), 7.54 (1H, s), 7.22–7.41 (5H, m), 6.25 (1H, d, J=7.6 Hz), 5.01 (1H, t, J=6.4 Hz), 3.76 (1H, dd, J=4.7, 13.5 Hz), 3.67 (1H, dd, J=6.6, 13.5 Hz), 2.77–2.83 (1H, m), 2.65 (3H, s), 1.03–1.10 (2H, m), 0.86–0.92 (2H, m). LCMS (M+H)+ m/z 477 (t=1.43 min.).

EXAMPLE 404

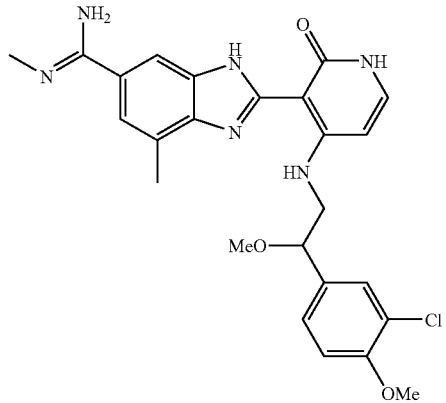

(±)-2-{4-[2-(3-Chloro-4-methoxy-phenyl)-2-methoxy-ethylamino]-2-oxo-1,2-dihydro-pyridin-3-yl}-7,N-dimethyl-3H-benzimidazole-5-carboxamidine: $^1$H NMR (300 MHz, CD$_3$OD) δ 7.79 (1H, narrow d, J=1.0 Hz), 7.45 (1H, narrow d, J=1.5 Hz), 7.38 (1H, s), 7.28–7.31 (2H, m), 7.02 (1H, d, J=6.4 Hz), 6.22 (1H, d, J=5.7 Hz), 4.52 (1H, t, J=5.9 Hz), 3.83 (3H, s), 3.60–3.71 (2H, m), 3.36 (3H, s), 3.13 (3H, s), 2.65 (3H, s). LCMS (M+H)+ m/z 495 (t=1.64 min.).

EXAMPLE 405

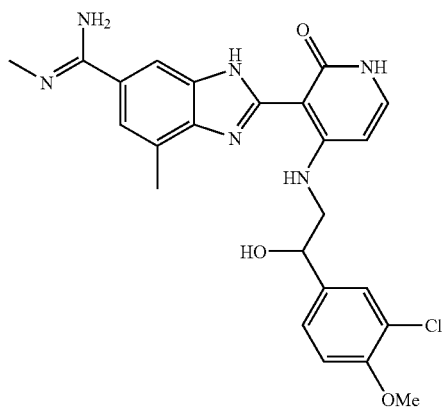

(±)-2-[4-[2-(3-Chloro-4-methoxy-phenyl)-2-hydroxy-ethylamino]-2-oxo-1,2-dihydro-pyridin-3-yl]-7,N-dimethyl-3H-benzimidazole-5-carboxamidine: To a solution of 2-{4-[2-(3-chloro-4-methoxy-phenyl)-2-methoxy-ethylamino]-2-oxo-1,2-dihydro-pyridin-3-yl}-7,N-dimethyl-3H-benzimidazole-5-carboxamidine (40 mg, 0.08 mmol) in methanol (5 mL) was added 2 N NaOH (0.5 mL) and the reaction mixture was stirred at room temperature for 14 h. After concentration in vacuo, the residue was purified by prep. HPLC to yield the title compound (7.2 mg, 19%) as oil. $^1$H NMR (300 MHz, CD$_3$OD) δ 7.78 (1H, narrow d, J=1.6 Hz), 7.52 (1H, narrow d, J=2.1 Hz), 7.30–7.36 (3H, m), 6.99 (1H, d, J=8.5 Hz), 6.27 (1H, d, J=7.6 Hz), 4.94 (1H, t, J=5.9 Hz), 3.82 (3H, s), 3.68–3.72 (2H, m), 3.13 (3H, s), 2.63 (3H, s). LCMS (M+H)+ m/z 481 (t=1.44 min.).

EXAMPLE 406

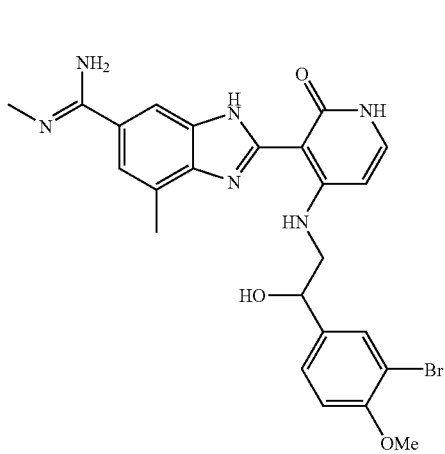

(±)-2-{4-[2-(3-Bromo-4-methoxy-phenyl)-2-hydroxy-ethylamino]-2-oxo-1,2-dihydro-pyridin-3-yl}-7,N-dimethyl-3H-benzimidazole-5-carboxamidine: $^1$H NMR (400 MHz, CD$_3$OD) δ 7.77 (1H, s), 7.67 (1H, s), 7.29–7.39 (3H, m), 6.95 (1H, d, J=8.4 Hz), 6.23 (1H, d, J=4.4 Hz), 4.92 (1H, m), 3.80 (3H, s), 3.69 (2H, m), 3.13 (3H, s), 2.61 (3H, s). LCMS (M+H)$^+$ m/z 525 (t=1.44 min.).

EXAMPLE 407

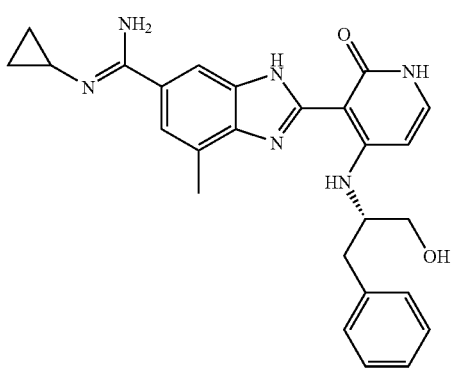

(S)-N-Cyclopropyl-2-[4-(1-hydroxymethyl-2-phenyl-ethylamino)-2-oxo-1,2-dihydro-pyridin-3-yl]-7-methyl-3H-benzimidazole-5-carboxamidine: $^1$H NMR (300 MHz, CD$_3$OD) δ 7.81 (1H, s), 7.37 (1H, s), 7.10–7.30 (6H, m), 6.16 (1H, d, J=7.6 Hz), 4.03–4.08 (1H, m), 3.74–3.76 (2H, m), 3.15 (1H, dd, J=5.3, 13.6 Hz), 2.96 (1H, dd, J=8.1, 13.6 Hz), 2.78–2.84 (1H, m), 2.67 (3H, s), 1.03–1.10 (2H, m), 0.87–0.92 (2H, m). LCMS (M+H)$^+$ m/z 457 (t=1.51 min.).

EXAMPLE 408

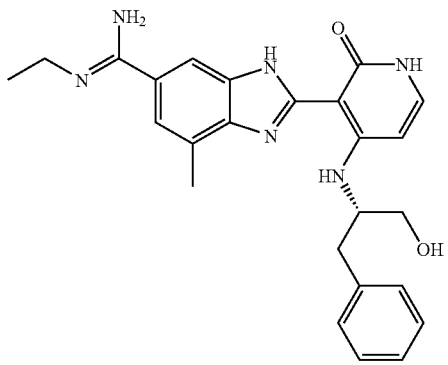

(S)-N-Ethyl-2-[4-(1-hydroxymethyl-2-phenyl-ethylamino)-2-oxo-1,2-dihydro-pyridin-3-yl]-7-methyl-3H-benzimidazole-5-carboxamidine: $^1$H NMR (400 MHz, CD$_3$OD) δ 7.82 (1H, s), 7.38 (1H, s), 7.12–7.30 (6H, m), 6.15 (1H, d, J=7.8 Hz), 4.04–4.07 (1H, m), 3.75–3.77 (2H, m), 3.51 (2H, q, J=7.3 Hz), 3.15 (1H, dd, J=5.4, 13.7 Hz), 2.96 (1H, dd, J=8.1, 13.7 Hz), 2.67 (3H, s), 1.40 (3H, t, J=7.3 Hz). LCMS (M+H)$^+$ m/z 445 (t=1.44 min.).

EXAMPLE 409

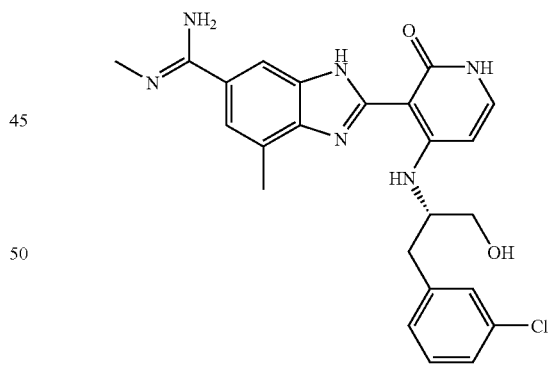

(S)-2-{4-[2-(3-Chloro-phenyl)-1-hydroxymethyl-ethylamino]-2-oxo-1,2-dihydro-pyridin-3-yl}-7,N-dimethyl-3H-benzimidazole-5-carboxamidine: $^1$H NMR (400 MHz, CD$_3$OD) δ 7.83 (1H, s), 7.38 (1H, s), 7.31 (1H, s), 7.10–7.24 (4H, m), 6.16 (1H, d, J=7.6 Hz), 4.06–4.09 (1H, m), 3.72–3.77 (2H, m), 3.16 (3H, s), 3.15 (1H, m), 2.96 (1H, dd, J=8.2, 13.7 Hz), 2.67 (3H, s). LCMS (M+H)$^+$ m/z 465 (t=1.49 min.).

EXAMPLE 410

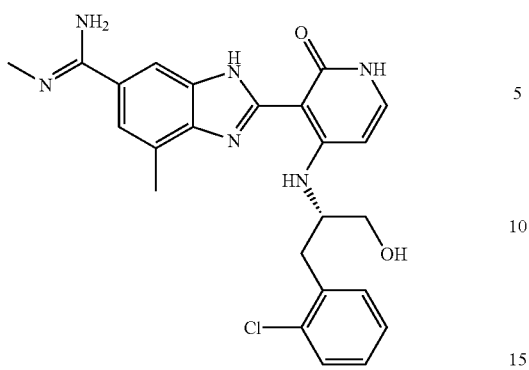

(S)-2-{4-[2-(2-Chloro-phenyl)-1-hydroxymethyl-ethylamino]-2-oxo-1,2-dihydro-pyridin-3-yl}-7,N-dimethyl-3H-benzimidazole-5-carboxamidine: ¹H NMR (400 MHz, CD₃OD) δ 7.84 (1H, s), 7.41 (1H, s), 7.32–7.35 (2H, m), 7.06–7.18 (3H, m), 6.10 (1H, d, J=7.5 Hz), 4.20–4.24 (1H, m), 3.76–3.85 (2H, m), 3.30–3.34 (1H, m), 3.06–3.14 (1H, m), 3.13 (3H, s), 2.64 (3H, s). LCMS (M+H)⁺ m/z 465 (t=1.48 min.).

EXAMPLE 411

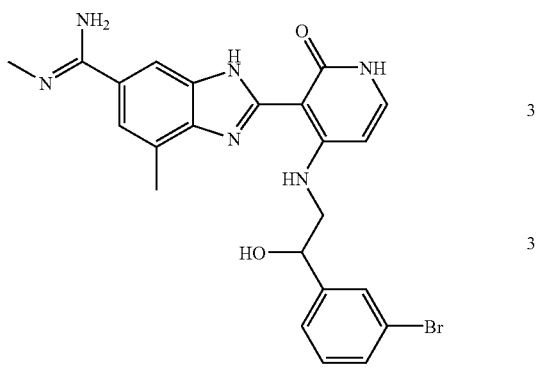

(±)-2-{4-[2-(3-Bromo-phenyl)-2-hydroxy-ethylamino]-2-oxo-1,2-dihydro-pyridin-3-yl}-7,N-dimethyl-3H-benzimidazole-5-carboxamidine: ¹H NMR (300 MHz, CD₃OD) δ 7.80 (1H, s), 7.69 (1H, s), 7.20–7.45 (5H, m), 6.25 (1H, d, J=7.3 Hz), 5.00 (1H, t, J=5.9 Hz), 3.64–3.80 (2H, m), 3.12 (3H, s), 2.66 (3H, s). LCMS (M+H)⁺ m/z 495 (t=1.49 min.).

EXAMPLE 412

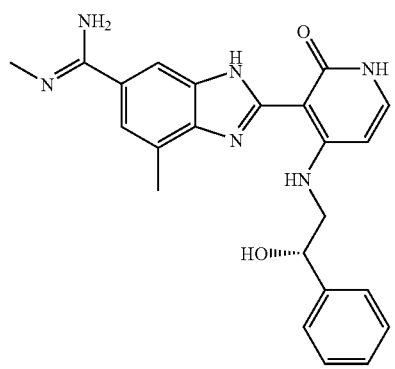

(S)-2-[4-(2-Hydroxy-2-phenyl-ethylamino)-2-oxo-1,2-dihydro-pyridin-3-yl]-7,N-dimethyl-3H-benzimidazole-5-carboxamidine: ¹H NMR (400 MHz, CD₃OD) δ 7.78 (1H, s), 7.24–7.49 (7H, m), 6.21 (1H, d, J=7.0 Hz), 4.00–5.05 (1H, m), 3.61–3.74 (2H, m), 3.12 (3H, s), 2.63 (3H, s). LCMS (M+H)⁺ m/z 417 (t=1.28 min.).

| Example # | Name | Structure | T (min.) | Mass (M + H)⁺ m/z |
|---|---|---|---|---|
| 413 | (±)-4-[2-(3-Chloro-phenyl)-2-hydroxy-ethylamino]-3-[6-(1-imino-1-morpholin-4-yl-methyl)-4-methyl-1H-benzimidazol-2-yl]-1H-pyridin-2-one | 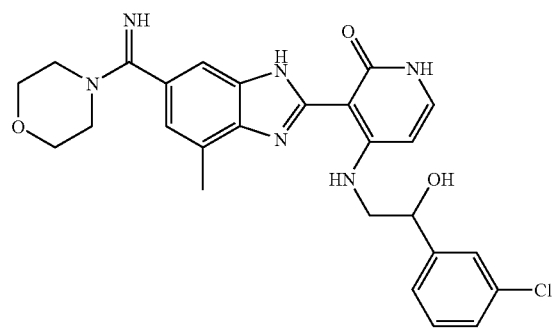 | 1.55 (f) | 507 |

| Example # | Name | Structure | T (min.) | Mass (M + H)+ m/z |
|---|---|---|---|---|
| 414 | (±)-4-[2-(3-Bromo-4-methoxy-phenyl)-2-hydroxy-ethylamino]-3-[6-(4,5-dihydro-1H-imidazol-2-yl)-4-methyl-1H-benzimidazol-2-yl]-1H-pyridin-2-one | 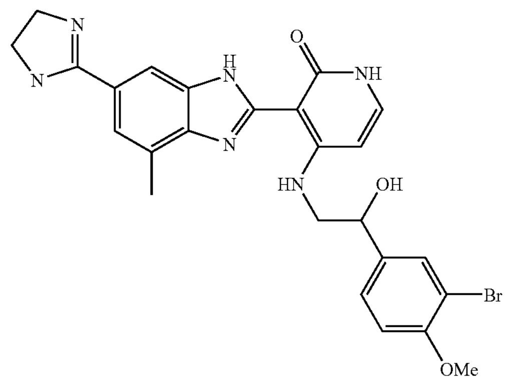 | 1.49 (b) | 537 |
| 415 | (±)-2-{4-[2-(3-Chloro-phenyl)-2-hydroxy-ethylamino]-2-oxo-1,2-dihydro-pyridin-3-yl}-N-(2,2-diethoxy-ethyl)-7-methyl-3H-benzimidazole-5-carboxamidine | 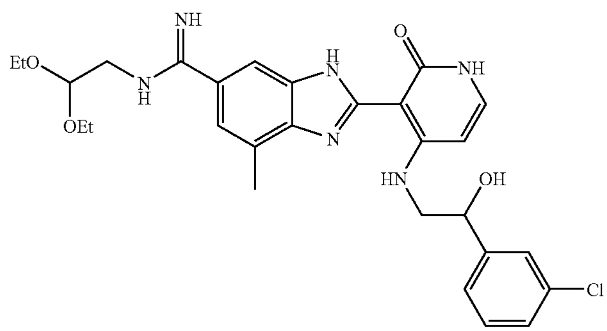 | 1.77 (f) | 553 |
| 416 | (±)-4-[2-(3-Chloro-phenyl)-2-hydroxy-ethylamino]-3-[6-(1H-imidazol-2-yl)-4-methyl-1H-benzimidazol-2-yl]-1H-pyridin-2-one | 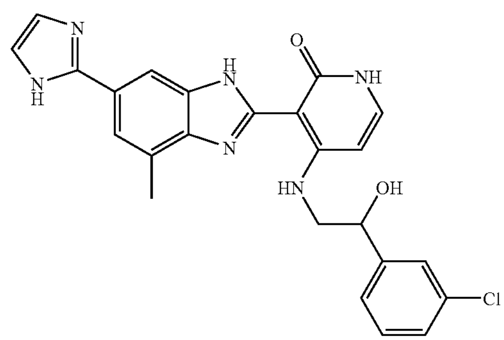 | 1.71 (f) | 461 |
| 417 | (±)-4-[2-(3-Chloro-phenyl)-2-hydroxy-ethylamino]-3-(7'-methyl-1H,3'H-[2,5']bibenzimidazolyl-2'-yl)-1H-pyridin-2-one | 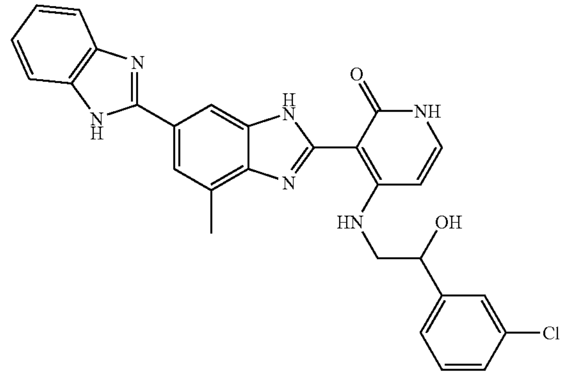 | 1.82 (b) | 511 |

| Example # | Name | Structure | T (min.) | Mass (M + H)+ m/z |
|---|---|---|---|---|
| 418 | (±)-Cis-4-[2-(3-chloro-phenyl)-2-hydroxy-ethylamino]-3-(7'-methyl-3a,4,5,6,7,7a-hexahydro-1H,3'H-[2,5']bibenzimidazolyl-2'-yl)-1H-pyridin-2-one | 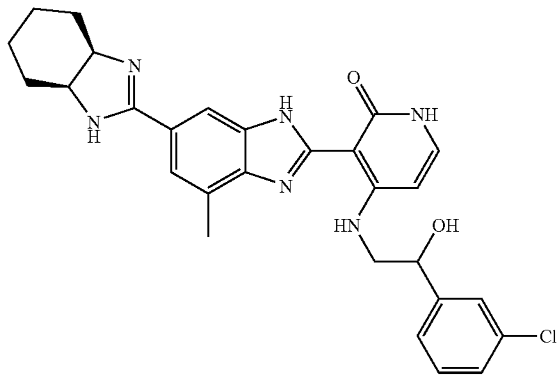 | 1.75 (b) | 517 |
| 419 | (±)-Trans-4-[2-(3-chloro-phenyl)-2-hydroxy-ethylamino]-3-(7'-methyl-3a,4,5,6,7,7a-hexahydro-1H,3'H-[2,5']bibenzimidazolyl-2'-yl)-1H-pyridin-2-one | 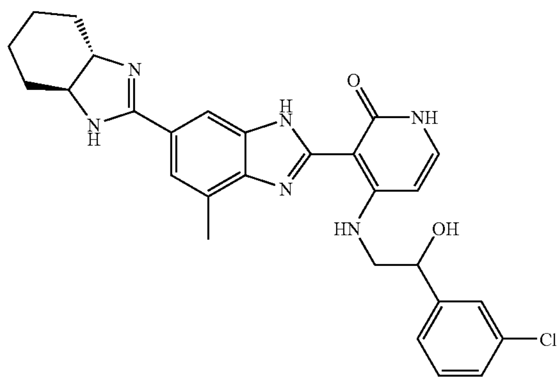 | 1.75 (b) | 517 |
| 420 | (±)-2-{4-[2-(3-Chloro-phenyl)-2-hydroxy-ethylamino]-2-oxo-1,2-dihydro-pyridin-3-yl}-N-cyclopentyl-7-methyl-3H-benzimidazole-5-carboxamidine | 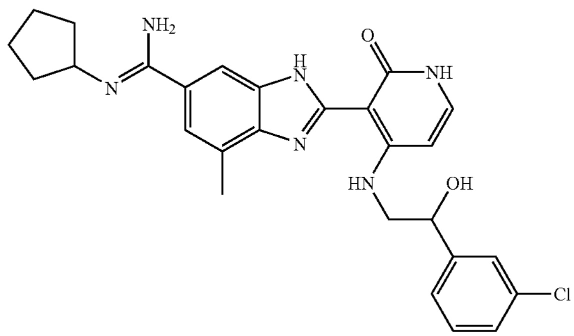 | 1.55 (b) | 505 |
| 421 | (±)-2-{4-[2-(3-Chloro-phenyl)-2-hydroxy-ethylamino]-2-oxo-1,2-dihydro-pyridin-3-yl}-N-cyclohexyl-7-methyl-3H-benzimidazole-5-carboxamidine | 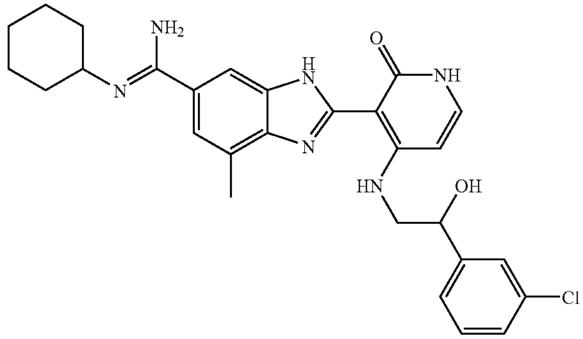 | 1.61 (b) | 519 |

-continued

| Example # | Name | Structure | T (min.) | Mass (M + H)+ m/z |
|---|---|---|---|---|
| 422 | (±)-2-{4-[2-(3-Chloro-phenyl)-2-hydroxy-ethylamino]-2-oxo-1,2-dihydro-pyridin-3-yl}-7-methyl-N-propyl-3H-benzimidazole-5-carboxamidine | 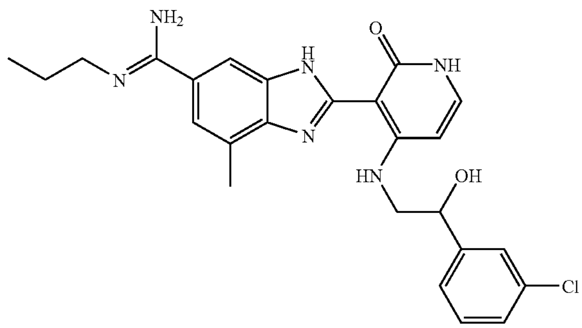 | 1.48 (b) | 479 |
| 423 | (±)-2-{4-[2-(3-Chloro-phenyl-2-hydroxy-ethylamino]-2-oxo-1,2-dihydro-pyridin-3-yl}-7-methyl-N,N'-dipropyl-3H-benzimidazole-5-carboxamidine | 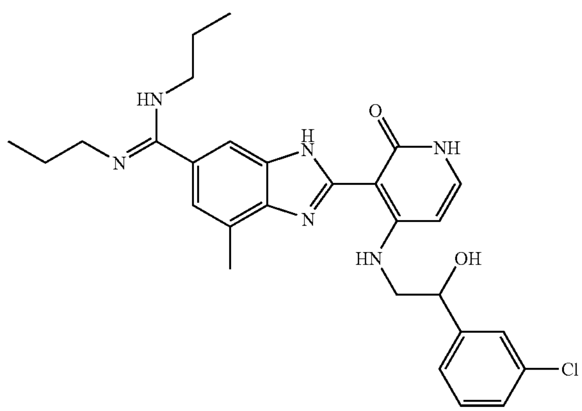 | 1.61 (b) | 521 |
| 424 | (±)-2-{4-[2-(3-Chloro-phenyl)-2-hydroxy-ethylamino]-2-oxo-1,2-dihydro-pyridin-3-yl}-N-isopropyl-7-methyl-3H-benzimidazole-5-carboxamidine | 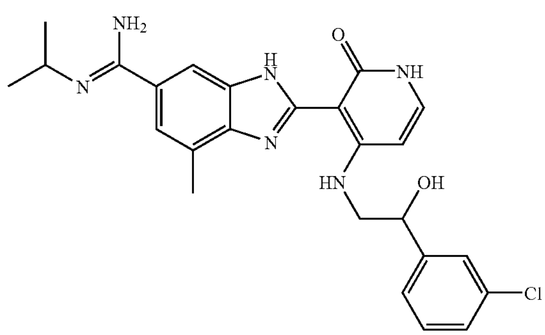 | 1.41 (b) | 479 |
| 425 | (±)-2-{4-[2-(3-Chloro-phenyl)-2-hydroxy-ethylamino]-2-oxo-1,2-dihydro-pyridin-3-yl}-7-methyl-N-(2-morpholin-4-yl-ethyl)-3H-benzimidazole-5-carboxamidine | 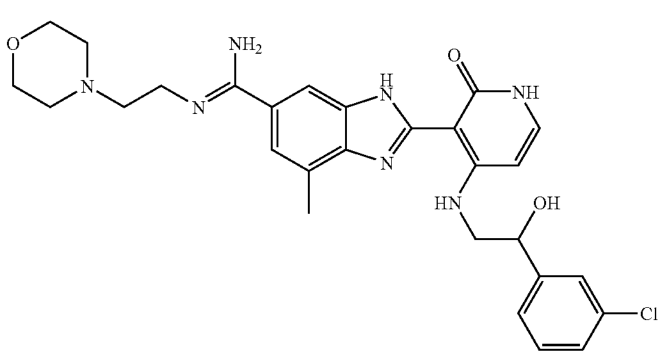 | 1.27 (b) | 550 |

-continued

| Example # | Name | Structure | T (min.) | Mass (M + H)+ m/z |
|---|---|---|---|---|
| 426 | (±)-2-{4-[2-(3-Chloro-phenyl)-2-hydroxy-ethylamino]-2-oxo-1,2-dihydro-pyridin-3-yl}-7-methyl-N,N'-bis-(2-morpholin-4-yl-ethyl)-3H-benzimidazole-5-carboxamidine | 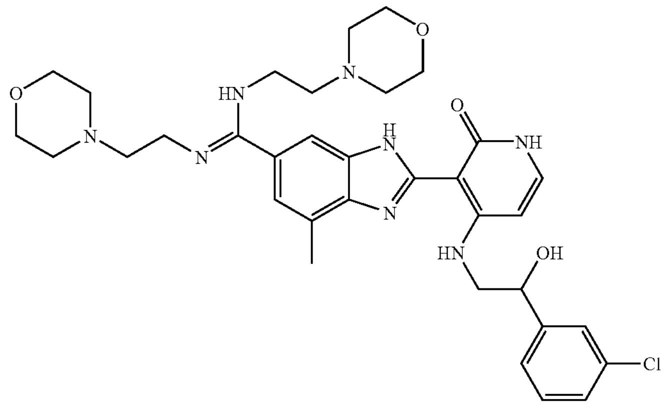 | 1.22 (b) | 663 |
| 427 | (±)-2-{4-[2-(3-Chloro-phenyl)-2-hydroxy-ethylamino]-2-oxo-1,2-dihydro-pyridin-3-yl}-N-(2-hydroxy-ethyl)-7-methyl-3H-benzimidazole-5-carboxamidine | 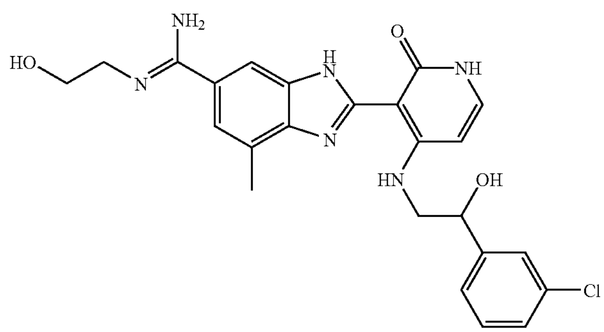 | 1.38 (b) | 481 |
| 428 | (±)-4-[2-(3-Chloro-phenyl)-2-hydroxy-ethylamino]-3-[4-methyl-6-(5-methyl-1H-imidazol-2-yl)-1H-benzimidazol-2-yl]-1H-pyridin-2-one | 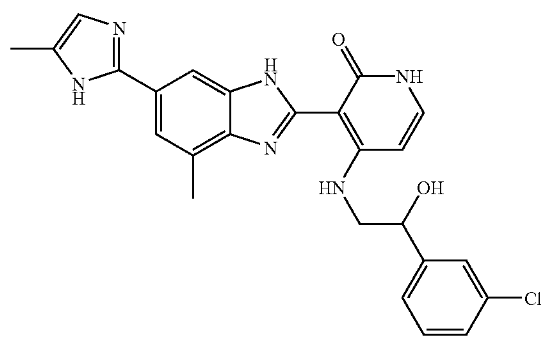 | 1.62 (b) | 475 |
| 429 | (±)-2-{4-[2-(3-Chloro-phenyl)-2-hydroxy-ethylamino]-2-oxo-1,2-dihydro-pyridin-3-yl}-4-methyl-1H-benzimidazole-6-carboxamidic acid hydrazide | 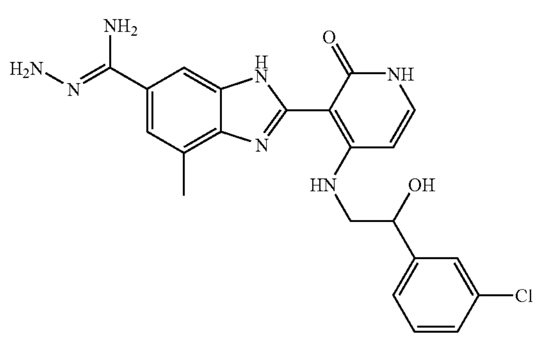 | 1.44 (f) | 452 |

| Example # | Name | Structure | T (min.) | Mass (M + H)+ m/z |
|---|---|---|---|---|
| 430 | (±)-2-{4-[2-(3-Chloro-phenyl)-2-hydroxy-ethylamino]-2-oxo-1,2-dihydro-pyridin-3-yl}-4-methyl-1H-benzimidazole-6-carboxamidic acid N-formylhydrazide | 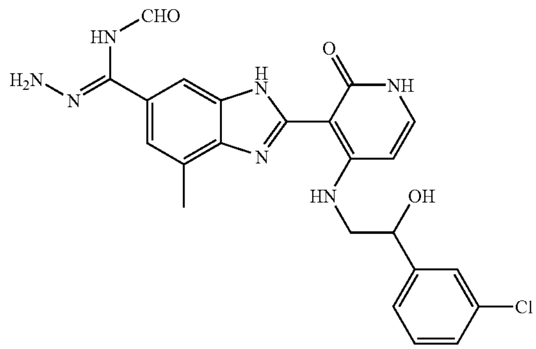 | 1.58 (f) | 480 |
| 431 | (±)-4-[2-(3-Chloro-phenyl)-2-hydroxy-ethylamino]-3-[4-methyl-6-(4H-[1,2,4]triazol-3-yl)-1H-benzimidazol-2-yl]-1H-pyridin-2-one | 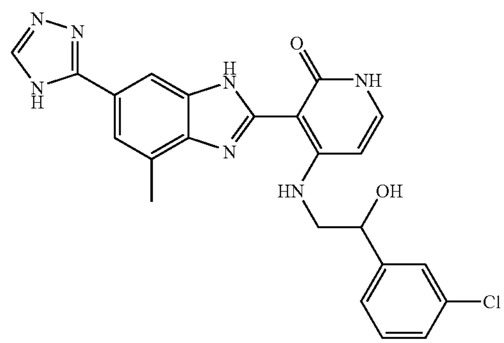 | 1.82 (f) | 462 |
| 432 | (±)-2-{4-[2-(3-Chloro-phenyl)-2-hydroxy-ethylamino]-2-oxo-1,2-dihydro-pyridin-3-yl}-N-hydroxy-7-methyl-3H-benzimidazole-5-carboxamidine | 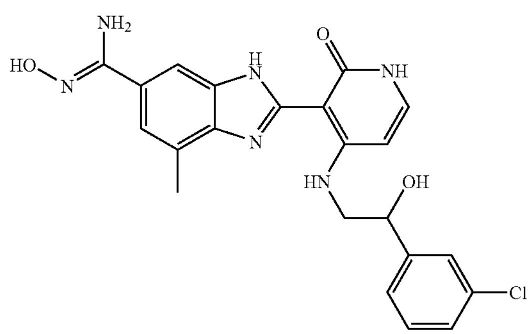 | 1.34 (f) | 453 |
| 433 | (±)-2-{4-[2-(3-Chloro-phenyl)-2-hydroxy-ethylamino]-2-oxo-1,2-dihydro-pyridin-3-yl}-N-methoxy-7-methyl-3H-benzimidazole-5-carboxamidine | 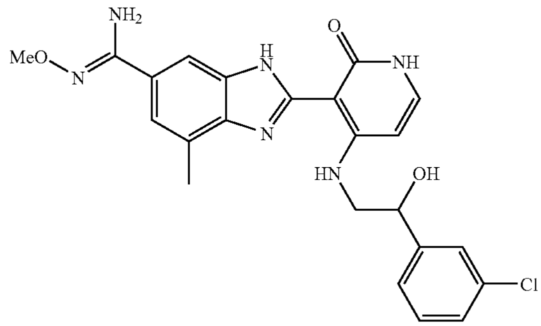 | 1.41 (f) | 467 |

-continued

| Example # | Name | Structure | T (min.) | Mass (M + H)+ m/z |
|---|---|---|---|---|
| 434 | (±)-2-{4-[2-(3-Chloro-phenyl)-2-hydroxy-ethylamino]-2-oxo-1,2-dihydro-pyridin-3-yl}-N-hydroxy-7,N-dimethyl-3H-benzimidazole-5-carboxamidine | 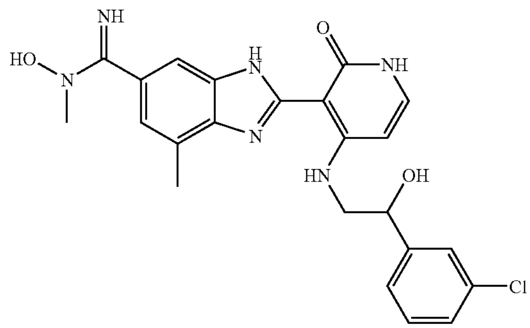 | 1.39 (f) | 467 |
| 435 | (±)-2-{4-[2-(3-Chloro-phenyl)-2-hydroxy-ethylamino]-2-oxo-1,2-dihydro-pyridin-3-yl}-N-ethyl-7-methyl-3H-benzimidazole-5-carboxamidine | 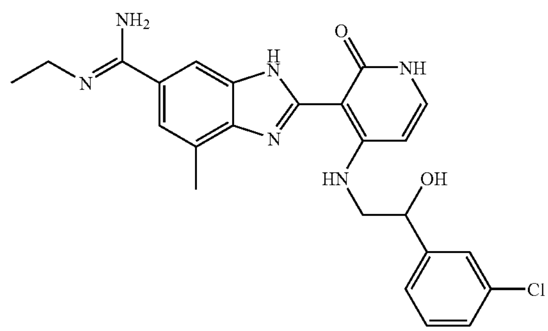 | 1.62 (f) | 465 |
| 436 | (±)-2-{4-[2-(3-Chloro-phenyl)-2-hydroxy-ethylamino]-2-oxo-1,2-dihydro-pyridin-3-yl}-7-methyl-N-(2,2,2-trifluoro-ethyl)-3H-benzimidazole-5-carboxamidine | 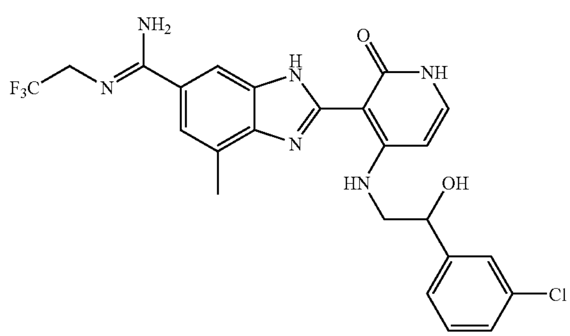 | 1.75 (f) | 519 |
| 437 | (±)-2-{4-[2-(3-Chloro-phenyl)-2-hydroxy-ethylamino]-2-oxo-1,2-dihydro-pyridin-3-yl}-7,N,N'-trimethyl-3H-benzimidazole-5-carboxamidine | 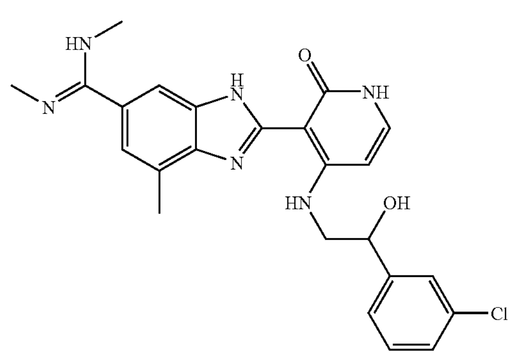 | 1.58 (f) | 465 |

-continued

| Example # | Name | Structure | T (min.) | Mass (M + H)+ m/z |
|---|---|---|---|---|
| 438 | (±)-2-{4-[2-(3-Fluoro-phenyl)-2-hydroxy-ethylamino]-2-oxo-1,2-dihydro-pyridin-3-yl}-7,N-dimethyl-3H-benzimidazole-5-carboxamidine | 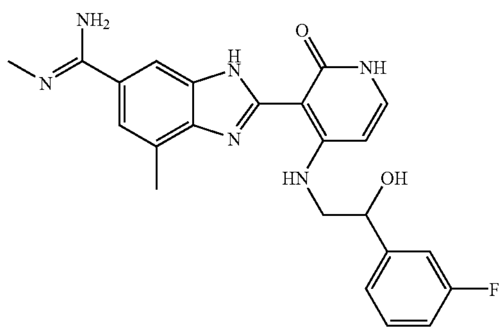 | 1.28 (b) | 435 |
| 439 | (±)-3-[6-(4,5-Dihydro-1H-imidazol-2-yl)-4-methyl-1H-benzimidazol-2-yl]-4-[2-(3-fluoro-phenyl)-2-hydroxy-ethylamino]-1H-pyridin-2-one | 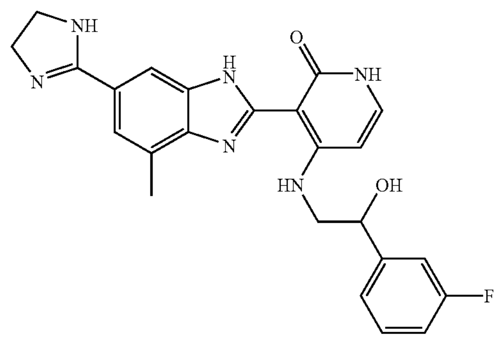 | 1.46 (b) | 447 |
| 440 | (±)-3-[6-(5,5-Dimethyl-4,5-dihydro-1H-imidazol-2-yl)-4-methyl-1H-benzimidazol-2-yl]-4-[2-(3-fluoro-phenyl)-2-hydroxy-ethylamino]-1H-pyridin-2-one | 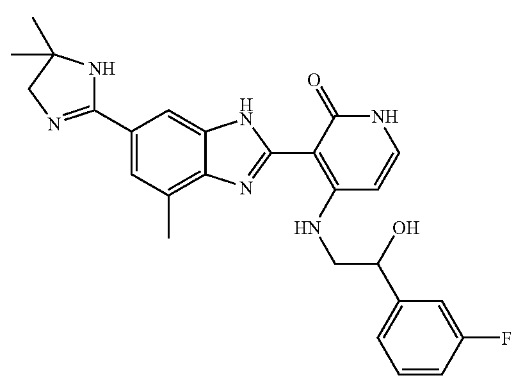 | 1.59 (b) | 475 |
| 441 | (S)-3-[6-(4,5-Dihydro-1H-imidazol-2-yl)-4-phenyl-1H-benzimidazol-2-yl]-4-(1-hydroxymethyl-2-phenyl-ethylamino)-1H-pyridin-2-one | 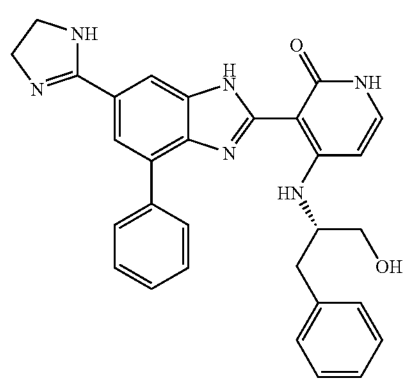 | 2.90 (b) | 505 |

-continued

| Example # | Name | Structure | T (min.) | Mass (M + H)+ m/z |
|---|---|---|---|---|
| 442 | (S)-3-[4-Bromo-6-(4,5-dihydro-1H-imidazol-2-yl)-1H-benzimidazol-2-yl]-4-(1-hydroxymethyl-2-phenyl-ethylamino)-1H-pyridin-2-one | 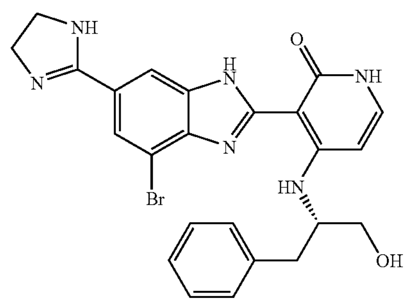 | 1.57 (b) | 507 |
| 443 | (±)-[2-Chloro-4-(1-hydroxy-2-{3-[4-methyl-6-(N-methylcarbamimidoyl)-1H-benzimidazol-2-yl]-2-oxo-1,2-dihydro-pyridin-4-ylamino}-ethyl)-phenyl]-carbamic acid isobutyl ester | 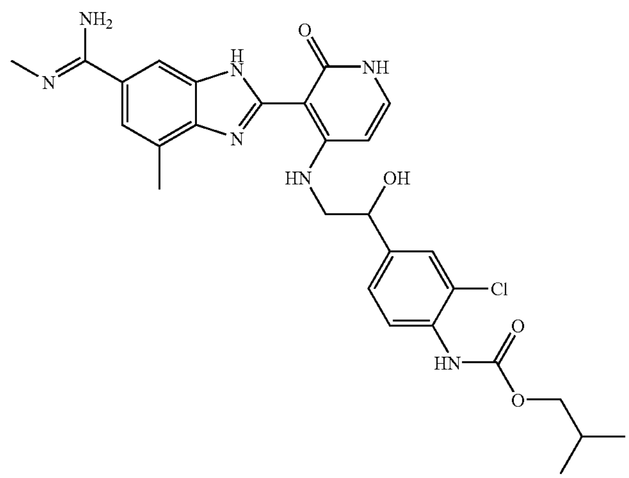 | 1.64 (b) | 566 |
| 444 | (S)-2-[4-(1-Hydroxymethyl-2-phenyl-ethylamino)-2-oxo-1,2-dihydro-pyridin-3-yl]-7-methyl-N-(2-morpholin-4-yl-ethyl)-3H-benzimidazole-5-carboxamidine | 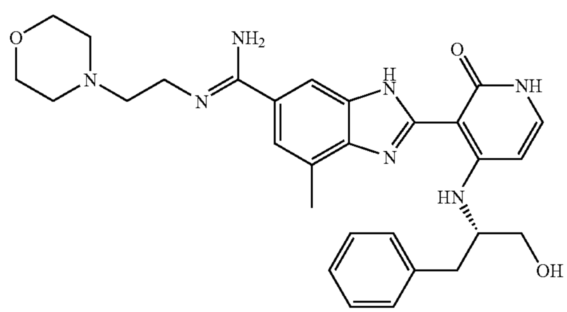 | 1.33 (b) | 530 |
| 445 | (S)-2-[4-(1-Hydroxymethyl-2-phenyl-ethylamino)-2-oxo-1,2-dihydro-pyridin-3-yl]-7-methyl-N-(2-thiophen-2-yl-ethyl)-3H-benzimidazole-5-carboxamidine | 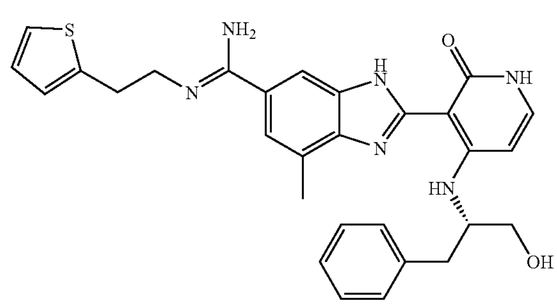 | 1.62 (b) | 527 |

| Example # | Name | Structure | T (min.) | Mass (M + H)+ m/z |
|---|---|---|---|---|
| 446 | (S)-2-[4-(1-Hydroxymethyl-2-phenyl-ethylamino)-2-oxo-1,2-dihydro-pyridin-3-yl]-7-methyl-N-(2-pyridin-2-yl-ethyl)-3H-benzimidazole-5-carboxamidine | 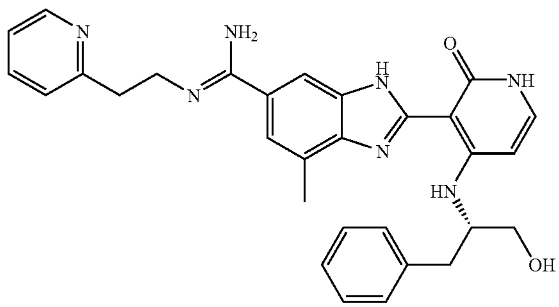 | 1.40 (b) | 522 |
| 447 | (S)-2-[4-(1-Hydroxymethyl-2-phenyl-ethylamino)-2-oxo-1,2-dihydro-pyridin-3-yl]-7-methyl-N-(2-pyridin-3-yl-ethyl)-3H-benzimidazole-5-carboxamidine | 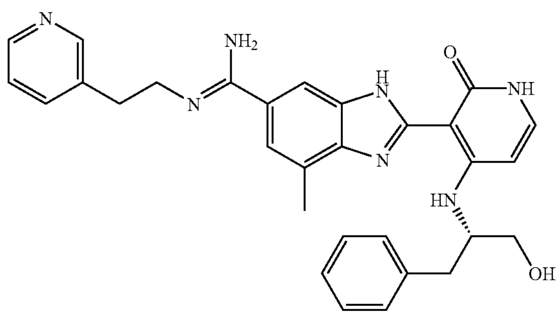 | 1.37 (b) | 522 |
| 448 | (S)-2-[4-(1-Hydroxymethyl-2-phenyl-ethylamino)-2-oxo-1,2-dihydro-pyridin-3-yl]-7-methyl-N-(2-pyridin-4-yl-ethyl)-3H-benzimidazole-5-carboxamidine | 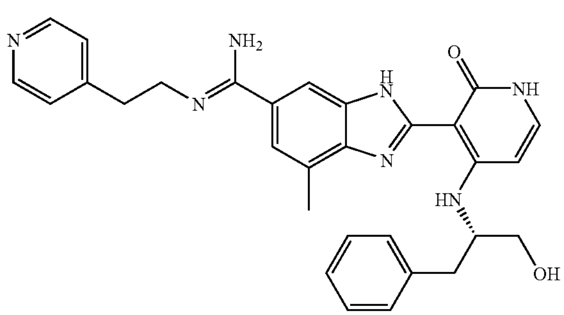 | 1.25 (b) | 522 |
| 449 | (S)-2-[4-(1-Hydroxymethyl-2-phenyl-ethylamino)-2-oxo-1,2-dihydro-pyridin-3-yl]-7-methyl-N,N'-bis-(2-pyridin-3-yl-ethyl)-3H-benzimidazole-5-carboxamidine | 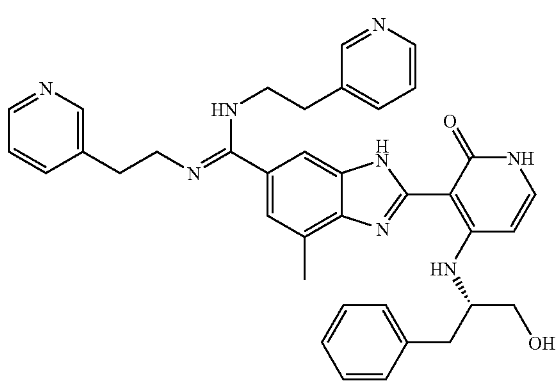 | 1.24 (b) | 627 |

-continued

| Example # | Name | Structure | T (min.) | Mass (M + H)+ m/z |
|---|---|---|---|---|
| 450 | (S)-2-[4-(1-Hydroxymethyl-2-phenyl-ethylamino)-2-oxo-1,2-dihydro-pyridin-3-yl]-7-methyl-N,N'-bis-(2-pyridin-4-yl-ethyl)-3H-benzimidazole-5-carboxamidine | 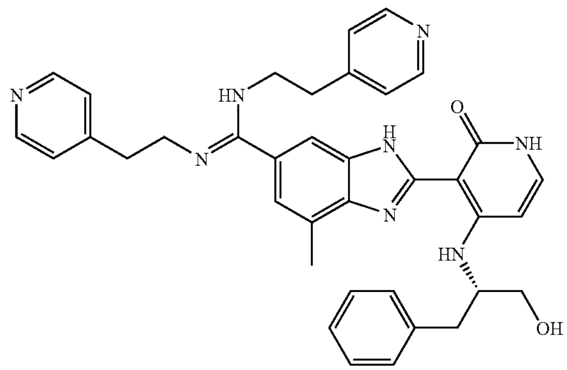 | 1.16 (b) | 627 |
| 451 | (S)-4-[2-(2-Chloro-phenyl)-1-hydroxymethyl-ethylamino]-3-[6-(4,5-dihydro-1H-imidazol-2-yl)-4-methyl-1H-benzimidazol-2-yl]-1H-pyridin-2-one | 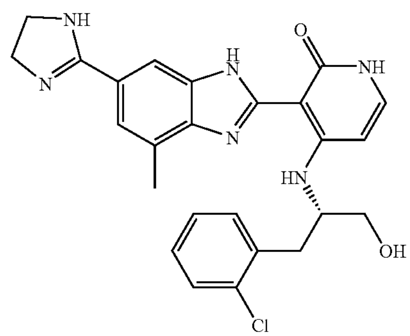 | 1.53 (b) | 477 |
| 452 | (S)-2-[4-(1-Hydroxymethyl-2-pyridin-3-yl-ethylamino)-2-oxo-1,2-dihydro-pyridin-3-yl]-7,N-dimethyl-3H-benzimidazole-5-carboxamidine | 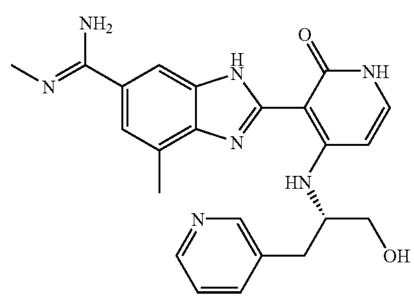 | 0.80 (b) | 432 |
| 453 | (S)-3-[6-(4,5-Dihydro-1H-imidazol-2-yl)-4-methyl-1H-benzimidazol-2-yl]-4-(1-hydroxymethyl-2-pyridin-3-yl-ethylamino)-1H-pyridin-2-one | 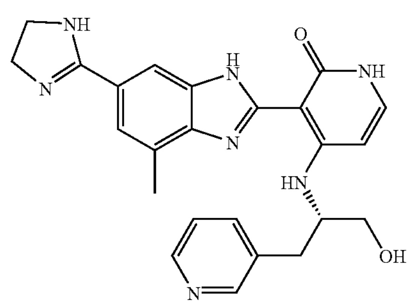 | 0.98 (b) | 444 |

-continued

| Example # | Name | Structure | T (min.) | Mass (M + H)+ m/z |
|---|---|---|---|---|
| 454 | (S)-2-[4-(1-Hydroxymethyl-2-pyridin-4-yl-ethylamino)-2-oxo-1,2-dihydro-pyridin-3-yl]-7,N-dimethyl-3H-benzimidazole-5-carboxamidine | 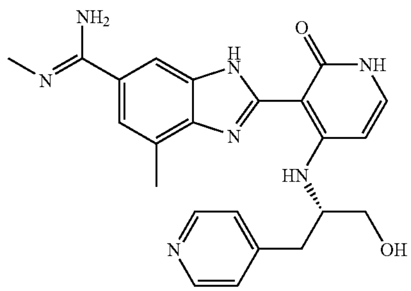 | 0.73 (b) | 432 |
| 455 | (S)-3-[6-(4,5-Dihydro-1H-imidazol-2-yl)-4-methyl-1H-benzimidazol-2-yl]-4-(1-hydroxymethyl-2-pyridin-4-yl-ethylamino)-1H-pyridin-2-one | 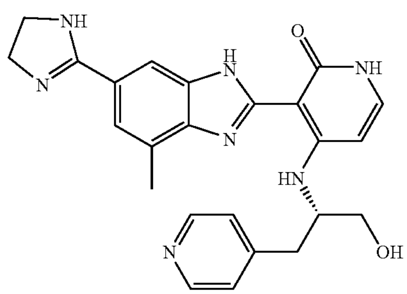 | 0.98 (b) | 444 |
| 456 | (S)-2-[4-(1-Hydroxymethyl-2-thiophen-2-yl-ethylamino)-2-oxo-1,2-dihydro-pyridin-4-yl]-7,N-dimethyl-3H-benzimidazole-5-carboxamidine | 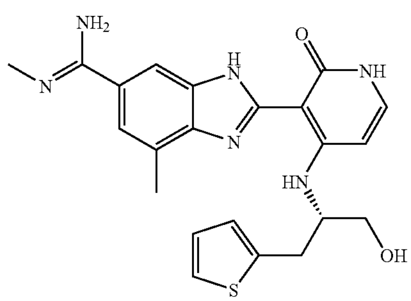 | 1.24 (b) | 437 |
| 457 | (S)-3-[6-(4,5-Dihydro-1H-imidazol-2-yl)-4-methyl-1H-benzimidazol-2-yl]-4-(1-hydroxymethyl-2-thiophen-2-yl-ethylamino)-1H-pyridin-2-one | 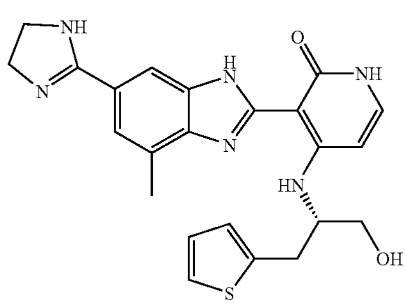 | 1.46 (b) | 449 |

-continued

| Example # | Name | Structure | T (min.) | Mass (M + H)+ m/z |
|---|---|---|---|---|
| 458 | (S)-2-[4-(2-Benzo[b]thiophen-3-yl-1-hydroxymethyl-ethylamino)-2-oxo-1,2-dihydro-pyridin-3-yl]-7,N-dimethyl-3H-benzimidazole-5-carboxamidine | 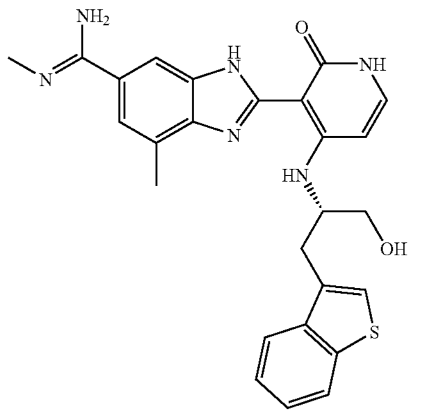 | 1.47 (b) | 487 |
| 459 | 7,N-Dimethyl-2-[2-oxo-4-(2-pyridin-2-yl-ethylamino)-1,2-dihydro-pyridin-3-yl]-3H-benzimidazole-5-carboxamidine | 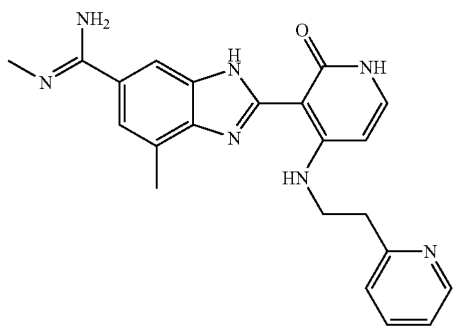 | 0.86 (b) | 402 |
| 460 | 3-[6-(4,5-Dihydro-1H-imidazol-2-yl)-4-methyl-1H-benzimidazol-2-yl]-4-(2-pyridin-2-yl-ethylamino)-1H-pyridin-2-one | 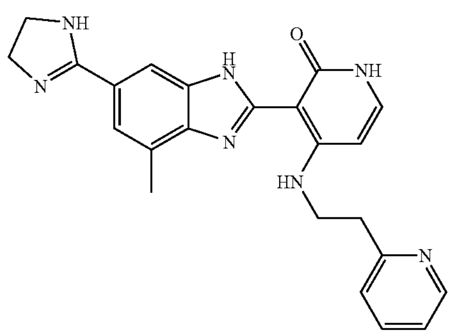 | 0.91 (b) | 414 |
| 461 | (S)-7-Bromo-2-[4(1-hydroxymethyl-2-phenyl-ethylamino)-2-oxo-1,2-diydro-pyridin-3-yl)-N-methyl-3H-benzimidazole-5-carboxamidine | 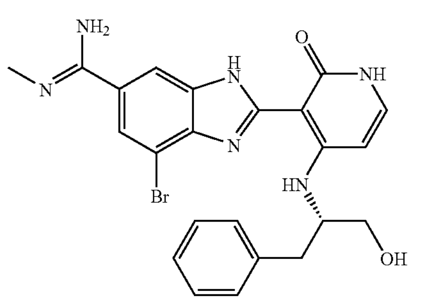 | 1.47 (b) | 495 |

-continued

| Example # | Name | Structure | T (min.) | Mass (M + H)+ m/z |
|---|---|---|---|---|
| 462 | (±)-2-{4-[2-(3-Chloro-phenyl)-2-hydroxy-ethylamino]-2-oxo-1,2-dihydro-pyridin-3-yl}-7-ethyl-N-methyl-3H-benzimidazole-5-carboxamidine | 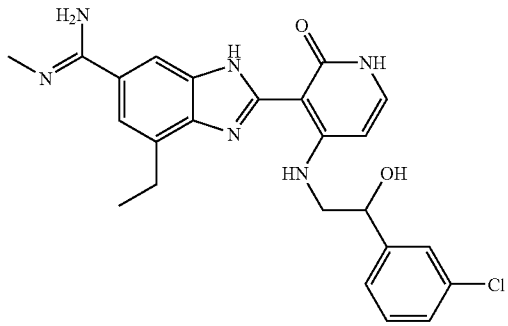 | 1.51 (d) | 465 |
| 463 | 7,N-Dimethyl-2-[2-oxo-4-(2-pyridin-2-ylmethylamino)-1,2-dihydro-pyridin-3-yl]-3H-benzimidazole-5-carboxamidine | 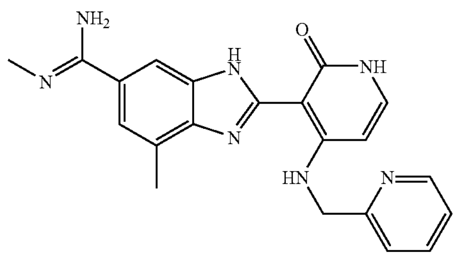 | 0.98 (b) | 388 |
| 464 | 3-[6-(4,5-Dihydro-1H-imidazol-2-yl)-4-methyl-1H-benzimidazol-2-yl]-4-[(pyridin-2-ylmethyl)-amino]-1H-pyridin-2-one | 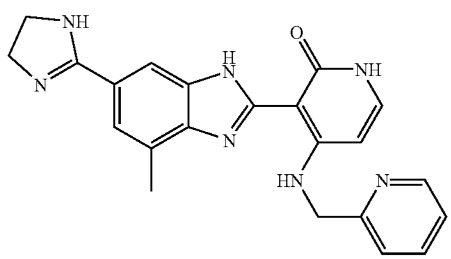 | 1.07 (b) | 400 |
| 465 | 7,N-Dimethyl-2-[2-oxo-4-(2-thiophen-2-yl-ethylamino)-1,2-dihydro-pyridin-3-yl]-3H-benzimidazole-5-carboxamidine | 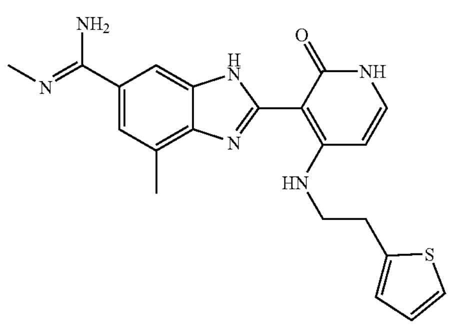 | 1.53 (b) | 407 |
| 466 | 3-[6-(4,5-Dihydro-1H-imidazol-2-yl)-4-methyl-1H-benzimidazol-2-yl]-4-(2-thiophen-2-yl-ethylamino)-1H-pyridin-2-one | 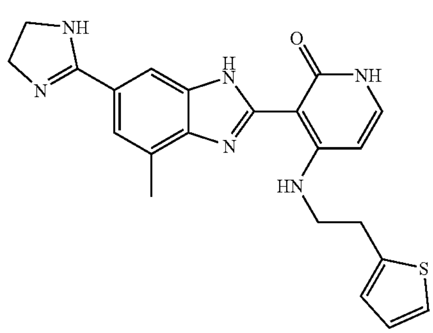 | 1.62 (b) | 419 |

-continued

| Example # | Name | Structure | T (min.) | Mass (M + H)+ m/z |
|---|---|---|---|---|
| 467 | (±)-2-{4-[2-(3-Chloro-phenyl)-ethylamino]-2-oxo-1,2-dihydro-pyridin-3-yl}-7,N-dimethyl-3H-benzimidazole-5-carboxamidine | 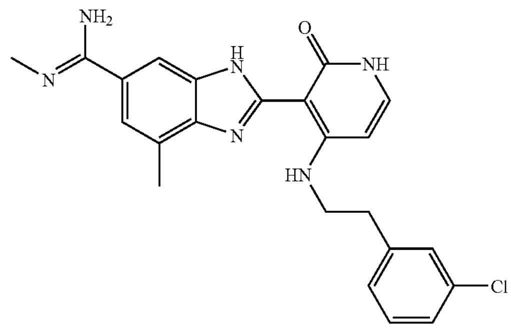 | 1.57 (b) | 435 |
| 468 | (±)-4-[2-(3-Chloro-phenyl)-ethylamino]-3-[6-(4,5-dihydro-1H-imidazol-2-yl)-4-methyl-1H-benzimidazol-2-yl]-1H-pyridin-2-one | 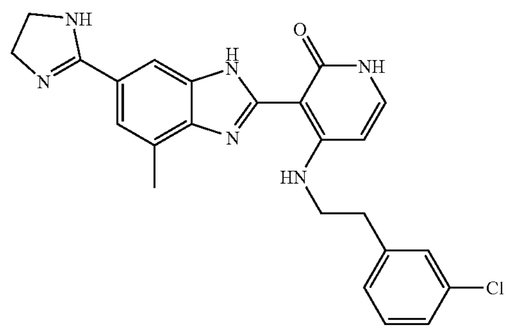 | 1.66 (b) | 447 |
| 469 | (±)-3-[4-Chloro-6-(4,5-dihydro-1H-imidazol-2-yl)-1H-benzimidazol-2-yl]-4-[2-(3-chloro-phenyl)-2-hydroxy-ethylamino]-1H-pyridin-2-one | 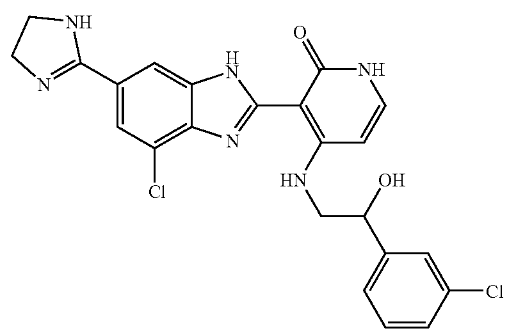 | 1.40 (d) | 483 |
| 470 | (±)-3-[4-Chloro-6-(5,5-dimethyl-4,5-dihydro-1H-imidazol-2-yl)-1H-benzimidazol-2-yl]-4-[2-(3-chloro-phenyl)-2-hydroxy-ethylamino]-1H-pyridin-2-one | 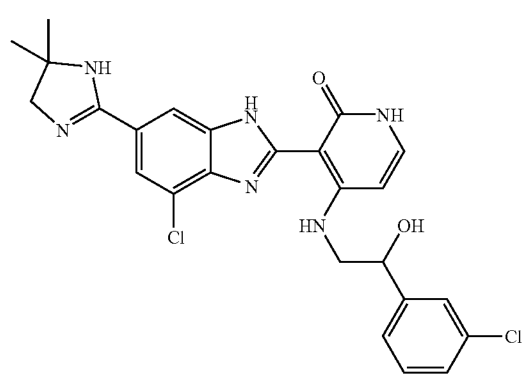 | 1.52 (d) | 511 |

-continued

| Example # | Name | Structure | T (min.) | Mass (M + H)+ m/z |
|---|---|---|---|---|
| 471 | (±)-4-[2-(3-Chloro-phenyl)-2-hydroxy-ethylamino]-3-[6-(5,5-dimethyl-4,5-dihydro-1H-imidazol-2-yl)-4-ethyl-1H-benzimidazol-2-yl]-1H-pyridin-2-one | 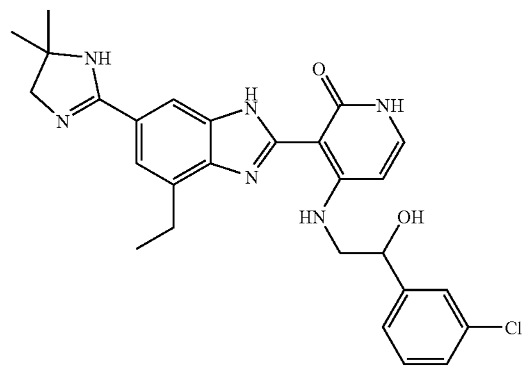 | 1.57 (d) | 505 |
| 472 | (±)-4-[2-(3-Chloro-phenyl)-2-hydroxy-ethylamino]-3-[6-(4,5-dihydro-1H-imidazol-2-yl)-4-ethyl-1H-benzimidazol-2-yl]-1H-pyridin-2-one | 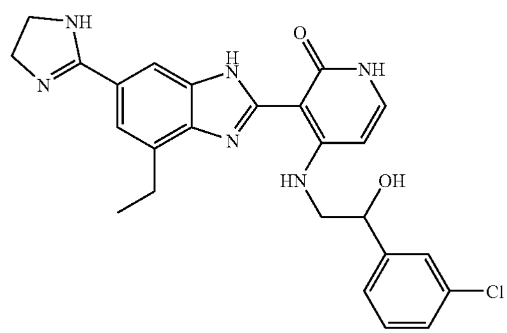 | 1.49 (d) | 477 |
| 473 | (S)-3-[6-(4,5-Dihydro-1H-imidazol-2-yl)-4-ethyl-1H-benzimidazol-2-yl]-4-(1-hydroxymethyl-2-phenyl-ethamino)-1H-pyridin-2-one | 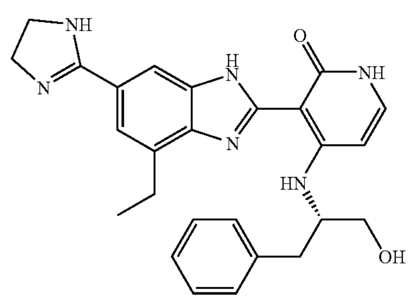 | 1.47 (d) | 457 |
| 474 | (S)-7-Ethyl-2-[4-(1-hydroxymethyl-2-phenyl-ethylamino)-2-oxo-1,2-dihydro-pyridin-3-yl]-N-methyl-3H-benzimidazole-5-carboxamidine | 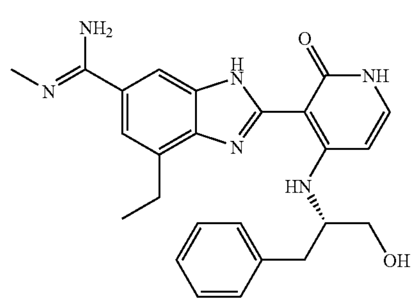 | 1.42 (d) | 445 |

Amide Formation

Intermediate Synthesis

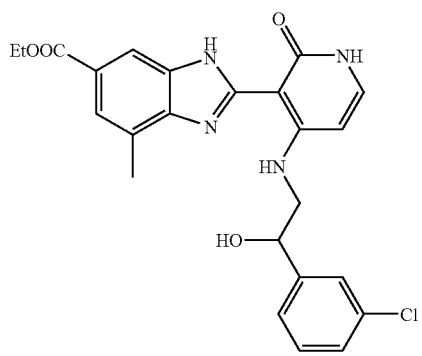

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid ethyl ester: A solution of (±)-2-{4-[2-(3-chloro-phenyl)-2-hydroxy-ethylamino-]-2-oxo-1,2-dihydro-pyridin-3-yl}-7-methyl-3H-benzimidazole-5-carboximidic acid ethyl ester (400 mg, 0.90 mmol) was diluted with 2 N HCl (20 mL) solution and the mixture was allowed to stir at room temperature for 14 h. After concentration to dryness, the crude product (419 mg, 100%) was used for the next step without purification. Small amount was purified by prep. HPLC to yield the title compound. $^1$H NMR (300 MHz, CD$_3$OD) δ 8.11 (1H, s), 7.74 (1H, s), 7.25–7.54 (5H, m), 6.25 (1H, d, J=7.6 Hz), 4.99 (1H, t, J=7.2 Hz), 4.38 (2H, q, J=7.1 Hz), 3.61–3.76 (2H, m), 2.61 (3H, s), 1.42 (3H, q, J=7.1 Hz). LCMS (M+H)$^+$ m/z 467 (t=2.23 min.).

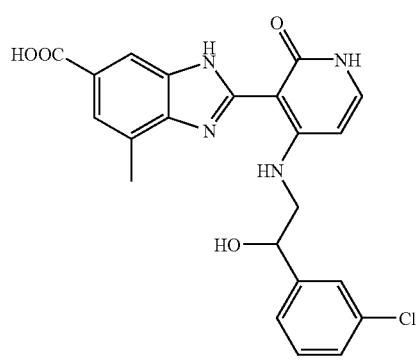

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid: The ethyl ester (419 mg, 0.90 mmol) obtained above was diluted with methanol (15 mL) and water (5 mL) followed by addition of sodium hydroxide (180 mg, 4.5 mmol). The mixture was stirred at room temperature for 14 h. After removal of methanol, the residue was neutralized with 2 N HCl solution. The resulting slurry was filtered and washed with ice-cold water. The solid was collected after drying over high vacuum. The crude product (395 mg, 100% yield, 80% pure) was used for the next step without further purification. $^1$NMR (300 MHz, CD$_3$OD) δ 8.20 (1H, s), 7.92 (1H, s), 7.27–7.47 (5H, m), 6.27 (1H, d, J=7.6 Hz), 4.85 (1H, m), 3.63 (2H, m), 2.67 (3H, s). LCMS (M+H)$^+$ m/z 439 (t=1.88 min.).

EXAMPLE 475

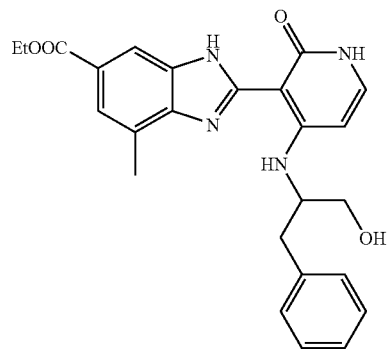

(S)-2-[4-(1-Hydroxymethyl-2-phenyl-ethylamino)-2-oxo-1,2-dihydro-pyridin-3-yl]-7-methyl-3H-benzimidazole-5-carboxylic acid ethyl ester: The imidate ester (30 mg, 0.067 mmol) was dilute with methanol (10 mL) and two drops of water was added. The reaction mixture was stirred at room temperature for 20 h. After concentration in vacuo, the residue was purified by prep. HPLC to yield the title compound (18.2 mg, 61%) as a white solid. $^1$H NMR (300 MHz, CD$_3$OD) δ 7.74 (1H, s), 7.11–7.30 (7H, m), 6.10 (1H, d, J=6.9 Hz), 4.37 (2H, q, J=6.6 Hz), 4.02 (1H, broad s), 3.69–3.81 (2H, m), 3.10 (1H, dd, J=4.8, 13.5 Hz), 2.93 (1H, dd, J=7.8, 13.5 Hz), 2.62 (3H, s), 1.41 (3H, t J=6.6 Hz). LCMS (M+H)$^+$ m/z 447 (t=1.95 min.).

Preparation of Amides Starting from (±)-2-{4-[2-(3-Chloro-phenyl)-2-hydroxy-ethylamino]-2-oxo-1,2-dihydro-pyridin-3-yl]-7-methyl-3H-benzimidazole-5-carboxylic acid, Examples 476–504, Scheme IV, 15

EXAMPLE 476

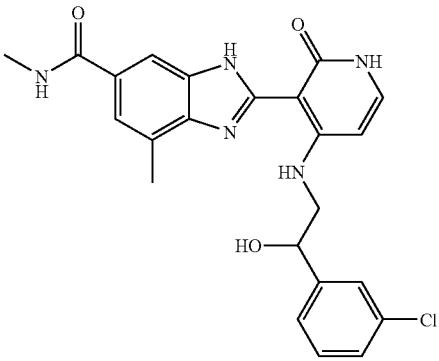

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid methylamide: To a solution of the acid (50 mg, 0.11 mmol) in DMF (5 mL) was added diphenylphosphoryl azide (38 mg, 0.14 mmol). The mixture was allowed to stir for 5 min. Then methylamine (2.0 M solution in THF) (0.11 mL, 0.22 mmol) was added. The mixture was stirred at room temperature for 14 h. After removal of DMF with high vacuum, the residue was purified by prep. HPLC to yield the title compound (18 mg, 36%) as a white solid. $^1$H NMR (300 MHz, CD$_3$OD) δ 7.89 (1H, s), 7.18–7.53 (6H, m), 6.23 (1H, d, J=7.6 Hz), 4.98 (1H, m), 3.70 (1H, dd, J=4.7, 13.5 Hz), 3.61 (1H, dd, J=7.0, 13.5 Hz), 2.94 (3H, s), 2.61 (3H, s). LCMS (M+H)$^+$ m/z 452 (t=1.57 min.).

EXAMPLE 477

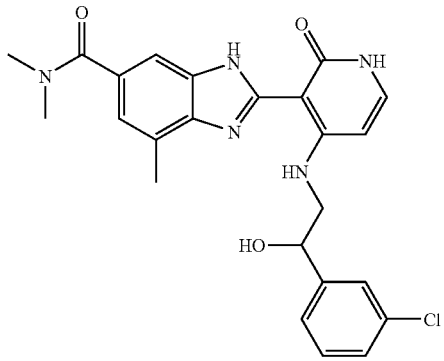

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid dimethylamide: $^1$H NMR (300 MHz, CD$_3$OD) δ 7.52 (1H, s), 7.24–7.40 (5H, m), 7.15 (1H, s), 6.25 (1H, d, J=7.6 Hz), 4.98 (1H, dd, J=5.0, 6.9 Hz), 3.70 (1H, dd, J=4.8, 13.5 Hz), 3.62 (1H, dd, J=7.0, 13.5 Hz), 3.3 (3H, s), 3.08 (3H, s), 2.62 (3H, s). LCMS (M+H)$^+$ m/z 466 (t=1.84 min.).

EXAMPLE 478

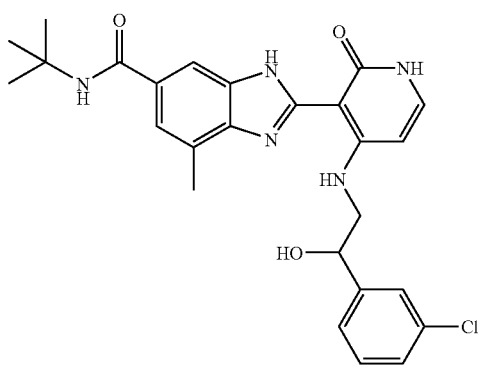

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid tert-butylamide: $^1$H NMR (300 MHz, CD$_3$OD) δ 7.82 (1H, s), 7.53 (1H, s), 7.48 (1H, s), 7.24–7.40 (4H, m), 6.25 (1H, d, J=7.6 Hz), 5.00 (1H, m), 3.64–3.70 (2H, m), 2.62 (3H, s), 1.49 (9H, s). LCMS (M+H)$^+$ m/z 494 (t=1.79 min.).

EXAMPLE 479

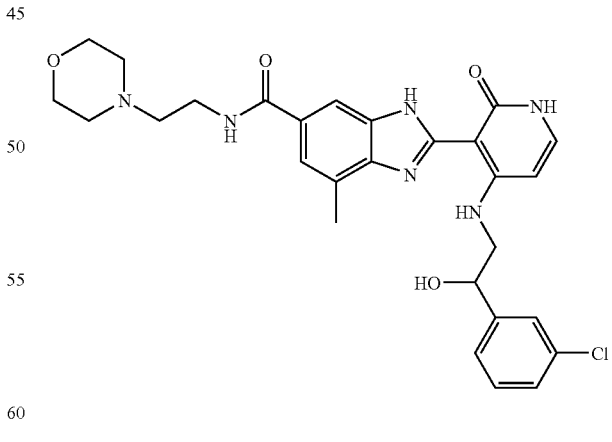

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid butyl-methyl-amide: $^1$H NMR (300 MHz, CD$_3$OD) δ 7.51 (1H, s), 7.48 (1H, s), 7.24–7.39 (4H, m), 7.13 (1H, s), 6.22 (1H, d, J=7.6 Hz), 4.95 (1H, m), 3.55–3.70 (3H, m), 3.34 (1H, m), 3.05 (3H, s), 2.62 (3H, s), 0.79–1.69 (7H, m). LCMS (M+H)$^+$ m/z 508 (t=1.88 min.).

EXAMPLE 480

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid (2-morpholine-4-yl-ethyl)-amide: $^1$H NMR (300 MHz, CD₃OD) δ 7.58 (1H, s), 7.52 (1H, s), 7.05–7.42 (5H, m), 6.22 (1H, d, J=7.6 Hz), 4.97 (1H, dd, J=4.9, 6.7 Hz), 2.60–4.07 (14H, m), 2.61 (3H, s). LCMS (M+H)⁺ m/z 551 (t=1.49 min.).

EXAMPLE 481

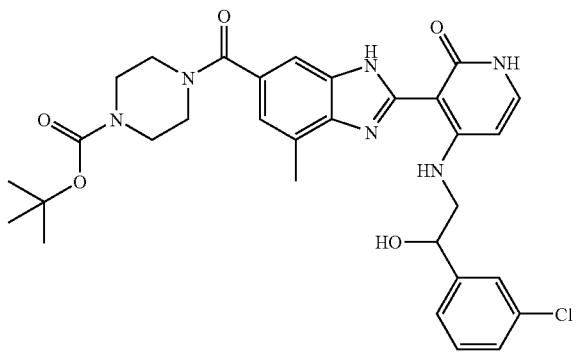

(±)-4-[1-(2-{4-[2-(3-Chloro-phenyl)-2-hydroxy-ethylamino]-2-oxo-1,2-dihydro-pyridin-3-yl}-7-methyl-3H-benzimidazol-5-yl)-methanoyl]-piperazine-1-carboxylic acid tert-butyl ester: ¹H NMR (300 MHz, CD₃OD) δ 7.52 (1H, s), 7.50 (1H, s), 7.24–7.38 (4H, m), 7.18 (1H, m), 6.22 (1H, d, J=7.6 Hz), 4.97 (1H, m), 3.49–3.69 (10H, m), 2.62 (3H, s), 1.47 (9H, s). LCMS (M+H)⁺ m/z 607 (t=1.90 min.).

EXAMPLE 482

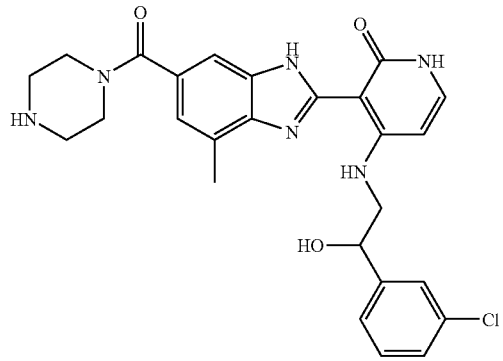

(±)-4-[2-(3-Chloro-phenyl)-2-hydroxy-ethylamino]-3-[4-methyl-6-(1-piperazin-1-yl-methanoyl)-1H-benzimidazol-2-yl]-1H-pyridin-2-one: To a solution of (±)-4-[1-(2-{4-[2-(3-chloro-phenyl)-2-hydroxy-ethylamino]-2-oxo-1,2-dihydro-pyridin-3-yl}-7-methyl-3H-benzimidazol-5-yl)-methanoyl]-piperazine-1-carboxylic acid tert-butyl ester (40 mg, 0.06 mmol) in methanol (5 mL) was added 4.0 M HCl dioxane solution (0.1 mL, excess). The reaction mixture was stirred at room temperature for 14 h. After concentration, the residue was purified by prep. HPLC to give the title compound (16 mg, 63%) as a white foam. ¹H NMR (300 MHz, CD₃OD) δ 7.56 (1H, s), 7.53 (1H, s), 7.23–7.41 (4H, m), 7.17 (1H, m), 6.26 (1H, d, J=7.6 Hz), 4.99 (1H, dd, J=4.7, 6.4 Hz), 3.91 (4H, broad s), 3.74 (1H, dd, J=4.7, 13.5 Hz), 3.65 (1H, dd, J=6.4, 13.5 Hz), 3.31 (4H, broad s), 2.63 (3H, s). LCMS (M+H)⁺ m/z 507 (t=1.38 min.).

EXAMPLE 483

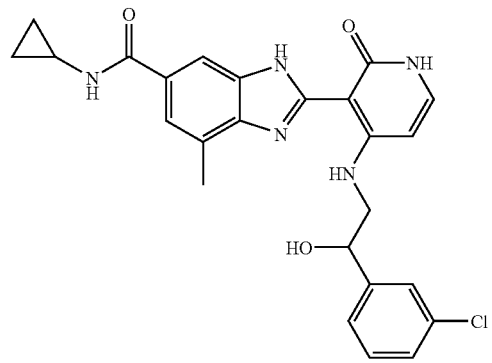

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid cyclopropylamide: ¹H NMR (300 MHz, CD₃OD) δ 7.80 (1H, s), 7.21–7.53 (6H, m), 6.22 (1H, d, J=7.6 Hz), 4.99 (1H, t, J=6.4 Hz), 3.59–3.76 (2H, m), 2.83–2.90 (1H, m), 2.60 (3H, s), 0.81–0.89 (2H, m), 0.64–0.73 (2H, m). LCMS (M+H)⁺ m/z 478 (t=1.60 min.).

EXAMPLE 484

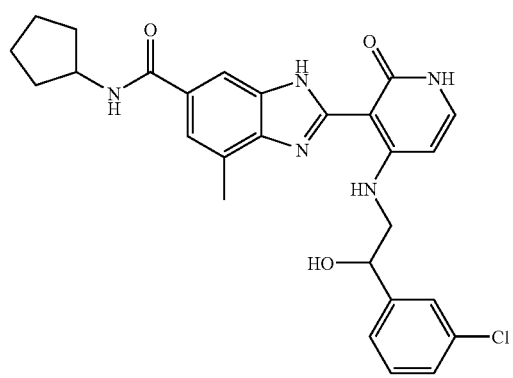

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid cyclopentylamide: ¹H NMR (300 MHz, CD₃OD) δ 7.97 (1H, s), 7.16–7.60 (6H, m), 6.22 (1H, d, J=7.6 Hz), 4.35 (1H, m), 3.58–3.68 (2H, m), 2.62 (3H, s), 1.29–2.07 (9H, m). LCMS (M+H)⁺ m/z 506 (t=1.86 min.).

EXAMPLE 485

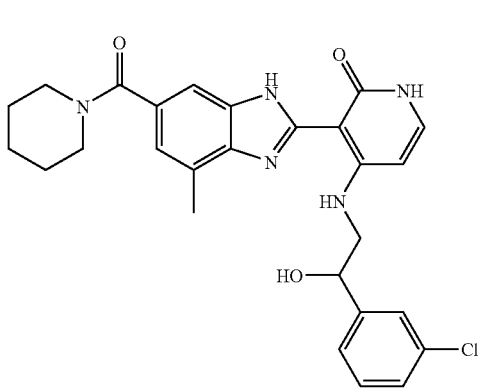

(±)-4-[2-(3-Chloro-phenyl)-2-hydroxy-ethylamino]-3-[4-methyl-6-(1-piperidin-1-yl-methanoyl)-1H-benzoimidazol-2-yl]-1H-pyridin-2-one: $^1$H NMR (300 MHz, CD$_3$OD) δ 7.53 (1H, s), 7.46 (1H, s), 7.18–7.41 (4H, m), 7.07 (1H, s), 6.23 (1H, d, J=7.6 Hz), 4.98 (1H, dd, J=4.8, 6.6 Hz), 3.60–3.74 (5H, m), 3.18–3.24 (1H, m), 2.60 (3H, m), 1.43–1.7 (6H, m). LCMS (M+H)$^+$ m/z 506 (t=1.78 min.).

EXAMPLE 486

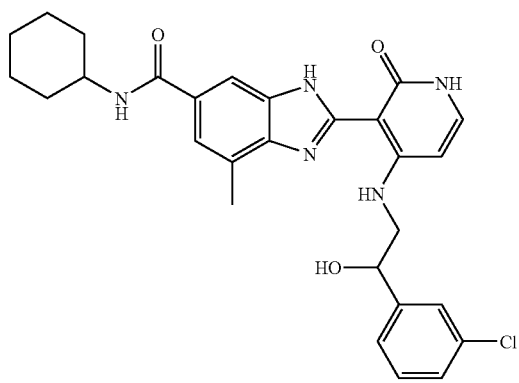

(±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid cyclohexylamide: $^1$H NMR (300 MHz, CD$_3$OD) δ 7.88 (1H, s), 7.54 (1H, s), 7.52 (1H, s), 7.16–7.40 (4H, m), 6.22 (1H, J=7.6 Hz), 4.97 (1H, dd, J=4.7, 6.9 Hz), 3.89 (H, m), 3.69 (1H, dd, J=4.7, 13.5 Hz), 3.61 (1H, dd, J=6.9, 13.5 Hz), 2.61 (3H, s), 1.19–2.00 (10H, m). LCMS (M+H)$^+$ m/z 520 (t=1.93 min.).

EXAMPLE 487

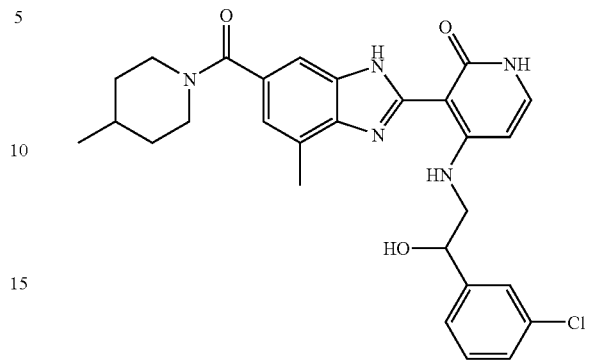

(±)-4-[2-(3-Chloro-phenyl)-2-hydroxy-ethylamino]-3-{4-methyl-6-[1-(4-methyl-piperidin-1-yl)-methanoyl]-1H-benzimidazol-2-yl}-1H-pyridin-2-one: $^1$H NMR (300 MHz, CD3OD) δ 7.51 (1H, s), 7.49 (1H, s), 7.21–7.39 (4H, m), 7.14 (1H, s), 6.24 (1H, d, J=7.6 Hz), 4.96 (1H, dd, J=4.7, 7.0 Hz), 3.68 (1H, dd, J=4.7,13.6 Hz), 3.60 (1H, dd, J=7.0, 13.6 Hz), 2.62 (3H, s), 1.93–1.72 (9H, m), 1.00 (3H, d, J=6.3 Hz). LCMS (M+H)$^+$ m/z 520 (t=1.97 min.).

EXAMPLE 488

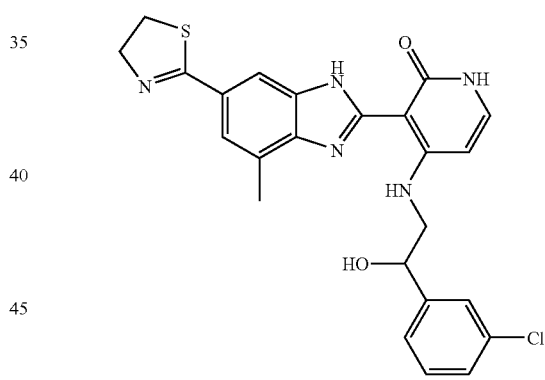

(±)-4-[2-(3-Chloro-phenyl)-2-hydroxy-ethylamino]-3-[6-(4,5-dihydro-thiazol-2-yl)-4-methyl-1H-benzimidazol-2-yl]-1H-pyridin-2-one: To a solution of (±)-2-{4-[2-(3-chloro-phenyl)-2-hydroxy-ethylamino]-2-oxo-1,2-dihydro-pyridin-3-yl}-7-methyl-3H-benzimidazole-5-carbonitrile (100 mg, 0.24 mmol) in methanol (20 mL) was added 2-aminoethanethiol hydrochloride (41 mg, 0.36 mmol) and triethylamine (0.1 mL, excess). The reaction mixture was heated to reflux for 14 h and cooled to room temperature. After concentration, the residue was purified by prep. HPLC to yield the title compound (76 mg, 66%) as a yellow solid. $^1$H NMR (300 MHz, CD$_3$OD) δ 8.10 (1H, s), 7.71 (1H, s), 7.66 (1H, s), 7.25–7.53 (4H, m), 6.33 (1H, d, J=7.6 Hz), 5.01 (1H, dd, J=4.2, 7.0 Hz), 4.58 (2H, t, J=8.6 Hz), 3.91 (2H, t, J=8.6 Hz), 3.73 (1H, dd, J=4.2, 13.7 Hz), 3.63 (1H, dd, J=7.0, 13.7 Hz), 2.64 (3H, s). LCMS (M+H)$^+$ m/z 480 (t=1.70 min.).

EXAMPLE 489

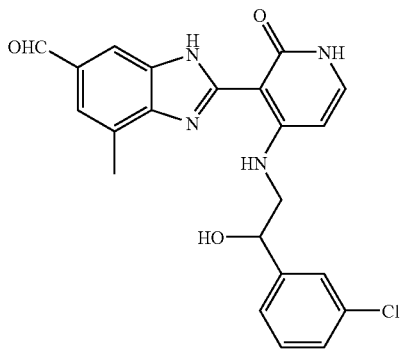

(±)-2-{4-[2-(3-Chloro-phenyl)-2-hydroxy-ethylamino]-2-oxo-1,2-dihydro-pyridin-3-yl}-7-methyl-3H-benzimidazole-5-carbaldehyde: To a suspension of (±)-2-{4-[2-(3-chloro-phenyl)-2-hydroxy-ethylamino]-2-oxo-1,2-dihydro-pyridin-3-yl }-7-methyl-3H-benzimidazole-5-carbonitrile (76 mg, 0.18 mmol) in toluene (anhydrous, 20 mL) was added diisobutylaluminium (1.4 M toluene solution) (0.65 mL, 0.97 mmol) at −78° C. under nitrogen. The mixture was stirred at —78° C. for 6 h. Ethyl acetate (1 mL) was then added followed by water (0.5 mL). The mixture was stirred at room temperature for 20 min. The mixture was then passed through a pad of celite and the filtrate was concentrated. The crude product was purified by prep. HPLC to yield the title compound (4 mg, 2.5%) as a brown solid. $^1$H NMR (300 MHz, CD$_3$OD) δ 7.65 (1H, s), 7.57 (1H, s), 7.24–7.50 (5H, m), 6.26 (1H, d, J=7.6 Hz), 5.49 (1H, s), 4.96 (1H, m), 3.53–3.79 (2H, m), 2.62 (3H, s). LCMS (M+H)$^+$ m/z 423 (t=1.79 min.).

EXAMPLE 490

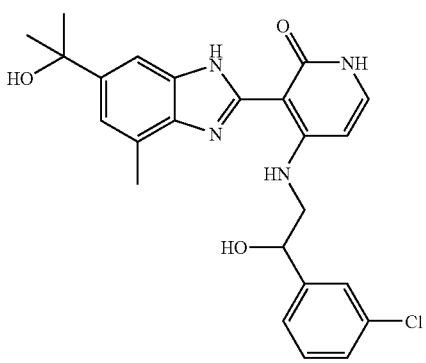

(±)-4-[2-(3-Chloro-phenyl)-2-hydroxy-ethylamino]-3-[6-(1-hydroxy-1-methyl-ethyl)-4-methyl-1H-benzimidazol-2-yl]-1H-pyridin-2-one: To a solution of (±)-2-{4-[2-(3-chloro-phenyl)-2-hydroxy-ethylamino]-2-oxo-1,2-dihydro-pyridin-3-yl}-7-methyl-3H-benzimidazole-5-carboxylic acid ethyl ester (40 mg, 0.08 mmol) in THF (5 mL) was added methyllithium (1.4 M THF solution, 0.57 mL, 0.8 mmol) at −78° C. under nitrogen. The reaction mixture was gradually warmed to room temperature overnight. After quenching with water, the mixture was partitioned between ethyl acetate and water. The organic layers were washed with brine, dried over Na$_2$SO$_4$, and concentrated in vacuo. The residue was purified by prep HPLC to yield the title compound (13 mg, 36%) as a colorless oil. $^1$H NMR (300 MHz, CD$_3$OD) δ 7.66 (1H, s), 7.47 (1H, s), 7.26–7.41 (5H, m), 6.26 (1H, d, J=7.6 Hz), 4.92 (1H, m), 3.54–3.61 (2H, m), 2.62 (3H, s), 1.60 (6H, s). LCMS (M+H)$^+$ m/z 453 (t=1.46 min.).

EXAMPLE 491

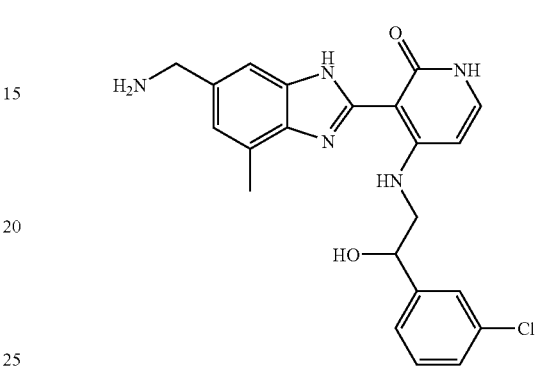

(±)-3-(6-Aminomethyl-4-methyl-1H-benzimidazol-2-yl)-4-[2-(3-chloro-phenyl)-2-hydroxy-ethylamino]-1H-pyridin-2-one: To a solution of (±)-2-{4-[2-(3-Chloro-phenyl)-2-hydroxyethyl amino]-2-oxo-1,2-dihydro-pyridin-3-yl}-7-methyl-3H-benzimidazole-5-carboxylic acid amide (20 mg, 0.046 mmol) in THF (1 mL) was added borane-tetrahydrofuran complex (1 M solution) (0.45 mL, 0.45 mmol). The reaction mixture was stirred at room temperature for 10 h and quenched with acetic acid (2 drops). After removal of most solvent, the residue was extracted with EtOAc, washed with brine, dried over Na$_2$SO$_4$. After concentration, the crude product was purified by prep. HPLC to yield the title compound (11.5 mg, 60%). $^1$H NMR (400 MHz, CD$_3$OD) δ 7.53 (1H, s), 7.50 (1H, s), 7.39 (1H, d, J=7.5 Hz), 7.24–7.32 (3H, m), 7.13 (1H, s), 6.26 (1H, d, J=7.5 Hz), 4.99 (1H, dd, J=4.8, 6.8 Hz), 4.19 (2H, s), 3.72 (1H, dd, J=4.8, 13.6 Hz), 3.64 (1H, dd, J=6.8, 13.6 Hz), 2.62 (3H, s). LCMS (M+H)$^+$ m/z 424 (t=2.10 min.).

EXAMPLE 492

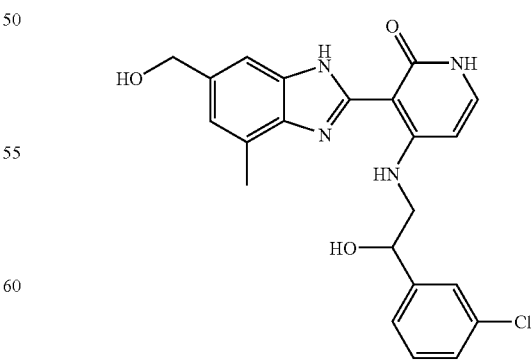

(±)-4-[2-(3-Chloro-phenyl)-2-hydroxy-ethylamino]-3-(6hydroxymethyl-4-methyl-1H-benzimidazol-2-yl)-1H-pyridin-2-one: To a solution of (±)-2-{4-[2-(3-Chloro-phenyl)-

2-hydroxy-ethylamino]-2-oxo-1,2-dihydro-pyridin-3-yl]}-3H-benzimidazole-5-carboxylic acid ethyl ester (25 mg, 0,054 mmol) in methanol (2 mL) and acetic acid (1 mL) was added NaBH₄ (10 mg, 0.27 mmol) at −20° C. The reaction mixture was stirred at −20° C. for 30 min. and quenched with isopropanol (5 drops). After removal of most solvent, the residue was extracted with EtOAc, washed with water and brine, dried over Na₂SO₄. After concentration, the crude product was purified by prep. HPLC to yield the title compound (18 mg, 62%). ¹H NMR (300 MHz, CD₃OD) δ 7.50 (1H, s), 7.48 (1H, s), 7.25–7.38 (4H, m), 7.22 (1H, s), 6.25 (1H, d, J=7.6 Hz), 4.89–4.94 (1H, m), 4.76 (2H, s), 3.51–3.62 (2H, m), 2.62 (3H, s). LCMS (M+H)⁺ m/z 425 (t=1.64 min.).

| Example # | Name | BMS-# | | T (min) | Mass (M + H)⁺ m/z |
|---|---|---|---|---|---|
| 493 | (±)-2-{4-[2-(3-Chloro-phenyl)-2-hydroxy-ethylamino]-2-oxo-1,2-dihydro-pyridin-3-yl}-7-methyl-3H-benzimidazole-5-carboxylic acid amide | | | 1.68 (f) | 437 |
| 494 | (±)-2-{4-[2-(3-Fluoro-phenyl)-2-hydroxy-ethylamino]-2-oxo-1,2-dihydro-pyridin-3-yl}-7-methyl-3H-benzimidazole-5-carboxylic acid ethyl ester | | | 1.90 (b) | 451 |
| 495 | (±)-7-Chloro-2-{4-[2-(3-chloro-phenyl)-2-hydroxy-ethylamino]-2-oxo-1,2-dihydro-pyridin-3-yl}-3H-benzimidazole-5-carboxylic acid ethyl ester | | | 2.06 (d) | 487 |
| 496 | (±)-7-Chloro-2-{4-[2-(3-chloro-phenyl)-2-hydroxy-ethylamino]-2-oxo-1,2-dihydro-pyridin-3-yl}-3H-benzimidazole-5-carboxylic acid amide | | | 1.54 (d) | 458 |

-continued

| Example # | Name | BMS-# | T (min) | Mass (M + H)+ m/z |
|---|---|---|---|---|
| 497 | (±)-7-Chloro-2-{4-[2-(3-chloro-phenyl)-2-hydroxy-ethylamino]-2-oxo-1,2-dihydro-pyridin-3-yl}-3H-benzimidazole-5-carboxylic acid | | 1.69 (d) | 459 |
| 498 | (±)-2-{4-[2-(3-Chloro-phenyl)-2-hydroxy-ethylamino]-2-oxo-1,2-dihydro-pyridin-3-yl}-7-ethyl-3H-benzimidazole-5-carboxylic acid ethyl ester | | 1.98 (d) | 481 |
| 499 | (±)-2-{4-[2-(3-Chloro-phenyl)-2-hydroxy-ethylamino]-2-oxo-1,2-dihydro-pyridin-3-yl}-7-ethyl-3H-benzimidazole-5-carboxylic acid amide | | 1.51 (d) | 452 |
| 500 | (S)-7-Bromo-2-[4-(1-hydroxymethyl-2-phenyl-ethylamino)-2-oxo-1,2-dihydro-pyridin-3-yl]-3H-benzimidazole-5-carboxylic acid ethyl ester | | 2.06 (b) | 511 |

-continued

| Example # | Name | BMS-# | T (min) | Mass (M + H)+ m/z |
|---|---|---|---|---|
| 501 | (±)-2-{4-[2-(3-Bromo-phenyl)-2-hydroxy-ethylamino]-2-oxo-1,2-dihydro-pyridin-3-yl}-7-methyl-3H-benzimidazole-5-carboxylic acid ethyl ester | | 1.99 (b) | 511 |
| 502 | (S)-2-{4-[2-(2-Chloro-phenyl)-1-hydroxymethyl-ethylamino]-2-oxo-1,2-dihydro-pyridin-3-yl}-7-methyl-3H-benzimidazole-5-carboxylic acid ethyl ester | | 1.89 (b) | 481 |
| 503 | (S)-2-[4-(2-Hydroxy-2-phenyl-ethylamino)-2-oxo-1,2-dihydro-pyridin-3-yl]-7-methyl-3H-benzimidazole-5-carboxylic acid ethyl ester | | 1.84 (b) | 433 |
| 504 | (±)-4-[2-(3-Chloro-phenyl)-2-hydroxy-ethylamino]-3-[4-methyl-6-(1H-tetrazol-5-yl)-1H-benzimidazol-2-yl]-1H-pyridin-2-one | | 1.92 (f) | 463 |

General Procedure for Suzuki Couplings, Example 505–509 (Scheme V, 18)

EXAMPLE 505

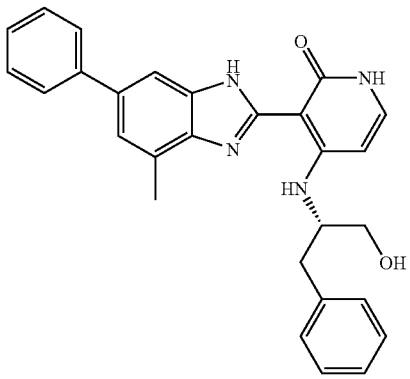

(S)-4-(1-Benzyl-2-hydroxy-ethylamino)-3-(4-methyl-6-phenyl-1H-benzimidazol-2-yl)-1H-pyridin-2-one: To a solution of (S)-4-(1-benzyl-2-trityloxy-ethylamino)-3-[6-bromo-4-methyl-1H-benzimidazole-2-yl]-1H-pyridin-2-one (50 mg, 0.072 mmol), phenylboronic acid (13 mg, 0.11 mmol), and 2 M K$_2$CO$_3$ (0.108 mL, 0.22 mmol) in THF (5 mL) was added Pd(PPh$_3$)$_4$ (8.3 mg, 0.007 mmol). The mixture was heated to reflux 14 h. Upon cooling, the reaction mixture was diluted with CH$_2$Cl$_2$, washed with saturated NaHCO$_3$, dried over Na$_2$SO$_4$, and concentrated in vacuo. The residue was used for the next step without purification. LCMS (M+H)$^+$ m/z 693 (t=2.82 min.). The crude product was treated with 4 N HCl dioxane solution (5 mL) at room temperature for 6 h. After concentration in vacuo, the residue was purified by prep. HPLC to yield the title compound (17 mg, 34%) as a white solid. $^1$H NMR (300 MHz, CD$_3$OD) δ 7.13–7.67 (13H, m), 6.15 (1H, d, J=7.4 Hz), 3.99–4.11 (1H, m), 3.74–3.77 (2H, m), 3.16 (1H, dd, J=5.4, 13.6 Hz), 2.97 (1H, dd, J=7.8, 13.6 Hz), 2.69 (3H, s). LCMS (M+H)$^+$ m/z 451 (t=2.04 min.).

EXAMPLE 506

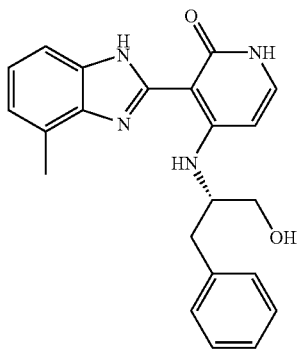

(S)-4-(1-Benzyl-2-hydroxy-ethylamino)-3-(4-methyl-1H-benzimidazol-2-yl)-1H-pyridin-2-one: $^1$H NMR (300 MHz, CD$_3$OD) δ 6.98–7.46 (9H, m), 6.15 (1H, d, J=7.5 Hz), 3.99–4.04 (1H, m), 3.75 (2H, d, J=5.1 Hz), 3.16 (1H, dd, J=5.1, 13.6 Hz), 2.95 (1H, dd, J=8.1, 13.6 Hz), 2.61 (3H, s). LCMS (M+H)$^+$ m/z 375 (t=1.72 min.).

EXAMPLE 507

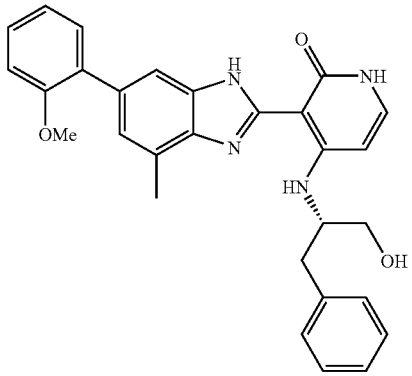

(S)-4-(1-Benzyl-2-hydroxy-ethylamino)-3-[6-(2-methoxy-phenyl)-4-methyl-1H-benzimidazol-2-yl]-1H-pyridin-2-one: $^1$H NMR (300 MHz, CD$_3$OD) δ 6.99–7.59 (12H, m), 6.16 (1H, d, J=7.5 Hz), 4.04 (1H, m), 3.81 (3H, s), 3.76 (2H, d, J=4.1 Hz), 2.96–3.20 (2H, m), 2.66 (3H, s). LCMS (M+H)$^+$ m/z 481 (t=2.00 min.).

EXAMPLE 508

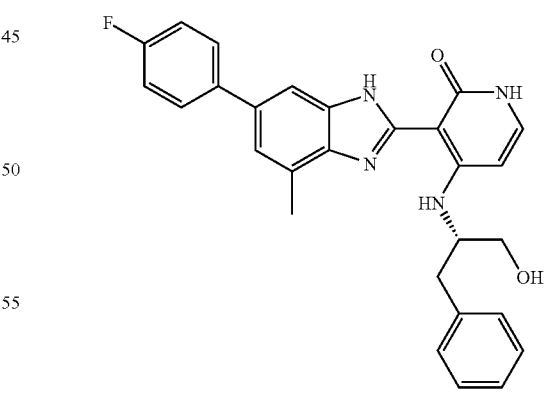

(S)-4-(1-Benzyl-2-hydroxy-ethylamino)-3-[6-(4-fluoro-phenyl)-4-methyl-1H-benzimidazol-2-yl]-1H-pyridin-2-one: $^1$H NMR (300 MHz, CD3OD) δ 7.10–7.66 (12H, m), 6.13 (1H, d, J=7.6 Hz), 3.99–4.04 (1H, m), 3.76 (2H, d, J=5.0 Hz), 3.16 (1H, dd, J=5.0, 13.6 Hz), 2.96 (1H, dd, J=8.1, 13.6 Hz), 2.65 (3H, s). LCMS (M+H)$^+$ m/z 469 (t=2.07 min.).

EXAMPLE 509

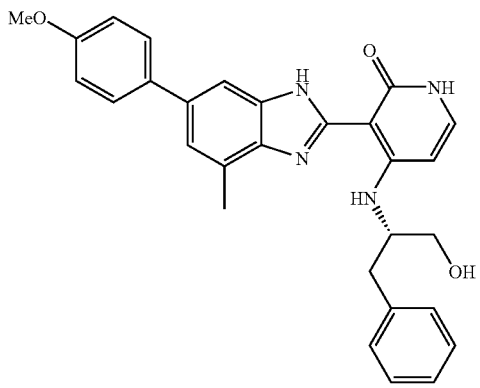

(S)-4-(1-Benzyl-2-hydroxy-ethylamino)-3-[6-(4-methoxy-phenyl)-4-methyl-1H-benzimidazol-2-yl]-1H-pyridin-2-one: $^1$H NMR (300 MHz, CD3OD) δ 6.97–7.65 (12H, m), 6.14 (1H, d, J=7.6 Hz), 4.00–4.04 (1H, m), 3.83 (3H, s), 3.76 (2H, d, J=5.0 Hz), 2.95–3.19 (2H, m), 2.67 (3H, s). LCMS (M+H)$^+$ m/z 481 (t=2.01 min.).

General Procedure for Buchwald Couplings, Examples 510–516 Scheme V, 19

EXAMPLE 510

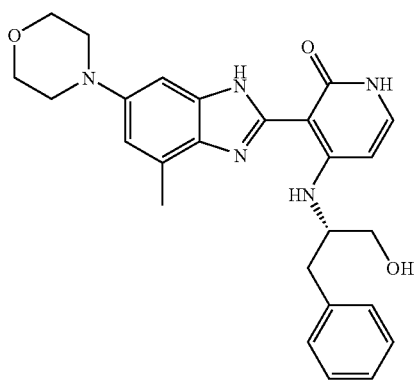

(S)-4-(1-Benzyl-2-hydroxy-ethylamino)-3-(4-methyl-6-morpholin-4-yl-1H-benzimidazol-2-yl)-1H-pyridin-2-one: A mixture of (S)-4-(1-benzyl-2-trityloxy-ethylamino)-3-[6-bromo-4-methyl-1H-benzimidazol-2-yl]-1H-pyridin-2-one (150 mg, 0.216 mmol), morpholine (28.2 mg, 0.324 mmol), palladium acetate (2.4 mg, 0.01 mmol), tri-tert-buylphosphine (4.4 mg, 0.02 mmol), and sodium tert-butoxide (104 mg, 1.08 mmol) in toluene (5 mL) was heated to 100° C. for 14 h under nitrogen. The reaction mixture was cooled to room temperature and diluted with EtOAc. After extraction, the combined organic layers were washed with water, brine, dried over Na$_2$SO$_4$. Concentration gave a brownish residue, which was treated with 4 N HCl dioxane solution (3 mL) at room temperature for 6 h. After removal of the solvent, the residue was purified by prep. HPLC to yield the title compound (18 mg, 18%). $^1$H NMR (400 MHz, CD$_3$OD) δ 7.59 (1H, s), 7.12–7.28 (7H, m), 6.12 (1H, d, J=7.6 Hz), 4.01–4.08 (5H, m), 3.76 (1H, dd, J=4.8, 11.1 Hz), 3.71 (1H, dd, J=5.2, 11.1 Hz), 3.32–3.10 (4H, m), 3.09 (1H, dd, J=5.6, 13.7 Hz), 2.92 (1H, dd, J=8.0, 13.7 Hz), 2.65 (3H, s). LCMS (M+H)$^+$ m/z 460 (t=1.30 min.).

EXAMPLE 511

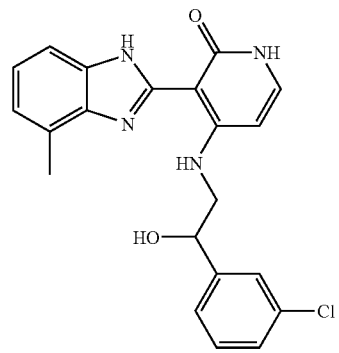

(±)-4-[2-(3-Chloro-phenyl)-2-hydroxy-ethylamino]-3-(4-methyl-1H-benzimidazol-2-yl)-1H-pyridin-2-one: $^1$H NMR (300 MHz, CD$_3$OD) δ 7.17–7.64 (8H, m), 6.23 (1H, d, J=10.2 Hz), 4.94 (1H, m), 3.61 (1H, dd, J=4.8, 13.8 Hz), 3.54 (1H, dd, J=7.4, 13.8 Hz), 2.61 (3H, s). LCMS (M+H)$^+$ m/z 395 (t=1.65 min.).

EXAMPLE 512

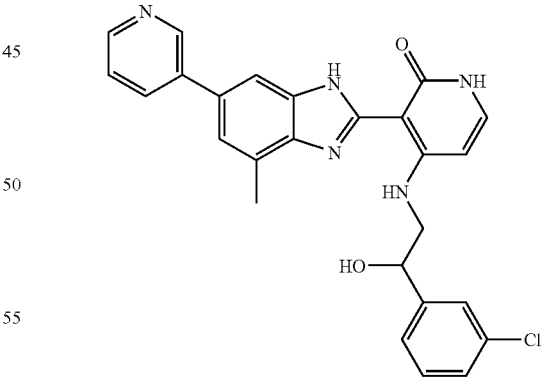

(±)-4-[2-(3-Chloro-phenyl)-2-hydroxy-ethylamino]-3-(4-methyl-6-pyridin-3-yl-1H-benzimidazol-2-yl)-1H-pyridin-2-one: $^1$H NMR (300 MHz, CD$_3$OD) δ 9.14 (1H, s), 8.88 (1H, d, J=8.2 Hz), 8.72 (1H, d, J=5.4 Hz), 8.08 (1H, dd, J=5.8, 8.2 Hz), 7.82 (1H, s), 7.56 (1H, s), 7.24–7.45 (5H, m), 6.26 (1H, d, J=7.6 Hz), 5.02 (1H, dd, J=5.0, 6.5 Hz), 3.77 (1H, dd, J=5.0, 13.5 Hz), 3.68 (1H, dd, J=6.5, 13.5 Hz), 2.68 (3H, s). LCMS (M+H)$^+$ m/z 472 (t=1.66 min.).

| Example # | Name | Structure | T (min) | Mass (M + H)+ m/z |
|---|---|---|---|---|
| 513 | (±)-3-(6-Bromo-4-methyl-1H-benzimidazol-2-yl)-4-[2-(3-chloro-phenyl)-2-hydroxy-ethylamino]1H-pyridin-2-one | 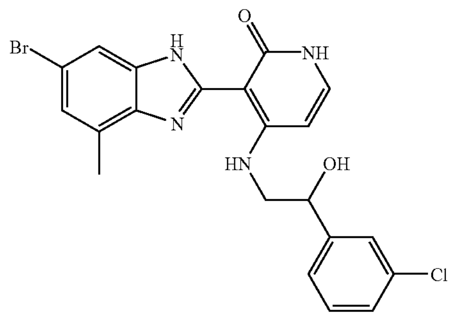 | 2.08 (f) | 473 |
| 514 | (±)-4-[2-(3-Chloro-phenyl)-2-hydroxy-ethylamino]-3-[6-(4-methoxy-phenyl)-4-methyl-1H-benzimidazol-2-yl]-1H-pyridin-2-one | 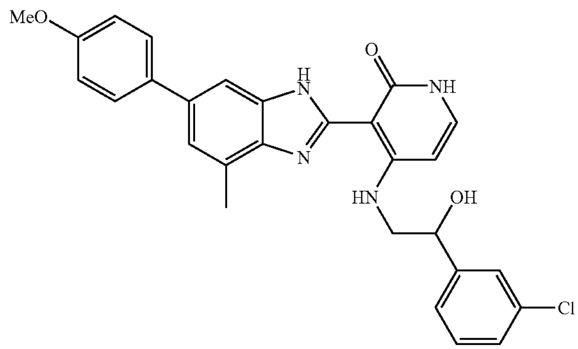 | 1.96 (f) | 501 |
| 515 | (±)-4-[2-(3-Chloro-phenyl)-2-hydroxy-ethylamino]-3-(4-methyl-1H-benzimidazol-2-yl)-1H-pyridin-2-one | 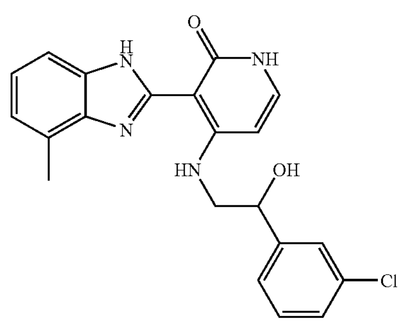 | 1.65 (f) | 395 |
| 516 | (S)-4-(1-Benzyl-2-hydroxy-ethylamino)-3-(4-methyl-6-piperidin-1-yl-1H-benzimidazol-2-yl)-1H-pyridin-2-one | 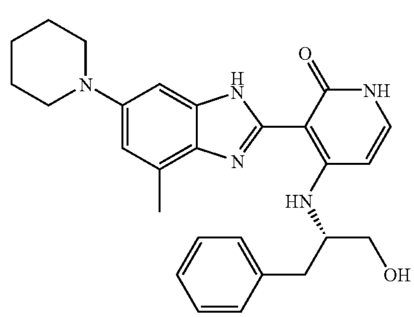 | 1.39 (b) | 458 |

The Following Examples 517–519 were Prepared According to Schemes VII and III

EXAMPLE 517

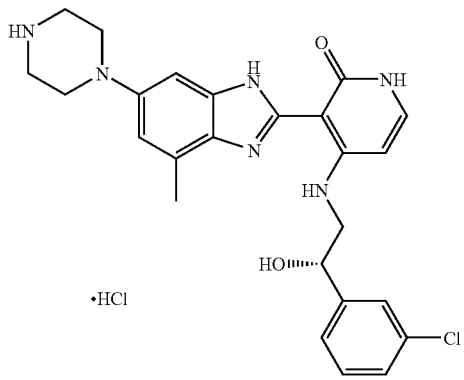

•HCl (S)-4-[2-(3-Chloro-phenyl)-2-hydroxy-ethylamino]-3-(4-methyl-6-piperazin-1-yl-1H-benzoimidazol-2-yl)-1H-pyridin-2-one: $^1$H NMR (500 MHz, CD$_3$OD) δ 7.54 (brs, 1H), 7.40–7.20 (m, 4H), 7.03 (brs, 1H), 6.84 (brs, 1H), 6.25 (d, 1H, J=7.60 Hz), 5.01–4.91 (m, 1H), 3.73 (dd, 1H), 3.65 (dd, 1H), 3.45–3.25 (m, 8H), 2.56 (s, 3H); LCMS (M+H)$^+$ m/z 479, 481.

EXAMPLE 518

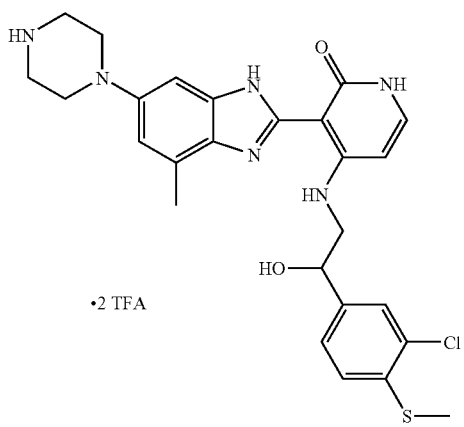

•2 TFA (±)-4-[2-(3-Chloro-4-methylsulfanyl-phenyl)-2-hydroxy-ethylamino]-3-(4-methyl-6-piperazin-1-yl-1H-benzoimidazol-2-yl)-1H-pyridin-2-one: $^1$H NMR (500 MHz, CD$_3$OD) δ 7.47 (brs, 1H), 7.38–7.29 (m, 2H), 7.19 (d, 1H, J=8.3 Hz), 7.03 (brs, 1H), 6.98 (brs, 1H), 6.26 (d, 1H, J=7.7 Hz), 4.90–4.81 (m, 1H), 3.65–3.35 (m, 10H), 2.56 (s, 3H), 2.42 (s, 3H); LCMS (M+H)$^+$ m/z 525, 527.

EXAMPLE 519

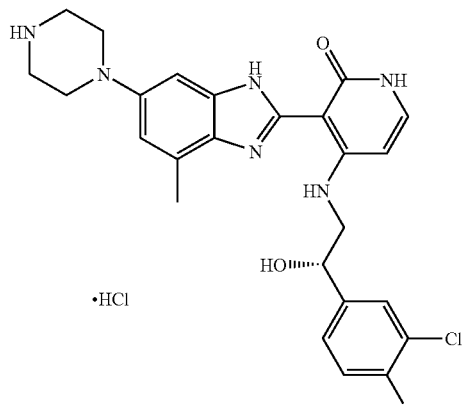

•HCl (S)-4-[2-(3-Chloro-4-fluoro-phenyl)-2-hydroxy-ethylamino]-3-(4-methyl-6-piperazin-1-yl-1H-benzoimidazol-2-yl)-1H-pyridin-2-one: $^1$H NMR (500 MHz, CD$_3$OD) δ 7.61 (dd, 1H, J=2.1, 7.2 Hz), 7.40 (ddd, 1H), 7.28 (d, 1H, J=7.5 Hz), 7.17 (dd, 1H, J=8.9, 8.8 Hz), 7.02 (brs, 1H), 6.87 (brs, 1H), 6.25 (d, 1H, J=7.6 Hz), 4.99–4.90 (m, 1H), 3.73–3.60 (m, 2H), 3.45–3.30 (m, 8H), 2.54 (s, 3H); LCMS (M+H)$^+$ m/z 497, 499.

The Following Examples (520–522) were Prepared According to Scheme VII and III and Illustrate the Alkylation of a Piperazine Derivative

EXAMPLE 520

General Procedure for Examples 520–522

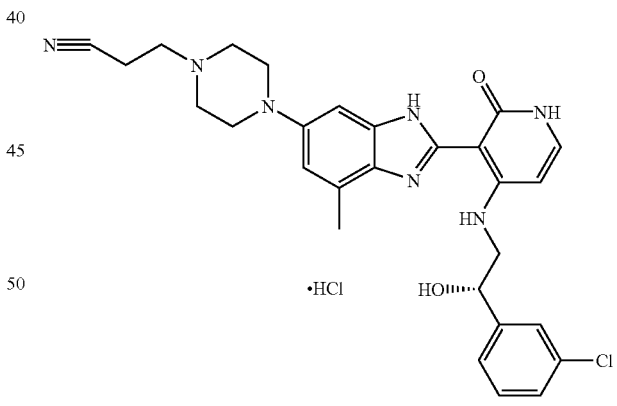

•HCl (S)-3-[4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazin-1-yl]-propionitrile: To a stirred solution of 4-[2-(3-Chloro-phenyl)-2-hydroxy-ethylamino]-3-(4-methyl-6-piperazin-1-yl-1H-benzoimidazol-2-yl)-1H-pyridin-2-one (17 mg, 0.021 mmol) in anhydrous methanol (1 mL) was added Hunigs base (36 μL). The resulting solution was cooled to 0° C. and acrylonitrile (5 μL) was added in portions until the reaction was complete as judged by LCMS. The reaction was warmed to room temperature and the solvent evaporated in vacuo. The resulting residue was purified on reverse phase preparative HPLC using a methanol/water/0.1% trifluoroacetic acid gradient. The fractions were evaporated to give the title compound as a trifluoroacetic acid salt (12.1 mg): $^1$H NMR (500 MHz, CD$_3$OD) δ 7.49 (brs, 1H), 7.39–7.23 (m, 4H), 7.15 (brs, 1H), 7.06 (brs, 1H), 6.25 (d, 1H, J=7.7 Hz), 4.97–4.88 (m, 1H), 3.70–3.40 (m, 12H), 3.06 (t, 2H, J=7.0 Hz), 2.59 (s, 3H); LCMS (M+H)$^+$ m/z 532, 534. The trifluoroaceticacid salt of the pure title compound was dissolved in methanol and applied to a Varian Mega Bond-Elute SCX cartridge. Elution with methanol followed by 2.0 M NH3/MeOH gave the free base. This material was suspended in MeOH and 1.00 N aqueous HCl (2 equiv.) was added. The resulting solution was filtered through a 45 μm filter and evaporated to give the bis HCl salt of the title compound: $^1$H NMR (300 MHz, CD$_3$OD) δ 7.50–7.25 (m, 5H), 7.16 (brs, 1H), 7.13 (brs, 1H), 6.27 (d, 1H, J=7.7 Hz), 4.95–4.87 (m, 1H), 3.70–3.40 (m, 12H), 3.13 (t, 2H, J=7.0 Hz), 2.62 (s, 3H); LCMS (M+H)$^+$ m/z 532,534.

EXAMPLE 521

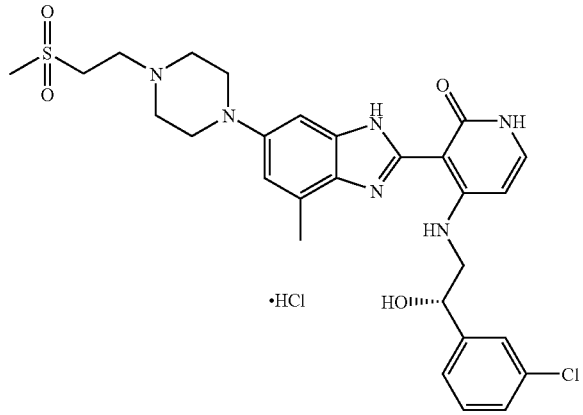

(S)-4-[2-(3-Chloro-phenyl)-2-hydroxy-ethylamino]-3-{6-[4-(2-methanesulfonyl-ethyl)-piperazin-1-yl]-4-methyl-1H-benzoimidazol-2-yl}-1H-pyridin-2-one: $^1$H NMR (500 MHz, CD$_3$OD) δ 7.53 (brs, 1H), 7.41–7.20 (m, 4H), 7.13 (brs, 1H), 6.92 (brs, 1H), 6.24 (d, 1H, J=7.6 Hz), 5.00–4.92 (m, 1H), 3.80–3.25 (m, 14H), 3.13 (s, 3H), 2.57 (s, 3H); LCMS (M+H)$^+$ m/z 585, 587.

EXAMPLE 522

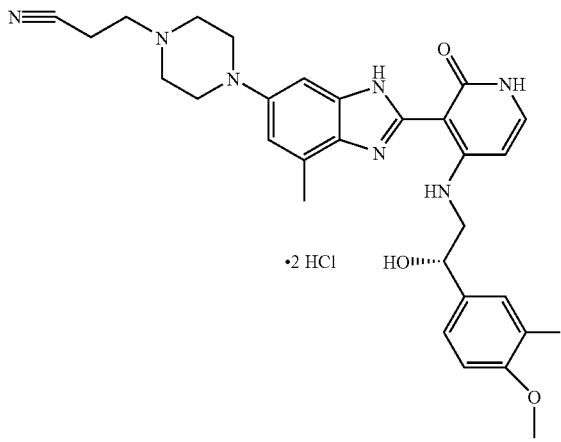

(S)-3-[4-(2-{4-[2-(3-Bromo-4-methoxy-phenyl)-2-hydroxy-ethylamino]-2-oxo-1,2-dihydro-pyridin-3-yl)-7-methyl-3H-benzoimidazol-5-yl)-piperazin-1-yl]-propionitrile: $^1$H NMR (500 MHz, CD$_3$OD) δ 7.59 (brs, 1H), 7.41 (d, 1H, J=7.5 Hz), 7.34 (dd, 1H, J=2.0, 8.5 Hz), 7.17 (brs, 1H), 7.12 (brs, 1H), 7.00 (d, 1H, J=8.5 Hz), 6.25 (d, 1H, J=7.5 Hz), 4.85–4.76 (m, 1H), 3.85 (s, 3H), 3.80–3.30 (m, 12H), 3.16 (t, 2H, J=7.0 Hz), 2.55 (s, 3H); LCMS (M+H)$^+$ m/z 606, 608.

The Following Examples (523–528) were Prepared According to Scheme VII and III and Illustrate the Carbamoylation of a Piperazine Derivative

EXAMPLE 523

General Procedure for Examples 523–528

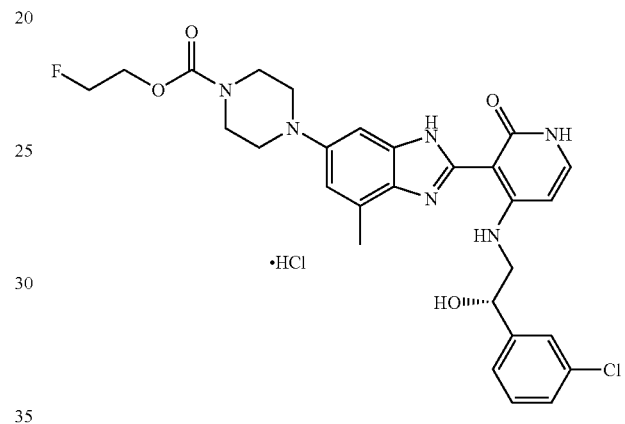

(S)-4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazine-1-carboxylic acid 2-fluoro-ethyl ester: To a stirred solution of 4-[2-(3-Chloro-phenyl)-2-hydroxy-ethylamino]-3-(4-methyl-6-piperazin-1-yl-1H-benzoimidazol-2-yl)-1H-pyridin-2-one (~2 TFA salt, 80 mg, ~0.1 mmol) in methanol (2 mL) at 0° C. was added N,N-diisopropylethylamine (170 μL) and 2-fluoroethyl chloroformate (37 mg). The cooling bath was removed and the solution was stirred at room temperature for 30 minutes, after which LC/MS analysis showed the reaction to be complete. The reaction mixture was then purified on reverse phase preparative HPLC using a methanol/water/0.1% trifluoroacetic acid gradient. The fractions were evaporated to give the title compound as a trifluoroacetic acid salt, which was dissolved in methanol and applied to a Varian Mega Bond-Elute SCX cartridge. Elution with methanol followed by 2.0 M NH3/MeOH gave the free base (46.2 mg). This material was suspended in MeOH and 1.00 N aqueous HCl (1 equiv.) was added. The resulting solution was filtered through a 45 μm filter and evaporated to give the mono HCl salt of the title compound (46 mg): $^1$H NMR (500 MHz, CD$_3$OD) δ 7.50 (brs, 1H), 7.45–7.20 (m, 6H), 6.26 (d, 1H, J=7.7 Hz), 4.98–4.91 (m, 1H), 4.64 (dm, 2H, J=47.9 Hz), 4.39 (dm, 2H, J=29 Hz), 3.95–3.50 (m, 10H), 2.63 (s, 3H); LCMS (M+H)$^+$ m/z 569, 571.

EXAMPLE 524

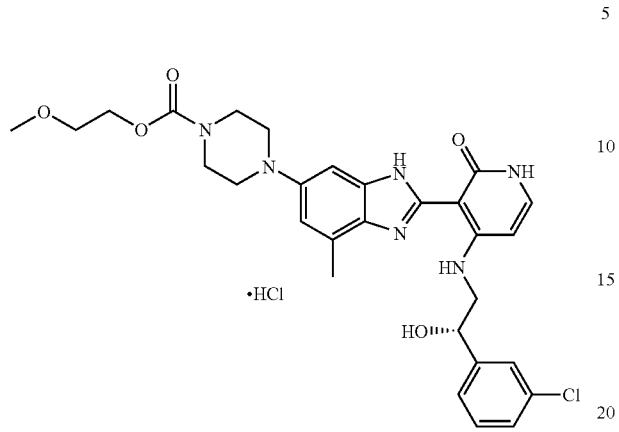

•HCl (S)-4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazine-1-carboxylic acid 2-methoxy-ethyl ester: $^1$H NMR (500 MHz, CD$_3$OD) δ 7.53–7.22 (m, 7H), 6.26 (d, 1H, J=7.6 Hz), 4.96 (dd, 1H, J=7.0, 4.6 Hz), 4.31–4.27 (m, 2H), 4.05–3.55 (m, 12H), 3.39 (s, 3H), 2.64 (s, 3H); LCMS (M+H)$^+$ m/z 581, 583.

EXAMPLE 525

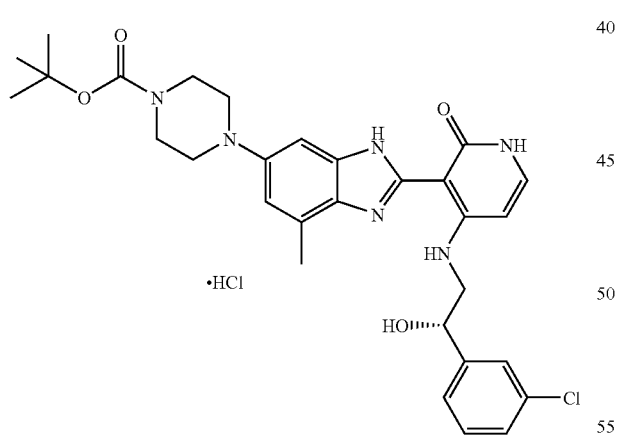

•HCl (S)-4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazine-1-carboxylic acid tert-butyl ester: $^1$H NMR (500 MHz, CD$_3$OD) δ 7.51 (brs, 1H), 7.40–7.22 (m, 6H), 6.26 (d, 1H, J=7.7 Hz), 4.96–4.90 (m, 1H), 3.90–3.30 (m, 10H), 2.64 (s, 3H), 1.51 (s, 9H); LCMS (M+H)$^+$ m/z 579, 581.

EXAMPLE 526

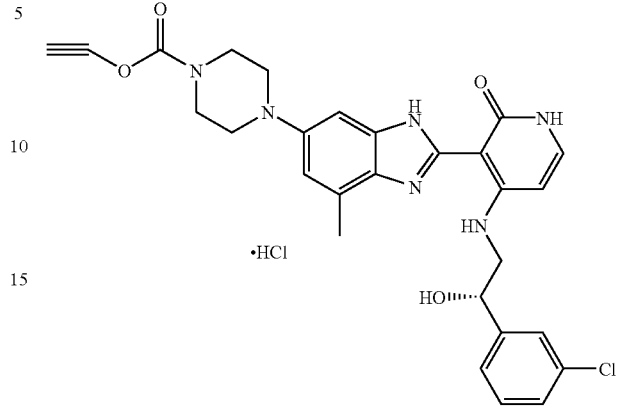

•HCl (S)-4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazine-1-carboxylic acid prop-2-ynyl ester: $^1$H NMR (500 MHz, CD$_3$OD) δ 7.50 (brs, 1H), 7.43–7.20 (m, 5H), 7.19 (brs, 1H), 6.25 (d, 1H, J=7.6 Hz), 4.98–4.90 (m, 1H), 4.78 (d, 2H, J=2.5 Hz), 3.95–3.30 (m, 10H), 2.97 (t, 1H, J=2.5 Hz), 2.62 (s, 3H); LCMS (M+H)$^+$ m/z 561, 563.

EXAMPLE 527

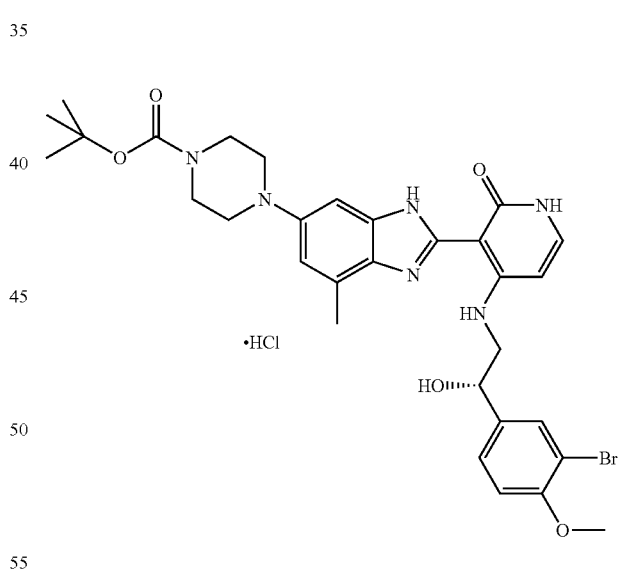

•HCl (S)-4-(2-{4-[2-(3-Bromo-4-methoxy-phenyl)-2-hydroxy-ethylamino]-2-oxo-1,2-dihydro-pyridin-3-yl}-7-methyl-3H-benzoimidazol-5-yl)-piperazine-1-carboxylic acid tert-butyl ester: $^1$H NMR (300 MHz, CD$_3$OD) δ 7.65 (brs, 1H), 7.48–7.28 (m, 3H), 7.25 (brs, 1H), 6.97 (d, 1H, J=8.5 Hz), 6.25 (d, 1H, J=7.7 Hz), 4.94–4.86 (m, 1H), 3.90–3.45 (m, 10H), 3.82 (s, 3H), 2.61 (s, 3H), 1.52 (s, 9H); LCMS (M+H)$^+$ m/z 653, 655.

EXAMPLE 528

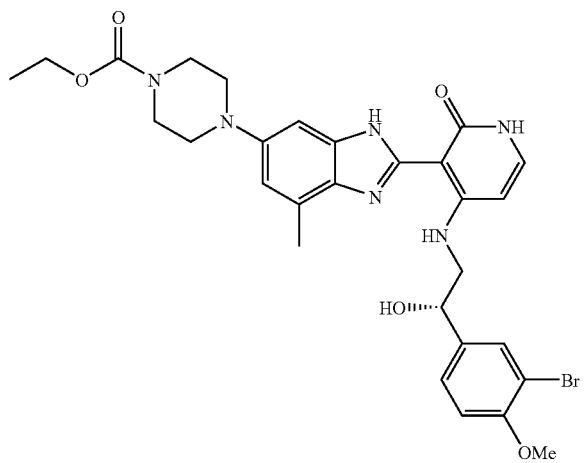

(S)-4-(2-{4-[2-(3-Bromo-4-methoxy-phenyl)-2-hydroxy-ethylamino]-2-oxo-1,2-dihydro-pyridin-3-yl}-7-methyl-3H-benzimidazol-5-yl)-piperazine-1-carboxylic acid ethyl ester: $^1$H NMR (400 MHz, CD$_3$OD) δ 7.80 (1H, s), 7.63 (1H, narrow d, J=1.8 Hz), 7.52 (1H, s), 7.42 (1H, d, J=7.5 Hz), 7.37 (1H, dd, J=1.8, 8.4 Hz), 7.00 (1H, d, J=8.4 Hz), 6.31 (1H, d, J=7.5 Hz), 4.89 (1H, m), 4.22 (2H, q, J=7.1 Hz), 3.98 (4H, br s), 3.84 (3H, s), 3.70–3.72 (4H, m), 3.59–3.60 (2H, m), 2.67 (3H, s), 1.31 (3H, t, J=7.1 Hz). LCMS (M+H)$^+$ m/z 625 (t=1.45 min.).

The Following Examples (529–540) were Prepared According to Scheme VII and III and Illustrate an Alternative Method of Alkylation of a Piperazine Derivative

EXAMPLE 529

General Procedure for Examples 529–540

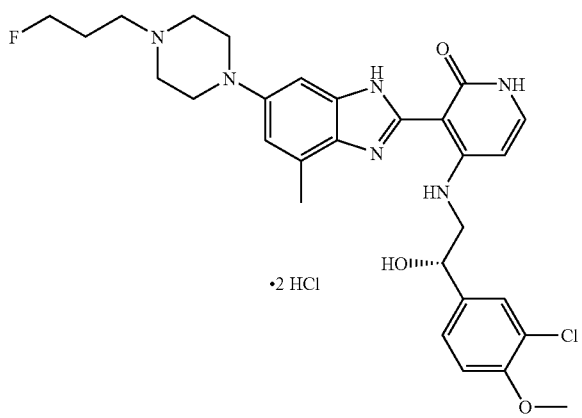

(S)-4-[2-(3-Chloro-4-methoxy-phenyl)-2-hydroxy-ethylamino]-3-{6-[4-(3-fluoro-propyl)-piperazin-1-yl]-4-methyl-1H-benzoimidazol-2-yl}-1H-pyridin-2-one: To a stirred solution of 4-[2-(3-Chloro-4-methoxy-phenyl)-2-hydroxy-ethylamino]-3-(4-methyl-6-piperazin-1-yl-1H-benzoimidazol-2-yl)-1H-pyridin-2-one (100 mg, 0.162 mmol) in 1,4-dioxane (4.0 mL), ethanol (0.8 mL), methanol (0.8 mL) was added N,N-diisopropylethylamine (0.30 mL) and 1-bromo-3-fluoropropane (85 μl). The reaction was heated at 80° C. for 12 h. The reaction mixture was then purified on reverse phase preparative HPLC using a methanol/water/0.1% trifluoroacetic acid gradient. The fractions were evaporated to give the title compound as a trifluoroacetic acid salt, which was dissolved in methanol and applied to a Varian Mega Bond-Elute SCX cartridge. Elution with methanol followed by 2.0 M NH3/MeOH gave the free base (39.3 mg). This material was suspended in MeOH and 1.00 N aqueous HCl (2 equiv.) was added. The resulting solution was filtered through a 45 μm filter and evaporated to give the bis HCl salt of the title compound (43.5 mg): $^1$H NMR (400 MHz, CD$_3$OD) δ 7.43–7.37 (m, 2H), 7.28 (dd, 1H, J=2.0, 8.6 Hz), 7.16 (brs, 1H), 7.08 (d, 1H, J=1.7 Hz), 7.01 (d, 1H, J=8.5 Hz), 6.24 (d, 1H, J=7.7 Hz), 4.84–4.78 (m, 1H), 4.60 (dt, 2H, J=5.7, 47.1 Hz), 3.95–3.88 (m, 2H), 3.83 (s, 3H), 3.78–3.71 (m, 2H), 3.53–3.14 (m, 8H), 2.59 (s, 3H), 2.31–2.16 (m, 2H); LCMS (M+H)$^+$ m/z 569, 571.

EXAMPLE 530

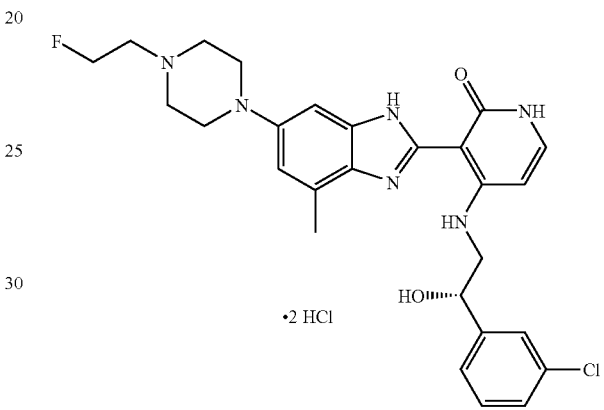

(S)-4-[2-(3-Chloro-phenyl)-2-hydroxy-ethylamino]-3-{6-[4-(2-fluoro-ethyl)-piperazin-1-yl]-4-methyl-1H-benzoimidazol-2-yl}-1H-pyridin-2-one: $^1$H NMR (400 MHz, CD$_3$OD) δ 7.45–7.20 (m, 5H), 7.16 (brs, 1H), 7.09 (brs, 1H), 6.25 (d, 1H, J=7.6 Hz), 5.00–4.92 (m, 1H), 4.92–4.78 (m, 2H), 3.98–3.15 (m, 12H), 2.60 (s, 3H); LCMS (M+H)$^+$ m/z 525, 527.

EXAMPLE 531

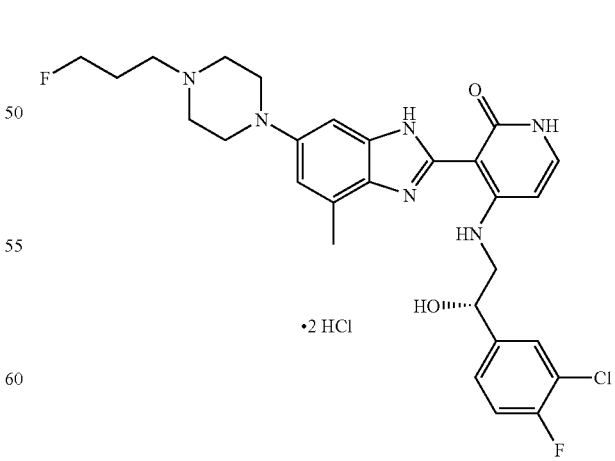

(S)-4-[2-(3-Chloro-4-fluoro-phenyl)-2-hydroxy-ethylamino]-3-{6-[4-(3-fluoro-propyl)-piperazin-1-yl]-4-methyl-1H-benzoimidazol-2-yl}-1H-pyridin-2-one: $^1$H NMR (400 MHz, CD$_3$OD) δ 7.52 (dd, 1H, J=2.1, 7.2 Hz), 7.40 (d, 1H, J=7.6 Hz), 7.35–7.12 (m, 3H), 7.08 (d, 1H, J=1.7 Hz), 6.25 (d, 1H, J=7.7 Hz), 4.90–4.82 (m, 1H), 4.60 (dt, 2H, J=5.4, 47.1 Hz), 3.96–3.10 (m, 12H), 2.60 (s, 3H), 2.28–2.13 (m, 2H); LCMS (M+H)$^+$ m/z 557, 559.

EXAMPLE 532

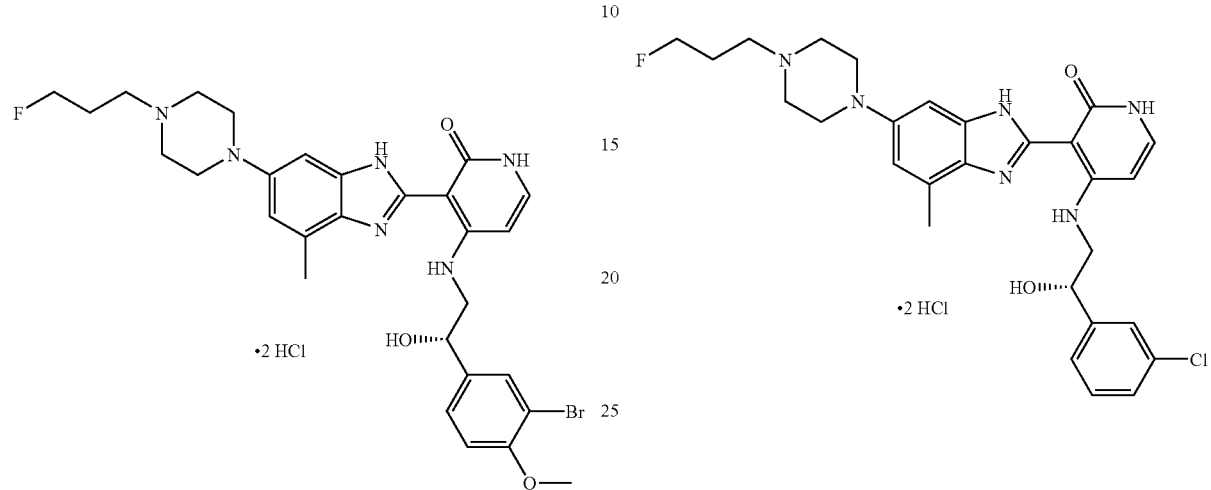

(S)-4-[2-(3-Bromo-4-methoxy-phenyl)-2-hydroxy-ethylamino]-3-{6-[4-(3-fluoro-propyl)-piperazin-1-yl]-4-methyl-1H-benzoimidazol-2-yl}-1H-pyridin-2-one: $^1$H NMR (400 MHz, CD$_3$OD) δ 7.58 (d, 1H, J=2.0 Hz), 7.43 (d, 1H, J=7.6 Hz), 7.34 (dd, 1H, J=2.0, 8.5 Hz), 7.19 (brs, 1H), 7.11 (brs, 1H), 7.00 (d, 1H, J=8.5 Hz), 6.26 (d, 1H, J=7.7 Hz), 5.90–4.82 (m, 1H), 4.61 (dt, 2H, J=5.4, 47.1 Hz), 3.95–3.12 (m, 12H), 3.85 (s, 3H), 2.62 (s, 3H), 2.30–2.14 (m, 2H); LCMS (M+H)$^+$ m/z 613, 615.

EXAMPLE 533

(S)-4-[2-(3-Chloro-phenyl)-2-hydroxy-ethylamino]-3-{4-methyl-6-[4-(3,3,3-trifluoro-propyl)-piperazin-1-yl]-1H-benzoimidazol-2-yl}-1H-pyridin-2-one: $^1$H NMR (300

MHz, CD$_3$OD) δ 7.50–7.10 (m, 7H), 6.26 (d, 1H, J=7.5 Hz), 4.96–4.88 (m, 1H), 4.00–3.15 (m, 12H), 3.00–2.82 (m, 2H), 2.61 (s, 3H); LCMS (M+H)$^+$ m/z 575, 577.

EXAMPLE 534

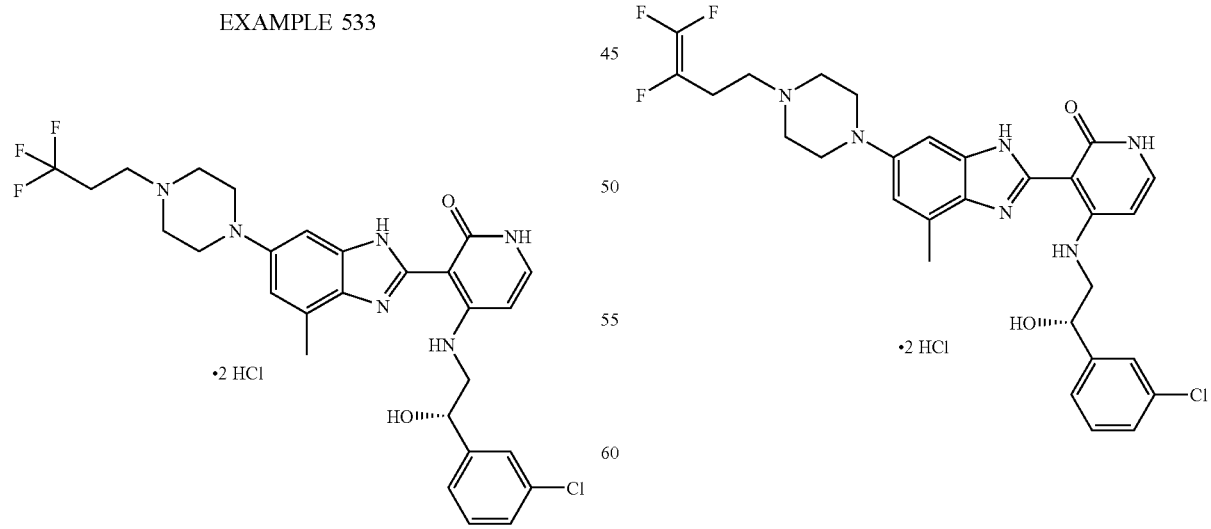

(S)-4-[2-(3-Chloro-phenyl)-2-hydroxy-ethylamino]-3-{6-[4-(3-fluoro-propyl)-piperazin-1-yl]-4-methyl-1H-benzoimidazol-2-yl}-1H-pyridin-2-one: $^1$H NMR (300 MHz, CD$_3$OD) δ 7.46–7.25 (m, 5H), 7.19 (brs, 1H), 7.11 (brs, 1H), 6.27 (d, 1H, J=7.7 Hz), 4.95–4.86 (m, 1H), 4.62 (dt, 2H, J=5.4, 47.1 Hz), 3.98–3.15 (m, 12H), 2.62 (s, 3H), 2.35–2.12 (m, 2H); LCMS (M+H)$^+$ m/z 539, 541.

EXAMPLE 535

(S)-4-[2-(3-Chloro-phenyl)-2-hydroxy-ethylamino]-3-{4-methyl-6-[4-(3,4,4-trifluoro-but-3-enyl)-piperazin-1-yl]-1H-benzoimidazol-2-yl}-1H-pyridin-2-one: LCMS (M+H)$^+$ m/z 587, 589.

EXAMPLE 536

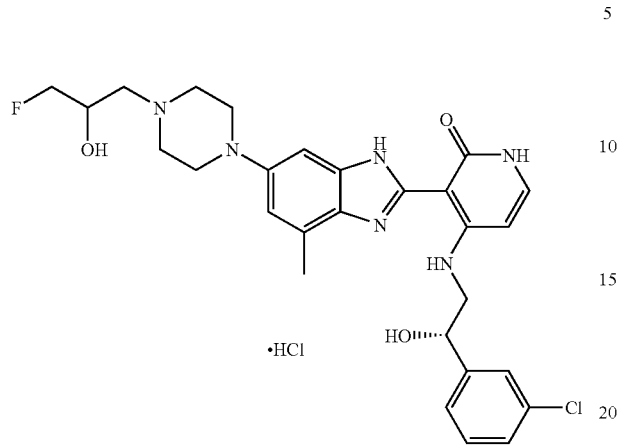

4-[2-(3-Chloro-phenyl)-2(S)-hydroxy-ethylamino]-3-{6-[4-(3-fluoro-2-hydroxy-propyl)-piperazin-1-yl]-4-methyl-1H-benzoimidazol-2-yl}-1H-pyridin-2-one: LCMS (M+H)+ m/z 555, 557.

EXAMPLE 537

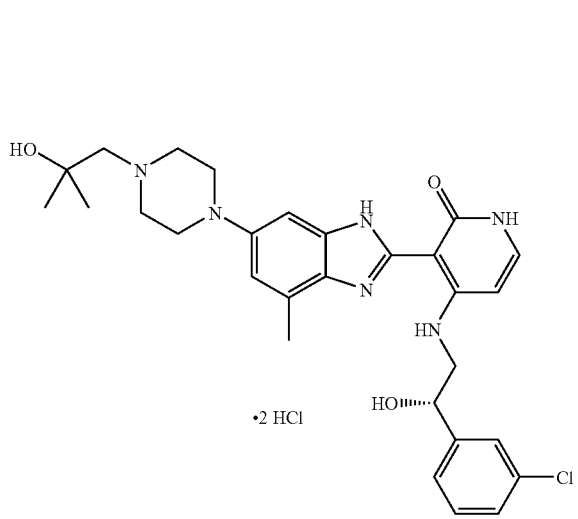

(S)-4-[2-(3-Chloro-phenyl)-2-hydroxy-ethylamino]-3-{6-[4-(2-hydroxy-2-methyl-propyl)-piperazin-1-yl]-4-methyl-1H-benzoimidazol-2-yl}-1H-pyridin-2-one: $^1$H NMR (400 MHz, CD$_3$OD) δ 7.44–7.22 (m, 5H), 7.15 (brs, 1H), 7.08 (brs, 1H), 6.25 (d, 1H, J=7.6 Hz), 4.88–4.80 (m, 1H), 3.86–3.81 (m, 4H), 3.55–3.32 (m, 6H), 3.28 (s, 2H), 2.60 (s, 3H), 1.38 (s, 6H); LCMS (M+H)+ m/z 551, 553.

EXAMPLE 538

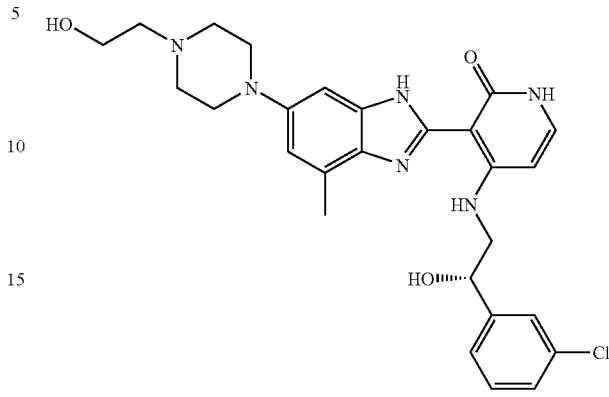

(S)-4-[2-(3-Chloro-phenyl)-2-hydroxy-ethylamino]-3-{6-[4-(2-hydroxy-ethyl)-piperazin-1-yl]-4-methyl-1H-benzimidazol-2-yl}-1H-pyridin-2-one: $^1$HNMR (400 MHz, CD$_3$OD) δ 7.50 (1H, s), 7.25–7.35 (4H, m), 7.04 (1H, s), 6.97 (1H, s), 6.22 (1H, d, J=6.8 Hz), 4.93–4.95 (1H, m), 3.21–3.96 (14H, m), 2.57 (3H, s). LCMS (M+H)+ m/z 523 (t=1.11 min.).

EXAMPLE 539

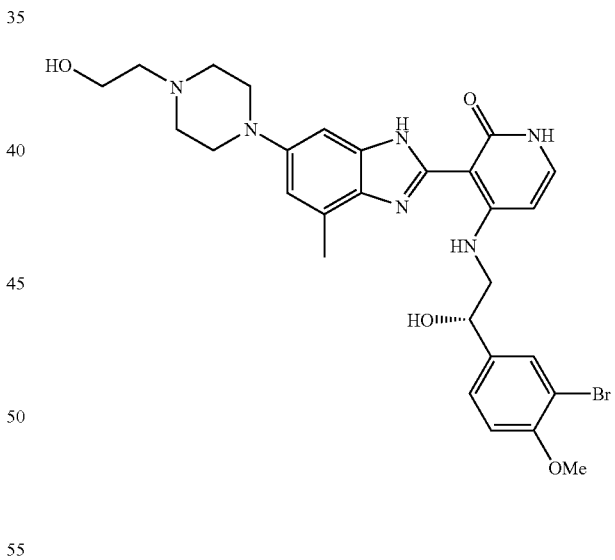

(S)-4-[2-(3-Bromo-4-methoxy-phenyl)-2-hydroxy-ethylamino]-3-{6-[4-(2-hydroxy-ethyl)-piperazin-1]-4-methyl-1H-benzimidazol-2-yl}-1H-pyridin-2-one: $^1$H NMR (400 MHz, CD$_3$OD) δ 7.60 (1H, narrow d, J=2.0 Hz), 7.40 (1H, d, J=7.6 Hz), 7.35 (1H, dd, J=2.0, 8.4 Hz), 7.13 (1H, s), 7.09 (1H, s), 6.99 (1H, d, J=8.4 Hz), 6.25 (1H, d, J=7.6 Hz), 4.82–4.87 (1H, m), 3.76 –3.97 (6H, m), 3.84 (3H, s), 3.24–3.52 (8H, m), 2.60 (3H, s). LCMS (M+H)+ m/z 597 (t=1.09 min.).

EXAMPLE 540

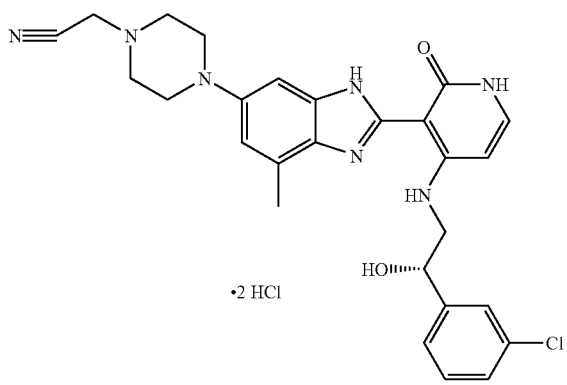

•2 HCl (S)-[4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazin-1yl]-acetonitrile: $^1$H NMR (400 MHz, CD$_3$OD) δ 7.50–7.25 (m, 7H), 6.28 (d, 1H, J=8.0 Hz), 4.95–4.88 (m, 1H), 4.32 (s, 2H), 3.75–3.62 (m, 4H), 3.60–3.35 (m, 6H), 2.63 (s, 3H); LCMS (M+H)$^+$ m/z 518, 520.

The Following Examples (541–553) were Prepared According to Scheme VII and III and Illustrate the Acylation of a Piperazine Derivative

EXAMPLE 541

General Procedure for Examples 541–553

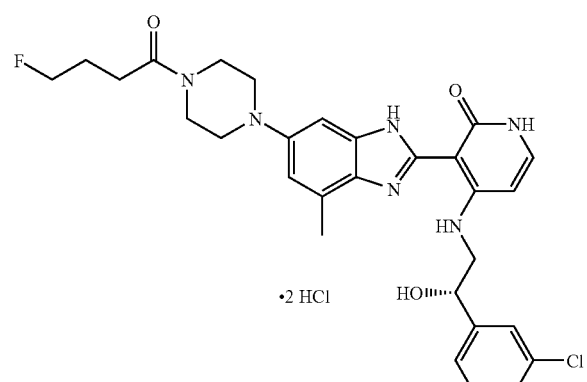

•2 HCl (S)-4-[2-(3-Chloro-phenyl)-2-hydroxy-ethylamino]-3-{6-[4-(4-fluoro-butyryl)-piperazin-1-yl]-4-methyl-1H-benzoimidazol-2-yl}-1H-pyridin-2-one: To a stirred solution of 4-[2-(3-Chloro-phenyl)-2-hydroxy-ethylamino]-3-(4-methyl-6-piperazin-1-yl-1H-benzoimidazol-2-yl)-1H-pyridin-2-one (70 mg, 0.136 mmol) in anhydrous N,N-dimethylformamide (750 μl) was added 1-(3-dimethylaminopropyl)-3-ethylcarbodiimide hydrochloride (112 mg, 0.584 mmol), 1-hydroxybenzotriazole hydrate (59 mg, 0.438 mmol), N-methylmorpholine (0.048 mL, 0.438 mmol) and 4-fluorobutyric acid (31 mg, 0.291 mmol; see O'Hagan, D., *J. Fluorine Chem.*, 43, (1989), 371–377) and the mixture heated to 80° C. for 3 h. The reaction mixture was then purified on reverse phase preparative HPLC using a methanol/water/0.1% trifluoroacetic acid gradient. The fractions were evaporated to give the title compound as a trifluoroacetic acid salt, which was dissolved in methanol and applied to a Varian Mega Bond-Elute SCX cartridge. Elution with methanol followed by 2.0 M NH3/MeOH gave the free base (35.9 mg). This material was suspended in MeOH and 1.00 N aqueous HCl (2 equiv.) was added. The resulting solution was filtered through a 45 μm filter and evaporated to give the bis HCl salt of the title compound (37.6 mg): $^1$H NMR (400 MHz, CD$_3$OD) δ 7.61 (brs, 1H), 7.47 (brs, 1H), 7.44–7.20 (m, 5H), 6.27 (d, 1H, J=7.6 Hz), 4.92 (dd, 1H, J=4.4, 7.3 Hz), 4.50 (dt, 2H, J=5,9, 47.3 Hz), 4.05–3.40 (m, 10H), 2.64 (s, 3H), 2.63 (t, 2H, J=7.6 Hz), 2.09–1.95 (m, 2H); LCMS (M+H)$^+$ m/z 567, 569.

EXAMPLE 542

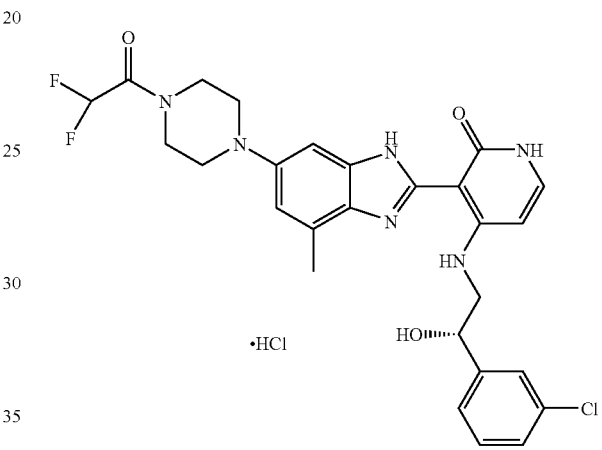

•HCl (S)-4-[2-(3-Chloro-phenyl)-2-hydroxy-ethylamino]-3-{6-[4-(2,2-difluoro-acetyl)-piperazin-1-yl]-4-methyl-1H-benzoimidazol-2-yl}-1H-pyridin-2-one: LCMS (M+H)$^+$ m/z 557, 559.

EXAMPLE 543

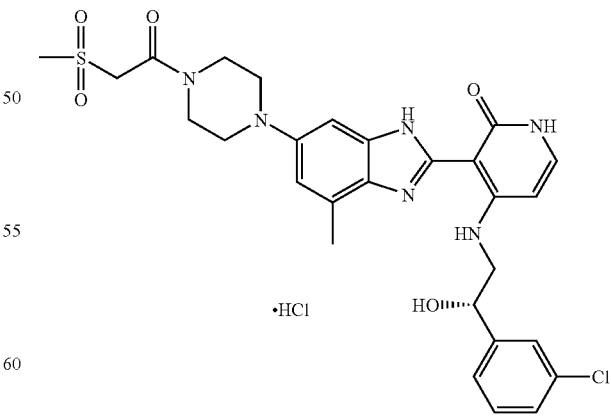

•HCl (S)-4-[2-(3-Chloro-phenyl)-2-hydroxy-ethylamino]-3-[6-[4-(2-methanesulfonyl-acetyl)-piperazin-1-yl]-4-methyl-1H-benzoimidazol-2-yl}-1H-pyridin-2-one: LCMS (M+H)$^+$ m/z 599, 601.

EXAMPLE 544

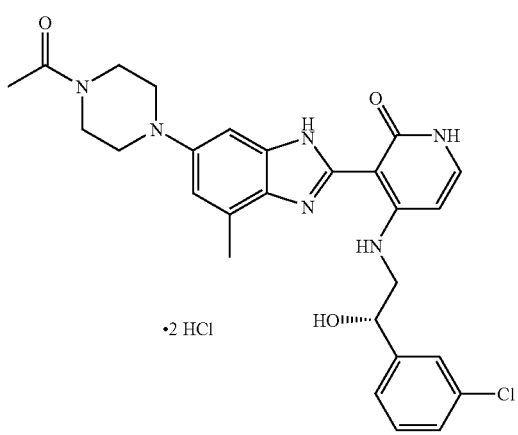

•2 HCl (S)-3-[6-(4-Acetyl-piperazin-1-yl)-4-methyl-1H-benzoimidazol-2-yl]-4-[2-(3-chloro-phenyl)-2-hydroxy-ethylamino]-1H-pyridin-2-one: $^1$H NMR (500 MHz, CD$_3$OD) δ 7.57 (brs, 1H), 7.49 (brs, 1H), 7.40–7.20 (m, 5H), 6.29 (d, 1H, J=7.6 Hz), 4.98–4.90 (m, 1H), 4.02–3.91 (m, 4H), 3.70–3.50 (m, 6H), 2.66 (s, 3H), 2.21 (s, 3H); LCMS (M+H)$^+$ m/z 521, 523.

EXAMPLE 545

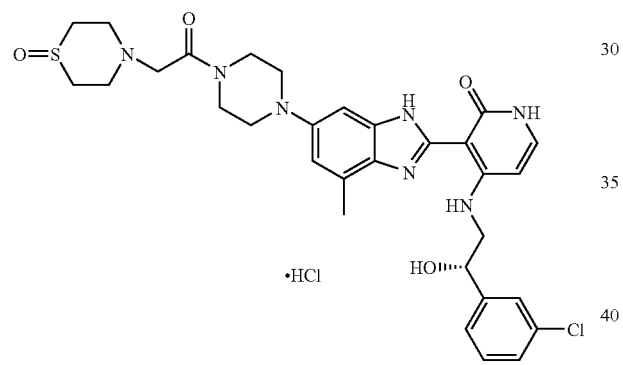

•HCl (S)-4-[2-(3-Chloro-phenyl)-2-hydroxy-ethylamino]-3-(4-methyl-6-{4-[2-(1-oxo-1λ4-thiomorpholin-4-yl)-acetyl]-piperazin-1-yl]-1H-benzoimidazol-2-yl)-1H-pyridin-2-one: LCMS (M+H)$^+$ m/z 638, 640.

EXAMPLE 546

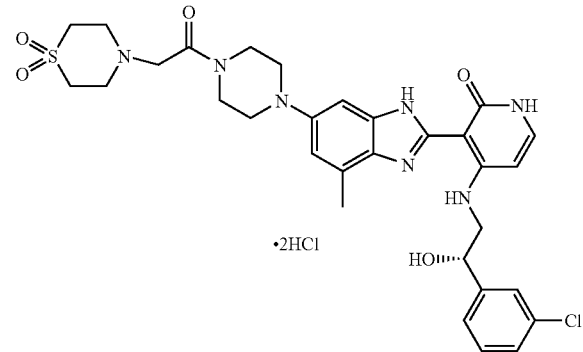

•2HCl (S)-4-[2-(3-Chloro-phenyl)-2-hydroxy-ethylamino]-3-(6-{4-[2-(1,1-dioxo-1λ6-thiomorpholin-4-yl)-acetyl]-piperazin-1-yl}-4-methyl-1H-benzoimidazol-2-yl)-1H-pyridin-2-one: LCMS (M+H)$^+$ m/z 654, 656.

EXAMPLE 547

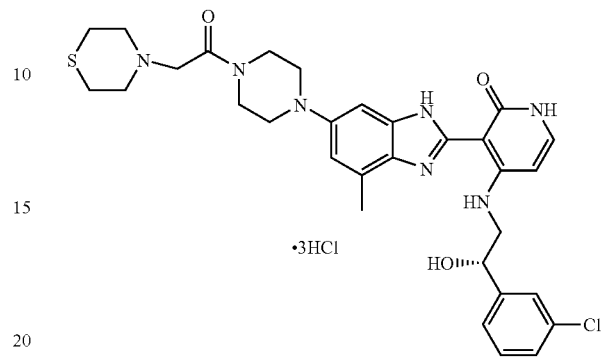

•3HCl (S)-4-[2-(3-Chloro-phenyl)-2-hydroxy-ethylamino]-3-{4-methyl-6-[4-(2-thiomorpholin-4-yl-acetyl)-piperazin-1-yl]-1H-benzoimidazol-2-yl}-1H-pyridin-2-one: LCMS (M+H)$^+$ m/z 622, 624.

EXAMPLE 548

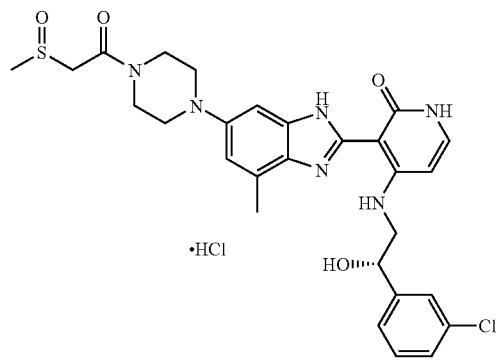

•HCl

4-[2-(3-Chloro-phenyl)-2(S)-hydroxy-ethylamino]-3-{6-[4-(2-methanesulfinyl-acetyl)-piperazin-1-yl]-4-methyl-1H-benzoimidazol-2-yl}-1H-pyridin-2-one: LCMS (M+H)$^+$ m/z 583, 585.

EXAMPLE 549

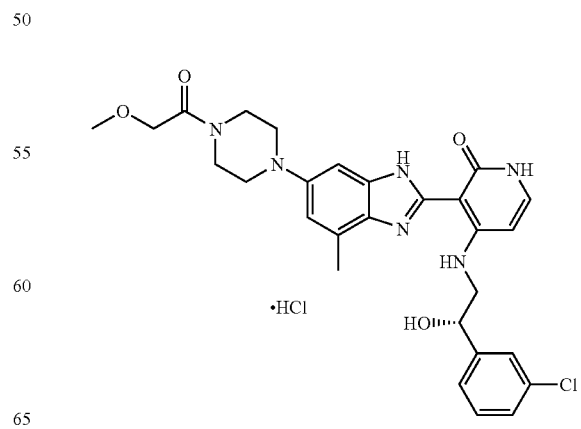

•HCl (S)-4-[2-(3-Chloro-phenyl)-2-hydroxy-ethylamino]-3-{6-[4-(2-methoxy-acetyl)-piperazin-1-yl]-4-methyl-1H-benzoimidazol-2-yl}-1H-pyridin-2-one: $^1$H NMR (500 MHz, CD$_3$OD) δ 7.49 (brs, 1H), 7.40–7.18 (m, 6H), 6.26 (d, 1H, J=7.7 Hz), 4.98–4.90 (m, 1H), 4.25 (s, 2H), 3.95–3.46 (m, 10H), 3.44 (s, 3H), 2.63 (s, 3H); LCMS (M+H)$^+$ m/z 551, 553.

EXAMPLE 550

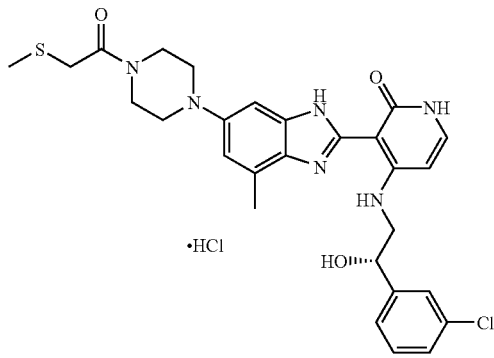

(S)-4-[2-(3-Chloro-phenyl)-2-hydroxy-ethylamino]-3-{4-methyl-6-[4-(2-methylsulfanyl-acetyl)-piperazin-1-yl]-1H-benzoimidazol-2-yl}-1H-pyridin-2-one: $^1$H NMR (500 MHz, CD$_3$OD) δ 7.49 (brs, 1H), 7.45–7.20 (m, 6H), 6.26 (d, 1H, J=7.60 Hz), 4.98–4.90 (m, 1H), 3.97–3.40 (m, 12H), 2.63 (s, 3H), 2.20 (s, 3H); LCMS (M+H)$^+$ m/z 567, 569.

EXAMPLE 551

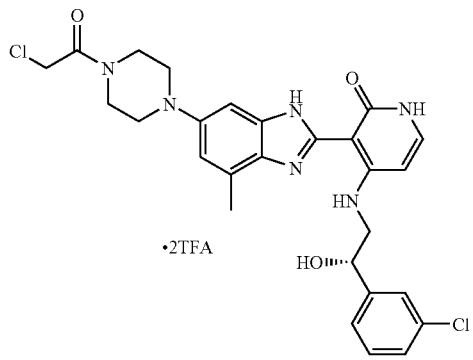

(S)-3-{6-[4-(2-Chloro-acetyl)-piperazin-1-yl]-4-methyl-1H-benzoimidazol-2-yl}-4-[2-(3-chloro-phenyl)-2-hydroxy-ethylamino]-1H-pyridin-2-one: $^1$H NMR (500 MHz, CD$_3$OD) δ 7.49 (brs, 1H), 7.38–7.20 (m, 5H), 7.15 (brs, 1H), 6.25 (d, 1H, J=7.6 Hz), 4.98–4.90 (m, 1H), 4.35 (s, 2H), 3.90–3.80 (m, 4H), 3.66–3.30 (m, 6H), 2.61 (s, 3H); LCMS (M+H)$^+$ m/z 555, 557.

EXAMPLE 552

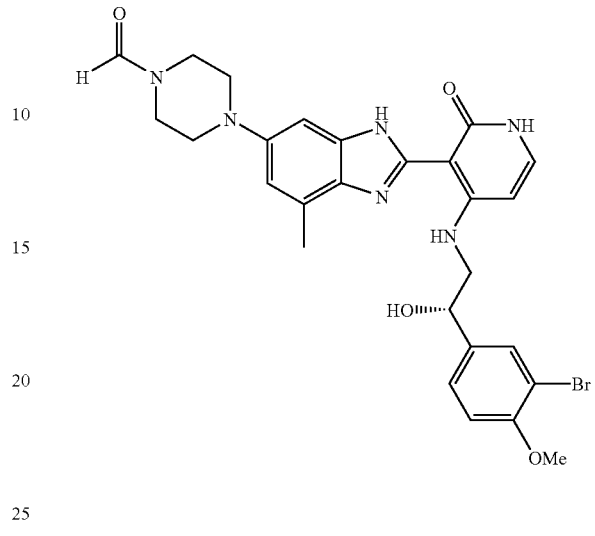

(S)-4-(2-{4-[2-(3-Bromo-4-methoxy-phenyl)-2-hydroxy-ethylamino]-2-oxo-1,2-dihydro-pyridin-3-yl}-7-methyl-3H-benzimidazol-5-yl)-piperazine-1-carbaldehyde: $^1$H NMR (400 MHz, CD$_3$OD) δ 8.18 (1H, s), 7.65 (1H, s), 7.61 (1H, narrow d, J=2.0 Hz), 7.46 (1H, s), 7.43 (1H, d, J=7.6 Hz), 7.36 (1H, dd, J=2.0, 8.5 Hz), 7.00 (1H, d, J=8.5 Hz), 6.32 (1H, d, J=7.6 Hz), 4.86–4.89 (1H, m), 3.91–3.96 (4H, m), 3.84 (3H, s), 3.57–3.67 (7H, m), 2.66 (3H, s). LCMS (M+H)$^+$ m/z 581 (t=1.24 min.).

EXAMPLE 553

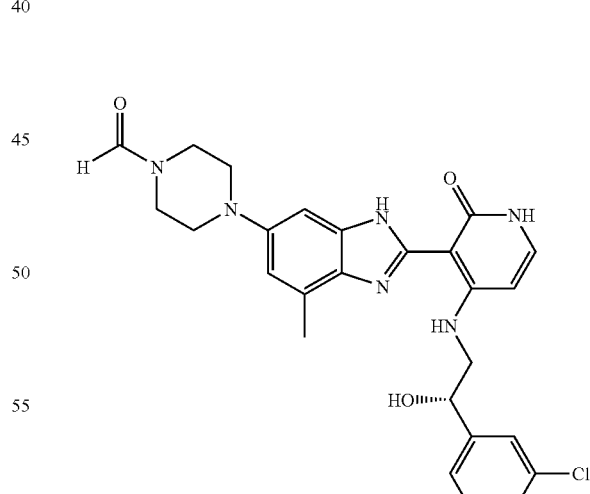

(S)-4-(2-{4-[2-(3-Chloro-phenyl)-2-hydroxy-ethylamino]-2-oxo-1,2-dihydro-pyridin-3-yl}-7-methyl-3H-benzimidazol-5-yl)-piperazine-1-carbaldehyde: $^1$H NMR (400 MHz, CD$_3$OD) δ 8.12 (1H, s), 7.50 (1H, s), 7.24–7.38

(6H, m), 6.23 (1H, d, J=7.6 Hz), 4.93–4.96 (1H, m), 3.54–3.79 (10H, m), 2.58 (3H, s). LCMS (M+H)⁺ m/z 507 (t=1.29 min.).

The Following Examples (Examples 554–575) were Prepared According to Scheme VII and III

EXAMPLE 554

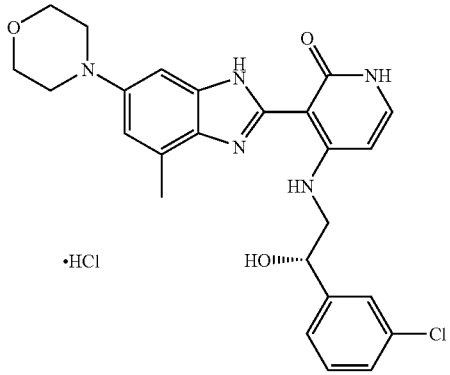

(S)-4-[2-(3-Chloro-phenyl)-2-hydroxy-ethylamino]-3-(4-methyl-6-morpholin-4-yl-1H-benzoimidazol-2-yl)-1H-pyridin-2-one: To a suspension of 4-Chloro-3-(4-methyl-6-morpholin-4-yl-1H-benzoimidazol-2-yl)-1H-pyridin-2-one and the corresponding iodo compound 4-Iodo-3-(4-methyl-6-morpholin-4-yl-1H-benzoimidazol-2-yl)-1H-pyridin-2-one (4.43 g, 11 mmol) in acetonitrile (100 ml) triethylamine (7.0 ml, 50 mmol) and 2-(S)-2-(3-Chloro-phenyl)-2-hydroxy-ethylamine hydrochloride (2.55 g, 12.2 mmol) were added. The mixture was stirred at 85° C. overnight. LCMS showed some starting material pyridone left. 2-(S)-2-(3-Chloro-phenyl)-2-hydroxy-ethylamine hydrochloride (0.22 g, 1.06 mmol) was added and the mixture stirred at 85° C. another 24 hours. After evaporation of volatiles an aqueous solution of Cs₂CO₃ (200 ml, 10%) was added, the suspension sonicated for 5 minutes and stirred overnight. The product was filtered, washed with water and recrystallized from methanol-chloroform. The title compound was isolated as yellow crystals. (3.951 g, 75%). LCMS (M+H)⁺ m/z 480 (t=1.31 min.). HPLC t=4.93 min, YMC-Pack ODS-A 3.0×50 mm; 0–100% gradient over 8 min; 2.5 mL/min flow rate. ¹H NMR of mono-HCl salt (500 MHz, DMSO-d₆) δ 13.3 (1H, broad s), 11.22 (1H, s), 10.9 (1H, broad s), 7.65 (1H, broad s), 7.60 (1H, s), 7.45 (d, J=7.6 Hz), 7.38–7.30 (4H, m) 6.19 (1H, d, J=7.5 Hz), 4.92 (1H, t, J=5.3 Hz), 4.00 (6H, broad), 3.67 (1H, m), 3.52 (5H, m), 2.58 (3H, s).

General Procedure for Preparation of mono- and bis-HCl Salts

A solution or suspension of free base in methanol is treated with 1.00 (or 2.00 resp.) equivalent of 1.00 N aqueous HCl. If significant amounts of compound remain insoluble an equal volume of dichlorethane is added to improve solubility. The mixture is filtered and concentrated in vacuo. Small amounts were evaporate to dryness, large-scale preparations for in vivo studies were concentrated until most of the compound crystallized, then filtered.

EXAMPLE 555

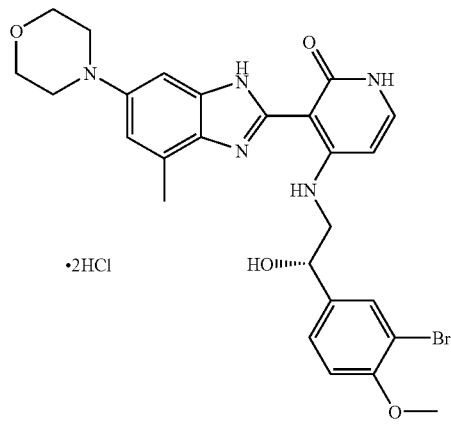

(S)-4-[2-(3-Bromo-4-methoxy-phenyl)-2-hydroxy-ethylamino]-3-(4-methyl-6-morpholin-4-yl-1H-benzoimidazol-2-yl)-1H-pyridin-2-one: ¹H NMR (300 MHz, CD₃OD) δ 7.68–7.60 (m, 2H), 7.43–7.28 (m, 3H), 6.98 (d, 1H, J=8.50 Hz), 6.26 (d, 1H, J=7.7 Hz), 4.97–4.89 (m, 1H), 4.18–4.04 (m, 4H), 3.82 (s, 3H), 3.73–3.55 (m, 6H), 2.63 (s, 3H); LCMS (M+H)⁺ m/z 554, 556.

EXAMPLE 556

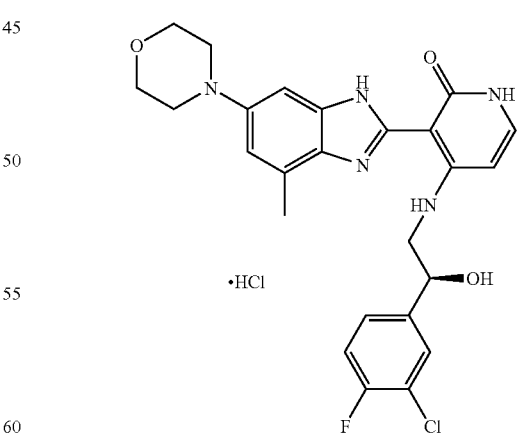

(S)-4-[2-(3-Chloro-4-fluoro-phenyl)-2-hydroxy-ethylamino]-3-(4-methyl-6-morpholin-4-yl-1H-benzoimidazol- 2-yl)-1H-pyridin-2-one: $^1$H NMR (300 MHz, CD$_3$OD) δ 7.65–7.50 (m, 2H), 7.43–7.20 (m, 3H), 7.18 (dd, 1H, J=8.9, 8.8 Hz), 6.27 (d, 1H, J=7.6 Hz), 5.00–4.91 (m, 1H), 4.15–4.02 (m, 4H), 3.75–3.60 (m, 6H), 2.64 (s, 3H); LCMS (M+H)$^+$ m/z 498, 500.

EXAMPLE 557

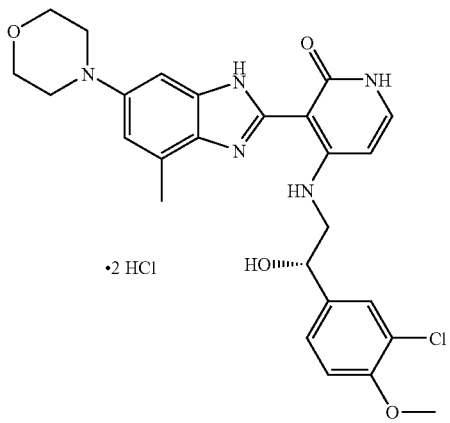

(S)-4-[2-(3-Chloro-4-methoxy-phenyl)-2-hydroxy-ethylamino]-3-(4-methyl-6-morpholin-4-yl-1H-benzoimidazol-2-yl)-1H-pyridin-2-one: $^1$H NMR (400 MHz, CD$_3$OD) δ 7.67 (brs, 1H), 7.45 (brs, 1H), 7.40–7.28 (m, 3H), 7.00 (d, 1H, J=8.4 Hz), 6.27 (d, 1H, J=7.6 Hz), 4.95–4.84 (m, 1H), 4.15–4.05 (m, 4H), 3.82 (s, 3H), 3.75–3.55 (m, 6H), 2.64 (s, 3H); LCMS (M+H)$^+$ m/z 510, 512.

EXAMPLE 558

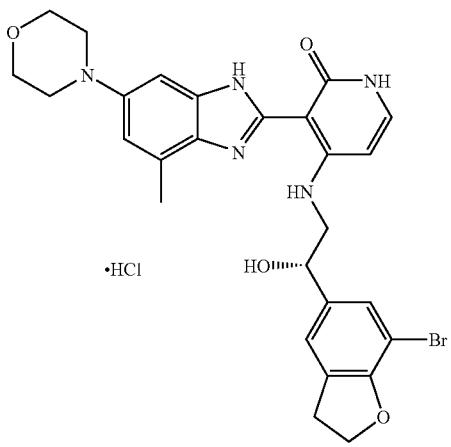

(S)-4-[2-(7-Bromo-2,3-dihydro-benzofuran-5-yl)-2-hydroxy-ethylamino]-3-(4-methyl-6-morpholin-4-yl-1H-benzoimidazol-2-yl)-1H-pyridin-2-one: $^1$H NMR (400 MHz, CD$_3$OD) δ 7.54 (brs, 1H), 7.35–7.30 (m, 2H), 7.27 (brs, 1H), 7.22 (brs, 1H), 6.27 (d 1H, J=7.6 Hz), 4.95–4.87 (m, 1H), 4.60–4.50 (m, 2H), 4.10–4.00 (m, 4H), 3.75–3.60 (m, 6H), 3.25–3.13 (m, 2H), 2.62 (s, 3H); LCMS (M+H)$^+$ m/z 566, 568.

EXAMPLE 559

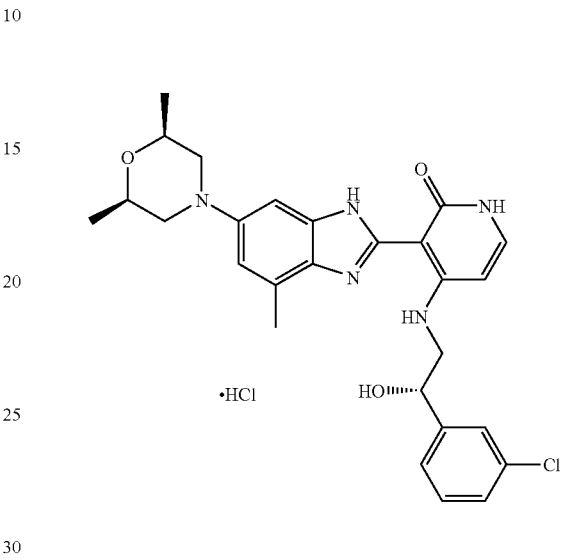

4-[2-(3-Chloro-phenyl)-2(S)-hydroxy-ethylamino]-3-[4-methyl-6-[2(S),6(R)-dimethyl-morpholine-4-yl]-1H-benzoimidazol-2-yl]-1H-pyridine-2-one. $^1$H NMR (400 MHz, CD$_3$OD) δ 7.23–7.57 (7H, –m), 6.22 (1H, d, J=7.6 Hz), 4.97 (1H, m), 4.06 (2H, m), 3.62–3.68 (4H, m), 3.20–3.34 (2H, m), 2.63 (3H, s), 1.30 (6H, d, J=6.28 Hz), LCMS (M+H)$^+$ m/z 508 (t=2.12 min.)

EXAMPLE 560

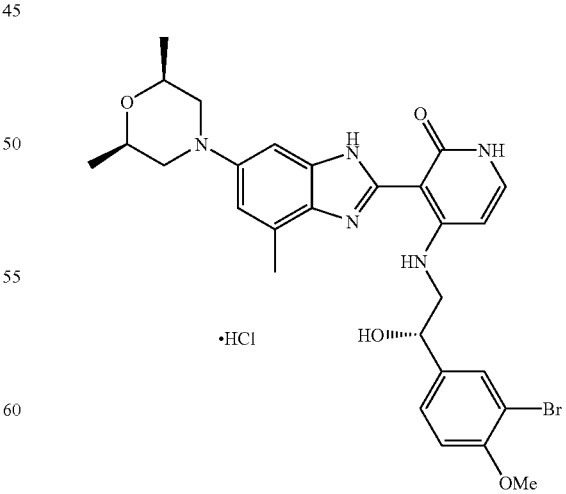

4-[2-(3-Bromo-4-methoxy-phenyl)-2(S)-hydroxy-ethylamino]-3-[4-methyl-6-[2(S),6(R)-dimethyl-morpholine-4-yl]-1H-benzoimidazol-2-yl]-1H-pyridine-2-one. $^1$H NMR (400 MHz, CD$_3$OD) δ 7.73 (1H-s), 7.63 (1H, s), 7.42 (1H, s), 7.34 (2H, m), 6.96 (1H, d, J=8.48 Hz), 6.21 (1H, d, J=7.48 Hz), 4.87 (1H, m), 4.23 (2H, m), 3.57–3.67(4H, m), 3.34 (3H, s) 3.30–3.32(2H, m), 2.60 (1H, s), 1.30 (6H, d, J=6.2 Hz) LCMS (M+H)$^+$ m/z 582 (t=2.03 min.)

EXAMPLE 561

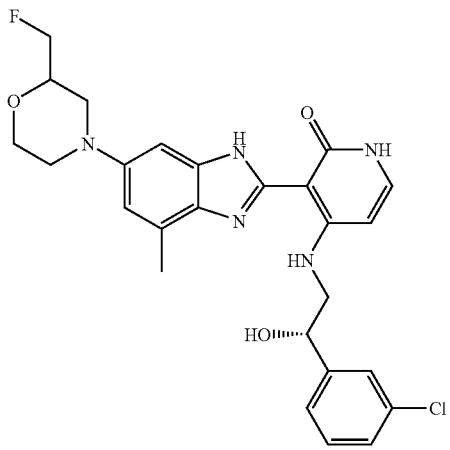

4-[2-(3-Chloro-phenyl)-(S)-2-hydroxy-ethylamino]-3-{6-[(R)-2-fluoromethyl-morpholin-4-yl]-4-methyl-1H-benzimidazol-2-yl}-1H-pyridin-2-one and 4-[2-(3-chloro-phenyl)-(S)-2-hydroxy-ethylamino]-3-{6-[(S)-2-fluoromethyl-morpholin-4-yl]-4-methyl-1H-benzimidazol-2-yl}-1H-pyridin-2-one: $^1$H NMR (400 MHz, CD$_3$OD) δ 7.47 (1H, s), 7.23–7.43 (6H, m), 6.22 (1H, d, J=7.2 Hz), 4.87–4.94 (1H, m), 4.60 (1H, d, J=3.4 Hz), 4.48 (1H, d, J=3.4 Hz), 4.04–4.15 (3H, m), 3.28–3.62 (6H, m), 2.56 (3H, s). LCMS (M+H)$^+$ m/z 512 (t=1.35 min.).

EXAMPLE 562

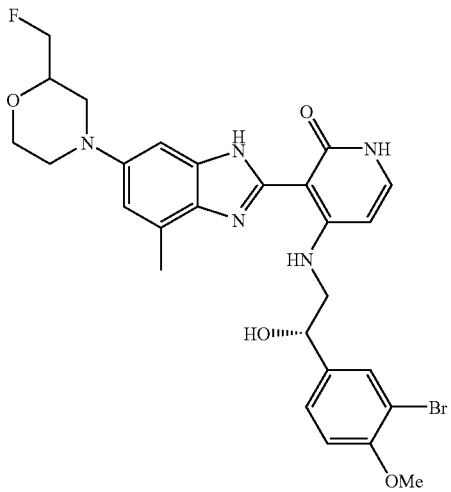

4-[2-(3-Bromo-4-methoxy-phenyl)-(S)-2-hydroxy-ethylamino]-3-{6-[(R)-2-fluoromethyl-morpholin-4-yl]-4-methyl-1H-benzimidazol-2-yl}-1H-pyridin-2-one and 4-[2-(3-bromo-4-methoxy-phenyl)-(S)-2-hydroxy-ethylamino]-3-{6-[(S)-2-fluoromethyl-morpholin-4-yl]-4-methyl-1H-benzimidazol-2-yl}-1H-pyridin-2-one: $^1$H NMR (400 MHz, CD$_3$OD) δ 7.60 (1H, narrow d, J=2.0 Hz), 7.56 (1H, s), 7.39 (1H, br s), 7.34 (1H, dd, J=2.0, 8.4 Hz), 6.97 (1H, d, J 8.4 Hz), 6.27 (1H, d, J=6.4 Hz), 4.86 (1H, m), 4.61 (1H, m), 4.50 (1H, m), 4.77–4.19 (3H, m), 3.82 (3H, s), 3.38–3.74 (8H, m), 2.63 (3H, s). LCMS (M+H)$^+$ m/z 586 (t=1.31 min.).

EXAMPLE 563

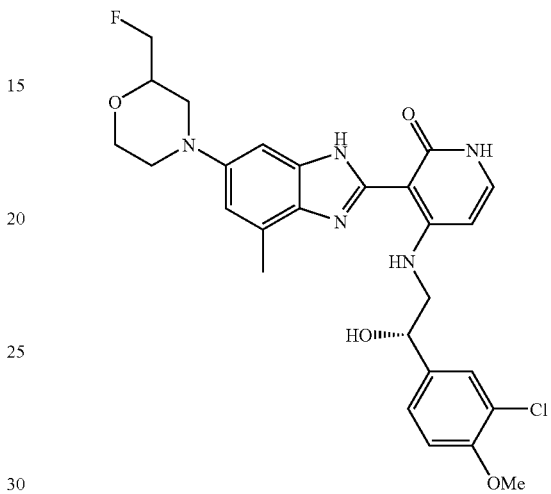

4-[2-(3-Chloro-4-methoxy-phenyl)-(S)-2-hydroxy-ethylamino]-3-{6-[(R)-2-fluoromethyl-morpholin-4-yl]-4-methyl-1H-benzimidazol-2-yl}-1H-pyridin-2-one and 4-[2-(3-chloro-4-methoxy-phenyl)-(S)-2-hydroxy-ethylamino]-3-{6-[(S)-2-fluoromethyl-morpholin-4-yl]-4-methyl-1H-benzimidazol-2-yl}-1H-pyridin-2-one: $^1$H NMR (400 MHz, CD$_3$OD) δ 7.45 (1H, s), 7.28–7.30 (3H, m), 7.10 (1H, s), 6.97 (1H, d, J=8.0 Hz), 6.20 (1H, d, J=6.4 Hz), 4.85 (1H, m), 4.58 (1H, br s), 4.46 (1H, br s), 3.93–4.10 (3H, m), 3.80 (3H, s), 3.59 (4H, m), 3.07–3.29 (2H, m), 2.55 (3H, s). LCMS (M+H)$^+$ m/z 542 (t=1.28 min.).

EXAMPLE 564

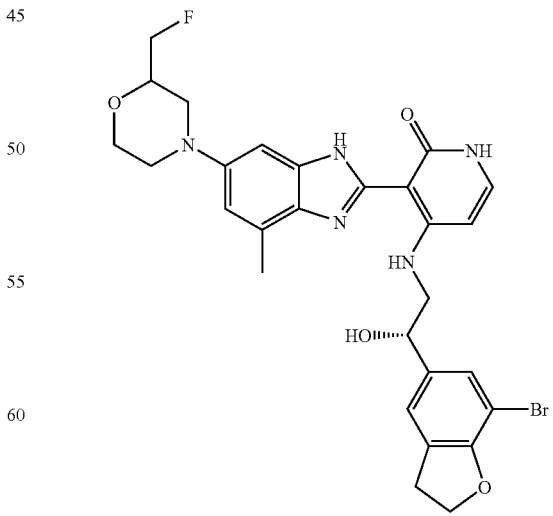

4-[2-(7-Bromo-2,3-dihydro-benzofuran-5-yl)-(S)-2-hydroxy-ethylamino]-3-{6-[(R)-2-fluoromethyl-morpholin-4- yl]-4-methyl-1H-benzimidazol-2-yl}-1H-pyridin-2-one and 4-[2-(7-bromo-2,3-dihydro-benzofuran-5-yl)-(S)-2-hydroxy-ethylamino]-3-{6-[(S)-2-fluoromethyl-morpholin-4-yl]-4-methyl-1H-benzimidazol-2-yl}-1H-pyridin-2-one: $^1$H NMR (400 MHz, CD$_3$OD) δ 7.26–7.40 (4H, m), 7.19 (1H, s), 6.24 (1H, d, J=7.6 Hz), 4.81–4.82 (1H, m), 4.49–4.61 (4H, m), 3.18–4.18 (1H, m), 2.59 (3H, s). LCMS (M+H)$^+$ m/z 598 (t=1.32 min.).

methyl-1H-benzimidazol-2-yl}-1H-pyridin-2-one and 4-[2-(3-bromo-4-methoxy-phenyl)-(S)-2-hydroxy-ethylamino]-3-{6-[(S)-2-hydroxy-methyl-morpholin-4-yl]-4-methyl-1H-benzimidazol-2-yl}-1H-pyridin-2-one: $^1$H NMR (400 MHz, CD$_3$OD) δ 7.62 (1H, narrow d, J=2.0 Hz), 7.54 (1H, s), 7.29–7.36 (3H, m), 6.95 (1H, d, J=8.4 Hz), 6.23 (1H, d, J=7.6 Hz), 4.88–4.89 (1H, m), 3.56–4.19 (1H, m), 3.80 (3H, s), 2.60 (3H, s). LCMS (M+H)$^+$ m/z 584 (t=1.16 min.).

EXAMPLE 565

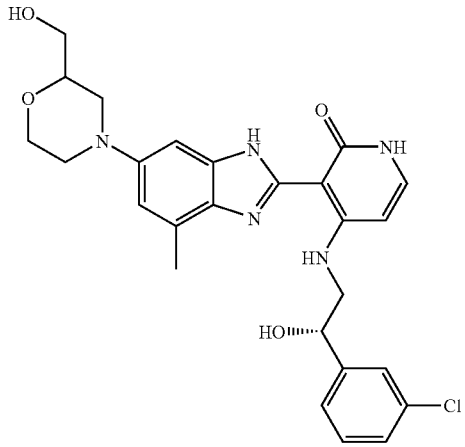

4-[2-(3-Chloro-phenyl)-(S)-2-hydroxy-ethylamino]-3-{6-[(R)-2-hydroxymethyl-morpholin-4-yl]-4-methyl-1H-benzimidazol-2-yl}-1H-pyridin-2-one and 4-[2-(3-chloro-phenyl)-(S)-2-hydroxy-ethylamino]-3-{6-[(S)-2-hydroxy-methyl-morpholin-4-yl]-4-methyl-1H-benzimidazol-2-yl}-1H-pyridin-2-one: $^1$H NMR (400 MHz, CD$_3$OD) δ 7.49 (1H, s), 7.23–7.37 (6H, m), 7.10 (1H, s), 6.24 (1H, d, J=7.6 Hz), 4.95–4.96 (1H, m), 4.19 (1H, m), 3.94–4.80 (2H, m), 3.59–3.71 (8H, m), 2.63 (3H, s). LCMS (M+H)$^+$ m/z 510 (t=1.21 min.).

EXAMPLE 566

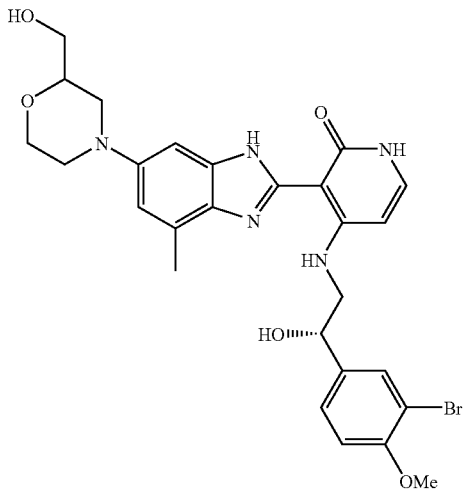

4-[2-(3-Bromo-4-methoxy-phenyl)-(S)-2-hydroxy-ethylamino]-3-{6-[(R)-2-hydroxymethyl-morpholin-4-yl]-4-

EXAMPLE 567

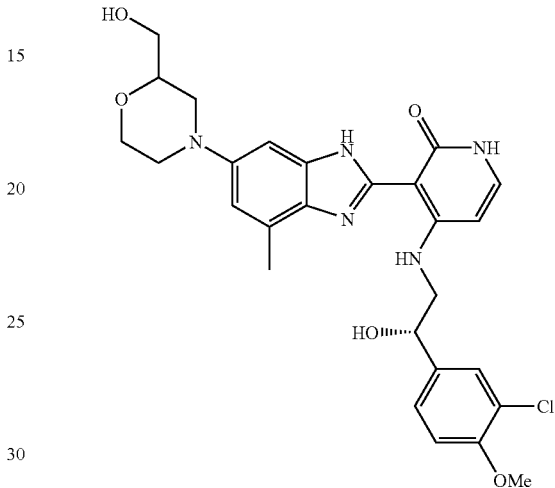

4-[2-(3-Chloro-4-methoxy-phenyl)-(S)-2-hydroxy-ethylamino]-3-{6-[(R)-2-hydroxymethyl-morpholin-4-yl]-4-methyl-1H-benzimidazol-2-yl}-1H-pyridin-2-one and 4-[2-(3-chloro-4-methoxy-phenyl)-(S)-2-hydroxy-ethylamino]-3-{6-[(S)-2-hydroxy-methyl-morpholin-4-yl]-4-methyl-1H-benzimidazol-2-yl}-1H-pyridin-2-one: $^1$H NMR (400 MHz, CD$_3$OD) δ 7.68 (1H, s), 7.54 (1H, s), 7.45 (1H, s), 7.39 (1H, s), 7.30–7.32 (2H, m), 6.98 (1H, d, J=8.4 Hz), 6.22 (1H, d, J=7.6 Hz), 4.89 (1H, m), 4.11–4.19 (3H, m), 3.80 (3H, s), 3.49–3.72 (8H, m), 2.60 (3H, s). LCMS (M+H)$^+$ m/z 540 (t=1.09 min.).

EXAMPLE 568

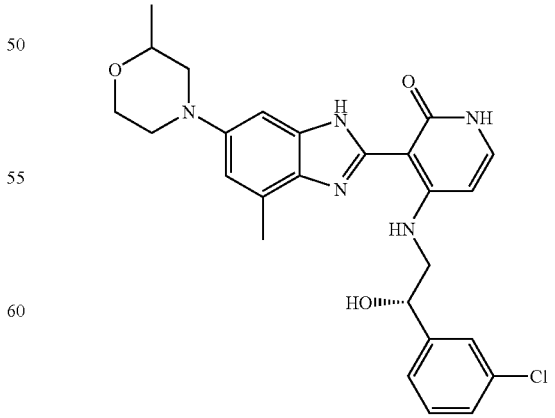

4–12-(3-Chloro-phenyl)-(S)-2-hydroxy-ethylamino]-3-{6-[(R)-2-methyl-morpholin-4-yl]-4-methyl-1H-benzimidazol-2-yl}-1H-pyridin-2-one and 4-[2-(3-chloro-phenyl)-(S)-2-hydroxy-ethylamino]-3-{6-[(S)-2-methyl-morpholin-4-yl]-4-methyl-1H-benzimidazol-2-yl}-1H-pyridin-2-one: $^1$H NMR (400 MHz, CD$_3$OD) δ 7.75 (1H, s), 7.48 (1H, s), 7.42 (1H, s), 7.23–7.37 (4H, m), 6.24 (1H, d, J=7.2 Hz), 4.94–4.97 (1H, m), 4.11–4.16 (3H, m), 3.61–3.68 (5H, m), 3.38 (1H, m), 2.64 (3H, s), 1.29 (3H, d, J=6.4 Hz). LCMS (M+H)$^+$ m/z 494 (t=1.32 min.).

EXAMPLE 569

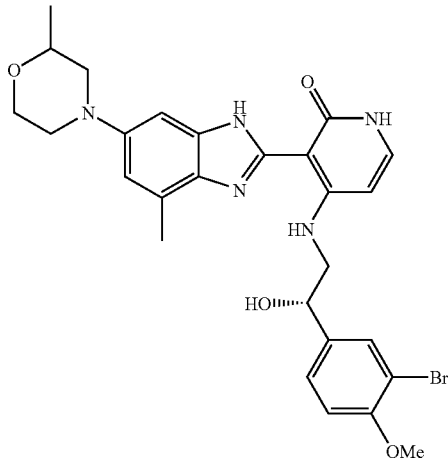

4-[2-(3-Bromo-4-methoxy-phenyl)-(S)-2-hydroxy-ethylamino]-3-{6-[(R)-2-methyl-morpholin-4-yl]-4-methyl-1H-benzimidazol-2-yl}-1H-pyridin-2-one and 4-[2-(3-bromo-4-methoxy-phenyl)-(S)-2-hydroxy-ethylamino]-3-{6-[(S)-2-methyl-morpholin-4-yl]-4-methyl-1H-benzimidazol-2-yl}-1H-pyridin-2-one: $^1$H NMR (400 MHz, CD$_3$OD) δ 7.63 (1H, s), 7.62 (1H, s), 7.30–7.61 (3H, m), 6.95 (1H, d, J=8.4 Hz), 6.22 (1H, d, J=7.6 Hz), 4.88–4.90 (1H, m), 4.08–4.18 (3H, m), 3.80 (3H, s), 3.61–3.67 (5H, m), 3.32–3.34 (1H, m), 2.60 (3H, s), 1.28 (3H, d, J=6.0 Hz). LCMS (M+H)$^+$ m/z 568 (t=1.31 min.).

EXAMPLE 570

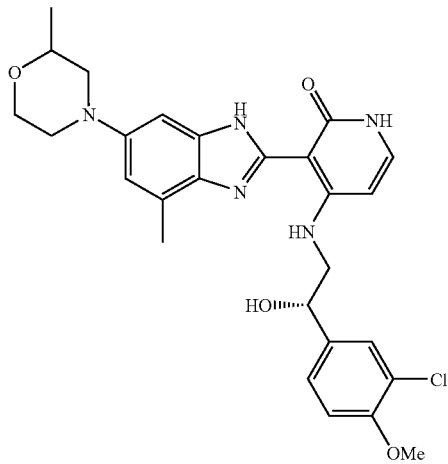

4-[2-(3-Chloro-4-methoxy-phenyl)-(S)-2-hydroxy-ethylamino]-3-{6-[(R)-2-methyl-morpholin-4-yl]-4-methyl-1H-benzimidazol-2-yl}-1H-pyridin-2-one and 4-[2-(3-chloro-4-methoxy-phenyl)-(S)-2-hydroxy-ethylamino]-3-{6-[(S)-2-methyl-morpholin-4-yl]-4-methyl-1H-benzimidazol-2-yl}-1H-pyridin-2-one: $^1$H NMR (400 MHz, CD$_3$OD) δ 7.48 (1H, narrow d, J=2.0 Hz), 7.40 (1H, br s), 7.31 (1H, narrow d, J=2.0 Hz), 7.29 (1H, narrow d, J=2.0 Hz), 6.97 (1H, d, J=8.4 Hz), 6.22 (1H, d, J=7.6 Hz), 4.87–4.90 (1H, m), 4.11 (1H, m), 3.95–4.01 (2H, m), 3.80 (3H, s), 3.47 (4H, m), 3.32 (1H, m), 3.25 (1H, m), 2.57 (3H, s), 1.27 (3H, d, J=6.4 Hz). LCMS (M+H)$^+$ m/z 525 (t=1.27 min.).

EXAMPLE 571

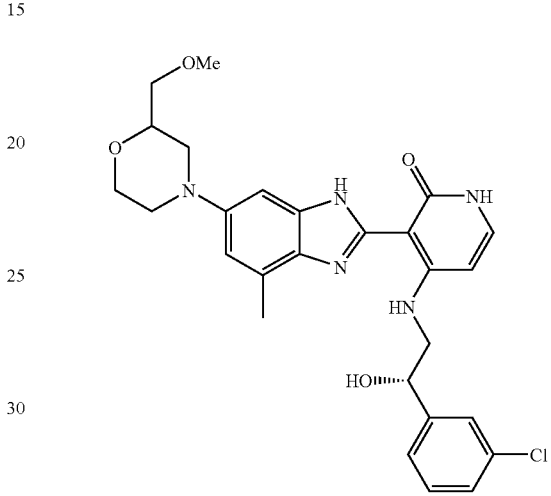

4-[2-(3-Chloro-phenyl)-(S)-2-hydroxy-ethylamino]-3-{6-[(R)-2-methoxymethyl-morpholin-4-yl]-4-methyl-1H-benzimidazol-2-yl}-1H-pyridin-2-one and 4-[2-(3-chloro-phenyl)-(S) -2-hydroxy-ethylamino]-3-{6-[(S)-2-methoxymethyl-morpholin-4-yl]-4-methyl-1H-benzimidazol-2-yl}-1H-pyridin-2-one: $^1$H NMR (400 MHz, CD$_3$OD) δ 7.49 (1H, narrow d, J=2.0 Hz), 7.23–7.36 (6H, m), 6.22 (1H, d, J=7.2 Hz), 4.93–4.96 (1H, m), 4.08–4.21 (1H, m), 3.38 (3H, s), 2.60 (3H, s), 1.27 (3H, d, J=6.4 Hz). LCMS (M+H)$^+$ m/z 524 (t=1.35 min.).

EXAMPLE 572

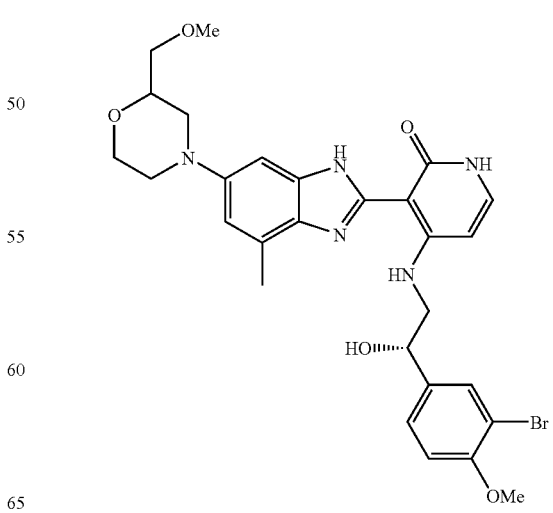

4-[2-(3-Bromo-4-methoxy-phenyl)-(S)-2-hydroxy-ethylamino]-3-{6-[(R)-2-methoxymethyl-morpholin-4-yl]-4-methyl-1H-benzimidazol-2-yl}-1H-pyridin-2-one and 4-[2-(3-bromo-4-methoxy-phenyl)-(S)-2-hydroxy-ethylamino]-3-{6-[(S)-2-methoxymethyl-morpholin-4-yl]-4-methyl-1H-benzimidazol-2-yl}-1H-pyridin-2-one: $^1$H NMR (400 MHz, CD$_3$OD) δ 7.63 (1H, narrow d, J=2.0 Hz), 7.40 (1H, br s), 7.30–7.36 (3H, m), 7.19 (1H, br s), 6.95 (1H, d, J=8.4 Hz), 6.23 (1H, d, J=7.2 Hz), 4.87–4.89 (1H, m), 4.18 (1H, m), 3.97–4.03 (3H, m), 3.80 (3H, s), 3.54–3.66 (7H, m), 3.39 (3H, s), 2.59 (3H, s). LCMS (M+H)$^+$ m/z 598 (t=1.31 min.).

EXAMPLE 573

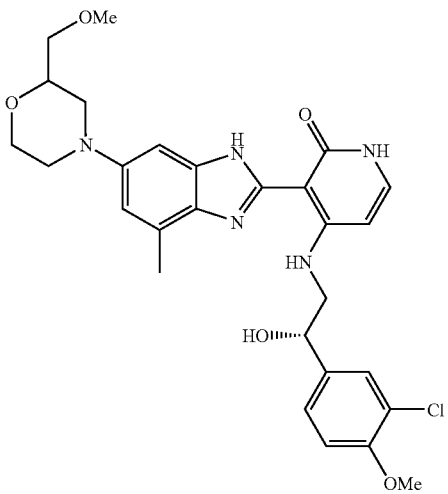

4-[2-(3-Chloro-4-methoxy-phenyl)-(S)-2-hydroxy-ethylamino]-3-{6-[(R)-2-methoxymethyl-morpholin-4-yl]-4-methyl-1H-benzimidazol-2-yl}-1H-pyridin-2-one and 4-[2-(3-chloro-4-methoxy-phenyl)-(S)-2-hydroxy-ethylamino]-3-{6-[(S)-2-methoxymethyl-morpholin-4-yl]-4-methyl-1H-benzimidazol-2-yl}-1H-pyridin-2-one: $^1$H NMR (400 MHz, CD$_3$OD) δ 7.52 (1H, s), 7.46 (1H, narrow d, J=1.6 Hz), 7.29–7.34 (3H, m), 6.99 (1H, d, J=8.4 Hz), 6.24 (1H, d, J=7.2 Hz), 4.89 (1H, m), 4.06–4.17 (3H, m), 3.81 (3H, s), 3.54–3.68 (8H, m), 3.38 (3H, s), 2.60 (3H, s). LCMS (M+H)$^+$ m/z 554 (t=1.28 min.).

EXAMPLE 574

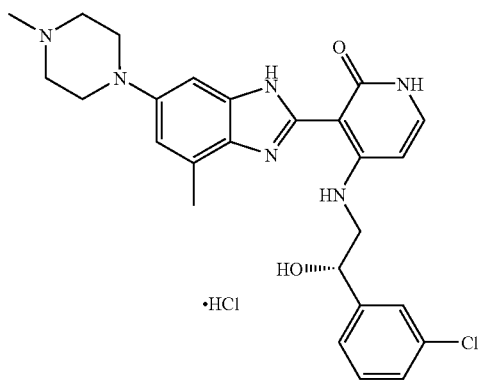

4-[2-(3-Chloro-phenyl)-2(S)-hydroxy-ethylamino]-3-[4-methyl-6-(4-methyl-piperazin-1-yl)-1H-benzoimidazol-2-yl]-1H-pyridine-2-one. $^1$H NMR (400 MHz, CD$_3$OD) δ 7.46 (1H, s), 7.24–7.36 (m, 4H), 7.04 (2H, s), 6.22 (1H, d, J=7.64 Hz), 4.89 (1H, m), 3.30–3.82 (10H, m) 2.97 (3H, s), 2.57 (3H, s). LCMS (M+H)$^+$ m/z 493 (t=1.56 min.)

EXAMPLE 575

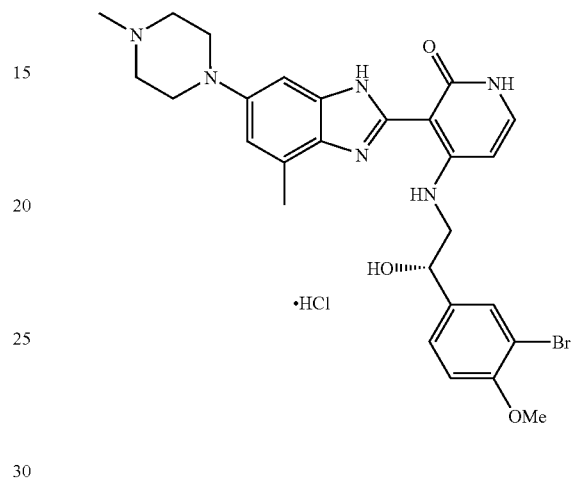

4-[2-(3-Bromo-4-methoxy-phenyl)-2(S)-hydroxy-ethylamino]-3-[4-methyl-6-(4-methyl-piperazin-1-yl)-1H-benzoimidazol-2-yl]-1H-pyridine-2-one. $^1$H NMR (400 MHz, CD$_3$OD) δ 7.61 (1H, d, J=2.0 Hz), 7.32–7.37 (2H, m), 7.05 (2H, s), 6.97 (1H, d, J=8.52 Hz), 6.24 (1H, d, J=7.64 Hz), 4.82 (1H, m), 3.82 (3H, s) 3.30–3.64 (10H, m), 2.98 (3H, s), 2.56 (3H, s) LCMS (M+H)$^+$ m/z 567 (t=1.53 min.)

The following Examples (576–581) were Prepared According to Scheme VII and III and Illustrate the Acylation of a 4-amino-piperidine Derivative

EXAMPLE 576

General Procedure for Examples 576–581

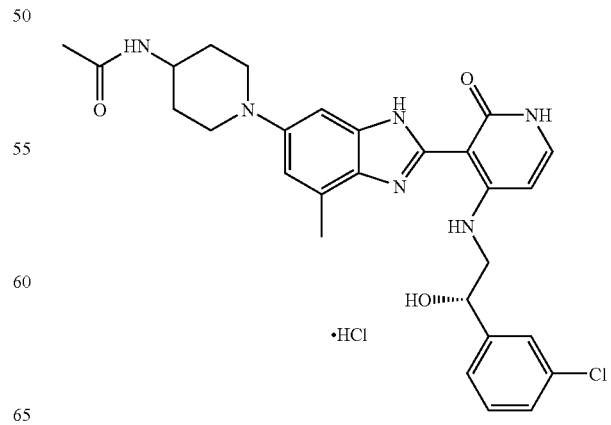

4-[2-(3-Chloro-phenyl)-2-hydroxy-ethylamino]-3-{6-[4-(acetamido)-piperidin-1-yl]-4-methyl-1H-benzoimidazol-2-yl}-1H-pyridin-2-one: A solution of the 4-amino-piperidine compound (~50–100 umol) in 5 ml MeOH is cooled to 0° C. Then ~10 equivalent of Huenigs base and ~3 equivalent of acyl chloride are added. The vial is shaken once and allowed to stand at ambient temperature for 1 hour. Evaporation of volatiles and purification by prep. HPLC gives the 4-acyl-aminopiperidine compounds. $^1$H NMR (500 MHz, CD$_3$OD) δ 8.06 (1H, s), 7.68 (1H, s), 7.49 (1H, s), 7.44 (1H, d, J=7.6), 7.27–7.38 (4H, m), 6.33 (1H, d, J=7.6 Hz), 4.96 (1H, dd, J=4.1, 7.6 Hz), 4.17 (1H, m), 3.87 (4H, m), 3.65 (1H, dd, J=4.2, 14 Hz), 3.58 (1H, dd, J=7.8, 13.8 Hz), 2.72 (3H, s), 2.31 (2H, m), 2.19 (2H, m), 2.02 (3H, s). LCMS (M+H)$^+$ m/z 535 (t=1.03 min, YMC Xterra C18 S7 3.0×50 mm; 0–100% gradient over 1.5 min; 5 mL/min flow rate).

EXAMPLE 577

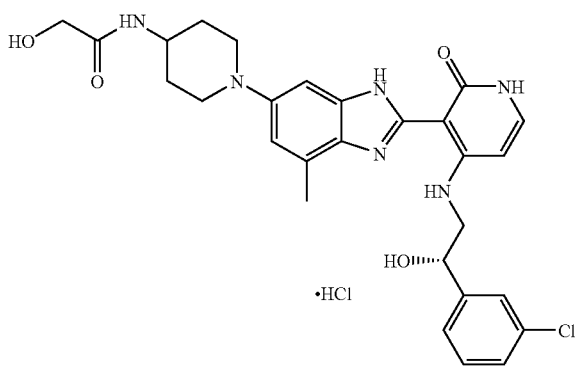

4-[2-(3-Chloro-phenyl)-2-hydroxy-ethylamino]-3-{6-[4-(2-hydroxyacetamido)-piperidin-1-yl]-4-methyl-1H-benzoimidazol-2-yl}-1H-pyridin-2-one: LCMS (M+H)$^+$ m/z 551 (t=1.27 min.). HPLC t=5.01 min, Waters Xterra C18 S5 4.6×30 mm; 0–100% gradient over 12 min; 5 mL/min flow rate.

EXAMPLE 578

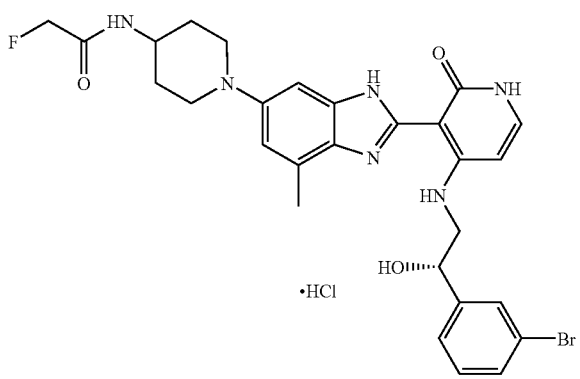

4-[2-(3-Chloro-phenyl)-2-hydroxy-ethylamino]-3-{6-[4-(2-fluoroacetamido)-piperidin-1-yl]-4-methyl-1H-benzoimidazol-2-yl}-1H-pyridin-2-one: LCMS (M+H)$^+$ m/z 597 (t=1.31 min.). HPLC t=6.90 min, YMC-Pack ODS-A 3.0×50 mm, 0–100% gradient over 12 min; 2.5 mL/min flow rate.

EXAMPLE 579

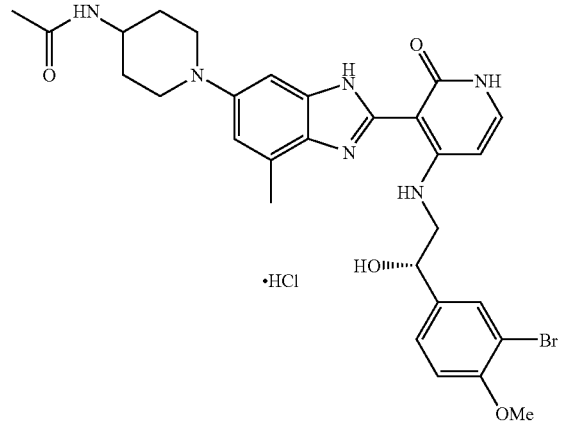

4-[2-(3-Bromo-4-methoxy-phenyl)-2-hydroxy-ethylamino]-3-{6-[4-(acetamido)-piperidin-1-yl]-4-methyl-1H-benzoimidazol-2-yl}-1H-pyridin-2-one: LCMS (M+H)$^+$ m/z 609 (t=1.27 min.). HPLC t=5.00 min, Waters Xterra C18 S5 4.6×30 mm; 0–100% gradient over 12 min; 5 mL/min flow rate.

EXAMPLE 580

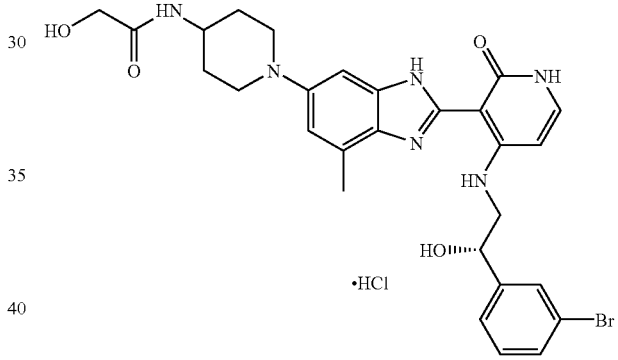

4-[2-(3-Bromo-phenyl)-2-hydroxy-ethylamino]-3-{6-[4-(2-hydroxyacetamido)-piperidin-1-yl]-4-methyl-1H-benzoimidazol-2-yl}-1H-pyridin-2-one: LCMS (M+H)$^+$ m/z 595 (t=1.30 min.). HPLC t=5.09 min, Waters Xterra C18 S5 4.6×30 mm; 0–100% gradient over 12 min; 5 mL/min flow rate.

EXAMPLE 581

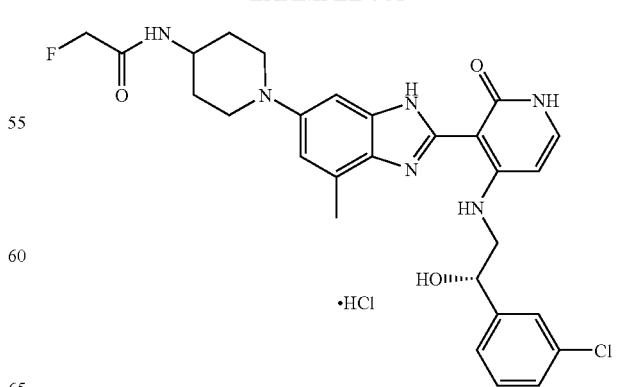

4-[2-(3-Chloro-phenyl)-2-hydroxy-ethylamino]-3-{6-[4-(2-fluoroacetamido)-piperidin-1-yl]-4-methyl-1H-benzoimidazol-2-yl}-1H-pyridin-2-one: LCMS (M+H)$^+$ m/z 553 (t=1.35 min.). HPLC t=5.90 min, YMC-Pack ODS-A 3.0×50 mm; 0–100% gradient over 10 min; 2.5 mL/min flow rate.

The Following Examples (582–584) were Prepared According to Scheme VII and III and Illustrate the Carbamoylation of a 4-amino-piperidine Derivative General Procedure for Examples 582–584

A solution of the 4-amino-piperidine compound (~50–100 umol) in 5 ml MeOH is cooled to 0° C. Then 10 equivalent of Huenigs base and ~3 equivalent of carbamoyl chloride are added. The vial is shaken once and allowed to stand at ambient temperature overnight. Evaporation of volatiles and purification by prep. HPLC gives the 4-carbamoyl-aminopiperidine compounds.

EXAMPLE 582

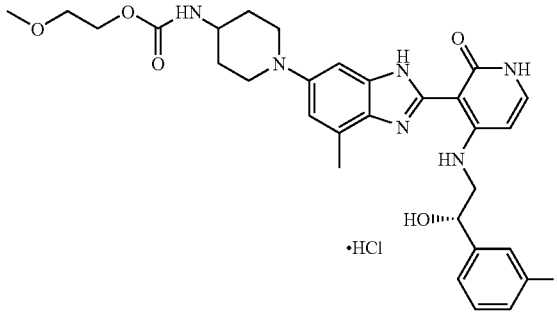

4-[2-(3-Chloro-phenyl)-2-hydroxy-ethylamino]-3-{6-[4-(2-methoxyethoxycarbamoyl)-piperidin-1-yl]-4-methyl-1H-benzoimidazol-2-yl}-1H-pyridin-2-one: $^1$H NMR (500 MHz, CD$_3$OD) δ 7.90 (1H, s), 7.26–7.52 (6H, m), 6.29 (1H, d, J=7.5 Hz), 4.97 (1H, dd, J=4.1, 7.0 Hz), 4.20 (2H, m), 3.93 (1H, m), 3.60–3.84 (8H, m), 3.37 (3H, s), 2.69 (3H, s), 2.33 (2H, m), 2.13 (2H, m). LCMS (M+H)$^+$ m/z 595 (t=1.09 min, YMC Xterra C18 S7 3.0×50 mm; 0–100% gradient over 1.5 min; 5 mL/min flow rate).

EXAMPLE 583

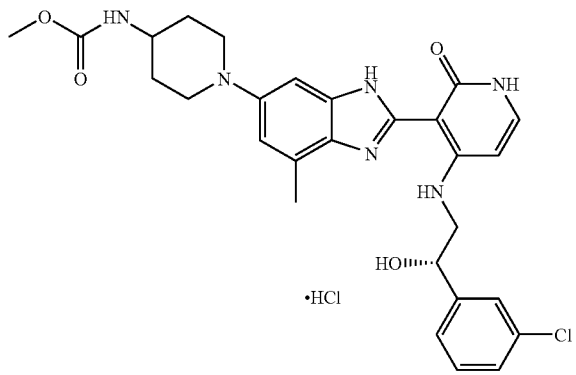

4-[2-(3-Chloro-phenyl)-2-hydroxy-ethylamino]-3-{6-[4-(methoxycarbamoyl)-piperidin-1-yl]-4-methyl-1H-benzoimidazol-2-yl}-1H-pyridin-2-one: $^1$H NMR (500 MHz, CD$_3$OD) δ 8.00 (1H, s), 7.63 (1H, s), 7.26–7.49 (5H, m), 6.32 (1H, d, J=7.6 Hz), 4.96 (1H, dd, J=4.2, 7.6 Hz), 3.93 (1H, m), 3.79–3.88 (4H, m), 3.67 (3H, s), 3.56–3.65 (2H, m), 2.71 (3H, s), 2.32 (2H, m), 2.17 (2H, m). LCMS (M+H)$^+$ m/z 551 (t=1.07 min, YMC Xterra C18 S7 3.0×50 mm; 0–100% gradient over 1.5 min; 5 mL/min flow rate).

EXAMPLE 584

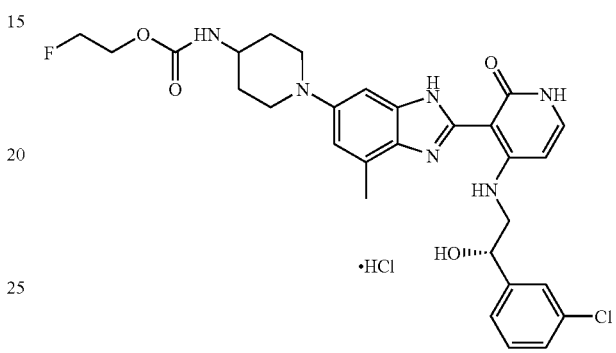

4-[2-(3-Chloro-phenyl)-2-hydroxy-ethylamino]-3-{6-[4-(2-fluoroethoxy carbamoyl)-piperidin-1-yl]-4-methyl-1H-benzoimidazol-2-yl}-1H-pyridin-2-one: $^1$H NMR (500 MHz, CD$_3$OD) δ 7.92 (1H, s), 7.26–7.54 (6H, m), 6.3 (1H, d, J=7.5 Hz), 4.97 (1H, dd, J=4.5, 7.5 Hz), 4.63 (1H, broad s), 4.53 (1H, d, J=2.5 Hz), 4.32 (1H, broad s), 4.27 (1H, broad s), 3.93 (1H, m), 3.79–3.85 (4H, m), 3.58–3.72 (2H, m), 2.70 (3H, s), 2.33 (2H, m), 2.15 (2H, m). LCMS (M+H)$^+$ m/z 583 (t=1.29 min, YMC Xterra C18 S7 3.0×50 mm; 0–100% gradient over 2 min; 5 mL/min flow rate).

The Following Examples (585–590) were Prepared According to Scheme VII and III and Illustrate the use of an Alcohol as the Nucleophile in Scheme VII

EXAMPLE 585

General Procedure for Examples 585–590

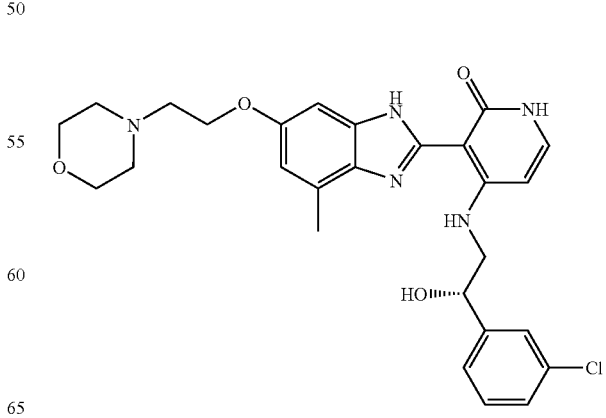

(S)-4-[2-(3-Chloro-phenyl)-2-hydroxy-ethylamino]-3-[4-methyl-6-(2-morpholin-4-yl-ethoxy)-1H-benzimidazol-2-yl]-1H-pyridin-2-one: $^1$H NMR (400 MHz, CD$_3$OD) δ 7.53 (1H, s), 7.37–7.39 (1H, m), 7.23–7.30 (3H, m), 7.01 (1H, s), 6.75 (1H, s), 6.21 (1H, d, J=7.2 Hz), 4.98 (1H, t, J=5.6 Hz), 4.40 (2H, br s), 3.97 (4H, br s), 3.45–3.73 (8H, m), 2.54 (3H, s). LCMS (M+H)$^+$ m/z 524 (t=1.24 min.).

EXAMPLE 586

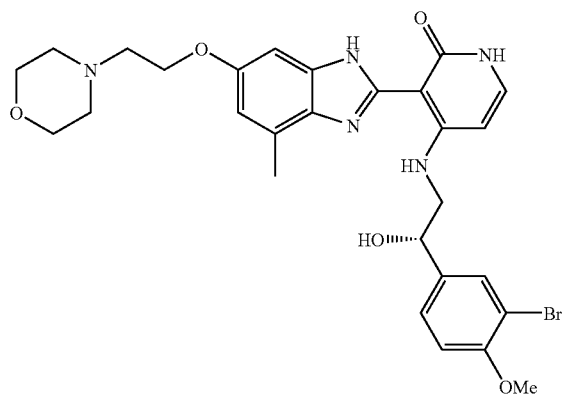

(S)-4-[2-(3-Bromo-4-methoxy-phenyl)-2-hydroxy-ethylamino]-3-[4-methyl-6-(2-morpholin-4-yl-ethoxy)-1H-benzimidazol-2-yl]-1H-pyridin-2-one: $^1$H NMR (400 MHz, CD$_3$OD) δ 7.67 (1H, narrow d, J=1.6 Hz), 7.36 (1H, dd, J=1.6, 8.4 Hz), 7.25 (1H, d, J=7.2 Hz), 6.98 (1H, s), 6.92 (1H, d, J=8.4 Hz), 6.75 (1H, s), 6.22 (1H, d, J=7.2 Hz), 4.89–4.92 (1H, m), 4.41 (2H, br s), 3.97 (4H, br s), 3.79 (3H, s), 3.34–3.66 (8H, m), 2.51 (3H, s). LCMS (M+H)$^+$ m/z 598 (t=1.22 min.).

EXAMPLE 587

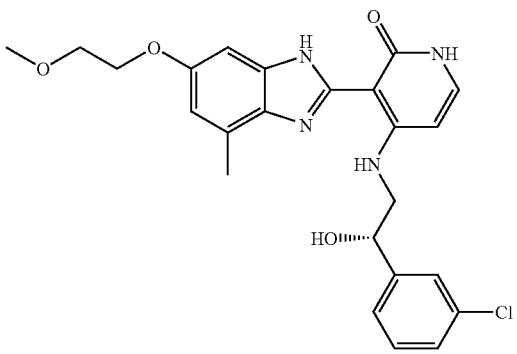

(S)-4-[2-(3-Chloro-phenyl)-2-hydroxy-ethylamino]-3-[4-methyl-6-(2-methoxy-ethoxy)-1H-benzimidazol-2-yl]-1H-pyridin-2-one: $^1$H NMR (400 MHz, CD$_3$OD) δ 7.48 (1H, s), 7.25–7.36 (4H, m), 6.96 (1H, s), 6.81 (1H, s), 6.20 (1H, d, J=7.4 Hz), 4.90–4.93 (1H, m), 4.13–4.14 (2H, m), 3.76–3.77 (2H, m), 3.50–3.61 (2H, m), 3.43 (3H, s), 2.53 (3H, s). LCMS (M+H)$^+$ m/z 469 (t=1.52 min.).

EXAMPLE 588

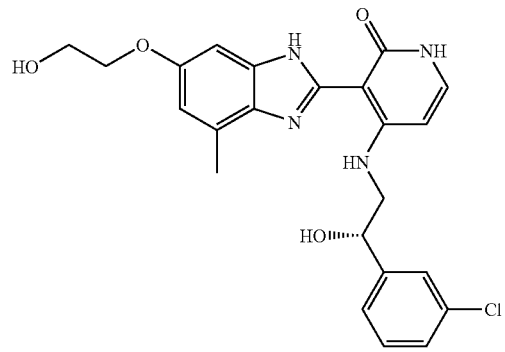

(S)-4-[2-(3-Chloro-phenyl)-2-hydroxy-ethylamino]-3-[4-methyl-6-(2-hydroxy-ethoxy)-1H-benzimidazol-2-yl]-1H-pyridin-2-one: $^1$H NMR (400 MHz, CD$_3$OD) δ 7.43–7.45 (2H, m), 7.27–7.34 (3H, m), 7.08 (1H, s), 7.04 (1H, narrow d, J=1.0 Hz), 6.28 (1H, d, J=7.6 Hz), 4.87 (1H, m), 4.13 (2H, t, J=4.6 Hz), 3.92 (2H, t, J=4.6 Hz), 3.45–3.54 (2H, m), 2.60 (3H, s). LCMS (M+H)$^+$ m/z 455 (t=1.35 min.).

EXAMPLE 589

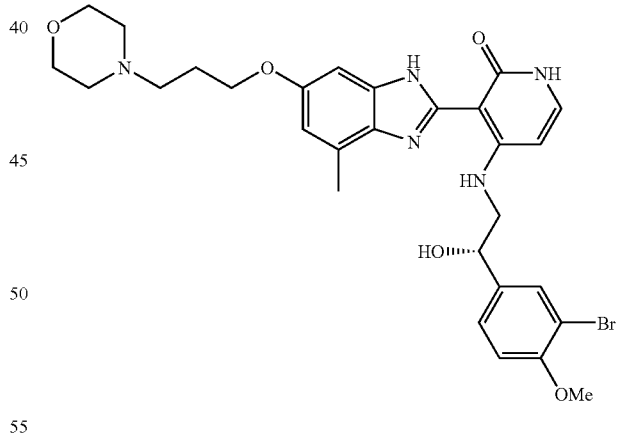

(S)-4-[2-(3-Bromo-4-methoxy-phenyl)-2-hydroxy-ethylamino]-3-[4-methyl-6-(3-morpholin-4-yl-propoxy)-1H-benzimidazol-2-yl]-1H-pyridin-2-one: $^1$H NMR (400 MHz, CD$_3$OD) δ 7.66 (1H, s), 7.35 (1H, dd, J=1.6, 7.9 Hz), 7.25 (1H, br s), 6.93 (1H, s), 6.91 (1H, s), 6.68 (1H, s), 6.19 (1H, br s), 4.86 (1H, m), 4.05–4.10 (4H, br s), 3.79 (3H, s), 3.17–3.73 (12H, m), 2.50 (3H, s). LCMS (M+H)$^+$ m/z 612 (t=1.6 min.).

EXAMPLE 590

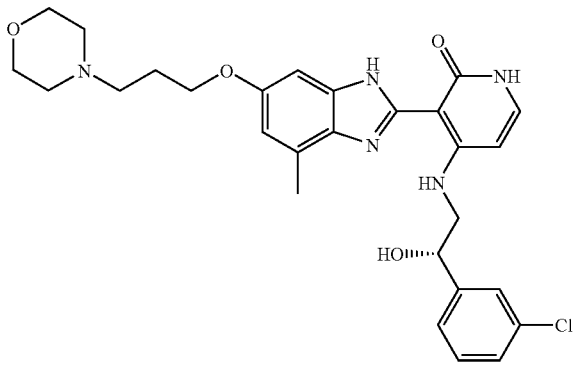

(S)-4-[2-(3-Chloro-phenyl)-2-hydroxy-ethylamino]-3-[4-methyl-6-(3-morpholin-4-yl-propoxy)-1H-benzimidazol-2-yl]-1H-pyridin-2-one: $^1$H NMR (400 MHz, CD$_3$OD) δ 7.52 (1H, s), 7.36–7.38 (1H, m), 7.23–7.30 (3H, m), 6.92 (1H, s), 6.67 (1H, s), 6.18 (1H, d, J=6.9 Hz), 4.96 (1H, t, J=5.9 Hz), 4.04–4.08 (4H, m), 3.82 (2H, m), 3.56–3.65 (8H, m), 3.15–3.18 (2H, m), 2.52 (3H, s). LCMS (M+H)$^+$ m/z 538 (t=1.19 min.).

The Following Examples (591–593) were Prepared According to Scheme VII and III Wherein a Cyano Group (Scheme IV) is Converted to an Aldehyde Which Undergo Reductive Amination with an Amine

EXAMPLE 591

General Procedure for Examples 591–593

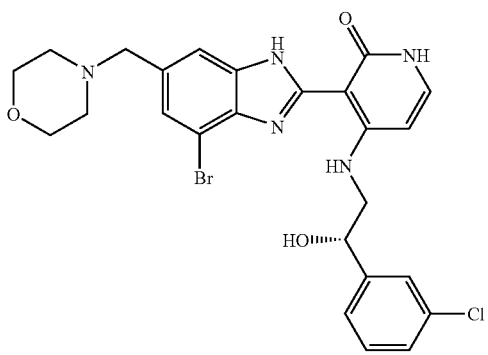

(S)-3-(4-Bromo-6-morpholin-4-ylmethyl-1H-benzimidazol-2-yl)-4-[2-(3-chloro-phenyl)-2-hydroxy-ethylamino]-1H-pyridin-2-one: To a solution of (S)-7-Bromo-2-{4-[2-(3-chloro-phenyl)-2-hydroxy-ethylamino]-2-oxo-1,2-dihydro-pyridin-3-yl}-3H-benzimidazole-5-carbaldehyde (130 mg, 0.27 mmol) in methanol (60 mL) was added morpholine (0.2 mL, excess). The reaction mixture was stirred 1 h at room temperature. Then NaCNBH$_3$ (1M THF solution, 1.35 mL, 1.35 mmol) was added. The reaction mixture was stirred at room temperature overnight and concentrated in vacuo. The residue was purified by prep. HPLC to yield the title compound (68 mg, 45%). $^1$H NMR (400 MHz, CD$_3$OD) δ 7.83 (1H, s), 7.69 (1H, s), 7.68 (1H, s), 7.24–7.54 (4H, m), 6.30 (1H, d, J=7.6 Hz), 4.89–5.02 (1H, m), 4.50 (2H, s), 3.66–3.71 (4H, m), 3.17–3.43 (6H, m). LCMS (M+H)$^+$ m/z 558 (t=1.41 min.).

EXAMPLE 592

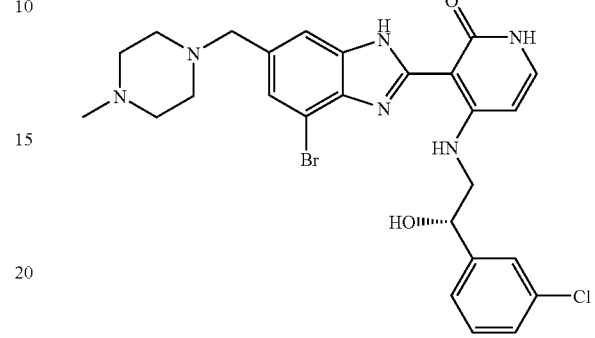

(S)-3-[4-Bromo-6-(4-methyl-piperazin-1-ylmethyl)-1H-benzimidazol-2-yl]-4-[2-(3-chloro-phenyl)-2-hydroxy-ethylamino]-1H-pyridin-2-one: $^1$H NMR (400 MHz, CD$_3$OD) δ 7.70 (1H, s), 7.55 (2H, s), 7.42 (1H, d, J=7.6 Hz), 7.24–7.32 (3H, m), 6.22 (1H, d, J=7.6 Hz), 5.01 (1H, t, J=6.2 Hz), 4.35 (2H, br s), 3.48–3.71 (10H, m), 2.98 (3H, s). LCMS (M+H)$^+$ m/z 571 (t=1.37 min.).

EXAMPLE 593

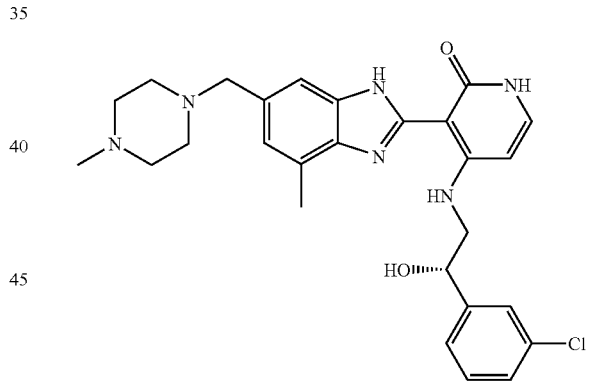

(S)-4-[2-(3-Chloro-phenyl)-2-hydroxy-ethylamino]-3-[4-methyl-6-(4-methyl-piperazin-1-ylmethyl)-1H-benzimidazol-2-yl]-1H-pyridin-2-one: Through a mixture of (S)-3-[4-Bromo-6-(4-methyl-piperazin-1-ylmethyl)-1H-benzimidazol-2-yl]-4-[2-(3-chloro-phenyl)-2-hydroxy-ethylamino]-1H-pyridin-2-one (80 mg, 0.14 mmol), tetramethyl tin (2.5 mL, excess), PdCl2 (PPh3)4 (10 mg, 0.014 mmol), and KF (40 mg, 0.7 mmol) in DMF (2 mL) in a vial was bubbled nitrogen, sealed, and heated to 100° C. for two days. The reaction mixture was passed through a small pad of celite. After concentration, the residue was purified by prep. HPLC to give the titled compound (34 mg, 48%). $^1$H NMR (400 MHz, CD$_3$OD) δ 7.53 (1H, s), 7.45 (1H, s), 7.24–7.40 (4H, m), 7.09 (1H, s), 6.22 (1H, d, J=7.6 Hz), 4.99 (1H, t, J=6.4 Hz), 4.04 (2H, br s), 3.61–3.74 (2H, m), 2.98–3.34 (8H, m), 2.80 (3H, s), 2.58 (3H, s). LCMS (M+H)$^+$ m/z 507 (t=1.29 min.).

The Following Examples (594–595) were Prepared According to Scheme VII and III and Illustrate the use of Tetrahydropyrimidine as the Nucleophile in Scheme VII

EXAMPLE 594

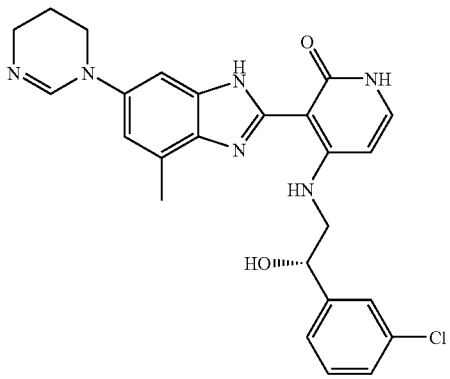

4-[2-(3-Chloro-phenyl)-2(S)-hydroxy-ethylamino]-3-[4-methyl-6-(1,4,5,6-tetrahydropyrimidine-1-yl)-1H-benzoimidazol-2-yl]-1H-pyridine-2-one: $^1$H NMR (400 MHz, CD$_3$OD) δ 8.38 (1H, s), 7.52 (1H,s), 7.21–7.41 (5H, m), 7.04 (1H, d, J=1.2 Hz), 6.21(1H, d, J=7.6 Hz), 4.97 (1H, t, J=4.9 Hz) 3.97(2H, m) 3.60–3.73 (2H, m),3.52(2H, t, J=5.74 Hz) 2.60 (3H, s), 2.25 (2H, m) LCMS (M+H)$^+$ m/z 477 (t=1.79 min.)

EXAMPLE 595

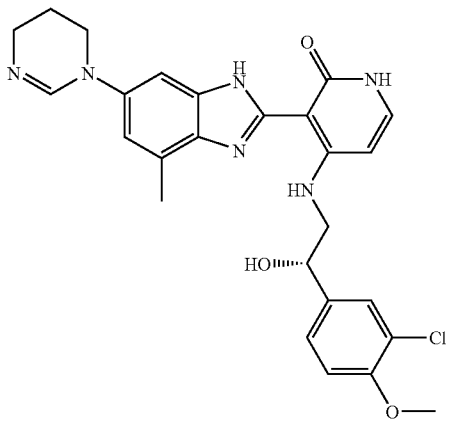

4-[2-(4-Methoxy-3-chloro-phenyl)-2(S)-hydroxy-ethylamino]-3-[4-methyl-6-(1,4,5,6-tetrahydropyrimidine-1-yl)-1H-benzoimidazol-2-yl]-1H-pyridine-2-one: $^1$H NMR (400 MHz, CD$_3$OD) δ 8.37 (1H, s), 7.52 (1H,s), 7.04–7.52(4H, m), 7.04 (1H, d, J=1.2 Hz), 6.21(1H, d, J=7.6 Hz), 4.98 (1H, t, J=4.92 Hz) 3.97(5H, m) 3.60–3.73 (2H, m), 3.52 (2H, t, J=5.74 Hz), 2.60 (3H, s), 2.26 (2H, m). LCMS (M+H)$^+$ m/z 507 (t=1.67 min.)

EXAMPLE 596

(SCHEME VIII) 4-[2-(3-Chloro-4-methoxy-phenyl)-2-hydroxy-ethylamino]-3-(4-methyl-6-morpholin-4-yl-1H-benzoimidazol-2-yl)-1,5-dihydro-pyrrol-2-one

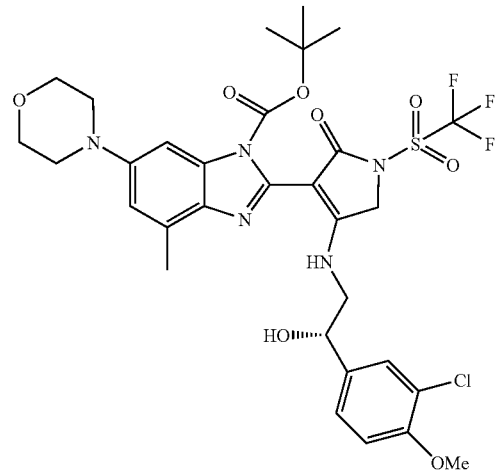

4-[2-(3-Chloro-4-methoxy-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one: 4-Hydroxy-3-(1-tert-butyloxycarbonyl-4-methyl-6-morpholin-4-yl-1H-benzoimidazol-2-yl)-1,5-dihydro-pyrrol-2-one (0.032 g, 0.059 mmol) was reacted as described in the procedure used to synthesize (S)-4-[2-(3-chloro-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one and by using acetonitrile instead of N,N-dimethylformamide. This gave the title material (0.018 g, 35%). LCMS ($^+$ESI, M+H$^+$) m/z 730; $^1$H NMR (400 MHz, methanol-d$_4$) δ (ppm): 1.55 (9H, s), 2.57 (3H, s), 3.20 (4H, m), 3.40 (2H, d, J=5.9 Hz), 3.85 (7H, m), 4.31 (1H, d, J=17.5 Hz), 4.44 (1H, d, J=17.6 Hz), 4.72 (1H, t, J=5.7 Hz), 7.02–7.04 (2H, m), 7.18 (1H, s), 7.30 (1H, d, J=8.4 Hz), 7.44 (1H, s).

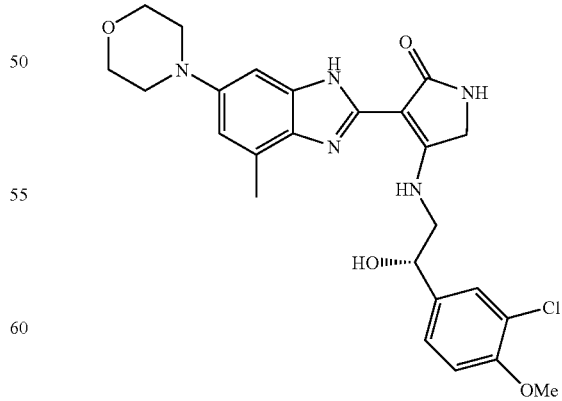

4-[2-(3-Chloro-4-methoxy-phenyl)-2-hydroxy-ethylamino]-3-(4-methyl-6-morpholin-4-yl-1H-benzoimidazol-2-yl)-1,5-dihydro-pyrrol-2-one: 4-[2-(3-Chloro-4-methoxyphenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one (0.017 g, 0.023 mmol) was reacted according to the procedure used to synthesize (S)-4-[2-(3-chloro-phenyl)-2-hydroxy-ethylamino]-3-(4-methyl-6-morpholin-4-yl-1H-benzoimidazol-2-yl)-1,5-dihydro-pyrrol-2-one and afforded the title material (0.0069 g, 59%) as a white solid. HPLC: 91% (220 nm), LCMS (+ESI, M+H+) m/z 498, HRMS calcd for $C_{25}H_{28}N_5O_4Cl$=497.1830, found: 497.1815; IR ν (cm$^{-1}$): 3386, 1636, 1558; $^1$H NMR (400 MHz, methanol-d$_4$) δ (ppm): 2.48 (3H, s), 3.11 (4H, br dd), 3.49 (1H, dd, J=13.9 and 6.8 Hz), 3.57 (1H, dd, J=13.9 and 4.3 Hz), 3.85–3.87 (7H, m), 4.14 (2H, 2d J$_{AB}$=18.1 Hz), 4.85–4.88 (1H, m), 6.75 (1H, s), 6.92 (1H, s), 7.02 (1H, d, J=8.4 Hz), 7.33 (1H, dd, J=8.4 and 1.8 Hz), 7.47 (1H, d, J=1.8 Hz).

EXAMPLE 597

(SCHEME VIII) 4-[2-(3-Bromo-4-methoxy-phenyl)-2-hydroxy-ethylamino]-3-(4-methyl-6-morpholin-4-yl-1H-benzoimidazol-2-yl)-1,5-dihydro-pyrrol-2-one

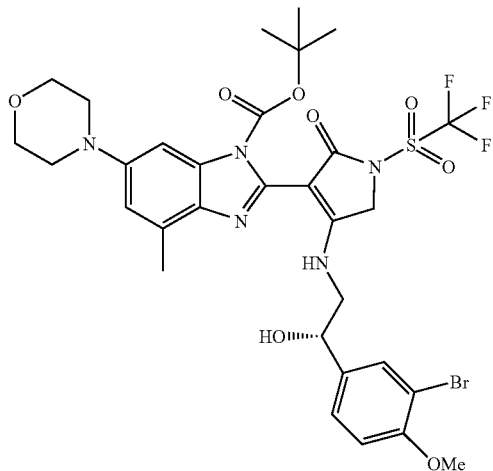

4-[2-(3-Bromo-4-methoxy-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one: 4-Hydroxy-3-(1-tert-butyloxycarbonyl-4-methyl-6-morpholin-4-yl-1H-benzoimidazol-2-yl)-1,5-dihydro-pyrrol-2-one (0.022 g, 0.053 mmol) was reacted as described in the procedure used to synthesize (S)-4-[2-(3-chloro-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one and by using acetonitrile instead of N,N-dimethylformamide. This gave the title material (0.018 g, 44%). LCMS ($^{+ESI, M+H+}$) m/z 774; $^1$H NMR (400 MHz, methanol-d$_4$) δ (ppm): 1.55 (9H, s), 2.58 (3H, s), 3.20 (4H, br dd), 3.40 (2H, d, J=5.6 Hz), 3.85–3.86 (7H, m), 4.32 (1H, d, J=17.2 Hz), 4.44 (1H, d, J=17.2 Hz), 4.72 (1H, t, J=5.7 Hz), 7.01 (1H, d, J=8.3 Hz), 7.04 (1H, br s), 7.18 (1H, d, J=1.5 Hz), 7.34 (1H, dd, J=8.3 and 1.8 Hz), 7.62 (1H, d, J=1.8 Hz).

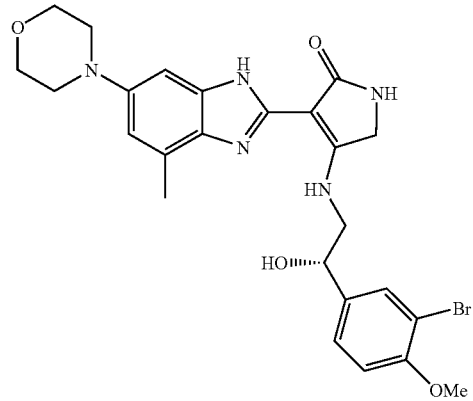

4-[2-(3-Bromo-4-methoxy-phenyl)-2-hydroxy-ethylamino]-3-(4-methyl-6-morpholin-4-yl-1H-benzoimidazol-2-yl)-1,5-dihydro-pyrrol-2-one: 4-[2-(3-Bromo-4-methoxy-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one (0.018 g, 0.023 mmol) was reacted according to the procedure used to synthesize (S)-4-[2-(3-chloro-phenyl)-2-hydroxy-ethylamino]-3-(4-methyl-6-morpholin-4-yl-1H-benzoimidazol-2-yl)-1,5-dihydro-pyrrol-2-one and afforded the title material (0.0068 g, 54%) as a beige solid. HPLC: 98% (220 nm), LCMS (+ESI, M+H+) m/z 542, 544, HRMS calcd for $C_{25}H_{28}N_5O_4Br$=541.1325, found: 541.1331; $^1$H NMR (400 MHz, methanol-d$_4$) δ (ppm): 2.48 (3H, s), 3.11 (4H, br dd), 3.49 (1H, dd, J=13.8 and 6.7 Hz), 3.57 (1H, dd, J=13.8 and 4.3 Hz), 3.84–3.87 (7H, m), 4.13 (2H, 2d, J=18.0 Hz), 4.85–4.94 (1H, m), 6.75 (1H, s), 6.92 (1H, s), 6.99 (1H, d, J=8.6 Hz), 7.37 (1H, dd, J=8.6 and 2.0 Hz), 7.64 (1H, d, J=2.0 Hz).

EXAMPLE 598

(SCHEME VIII) (S)-4-[2-(3-Chloro-phenyl)-2-hydroxy-ethylamino]-3-(4-methyl-6-morpholin-4-yl-1H-benzoimidazol-2-yl)-1,5-dihydro-pyrrol-2-one

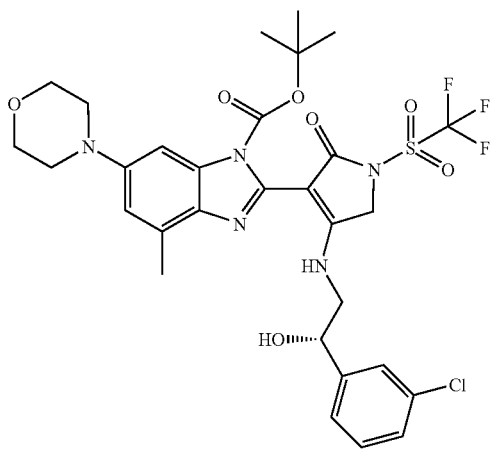

(S)-4-[2-(3-Chloro-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one: To a stirred solution of 4-hydroxy-3-(1-tert-butyloxycarbonyl-4-methyl-6-morpholin-4-yl-1H-benzoimidazol-2-yl)-1,5-dihydro-pyrrol-2-one (0.034 g, 0.082 mmol) in dichloromethane (4 mL) at 0° C. was added 2,6-di-tert-butyl-4amino-pyridine (0.050 g, 0.246 mmol) followed by trifluoromethanesulfonic anhydride (30 µL, 0.180 mmol). The mixture was stirred at 0° C. for about 10 minutes then water was added and this was extracted with dichloromethane (3×). The combined organic layers were dried over anhydrous magnesium sulfate, filtered and concentrated. The residue was then treated with a solution of (S)-2-amino-1-[3-chlorophenyl]ethanol (0.040 g, 0.233 mmol) in N,N-dimethylformamide (2 mL) at RT. The reaction was purified by Prep HPLC (acetonitrile/ammonium acetate/water) to give the title material (0.012 g, 21%) along with 4-trifluoromethanesulfonyloxy-3-(1-tert-butyloxycarbonyl-4-methyl-6-morpholin-4-yl-1H-benzoimidazol-2-yl)-1,5-dihydro-pyrrol-2-one (0.017 g, 38%), LCMS (+ESI, M+H+) m/z 547. Title material: LCMS (+ESI, M+H+) m/z 700; ¹H NMR (400 MHz, DMSO-d₆) δ (ppm): 1.46 (9H, s), 2.51 (3H, s), 3.13 (4H, br dd), 3.76 (5H, m), 4.30 (1H, m), 4.44 (2H, br s), 4.70 (1H, br qa), 5.80 (1H, d, J=4.3 Hz), 7.02 (1H, s), 7.07 (1H, s), 7.31–7.38 (3H, m), 7.43 (1H, s), 8.10 (1H, br t).

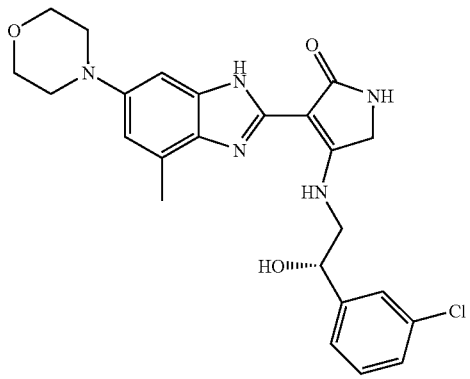

(S)-4-[2-(3-Chloro-phenyl)-2-hydroxy-ethylamino]-3-(4-methyl-6-morpholin-4-yl-1H-benzoimidazol-2-yl)-1,5-dihydro-pyrrol-2-one: To a stirred solution of (S)-4-[2-(3-chloro-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one (0.014 g, 0.020 mmol) in N,N-dimethylformamide (2 mL) was added saturated sodium bicarbonate (10 drops) and this was heated at 80° C. for 6 hours. The reaction was cooled down to RT and water and dichloromethane were added. The pH of the aqueous phase was adjusted to 7 with 0.5 N hydrochloric acid. The aqueous phase was extracted with dichloromethane (5×). The combined organic layers were dried over anhydrous magnesium sulfate, filtered and concentrated. The residue (0.012 g) was dissolved in dichloromethane (1.5 mL) and treated with SCX resin (0.750 g). This mixture was stirred at RT for 2 hours, then the resin was washed with dichloromethane, followed by ammonia (2N in methanol, diluted with dichloromethane (3 parts)). The ammonia solution was evaporated to give a residue (0.013 g) which was purified by Prep HPLC (acetonitrile/ammonium acetate/water) and afforded the acetic acid salt of the title material (0.0054 g, 51%) as a beige solid. HPLC: 95% (220 nm), LCMS (+ESI, M+H+) m/z 468, HRMS calcd for C₂₄H₂₆N₅O₃Cl=467.1724, found: 467.1715; IR ν (cm⁻¹): 3382, 2922, 1636, 1597. ¹H NMR (400 MHz, methanol-d₄) δ (ppm): 1.89 (3H, s), 2.50 (3H, s), 3.11 (4H, br dd), 3.49 (1H, dd, J=13.7 and 7.9 Hz), 3.60 (1H, dd, J=13.7 and 4.1 Hz), 3.86 (4H, br dd), 4.15 (2H, d, JAB=18.1 Hz), 4.92 (1H, dd, J=7.0 and 4.3 Hz), 6.76 (1H, br s), 6.94 (1H, br s), 7.27–7.39 (3H, m), 7.50 (1H, s).

EXAMPLE 599

(SCHEME VIII) (S,S and S,R)-4-[2-(3-Chloro-phenyl)-2-hydroxy-ethylamino]-5-methyl-3-(4-methyl-6-morpholin-4-yl-1H-benzoimidazol-2-yl)-1,5-dihydro-pyrrol-2-one

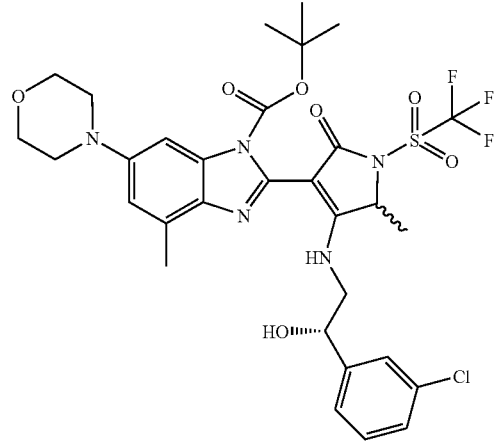

(S,S and S,R)-4-[2-(3-Chloro-phenyl)-2-hydroxy-ethylamino]-5-methyl-3-(1-tert-butyloxycarbonyl-4-methyl-6-morpholin-4-yl-1H-benzoimidazol-2-yl)-1-trifluoromethanesulfonyl-1,5-dihydro-pyrrol-2-one: (S and R)-4-Hydroxy-5-methyl-3-(1-tert-butyloxycarbonyl-4-methyl-6-morpholin-4-yl-1H-benzoimidazol-2-yl)-1,5-dihydro-pyrrol-2-one (0.023 g, 0.0536 mmol) was reacted as described in the procedure used to synthesize (S)-4-[2-(3-chloro-phenyl)-2-hydroxy-ethylamino]-3-(1-tert-butyloxycarbonyl-4-methyl-6-morpholin-4-yl-1H-benzoimidazol-2-yl)-1-trifluoromethanesulfonyl-1,5-dihydro-pyrrol-2-one and by using acetonitrile instead of N,N-dimethylformamide. This gave the title material (0.014 g, 37%). LCMS (+ESI, M+H+) m/z 714; ¹H NMR (400 MHz, acetone-d₆) δ (ppm): 1.50 (9H, s), 1.57 (3H, s), 2.54 (3H, s), 3.21 (4H, m), 3.81 (4H, m), 4.67 (2H, m), 4.98 (1H, m), 5.15 (1H, m), 7.08–7.35 (6H, m).

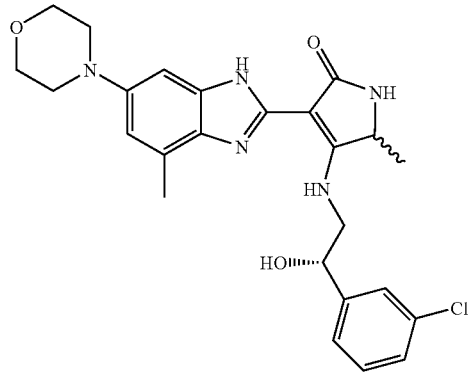

(S,S and S,R)-4-[2-(3-Chloro-phenyl)-2-hydroxy-ethylamino]-5-methyl-3-(4-methyl-6-morpholin-4-yl-1H-benzoimidazol-2-yl)-1,5-dihydro-pyrrol-2-one: (S,S and S,R)-4-[2-(3-chloro-phenyl)-2-hydroxy-ethylamino]-5-methyl-3-

(1-tert-butyloxycarbonyl-4-methyl-6-morpholin-4-yl-1H-benzoimidazol-2-yl )-1-trifluoromethanesulfonyl-1,5-dihydro-pyrrol-2-one (0.017 g, 0.024 mmol) was reacted according to the procedure used to synthesize (S)-4-[2-(3-chloro-phenyl)-2-hydroxy-ethylamino]-3-(4-methyl-6-morpholin-4-yl-1H-benzoimidazol-2-yl)-1,5-dihydro-pyrrol-2-one and afforded the title material (0.0071 g, 63%) as a white solid. HPLC: 100% (220 nm), LCMS (+ESI, M+H+) m/z 482, HRMS calcd for $C_{25}H_{28}N_5O_3Cl$=481.1881, found: 481.1868; $^1$H NMR (400 MHz, methanol-$d_4$) δ (ppm): 1.41 and 1.45 (3H, 2d, J=6.8 and 6.6 Hz), 2.48 and 2.52 (3H, 2s), 3.11 (4H, m), 3.60 (1H, m), 3.69–3.77 (1H, m), 3.86 (4H, m), 4.29 and 4.47 (1H, 2m), 4.83–4.93 (1H, m overlapped by HDO), 6.76 (1H, br d), 6.92 (1H, br s), 7.26–7.48 (4H, m).

EXAMPLE 600

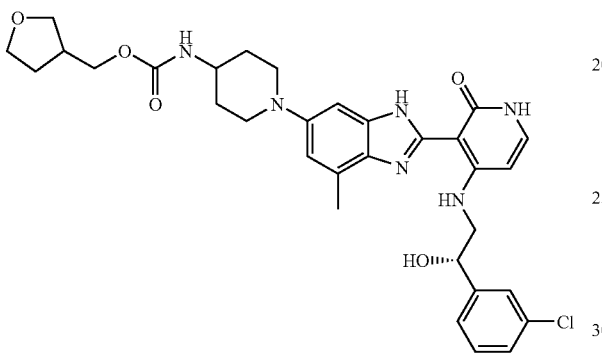

[1-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperidin-4-yl]-carbamic acid tetrahydro-furan-3-ylmethyl ester: To a solution of the Tetrahydro-3-furanmethanol (1 mmol) in THF (1 ml) was added NaH (100 mg, 2.5mmol). After 5 min, a solution of Isocyanate compound (100 mg, 0.19 mmol) in THF (1 ml) was added. The reaction mixture was stirred at room temperature for 30 min and concentrated, then purified by prep. HPLC to give the title compound (20 mg, 17%). The title compound was converted to mono HCl salt via a procedure described in example 520. LCMS (M+H)+ m/z 621 (t=1.4 min, YMC Xterra C18 7u 3.0×50 mm; 0–100% gradient over 2 min; 5 mL/min flow rate).

EXAMPLE 601

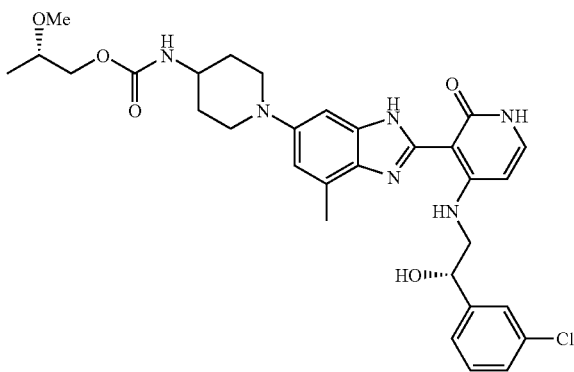

[1-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperidin-4-yl]-carbamic acid 2-methoxy-propyl ester: To a solution of the (S)-(+)-2-Methoxypropanol (1 mmol) in THF (1 ml) was added NaH (100 mg, 2.5 mmol). After 5 min, a solution of Isocyanate compound (100 mg, 0.19 mmol) in THF (1 ml) was added. The reaction mixture was stirred at room temperature for 30 min and concentrated, then purified by prep. HPLC to give the title compound (25 mg, 23%). The title compound was converted to mono HCl salt via a procedure described in example 520. LCMS (M+H)+ m/z 609 (t=1.36 min, YMC Xterra C18 7u 3.0×50 mm; 0–100% gradient over 2 min; 5 mL/min flow rate).

EXAMPLE 602

(S)-4-(2-{4-[2-(3-Bromo-phenyl)-2-hydroxy-ethylamino]-2-oxo-1,2-dihydro-pyridin-3-yl}-7-methyl-3H-benzoimidazol-5-yl)-piperazine-2-ethanol

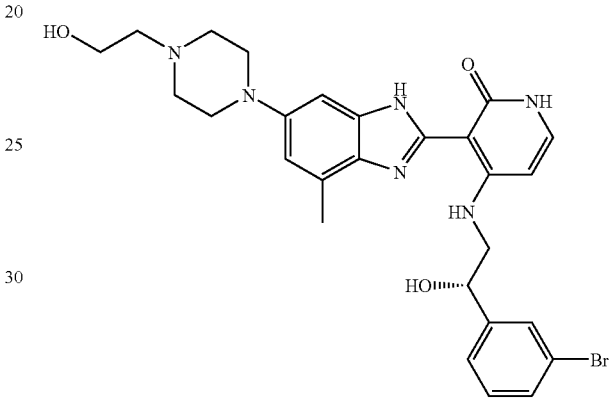

(S)-4-[2-(3-Bromo-phenyl)-2-hydroxy-ethylamino]-3-{6-[4-(2-hydroxy-ethyl)-piperazin-1-yl]-4-methyl-1H-benzimidazol-2-yl}-1H-pyridin-2-one: $^1$HNMR (500 MHz, CD$_3$OD) δ 7.60 (1H, s), 7.22–7.49 (4H, m), 7.04 (1H, s), 7.15 (1H, s), 6.36 (1H, d, J=6.8 Hz), 4.88 (1H, m), 3.30–3.97 (14H, m), 2.63 (3H, s). LCMS (M+H)+ m/z 567 (t=1.57 min.).

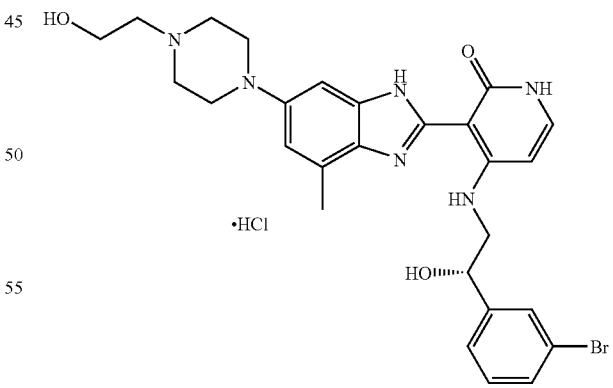

(S)-4-(2-{4-[2-(3-Bromo-phenyl)-2-hydroxy-ethylamino]-2-oxo-1,2-dihydro-pyridin-3-yl}-7-methyl-3H-benzoimidazol-5-yl)-piperazine-2-ethanol: To a stirred solution of 4-[2-(3-Chloro-phenyl)-2-hydroxy-ethylamino]-3-(4-methyl-6-piperazin-1-yl-1H-benzoimidazol-2-yl)-1H-pyridin-2-one (2 TFA salt, 80 mg, ~0.1 mmol) in methanol (2 mL) at 0° C. was added N,N-diisopropylethylamine (170

μL) and 2-fluoroethyl chloroformate (37 mg). The cooling bath was removed and the solution was stirred at room temperature for 30 minutes, after which LC/MS analysis showed the reaction to be complete. The reaction mixture was then purified on reverse phase preparative HPLC using a methanol/water/0.1% trifluoroacetic acid gradient. The fractions were evaporated to give the title compound as a trifluoroacetic acid salt, which was dissolved in methanol and applied to a Varian Mega Bond-Elute SCX cartridge. Elution with methanol followed by 2.0 M NH3/MeOH gave the free base (46.2 mg). This material was suspended in MeOH and 1.00 N aqueous HCl (1 equiv.) was added. The resulting solution was filtered through a 45 μm filter and evaporated to give the mono HCl salt of the title compound (46 mg): $^1$H NMR (500 MHz, CD$_3$OD) δ 7.50 (brs, 1H), 7.45–7.20 (m, 6H), 6.26 (d, 1H, J=7.7 Hz), 4.98–4.91 (m, 1H), 4.64 (dm, 2H, J=47.9 Hz), 4.39 (dm, 2H, J=29 Hz), 3.95–3.50 (m, 10H), 2.63 (s, 3H); . LCMS (M+H)$^+$ m/z 569,571.

EXAMPLE 603

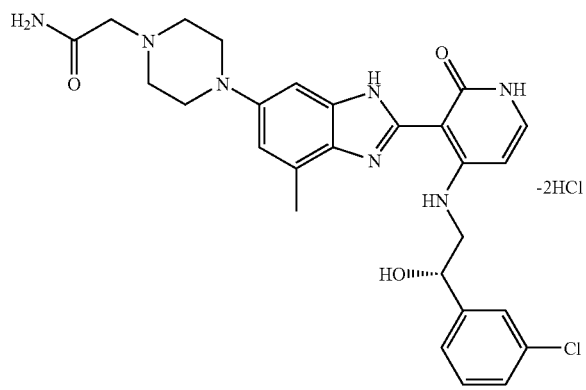

(S)-2-[4-(2-{4-[2-(3-Chloro-phenyl)-2-hydroxy-ethylamino]-2-oxo-1,2-dihydro-pyridin-3-yl}-7-methyl-3H-benzoimidazol-5-yl)-piperazin-1-yl]-acetamide Bis hydrochloride: $^1$H NMR (400 MHz, CD$_3$OD) δ 7.45–7.24 (m, 5H), 7.12 (br s, 1H), 7.09 (br s, 1H), 6.24 (d, J=7.6 Hz, 1H), 4.95–4.88 (m, 1H), 4.07 (s, 2H), 3.95–3.30 (m, 10H), 2.59 (s, 3H); LCMS (M+H)$^+$ m/z 536.

EXAMPLE 604

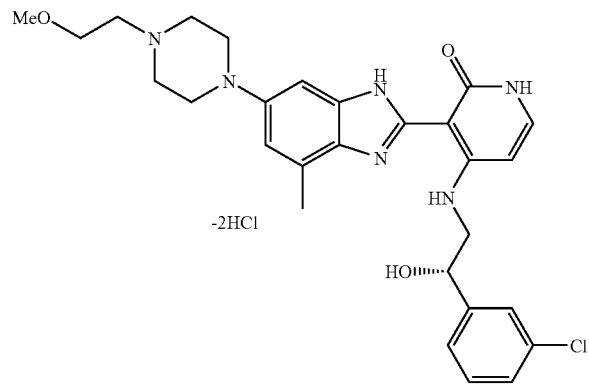

(S)-4-[2-(3-Chloro-phenyl)-2-hydroxy-ethylamino]-3-{6 [4-(2-methyoxy-ethyl)-piperazin-1-yl]-4-methyl-1H-benzoimidazol-2-yl1H-pyridin-2-one bis-hydrochloride: To a stirred solution of 4-[2-(3-Chloro-pheny)-2-hydroxy-ethylamino]-3-(4-methyl-6-piperazin-1-yl-1H-benzomidazol-2-yl)-1H-pyridin-2-one (100 mg, 0.123 mmol) in 1,4-dioxane (4 ml), ethanol (800ul), and methanol (800 ul) was added Hunigs base (214 ul). 2-Bromoethyl methyl ether (138 ul) was added and the reaction was flushed with nitrogen and heated to 80° C. until the reaction was complete as judged by LCMS. The reaction was cooled to room temperature and the solvents were evaporated in vacuo. The resulting residue was purified on reverse phase prepartive HPLC using a methanol/water/0.1% trifluoroacetic acid gradient. The fractions were evaporated to give the title compound as a trifluoroacetic acid salt. The trifluoroacetic acid salt of the pure title compound was dissolved in methanol and applied to a Varian Mega Bond-Elute SCX cartridge. Elution with methanol followed by 2.0 M NH3/MeOH gave the free base (27.3 mg). This material was suspended in MeOH and 1.00 N aqueous HCl (2 equiv.) was added. The resulting solution was filtered through a 45 μm filter and evaporated to give the bis HCl salt of the title compound (25.8 mg): $^1$H NMR (400 MHz, CD3OD) δ 7.45–7.23 (m, 5H), 7.16 (brs, 1H), 7.08 (brs, 1H), 6.25 (d,1H, J=7.6 Hz), 4.95–4.87 (m, 1H), 3.92–3.20 (m, 14H), 3.44 (s, 3H), 2.60 (s, 3H); LCMS (M+H)$^+$ m/z 537,539.

EXAMPLE 605

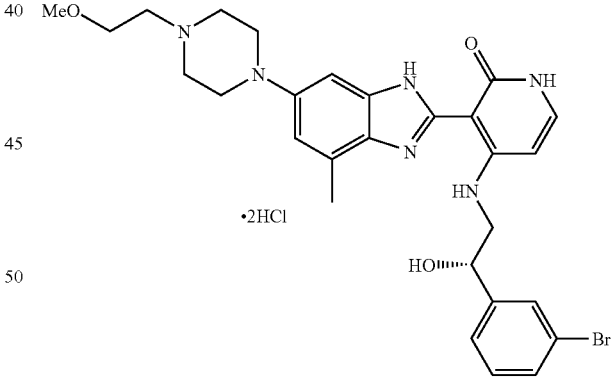

(S)-4-[2-(3-Bromo-phenyl)-2-hydroxy-ethylamino]-3-{6 [4-(2-methyoxy-ethyl)-piperazin-1-yl]-4-methyl-1H-benzoimidazol-2-yl-1H-pyridin-2-one bis hydrochloride: $^1$H NMR (400 MHz) δ 7.58 (brs, 1H), 7.43–7.33 (m, 3H), 7.25 (t, 1H), 7.15 (brs, 1H), 7.09 (brs, 1H), 6.24 (d, J=7.6 Hz, 1H), 4.92–4.84 (m, 1H), 3.83–3.24 (m, 14H), 3.43 (s, 3H), 2.60 (brs, 3H); LCMS [M+H]$^+$581,583.

EXAMPLE 606

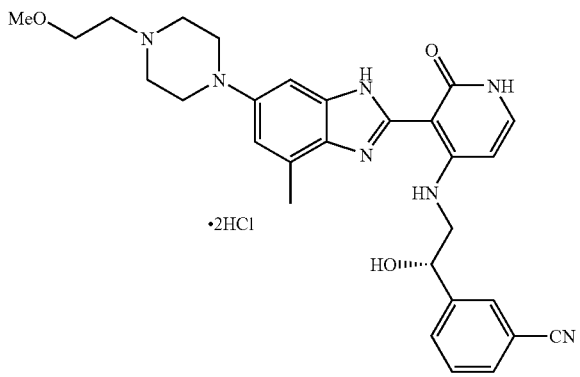

(S)-4-[2-(3-Cynao-phenyl)-2-hydroxy-ethylamino]-3-{6-[4-(2-methyoxy-ethyl)-piperazin-1-yl]-4-methyl-1H-benzoimidazol-2-yl1H-pyridin-2-one bis hydrochloride: $^1$H NMR (500 MHz) δ 7.79 (brs, 1H), 7.75 (d, J=8 Hz, 1H), 7.66 (d, J=8 Hz, 1H), 7.54 (t, J=7.5 Hz, 1H), 7.46 (d, J=7.5 Hz, 1H), 7.2 (brs, 1H), 7.14 (brs, 1H), 6.33 (d, J=7.5 Hz, 1H), 4.96–4.88 (m, 1H), 3.85–3.26 (m, 14H), 3.45 (s, 3H), 2.62 (brs, 3H); LCMS [M+H]$^+$528.

EXAMPLE 607

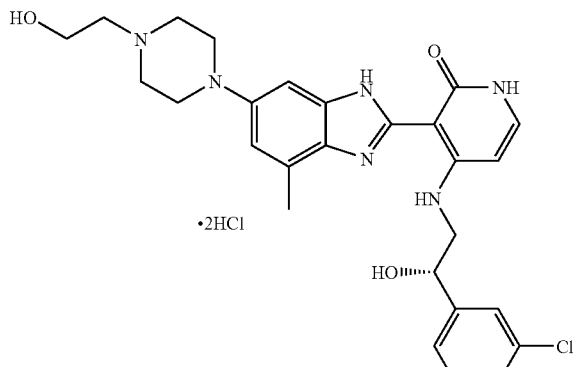

(S)-4-[2-(3-Chloro-phenyl)-2-hydroxy-ethylamino]-3-{6-[4-(2-hydroxy-ethyl)-piperadin-1-yl]-4-methyl-1H-benzimidazol-2-yl}-1H-pyridin-2-one bis hydrochloride: $^1$H NMR (500 MHz, CD3OD) δ 7.62 (s, 1H), 7.50–7.28 (m, 6H), 6.32 (d, J=8 Hz, 1H), 4.99–4.88 (m, 1H), 3.82–3.58 (m, 8H), 2.71 (s, 3H), 2.22–1.60 (m, 7H); LCMS [M+H]$^+$522, 524.

EXAMPLE 608

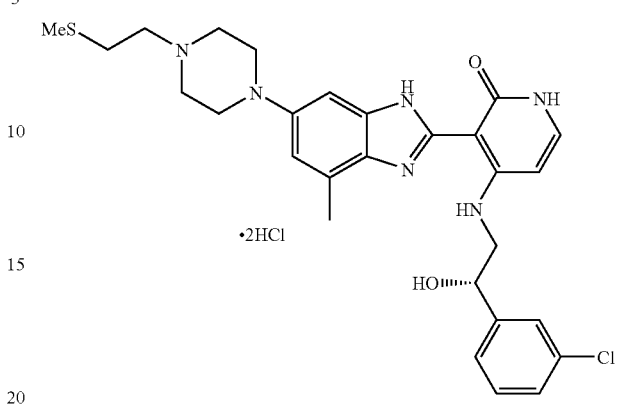

(S)-4-[2-(3-Chloro-phenyl)-2-hydroxy-ethylamino]-3-{4-methyl-6-[4-(2-methylsulfanyl-ethyl)-piperazin-1-yl]-1H-benzoimidazol-2-yl}-1H-pyridin-2-one bis hydrochloride: The product of Example 550 (60 mg) was treated with a solution of borane-tetrahydrofuran complex (1.0M in THF; 2.0 mL) and stirred for 5 min. A solution of 0.1% TFA in 95:5 methanol/water was added (3.0 mL) followed by 0.5 mL neat TFA. The reaction mixture was then purified on reverse phase preparative HPLC using a methanol/water/0.1% trifluoroacetic acid gradient. The fractions were evaporated to give the title compound as a trifluoroacetic acid salt. The trifluoroacetic acid salt of the pure title compound was dissolved in methanol and applied to a Varian Mega Bond-Elute SCX cartridge. Elution with methanol followed by 2.0 M NH3/MeOH gave the free base. This material was suspended in MeOH and 1.00 N aqueous HCl (2 equiv.) was added. The resulting solution was filtered through a 45 μm filter and evaporated to give 141 mg of the bis HCl salt of the title compound: $^1$H NMR (500 MHz, CD3OD) δ 7.47–7.40 (m, 2H), 7.37–7.25 (m, 3H), 7.19 (br s, 1H), 7.11 (br s. 1H), 6.28 (d, J=7.5 Hz, 1H), 4.95–4.88 (m, 1H), 3.95–3.20 (m, 12H), 3.00–2.93 (m, 2H), 2.62 (s, 3H), 2.22 (s, 3H); LCMS (M+H)$^+$ m/z 553, 555.

EXAMPLE 609

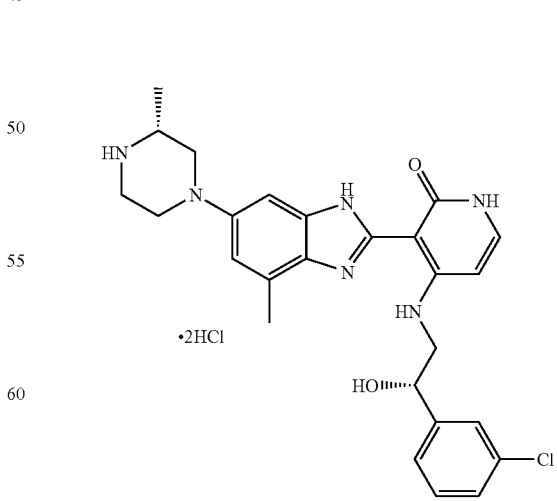

(S)4-[2-(3-Chloro-phenyl)-2-hydroxy-ethylamino]-3-[4-methyl-6-(3R-methyl-piperazin-1-yl)-1H-benzoimidazol-2- yl]-1H-pyridin-2-one bis hydrochloride: Using the method described for the preparation of Example 517, R-2-methyl piperazine was used to give the titled compound; LCMS (M+H)⁺ m/z 493, 495.

EXAMPLE 610

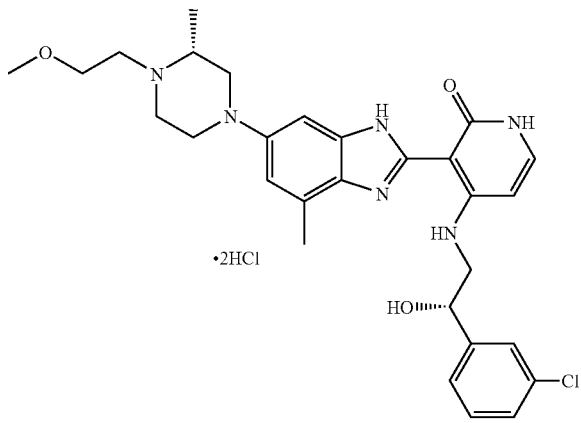

(S)4-[2-(3-Chloro-phenyl)-2-hydroxy-ethylamino]-3-{6-[4-(2-methoxy-ethyl)-3(R)-methyl-piperazin-1-yl]-4-methyl-1H-benzoimidazol-2-yl}-1H-pyridin-2-one bis hydrochloride: was prepared starting with (S)4-[2-(3-Chlorophenyl)-2-hydroxy-ethylamino]-3-[4-methyl-6-(3R-methyl-piperazin-1-yl)-1H-benzoimidazol-2-yl]-1H-pyridin-2-one and using the method employed for the synthesis of Example 604. ¹H NMR (400 MHz, CD3OD) δ 7.45–7.23 (m, 5H), 7.16 (br s, 1H), 7.09 (br s, 1H), 6.24 (d, J=7.6 Hz, 1H), 4.95–4.87 (m, 1H), 3.92–3.20 (m, 13H), 3.43 (s, 3H), 2.60 (s, 3H), 1.51 (d, 3H); LCMS (M+H)⁺ m/z 551, 553.

It is understood that the examples described above in no way serve to limit the true scope of this invention, but rather are presented for illustrative purposes. All references cited herein are incorporated by reference in their entirety.

We claim:

1. A compound according to formula I

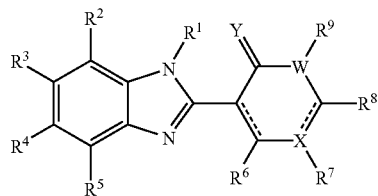

its enantiomers, diastereomers, pharmaceutically acceptable salts, hydrates, prodrugs and solvates thereof;
wherein
X is C;
Y is O;
W is N,
$R^3$ is an optionally substituted morpholine, or homomorpholine;
$R^1$, $R^2$, $R^4$, $R^5$, $R^6$, $R^7$, $R^8$, and $R^9$ are each independently selected from the group consisting of H, $C_{1-6}$ alkyl, alkenyl, alkynyl, cycloalkyl, halo, amino, —$OR^{60}$, —$NO_2$, —OH, —$SR^{60}$, —$NR^{60}R^{61}$, —CN, —$CO_2R^{60}$, —$CONR^{60}R^{61}$, $OCONR^{60}R^{61}$, —$NR^{62}CONR^{60}R^{61}$, —$NR^{60}SO_2R^{61}$, —$SO_2NR^{60}R^{61}$, —$SO_2R^{63}$, —$C(NR^{62})NR^{60}R^{61}$, aryl, —$(CH_2)_nOR^{60}$, —$(CH_2)_nNR^{60}R^{61}$, —$(CH_2)_nSR^{60}$, —$(CH_2)_n$aryl, —NH-Z-aryl, and;
wherein n is 1 to 3; and
Z is selected from the group consisting of $C_1$–$C_4$ alkyl, alkenyl, and alkynyl chain; Z having one or more hydroxy, thiol, alkoxy, thioalkoxy, amino, halo, $NR^{60}SO_2R^{61}$ groups; Z optionally incorporating one or more groups selected from the group consisting of CO, CNOH, $CNOR^{60}$, $CNNR^{60}$, $CNNCOR^{60}$ and $CNNSO_2R^{60}$; and
$R^{60}$, $R^{61}$, $R^{62}$, and $R^{63}$ are independently selected from the group consisting of H, alkyl, alkenyl, alkynyl, cycloalkyl, cycloalkylalkyl, hydroxy, alkoxy, aryl, and alkyl-$R^{25}$;
$R^{25}$ is hydrogen, alkenyl, hydroxy, thiol, alkoxy, thioalkoxy, amino, alkylamino, dialkylamino, aryl, cyano, halo, sulfoxy, sulfonyl, —$NR^{30}COOR^{31}$, —$NR^{30}C(O)R^{31}$, —$NR^{30}SO_2R^{31}$, —$C(O)NR^{30}R^{31}$; and
$R^{30}$ and $R^{31}$ are, independently, hydrogen, alkyl, or cycloalkyl.

2. The compound according to claim 1 wherein
$R^1$, $R^7$, $R^8$ and $R^9$ are H;
$R^2$ and $R^4$ are H or F;
$R^5$ is selected from the group consisting of H, methyl, ethyl, isopropyl, secondary butyl, cyclopropyl, F, and $CF_3$;
$R^6$ is selected from the group consisting of H, $NHCH_2CH(OH)$aryl, and $NHCH(CH_2OH)CH_2$aryl;
$R^{60}$ is selected from the group consisting of H, alkyl, cycloalkyl, and alkyl-$R^{25}$ wherein $R^{25}$ is hydrogen, alkenyl, hydroxy, thiol, thioalkoxy, alkoxy, thioalkoxy, halo, cyano, sulfoxy, sulfonyl, —$NR^{30}COOR^{31}$, —$NR^{30}C(O)R^{31}$, —$NR^{30}SO_2R^{31}$, or $(O)NR^{30}R^{31}$; and
$R_{30}$ and $R_{31}$ are, independently, hydrogen, alkyl, or cycloalkyl.

3. A compound according to claim 2 wherein $R^3$ is morpholine, homomorpholine.

4. The compound according to claim 3 wherein said morpholine, or homomorpholine is substituted with hydroxy, thiol, amino, alkylamino, dialkylamino, alkoxy, thioalkoxy, alkyl-$R^{25}$ —$NHC(O)R^{15}$, or —$NHCO_2R^{15}$, wherein $R^{15}$ is hydrogen, alkyl, aryl or alkyl-$R^{25}$.

5. The compound according to claim 1 wherein $R^1$ is —$CO_2R^{60}$.

6. The compound according to claim 1 wherein $R^9$ is —$SO_2R^{63}$ and $R^{63}$ is a haloalkyl.

7. The compound according to claim 2 wherein $R^6$ is selected from the group consisting of H, $NHCH_2CH(OH)$aryl, and $NHCH(CH_2OH)CH_2$aryl.

8. The compound according to claim 7 wherein said aryl is an optionally substituted phenyl.

9. The compound according to claim 8 wherein said phenyl is substituted with at least one Br, Cl, F, —CN, methoxy, or —$NHSO_2CH_3$.

10. The compound according to claim 8 wherein said substituent is 3-Br, 3-Cl or 3-F.

11. The compound according to claim 8 wherein said substituent is 4-F or 4-methoxy.

12. A compound having the formula:

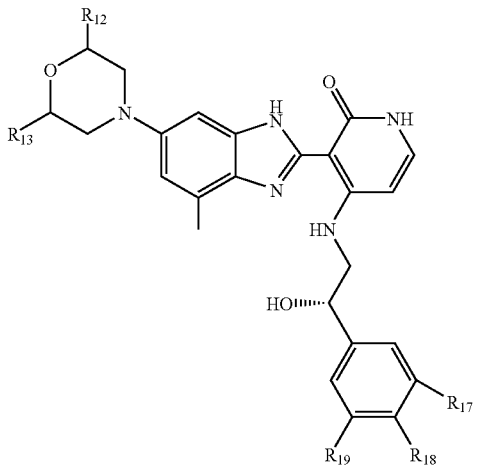

wherein $R^{12}$ and $R^{13}$ are, independently, hydrogen, alkyl, or alkyl-$R^{25}$ wherein
$R^{25}$ is hydrogen, hydroxy, thiol, alkenyl, amino, alkoxy, thioalkoxy, halo, cyano, sulfoxy, sulfonyl, —$CO_2H$, —$C(O)NR^{30}R^{31}$, —$NR^{30}SO_2R^{31}$, —$NR^{30}C(O)R^{31}$, —$NR^{30}C(O)OR^{31}$;
$R^{17}$, $R^{18}$ and $R^{19}$ are, independently, hydrogen, halogen, or alkoxy; and
$R^{30}$ and $R^{31}$ are, independently, hydrogen, or alkyl.

13. The compound according to claim 12 wherein $R^{12}$ is hydrogen, methyl, hydroxymethyl, methoxymethyl, $CH_2F$, $CH_2CN$, $CO_2H$, or —$CONR^{30}R^{31}$ wherein $R^{30}$ and $R^{31}$ are, hydrogen.

14. The compound according to claim 12 wherein $R^{12}$ and $R^{13}$ are each independently H or methyl; $R^{17}$ is Br, F, or Cl; $R^{18}$ is methoxy or fluoro; and $R^{19}$ is H.

15. The compound according to claim 12 wherein $R^{12}$ and $R^{13}$ are methyl; $R^{17}$ is Br, F or Cl, $R^{18}$ is hydrogen or methoxy; and $R^{19}$ is H.

16. A pharmaceutical composition comprising a compound according to claim 1 and a pharmaceutically acceptable carrier.

17. The pharmaceutical composition according to claim 16 further comprising at least one other anti-cancer agent formulated as a fixed dose.

18. The pharmaceutical composition according to claim 17, wherein said anti-cancer agent is selected from the group consisting of: tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone, Iressa, OSI-774, angiogenesis inhibitors, EGF inhibitors, MEK inhibitors, VEGF inhibitors, CDK inhibitors, Her1 and Her2 inhibitors and monoclonal antibodies.

19. A compound according to claim 1 having the formula (S)-4-[2-(3-Chloro-phenyl)-2-hydroxy-ethylamino]-3-(4-methyl-6-morpholin-4-yl-1H-benzoimidazol-2-yl)-1H-pyridin-2-one.

20. A compound according to claim 1 selected from the group consisting of:
(±)-4-[2-(3-Chloro-phenyl)-2-hydroxy-ethylamino]-3-(4-methyl-6-morpholin-4-yl-1H-benzimidazol-2-yl)-1H-pyridin-2-one;
(±)-4-[2-(3-Bromo-phenyl)-2-hydroxy-ethylamino]-3-(4-methyl-6-morpholin-4-yl-1H-benzimidazol-2-yl)-1H-pyridin-2-one;
(±)-4-[2-(3-Bromo-4-methoxy-phenyl)-2-hydroxy-ethylamino]-3-(4-methyl-6-morpholin-4-yl-1H-benzimidazol-2-yl)-1H-pyridin-2-one;
(S)-4-[2-(3-Chloro-phenyl)-2-hydroxy-ethylamino]-3-(4-methyl-6-morpholin-4-yl-1H-benzoimidazol -2-yl)-1H-pyridin-2-one;
(S)-4-[2-(3-Bromo-4-methoxy-phenyl)-2-hydroxy-ethylamino]-3-(4-methyl-6-morpholin-4-yl-1H-benzoimidazol-2-yl)-1H-pyridin-2-one;
(S)-4-[2-(3-Chloro-4-fluoro-phenyl)-2-hydroxy-ethylamino]-3-(4-methyl-6-morpholin-4-yl-1H-benzoimidazol-2-yl)-1H-pyridin-2-one;
(S)-4-[2-(3-Chloro-4-methoxy-phenyl)-2-hydroxy-ethylamino]-3-(4-methyl-6-morpholin-4-yl-1H-benzoimidazol-2-yl)-1H-pyridin-2-one;
4-[2-(3-Chloro-phenyl)-2(S)-hydroxy-ethylamino]-3-[4-methyl-6-[2(S),6(R)-dimethyl-morpholine-4-yl]-1H-benzoimidazol-2-yl]-1H-pyridine-2-one;
4-[2-(3-Bromo-4-methoxy-phenyl)-2(S)-hydroxy-ethylamino]-3-[4-methyl-6-[2(S),6(R)-dimethyl-morpholine-4-yl]-1H-benzoimidazol-2-yl]-1H-pyridine-2-one;
4-[2-(3-Chloro-phenyl)-(S)-2-hydroxy-ethylamino]-3-{6-[(R)-2-fluoromethyl-morpholin-4-yl]-4-methyl-1H-benzimidazol-2-yl}-1H-pyridin-2-one;
4-[2-(3-chloro-phenyl)-(S)-2-hydroxy-ethylamino]-3-{6-[(S)-2-fluoromethyl-morpholin-4-yl]-4-methyl-1H-benzimidazol-2-yl}-1H-pyridin-2-one;
4-[2-(3-Bromo-4-methoxy-phenyl)-(S)-2-hydroxy-ethylamino]-3-{6-[(R)-2-fluoromethyl-morpholin-4-yl]-4-methyl-1H-benzimidazol-2-yl}-1H-pyridin-2-one;
4-[2-(3-bromo-4-methoxy-phenyl)-(S)-2-hydroxy-ethylamino]-3-{6-[(S)-2-fluoromethyl-morpholin-4-yl]-4-methyl-1H-benzimidazol-2-yl}-1H-pyridin-2-one;
4-[2-(3-Chloro-4-methoxy-phenyl)-(S)-2-hydroxy-ethylamino]-3-{6-[(R)-2-fluoromethyl-morpholin-4-yl]-4-methyl-1H-benzimidazol-2-yl}-1H-pyridin-2-one;
4-[2-(3-chloro-4-methoxy-phenyl)-(S)-2-hydroxy-ethylamino]-3-{6-[(S)-2-fluoromethyl-morpholin-4-yl]-4-methyl-1H-benzimidazol-2-yl}-1H-pyridin-2-one;
4-[2-(7-Bromo-2,3-dihydro-benzofuran-5-yl)-(S)-2-hydroxy-ethylamino]-3-{6-[(R)-2-fluoromethyl-morpholin-4-yl]-4-methyl-1H-benzimidazol-2-yl}-1H-pyridin-2-one;
4-[2-(3-Chloro-phenyl)-(S)-2-hydroxy-ethylamino]-3-{6-[(R)-2-hydroxymethyl-morpholin-4-yl]-4-methyl-1H-benzimidazol-2-yl}-1H-pyridin-2-one;
4-[2-(3-chloro-phenyl)-(S)-2-hydroxy-ethylamino]-3-{6-[(S)-2-hydroxy-methyl-morpholin-4-yl]-4-methyl-1H-benzimidazol-2-yl}-1H-pyridin-2-one;
4-[2-(3-Bromo-4-methoxy-phenyl)-(S)-2-hydroxy-ethylamino]-3-{6-[(R)-2-hydroxymethyl-morpholin-4-yl]-4-methyl-1H-benzimidazol-2-yl}-1H-pyridin-2-one;
4-[2-(3-bromo-4-methoxy-phenyl)-(S)-2-hydroxy-ethylamino]-3-{6-[(S)-2-hydroxy-methyl-morpholin-4-yl]-4-methyl-1H-benzimidazol-2-yl}-1H-pyridin-2-one;
4-[2-(3-Chloro-4-methoxy-phenyl)-(S)-2-hydroxy-ethylamino]-3-{6-[(R)-2-hydroxymethyl-morpholin-4-yl]-4-methyl-1H-benzimidazol-2-yl}-1H-pyridin-2-one;

4-[2-(3-chloro-4-methoxy-phenyl)-(S)-2-hydroxy-ethylamino]-3-{6-[(S)-2-hydroxy-methyl-morpholin-4-yl]-4-methyl-1H-benzimidazol-2-yl}-1H-pyridin-2-one;

4-[2-(3-Chloro-phenyl)-(S)-2-hydroxy-ethylamino]-3-{6-[(R)-2-methyl-morpholin-4-yl]-4-methyl-1H-benzimidazol-2-yl}-1H-pyridin-2-one;

4-[2-(3-chloro-phenyl)-(S)-2-hydroxy-ethylamino]-3-{6-[(S)-2-methyl-morpholin-4-yl]-4-methyl-1H-benzimidazol-2-yl}-1H-pyridin-2-one;

4-[2-(3-Bromo-4-methoxy-phenyl)-(S)-2-hydroxy-ethylamino]-3-{6-[(R)-2-methyl-morpholin-4-yl]-4-methyl-1H-benzimidazol-2-yl}-1H-pyridin-2-one;

4-[2-(3-bromo-4-methoxy-phenyl)-(S)-2-hydroxy-ethylamino]-3-{6-[(S)-2-methyl-morpholin-4-yl]-4-methyl-1H-benzimidazol-2-yl}-1H-pyridin-2-one;

4-[2-(3-Chloro-4-methoxy-phenyl)-(S)-2-hydroxy-ethylamino]-3-{6-[(R)-2-methyl-morpholin-4-yl]-4-methyl-1H-benzimidazol-2-yl}-1H-pyridin-2-one;

4-[2-(3-chloro-4-methoxy-phenyl)-(S)-2-hydroxy-ethylamino]-3-{6-[(S)-2-methyl-morpholin-4-yl]-4-methyl-1H-benzimidazol-2-yl}-1H-pyridin-2-one;

4-[2-(3-Chloro-phenyl)-(S)-2-hydroxy-ethylamino]-3-{6-[(R)-2-methoxymethyl-morpholin-4-yl]-4-methyl-1H-benzimidazol-2-yl}-1H-pyridin-2-one;

4-[2-(3-chloro-phenyl)-(S)-2-hydroxy-ethylamino]-3-{6-[(S)-2-methoxy-methyl-morpholin-4-yl]-4-methyl-1H-benzimidazol-2-yl}-1H-pyridin-2-one;

4-[2-(3-Bromo-4-methoxy-phenyl)-(S)-2-hydroxy-ethylamino]-3-{6-[(R)-2-methoxymethyl-morpholin-4-yl]-4-methyl-1H-benzimidazol-2-yl}-1H-pyridin-2-one;

4-[2-(3-bromo-4-methoxy-phenyl)-(S)-2-hydroxy-ethylamino]-3-{6-[(S)-2-methoxymethyl-morpholin-4-yl]-4-methyl-1H-benzimidazol-2-yl}-1H-pyridin-2-one;

4-[2-(3-Chloro-4-methoxy-phenyl)-(S)-2-hydroxy-ethylamino]-3-{6-[(R)-2-methoxymethyl-morpholin-4-yl]-4-methyl-1H-benzimidazol-2-yl}-1H-pyridin-2-one; and 4-[2-(3-chloro-4-methoxy-phenyl)-(S)-2-hydroxy-ethylamino]-3-{6-[(S)-2-methoxymethyl-morpholin-4-yl]-4-methyl-1H-benzimidazol-2-yl}-1H-pyridin-2-one.

\* \* \* \* \*